US007442554B2

(12) United States Patent
Doweyko et al.

(10) Patent No.: US 7,442,554 B2
(45) Date of Patent: Oct. 28, 2008

(54) COMPOSITIONS AND METHODS INVOLVING GLUCOCORTICOID RECEPTOR SITE II

(75) Inventors: Arthur M. P. Doweyko, Long Valley, NJ (US); Steven G. Nadler, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 641 days.

(21) Appl. No.: 10/621,807

(22) Filed: Jul. 17, 2003

(65) Prior Publication Data

US 2006/0223110 A1    Oct. 5, 2006

Related U.S. Application Data

(60) Provisional application No. 60/396,907, filed on Jul. 18, 2002.

(51) Int. Cl.
*G01N 31/00* (2006.01)
*G01N 33/00* (2006.01)
*G06F 19/00* (2006.01)

(52) U.S. Cl. .......................................... 436/86; 702/27
(58) Field of Classification Search ........................ None
See application file for complete search history.

(56) References Cited

U.S. PATENT DOCUMENTS

| 5,759,785 | A | 6/1998 | Tsai et al. | |
|---|---|---|---|---|
| 5,856,116 | A | 1/1999 | Wilson et al. | |
| 6,236,946 | B1 | 5/2001 | Scanlan et al. | |
| 6,965,850 | B2 * | 11/2005 | Baxter et al. | 703/11 |
| 2005/0181362 | A1 * | 8/2005 | Apolito et al. | 435/6 |

FOREIGN PATENT DOCUMENTS

| EP | 1375517 A | 2/2004 |
|---|---|---|
| WO | WO 00/52050 | 9/2000 |
| WO | WO 03/015692 | 2/2003 |
| WO | WO 03/090666 | 6/2003 |
| WO | WO 2004/009017 | 1/2004 |

OTHER PUBLICATIONS

Arriza, J.L. et al., "Cloning of Human Mineralocorticoid Receptor Complementary DNA: Structural and Functional Kinship with the Glucocorticoid Receptor", Science, vol. 237, pp. 268-275 (1987).
Baldwin, Jr., A.S., "The transcription factor NF-κB and human disease", The Journal of Clinical Investigation, vol. 107, No. 1, pp. 3-6 (2001).
Bamberger, C.M. et al., "Glucocorticoid Receptor β, a Potential Endogenous Inhibitor of Glucocorticoid Action in Humans", The Journal of Clinical Investigation, vol. 95, pp. 2435-2441 (1995).
Bledsoe, R.K. et al., "Crystal Structure of the Glucocorticoid Receptor Ligand Binding Domain Reveals a Novel Mode of Receptor Dimerization and Coactivator Recognition", Cell, vol. 110, pp. 93-105 (2002).
Bourguet, W. et al., "Crystal structure of the ligand-binding domain of the human nuclear receptor RXR-α", Nature, vol. 375, pp. 377-382 (1995).
Brandon, D.D. et al., "Genetic variation of the glucocorticoid receptor from a steroid-resistant primate", Journal of Molecular Endocrinology, vol. 7, pp. 89-96 (1991).
Caldenhoven, E. et al., "Negative Cross-Talk between ReIA and the Glucocorticoid Receptor: A Possible Mechanism for the Antiinflammatory Action of Glucocorticoids", Molecular Endocrinology, vol. 9, No. 4, pp. 401-412 (1995).
Chakravarti, D. et al., "Role of CBP/P300 in nuclear receptor signalling", Nature, vol. 383, pp. 99-103 (1996).
Coghlan, M.J. et al., "Synthesis and Characterization of Non-Steroidal Ligands for the Glucocorticoid Receptor: Selective Quinoline Derivatives with Prednisolone-Equivalent Functional Activity", J. Med. Chem., vol. 44, pp. 2879-2885 (2001).
Da Silva, J.A. et al., "Optimizing Glucocorticoid Therapy in Rheumatoid Arthritis", Neuroendocrine Mechanisms in Rheumatic Disease, Rheumatic Disease Clinics of North America, vol. 26, No. 4, pp. 859-880 (2000).
Danielsen, M. et al., "The mouse glucocorticoid receptor: mapping of functional domains by cloning, sequencing and expression of wild-type and mutant receptor proteins", The EMBO Journal, vol. 5, No. 10, pp. 2513-2522 (1986).
Darimont, B.D. et al., "Structure and specificity of nuclear receptor-coactivator interactions", Genes & Development, vol. 12, pp. 3343-3356 (1998).
Diamond, M.I. et al., "Transcription Factor Interactions: Selectors of Positive or Negative Regulation from a Single DNA Element", Science, vol. 249, pp. 1266-1272 (1990).
Eisenmann, G. et al., "Quand Les Cellules Scintillent", Le Technoscope De Biofutur, No. 151, p. 8 (1995).
Elmore, S.W. et al., "Nonsteroidal Selective Glucocorticoid Modulators: the Effect of C-5 Alkyl Substitution on the Transcriptional Activation/Repression Profile of 2,5-Dihydro-10-methoxy-2,2,4-trimethyl-1H-[1]benzopyrano[3,4-f]luinolines", J. Med. Chem., vol. 44, pp. 4481-4491 (2001).
Evans, R.M., "The Steroid and Thyroid Hormone Receptor Superfamily", Science, vol. 240, pp. 889-895 (1988).
Firestein, G.S. et al., "Signal Transduction and Transcription Factors in Rheumatic Disease", Arthritis & Rheumatism, vol. 42, No. 4, pp. 609-621 (1999).
Francis, G.A. et al., "Nuclear Receptors and the Control of Metabolism", Annu. Rev. Physiol., vol. 65, pp. 261-311 (2003).

(Continued)

*Primary Examiner*—Nashaat T. Nashed
*Assistant Examiner*—Jae W Lee
(74) *Attorney, Agent, or Firm*—Melissa Handler

(57) ABSTRACT

A binding site in nuclear hormone receptors is described and its structural coordinates are provided. The invention provides machine-readable data storage media comprising structure coordinates of Site II and computer systems comprising the machine-readable data storage media. The invention provides methods used in the design and identification of ligands of Site II and of modulators of nuclear hormone receptors. The invention provides ligands of Site II, modulators of NHRs, pharmaceutical compositions comprising modulators of NHRs, methods of modulating NHRs, and methods of treating diseases by administering modulators of an NHR. Also provided are methods of designing mutants, mutant NHRs, Site II binding assays, and models of Site II.

7 Claims, 16 Drawing Sheets
(2 of 16 Drawing Sheet(s) Filed in Color)

OTHER PUBLICATIONS

Giguère, V. et al., "Functional Domains of the Human Glucocorticoid Receptor", Cell, vol. 46, pp. 645-652 (1986).
Giguère, V. et al., "Identification of a new class of steroid hormone receptors", Nature, vol. 331, pp. 91-94 (1988).
Giguère, V. et al., "Orphan Nuclear Receptors: From Gene to Function", Endocrine Reviews, vol. 20, No. 5, pp. 689-725 (1999).
Grange, T. et al., "In vivo analysis of the model tyrosine aminotransferase gene reveals multiple sequential steps in glucocorticoid receptor action", Oncogene, vol. 20, pp. 3028-3038 (2001).
Green, S. et al., "Human oestrogen receptor cDNA: sequence, expression and homology to v-erb-A", Nature, vol. 320, pp. 134-139 (1986).
Greene, M.E. et al., "Isolation of the Human Peroxisome Proliferator Activated Receptor Gamma cDNA: Expression in Hemotopoietic Cells and Chromosomal Mapping", Gene Expression, vol. 4, pp. 281-299 (1995).
Greschik, H. et al., "Structural and Functional Evidence for Ligand-Independent Transcriptional Activation by the Estrogen-Related Receptor 3", Molecular Cell, vol. 9, pp. 303-313 (2002).
Hager, L.J. et al., "Transcriptional regulation of mouse liver metallothionein-I gene by glucocorticoids", Nature, vol. 291, pp. 340-342 (1981).
Hofmann, T.G. et al., "Various glucocorticoids differ in their ability to induce gene expression, apoptosis and to repress NF-κB-dependent transcription", FEBS Letters, vol. 441, pp. 441-446.
Hollenberg, S.M. et al., "Primary structure and expression of a functional human glucocorticoid receptor cDNA", Nature, vol. 318, pp. 635-641 (1985).
Huang, X. et al., "Elucidating the Inhibiting Mode of AHPBA Derivatives against HIV-1 Protease and Building Predictive 3D-QSAR Models", J. Med. Chem., vol. 45, pp. 333-343 (2002).
Jonat, C. et al., "Antihumor Promotion and Antiinflammation: Down-Modulation of AP-1 (Fos/Jun) Activity by Glucocorticoid Hormone", Cell, vol. 62, pp. 1189-1204 (1990).
Jones, D.C. et al., "Nuclear Receptor Peroxisome Proliferator-activated Receptor α (PPARα) Is Expressed in Resting Murine Lymphocytes", The Journal of Biological Chemistry, vol. 277, No. 9, pp. 6838-6845 (2002).
Kalkhoven, E. et al., "Negative Interaction between the RelA(p65) Subunit of NF-κB and the Progesterone Receptor", The Journal of Biological Chemistry, vol. 271, No. 11, pp. 6217-6224 (1996).
Kallio, P.J. et al., "Androgen Receptor-Mediated Transcriptional Regulation in the Absence of Direct Interaction with a Specific DNA Element", Molecular Endocrinology, vol. 9, No. 8, pp. 1017-1028 (1995).
Kamei, Y. et al., "A CBP Integrator Complex Mediates Transcriptional Activation and AP-1 Inhibition by Nuclear Receptors", Cell, vol. 85, pp. 403-414 (1996).
Kauppi, B. et al., "The Three-dimensional Structures of Antagonistic and Agonistic Forms of the Glucocorticoid Receptor Ligand-binding Domain", The Journal of Biological Chemistry, vol. 278, No. 25, pp. 22748-22754 (2003).
Keightley, M.-C. et al., "Unique Sequences in the Guinea Pig Glucocorticoid Receptor Induce Constitutive Transactivation and Decrease Steroid Sensitivity", Molecular Endocrinology, vol. 8, No. 4, pp. 431-439 (1994).
Keller, E.T. et al., "Inhibition of NF κB Activity through Maintenance of IκBαLevels Contributes to Dihydrotestosterone-mediated Repression of the Interleukin-6 Promoter", The Journal of Biological Chemistry, vol. 271, No. 42, pp. 26267-26275 (1996).
Laudet, V. et al., Chapter 4: "Molecular mechanisms of transcriptional regulation", The Nuclear Receptor FactsBook, Academic Press, publ., pp. 42-61 (2002).
Laudet, V. et al., "GR", The Nuclear Receptor FactsBook, Academic Press, publ., pp. 345-367 (2002).
Lind, U. et al., "Functional Probing of the Human Glucocorticoid Receptor Steroid-interacting Surface by Site-directed Mutagenesis", The Journal of Biological Chemistry, vol. 275, No. 25, pp. 19041-19049 (2000).
Lubahn, D.B. et al., "The Human Androgen Receptor: Complementary Deoxyribonucleic Acid Cloning, Sequence Analysis and Gene Expression in Prostate", Molecular Endocrinology, vol. 2, No. 12, pp. 1265-1275 (1988).
Mangelsdorf, D.J. et al., "Nuclear receptor that identifies a novel retinoic acid response pathway", Nature, vol. 345, pp. 224-229 (1990).
Matias, P.M. et al., "Structural Evidence for Ligand Specificity in the Binding Domain of the Human Androgen Receptor", The Journal of Biological Chemistry, vol. 275, No. 34, pp. 26164-26171 (2000).
Miesfeld, R. et al., "Characterization of a steroid hormone receptor gene and mRNA in wild-type and mutant cells", Nature, vol. 312, pp. 779-781 (1984).
Miesfeld, R. et al., "Genetic Complementation of a Glucocorticoid Receptor Deficiency by Expression of Cloned Receptor cDNA", Cell, vol. 46, pp. 389-399 (1986).
Misrahi, M. et al., "Complete Amino Acid Sequence of the Human Progesterone Receptor Deduced from Cloned cDNA", Biochemical and Biophysical Research Communications, vol. 143, No. 2, pp. 740-748 (1987).
Miura, T. et al., "Functional Modulation of the Glucocorticoid Receptor and Suppression of NF-κB-dependent Transcription by Ursodeoxycholic Acid", The Journal of Biological Chemistry, vol. 276, No. 50, pp. 47371-47378 (2001).
Nakai, A. et al., "Characterization of a Third Human Thyroid Hormone Receptor Coexpressed with Other Thyroid Hormone Receptors in Several Tissues", Molecular Endocrinology, vol. 2, No. 11, pp. 1087-1092 (1988).
Nolte, R.T. et al., "Ligand binding and co-activator assembly of the peroxisome proliferator-activated receptor-γ", Nature, vol. 395, pp. 137-143 (1998).
Palvimo, J.J. et al., "Mutual Transcriptional Interference between RelA and Androgen Receptor", The Journal of Biological Chemistry, vol. 271, No. 39, pp. 24151-24156 (1996).
Peltz, G., "Transcription factors in immune-mediated disease", Current Opinion in Biotechnology, vol. 8, pp. 467-473 (1997).
Petkovich, M. et al., "A human retinoic acid receptor which belongs to the family of nuclear receptors", Nature, vol. 330, pp. 444-450 (1987).
Reichardt, H.M. et al., "DNA Binding of the Glucocorticoid Receptor Is Not Essential for Survival", Cell, vol. 93, pp. 531-541 (1998).
Reichardt, H.M. et al., "Repression of inflammatory responses in the absence of DNA binding by the glucocorticoid receptor", The EMBO Journal, vol. 20, No. 24, pp. 7168-7173 (2001).
Renaud, J.-P. et al., "Crystal structure of the RAR-γ ligand-binding domain bound to all-trans retinoic acid", Nature, vol. 378, pp. 681-689 (1995).
Reynolds, P.D. et al., "Cloning and Expression of the Glucocorticoid Receptor from the Squirrel Monkey (Saimiri boliviensis boliviensis), a Glucocorticoid-Resistant Primate", Journal of Clinical Endocrinology and Metabolism, vol. 82, No. 2, pp. 465-472 (1997).
Ricote, M. et al., "The peroxisome proliferator-activated receptor-γ is a negative regulator of macrophage activation", Nature, vol. 391, pp. 79-82 (1998).
Ringold, G.M. et al., "Dexamethasone-Mediated Induction of Mouse Mammary Tumor Virus RNA: a System for Studying Glucocorticoid Action", Cell, vol. 6, pp. 299-305 (1975).
Rochel, N. et al., "The Crystal Structure of the Nuclear Receptor for Vitamin D Bound to its Natural Ligand", Molecular Cell, vol. 5, pp. 173-179 (2000).
Rusconi, S. et al., "Functional dissection of the hormone and DNA binding activities of the glucocorticoid receptor", The EMBO Journal, vol. 6, No. 5, pp. 1309-1315 (1987).
Scheidereit, C. et al., "The glucocorticoid receptor binds to defined nucleotide sequences near the promoter of mouse mammary tumour virus", Nature, vol. 304, pp. 749-752 (1983).
Shiau, A.K. et al., "Structural characterization of a subtype-selective ligand reveals a novel mode of estrogen receptor antagonism", Nature Structural Biology, vol. 9, No. 5, pp. 359-364 (2002).
Sierk, M.L. et al., "DNA Deformability as a Recognition Feature in the RevErb Response Element", Biochemistry, vol. 40, pp. 12833-12843 (2001).

Stanbury, R.M. et al., "Systemic corticosteriod therapy—side effects and their management", Br. J. Opthalmol., vol. 82, pp. 704-708 (1998).

Stöcklin, E. et al., "Functional interactions between Stat5 and the glucocorticoid receptor", Nature, vol. 383, pp. 726-728 (1996).

Takamatsu, Y. et al., "A New Method for Predicting Binding Free Energy Between Receptor and Ligand", Proteins: Structure, Function, and Genetics, vol. 33, pp. 62-73 (1998).

Tanenbaum, D.M. et al., "Crystallographic comparison of the estrogen and progesterone receptor's ligand binding domains", Proc. Natl. Acad. Sci. USA, vol. 95, pp. 5998-6003 (1998).

Valentine, J.E. et al., "Mutations in the Estrogen Receptor Ligand Binding Domain Discriminate between Hormone-dependent Transactivation and Transrepression", The Journal of Biological Chemistry, vol. 275, No. 33, pp. 25322-25329 (2000).

Van Hoorn, W.P., "Identification of a Second Binding Site in the Estrogen Receptor", J. Med. Chem., vol. 45, pp. 584-589 (2002).

Vayssière, B.M. et al., "Synthetic Glucocorticoids That Dissociate Transactivation and AP-1 Transrepression Exhibit Antiinflammatory Activity in Vivo", Molecular Endocrinology, vol. 11, No. 9, pp. 1245-1255 (1997).

Wang, Y. et al., "A Second Binding Site for Hydroxytamoxifen within the Ligand-Binding Domain of Estrogen Receptor β", The Endocrine Society, Meeting Jun. 2003, Presentation No. OR34-1, p. 106 (2003).

Wang, Z. et al., "Structure and function of Nurr1 identifies a class of ligand-independent nuclear receptors", Nature, vol. 423, pp. 555-560 (2003).

Watkins, R.E. et al., "The Human Nuclear Xenobiotic Receptor PXR: Structural Determinants of Directed Promiscuity", Science, vol. 292, pp. 2329-2333 (2001).

Weinberger, C. et al., "Identification of Human Glucocorticoid Receptor Complementary DNA Clones by Epitope Selection", Science, vol. 228, pp. 740-742 (1985).

Williams, S.P. et al., "Atomic structure of progesterone complexed with its receptor", Nature, vol. 393, pp. 392-396 (1998).

Yamamoto, K. et al., "Transcriptional Roles of Nuclear Factor κB and Nuclear Factor-Interleukin-6 in the Tumor Necrosis Factor α-Dependent Induction of Cyclooxygenase-2 in MC3T3-E1 Cells", The Journal of Biological Chemistry, vol. 270, No. 52, pp. 31315-31320 (1995).

Yang, K. et al., "Characterization of an ovine glucocorticoid receptor cDNA and developmental changes in its mRNA levels in the fetal sheep hypothalamus, pituitary gland and adrenal", Journal of Molecular Endocrinology, vol. 8, pp. 173-180 (1992).

Yang-Yen, H.-F. et al., "Transcriptional Interface between c-Jun and the Glucocorticoid Receptor: Mutual Inhibition of DNA Binding Due to Direct Protein-Protein Interaction", Cell, vol. 62, pp. 1205-1215 (1990).

Zhang, S. et al., "Role of the C Terminus of the Glucocorticoid Receptor in Hormone Binding and Agonist/Antagonist Discrimination", Molecular Endocrinology, vol. 10, No. 1, pp. 24-34 (1996).

Agius, C. et al., "Identification of a glucocorticoid receptor in the human leukemia cell line K562", J. Lab Clin Med, vol. 100, pp. 178-185 (1982).

Baumann, H. et al., "Refined Solution Structure of the Glucocorticoid Receptor DNA-Binding Domain", Biochemsitry, vol. 32, pp. 13463-13471 (1993).

Dey, R. et al., "Homology modelling of the ligand-binding domain of glucocorticoid receptor: binding site interactions with cortisol and corticosterone", Protein Engineering, vol. 14, No. 8, pp. 565-571 (2001).

Goldstein, R. et al., "Three-dimensional model for the hormone binding domains of steroid receptors", Proc Natl Acad Sci USA, vol. 90, pp. 9949-9953 (1993).

Makino, S. et al., "Automated Flexible Ligand Docking Method and Its Application for Database Search", J Comput Chem, vol. 18, pp. 1812-1825 (1997).

Tapia, O. et al., "Computer Assisted Simulations and Molecular Graphics Methods in Molecular Design. 1. Theory and Applications to Enzyme Active-Site Directed Drug Design", Molecular Engineering, vol. 3, pp. 377-414 (1994).

Wurtz, J.M. et al., "Three-Dimensional Models of Estrogen Receptor Ligand Binding Domain Complexes, Based on Related Crystal Structures and Mutational and Structure-Activity Relationship Data", J. Med. Chem., vol. 41, pp. 1803-1814 (1998).

* cited by examiner

FIGURE 2

```
RXRalpha   225  S......... ANEDM..... .......... .......... PVE.RI LEAE  LAVE. PKTET
RARgamma   182  L......... SPQ..LEE.. .......... .......... LIT.KV SKAH  QETF. P....
PR         682  .......... ........Q. .......LI. .........P PLINLL MSIE  ..PD. V....
AR         669  .......... .......... .........C Q........P IFLNVL EAIE  ..PG. V....
ERalpha    305  .......... .......... .......... .SLALSLTAD QMVSAL LDAE  ..PP. I....
ERbeta     261  .......... .......... .......... ....DALSPE QLVLTL LEAE  ..PP. H....
VitDR      120  .LRPKL.... SEE..QQR.. .......... .......... IIA.IL LDAH  HKTY. D....
PPARgamma  207  E......... SAD..LRA.. .........  .......... LAK.HL YDSY  IKSF. P....
MR         731  .......... ........S  RA.....LT. .........P SPVMVL ENIE  ..PE. I....
TRbeta     211  ......KPEP TDE..EWE.. .......... .......... LIK.TV EAH   VATNAQ....
GR         523  .......... .......... ..ATLPQLT. .........P TLVSLL EVIE  ..PE. V....

RXRalpha   249  YVEANMGLNP SSPNDPVTN. .......... .......IC. .......... ..........
RARgamma   203  .......... .......... .......... .........S LCQL.GKYTT N.........
PR         699  .......... .........I YAGHDNTKPD TSSSLLTS.. .......... ..........
AR         685  .......... .........V CAGHDNNQPD SFAALLSS.. .......... ..........
ERalpha    327  .......... .........L YSEYDPTRPF SEASMMGL.. .......... ..........
ERbeta     281  .......... .........V LISR...... TEASMMMS.. .......... ..........
VitDR      145  .......... .......... .......... .........P .......... .TYSDFCQFR
PPARgamma       .......... .......... .......... .......... .......... ..........
MR         750  .......... .........V YAGYDSSKPD TAENLLST.. .......... ..........
TRbeta     236  .......... .......... .......... .........G SHWKQKRKFL P.........
GR         544  .......... .........L YAGYDSSVPD STWRIMTT.. .......... ..........

RXRalpha        .......... .......... .......... .......... .......... ..........
RARgamma   214  ..SSADHRVQ L......... .......... .......... .......... ..........
PR              .......... .......... .......... .......... .......... ..........
AR              .......... .......... .......... .......... .......... ..........
ERalpha         .......... .......... .......... .......... .......... ..........
ERbeta          .......... .......... .......... .......... .......... ..........
VitDR      155  PPVRV..... .NDGGGSVTL ELS....... .......... .......... ..........
PPARgamma  228  .......... .......... ...LTKAKAR AILTGKTTDK SPFVIYDMNS LMMGEDKIKF
MR              .......... .......... .......... .......... .......... ..........
TRbeta     248  ..EDIGQAPK V......... .......... .......... .......... ..........
GR              .......... .......... .......... .......... .......... ..........

RXRalpha   271  .......... .......... ..Q...AADK QLFTLVEWAK RIPHFSELPL DDQVILLRAG
RARgamma   223  .......... ...DLGLWDK FSE...LATK CIIKIVEFAK RLPGFTGLSI ADQITLLKAA
PR         718  .......... .......... ...LNQLGER QLLSVVKWSK SLPGFRNLHI DDQITLIQYS
AR         705  .......... .......... ...LNELGER QLVHVVKWAK ALPGFRNLHV DDQMAVIQYS
ERalpha    345  .......... .......... ...LTNLADR HLVHMINWAK RVPGFVDLTL HDQVHLLECA
ERbeta     294  .......... .......... ...LTKLADK ELVHMISWAK KIPGFVELSL FDQVRLLESC
VitDR      172  .......... ...QLSMLPH LAD...LVSY SIQKVIGFAK MIPGFRDLTS EDQIVLLKSS
PPARgamma  265  KHITPLQEQS KEVAIRIFQG CQF...RSVE AVQEITEYAK SIPGFVNLDL NDQVTLLKYG
MR         769  .......... .......... ...LNRLAGK QMIQVVKWAK VLPGFKNLPL EDQITLIQYS
TRbeta     257  .......... ...DLEAFSH FTK...IITP AITRVVDFAK KLPMFCELPC EDQIILLKGC
GR         563  .......... .......... ...LNMLGGR QVIAAVKWAK AIPGFRNLHL DDQMTLLQYS
```

FIGURE 2 (continued)

```
RXRalpha   306  WNELLIASFS HRSIAV....  ..KDGILLAT GL...HVHRN ...S..AHSAG VG........
RARgamma   267  CLDILMLRIC TRY...TPE.  ..QDTMTFSD GL...TLNRT ..Q..MH... ..NAGF....
PR         755  WMSLMVFGLG WRSYK....H  VSGQMLYFAP DL...ILNEQ ..R..MKESS FY........
AR         742  WMGLMVFAMG WRSFT....N  VNSRMLYFAP DL...VFNEY ..RM.HKSRM Y.........
ERalpha    382  WLEILMIGLV WRSME.....  .HPGKLLFAP NL...LLDRN ..Q.GKCVEG MV........
ERbeta     331  WMEVLMMGLM WRSID.....  .HPGKLIFAP DL...VLDRD ..E.GKCVEG IL........
VitDR      216  AIEVIMLRSN ESF...TMD.  ...DMSWTCG N.QDYKYRVS ..D..VT... ..KAGH....
PPARgamma  322  VHEIIYTMLA SLM...NK..  ...DGVLISE GQ...GFMTR E.F..LK... ......SLRK
MR         806  WMCLSSFALS WRSYK....H  TNSQFLYFAP DL...VFNEE .KM..HQSAM YE........
TRbeta     301  CMEIMSLRAA VRY...DPE.  ..SETLTLNG EM...AVTRG ..Q..LK... ..NGGL....
GR         600  WMFLMAFALG WRSYR....Q  SSANLLCFAP DL...IINEQ .R...MTLPC MY........

RXRalpha   345  ...A.IF.DR VLTELVSKMR DMQMDKTELG CLRAIVL.FN PDSKG...LS ..........
RARgamma   305  ..GP.LT.DL VFAFAGQLL. PLEMDDTETG LLSAICL.IC GDRMD...LE ..........
PR         796  ...S.LC.LT MWQIPQEFV. KLQVSQEEFL CMKVLLL.LN .TIP.LEGLR ..........
AR         783  ...S.QC.VR MRHLSQEFG. WLQITPQEFL CMKALLL.FS .IIP.VDGLK ..........
ERalpha    422  ...E.IF.DM LLATSSRFR. MMNLQGEEFV CLKSIILLNS .GV...... YTF.LSSTLK
ERbeta     371  ...E.IF.DM LLATTSRFR. ELKLQHKEYL CVKAMILLNS .......... ...LVTAT.Q
VitDR      255  ..SLELI.EP LIKFQVGLK. KLNLHEEEHV LLMAICI.VS PDRPG...VQ ..........
PPARgamma  359  PFGD.FM.EP KFEFAVKFN. ALELDDSDLA IFTAVII.IS GDRPG...LL ..........
MR         848  ...L..C.QG MHQISLQFV. RLQLTFEEYT IMKVLLL.LS .TIP.KDGLK ..........
TRbeta     339  ..GV.VS.DA IFDLGMSLS. SFNLDDTEVA LLQAVLL.MS SDRPG...LA ..........
GR         641  ...D..QCKH MLYVSSELH. RLQVSYEEYL CMKTLLL.LS .SVP.KDGLK ..........

RXRalpha   386  ...NPAEVEA LREKVYASLE AYCKH..KYP EQPG...... ...RFAKLLL RLPALRSIGL
RARgamma   336  ...EPEKVDK LQEPLLEALR LYARR..RRP SQPY...... ...MFPRMLM KITDLRGIST
PR         837  ...SQTQFEE MRSSYIRELI KAIG...LRQ K...GVV...S SSQRFYQLTK LLDNLHDLVK
AR         824  ...NQKFFDE LRMNYIKELD RIIA...CKR K...NPT...S CSRRFYQLTK LLDSVQPIAR
ERalpha    467  SLEEKDHIHR VLDKITDTLI HLMA...KAG L...TLQ..Q QHERLAQLLL ILSHIRHMSN
ERbeta     411  DADSSRKLAH LLNAVTDALV WVIA...KSG I...SSQ..Q QSMRLANLLM LLSHVRHASN
VitDR      297  ...DAALIEA IQDRLSNTLQ TYIRC..RHP PP.L...... ...LYAKMIQ KLADLRSLNE
PPARgamma  402  ...NVKFEID IQDNLLQALE LQLKL..NHP ESSQ...... ...LFAKLLQ KMTDLRQIVT
MR         888  ...SQAAFEE MRTNYIKELR KMVT.KCPNN S...G....Q SWQRFYQLTK LLDSMHDLVS
TRbeta     380  ...CVERIEK YQDSFLLAFE HYINY..RKH HVTH...... ...FWPKLLM KVTDLRMIGA
GR         681  ...SQELFDE IRMTYIKELG KAIV...KRE G...N..SSQ NWQRFYQLTK LLDSMHEVVE RXRalpha   432  KCLEHLFFFK LIGDTPIDTF LMEMLEAPHQ MT........ .......... ..........
RARgamma   382  KGAERA.... .......... .......... ...ITLKMEI PGP....MPP LIREMLENP.
PR         886  QLHLYC.... .......... .......... .......... .......... .........L
AR         873  ELHQFT.... .......... .......... .......... .......... .........F
ERalpha    519  KGMEHL.... .......... .......... .......... .......... .........Y
ERbeta     463  KGMEHL.... .......... .......... .......... .......... .........L
VitDR      342  EHSKQY.... .......... .......... ...RCLSFQP ECSMK..LTP LVLEVFG...
PPARgamma  448  EHVQLL.... .......... .......... ..QVIKKTET DMS....LHP LLQEIYKDL.
MR         937  DLLEFC.... .......... .......... .......... .......... .........F
TRbeta     426  CHASRF.... .......... .......... ...LHMKVEC PT...ELFPP LFLEVFE...
GR         730  NLLNYC.... .......... .......... .......... .......... .........F
```

FIGURE 2 (continued)

```
RXRalpha          ..........  ..........  ..........  ..........  ..........  ..........
RARgamma          ..........  ..........  ..........  ..........  ..........  ..........
PR         893    .NTFIQSRAL  SVEFPEMMSE  VIAAQLPKIL  AGMVKPLLFH  K.........  ..........
AR         880    .DLLIKSHMV  SVDFPEMMAE  IISVQVPKIL  SGKVKPIYFH  T.........  ..........
ERalpha    526    .SMKCKNV..  ..........  ..........  ..........  .VPLYDLLLE  ML........
ERbeta     470    NMKC......  ..........  ..........  ..........  ..........  ..KNVVPVYD
VitDR             ..........  ..........  ..........  ..........  ..........  ..........
PPARgamma         ..........  ..........  ..........  ..........  ..........  ..........
MR         944    .YTFRESHAL  KVEFPAMLVE  IISDQLPKVE  SGNAKPLYFH  R.........  ..........
TRbeta            ..........  ..........  ..........  ..........  ..........  ..........
GR         737    .QTFLDKTMS  IEFPEMLAEI  ITNQIPKYSN  GNIKKLLFHQ  K.........  ..........

RXRalpha          ..........  .....  (SEQ ID NO:3)
RARgamma          ..........  .....  (SEQ ID NO:4)
PR                ..........  .....  (SEQ ID NO:5)
AR                ..........  .....  (SEQ ID NO:6)
ERalpha           ..........  .....  (SEQ ID NO:7)
ERbeta     482    LLLEMLNAHV  LR...  (SEQ ID NO:8)
VitDR             ..........  .....  (SEQ ID NO:9)
PPARgamma  477    ..........  ...Y..  (SEQ ID NO:10)
MR         984    ..........  ...K.  (SEQ ID NO:11)
TRbeta     453    ..........  ....D  (SEQ ID NO:12)
GR                ..........  .....  (SEQ ID NO:13)
```

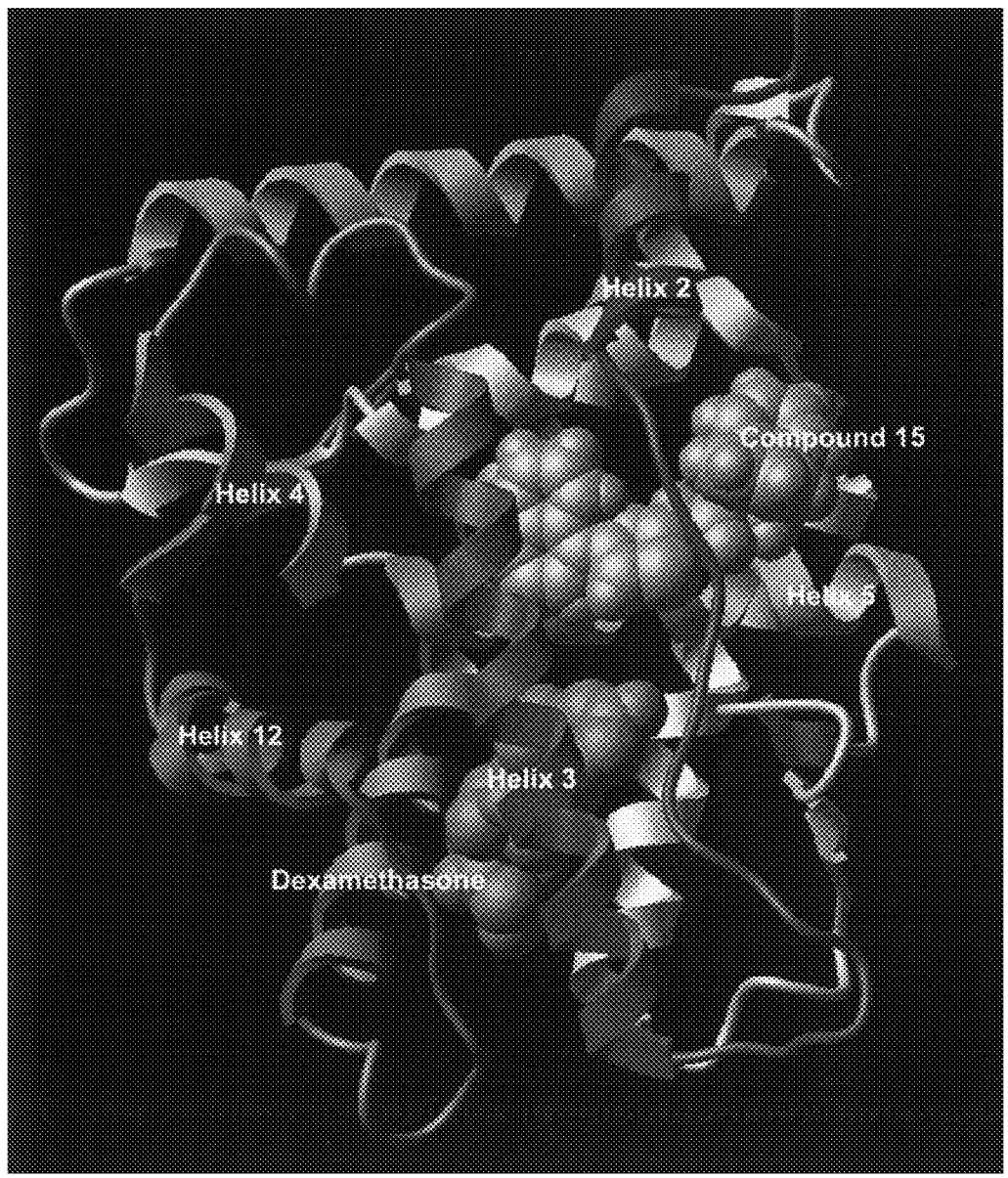

FIGURE 6

```
u87951 Squirrel      MDSKESLTP. GKEENPSSVL TQERGNVMDF CKILRGGATL KVSVSSTSLA
AF141371 Pig         .......... .......... .......... .......... ..........
113196 Guinea Pig    MDLKESVTSS ..KEVPSSVL GSERRNVIDF YKTVRGGATV KVSASSPSLA
u87953 Marmoset      MDSKESLTP. GKEENPSSVL TQERGNVMDF CKILRGGATL KVSVSSTSLA
u87952 Ma'z Monkey   MDSKESLTP. GKEENPSSVL TQERGNVMDF SKILRGGATL KVSVSSTSLA
Human                MDSKESLTP. GREENPSSVL AQERGDVMDF YKTLRGGATV KVSASSPSLA
m14053 rat           MDSKESLAPP GRDEVPGSLL GQGRGSVMDF YKSLRGGATV KVSASSPSVA
x04435 mouse         MDSKESLAPP GRDEVPSSLL GRGRGSVMDL YKTLRGGATV KVSASSPSVA u87951 Squirrel      AASQSDSKQQ RLLVDFPKGS VSNAQQ.... .......... ......PDLS
AF141371 Pig         .......... .VSASSPSLA AVSQPDSKQQ RLAVDFPKGS GSNAQQPDLS
113196 Guinea Pig    AAAQSDSKQR RLLVDFPKGS GSNAQQ.... .......... ......PDLS
u87953 Marmoset      AASQSDSKQQ RLLVDFPKGS VSNAQQ.... .......... ......PDLS
u87952 Ma'z Monkey   AASQSDSKQQ RLLVDFPKGS VSNAQQ.... .......... ......PDLS
Human                VASQSDSKQR RLLVDFPKGS VSNAQQ.... .......... ......PDLS
m14053 rat           AASQADSKQQ RILLDFSKGS TSNVQQRQQQ QQQQQQQQQQ QQQQQQPGLS
x04435 mouse         AASQADSKQQ RILLDFSKGS ASNAQQ.... ........QQ QQQQPQPDLS u87951 Squirrel      KAVSLSMGLY MGETETKVMG NDLGFPQQGQ ISLSSGETDL QLLEESIANL
AF141371 Pig         KAVSLSMGLY MGETETKVMG SDLGFPQQGQ ISLSSGETDF RLLEESIANL
113196 Guinea Pig    KAVSLSMGLY MGETETKVMG NDLGFPQQGQ ISLPSGETDF RLLEESIANL
u87953 Marmoset      KAVSLSMGLY MGETETKVMG NDLGFPQQGQ ISLSSGETDL QLLEESIANL
u87952 Ma'z Monkey   KAVSLSMGLY MGETETKVMG NDLGFPQQGQ ISLSSGETDL QLLEESIANL
Human                KAVSLSMGLY MGETETKVMG NDLGFPQQGQ ISLSSGETDL KLLEESIANL
m14053 rat           KAVSLSMGLY MGETETKVMG NDLGYPQQGQ LGLSSGETDF RLLEESIANL
x04435 mouse         KAVSLSMGLY MGETETKVMG NDLGYPQQGQ LGLSSGETDF RLLEESIANL u87951 Squirrel      NRSTSVPENP KSSASSSVSA APKEKEFPKT HSDVSSEQQN LKGQTGSNGG
AF141371 Pig         SRSTSVPENP KSSASAAGPA APAEKAFPKT HSDGAPEQPN VKGQTGTNGG
113196 Guinea Pig    SRSTSVPENP KNSASA.VSG TPTE.EFPKT QSDLSSEQEN LKSQAGTNGG
u87953 Marmoset      NRSTSVPENP KSSASSSVSA APKEKEFPKT HSDVSSEQQN LKGQTGTNGG
u87952 Ma'z Monkey   NRSTSVPENP KSSASSSVSA APKEKEFPKT HSDVSSEQQN LKGQTGTNGG
Human                NRSTSVPENP KSSASTAVSA APTEKEFPKT HSDVSSEQQH LKGQTGTNGG
m14053 rat           NRSTSVPENP KSSTSATGCA TPTEKEFPKT HSDASSEQQN RKSQTGTNGG
x04435 mouse         NRSTSRPENP KSSTPAAGCA TPTEKEFPQT HSDPSSEQQN RKSQPGTNGG u87951 Squirrel      NVKLYTADQS TFDI....LQ DLEFSSGSPG KETNQSPWKS DLLIDENCLL
AF141371 Pig         NVKLFTTDQS TFDIWRKKLQ DLELPSGSPG KETSESPWSS DLLIDENCLL
113196 Guinea Pig    NVK.FPPDQS TFDI....LK DLEFSSGSPG KERSESPWRP DLLMDESCLL
u87953 Marmoset      NAKLCTADQS TFDI....LQ DLEFSSGSPG KETNQSPWRS DLLIDENCLL
u87952 Ma'z Monkey   NVKLYTADQS TFDI....LQ DLEFSSGSPG KETNQSPWRS DLLIDENCLL
Human                NVKLYTTDQS TFDI....LQ DLEFSSGSPG KETNESPWRS DLLIDENCLL
m14053 rat           SVKLYPTDQS TFDL....LK DLEFSAGSPS KDTNESPWRS DLLIDEN.LL
x04435 mouse         SVKLYTTDQS TFDI....LQ DLEFSAGSPG KETNESPWRS DLLIDEN.LL
```

FIGURE 6 (Continued)

```
u87951 Squirrel      SPLAGEEDSF LLEGNSNEDC KPLILPDTKP KIKDNGDLVL SSSSNVTLPQ
AF141371 Pig         SPLAGEEDPF LLEGSSTEDC KPLVLPDTKP KVKDNGELIL PSPNSVPLPQ
113196 Guinea Pig    SPLAGEDDPF LLEGNSNEDC KPLILPDTKP KIKDNGDGIL SSSNSVPQPQ
u87953 Marmoset      SPLAGEEDSF LLEGNSNEDC KPLILPDTKP KIKDNGDLVL SSSSNVTLPQ
u87952 Ma'z Monkey   SPLAGEEDSF LLEGNSNEDC KPLILPDTKP KIKDNGDLVL SSSSNVTLPQ
Human                SPLAGEDDSF LLEGNSNEDC KPLILPDTKP KIKDNGDLVL SSPSNVTLPQ
m14053 rat           SPLAGEDDPF LLEGNTNEDC KPLILPDTKP KIKDTGDTIL SSPSSVALPQ
x04435 mouse         SPLAGEDDPF LLEGDVNEDC KPLILPDTKP KIQDTGDTIL SSPSSVALPQ u87951 Squirrel      VKTEKEDFIE LCTPGVIKQE KLSTVYCQAS FPGANIIGNK MSAISIHGVS
AF141371 Pig         VKTEKEDFIE LCTPGVIKQE KLGPAYCQAS FSGANIIGGK MSAISVHGVS
113196 Guinea Pig    VKIGKEDFIE LCTPGVIKQE KLGPVYCQAS FSGANIIGNK MSAISVHGVS
u87953 Marmoset      VKTEKEDFIE LCTPGVIKQE KLSTVYCQAS FPGANIIGNK MSAISIHGVS
u87952 Ma'z Monkey   VKTEKEDFIE LCTPGVIKQE KLSTVYCQAS FPGANVIGNK MSAISIHGVS
Human                VKTEKEDFIE LCTPGVIKQE KLGTVYCQAS FPGANIIGNK MSAISVHGVS
m14053 rat           VKTEKDDFIE LCTPGVIKQE KLGPVYCQAS FSGTNIIGNK MSAISVHGVS
x04435 mouse         VKTEKDDFIE LCTPGVIKQE KLGPVYCQAS FSGTNIIGNK MSAISVHGVS u87951 Squirrel      TSGGQMYHYD MNTA.SLSQQ QDQKPIFNVI PPIPVGSENW NRCQGSGDDN
AF141371 Pig         TSGGQLYHYD MNTAASLSKQ QEQKPLFNVI PPIPVGSENW NRCQGSGDDN
113196 Guinea Pig    TSGGQMYHYD MNTA.SLSQQ QDQKPIFNVI PPIPVGSENW NRCQGSGEDN
u87953 Marmoset      TSGGQMYHYD MNTA.SLSQQ QDQKPIFNVI PPIPVGSENW NRCQGSGDDN
u87952 Ma'z Monkey   TSGGQMYHYD MNTA.SLSQQ QDQKPIFNVI PPIPVGSENW NRCQGSGDDN
Human                TSGGQMYHYD MNTA.SLSQQ QDQKPIFNVI PPIPVGSENW NRCQGSGDDN
m14053 rat           TSGGQMYHYD MNTA.SLSQQ QDQKPVFNVI PPIPVGSENW NRCQGSGEDS
x04435 mouse         TSGGQMYHYD MNTA.SLSQQ QDQKPVFNVI PPIPVGSENW NRCQGSGEDN u87951 Squirrel      LTSLGTLNFP GRTVFSNGYS SPSMRPDVSS PPSSSSTATT GPPPKLCLVC
AF141371 Pig         LTSLGTLNFS GRSVFSNGYS SPGMRPDVSS PPSSSSAAT. GPPPKLCLVC
113196 Guinea Pig    LTSLGTVNFP GRSVFSNGYS SPGLRPDVSS PPSSSST.TT GPPPKLCLVC
u87953 Marmoset      LTSLGTLNFP GRTVFSNGYS SPSMRPDVSS PPSSSSTATT GPPPKLCLVC
u87952 Ma'z Monkey   LTSLGTLNFP GRTVFSNGYS SPSMRPDVSS PPSSSSTATT GPPPKLCLVC
Human                LTSLGTLNFP GRTVFSNGYS SPSMRPDVSS PPSSSSTATT GPPPKLCLVC
m14053 rat           LTSLGALNFP GRSVFSNGYS SPGMRPDVSS PPSSSSAAT. GPPPKLCLVC
x04435 mouse         LTSLGAMNFA GRSVFSNGYS SPGMRPDVSS PPSSSSTAT. GPPPKLCLVC u87951 Squirrel      SDEASGCHYG VLTCGSCKVF FKRAVEGQHN YLCAGRNDCI IDKIRRKNCP
AF141371 Pig         SDEASGCHYG VLTCGSCKVF FKRAVEGQHN YLCAGRNDCI IDKIRRKNCP
113196 Guinea Pig    SDELSGCHYG VLTCGSCKVF FKRAVEGQHN YLCAGRNDCI IDKIRRENCP
u87953 Marmoset      SDEASGCHYG VLTCGSCKVF FKRAVEGQHN YLCAGRNDCI IDKIRRKNCP
u87952 Ma'z Monkey   SDEASGCHYG VLTCGSCKVF FKRAVEGQHN YLCAGRNDCI IDKIRRKNCP
Human                SDEASGCHYG VLTCGSCKVF FKRAVEGQHN YLCAGRNDCI IDKIRRKNCP
m14053 rat           SDEASGCHYG VLTCGSCKVF FKRAVEGQHN YLCAGRNDCI IDKIRRKNCP
x04435 mouse         SDEASVCHYG VLTCGSCKVF FKRAVEGQHN YLCAGRNDCI IDKIRRKNCP
```

FIGURE 6 (Continued)

```
u87951 Squirrel       ACRYRKCLQA GMNLEARKTK KKIKGIQQAT TGVSQETSEN PANKTIVPAT
AF141371 Pig          ACRYRKCLQA GMNLEARKTK KKIKGIQQAT TGVSQETSEN SANKTIVPAT
113196 Guinea Pig     ACRYRKCLQA GMNLQARKTK KKIKGIQQAT TGVSQNTSEN P.NKTIVPAT
u87953 Marmoset       ACRYRKCLQA GMNLEARKTK KKIKGIQQAT TGVSQETSEN PANKTIVPAT
u87952 Ma'z Monkey    ACRYRKCLQA GMNLEARKTK KKIKGIQQAT TGVSQETSEN PANKTIVPAT
Human                 ACRYRKCLQA GMNLEARKTK KKIKGIQQAT TGVSQETSEN PGNKTIVPAT
m14053 rat            ACRYRKCLQA GMNLEARKTK KKIKGIQQAT AGVSQDTSEN P.NKTIVPAA
x04435 mouse          ACRYRKCLQA GMNLEARKTK KKIKGIQQAT AGVSQDTSEN .ANKTIVPAA u87951 Squirrel   525 LPQLTPTLVS LLEVIEPEVL YAGYDSTVPD STWRIMTTLN MLGGRQVIAA
AF141371 Pig      489 LPQLTPTLVS LLEVIEPEVL YAGYDSSIPD STWRIMTALN MLGGRQVIAA
113196 Guinea Pig 519 LPQLTPTLVS LLEVIEPEVI HSGYDSTSPD STWRIMTTLN MLGGRQVIAA
u87953 Marmoset   525 LPQLTPTLVS LLEVIEPEVL YAGYDSTVPD STWRIMTTLN MLGGRQVIAA
u87952 Ma'z Monkey 525 LPQLTPTLVS LLEVIEPEVL YAGYDSTVPD STWRIMTTLN MLGGRQVIAA
Human             525 LPQLTPTLVS LLEVIEPEVL YAGYDSTVPD STWRIMTTLN MLGGRQVIAA
m14053 rat        543 LPQLTPTLVS LLEVIEPEVL YAGYDSSVPD SAWRIMTTLN MLGGRQVIAA
x04435 mouse      531 LPQLTPTLVS LLEVIEPEVL YAGYDSSVPD SAWRIMTTLN MLGGRQVIAA u87951 Squirrel   575 VKWAKAIPGF RNLHLDDQMT LLQYSWMFLM AFALGWRSYR QASSNLLCFA
AF141371 Pig      539 VKWAKAIPGF RNLHLDDQMT LLQYSWMFLM VFALGWRSYR QSSASLLCFA
113196 Guinea Pig 569 VKWAKAIPGF KNLHLDDQMT LLQYSWMFLM AFALGWRSYK QSNGSLLCFA
u87953 Marmoset   575 VKWAKAIPGF RNLHLDDQMT LLQYSWMFLM AFALGWRSYR QASSNLLCFA
u87952 Ma'z Monkey 575 VKWAKAIPGF RNLHLDDQMT LLQYSWMFLM AFALGWRSYR QASSNLLCFA
Human             575 VKWAKAIPGF RNLHLDDQMT LLQYSWMFLM AFALGWRSYR QSSANLLCFA
m14053 rat        593 VKWAKAILGL RNLHLDDQMT LLQYSWMFLM AFALGWRSYR QSSGNLLCFA
x04435 mouse      581 VKWAKAIPGF RNLHLDDQMT LLQYSWMFLM AFALGWRSYR QASGNLLCFA u87951 Squirrel   625 PDLIINEQRM TLPCMYDQCK HMLYVSSELH RLQVSYEEYL CMKTLLLLSS
AF141371 Pig      589 PDLVINEQRM ALPCMYDQCK HMLYVSSELQ RLQVSYEEYL CMKTLLLLSS
113196 Guinea Pig 619 PDLIINEQRM SLPWMYDQCK YMLYVSSELK RLQVSYEEYL CMKTLLLLSS
u87953 Marmoset   625 PDLIINEQRM TLPCMYDQCK HMLYVSSELH RLQVSYEEYL CMKTLLLLSS
u87952 Ma'z Monkey 625 PDLIINEQRM TLPCMYDQCK HMLYVSSELH RLQVSYEEYL CMKTLLLLSS
Human             625 PDLIINEQRM TLPCMYDQCK HMLYVSSELH RLQVSYEEYL CMKTLLLLSS
m14053 rat        643 PDLIINEQRM SLPCMYDQCK HMLFVSSELQ RLQVSYEEYL CMKTLLLLSS
x04435 mouse      631 PDLIINEQRM TLPCMYDQCK HMLFISTELQ RLQVSYEEYL CMKTLLLLSS u87951 Squirrel       VPKDGLKSQE LFDEIRMTYI KELGKAIVKR EGNSSQNWQR FYQLTKLLDS
AF141371 Pig          VPKDGLKSQE LFDEIRMTYI KELGKAIVKR EGNSSQNWQR FYQLTKLLDS
113196 Guinea Pig     VPKEGLKSQE LFDEIRMTYI KELGKAIVKR EGNSSQNWQR FYQLTKLLDS
u87953 Marmoset       VPKDGLKSQE LFDEIRMTYI KELGKAIVKR EGNSSQNWQR FYQLTKLLDS
u87952 Ma'z Monkey    VPKDGLKSQE LFDEIRMTYI KELGKAIVKR EGNSSQNWQR FYQLTKLLDS
Human                 VPKDGLKSQE LFDEIRMTYI KELGKAIVKR EGNSSQNWQR FYQLTKLLDS
m14053 rat            VPKEGLKSQE LFDEIRMTYI KELGKAIVKR EGNSSQNWQR FYQLTKLLDS
x04435 mouse          VPKEGLKSQE LFDEIRMTYI KELGKAIVKR EGNSSQNWQR FYQLTKLLDS
                  675
```

FIGURE 6 (Continued)

```
u87951 Squirrel      MHEVVENLLN YCFQTFLDKT MSIEFPEMLA EIITNQLPKY SNGNIKKLLF
AF141371 Pig         MHDVVENLLN YCFQT..... .......... .......... ..........
113196 Guinea Pig    LHEIVGNLLN ICFKTFLDKT MNIEFPEMLA EIITNQLPKY SNGDIKKLLF
u87953 Marmoset      MHEVVENLLN YCFQTFLDKT MSIEFPEMLA EIITNQLPKY SNGNIRKLLF
u87952 Ma'z Monkey   MHEVVENLLN YCFQTFLDKT MSIEFPEMLA EIITNQLPKY SNGNIKKLLF
Human                MHEVVENLLN YCFQTFLDKT MSIEFPEMLA EIITNQIPKY SNGNIKKLLF
m14053 rat           MHEVVENLLT YCFQTFLDKT MSIEFPEMLA EIITNQIPKY SNGNIKKLLF
x04435 mouse         MHDVVENLLS YCFQTFLDKS MSIEFPEMLA EIITNQIPKY SNGNIKKLLF u87951 Squirrel      HQK (SEQ ID NO:14)
AF141371 Pig         ... (SEQ ID NO:15)
113196 Guinea Pig    HQK (SEQ ID NO:16)
u87953 Marmoset      HQK (SEQ ID NO:17)
u87952 Ma'z Monkey   HQK (SEQ ID NO:18)
Human                HQK (SEQ ID NO:19)
m14053 rat           HQK (SEQ ID NO:20)
x04435 mouse         HQK (SEQ ID NO:21)
```

COMPOSITIONS AND METHODS INVOLVING GLUCOCORTICOID RECEPTOR SITE II

This invention claims priority from provisional U.S. application Ser. No. 60/396,907, filed Jul. 18, 2002, which is incorporated herein by reference in its entirety.

FIELD OF THE INVENTION

The present invention generally relates to a binding site, termed Site II, in nuclear hormone receptors. The present invention relates to: machine-readable data storage media comprising structure coordinates of Site II; computer systems capable of producing three-dimensional representations of all or any part of Site II; methods used in the design and identification of ligands of Site II and of modulators of nuclear hormone receptors (NHRs); ligands of Site II; modulators of NHRs; methods of modulating NHRs; pharmaceutical compositions comprising modulators of NHRs; methods of treating diseases by administering modulators of an NHR; methods of designing mutants; mutant NHRs or portions of mutant NHRs; methods of measuring the binding of a test molecule to Site II; and models of Site II.

BACKGROUND OF THE INVENTION

The nuclear hormone receptor (NHR) family of transcription factors bind low molecular weight ligands and either stimulate or repress transcription. (in The Nuclear Receptor Facts Book, V. Laudet and H. Gronemeyer, Academic Press, p 345, 2002). NHRs stimulate transcription by binding to DNA and inducing transcription of specific genes. NHRs may also stimulate transcription by not binding to DNA itself, rather they may modulate the activity of other DNA binding proteins (Stocklin, E., et al., Nature (1996) 383:726-8). The process of stimulation of transcription is called transactivation. NHRs repress transcription by interacting with other transcription factors or coactivators and inhibiting the ability of these other transcription factors or coactivators to induce transcription of specific genes. The process of repression of transcription is called transrepression. (for a review see The Nuclear Receptor Factsbook, V. Laudet and H. Gronemeyer, Academic Press, p 42, 2002). For example, the glucocorticoid receptor, estrogen receptor, androgen receptor and peroxisome proliferator activated receptors α and γ have been shown to repress the activity of the transcription factors AP-1 and NF-κB (Jonat, C., et al., Cell, 62, p 1189-1204, (1990) Kallio, P. J., et al., Mol. Endocrinol., 9, p 017-1028 (1995), Keller, E. T., et al., J. Biol. Chem., 271, p 26267-26275 (1996), Jones, D. C., et al., J. Biol. Chem., 277 (9), p 6838-6845, (2002), Ricote, M., et al., Nature, 391, p 79-82, (1998), Valentine, J. E., et al, J. Biol. Chem., 275, p 25322-25329, (2000).

The nuclear hormone receptor family includes the glucocorticoid receptor (Hollenberg, S. M. et al. (1985) Nature, 318, p 635), progesterone receptor (Misrahi, M. et al. (1987) Biochem. Biophys. Res. Commun. 143, p 740), androgen receptor (Lubahn D. B., et al (1988), estrogen receptors (Green, S., et al. (1986) Nature 320, p 134), mineralocorticoid receptor (Arriza, J. L., et al., (1987) Science 237, p 268), retinoid receptors (RXRs and RARs) (Mangelsdorf, et al. (1990) Nature, 345, p 224 and Petkovich M., et al (1987) Nature 330, p 444), Vitamin D receptor, thyroid receptor (TR) (Nakai, A. et al., (1988) Mol. Endocrinol. 2, p 1087), peroxisome proliferator activated receptor (PPAR) (Greene, M. E., et al. (1995) Gene Expression 4, p 281), orphan nuclear receptors and others. Glucocorticoid receptor, progesterone receptor, androgen receptor, estrogen receptor, and mineralocorticoid receptor are steroid hormone receptors (SHRs).

Although the sequences vary amongst the various nuclear hormone receptors, they can be divided into functional domains including an N-terminal transactivation domain, a central DNA binding domain and a C-terminal ligand and dimerization domain. The ligands which bind these receptors act in a ligand, cell type, and promoter dependent fashion and include: glucocorticoids, progestins, retinoids, mineralocorticoids, and others. In addition to steroids, recent studies have shown that non-steroids can bind to nuclear hormone receptors and induce a biologic response (Coghlan, M J, et al, J. Med. Chem. 44, p 2879, 2001). Ligand cross-talk can occur between the receptors, for example, progesterone can bind not only the progesterone receptor but the glucocorticoid receptor as well (Zhang, S., Mol. Endocrinology 10, p 24, 1996).

Three-dimensional structures of some of the nuclear hormone receptors have been elucidated through crystallization or homology modeling. A homology model of the glucocorticoid receptor is disclosed in WO 00/52050, published Sep. 8, 2000.

Recent publications by the same research group: Bledsoe, et. al., Cell, online publication by Cell Press, Jul. 1, 2002, DOI: 10.1016/S0092867402008176; Cell, Vol 110, 93-105, 12 Jul. 2002; and Apolito, et. al., in WO 03/015692 A2, published Feb. 27, 2003; describe the successful crystallization and xray structural elucidation of the glucocorticoid receptor LBD as the dimer. X-ray structure coordinates were provided in WO 03/015692. Disruption of the dimeric structure was found to occur upon mutation of selected residues at the dimerization interface. Despite structural similarity to other steroid receptors, the GR LBD dimer represents a unique dimer configuration. The GR LBD used for this crystalization was a mutant (F602S) designed to provide a more soluble LBD construct.

Also recently, Kauppi et. al. published the stucture of the GR LBD bound to an antagonist, RU-486, in: the Journal of Biological Chemistry Online, JBC Papers In Press as DOI: 10.1074/JBC.M212711200, Apr. 9, 2003; and in J. Biol. Chem., Vol. 278, Issue 25, 22748-22754, Jun. 20, 2003. In this structure, the GR LBD exhibits a significant displacement of helix 12, typical of antagonist action. In addition to the antagonist-bound LBD, a dimer structure similar to that reported by Bledsoe, et. al. was also described. The structure of the GR LBD-RU-486 complex was deposited in with the RCSB (1nhz.pdb)

Three dimensional structures of other nuclear hormone receptors are disclosed as follows, with RCSB (Research Collaboratory for Structural Bioinformatics, pdb file format) references in parentheses: RXRalpha (1lbd) Bourguet, W., Ruff, M., Chambon, P., Gronemeyer, H., Moras, D. Nature 375 pp. 377 (1995); PPAR-gamma (2prg) Nolte, R. T., Wisely, G. B., Westin, S., Cobb, J. E., Lambert, M. H., Kurokawa, R., Rosenfeld, M. G., Willson, T. M., Glass, C. K., Milburn, M. V. Nature 395 pp. 137 (1998); RARgamma (2lbd) Renaud, J. P., Rochel, N., Ruff, M., Vivat, V., Chambon, P., Gronemeyer, H., Moras, D. Nature 378 pp. 681 (1995); PR (1a28) Williams, S. P., Sigler, P. B. Nature 393 pp. 392 (1998); VitDR (1db1) Rochel, N., Wurtz, J. M., Mitschler, A., Klaholz, B., Moras, D. Mol. Cell 5 pp. 173 (2000); AR (1e3g) Matias, P. M., Donner, P., Coelho, R., Thomaz, M., Peixoto, C., Macedo, S., Otto, N., Joschko, S., Scholz, P., Wegg, A., Basler, S., Schafer, M., Egner, U., Carrondo, M. A. J. Biol. Chem. 275 pp. 26164 (2000); ERalpha (1a52) Tanenbaum, D. M., Wang, Y., Williams, S. P., Sigler, P.

B. Proc Natl Acad Sci USA 95 pp. 5998 (1998); ERbeta (112j) Shiau, A. K., Barstad, D., Radek, J. T., Meyers, M. J., Nettles, K. W., Katzenellenbogen, B. S., Katzenellenbogen, J. A., Agard, D. A., Greene, G. L. Nat. Struct. Biol. 9 pp. 359 (2002). It is generally thought that all steroid ligands bind to nuclear hormone receptors at the classical ligand binding site, which we term site I (Evans, R. M. Science 240, p 889, 1988). Limited proteolysis studies and cell transfection/mutagenesis studies have delineated the functional domains of nuclear hormone receptors which include a DNA binding domain, ligand binding domain and a transactivation domain. These studies provided the evidence that hormones bind to the ligand binding domain. Mutagenesis of GR has defined the dexamethasone interacting surface, defined as Site I, which includes amino acids Met-560, Met-639, Gln-642 and Thr-739 (Lind, U., et al. J. Biol. Chem. 275, p 19041, 2000).

Recently, a second ligand binding site in ER-α and ER-β has been reported based on computational analysis and docking experiments with steroids. (van Horn, W. J. Med. Chem. 45, p 584, 2002). This second binding site is not completely delineated. It is reported to have no obvious function, to be an evolutionary remnant, and to be absent in other nuclear receptors such as RARγ. Furthermore, there is no discussion of transrepression whatsoever. In addition, Endocrine Society Meeting June 2003, presentation OR34-1, Wang, Y., Chirgadze, N Y, Briggs, S L, Khan, S., Jensen, E V., Burris, T P., A second binding site for hydroxytamoxifen with the ligand binding domain of estrogen receptor beta, describes the crystal structure of estrogen receptor bound with 4-hydroxytamoxifen, in which the ligand is found in two locations: the usual steroid binding pocket and a second site located along the hydrophobic groove near the cofactor binding region. This second site is remote from the Site II location described in this application.

The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the human (Weinberger, et al. Science 228, p 740-742, 1985, Weinberger, et al. Nature, 318, P635-641, 1985) and rat (Miesfeld, R. Nature, 312, p 779-781, 1985) glucocorticoid receptors. Subsequently, glucocorticoid receptors from other species were cloned including mouse (Danielson, M. et al. EMBO J., 5, 2513), sheep (Yang, K., et al. J. Mol. Endocrinol. 8, p 173-180, 1992), and marmoset (Brandon, D. D., et al, J. Mol. Endocrinol. 7, p 89-96, 1991). There is also a C-terminally distinct isoform of GR termed GR-beta. This isoform is identical to GR up to amino acid 727 and then diverges in the last C-terminal 15 amino acids. GR-beta is not known to bind glucocorticoids, is unable to transactivate, but does bind DNA (Hollenberg, S M. et al. Nature, 318, p 635, 1985, Bamberger, C. M. et al. J. Clin Invest. 95, p 2435, 1995). It is possible that GR-beta binds compounds other than the typical glucocorticoids.

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription (Jonat, C., et al. Cell, 62, p 1189, 1990, Yang-Yen, H. F., et al. Cell 62, p 1205, 1990, Diamond, M. I. et al. Science 249, p 1266, 1990, Caldenhoven, E. et al., Mol. Endocrinol. 9, p 401, 1995). Other mechanisms such as sequestration of co-activators by GR have also been proposed (Kamer Y, et al., Cell 85, p 403, 1996, Chakravarti, D. et al., Nature 383, p 99, 1996). NF-κB and AP-1 play key roles in the initiation and perpetuation of inflammatory and immunological disorders (Baldwin, A S, Journal of Clin. Investigation 107, p 3, 2001, Firestein, G. S., and Manning, A. M. Arthritis and Rheumatism, 42, p 609, 1999, Peltz, G., Curr. Opin, in Biotech. 8, p 467, 1997). NF-κB and AP-1 are involved in regulating the expression of a number of important inflammatory and immunomodulatory genes including: TNF-alpha, IL-1, IL-2, IL-5, adhesion molecules (such as E-selectin), chemokines (such as Eoxtaxin and Rantes), Cox-2, and others.

Although glucocorticoids are very effective anti-inflammatory agents, their systemic use is limited by their side effects which include diabetes, osteoporosis, glaucoma, Cushingoid syndrome, muscle loss, facial swelling, personality changes, and others. (Stanbury, R M, and Graham, E M, Br. J. Opthalmology 82, p 704, 1998, Da Silva, J A P., Bijlsma, J. Rheumatic Disease Clinics of North America, 26, p 859, 2000)

In addition to leading to transrepression, the interaction of a glucocorticoid with GR can lead to stimulation by GR of transcription of certain genes. This stimulation of transcription is termed transactivation. Transactivation requires dimerization of GR and binding to a glucocorticoid response element (GRE). DNA binding is mediated via Zn fingers in the DNA binding domain (Giguere, V. et al Cell 46, p 645, 1986; Rusconi, S. and Yamamoto, K. R. EMBO J., 6, p 1309, 1987). DNA sequence specific interactions are determined by the C-terminal part of the first Zn finger (Danielsen, M., et al. Cell 57, p 1131, 1989). Several GR target genes have been identified including MMTV, metallothionein, and tyrosine amino transferase (Ringold, G M et al, Cell 6, p 299,1975; Scheidereit, C., et al Nature, 304, p 749, 1983; Hager, L J, Palmiter R D, Nature 291, 340, 1981; Grange, T., et al. Oncogene, 20, p 3028, 2001). Transrepression, as opposed to transactivation, can occur in the absence of dimerization, and as mentioned above is believed to involve the direct interaction of GR with AP-1 and NF-κB.

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. (Tuckermann, J. et al. Cell 93, p 531, 1998; Reichardt, H M. EMBO J., 20, p 7168, 2001).

Compounds which can induce transrepression of GR with none to minimal induction of transactivation have been termed "dissociated steroids" (Vayassiere, B M, et al., Mol. Endocrinology, 11, p 1249, 1997). Such "dissociated" compounds would be useful to treat inflammatory diseases. See FIG. 1 for a graphical description of transactivation mediated by GR dimers versus transrepression mediated by GR monomers. It is possible that these "dissociated" compounds bind to GR without inducing dimerization yet allow the monomer to transrepress AP-1 and NF-κB. Another plausible explanation is that "dissociated" compounds may alter the conformation of GR to enable transrepression without inducing a DNA binding conformation.

There are several examples in the literature of compounds that possess dissociated activity as defined by the ratio of the effective concentration required to induce DNA binding in a cellular assay relative to the effective concentration required to transrepress, or inhibit AP-1 or NF-κB activity. The first report of a "dissociated steroid" published by Vayssiere, et al. Molecular Endocrinology, 11, p 1245, 1997, showed that a derivative of dexamethasone had potent in vitro and in vivo anti-inflammatory activity with minimal induction of DNA binding. Subsequent studies (Coghlan, M J, et al., J. Med. Chem. 44, p 4481, 2001) have shown that non-steroidal compounds can bind to GR and elicit transrepressive activity with moderate transactivation activity. It is believed that each of the compounds described above act via the dexamethasone binding site.

Ursodeoxycholic acid (UDCA) has recently been shown to repress NF-κB activity via a GR mediated pathway. The compound appears to be "dissociated" as it does not induce DNA binding in a cellular assay. This compound, although acting in a GR dependent fashion, does not compete for dexamethasone binding to GR. Although direct binding of UDCA to GR has not been demonstrated, mutagenesis studies suggest that the ligand binding domain (LBD) of GR is required for activity. (Miura, T., J. Biol. Chem. 276, p 47371, 2001). However, these studies did not delineate the specific amino acids which are involved in UDCA activity.

The art is in need of modulators of NHRs. A modulator of an NHR may be useful in treating NHR-associated diseases, that is diseases associated with the expression products of genes whose transcription is stimulated or repressed by NHRs. For instance, the art is in need of modulators of NHR that induce inhibition of AP-1 and NF-κB, as such modulators would be useful in the treatment of inflammatory and immune associated diseases and disorders, such as osteoarthritis, rheumatoid arthritis, multiple sclerosis, asthma, inflammatory bowel disease, transplant rejection, and graft vs. host disease.

The art is in need of compounds that possess dissociated activity, as such compounds would be useful in treating inflammatory and immune associated diseases and disorders without exhibiting unwanted side effects. For instance, in the case of GR, although glucocorticoids are potent anti-inflammatory agents, their systemic use is limited by side effects. A dissociated compound that retained the anti-inflammatory efficacy of glucocorticoids while minimizing the side effects such as diabetes, osteoporosis and glaucoma would be of great benefit to a very large number of patients with inflammatory diseases.

The art is in need of compounds that antagonize transactivation. For instance, in the case of GR, such compounds may be useful in treating metabolic diseases associated with increased levels of glucocorticoid, such as diabetes, osteoporosis and glaucoma.

The art is in need of compounds that induce transactivation. For instance, in the case of GR, such compounds may be useful in treating metabolic diseases associated with a deficiency in glucocorticoid. Such diseases include Addison's disease.

In order to design compounds that modulate an NHR in specific ways, one needs to understand how ligands bind to an NHR and modulate the activity of the NHR.

SUMMARY OF THE INVENTION

We have identified a second binding site in the ligand binding domain of nuclear hormone receptors (NHRs). We refer to this second binding site as Site II.

Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I. Table I is located under the heading for Example 21.

FIG. 2 shows the amino acids of Site II in various human NHRs. The structure coordinates of Site II in the NHRs of FIG. 2 are given in Table III, located under the heading for Example 22. Two sets of xray structure coordinates of Site II in GR are given in Table IV, located under the heading for Example 23, and Table V, located under the heading for Example 24. FIG. 6 shows the amino acids of Site II in the GR of various species.

We have found that ligands of Site II modulate NHRs. Ligands of Site II induce transrepression. Ligands of Site II possess dissociated activity. Ligands of Site II antagonize transactivation.

The invention provides machine-readable data storage media comprising data storage material encoded with machine readable data comprising all or any part of the structure coordinates of Site II. The invention provides computer systems comprising the machine-readable data storage media of the invention capable of producing three-dimensional representations of all or any part of Site II.

The invention provides methods used in the design and identification of ligands of Site II and modulators of NHRs. The invention provides: methods of docking a test molecule into all or any part of the cavity circumscribed by Site II; methods comprising identifying structural and chemical features of all or any part of Site II; methods of designing a ligand of Site II comprising modeling all or any part of Site II and designing a chemical entity that has structural and chemical complementarity with all or any part of Site II; methods of evaluating the potential of a chemical entity to bind to all or any part of Site II; methods for identifying a modulator of an NHR; and methods for identifying a ligand of Site II.

The invention provides ligands of Site II. The invention provides modulators of NHRs.

The invention provides methods of modulating an NHR.

The invention provides pharmaceutical compositions comprising modulators of NHRs.

The invention provides methods of treating diseases by administering a modulator of an NHR. Such diseases include NHR-associated diseases, diseases associated with NHR transactivation, diseases associated with NHR transrepression, diseases associated with AP-1-dependent gene expression, diseases associated with NF-κB-dependent gene expression, inflammatory or immune associated diseases and disorders, diseases treatable by inducing NHR transrepression, and diseases treatable by antagonizing NHR transactivation.

The invention provides methods of designing mutants comprising mutating Site II by making an amino acid substitution, deletion or insertion, and the resultant mutant NHRs, or portions of mutant NHRs, comprising a mutation in Site II.

The invention provides methods of measuring the binding of a test molecule to Site II.

The invention provides models of Site II.

All documents referred to herein, including but not limited to U.S. patent applications, are incorporated herein by reference in their entirety.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2. Consensus alignments carried out using ICM (Molsoft LLC, La Jolla, Calif.) between human GR (glucocorticoid receptor) LBD and other human NHR LBDs, indicating by shading the residues of Site II, i.e. residues corresponding to residues of GR Site II. Dots are spaceholders and do not represent amino acids. Numbers refer to the first residue in each line, are specific for each NHR and are based on the full-length NHR. For the NHRs listed below, with the exception of GR and MR, structural data was obtained from the RCSB references listed below, and the numbering system in the RCSB references was used. For GR and MR, structural data was obtained by homology modeling using the literature references below, and the numbering system in those literature references was used. The RCSB references (in parentheses) and literature references for the various NHRs are as follows:

RXRalpha (SEQ ID NO:3) (1lbd) Bourguet, W., Ruff, M., Chambon, P., Gronemeyer, H., Moras, D. Nature 375 pp. 377 (1995); PPAR-gamma (SEQ ID NO:10) (2prg) Nolte, R. T., Wisely, G. B., Westin, S., Cobb, J. E., Lambert, M. H., Kurokawa, R., Rosenfeld, M. G., Willson, T. M., Glass, C. K., Milburn, M. V. Nature 395 pp. 137 (1998); RARgamma (SEQ ID NO:4) (2lbd) Renaud, J. P., Rochel, N., Ruff, M., Vivat, V., Chambon, P., Gronemeyer, H., Moras, D. Nature 378 pp. 681 (1995); PR (SEQ ID NO:5) (1a28) Williams, S. P., Sigler, P. B. Nature 393 pp. 392 (1998); VitDR (SEQ ID NO:9) (1db1) Rochel, N., Wurtz, J. M., Mitschler, A., Klaholz, B., Moras, D. Mol. Cell 5 pp. 173 (2000); AR (SEQ ID NO:6) (1e3g) Matias, P. M., Donner, P., Coelho, R., Thomaz, M., Peixoto, C., Macedo, S., Otto, N., Joschko, S., Scholz, P., Wegg, A., Basler, S., Schafer, M., Egner, U., Carrondo, M. A. J. Biol. Chem. 275 pp. 26164 (2000); ERalpha (SEQ ID NO:7) (1a52) Tanenbaum, D. M., Wang, Y., Williams, S. P., Sigler, P. B. Proc Natl Acad Sci USA 95 pp. 5998 (1998); ERbeta (SEQ ID NO:8) (1l2j) Shiau, A. K., Barstad, D., Radek, J. T., Meyers, M. J., Nettles, K. W., Katzenellenbogen, B. S., Katzenellenbogen, J. A., Agard, D. A., Greene, G. L. Nat. Struct. Biol. 9 pp. 359 (2002); TRbeta (SEQ ID NO:12) (1bsx) Wagner, R. L., Darimont, B. D., Apriletti, J. W., Stallcup, M. R., Kushner, P. J., Baxter, J. D., Fletterick, R. J., Yamamoto, K. R. Genes Dev. 12 pp. 3343 (1998). MR and GR structural data were obtained by homology modeling to PR using the sequences from the following references: GR (SEQ ID NO:13), PIR Accession Number QRHUGA, Hollenberg, S. M., Weinberger, C., Ong, E. S., Cerelli, G., Oro, A., Leba, R., Thompson, E. B., Rosenfeld, M. G., Evans, R. M. Nature (1985) 318: 635-641; MR (SEQ ID NO:11), PIR Accession Number A29613, Arriza, J. L.; Weinberger, C., Cerelli, G., Glaser, T. M., Handelin, B. L., Housman, D. E., Evans, R. M., Science (1987) 237: 268-275.

FIG. 3. GR homology model displayed in ribbon format with dexamethasone (green) and Compound 15 (violet) displayed as space-filling models docked in Site I and Site II, respectively. The location of Site I (dexamethasone site) represents the classical steroid binding site (eg, consistent with the location of progesterone in PR, 1A28). The location of Site II (Compound 15 site) represents the novel binding site which is the subject of this invention.

Figure 1:
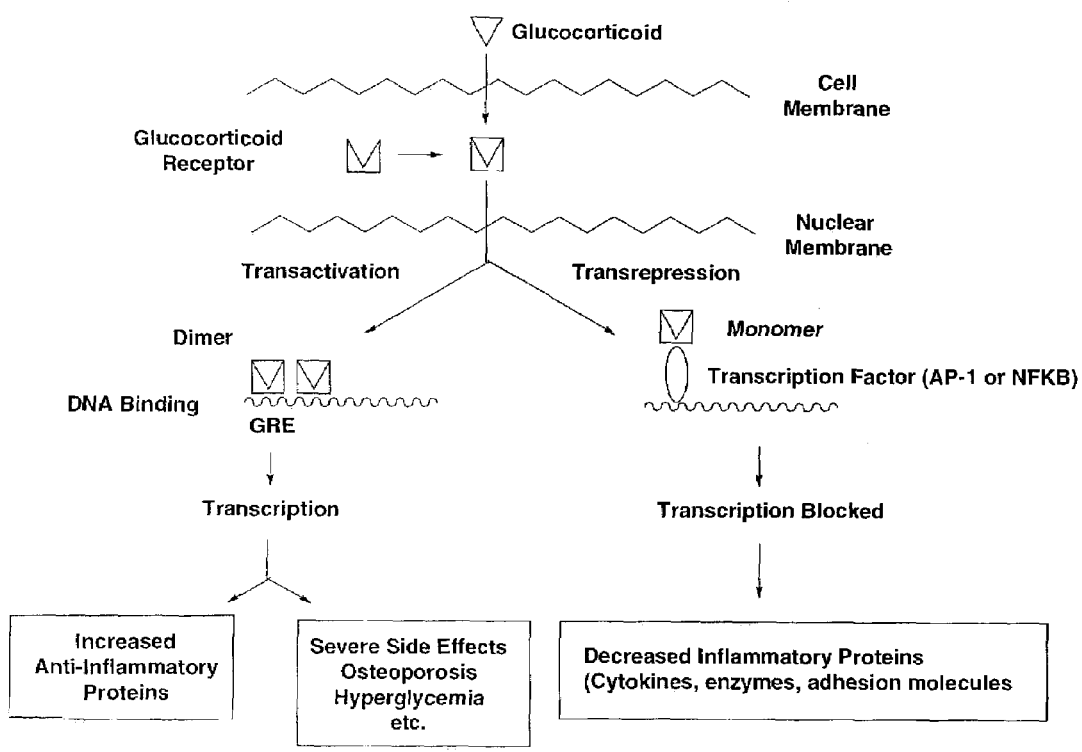
FIG. 1. Graphical description of transactivation mediated by GR dimers versus transrepression mediated by GR monomers.
Figure 4:
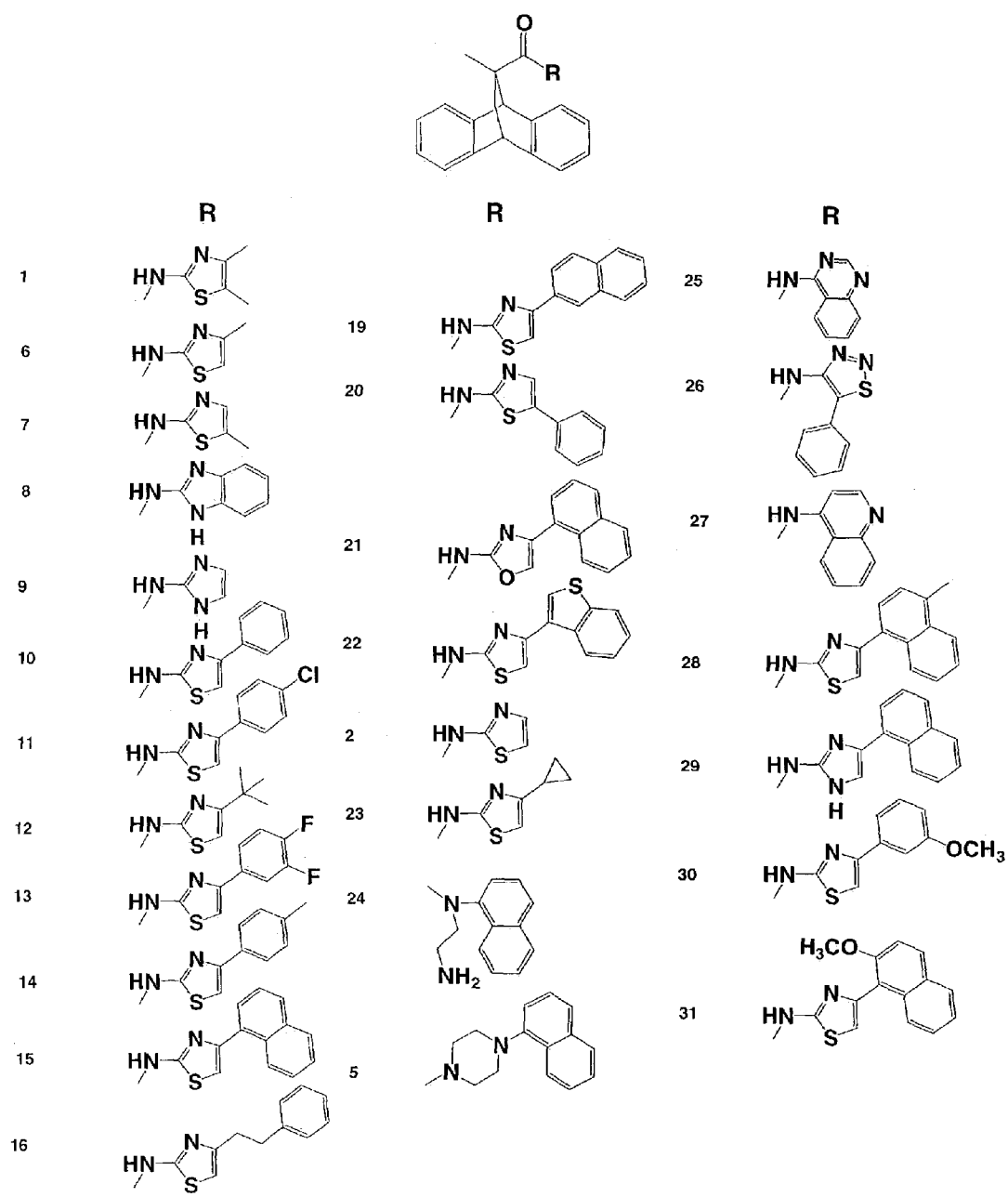

FIG. 4. Twenty-seven analogues used in the correlation of observed AP-1 inhibition and calculated contact energy scores as derived from docking into the homology model of GR Site II. Compound numbers are given to the left of each compound.

Figure 5:
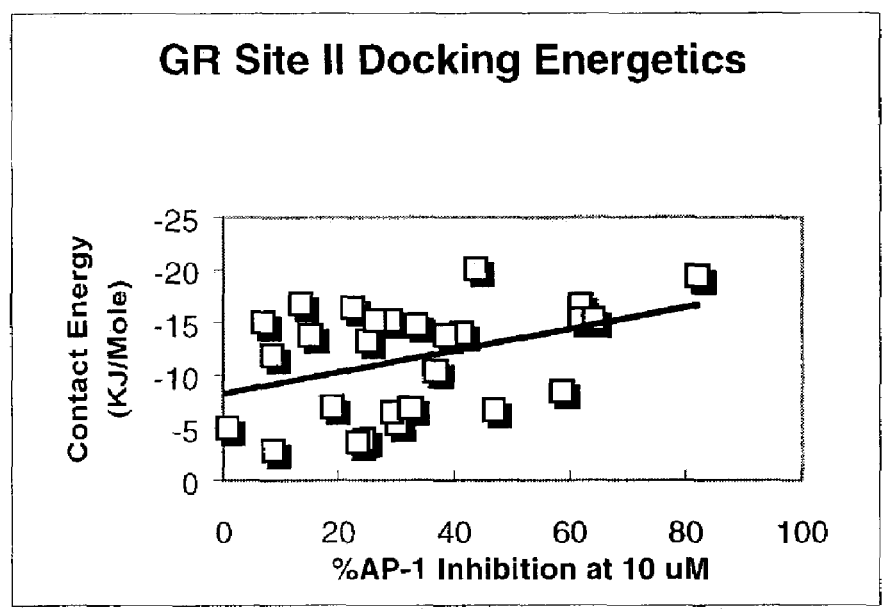

FIG. 5. The relationship between calculated contact energies of a series of twenty-seven analogues of Compound 15 and their % AP-1 inhibition (at 10 µM). Each analogue was modeled as the S-enantiomer and manually positioned in GR Site II in a manner consistent with the orientation depicted in FIG. 3. Energetics were calculated after geometry/energy minimization using Flo (Colin McMartin, Thistlesoft, Colebrook, Conn.).

FIG. 6. Sequence alignments of the GR from various species conducted using the program LOOK (Version 3.5.2, Molecular Applications Group, Palo Alto, Calif.). The sequence for each GR starts at residue 1. Alignments were made based on pair-wise sequence identity. Site II residues are shaded. Dots are spaceholders and do not represent amino acids. Numbers refer to the first residue in each line, are specific for each GR, and are based on the full-length GR. GR sequences were obtained from the following sources: Squirrel (SEQ ID NO:14) (Saimiri boliviensis boliviensis) (GenBank U87951) Reynolds, P. D., Pittler, S. J. and Scammell, J. G. J. Clin. Endocrinol. Metab. 82 (2), 465-472 (1997); Pig GR (SEQ ID NO:15) (GenBank AF141371) Gutscher, M., Eder, S., Mueller, M. and Claus, R. Submitted to GenBank (08-APR-1999) Institut fuer Tierhaltung und Tierzuechtung (470), FG Tierhaltung und Leistungsphysiologie, Universitaet Hohenheim, Garbenstr. 17, Stuttgart 70599, Germany; Guinea Pig (SEQ ID NO:16) (GenBank L13196) Keightley, M. C. and Fuller, P. J. Mol. Endocrinol. 8 (4), 431-439 (1994); Marmoset (SEQ ID NO:17) (GenBank U87953) Reynolds, P. D., Pittler, S. J. and Scammell, J. G. J. Clin. Endocrinol. Metab. 82 (2), 465-472 (1997); Ma'z Monkey (SEQ ID NO:18) (GenBank U87952) Reynolds, P. D., Pittler, S. J. and Scammell, J. G. J. Clin. Endocrinol. Metab. 82 (2), 465-472 (1997); rat (SEQ ID NO:19) (GenBank M14053) Miesfeld, R., Rusconi, S., Godowski, P. J., Maler, B. A., Okret, S., Wikstrom, A. C., Gustafsson, J. A. and Yamamoto, K. R. Cell 46 (3), 389-399 (1986); mouse (SEQ ID NO:20) (GenBank X04435) Danielsen, M., Northrop, J. P. and Ringold, G. M. EMBO J. 5 (10), 2513-2522 (1986); Human (SEQ ID NO:21) (PIR Accession Number QRHUGA) Hollenberg, S. M., Weinberger, C., Ong, E. S., Cerelli, G., Oro, A., Leba, R., Thompson, E. B., Rosenfeld, M. G., Evans, R. M., Nature (1985) 318: 635-641.

Figure 7:
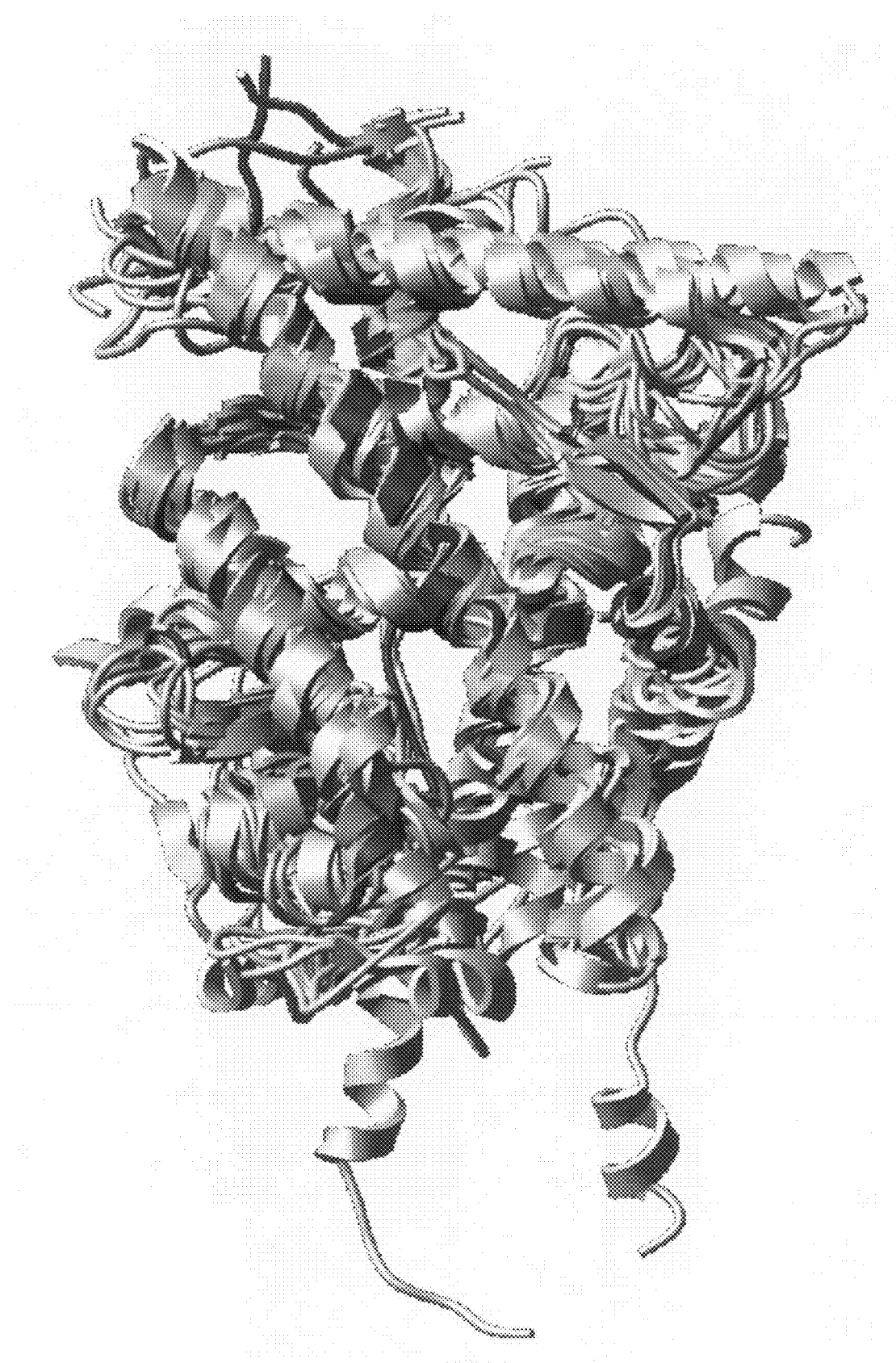

FIG. 7. Ribbon diagram of the LBDs of 11 NHRs detailed in FIG. 2, based on a consensus alignment paradigm (ICM, Molsoft LLC, La Jolla, Calif.). The glucocorticoid receptor (GR) homology model is represented by the blue ribbon.

Figure 8:
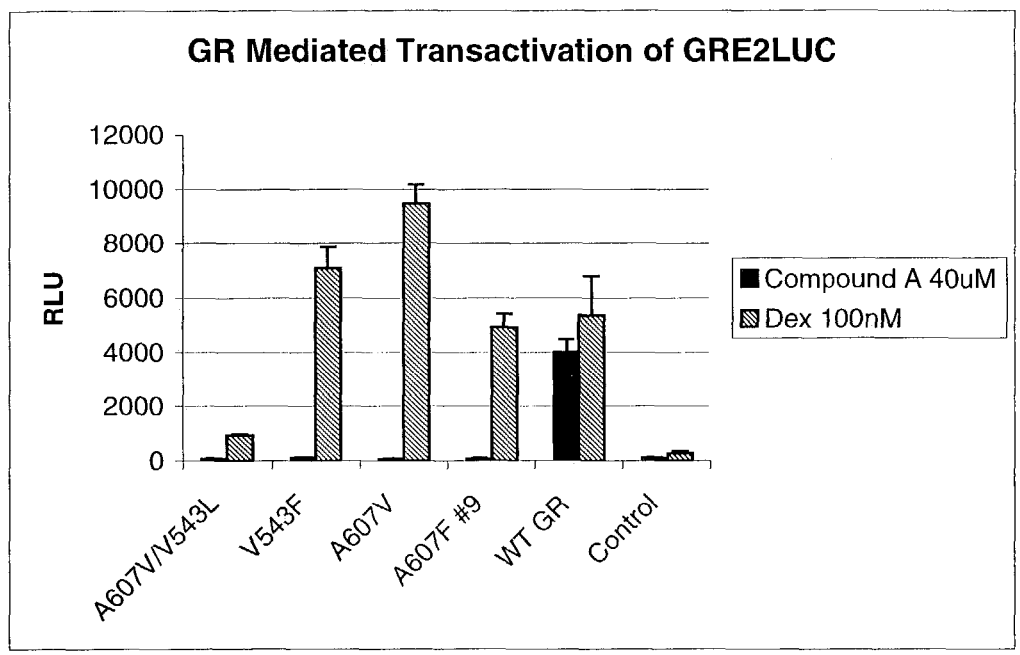

FIG. 8. Graphic demonstration that in a highly sensitive, artificial assay, mutations in Site II inhibit the ability of Site II ligands to induce transactivation, whereas there was a minimal effect on the Site I compound dexamethasone. RLU on the Y-axis is relative light units, a measurement of transactivation. Various mutants and the wild-type are given on the X-axis. Compound A, a Site II ligand, is indicated by the left, darker, solid bar in each pair of bars. Dexamethasone is indicated by the right, lighter, hatched bar in each pair of bars.

Figure 9:
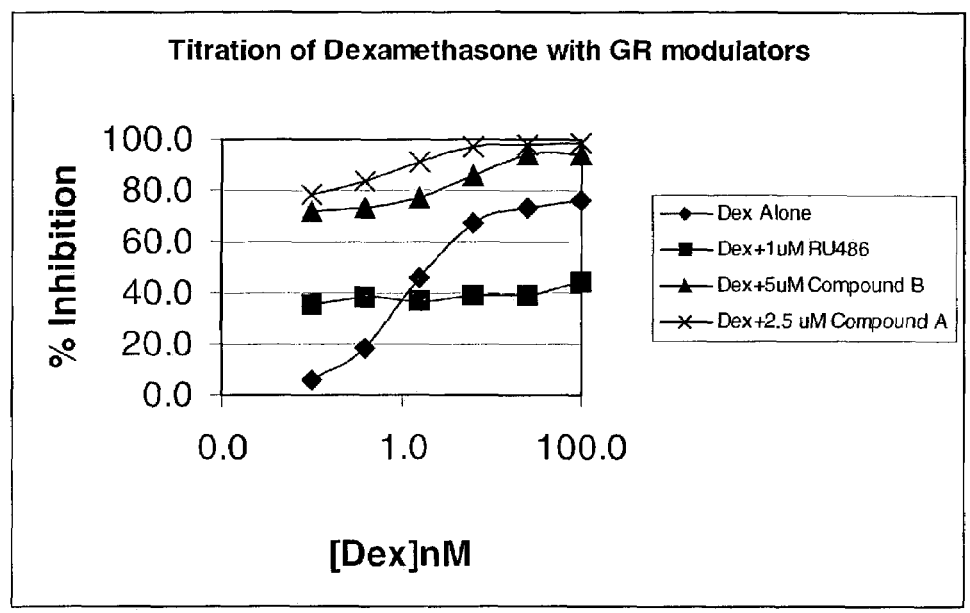

FIG. 9. Graphic demonstration that the Site I antagonist RU486 inhibits dexamethasone-mediated repression of AP-1 activity, whereas Site II compounds, such as Compound A and Compound B, act in an additive fashion with dexamethasone to repress AP-1 activity. The Y-axis denotes % inhibition of AP-1 activity. The X-axis denotes concentration of dexarnethasone. Concentrations of RU486, Compound A, and Compound B are denoted by the indicated symbols.

Figure 10:
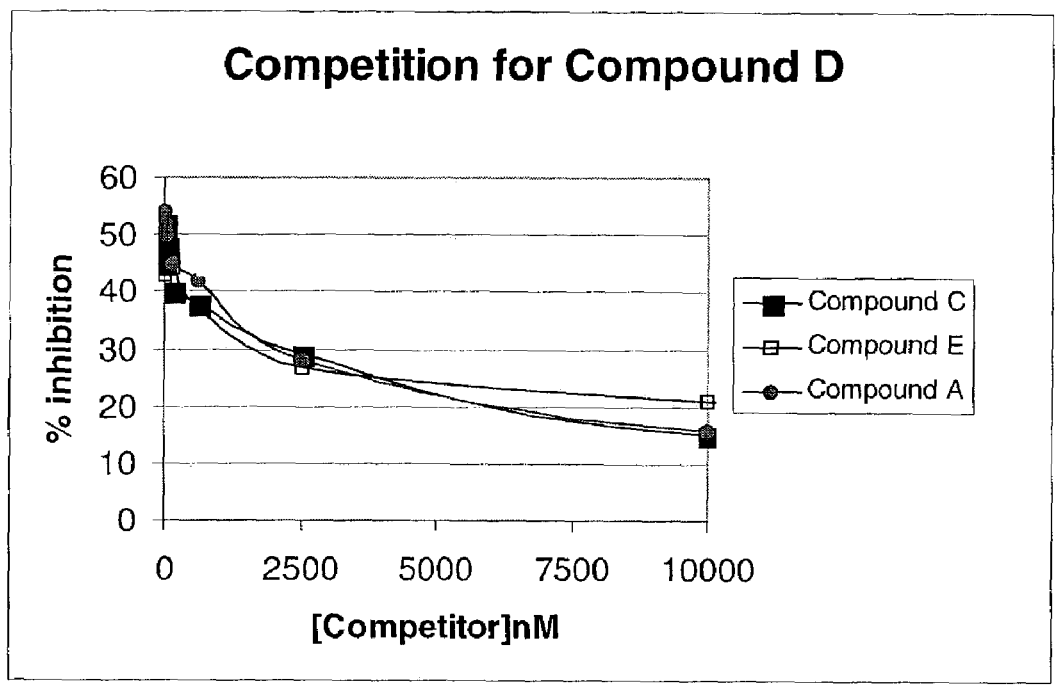

FIG. 10. Graphic demonstration of an assay to indirectly measure the interaction of Site II ligands with GR showing that Site II ligands which do not inhibit dexamethasone on their own can displace other Site II ligands which do inhibit dexamethasone, thereby allowing dexamethasone to bind to GR. Compound D is a Site II ligand that does inhibit dexamethasone. Compound A, Compound B, and Compound C are Site II ligands that do not inhibit dexamethasone on their own. Compound A, Compound B, and Compound C are denoted by the indicated symbols and are the competitor compounds whose concentration is denoted on the X-axis. The Y-axis denotes % inhibition of dexamethasone binding.

Figure 11A:
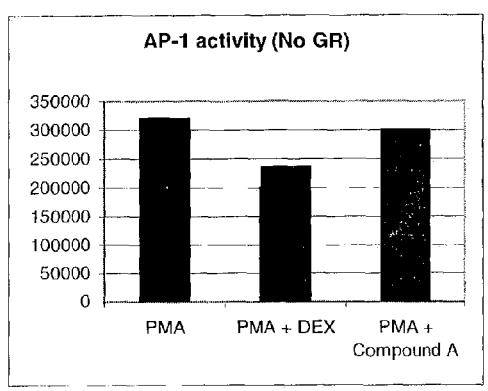
Figure 11B:
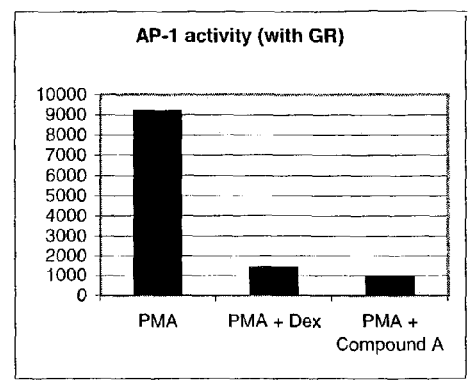

FIGS. 11a and 11b. Graphic demonstrations that a Site II ligand inhibits AP-1-mediated transcription in a GR dependent fashion. The Y-axes denote relative light units (RLU), a measurement of AP-1 activity. On the X-axes, Compound A is a Site II ligand, DEX is dexamethasone, and PMA is phorbol myristic acid. In FIG. 11a, AP-1 activity is measure without the presence of GR. In FIG. 11b, AP-1 activity is measured in the presence of GR.

DETAILED DESCRIPTION OF THE INVENTION

We have identified a second binding site in the ligand binding domain of nuclear hormone receptors (NHRs). We refer to this second binding site as Site II.

Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I. That is, a Site II is any structure that falls within the given root mean square deviation. Table I is located under the heading for Example 21.

FIG. 2 shows the amino acids of Site II in various human NHRs. The structure coordinates of Site II in the NHRs of FIG. 2 are given in Table III, located under the heading for Example 22. Two sets of xray structure coordinates of Site II in GR are given in Table IV, located under the heading for Example 23, and Table V, located under the heading for Example 24. FIG. 6 shows the amino acids of Site II in the GR of various species.

We have found that ligands of Site II modulate NHRs. Ligands of Site II induce transrepression. Ligands of Site II possess dissociated activity. Ligands of Site II antagonize transactivation.

For all of the present inventions described further below, the following information on possible and preferable embodiments applies.

Said Site II preferably is a nuclear hormone receptor (NHR) Site II, more preferably steroid hormone receptor (SHR) Site II, most preferably a glucocorticoid receptor (GR) Site II.

Said NHR is preferably an SHR, more preferably a GR.

Preferably said NHR is selected from the group consisting of: RXR-alpha; RXR-beta; progesterone receptor (PR); androgen receptor (AR); estrogen receptor-alpha (ER-alpha); ER-beta; vitamin D receptor (VitDR); peroxisome proliferator activated receptor-gamma (PPAR-gamma); thyroid receptor-alpha (TR-alpha); TR-beta; mineralocorticoid receptor (MR); and glucocorticoid receptor (GR). More preferably, said NHR is selected from the group consisting of: RXR-alpha; RXR-beta; progesterone receptor (PR); androgen receptor (AR); vitamin D receptor (VitDR); peroxisome proliferator activated receptor-gamma (PPAR-gamma); thyroid receptor-alpha (TR-alpha); TR-beta; mineralocorticoid receptor (MR); and glucocorticoid receptor (GR). Most preferably, said NHR is selected from the group consisting of: RXR-alpha; RXR-beta; androgen receptor (AR); vitamin D receptor (VitDR); peroxisome proliferator activated receptor-gamma (PPAR-gamma); thyroid receptor-alpha (TR-alpha); TR-beta; mineralocorticoid receptor (MR); and glucocorticoid receptor (GR).

Preferably said SHR is selected from the group consisting of: PR; AR; ER-alpha; ER-beta; MR; and GR. More preferably, said SHR is selected from the group consisting of: PR; AR; MR; and GR. Most preferably said SHR is selected from the group consisting of: AR; MR; and GR.

Said RXR-alpha Site II preferably is composed of amino acids L236-P244, A272-A273, Q276-W283, G305-S313, H316-R317, A320-V321, T329, L368-G369, and R372 of SEQ ID NO:3 according to FIG. 2. Preferably said structure coordinates of said RXR-alpha Site II define the structure of amino acids L236-P244, A272-A273, Q276-W283, G305-S313, H316-R317, A320-V321, T329, L368-G369, and R372 of SEQ ID NO:3 according to Table III, or define the structure of the conserved residue backbone atoms according to Table III. By this it is meant that preferably said structure coordinates define the same shape as the structure of the amino acids according to Table III, or as the structure of the residue backbone atoms according to Table II, but not necessarily that the structure coordinates are identical to those of the amino acids or residue backbone atoms in the table, as the structure coordinates may be of a coordinate system other than Cartesian coordinates. More preferably, said structure coordinates of said Site II are the structure coordinates of Site II amino acids L236-P244, A272-A273, Q276-W283, G305-S313, H316-R317, A320-V321, T329, L368-G369, and R372 of SEQ ID NO:3 according to Table III.

Said RAR-gamma Site II preferably is composed of amino acids S194-P202, L233-A234, C237-F244, A266-R274, T277-R278, T280-E282, D290, T328-G329 and S332 of SEQ ID NO:4 according to FIG. 2. Preferably said structure coordinates of said RAR-gamma Site II define the structure of amino acids S 194-P202, L233-A234, C237-F244, A266-R274, T277-R278, T280-E282, D290, T328-G329 and S332 of SEQ ID NO:4 according to Table III, or define the structure of the conserved residue backbone atoms according to Table III. More preferably, said structure coordinates of said Site II are the structure coordinates of Site II amino acids S194-P202, L233-A234, C237-F244, A266-R274, T277-R278, T280-E282, D290, T328-G329 and S332 of SEQ ID NO:4 according to Table III.

Said PR preferably is composed of amino acids M692-V698, L721-G722, Q725-W732, S754-G762, W765-R766, K769-H770, P780, F818-L819 and K822 of SEQ ID NO:5 according to FIG. 2. Preferably said structure coordinates of said PR Site II define the structure of amino acids M692-V698, L721-G722, Q725-W732, S754-G762, W765-R766, K769-H770, P780, F818-L819 and K822 of SEQ ID NO:5 according to Table III, or define the structure of the conserved residue backbone atoms according to Table III. More preferably, said structure coordinates of said Site II are the structure coordinates of Site II amino acids M692-V698, L721-G722, Q725-W732, S754-G762, W765-R766, K769-H770, P780, F818-L819 and K822 of SEQ ID NO:5 according to Table III.

Said AR Site II preferably is composed of amino acids E678-V684, L708-G709, Q712-W719, S741-A749, W752-R753, T756-N757, P767, F805-L806 and K809 of SEQ ID NO:6 according to FIG. 2. Preferably said structure coordinates of said AR Site II define the structure of amino acids E678-V684, L708-G709, Q712-W719, S741-A749, W752-

R753, T756-N757, P767, F805-L806 and K809 of SEQ ID NO:6 according to Table III, or define the structure of the conserved residue backbone atoms according to Table III. More preferably, said structure coordinates of said Site II are the structure coordinates of Site II amino acids E678-V684, L708-G709, Q712-W719, S741-A749, W752-R753, T756-N757, P767, F805-L806 and K809 of SEQ ID NO:6 according to Table III.

Said ER-alpha Site II preferably is composed of amino acids L320-1326, L348-A349, E352-W359, A381-G389, W392-R393, E396, P405, F444-V445 and K448 of SEQ ID NO:7 according to FIG. 2. Preferably said structure coordinates of said ER-alpha Site II define the structure of amino acids L320-1326, L348-A349, E352-W359, A381-G389, W392-R393, E396, P405, F444-V445 and K448 of SEQ ID NO:7 according to Table III, or define the structure of the conserved residue backbone atoms according to Table III. More preferably, said structure coordinates of said Site II are the structure coordinates of Site II amino acids L320-1326, L348-A349, E352-W359, A381-G389, W392-R393, E396, P405, F444-V445 and K448 of SEQ ID NO:7 according to Table III.

Said ER-beta Site II preferably is composed of amino acids L273-H279, L297-A298, E301-W308, C330-G338, W341-R342, D345, P354, Y393-L394 and K397 of SEQ ID NO:8 according to FIG. 2. Preferably said structure coordinates of said ER-beta Site II define the structure of amino acids L273-H279, L297-A298, E301-W308, C330-G338, W341-R342, D345, P354, Y393-L394 and K397 of SEQ ID NO:8 according to Table III, or define the structure of the conserved residue backbone atoms according to Table III. More preferably, said structure coordinates of said Site II are the structure coordinates of Site II amino acids L273-H279, L297-A298, E301-W308, C330-G338, W341-R342, D345, P354, Y393-L394 and K397 of SEQ ID NO:8 according to Table III.

Said VitDR Site II preferably is composed of amino acids L136-D144, L182-VI 83, S186-F193, S215-R223, E226-S227, T229-D231, G238, H279-V280 and M283 of SEQ ID NO:9 according to FIG. 2. Preferably said structure coordinates of said VitDR Site II define the structure of amino acids L136-D144, L182-V183, S186-F193, S215-R223, E226-S227, T229-D231, G238, H279-V280 and M283 of SEQ ID NO:9 according to Table III, or define the structure of the conserved residue backbone atoms according to Table III. More preferably, said structure coordinates of said Site II are the structure coordinates of Site II amino acids L136-D144, L182-V183, S186-F193, S215-R223, E226-S227, T229-D231, G238, H279-V280 and M283 of SEQ ID NO:9 according to Table III.

Said PPAR-gamma Site II preferably is composed of amino acids Y219-P227, R288-S289, A292-Y299, G321-M329, S332-L333, N335-K336, E343, L384-A385 and I388 of SEQ ID NO:10 according to FIG. 2. Preferably said structure coordinates of said PPAR-gamma Site II define the structure of amino acids Y219-P227, R288-S289, A292-Y299, G321-M329, S332-L333, N335-K336, E343, L384-A385 and I388 of SEQ ID NO:10 according to Table III, or define the structure of the conserved residue backbone atoms according to Table III. More preferably, said structure coordinates of said Site II are the structure coordinates of Site II amino acids Y219-P227, R288-S289, A292-Y299, G321-M329, S332-L333, N335-K336, E343, L384-A385 and I388 of SEQ ID NO:10 according to Table III.

Said MR Site II preferably is composed of amino acids E743-1749, L772-A773, Q776-W783, S805-A813, W816-R817, K820-H821, P831, Y869-T870 and K873 of SEQ ID NO:11 according to FIG. 2. Preferably said structure coordinates of said MR Site II define the structure of amino acids E743-1749, L772-A773, Q776-W783, S805-A813, W816-R817, K820-H821, P831, Y869-T870 and K873 of SEQ ID NO:11 according to Table III, or define the structure of the conserved residue backbone atoms according to Table III. More preferably, said structure coordinates of said Site II are the structure coordinates of Site II amino acids E743-1749, L772-A773, Q776-W783, S805-A813, W816-R817, K820-H821, P831, Y869-T870 and K873 of SEQ ID NO:11 according to Table III.

Said TR-beta Site II preferably is composed of amino acids T226-Q235, 1267-1268, A271-F278, C300-R308, V311-R312, D314-E316, G324, V362-A363 and Q366 of SEQ ID NO:12 according to FIG. 2. Preferably said structure coordinates of said TR-beta Site II define the structure of amino acids T226-Q235, 1267-1268, A271-F278, C300-R308, V311-R312, D314-E316, G324, V362-A363 and Q366 of SEQ ID NO:12 according to Table III, or define the structure of the conserved residue backbone atoms according to Table III. More preferably, said structure coordinates of said Site II are the structure coordinates of Site II amino acids T226-Q235, 1267-1268, A271-F278, C300-R308, V311-R312, D314-E316, G324, V362-A363 and Q366 of SEQ ID NO:12 according to Table III.

Said GR Site II preferably is composed of amino acids E537-V543, L566, G567, Q570-W577, S599-A607, W610, R611, R614, Q615, P625, Y663, L664 and K667 of SEQ ID NO:13 according to FIG. 2. Preferably said structure coordinates of said GR Site II define the structure of amino acids E537-V543, L566, G567, Q570-W577, S599-A607, W610, R611, R614, Q615, P625, Y663, L664 and K667 of SEQ ID NO:13 according to Table I, Table III, Table IV or Table V, or define the structure of the aforementioned amino acids according to the structure coordinates disclosed in Bledsoe, et. al., Cell, online publication by Cell Press, Jul. 1, 2002; DOI: 10.1016/S0092867402008176, or define the structure of the conserved residue backbone atoms according to any of the aforementioned. Preferably, said structure coordinates of said Site II are the structure coordinates of Site II amino acids E537-V543, L566, G567, Q570-W577, S599-A607, W610, R611, R614, Q615, P625, Y663, L664 and K667 of SEQ ID NO:13 according to Table I, Table III, Table IV or Table V.

Said GR Site II is preferably selected from the group consisting of: human GR Site II composed of amino acids E537-V543, L566, G567, Q570-W577, S599-A607, W610, R611, R614, Q615, P625, Y663, L664 and K667 of SEQ ID NO:19 according to FIG. 6; squirrel GR Site II composed of amino acids E537-V543, L566, G567, Q570-W577, S599-A607, W610, R611, R614, Q615, P625, Y663, L664 and K667 of SEQ ID NO:14 according to FIG. 6; pig GR Site II composed of amino acids E501-V507, L530, G531, Q534-W541, S563-A571, W574, R575, R578, Q579, P589, Y627, L628 and K631 of SEQ ID NO:15 according to FIG. 6; guinea pig GR Site II composed of amino acids E531-V537, L560, G561, Q564-W571, S593-A601, W604, R605, K608, Q609, P619, Y557, L558 and K561 of SEQ ID NO:16 according to FIG. 6; marmoset GR Site II composed of amino acids E537-V543, L566, G567, Q570-W577, S599-A607, W610, R611, R614, Q615, P625, Y663, L664 and K667 of SEQ ID NO:17 according to FIG. 6; ma'z monkey GR Site II composed of amino acids E537-V543, L566, G567, Q570-W577, S599-A607, W610, R611, R614, Q615, P625, Y663, L664 and K667 of SEQ ID NO:18 according to FIG. 6; rat GR Site II E555-V561, L584, G585, Q588-W595, S617-A625, W628, R629, R632, Q633, P643, Y681, L682 and K685 of SEQ ID NO:20 according to FIG. 6; and mouse GR Site II E543-V549, L572, G573, Q576-W583, S605-A613, W616, R617, R620, Q621, P631, Y669, L670 and K673 of SEQ ID NO:21 according to FIG. 6.

Said nuclear hormone receptor can be of any source, preferably human.

Said glucocorticoid receptor can be of any source, preferably human, rat, mouse, sheep, marmoset, squirrel, pig, guinea pig, or ma'z monkey. Most preferably said glucocorticoid receptor is human.

Said NHR Site II may be native or mutant. Preferably said NHR Site II is a native NHR Site II. Said SHR Site II maybe native or mutant. Preferably said SHR Site II is a native SHR Site II. Said GR Site II may be native or mutant. Preferably said GR Site II is a native GR Site II.

Said Site II may be found on a protein of any source, including mammalian, fungal, bacterial and plant. Preferably said Site II is found on a mammalian protein, more preferably on a human protein.

Preferably the conserved residue backbone atoms of said Site II have a root mean square deviation of less than 1.9, 1.8, 1.7, 1.6 or 1.5 Å, more preferably of less than 1.4, 1.3, 1.2, 1.1, 1.03, 1.02, or 1.0 Å, yet more preferably of less than 0.93, 0.92, 0.9, 0.8, 0.7, 0.6 0.5, 0.4, 0.3, 0.2, or 0.1 Å, most preferably 1.02, 0.92 or 0.0 Å from the conserved residue backbone atoms described by the structure coordinates of amino acids E537-V543, L566, G567, Q570-W577, S599-A607, W610, R611, R614, Q615, P625, Y663, L664 and K667 according to Table I.

Preferably the conserved residue backbone atoms of said Site II have a root mean square deviation of less than 2.0, 1.9, 1.8, 1.7, 1.6 or 1.5 Å, more preferably of less than 1.4, 1.3, 1.2, 1.1, 1.03, 1.02, or 1.0 Å, yet more preferably of less than 0.93, 0.92, 0.9, 0.8, 0.7, 0.6 0.5, 0.4, 0.3, 0.2, or 0.1 Å, most preferably 1.02, 0.92 or 0.0 Å from the conserved residue backbone atoms described by the structure coordinates of amino acids E537-V543, L566, G567, Q570-W577, S599-A607, W610, R611, R614, Q615, P625, Y663, L664 and K667 according to Table IV.

Preferably the conserved residue backbone atoms of said Site II have a root mean square deviation of less than 2.0, 1.9, 1.8, 1.7, 1.6 or 1.5 Å, more preferably of less than 1.4, 1.3, 1.2, 1.1, 1.03, 1.02, or 1.0 Å, yet more preferably of less than 0.93, 0.92, 0.9, 0.8, 0.7, 0.6 0.5, 0.4, 0.3, 0.2, or 0.1 Å, most preferably 1.02, 0.92 or 0.0 Å from the conserved residue backbone atoms described by the structure coordinates of amino acids E537-V543, L566, G567, Q570-W577, S599-A607, W610, R611, R614, Q615, P625, Y663, L664 and K667 according to Table V.

Said structure coordinates may be those determined for a Site II to which a ligand is bound or to which no ligand is bound. Said structure coordinates may be those determined for a Site II of a ligand binding domain in which a Site I ligand is bound to Site I. Said structure coordinates may be those determined for a Site II of an NHR that is in monomer, dimer, or other form.

As is illustrated in FIG. 3, the cavity circumscribed by Site II and the cavity circumscribed by Site I (in GR, the dexamethasone binding site) share a common wall section. That is, some amino acids are common to both Site II and Site I. However the cavity circumscribed by Site II is distinct from the cavity circumscribed by Site I, as the two cavities are on opposite sides of the common wall. We manually docked dexamethasone into GR Site I (see Example 10) and determined that the following amino acid residues are in contact distance, i.e. within 2-3 Angstroms, of dexamethasone and thus make up GR Site I: M560, L563, N564, L566, G567, Q570, M601, M604, A605, L608, R611, F623, M639, Q642, M646, L732, Y735, C736, T739 and E748. The following amino acid residues are common to both GR Site I and Site II: L566, G567, Q570, M601, M604, A605 and R611. The following amino acid residues are unique to GR Site II, i.e. they are not part of GR Site I: E537-V543, V571-W577, S599-W600, F602-L603, F606-A607, W610, R614, Q615, P625, Y663, L664 and K667. The following amino acid residues are unique to GR Site I, i.e. they are not part of GR Site II: M560, L563, N564, L608, F623, M639, Q642, M646, L732, Y735, C736, T739 and E748. The amino acids in other NHRs and non-human GR corresponding to the above-recited GR amino acids can be seen in FIGS. 2 and 6 respectively. We have identified Site II in NHRs as a binding site whose ligands modulate NHRs.

We defined Site II through use of structure coordinates of the ligand binding domain (LBD) of the glucocorticoid receptor (GR), which are provided in Table I. The structure coordinates of the LBD of GR were determined using homology modeling, and later confirmed based on the xray structural elucidation of the GR LBD provided in Apolito, et. al., in WO 03/015692 A2, published Feb. 27, 2003, and Kauppi et. al. in the Journal of Biological Chemistry Online, JBC Papers In Press as DOI:10.1074/JBC.M212711200, Apr. 9, 2003. Thus, some description of homology models and structure coordinates is appropriate here.

Homology models are useful when there is no experimental information available on the three-dimensional structure of the protein of interest. A three dimensional model can be constructed on the basis of the known structure of a homologous protein (Greer et. al., 1991, Lesk, et. al., 1992, Cardozo, et. al., 1995, Sali, et. al., 1995). Those of skill in the art will understand that a homology model is constructed on the basis of first identifying a template, or, protein of known structure which is similar to the protein without known structure. This can be accomplished through pairwise alignment of sequences using such programs as the MODELLER module found in InsightII (Accelrys, Inc., San Diego, Calif.).

Those of skill in the art will understand that a set of structure coordinates for a protein or part of a protein is a relative set of points that define a shape in three dimensions. For a number of reasons, including those that follow below, the structure coordinates that define two identical or almost identical shapes may vary slightly. If variations are within an acceptable standard error as compared to the original coordinates, the resulting three-dimensional shape is considered to be equivalent. Thus, for example, a ligand that bound to the structure defined by the structure coordinates of amino acids E537-V543, L566, G567, Q570-W577, S599-A607, W610, R611, R614, Q615, P625, Y663, L664 and K667 according to Table I would also be expected to bind to a site having a shape that fell within the acceptable error. Such sites with structures within the acceptable standard error are also within the scope of this invention.

Various computational analyses are therefore necessary to determine whether a molecule or a portion thereof is sufficiently similar to all or parts of the disclosed homology model to be considered equivalent. Such analyses may be carried out in current software applications, such as InsightII (Accelrys Inc., San Diego, Calif.) Version 2000 as described in the User's Guide, online or software applications available in the SYBYL software suite (Tripos Inc., St. Louis, Mo.).

Using the superimposition tool in the program InsightII, for instance, comparisons can be made between different structures and different conformations of the same structure. The procedure used in InsightII to compare structures is divided into four steps: 1) load the structures to be compared; 2) define the atom equivalencies in these structures; 3) per-form a fitting operation; and 4) analyze the results. Each structure is identified by a name. One structure is identified as the target (i.e., the fixed structure); the second structure (i.e., moving structure) is identified as the source structure. Since atom equivalency within InsightII is defined by user input, for the purpose of this invention we will define equivalent atoms as protein backbone atoms, also known as residue backbone atoms, (N, Cα, C and O) for all residues between the two structures being compared. We will also consider only rigid fitting operations. When a rigid fitting method is used, the moving structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in Angstroms (Å), is reported by InsightII.

Three-dimensional coordinates give the location of the centers of all atoms in a protein molecule and are typically expressed as Cartesian coordinates (eg, distances in three directions, each perpendicular to the other), or polar coordinates (eg, sets of angle/distance pairs from a universal origin), or internal coordinates (eg, sets of angle/distance pairs from one atom center to the next). Thus, it is possible that an entirely different set of coordinates could define an identical or similar shape, depending on which coordinate system is used.

Slight variations in the individual coordinates, as emanate from generation of similar homology models using different alignment templates, and/or using different methods in generating the homology model, will have minor effects on the overall shape.

Variations in coordinates may also be generated because of mathematical manipulations of the structure coordinates. For example, the structure coordinates set forth in Table I could be manipulated by fractionalization of the structure coordinates, integer additions or subtractions to sets of the structure coordinates, inversion of the structure coordinates or any combination of the above.

The structure coordinates of an actual xray structure of a protein would be expected to have some variation from the homology model of that very same protein. For example, the location of sidechains may vary to some extent. As examples, the homology model GR Site II coordinates were compared to the GR Site II x-ray structure coordinates available from the disclosures in WO 03/015692 A2, Feb. 27, 2003 Apolito, et. al. and Kauppi et. al., in the Journal of Biological Chemistry Online, JBC Papers In Press as DOI:10.1074/jbc.M212711200, Apr. 9, 2003, RCSB file: 1nhz.pdb (GR LBD bound to an antagonist, RU 486). When the backbone atoms of the homology model Site II residues, ie, E537-V543, L566, G567, Q570-W577, S599-A607, W610, R611, R614, Q615, P625, Y663, L664 and K667 of SEQ ID NO;13 according to Table I were compared, root mean square deviations (rmsds) of 0.92 and 1.02 Å were obtained between the homology model of Table I Site II residues and the Apolito Site II residues, and between the homology model of Table I Site II residues and the Kauppi Site II residues, respectively. These observations underscore the similarity of the Site II homology model structure to actual crystal structures.

Variations in structure coordinates can be due to mutations, additions, substitutions, and/or deletions of amino acids of a protein being studied.

Variations in structure coordinates can be due to variations in proteins whose shape is being described by the structure coordinates given. For instance, rigid fitting operations conducted (see Example 13) between the GR LBD homology model and several closely-related NHRs known to have similar structure and function (ie, progesterone receptor LBD, androgen receptor LBD, estrogen receptor alpha LBD and estrogen receptor beta LBD as examples) yielded Site II root mean square (rms) deviations in conserved residue backbone atom comparisons of 0.57-0.71 Å. These Site II rms deviations could be greater if other variation factors described above were present in the calculations. GR LBDs from non-human species may also have slight variations in shape from that of human GR LBD defined by the structure coordinates in Table 1.

For the purpose of this invention, any structure that has a root mean square deviation of residue backbone atoms (N, Cα, C, O) of less than 2.0 Angstroms (Å) when superimposed on the relevant residue backbone atoms described by structure coordinates listed in Table I is considered to be equivalent. Preferably the root mean square deviation is less than 1.9, 1.8, 1.7, 1.6 or 1.5 Å, more preferably of less than 1.4, 1.3, 1.2, 1.1, 1.03, 1.02, or 1.0 Å, yet more preferably of less than 0.93, 0.92, 0.9, 0.8, 0.7, 0.6 0.5, 0.4, 0.3, 0.2, or 0.1 Å, most preferably 1.02, 0.92 or 0.0 Å.

Within the context of the present invention, "conserved" refers to a portion of a protein backbone which is found in common between two proteins. That is, if portions of two proteins are aligned and compared using the three-dimensional coordinates of their residue backbone atoms for super-positioning, and comparison of the structure coordinates of the residue backbone atoms yields an rms of 2.0 Å or less, then the residue backbone atoms are considered to be conserved between the two proteins.

We made the claimed inventions through a series of experiments described below in the Examples. To help in understanding the invention, that series of experiments is summarized here.

Twenty-seven compounds, which are analogues, were synthesized and shown to inhibit GR binding in GR Site I binding assays and to induce transrepression in AP-1 cellular transrespressional assays. Some of these compounds were tested in cellular transcriptional assays and shown to induce none to minimal transactivation. Thus these compounds were shown to have dissociated activity.

Twelve analogues of the twenty-seven compounds (some of which are among the twenty-seven compounds) were synthesized and the racemic mixtures were separated into enantiomers. Each of these twenty-four enantiomers was tested in the GR binding assay and the cellular transrepressional assay. It was observed that the S enantiomer of each pair induced AP-1 inhibitory activity when GR was present but did not inhibit well dexamethasone binding to GR, while the R enantiomer of each pair induced minimal AP-1 inhibitory activity when GR was present and inhibited well dexamethasone binding to GR. Each enantiomer was also tested in the cellular transcriptional assay and induced none to minimal transactivation. This suggested that there is an alternate site on GR to which these compounds bind that does not result in inhibition of dexamethasone binding to GR.

A homology model of the ligand binding domain (LBD) of GR was constructed using the known crystal structure of the progesterone receptor (PR). Site II in the LBD of GR was identified by the complementarity of three-dimensional shape and functional features between the Site II and compounds having AP-1 inhibitory activity. Manual docking of one such compound was performed and confirmed the identity of Site II and its role in transrepression. Binding energetics of the S enantiomer of the twenty-seven compounds to Site II were calculated and correlated with AP-1 inhibitory activity of these compounds. This positive correlation further confirmed the identity and role of Site II.

As binding energetics to Site II correlates to AP-1 inhibitory activity and all compounds that were tested for binding to Site II are dissociated compounds, Site II was determined to be a target for compounds that have AP-1 inhibitory activity as well as compounds that have dissociated activity.

Additional studies were performed to elucidate the relationship between binding at Site II and binding at Site I. One S enantiomer and dexamethasone were used concurrently in cellular transrepressional assays and cellular transcriptional assays. In the cellular transrepressional assays, it was observed that the dissociated compound (i.e. the S enantiomer) and dexamethasone had an additive effect on AP-1 inhibitory activity. In the cellular transcriptional assays, it was observed that the presence of a dissociated compound along with dexamethasone reduced transactivation as compared to dexamethasone alone.

The cellular transcriptional assay was performed with a titration of dexamethasone in the presence or absence of each of both enantiomers of a pair. Again, an additive effect on AP-1 inhibitory activity was seen with each of the enantiomers and dexamethasone. In contrast, the Site I antagonist RU 486 inhibited the ability of dexamethasone to induce transrepression.

Other studies performed have shown that mutations in Site II alter the ability of an S enantiomer to modulate GR function. In a highly sensitive, artificial assay system to measure transactivation, it was shown that mutations of residues 543 or 607 prevented the compound from inducing transactivation, whereas, in the wild type protein transactivation was seen. Dexamethasone induced transactivation in both the mutants and the wild type protein.

A further study demonstrated that both an S enantiomer and dexamethasone act in a GR-dependent fashion.

The studies performed to date suggest that both enantiomers interact with Site II. Example 17 shows that both enantiomers R (Compound B) and S (Compound A) act in an additive fashion with saturating levels of dexamethasone to suppress AP-1 activity. Since dexamethasone binds to Site I, it is most likely that the R and S enantiomers interact with Site II to allosterically enhance the repressive activity.

The following definitions are provided to more fully describe the present invention in its various aspects. The definitions are intended to be useful for guidance and elucidation, and are not intended to limit the disclosed invention and its embodiments. Additional definitions may be provided elsewhere in the specification.

The terms "nuclear hormone receptor" and "NHR," as used herein, refer to a member of the nuclear hormone receptor family of transcription factors which bind low molecular weight ligands and stimulate or repress transcription. NHRs include, but are not limited to, glucocorticoid receptors (GRs), progesterone receptors (PRs), androgen receptors (ARs), estrogen receptors (ERs), mineralocorticoid receptors (MRs), retinoid receptors (RXRs and RARs), Vitamin D receptors (VitDRs), thyroid receptors (TRs), peroxisome proliferator activated receptors (PPARs), and orphan nuclear receptors (i.e. receptors for which the ligands are not yet identified) that bind nuclear hormones. "Nuclear hormone receptor" includes orphan nuclear receptors, which are gene products that embody structural features of nuclear hormone receptors and were identified without any prior knowledge of their association with a putative ligand.

The structural features that define a nuclear hormone receptor, including an orphan nuclear receptor, are the four following features (as disclosed in Giguere, V. (1999) Endocrine Reviews 20(5) p 689: 1. An NHR has a modulator domain including the AF-1 domain responsible in part for transcriptional activation function. Modulator domains can also include regions for promoters and cell-specific cofactors and can interact with steroid receptor co-activators (SRCs). 2. An NHR has a DNA binding domain (DBD) composed of two zinc finger modules composed of 60-70 amino acids and a carboxy-terminal extension (CTE) that providesprotein-protein and protein-DNA interactions upon homo- or heterodimer receptorbinding. 3. An NHR has a hinge region that is the hinge between the DBD and the carboxy-terminal ligand binding domain. The hinge region is variable is primary structure and amino acid sequence length. 4. An NHR has a ligand binding domain (LBD) that contains the AF-2 motif (which corresponds to helix 12 of NHRs) and provides a structured region whereby AF-2 (helix 12) is packed closely to the LBD core forming an interface with at least 3 other helices of the core. The interface is involved with binding of co-activator or co-repressor polypeptides.

"Nuclear hormone receptor" and "NHR," as used herein, refer to NHRs from any source, including but not limited to: glucocorticoid receptor as disclosed in Hollenberg, S. M., Weinberger, C., Ong, E. S., Cerelli, G., Oro, A., Leba, R., Thompson, E. B., Rosenfeld, M. G., Evans, R. M., Nature (1985) 318: 635-641 progesterone receptor as disclosed in Misrahi, M. et al. (1987) Biochem. Biophys. Res. Commun. 143, p 740; androgen receptor as disclosed in Lubahn D. B., et al (1988); estrogen receptors as disclosed in Green, S., et al. (1986) Nature 320, p 134); mineralocorticoid receptor as disclosed in Arriza, J. L., et al., (1987) Science 237, p 268; retinoid receptors (RXRs and RARs) as disclosed in Mangelsdorf, et al. (1990) Nature, 345, p 224 and Petkovich M., et al (1987) Nature 330, p 444; Vitamin D receptor, thyroid receptor (TR) as disclosed in Nakai, A. et al., (1988) Mol. Endocrinol. 2, p 1087; peroxisome proliferator activated receptor (PPAR) as disclosed in Greene, M. E., et al. (1995) Gene Expression 4, p 281; RXRalpha (1lbd) as disclosed in Bourguet, W., Ruff, M., Chambon, P., Gronemeyer, H., Moras, D. Nature 375 pp. 377 (1995); PPARgamma (2prg) as disclosed in Nolte, R. T., Wisely, G. B., Westin, S., Cobb, J. E., Lambert, M. H., Kurokawa, R., Rosenfeld, M. G., Willson, T. M., Glass, C. K., Milburn, M. V. Nature 395 pp. 137 (1998); RARgamma (2lbd) as disclosed in Renaud, J. P., Rochel, N., Ruff, M., Vivat, V., Chambon, P., Gronemeyer, H., Moras, D. Nature 378 pp. 681 (1995); PR (1a28) as disclosed in Williams, S. P., Sigler, P. B. Nature 393 pp. 392 (1998); VitDR (1db1) as disclosed in Rochel, N., Wurtz, J. M., Mitschler, A., Klaholz, B., Moras, D. Mol. Cell 5 pp. 173 (2000); AR (1e3g) as disclosed in Matias, P. M., Donner, P., Coelho, R., Thomaz, M., Peixoto, C., Macedo, S., Otto, N., Joschko, S., Scholz, P., Wegg, A., Basler, S., Schafer, M., Egner, U., Carrondo, M. A. J. Biol. Chem. 275 pp. 26164 (2000); ERalpha (1 as2) as disclosed in Tanenbaum, D. M., Wang, Y., Williams, S. P., Sigler, P. B. Proc Natl Acad Sci USA 95 pp. 5998 (1998); ERbeta (1l2j) as disclosed in Shiau, A. K., Barstad, D., Radek, J. T., Meyers, M. J., Nettles, K. W., Katzenellenbogen, B. S., Katzenellenbogen, J. A., Agard, D. A., Greene, G. L. Nat. Struct. Biol. 9 pp. 359 (2002); TRbeta (1bsx) as disclosed in Wagner, R. L., Darimont, B. D., Apriletti, J. W., Stallcup, M. R., Kushner, P. J., Baxter, J. D., Fletterick, R. J., Yamamoto, K. R. Genes Dev. 12 pp. 3343 (1998); GR, PIR Accession Number QRHUGA, as dislcosed in Hollenberg, S. M., Weinberger, C., Ong, E. S.; Cerelli, G., Oro, A., Leba, R., Thompson, E. B., Rosenfeld, M. G., Evans, R. M., Nature (1985) 318: 635-641; MR, PIR Accession Number A29613, as disclosed in Arriza, J. L.; Weinberger, C., Cerelli, G., Glaser, T.

M., Handelin, B. L., Housman, D. E., Evans, R. M., Science (1987) 237: 268-275. Orphan nuclear receptors include but are not limited to: Rev Erb (alpha) (1hlz) as disclosed in Sierk, M. L., et. al., Biochemistry (2001) 40: pp. 12833; Pxr (1ilh) as disclosed in Watkins, R. E., et. al., Science (2002) 292: pp. 2329; ERR3 (1 kv6) as disclosed in Greschik, H., et. al., Mol. Cell (2002) 9: pp. 303; Nurrl (1ovl) as disclosed in Wang, Z., et. al., Nature (2003) 423: pp. 555; ERR1 as disclosed in Guiguere, V., et al., Nature (1988) 331: 91-94. Other NHRs, including orphan nuclear receptors, include those disclosed in: The Nuclear Receptor Facts Book, V. Laudet and H. Gronemeyer, Academic Press, p 345, 2002; and Francis et al, Annu. Rev. Physiol. 2003, 65:261-311.

The terms "steroid hormone receptor" and "SHR," as used herein, refer to a member of the nuclear hormone receptor family of transcription factors which bind steroids and stimulate or repress transcription. SHRs include, but are not limited to, glucocorticoid receptors (GRs), progesterone receptors (PRs), androgen receptors (ARs), estrogen receptors (ERs), mineralocorticoid receptors (MRs), and orphan receptors (i.e. receptors for which the ligands are not yet identified) that bind steroids. These terms, as used herein, refer to steroid hormone receptors from any source, including but not limited to human.

The terms "glucocorticoid receptor" and "GR," as used herein, refer to a member of the nuclear hormone receptor family of transcription factors which bind glucocorticoids and stimulate or repress transcription, and to the GR-beta isoform. These terms, as used herein, refer to glucocorticoid receptor from any source, including but not limited to: human glucocorticoid receptor as disclosed in Weinberger, et al. Science 228, p 740-742, 1985, and in Hollenberg, S. M., Weinberger, C., Ong, E. S., Cerelli, G., Oro, A., Leba, R., Thompson, E. B., Rosenfeld, M. G., Evans, R. M.; Nature (1985) 318: 635-641; rat glucocorticoid receptor as disclosed in Miesfeld, R. Nature, 312, p 779-781, 1985; mouse glucocortoid receptor as disclosed in Danielson, M. et al. EMBO J., 5, 2513; sheep glucocorticoid receptor as disclosed in Yang, K., et al. J. Mol. Endocrinol. 8, p 173-180, 1992; marmoset glucocortoid receptor as disclosed in Brandon, D. D., et al, J. Mol. Endocrinol. 7, p 89-96, 1991; human GR-beta as disclosed in Hollenberg, S M. et al. Nature, 318, p 635, 1985, Bamberger, C. M. et al. J. Clin Invest. 95, p 2435, 1995; Squirrel (Saimiri boliviensis boliviensis) (GenBank U87951) as disclosed in Reynolds, P. D., Pittler, S. J. and Scammell, J. G. J. Clin. Endocrinol. Metab. 82 (2), 465-472 (1997); Pig GR (GenBank AF141371) as disclosed in Gutscher, M., Eder, S., Mueller, M. and Claus, R. Submitted to GenBank (08-APR-1999) Institut fuer Tierhaltung und Tierzuechtung (470), FG Tierhaltung und Leistungsphysiologie, Universitaet Hohenheim, Garbenstr. 17, Stuttgart 70599, Germany; Guinea Pig (GenBank L13196) as disclosed in Keightley, M. C. and Fuller, P. J. Mol. Endocrinol. 8 (4), 431-439 (1994); Marmoset (GenBank U87953) as disclosed in Reynolds, P. D., Pittler, S. J. and Scammell, J. G. J. Clin. Endocrinol. Metab. 82 (2), 465-472 (1997); Ma'z Monkey (GenBank U87952) as disclosed in Reynolds, P. D., Pittler, S. J. and Scammell, J. G. J. Clin. Endocrinol. Metab. 82 (2), 465-472 (1997); rat (GenBank M14053) as disclosed in Miesfeld, R., Rusconi, S., Godowski, P. J., Maler, B. A., Okret, S., Wikstrom, A. C., Gustafsson, J. A. and Yamamoto, K. R. Cell 46 (3), 389-399 (1986); mouse (GenBank X04435) as disclosed in Danielsen, M., Northrop, J. P. and Ringold, G. M. EMBO J. 5 (10), 2513-2522 (1986); Human (Protein Information Resource (PIR) Accession Number QRHUGA) as disclosed in Hollenberg, S. M., Weinberger, C., Ong, E. S., Cerelli, G., Oro, A., Leba, R., Thompson, E. B., Rosenfeld, M. G., Evans, R. M., Nature (1985) 318: 635-641.

The term "binding site," as used herein, refers to a region of a molecule or molecular complex that, as a result of its shape, favorably associates with, i.e. binds, another molecule, such other molecule being a ligand of the binding site. A binding site, such as Site II, is analogous to a wall and circumscribes a space referred to as a "cavity" or "pocket." The ligand of the binding site situates in the cavity.

The terms "binds" in all its grammatical forms, as used herein, refers to a condition of proximity between or amongst molecules, chemical compounds or chemical entities. The association may be non-covalent (i.e. non-bonded or reversible), wherein the juxtaposition is energetically favored by hydrogen bonding or van der Waals or electrostatic interactions, or it may be covalent (i.e. bonded or irreversible).

The term "soaked," as used herein, refers to a process in which the protein crystal is transferred to a solution containing the compound of interest.

The terms "at least a portion of," "a portion of," "any part of," and "any portion of," in all their grammatical forms, as used herein when referring to Site II, or the structure coordinates of Site II, or the cavity circumscribed by Site II, refer to all or any part of Site II, or the structure coordinates of Site II, or the cavity circumscribed by Site II, wherein Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 according to Table I. Preferably the terms relate to a sufficient number of residues or the corresponding structure coordinates so as to be useful in docking or modeling a ligand in the cavity circumscribed by Site II. Preferably, the terms comprise one or more of the following residues or the corresponding structure coordinates: E537-V543, V571-W577, S599-W600, F602-L603, F606-A607, W610, R614, Q615, P625, Y663, L664 and K667. These are the residues of Site II that are not also part of Site I. More preferably, the terms comprise one or more of the following residues or the corresponding structure coordinates: E537-V543, V571-W577, S599-W600, F602-L603, F606-A607, W610, R614, Y663, L664 and K667. Preferably, the terms relate to at least four amino acid residues, more preferably at least five amino acids, more preferably at least eight amino acid residues, more preferably at least fifteen amino acid residues, more preferably at least twenty amino acid residues, more preferably at least twenty-five amino acid residues, most preferably at least thirty amino acid residues.

The term "mutant," as used herein, refers to a protein, or portion of protein, having one or more amino acid deletions, insertions, inversions, repeats, or substitutions as compared to the relevant native protein or relevant portion of native protein. A native protein is one occurring in nature. A mutant Site II falls within the scope of this invention so long as the rms deviation in conserved residue backbone atoms between such mutant Site II and the the Site II residues according to Table I falls within 2.0 Angstroms. A mutant may have the same, similar, or altered activity as compared to the native protein. Activity refers to transrepression, transactivation, and ligand binding. Preferred mutants have at least 25% sequence identity, more preferably at least 50% sequence identity, more preferably at least 75% sequence identity, and most preferably at least 95% sequence identity to the native protein or portion of native protein.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein or portion of a protein from the relevant portion of the backbone of another protein, such as the LBD defined by the structure coordinates of Table I.

The term "structure coordinates," "structural coordinates," "atomic coordinates," or "atomic structure coordinates" refers to coordinates that specify the location of the centers of atoms in a protein molecule or molecular complex. The terms include, but are not limited to, Cartesian coordinates, polar coordinates, and internal coordinates. The structure coordinates may be generated by any means, including the building of a homology model or derivation from mathematical equations related to the patterns obtained on diffraction of a monochromatic beam of X-rays by the atoms (scattering centers) of a molecule or molecular complex in crystal form. The diffraction data are used to calculate an electron density map of the repeating unit of the crystal. The electron density maps are then used to establish the positions of the individual atoms of the molecule or molecular complex.

The term "molecule," as used herein, has the meaning generally used in the art and includes, but is not limited to, proteins, nucleic acids, and chemical compounds, including small organic compounds. "Small organic compounds" are also known as "small organic molecules" or "small molecules."

The term "complex" or "molecular complex," as used herein, refers to a covalent or non-covalent association of a molecule with its ligand.

The term "chemical entity," as used herein, refers to chemical compounds, complexes of at least two chemical compounds, and fragments of such chemical compounds or complexes. A modulator may be a chemical entity. A ligand may be a chemical entity.

The term "compound," as used herein, refers to a chemical compound.

The term "test molecule," as used herein, refers to a molecule, preferably a chemical compound, that is being tested for specific characteristics.

The term "ligand," as used herein, refers to a molecule that binds to another molecule or portion of another molecule.

The term "modulator," as used herein, refers to a molecule whose presence induces an activity in the molecule that it modulates. A modulator can bind to the molecule that it modulates, i.e. be a ligand of the molecule it modulates. A preferred modulator is a ligand of the molecule that it modulates. Modulators include, but are not limited to, small organic molecules, chemical compounds, peptides, peptidomimetics (eg., cyclic peptides, peptide analogs, or constrained peptides) and nucleic acids. Modulators can be natural or synthetic. Preferred modulators are small organic molecules.

The term "modeling" in all its grammatical forms, as used herein, refers to the development of a mathematical construct designed to mimic real molecular geometry and behavior in proteins and small molecules. These mathematical constructs include, but are not limited to: energy calculations for a given geometry of a molecule utilizing forcefields or ab initio methods known in the art; energy minimization using gradients of the energy calculated as atoms are shifted so as to produce a lower energy; conformational searching, ie, locating local energy minima; molecular dynamics wherein a molecular system (single molecule or ligand/protein complex) is propagated forward through increments of time according to Newtonian mechanics using techniques known to the art; calculations of molecular properties such as electrostatic fields, hydrophobicity and lipophilicity; calculation of solvent-accessible or other molecular surfaces and rendition of the molecular properties on those surfaces; comparison of molecules using either atom-atom correspondences or other criteria such as surfaces and properties; quantitiative structure-activity relationships in which molecular features or properties dependent upon them are correlated with activity or bio-assay data.

The term "fits spatially" in all its grammatical forms, as used herein, refers to when the three-dimensional structure of a compound is accommodated geometrically by a cavity or pocket of a protein, such as the cavity circumscribed by Site II.

The terms "docking" and "performing a fitting operation," in all their grammatical forms, as used herein, refer to the computational placement of a chemical entity (eg. a potential ligand, preferably a small organic molecule) within a space (i.e. cavity) at least partially enclosed by the protein structure (i.e. binding site) so that structural and chemical feature complementarity (i.e. binding contacts) between chemical entity and binding site components can be assessed in terms of interactions typical of protein/ligand complexes. Specifically, the structural and chemical features may include both bonded and non-bonded interactions, and more generally, the non-bonded interactions which occur in the bulk of reversible protein/ligand complexes would include forces such as hydrogen-bonding, electrostatic or charge interactions, vander Waal's interactions, and hydrophobic interactions. Such placement could be conducted manually or automatically using software designed for such purpose.

The term "transrepress" or "transrepression," in all their grammatical forms, is used herein to refer to the process in which an NHR represses transcription by inhibiting a transcription factor or coactivator from inducing transcription. The term is not limited to any specific mechanism of action, any specific transcription factor or coactivator, or any specific gene whose transcription is repressed. AP-1 and NF-κB are two transcription factors, among others, that can be inhibited by an NHR.

The term "transactivate" or "transactivation," in all their grammatical forms, is used herein to refer to the process in which an NHR stimulates transcription, either by binding to DNA and inducing transcription, or by modulating the activity of another DNA binding protein that induces transcription. The term is not limited to any specific mechanism of action or any specific gene whose transcription is stimulated.

The term, "NF-κB-dependent gene expression," as used herein, refers to the expression of those genes that are under the regulatory control of the NF-κB transcription factor. Such genes include, but are not limited to the immune-related and inflammatory genes encoding TNF-alpha, IL-1, IL-2, IL-5, adhesion molecules (such as E-selectin), chemokines (such Eoxtaxin and Rantes), and Cox-2.

The term, "AP-1-dependent gene expression," as used herein, refers to the expression of genes that are under the regulatory control of the AP-1 transcription factor. Such genes include, but are not limited to the immune-related and inflammatory genes encoding TNF-alpha, IL-1, IL-2, IL-5, adhesion molecules (such as E-selectin), chemokines (such Eoxtaxin and Rantes), and Cox-2.

The term "dissociated compound" is used herein to refer to a modulator of an NHR that induces transrepression and induces none to minimal transactivation. The term "dissociated activity" refers to the activity in which a dissociated compound induces transrepression and induces none to minimal transactivation.

The term "treat", "treating", or "treatment," in all grammatical forms, as used herein refers to the prevention, reduction, or amelioration, partial or complete alleviation, or cure of a disease, disorder, or condition.

The term "NHR-associated disease," as used herein, refers to a disease or disorder associated with the expression product of a gene whose transcription is stimulated or repressed by an NHR. Stimulation is through transactivation. Repression is through transrepression. Such diseases include, but are not limited to, inflammatory and immune associated diseases and disorders, diseases associated with AP-1-dependent gene expression, diseases associated with NF-κB-dependent gene expression, diseases associated with NHR transrepression, diseases associated with NHR transactivation, diseases treatable by inducing NHR transrepression, and diseases treatable by antagonizing NHR transactivation.

The term "SHR-associated disease," as used herein, refers to a disease or disorder associated with the expression product of a gene whose transcription is stimulated or repressed by an SHR. Stimulation is through transactivation. Repression is through transrepression. Such diseases include, but are not limited to, inflammatory and immune associated diseases and disorders, diseases associated with AP-1-dependent gene expression, diseases associated with NF-κB-dependent gene expression, diseases associated with SHR transrepression, diseases associated with SHR transactivation, diseases treatable by inducing SHR transrepression, and diseases treatable by antagonizing SHR transactivation.

The term "GR-associated disease," as used herein, refers to a disease or disorder associated with the expression product of a gene whose transcription is stimulated or repressed by a GR. Stimulation is through transactivation. Repression is through transrepression. Such diseases include, but are not limited to, inflammatory and immune associated diseases and disorders, diseases associated with AP-1-dependent gene expression, diseases associated with NF-κB-dependent gene expression, diseases associated with NHR transrepression, diseases associated with GR transactivation, diseases treatable by inducing GR transrepression, and diseases treatable by antagonizing GR transactivation.

The term "disease associated with NHR transrepression," as used herein, refers to a disease or disorder associated with the transcription product of a gene whose transcription is transrepressed by an NHR. Such diseases include, but are not limited to, inflammatory and immune associated diseases and disorders, diseases associated with NF-κB-dependent gene expression, diseases, diseases associated with AP-1-dependent gene expression, and diseases treatable by inducing NHR transrepression.

The term "disease associated with SHR transrepression," as used herein, refers to a disease or disorder associated with the transcription product of a gene whose transcription is transrepressed by an SHR. Such diseases include, but are not limited to, inflammatory and immune associated diseases and disorders, diseases associated with NF-κB-dependent gene expression, diseases, diseases associated with AP-1-dependent gene expression, and diseases treatable by inducing SHR transrepression.

The term "disease associated with GR transrepression," as used herein, refers to a disease or disorder associated with the transcription product of a gene whose transcription is transrepressed by a GR. Such diseases include, but are not limited to, inflammatory and immune associated diseases and disorders, diseases associated with NF-κB-dependent gene expression, diseases, diseases associated with AP-1-dependent gene expression, and diseases treatable by inducing GR transrepression.

The term "disease associated with NHR transactivation," as used herein, refers to a disease or disorder associated with the transcription product of a gene whose transcription is transactivated by an NHR. Such diseases include, but are not limited to: osteoporosis, diabetes, glaucoma, muscle loss, facial swelling, personality changes, hypertension, obesity, depression, AIDS, the condition of wound healing, prostate cancer, breast cancer, primary or secondary andrenocortical insufficiency, and Addison's disease.

The term "disease associated with SHR transactivation," as used herein, refers to a disease or disorder associated with the transcription product of a gene whose transcription is transactivated by an SHR. Such diseases include, but are not limited to: osteoporosis, diabetes, glaucoma, muscle loss, facial swelling, personality changes, hypertension, obesity, depression, and AIDS, the condition of wound healing, prostate cancer, breast cancer, primary or secondary andrenocortical insufficiency, and Addison's disease.

The term "disease associated with GR transactivation," as used herein, refers to a disease or disorder associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The term, "disease associated with NF-κB-dependent gene expression," as used herein, refers to a disease or disorder associated with the expression product of a gene under the regulatory control of NF-κB. Such diseases include, but are not limited to: inflammatory and immune associated diseases and disorders; cancer and tumor disorders, such as solid tumors, lymphomas and leukemia; fungal infections such as mycosis fungoides; ischemic or reperfusion injury such as ischemic or reperfusion injury that may have been incurred during organ transplantation, myocardial infarction, stroke or other causes; and DNA and RNA viral replication diseases, such herpes simplex type 1 (HSV-1), herpes simplex type 2 (HSV-2), hepatitis (including hepatitis B and hepatitis C), cytomegalovirus, Epstein-Barr, and human immunodeficiency virus (HIV).

The term, "disease associated with AP-1-dependent gene expression," as used herein, refers to a disease or disorder associated with the expression product of a gene under the regulatory control of AP-1. Such diseases include, but are not limited to: inflammatory and immune associated diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, juvenile diabetes, asthma, inflammatory bowel disease (such as Crohn's disease and ulcerative colitus), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia greata, autoimmune alopecia, autoimmune hypopituatarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, asthma, acute respiratory distress syndrome, Sezary's syndrome and vascular diseases which have an inflammatory and or a proliferatory component such as restenosis, stenosis and artherosclerosis. Inflammatory or immune associated diseases or disorders also includes, but is not limited to: endocrine disorders, rheumatic disorders, collagen diseases, dermatologic disease, allergic disease, opthalmic disease, respiratory disease, hematologic disease, gastrointestinal disease, inflammatory disease, autoimmune disease, Congenital adrenal hyperplasia, Nonsuppurative thyroiditis, Hypercalcemia associated with cancer, Psoriatic arthritis, Rheumatoid arthritis, including juvenile rheumatoid arthritis, Ankylosing spondylitis, Acute and subacute bursitis, Acute nonspecific tenosynovitis, Acute gouty arthritis, Post-traumatic osteoarthritis, Synovitis of osteoarthritis, Epicondylitis, Systemic lupus erythematosus, Acute rheumatic carditis, Pemphigus, Bullous dermatitis herpetiformis, Severe erythema multiforme, Exfoliative dermatitis, Psoriasis, Seborrheic dermatitis, Seasonal or perennial allergic rhinitis, Serum sickness, Bronchial asthma, Contact dermatitis, Atopic dermatitis, Drug hypersensitivity reactions, Allergic conjunctivitis, Keratitis, Herpes zoster ophthalmicus, Iritis and iridocyclitis, Chorioretinitis, Optic neuritis, Symptomatic sarcoidosis, Fulminating or disseminated pulmonary tuberculosis chemotherapy, Idiopathic thrombocytopenic purpura in adults, Secondary thrombocytopenia in adults, Acquired (autoimmune) hemolytic anemia, Leukemias and lymphomas in adults, Acute leukemia of childhood, Ulcerative colitis, Regional enteritis, Crohn's diease, Sjogren's syndrome, Autoimmune vasculitis, Multiple sclerosis, Myasthenia gravis, Anklyosing spondylitis, Chronic obstructive pulmonary disease, Solid organ transplant rejection, Sepsis, and Allergy.

The term "disease treatable by inducing NHR transrepression," as used herein, refers to a disease that can be treated by inducing NHR transrepression. Such diseases include, but are not limited to, inflammatory and immune associated diseases and disorders.

The term "disease treatable by inducing SHR transrepression," as used herein, refers to a disease that can be treated by inducing SHR transrepression. Such diseases include, but are not limited to, inflammatory and immune associated diseases and disorders.

The term "disease treatable by inducing GR transrepression," as used herein, refers to a disease that can be treated by inducing GR transrepression. Such diseases include, but are not limited to, inflammatory and immune associated diseases and disorders.

The term "disease treatable by antagonizing NHR transactivation," as used herein, refers to a disease that can be treated by antagonizing NHR transactivation. Such diseases include, but are not limited to: osteoporosis, diabetes, glaucoma, muscle loss, facial swelling, personality changes, hypertension, obesity, depression, and AIDS, the condition of wound healing, prostate cancer, breast cancer, and primary or secondary andrenocortical insufficiency.

The term "disease treatable by antagonizing SHR transactivation," as used herein, refers to a disease that can be treated by antagonizing SHR transactivation. Such diseases include, but are not limited to: osteoporosis, diabetes, glaucoma, muscle loss, facial swelling, personality changes, hypertension, obesity, depression, and AIDS, the condition of wound healing, prostate cancer, breast cancer, and primary or secondary andrenocortical insufficiency.

The term "disease treatable by antagonizing GR transactivation," as used herein, refers to a disease that can be treated by antagonizing GR transactivation. Such diseases include, but are not limited to: osteoporosis, diabetes, glaucoma, muscle loss, facial swelling, personality changes, hypertension, obesity, depression, and AIDS, the condition of wound healing, prostate cancer, breast cancer, and primary or secondary andrenocortical insufficiency.

Machine—Readable Data Storage Media, and Computer Systems

We have identified a second binding site in the ligand binding domain of NHRs, termed Site II, and provide herein the structure coordinates of Site II. The structure coordinates may be used in the design and identification of ligands of Site II and modulators of NHRs. In order to so-use structure coordinates, it may be necessary to convert them into a three-dimensional shape. This is achieved through the use of commercially available software that, in conjunction with a computer, is capable of generating three-dimensional graphical representations of molecules or portions thereof from a set of structure coordinates provided on a machine-readable data storage medium.

Therefore, the invention provides a machine-readable data storage medium comprising a data storage material encoded with machine-readable data comprising all or any part of structure coordinates of a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO: 13 according to Table I.

The invention also provides a machine-readable data storage medium comprising a data storage material encoded with machine readable data consisting of all or any part of structure coordinates of a Site II.

As is illustrated in FIG. 3, the cavity circumscribed by Site II and the cavity circumscribed by Site I share a common wall section. That is, some amino acids are common to both Site II and Site I. However the cavity circumscribed by Site II is distinct from the cavity circumscribed by Site I, as the two cavities are on opposite sides of the common wall. We manually docked dexamethasone into GR Site I (see Example 10) and determined that the following amino acid residues are in contact distance, i.e. within 2-3 Angstroms, of dexamethasone and thus make up GR Site I: M560, L563, N564, L566, G567, Q570, M601, M604, A605, L608, R611, F623, M639, Q642, M646, L732, Y735, C736, T739 and E748. The following amino acid residues are common to both GR Site I and Site II: L566, G567, Q570, M601, M604, A605 and R611. The following amino acid residues are unique to GR Site II, i.e. they are not part of GR Site I: E537-V543, V571-W577, S599-W600, F602-L603, F606-A607, W610, R614, Q615, P625, Y663, L664 and K667. The following amino acid residues are unique to GR Site I, i.e. they are not part of GR Site II: M560, L563, N564, L608, F623, M639, Q642, M646, L732, Y735, C736, T739 and E748. The amino acids in other NHRs and non-human GR corresponding to the above-recited GR amino acids can be seen in FIGS. 2 and 6 respectively. Site II and its function were newly identified by us, who were the first to identify Site II in NHRs as a binding site whose ligands modulate NHRs.

Thus the invention also provides a machine-readable data storage medium comprising a data storage material encoded with machine readable data, wherein the data: (a) comprises all or any part of the structure coordinates of a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; and (b) does not comprise structure coordinates that describe conserved residue backbone atoms having a root mean square deviation of not more than 2.0 Å from the conserved residue backbone atoms described by the structure coordinates of one or more of amino acids M560, L563, N564, L608, F623, M639, Q642, M646, L732, Y735, C736, T739 and E748 according to Table I. Preferably, said data does not comprise structure coordinates that describe conserved residue backbone atoms having a root mean square deviation of not more than 2.0 Å from the conserved residue backbone atoms described by the structure coordinates of all of amino acids M560, L563, N564, L608, F623, M639, Q642, M646, L732, Y735, C736, T739 and E748 according to Table I. Preferably, the root mean square deviation of part (b) is less than 1.9, 1.8, 1.7, 1.6 or 1.5 Å, more preferably of less than 1.4, 1.3, 1.2, 1.1, 1.03, 1.02, or 1.0 Å, yet more preferably of less than 0.93, 0,92, 0.9, 0.8, 0.7, 0.6 0.5, 0.4, 0.3, 0.2, or 0.1 Å, most preferably 1.02, 0.92 or 0.0 Å.

The machine-readable data storage media of the present invention are used in a computer. The computer is capable of producing a three-dimensional representation of Site II, and comprises various components, including the machine-readable storage medium, used to produce the three-dimensional representation.

Thus, the invention further provides a computer system capable of producing a three-dimensional representation of all or any part of a Site II, wherein said computer system comprises: (a) a machine-readable data storage medium comprising a data storage material encoded with machine readable data comprising all or any part of structure coordinates of Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; (b) a working memory for storing instructions for processing said machine-readable data; (c) a central-processing unit coupled to said working memory and to said machine-readable data storage medium for processing said machine readable data into said three-dimensional representation; and (d) a display coupled to said central-processing unit for displaying said three-dimensional representation.

The invention also provides a computer system as described above wherein the machine-readable data consists of all or any part of the structure coordinates of Site II.

The invention also provides a computer system capable of producing a three-dimensional representation of all or any part of Site II, wherein said computer system comprises: (a) a machine-readable data storage medium comprising a data storage material encoded with machine readable data, wherein the data: (i) comprises all or any part of the structure coordinates of a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; and (ii) does not comprise structure coordinates that describe conserved residue backbone atoms having a root mean square deviation of not more than 2.0 Å from the conserved residue backbone atoms described by the structure coordinates of one or more of amino acids M560, L563, N564, L608, F623, M639, Q642, M646, L732, Y735, C736, T739 and E748 according to Table I; (b) a working memory for storing instructions for processing said machine-readable data; (c) a central-processing unit coupled to said working memory and to said machine-readable data storage medium for processing said machine readable data into said three-dimensional representation; and (d) a display coupled to said central-processing unit for displaying said three-dimensional representation. Preferably, said data does not comprise structure coordinates that describe conserved residue backbone atoms having a root mean square deviation of not more than 2.0 Å from the conserved residue backbone atoms described by the structure coordinates of all of amino acids M560, L563, N564, L608, F623, M639, Q642, M646, L732, Y735, C736, T739 and E748 according to Table I.

For all of the present invention, preferably said structure coordinates are Cartesian coordinates, polar coordinates, or internal coordinates. Most preferably said structure coordinates are Cartesian coordinates.

For all of the present invention, preferably said structure coordinates are of at least four amino acids, more preferably of at least five amino acids, more, preferably of at least eight amino acids, more preferably of at least fifteen amino acids, more preferably of at least twenty amino acids, more preferably at least twenty-five amino acids, most preferably at least thirty amino acids.

For all of the present invention, said structure coordinates may be those determined for a Site II to which a ligand is bound or to which no ligand is bound. Said structure coordinates may be those determined for a Site II of an NHR that is in monomer, dimer, or other form.

One of ordinary skill in the art will recognize that there can be various embodiments of the components of the computer system. One embodiment of a computer system utilizes System 10 as disclosed in WO 98/11134, the disclosure of which is incorporated herein by reference in its entirety. Briefly, one version of the computer system comprises a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bidirectional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, keyboard may also be used as an input device.

Output hardware, coupled to the computer by output lines, may similarly be implemented by conventional devices. By way of example, output hardware may include a CRT display terminal for displaying a graphical representation of a region or domain of the present invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage, and accesses to and from the working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

For the purpose of the present invention, any magnetic data storage medium which can be encoded with machine-readable data would be sufficient for carrying out the storage requirements of the system. The medium could be a conventional floppy diskette or hard disk, having a suitable substrate, which may be conventional, and a suitable coating, which may be conventional, on one or both sides, containing magnetic domains whose polarity or orientation could be altered magnetically, for example. The medium may also have an opening for receiving the spindle of a disk drive or other data storage device.

The magnetic domains of the coating of a medium may be polarized or oriented so as to encode in a manner which may be conventional, machine readable data such as that described herein, for execution by a system such as the system described herein.

Another example of a suitable storage medium which could also be encoded with such machine-readable data, or set of instructions, which could be carried out by a system such as the system described herein, could be an optically-readable data storage medium. The medium could be a conventional compact disk read only memory (CD-ROM) or a rewritable medium such as a magneto-optical disk which is optically readable and magneto-optically writable. The medium preferably has a suitable substrate, which may be conventional, and a suitable coating, which may be conventional, usually of one side of substrate.

In the case of a CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Methods of Designing and Identifying Ligands of Site II and Modulators of NHRs

The present invention permits the use of structure-based or rational drug design and virtual screening to design or identify potential ligands and modulators of Site II.

The identity of Site II as disclosed herein permits the practice of the following techniques commonly practiced in structure-based design and virtual screening.

Using a three-dimensional model of all or any part of Site II, a test molecule, i.e. potential ligand or potential modulator, can be docked into the cavity circumscribed by Site II, i.e. a fitting operation can be performed between a test molecule and Site II. After docking, the test molecule may be analyzed for structural and chemical feature complementarity with all or any part of Site II. Structural and chemical features include, but are not limited to, any one of the following: van der Waals interactions, hydrogen bonding interactions, charge interaction, hydrophobic interactions, and dipole interactions.

Therefore, the invention provides a method of docking a test molecule comprising docking the test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I. The method may further comprise analyzing structural and chemical feature complementarity of the test molecule with all or any part of said Site II.

A three-dimensional model can be created using methods known in the art, including, but not limited to, using software such as InsightII (Accelrys, Inc., San Diego, Calif.), SYBYL (Tripos Associates, St. Louis, Mo.), and Flo (Colin McMartin, Thistlesoft, Colebrook, Conn.). Docking can be performed manually or using a variety of software, including but not limited to, DOCK (Kuntz et. al. 1982), GOLD (Cambridge Crystallographic Data Center, 12 Union Road, Cambridge, UK), or Flo (Thistlesoft, High Meadow, 603 Colebrook Raod, Colebrook, Conn.). Analyzing structural and chemical feature complementarity includes any process of a) quantifying features of atomic components found within a ligand molecule and protein molecule (eg, charge, size, shape, polarizability, hyprophobicity, etc), and b) quantifying interactions between such features in the ligand molecule, the protein molecule and the protein/ligand complex, as determined using any number of approaches known in the art (eg. molecular mechanics force fields and/or quantum mechanics). Analyzing stuructural and chemical feature complementarity can, for example, be ascertained visually or by scoring functions based on computed ligand-site interactions as implemented in DOCK, GOLD or Flo.

A three dimensional model of Site II can be used to identify structural and chemical features that may be involved in binding of ligands to Site II. Identified structural or chemical features can then be employed to design ligands or modulators of Site II or identify test molecules as ligands or modulators of Site II.

Therefore, the invention provides a method of identifying structural and chemical features comprising identifying structural and chemical features of all or any part of a Site II using a three-dimensional model of all or any part of said Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I. Identification of structural and chemical features may be performed by means known in the art, such as through use of DOCK, GOLD or Flo.

Structure-based design often involves modeling. Modeling is the development of a mathematical construct designed to mimic real molecular geometry and behavior in proteins and small molecules. These mathematical constructs include, but are not limited to: energy calculations for a given geometry of a molecule utilizing forcefields or ab initio methods known in the art; energy minimization using gradients of the energy calculated as atoms are shifted so as to produce a lower energy; conformational searching, ie, locating local energy minima; molecular dynamics wherein a molecular system (single molecule or ligand/protein complex) is propagated forward through increments of time according to Newtonian mechanics using techniques known to the art; calculations of molecular properties such as electrostatic fields, hydrophobicity and lipophilicity; calculation of solvent-accessible or other molecular surfaces and rendition of the molecular properties on those surfaces; comparison of molecules using either atom-atom correspondences or other criteria such as surfaces and properties; quantitiative structure-activity relationships in which molecular features or properties dependent upon them are correlated with activity or bio-assay data. A number of computer modeling systems are available in which a sequence and structure (i.e., structure coordinates) of a protein or portion of a protein can be input. Examples of such computer modeling systems include, but are not limited to, InsightII (Accelrys, Inc., San Diego, Calif.), SYBYL (Tripos Associates, St. Louis, Mo.), and Flo (Colin McMartin, Thistlesoft, Colebrook, Conn.). The computer system then generates the structural details of one or more regions in which a potential ligand binds so that complementary structural and chemical features of the potential ligands can be determined. Design in these modeling systems is generally based upon the compound being capable of structurally and chemically associating with the protein, i.e. have structural and chemical feature complementarity. In addition, the compound must be able to assume a conformation that allows it to associate with the protein. Some modeling and design systems estimate the potential inhibitory or binding effect of a potential modulator prior to actual synthesis and testing. Using modeling, compounds may be designed de novo using an empty binding site. Alternatively, compounds may be designed including some portion of a known ligand, i.e. grown in place. The known ligand may have been determined through virtual screening. Programs for design include, but are not limited to LUDI (Bohm 1992), LeapFrog (Tripos Associates, St. Louis Mo.) and DOCK (Kuntz et. al., 1982).

Therefore, the invention provides a method of designing a ligand of Site II comprising: (a) modeling all or any part of a Site II; and (b) based on said modeling, designing a chemical entity that has structural and chemical feature complementarity with all or any part of said Site II; wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I. The chemical entity is designed to fit spatially into all or any part of the cavity circumscribed by Site II. The chemical entity may be designed manually without the aid of computer software, either de novo or including some portion of a known ligand. The chemical entity may be designed by computer either de novo or including some portion of a known ligand. Design by computer may employ a database from which chemical entities are chosen based on the model. The method may further comprise: (c) docking the chemical entity into all or any part of the cavity circumscribed by said Site II; and (d) analyzing structural and chemical feature complementarity of the chemical entity with all or any part of said Site II. The method may further comprise analyzing structural and chemical feature complementarity of a second chemical entity with all or any part of said Site II, such as when the modeling operation grows a ligand in place.

The invention also provides a method of designing a modulator of an NHR comprising: (a) modeling all or any part of a Site II; and (b) based on said modeling, designing a chemical entity that has structural and chemical feature complementarity with all or any part of said Site II; wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I. The chemical entity is designed to fit spatially into all or any part of the cavity circumscribed by said Site II. The chemical entity may be designed manually without the aid of computer software, either de novo or including some portion of a known ligand. The chemical entity may be designed by computer either de novo or including some portion of a known ligand. Design by computer may employ a database from which chemical entities are chosen based on the model. The method may further comprise: (c) docking the chemical entity into all or any part of the cavity circumscribed by said Site II; and (d) analyzing structural and chemical feature complementarity of the chemical entity with all or any part of said Site II. The method may further comprise analyzing structural and chemical feature complementarity of a second chemical entity with all or any part of said Site II, such as when the modeling operation grows a ligand in place.

Virtual screening methods, i.e. methods of evaluating the potential of chemical entities to bind to a given protein or portion of a protein, are well known in the art. These methods often utilize databases as sources of the chemical entities and often are employed in designing ligands. Often these methods begin by visual inspection of the binding site on the computer screen. Selected chemical entities can then be placed, i.e. docked, in one or more positions and orientations within the binding site and chemical and structural feature complementarity can be analyzed.

In virtual screening, molecular docking can be accomplished using software such as InsightII, ICM (Molsoft LLC, La Jolla, Calif.), and SYBYL, followed by energy minimization and molecular dynamics with standard molecular mechanics forcefields such as CHARMM and MMFF. Examples of computer programs which assist in the selection of chemical entities useful in the present invention include, but are not limited to, GRID (Goodford, 1985), AUTODOCK (Goodsell, 1990), and DOCK (Kuntz et. al. 1982). Databases of chemical entities that may be used include, but are not limited to, ACD (Molecular Designs Limited), Aldrich (Aldrich Chemical Company), NCI (National Cancer Institute), Maybridge (Maybridge Chemical Company Ltd), CCDC (Cambridge Crystallographic Data Center), CAST (Chemical Abstract Service) and Derwent (Derwent Information Limited).

For example, programs such as DOCK (Kuntz et. al 1982) can be used with the structure coordinates of Site II to identify chemical entities from databases or virtual databases of small molecules. These molecules may therefore be suitable candidates for synthesis and testing. Such a virtual screening approach may include, but is not limited to, the following steps:

1) Selection of a chemical entity from a database or elsewhere and positioning the chemical entity in one or more orientations within all or any part of the cavity circumscribed by Site II, wherein Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I.
2) Characterization of the structural and chemical features of the chemical entity and binding site, such as van der Waals interactions, hydrogen bonding interactions, charge interaction, hydrophobic bonding interaction, and dipole interactions
3) Optionally, selection from a database or elsewhere of a chemical entity which can be joined to or replace the docked chemical entity and fit spatially into all or any part of the cavity circumscribed by Site II
4) Evaluation of the docked chemical entity using a combination of scoring schemes which account for van der Waals interactions, hydrogen bonding interactions, charge interaction and hydrophobic interactions, i.e. evaluation of structural and chemical feature complementarity.

Upon selection of preferred chemical entities, their relationship to each other and Site II can be visualized and then assembled into a single potential ligand. Programs useful in assembling the individual chemical entities include, but are not limited to, SYBYL and LeapFrog (Tripos Associates, St. Louis Mo.), LUDI (Bohm 1992) and 3D Database systems (Martin 1992).

Thus, the invention provides a method for evaluating the potential of a chemical entity to bind to all or any part of Site II comprising: a) docking a chemical entity into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; and b) analyzing structural and chemical feature complementarity between the chemical entity and all or any part of said Site II. The chemical entity may be selected from a database. The method may further comprise a step in which a second chemical entity is joined to the first chemical entity that was docked and analyzed, and the resultant chemical entity is docked and analyzed.

Ligands designed or identified using the methods described herein can then be synthesized and screened in an NHR Site II binding assay (such as is described in Examples 15 and 18), or in an assay designed to test functional activity (such as the cellular tranrepressional assay described in Example 3 and the cellular transcriptional assay described in Example 4, and the competition assays described in Examples 11 and 12). Examples of assays useful in screening of potential ligands or modulators include, but are not limited to, screening in silico, in vitro assays and high throughput assays.

Similarly and further to the method for evaluating the potential of a chemical entity to bind Site II, test molecules may be screened, using computational means and biological assays, to identify ligands of Site II and modulators of NHRs.

Thus, the invention provides a method for identifying a modulator of an NHR. The method comprises the following steps, which are preferably, but not necessarily, performed in the order given: a) docking a test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; b) analyzing structural and chemical feature complementarity between the test molecule and all or any part said Site II; and c) screening the test molecule in a biological assay of modulation of an NHR. A test molecule is identified as a modulator of an NHR if the structural and chemical feature complementarity and/or the modulation exceed a desired level. A compound which stimulates or inhibits a measured activity in a cellular assay by greater than 10% is a preferred modulator. The method may further comprise one or more of the following steps: d) screening the test molecule in an assay that characterizes binding to a Site II; and e) screening the test molecule in an assay that characterizes binding to Site I.

A biological assay of modulation of an NHR includes, but is not limited to: a transrepression assay, such as described in Example 3; a transactivation assay, such as described in Example 4; a transrepression competition assay, such as described in Example 11; and a transactivation competition assay, such as described in Example 12. An assay that characterizes binding to Site II includes, but is not limited to, any of the assays described in Examples 15 and 18.

The invention provides a method for identifying a ligand of Site II. The method comprises the following steps, which are preferably, but not necessarily, performed in the order given: a) docking a test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; b) analyzing structural and chemical feature complementarity between the test molecule and all or any part said Site II; and c) screening the test molecule in an assay that characterizes binding to a Site II. A test molecule that binds to Site II is identified as a ligand of Site II. The method may further comprise one or more of the following steps: d) screening the test molecule in a biological assay of modulation of an NHR; and e) screening the test molecule in an assay that characterizes binding to Site I.

In the above-described method of identifying a modulator of an NHR and method of identifying a ligand of Site II, the structure coordinates of a Site II of a first NHR may be used, while the biological assays (i.e. biological assay of modulation of an NHR, or assay that characterizes binding to Site II, or assay that characterizes binding to Site I) may be performed using a second NHR. Preferably, the structure coordinates of a Site II are of the same NHR as the NHR used in the biological assays.

In the present methods, a modulator of an NHR can induce one or more of the following four activities in the NHR. This list is not meant to be inclusive. (1) A modulator of an NHR can induce transrepression. (2) A modulator of an NHR can induce transactivation. (3) A modulator of an NHR can inhibit or antagonize the ability of another modulator from inducing transrepression. (4) A modulator of an NHR can inhibit or antagonize the ability of another modulator from inducing transactivation.

Preferably said modulator of an NHR is a modulator of an SHR, more preferably a modulator of GR.

A modulator of an NHR, SHR or GR that induces transrepression includes, but is not limited to, a dissociated compound.

Preferably said modulator of an NHR induces transrepression. More preferably said modulator of an NHR is a dissociated compound. More preferably said modulator of an NHR is an SHR dissociated compound. Most preferably said modulator of an NHR is a GR dissociated compound.

"All or any part of the cavity circumscribed by Site II" preferably relates to enough of the cavity so as to be useful in docking or modeling a ligand into the cavity. Preferably, all or any part of the cavity is circumscribed by one or more of the following residues: E537-V543, V571-W577, S599-W600, F602-L603, F606-A607, W610, R614, Q615, P625, Y663, L664 and K667. These are the residues of Site II that are not also part of Site I. Preferably, all or any part of the cavity is circumscribed by at least four amino acid residues, more preferably at least five amino acids, more preferably at least eight amino acid residues, more preferably at least fifteen amino acid residues, more preferably at least twenty amino acid residues, more preferably at least twenty-five amino acid residues, most preferably at least thirty amino acid residues.

The structure coordinates of Site II of a first NHR may be used in the above methods when one is interested in a second NHR. For instance, one may use the structure coordinates of GR Site II in a method when the end goal is to evaluate the potential of a chemical entity to bind to Site II of another NHR, for instance, androgen receptor. This is because, based on the structural similarity amongst various NHRs, it is possible that a modulator of GR Site II, or structural variants of a modulator of GR Site II, could bind to Site II in other NHRs. It is known in the art that a single steroid can bind to multiple NHRs. For example, cortisol can bind not only to GR but to the mineralocorticoid receptor as well. It is thought that this binding of cortisol occurs via Site I.

Ligands of Site II, and Modulators of NHRs

We have identified Site II in NHRs and identified ligands of Site II as modulators of NHRs and thus drug candidates.

Therefore, the invention provides a ligand of a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I.

A ligand can be identified by any art-recognized assay for binding to Site II, such as the assays described in Examples 15 and 18.

Preferred ligands have been identified according to a method of the invention described herein. That is, preferred ligands were identified by a method comprising: a) docking a test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; b) analyzing the structural and chemical feature complementarity between the test molecule and all or any part said Site II; and c) screening the test molecule in an assay that characterizes binding to a Site II. A test molecule that binds to Site II is identified as a ligand of Site II. The method may further comprise one or more of the following steps: d) screening the test molecule in a biological assay of modulation of an NHR; and e) screening the test molecule in an assay that characterizes binding to Site I.

Preferred ligands are ligands of an NHR Site II, more preferably of an SHR Site II, most preferably of a GR Site II.

The invention also provides a modulator of an NHR identified according to a method of the invention described herein. That is, the invention provides a modulator of an NHR, wherein said modulator has been identified by a method comprising: a) docking a test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; b) analyzing the structural and chemical feature complementarity between the test molecule and all or any part said Site II; and c) screening the test molecule in a biological assay of modulation of an NHR. A test molecule is identified as a modulator of an NHR if the structural and chemical feature complementarity and the modulation exceed a desired level. The method may further comprise one or more of the following steps: d) screening the test molecule in an assay that characterizes binding to a Site II; and e) screening the test molecule in an assay that characterizes binding to Site I.

Preferably said modulator of an NHR is a ligand of Site II. Preferred modulators are modulators of an NHR, more preferably of an SHR, most preferably of a GR.

The invention also provides a modulator of an NHR that is a ligand of a Site II. A modulator of an NHR that is a ligand of Site II is part of the invention regardless of how the modulator was identified.

As previously stated, the term "modulator," as used herein, refers to a molecule whose presence induces an activity in the molecule that it modulates. The following information on modulators applies to all of the present inventions.

A modulator can bind to the molecule that it modulates, i.e. be a ligand of the molecule it modulates. A preferred modulator is a ligand of the molecule that it modulates. In the present inventions, a preferred modulator is a ligand of Site II. Modulators include, but are not limited to, small organic molecules, chemical compounds, peptides, peptidomimetics (eg., cyclic peptides, peptide analogs, or constrained peptides) and nucleic acids. Modulators can be natural or synthetic. Preferred modulators are small organic molecules.

A modulator of an NHR can induce one or more of the following four activities in the NHR. This list is not meant to be inclusive. (1) A modulator of an NHR can induce transrepression. (2) A modulator of an NHR can induce transactivation. (3) A modulator of an NHR can inhibit or antagonize the ability of another modulator from inducing transrepression. (4) A modulator of an NHR can inhibit or antagonize the ability of another modulator from inducing transactivation.

One type of modulator of an NHR is one that induces transrepression. Examples of this type of modulator are steroids (such as glucocorticoids and dexamethasone) and dissociated compounds, both of which are discussed further below. Several such modulators are described in the Examples. Such a modulator is useful in treating inflammatory and immune associated diseases and disorders. A modulator that induces tranrepression and synergizes (i.e. has an additive effect) with another modulator that induces transrepression, such as described in Examples 11 and 17, is included in the definition of a modulator that induces transrepression.

Another type of modulator is a dissociated compound. A dissociated compound is a modulator that induces transrepression while inducing none or minimal transactivation. That is, a dissociated compound induces activity (1) above but induces no or little activity (2) above. Several such modulators are described in the Examples. A dissociated compound also may inhibit or antagonize the ability of another modulator from causing transactivation, i.e. a dissociated compound may cause activity (4) above, such as the compound described in Examples 11 and 12, Dissociated compounds that induce AP-1 and NF-κB inhibitory activity without causing DNA-binding activity are useful in treating inflammatory and immune associated diseases and disorders, such as in immunosuppressive therapy. AP-1 and NF-κB are transcription factors which regulate the expression of a large number of genes involved in immune and inflammatory responses. These genes include TNF-alpha, IL-2, IL-5, E-selectin, Eoxtaxin, Rantes, Cox-2, among others. By way of example, glucocorticoids, which inhibit the activity of both AP-1 and NF-κB are one of the most potent anti-inflammatory drugs known to date. Glucocorticoids are used to treat more than 50 diseases, however, their use in patients is often limited by the side effects of osteoporosis, diabetes, glaucoma, muscle loss, facial swelling, personality changes, and others. It is thought that a compound which inhibits NF-κB and AP-1 without inducing DNA binding (i.e. without causing transactivation) would possess most of the anti-inflammatory effects of glucocorticoids without the side effects.

Another type of modulator of is one that induces transactivation without inducing transrepression. In the case of GR, such a modulator that induces DNA binding and transcription may be useful in treating Addison's disease or other metabolic disorders where circulating glucocorticoid levels are lower than normal and where causing transrepression is not desireable.

Another type of modulator is one that induces both transrepression and transactivation. Examples of this type of modulator are steroids such as glucocorticoids and dexamethasone. Such a modulator is useful in treating inflammatory and immune associated diseases and disorders.

Another type of modulator is one that antagonizes a modulator that induces transactivation. These modulators inhibit transcription. Such a modulator is described in Example 12. These modulators may also induce transrepression. In the case of GR, a modulator that antagonizes a modulator that induces transactivation may be useful in treating metabolic diseases such as diabetes, hypertension, obesity, glaucoma, depression, and AIDS, and in wound healing. It is believed that some of these diseases are, at least in part, caused by higher than normal circulating levels of glucocorticoids. Inhibiting the transactivation or DNA binding induced by the increased circulating glucocorticoids may ameliorate or attenuate some or all of these diseases. Preferably, the GR modulator that antagonizes a modulator that induces transactivation does not also induce transrepression.

All modulators of NHRs and ligands of Site II may be useful in elucidating the mechanism of transcriptional regulation mediated by NHRs. These modulators and ligands could be used in cellular and animal studies to determine the requirement for NHRs in the induction or inhibition of gene expression, the association of coactivators and corepressors with NHRs, and the role of chaperones in regulating NHR activity, among other experiments.

Modulators of NHRs may be found by performing any art-recognized transrepression assay, transactivation assay, transrepression competition assay, or transactivation competition assay. Such assays include, but are not limited to, the assays described in Examples 3, 4, 11 and 12.

For a modulator of an NHR that induces transrepression, such as and including a dissociated compound, a preferred modulator induces transrepression at an IC50 of between 0.1 nM and 10 µM, more preferably between 0.1 nm and 1 µM (such as between 33 nM and 275 nM, or between 15 nm and 275 nm), more preferably between 0.1 nM and 100 nM, most preferably between 0.1 nM and 10 nM. Transrepression may be measured by any art-recognized method, such as the cellular transrepressional assays described in Example 3. An IC50 is the modulator concentration which causes a 50% repression of transcription.

For a modulator of an NHR that induces none to minimal transactivation, such as and including a dissociated compound, a preferred modulator induces transactivation at an EC50 of greater than 1M, preferably at greater than 100 nM, more preferably at greater than 1 µM, and most preferably at greater than 40 µM. Transactivation may be measured by any method known in the art, such as the cellular transcriptional assays described in Example 4. An EC50 is modulator concentration required to cause a 50% stimulation of transcription.

For a dissociated compound, a preferred dissociated compound has a dissociation constant of greater than 0.1, more preferably greater than 10, more preferably greater than 100 (such as between 167 and 1000, or between 137 and 1000), most preferably greater than 1000. The dissociation constant is calculated by dividing the EC50 for transactivation by the IC50 for transrepression.

For a modulator of an NHR that antagonizes a modulator that induces transactivation, a preferred modulator antagonizes at an IC50 of between 0.1 nM and 10 µM, more preferably between 0.1 nM and 1 µM, more preferably between 0.1 nM and 100 nM, most preferably between 0.1 nM and 10 nM.

For a modulator of an NHR that induces transactivation, a preferred modulator induces transactivation at an IC50 of between 0.1 nM and 10 µM, more preferably between 0.1 nM and 1 µM, more preferably between 0.1 nM and 100 nM, most preferably between 0.1 nM and 10 nM.

Methods of Modulating a Nuclear Hormone Receptor

The modulators of the present invention may be used to modulate an NHR.

Thus, the invention provides a method of modulating an NHR comprising administering a modulator of an NHR in an amount sufficient to modulate the NHR, wherein said modulator of an NHR is a ligand of a Site II or was identified by a method comprising: a) docking a test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; b) analyzing the structural and chemical feature complementarity structural and chemical feature complementarity between the test molecule and all or any part said Site II; and c) screening the test molecule in a biological assay of modulation of an NHR. A test molecule is identified as a modulator of an NHR if the structural and chemical feature complementarity and the modulation exceed a desired level. The method may further comprise one or more of the following steps: d) screening the test molecule in an assay that characterizes binding to a Site II; and e) screening the test molecule in an assay that characterizes binding to Site I.

The invention provides a method of inducing transrepression comprising administering a modulator of an NHR in an amount sufficient to cause transrepression, wherein said modulator on an NHR is a ligand of Site II or was identified by the method described above.

The invention provides a method of inhibiting AP-1-dependent gene expression comprising administering a modulator of an NHR in an amount sufficient to inhibit AP-1-dependent gene expression, wherein said modulator on an NHR is a ligand of Site II or was identified by the method described above.

The invention provides a method of inhibiting NF-κB-dependent gene expression comprising administering a modulator of an NHR in an amount sufficient to inhibit NF-κB-dependent gene expression, wherein said modulator on an NHR is a ligand of Site II or was identified by the method described above.

The invention provides a method of antagonizing transactivation comprising administering a modulator of an NHR in an amount sufficient to antagonize transactivation, wherein said modulator on an NHR is a ligand of Site II or was identified by the method described above.

Preferred ligands used in the methods of the present invention were identified by a method comprising: a) docking a test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; b) analyzing the structural and chemical feature complementarity between the test molecule and all or any part said Site II; and c) screening the test molecule in an assay that characterizes binding to a Site II. A test molecule that binds to Site II is identified as a ligand of Site II. The method may further comprise one or more of the following steps: d) screening the test molecule in a biological assay of modulation of an NHR; and e) screening the test molecule in an assay that characterizes binding to Site I.

The methods may be practiced in vitro or in vivo. When practiced in vitro, the method may employ any number of art-recognized in vitro systems, including the assays described in Examples 3 and 4. In vivo methods include, but are not limited to, any of the ways described in the section below on methods of treatment.

Pharmaceutical Compositions

The invention provides a pharmaceutical composition comprising: (a) a modulator of an NHR that was identified by a method comprising: (i) docking a test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; (ii) analyzing the structural and chemical feature complementarity between the test molecule and all or any part said Site II; and (iii) screening the test molecule in a biological assay of modulation of an NHR; and (b) a pharmaceutically acceptable carrier, adjuvant, excipient or vehicle. A test molecule is identified as a modulator of an NHR if the structural and chemical feature complementarity and the modulation exceed a desired level. The method used to identify a modulator of Site II may further comprise one or more of the following steps: d) screening the test molecule in an assay that characterizes binding to a Site II; and e) screening the test molecule in an assay that characterizes binding to Site I.

The invention provides a pharmaceutical composition comprising a modulator of an NHR that is a ligand of Site II and a pharmaceutically acceptable carrier, adjuvant, excipient or vehicle. Preferred ligands of Site II were identified by a method comprising: a) docking a test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; b) analyzing the structural and chemical feature complementarity between the test molecule and all or any part said Site II; and c) screening the test molecule in an assay that characterizes binding to a Site II. A test molecule that binds to Site II is identified as a ligand of Site II. The method may further comprise one or more of the following steps: d) screening the test molecule in a biological assay of modulation of an NHR; and e) screening the test molecule in an assay that characterizes binding to Site I.

In the present pharmaceutical compositions, a modulator of an NHR can induce one or more of the following four activities in the NHR. This list is not meant to be inclusive. (1) A modulator of an NHR can induce transrepression. (2) A modulator of an NHR can induce transactivation. (3) A modulator of an NHR can inhibit or antagonize the ability of another modulator from inducing transrepression. (4) A modulator of an NHR can inhibit or antagonize the ability of another modulator from inducing transactivation.

Preferably said modulator of an NHR is a modulator of an SHR, more preferably a modulator of GR.

A modulator of an NHR, SHR or GR that induces transrepression includes, but is not limited to, a dissociated compound.

Preferably said modulator of an NHR induces transrepression. More preferably said modulator of an NHR is a dissociated compound. More preferably said modulator of an NHR is an SHR dissociated compound. Most preferably said modulator of an NHR is a GR dissociated compound.

The pharmaceutical composition may further comprise at least one additional therapeutic agent. "Additional therapeutic agents" encompasses, but is not limited to, an agent or agents selected from the group consisting of an immunosuppressant, an anti-cancer agent, an anti-viral agent, an anti-inflammatory agent, an anti-fungal agent, an antibiotic, an anti-vascular hyperproliferation compound, an anti-diabetic agent, or an anti-depressant agent.

The term "pharmaceutically acceptable carrier, adjuvant or vehicle" refers to a carrier, adjuvant or vehicle that may be administered to a subject, together with a modulator of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agent(s) as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The modulators may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present modulators may, for example, be administered in a form suitable for immediate release or extended release. Immediate release or extended release may be achieved by the use of suitable pharmaceutical compositions comprising the present modulators, or, particularly in the case of extended release, by the use of devices such as subcutaneous implants or osmotic pumps. The present modulators may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present modulators may also be delivered through the oral cavity by sublingual and/or buccal administration. Molded tablets, compressed tablets or freeze-dried tablets are exemplary forms which may be used. Exemplary compositions include those formulating the present modulator(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a modulator of the present invention may be determined by one of ordinary skill in the art, and includes exemplary dosage amounts for an adult human of from about 0.1 to 500 mg/kg of body weight of active modulator per day, which may be administered in a single dose or in the form of individual divided doses, such as from 1 to 5 times per day. It will be understood that the specific dose level and frequency of dosage for any particular subject may be varied and will depend upon a variety of factors including the activity of the specific modulator employed, the metabolic stability and length of action of that modulator, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated diseases.

The modulators of the present invention may be employed alone or in combination with each other and/or other suitable therapeutic agent(s) useful in the treatment of NHR-associated diseases, such as immunosuppressants, anti-cancer agents, anti-viral agents, anti-inflammatory agents, anti-fungal agents, antibiotics, anti-vascular hyperproliferation agents, anti-diabetic agents, or anti-depressant agents. Such other therapeutic agent(s) may be administered prior to, simultaneously with or following the administration of the compound(s) of the present invention.

Exemplary such other therapeutic agents include the following: cyclosporins (e.g., cyclosporin A), CTLA4-Ig, antibodies such as anti-TNF-α (such as Remicade), anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD 154, fusion proteins constructed from CD40 and/or CD154/gp39 (e.g., CD40Ig and CD8gp39), inhibitors, such as nuclear translocation inhibitors, of NF-κB function, such as deoxyspergualin (DSG), non-steroidal antiinflammatory drugs (NSAIDs) such as ibuprofen, celecoxib, rofecoxib, cox-2 inhibitors, and aspirin, antibiotics such as penicillin, and tetracycline, steroids such as prednisone or dexamethasone, gold compounds, antiviral agents such as abacavir, antiproliferative agents such as mycophenolate, 5-fluorouracil, cisplatin, methotrexate, leflunomide, FK506 (tacrolimus, Prograf), cytotoxic drugs such as azathiprine and cyclophosphamide, TNF-α inhibitors such as tenidap, anti-TNF antibodies (such as Remicade) or soluble TNF receptor (such as Enbrel), and rapamycin (sirolimus or Rapamune) or derivatives thereof. The above other therapeutic agents, when employed in combination with the modulators of the present invention, may be used, for example, in those amounts indicated in the Physicians' Desk Reference (PDR) or as otherwise determined by one of ordinary skill in the art.

Methods of Treatment

The modulators of the present invention may be used to treat diseases.

The present invention provides a method of treating an NHR-associated disease comprising administering to a subject in need thereof, in an amount effective therefore, at least one modulator of an NHR, wherein said modulator of an NHR was identified by the method comprising: a) docking a test molecule into all or any part of the cavity circumscribed by a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; b) analyzing the structural and chemical feature complementarity between the test molecule and all or any part said Site II; and c) screening the test molecule in a biological assay of modulation of an NHR. A test molecule is identified as a modulator of an NHR if the structural and/or chemical feature complementarity and the modulation exceed a desired level. The method may further comprise one or more of the following steps: d) screening the test molecule in an assay that characterizes binding to a Site II; and e) screening the test molecule in an assay that characterizes binding to Site I.

The present invention provides a method of treating an NHR-associated disease comprising administering to a subject in need thereof, in an amount effective therefore, at least one modulator of an NHR that is a ligand of a Site II.

Preferably said NHR-associated disease is an SHR-associated disease and said modulator of an NHR is a modulator of an SHR. Most preferably said NHR-associated disease is a GR-associated disease and said modulator of an NHR is a modulator of GR.

The present invention provides a method of treating a disease associated with NHR transactivation comprising administering to a subject in need thereof, in an amount effective therefore, at least one modulator of an NHR, wherein said modulator of an NHR was identified by the method described above.

The present invention provides a method of treating a disease associated with NHR transactivation comprising administering to a subject in need thereof, in an amount effective therefore, at least one modulator of an NHR that is a ligand of a Site II.

The present invention provides a method of treating a disease associated with NHR transrepression comprising administering to a subject in need thereof, in an amount effective therefore, at least one modulator of an NHR, wherein said modulator of an NHR was identified by the method described above.

The present invention provides a method of treating a disease associated with NHR transrepression comprising administering to a subject in need thereof, in an amount effective therefore, at least one modulator of an NHR that is a ligand of a Site.

The invention provides a method of treating a disease associated with AP-1-dependent gene expression or NF-κB-dependent gene expression comprising administering to a subject in need thereof, in an amount effective therefore, at least one modulator of an NHR, wherein said modulator of an NHR was identified by the method described above.

The invention provides a method of treating a disease associated with AP-1-dependent gene expression or NF-κB-dependent gene expression comprising administering to a subject in need thereof, in an amount effective therefore, at least one modulator of an NHR that is a ligand of a Site II.

The invention provides a method of treating an inflammatory or immune associated disease or disorder comprising administering to a subject in need thereof, in an amount effective therefore, at least one modulator of an NHR, wherein said modulator of an NHR was identified by the method described above.

The invention provides a method of treating an inflammatory or immune disease or disorder comprising administering to a subject in need thereof, in an amount effective therefore, at least one modulator of an NHR that is a ligand of a Site II.

Preferably said methods of treating an inflammatory or immune disease or disorder comprise inhibiting AP-1-dependent gene expression or NF-κB-dependent gene expression by administering said modulator of an NHR in an amount effective to inhibit AP-1-dependent gene expression or NF-κB-dependent gene expression.

The present invention provides a method of treating a disease treatable by inducing NHR transrepression comprising administering to a subject in need thereof, in an amount effective therefore, at least one modulator of an NHR that induces transrepression, wherein said modulator of an NHR was identified by the method described above.

The present invention provides a method of treating a disease treatable by inducing NHR transrepression comprising administering to a subject in need thereof, in an amount effective therefore, at least one modulator of an NHR that induces transrepression, wherein said modulator of an NHR is a ligand of a Site II.

The present invention provides a method of treating a disease treatable by antagonizing NHR transactivation comprising administering to a subject in need thereof, in an amount effective therefore, at least one modulator of an NHR that antagonizes transactivation, wherein said modulator of an NHR was identified by the method described above.

The present invention provides a method of treating a disease treatable by antagonizing NHR transactivation comprising administering to a subject in need thereof, in an amount effective therefore, at least one modulator of an NHR that antagonizes transactivation, wherein said modulator of an NHR is a ligand of a Site II.

Preferred ligands of Site II used in the present methods of treatment were identified by a method comprising: a) docking a test molecule into all or any part of the cavity circumscribed by a Site II, wherein Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; b) analyzing the structural and chemical feature complementarity between the test molecule and all or any part said Site II; and c) screening the test molecule in an assay that characterizes binding to a Site II. A test molecule that binds to Site II is identified as a ligand of Site II. The method may further comprise one or more of the following steps: d) screening the test molecule in a biological assay of modulation of an NHR; and e) screening the test molecule in an assay that characterizes binding to Site I.

A preferred ligand of Site II was identified by screening a test molecule in an assay that characterizes binding to Site II.

Preferably said NHR is an SHR, more preferably a GR.

In the present methods of treatment, a modulator of an NHR can induce one or more of the following four activities in the NHR. This list is not meant to be inclusive. (1) A modulator of an NHR can induce transrepression. (2) A modulator of an NHR can induce transactivation. (3) A modulator of an NHR can inhibit or antagonize the ability of another modulator from inducing transrepression. (4) A modulator of an NHR can inhibit or antagonize the ability of another modulator from inducing transactivation.

Preferably said modulator of an NHR is a modulator of an SHR, more preferably a modulator of GR.

A modulator of an NHR, SHR or GR that induces transrepression includes, but is not limited to, a dissociated compound.

Preferably said modulator of an NHR induces transrepression. More preferably said modulator of an NHR is a dissociated compound. More preferably said modulator of an NHR is an SHR dissociated compound. Most preferably said modulator of an NHR is a GR dissociated compound.

Preferably said subject is a mammal, most preferably a human.

Other therapeutic agent(s), such as those described above in the section on pharmaceutical compositions, may be employed with the modulators in the present methods. In the methods of the present invention, such other therapeutic agent(s) may be administered prior to, simultaneously with or following the administration of the compound(s) of the present invention.

Modes of administration useful in the present invention are described above in the section of pharmaceutical compositions.

In a particular embodiment, the modulators of the present invention are useful for the treatment of the aforementioned exemplary disorders irrespective of their etiology, for example, for the treatment of transplant rejection, rheumatoid arthritis, inflammatory bowel disease, and viral infections.

Methods of Designing Mutants

We have identified Site II in NHRs as a binding site whose ligands modulate NHRs. Now that Site II is known to be a region of interest, mutants of NHRs, and mutants of portions of NHRs, in which Site II is mutated may be made.

Thus, the invention provides a method of designing a mutant comprising making one or more amino acid mutations in a Site II. The mutant so designed may be an NHR or a portion of an NHR, such as the LBD.

Preferably the mutation(s) is a deletion or substitution of one or more of the amino acids of said Site II. When the mutation(s) is an amino acid insertion, preferably the amino acid(s) inserted are inserted next to an amino acid of said Site II.

Preferably a mutation involves one or more of the following amino acids in human GR: E537-V543, V571-W577, S599-W600, F602-L603, F606-A607, W610, R614, Q615, P625, Y663, L664 and K667, or one or more of the corresponding amino acids in another NHR or non-human GR of SEQ ID NO:13 as can be seen in FIGS. 2 and 6 respectively. Preferably a mutation involves one or more of the following amino acids in human GR: E537-V543, V571-W577, S599-W600, F602-L603, F606-A607, W610, R614, Y663, L664 and K667, or one or more of the corresponding amino acids in another NHR or non-human GR of SEQ ID NO:13 as can be seen in FIGS. 2 and 6 respectively. Preferably the deletion or substitution is of one or more of the aforementioned amino acids or corresponding amino acids, and preferably the insertion is next to one or more the aforementioned amino acids or corresponding amino acids.

The method may further comprise using all or part of a model of a Site II to visualize all or part of Site II in its mutated or native form. Preferably said model is a three-dimensional model.

Mutation includes one or more amino acid deletions, insertions, inversions, repeats, or substitutions as compared to the native protein. Various methods of making mutations are known to one of ordinary skill in the art. A mutant may have the same, similar, or altered activity as compared to the native protein. Activity refers to transrepression, transactivation, and ligand binding. Preferred mutants have at least 25% sequence identity, more preferably 50% sequence identity, more preferably 75% sequence identity, and most preferably 95% sequence identity to the native protein.

A mutant designed by the method of the invention that has the same or similar biological activity as the native NHR or native portion of NHR may be useful for any purpose for which the native is useful. A mutant designed by the method of the invention that has altered biological activity as the native may be useful in binding assays to test the ability of a potential ligand to bind to or associate with Site II. A mutant designed by the method of the invention that has the altered biological activity from the native may be useful in further elucidating the biological role of Site II.

Example 16 illustrates designing mutants comprising making one or more amino acid mutations in Site II.

Mutants of Site II

The invention provides a mutant NHR, or a mutant portion of an NHR, comprising one or more amino acid mutations in Site II.

Said mutant portion of an NHR preferably comprises a mutant LBD of the NHR, more preferably consists of a mutant LBD of the NHR.

Preferably the mutation(s) is a deletion or substitution of one or more of the amino acids of Site II. When the mutation(s) is an amino acid insertion, preferably the amino acid(s) inserted are inserted next to an amino acid of Site II.

Preferably a mutation involves one or more of the following amino acids in human GR: E537-V543, V571-W577, S599-W600, F602-L603, F606-A607, W610, R614, Q615, P625, Y663, L664 and K667, or one or more of the corresponding amino acids in another NHR or non-human GR of SEQ ID NO:13 as can be seen in FIGS. 2 and 6 respectively. Preferably a mutation involves one or more of the following amino acids in human GR: E537-V543, V571-W577, S599-W600, F602-L603, F606-A607, W610, R614, Y663, L664 and K667, or one or more of the corresponding amino acids in another NHR or non-human GR of SEQ ID NO:13 as can be seen in FIGS. 2 and 6 respectively. Preferably the deletion or substitution is of one or more of the aforementioned amino acids or corresponding amino acids, and preferably the insertion is next to one or more the aforementioned amino acids or corresponding amino acids.

Mutation includes one or more amino acid deletions, insertions, inversions, repeats, or substitutions as compared to the native protein. Various methods of making mutations are known to one of ordinary skill in the art. A mutant may have the same, similar, or altered activity as compared to the native protein. Activity refers to transrepression, transactivation, and ligand binding. Preferred mutants have at least 25% sequence identity, more preferably 50% sequence identity, more preferably 75% sequence identity, and most preferably 95% sequence identity to the native protein.

A mutant of the present invention that has the same or similar biological activity as the native NHR, or native portion of NHR, may be useful for any purpose for which the native is useful. A mutant of the present invention that has altered biological activity as the native may be useful in binding assays to test the ability of a potential ligand to bind to or associate with Site II. A mutant of the present invention that has the altered biological activity from the native may be useful in further elucidating the biological role of Site II.

In preferred mutants, the mutation consists of five or fewer substitutions, more preferably four or fewer substitutions, more preferably three or fewer substitutions, more preferably two or fewer substitutions, most preferably one substitution. A substitution is preferably a conservative amino acid substitution.

In preferred mutants, the mutation consists of three or fewer deletions, more preferably two or fewer deletions, most preferably one deletion.

In preferred mutants, the mutation consists of two or fewer substitutions and two or fewer deletions.

Example 16 illustrates mutants comprising making one or more amino acid mutations in Site II.

Site II Binding Assay

The invention provides a method of measuring the binding of a test molecule to Site II comprising: (a) incubating an NHR with a ligand of Site II and said test molecule; and (b) measuring the ability of said test molecule to compete for binding to said Site II with said ligand; wherein said ability to compete is the measure of binding of said test molecule to Site II. The method may further comprise comparing the ability of said test molecule to modulate a native NHR and to modulate an NHR mutated in Site II.

The ligand of Site II may be identified by any art-recognized method, such as those described in Examples 15 and 16.

The NHR may be in a purified form, in a partially purified form, or in a cell lysate.

In order to measure the ability of said test molecule to compete for binding to Site II with said ligand, the ligand can be labeled, such as radiolabeled or fluorescently labeled. Binding can be measured using any art-recognized technique, such as fluorescence quenching, fluorescence polarization, filter binding, scintillation proximity assay, among others. The ability to compete is determined by comparing the measured value with the labeled compound alone to the measured value in the presence of the unlabeled test molecule. A decrease in the measured signal indicates binding of the test molecule.

The ability of said test molecule to modulate a native NHR and to modulate an NHR mutated in Site II can be determined by measuring transrepression and transactivation using methods such as described in Examples 3 and 4.

One such Site II binding assay is described in Example 18. Example 18 provides a method of measuring the binding of a test molecule to Site II by: incubating said test molecule with an NHR, a Site I ligand (such as FITC-dexamethasone), and a known Site II ligand that inhibits the binding of the Site I ligand to Site I. A test molecule that does not inhibit the binding of the Site I ligand to Site I and does bind to Site II will displace the known Site II ligand, thus allowing the Site I ligand to bind to Site I. The binding of the Site I ligand to Site I can be measured. The comparison of the Site I ligand binding to Site I in the presence of the Site II ligand with and without the test molecule provides a measurement of relative binding of the test molecule to Site II. In order to measure the ability of said Site I ligand to bind to Site I, the Site I ligand can be labeled, such as radiolabeled or fluorescently labeled. Binding can be measured using any art-recognized technique, such as fluorescence quenching, fluorescence polarization, filter binding, scintillation proximity assay, among others.

Models of Site II

We have identified Site II in NHRs as a binding site whose ligands modulate NHRs. We have focused on Site II as a region of interest in NHRs. Now that Site II is known to be a region of interest, models of Site II, such as three-dimensional models, useful in drug design may be made.

Thus, the invention provides a model comprising all or any part of a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I.

In a preferred embodiment the model consists of all or any part of Site II.

In another preferred embodiment the model: (a) comprises all or any part of a Site II, wherein said Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:13 according to Table I; and (b) does not comprise structure coordinates that describe conserved residue backbone atoms having a root mean square deviation of not more than 2.0 Å from the conserved residue backbone atoms described by the structure coordinates of one or more of amino acids M560, L563, N564, L608, F623, M639, Q642, M646, L732, Y735, C736, T739 and E748 of SEQ ID NO:13 according to Table I. Preferably, said data does not comprise structure coordinates that describe conserved residue backbone atoms having a root mean square deviation of not more than 2.0 Å from the conserved residue backbone atoms described by the structure coordinates of all of amino acids M560, L563, N564, L608, F623, M639, Q642, M646, L732, Y735, C736, T739 and E748 of SEQ ID NO:13 according to Table I. Preferably, the root mean square deviation of part (b) is less than 1.5 Å, more preferably less that 1.0 Å, yet more preferably less than 0.9, 0.8, 0.7, 0.6 0.5, 0.4, 0.3, 0.2, or 0.1 Å, most preferably 0.0 Å.

A model of a Site II of the present invention may be any type of art-recognized model, including but not limited to: three-dimensional models; and steric/electrostatic field definition models that can be used to study/compute the putative interactions ligands might undergo. A three-dimensional model may be produced through use of structure coordinates, such as are ribbon diagrams.

A three-dimensional model of a Site II of the present invention is useful for designing and identifying ligands and modulators of NHRs.

It should be understood that one skilled in the field is able to make various modifications to the compositions and methods described above, applying the ordinary level of skill in the field, without departing from the spirit or scope of the invention. All such modifications are intended to be included within the invention as defined in the appended claims.

EXAMPLES

The examples below are provided to illustrate the subject invention and are not intended to limit the invention.

Example 1

Compound Synthesis

The fifty-one compounds used in the following examples were synthesized as follows. These compounds and their synthesis are described in the provisional application entitled "Modulators of the Glucocorticoid Receptor and Method," U.S. Application No. 60/396,877, filed on Jul. 18, 2002, and in utility application entitled "Modulators of the Glucocorticoid Receptor and Method," U.S. application Ser. No. 10/621,909, filed concurrently herewith. The contents of U.S. Application No. 60/396,877 and QA266NP are incorporated herein by reference in their entirety.

Preparations

The preparations set out below are for the synthesis of reagents that were not obtained from commercial sources and were employed for the preparation of compounds. All chemical structures in the tables and schemes are racemic unless specified otherwise.

Preparation 1

4-[1-(4-Fluoro)naphthyl]aminothiazole 1a

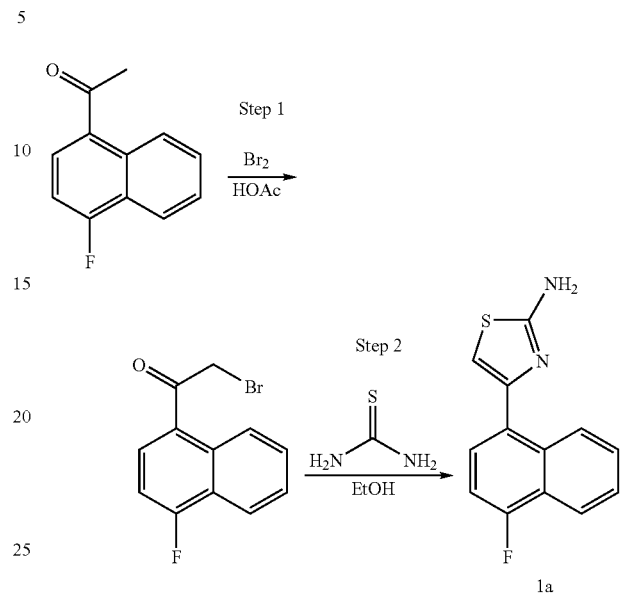

Step 1

To a solution of 4'-fluoro-1'-acetonaphthone (28.69 mmol, 5.4 g) in 1,4-dioxane (18.0 mL) at 0° C. was added bromine (35.13 mmol, 5.61 g). After 3 hours at room temperature the reaction mixture was concentrated in vacuo to give 7.66 g (Y: 100%) of the product of step 1.

Step 2

To a solution of the product of step 1 (28.69 mmol, 7.66 g) in ethyl alcohol (20 mL) at room temperature was added thiourea (36.13 mmol, 2.75 g). After 1 hour at room temperature a precipitate formed. To the reaction mixture was added water (100 mL) and the solid was collected by vacuum filtration. The solid was then washed with water (3×100 mL) and dichloromethane (3×100 mL). The solid was then dried in vacuo to give 5.5 g (Y: 75%) of the title compound 1a. MS (E+) m/z: 245 (MH$^+$).

In a similar manner the following compounds were prepared from the corresponding ketone.

| Preparation | Structure |
|---|---|
| 1b | 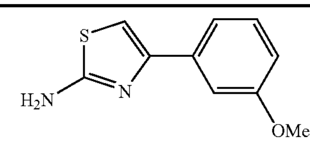 |
| 1q | 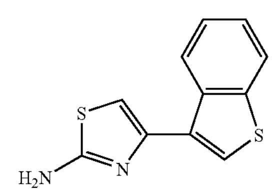 |

-continued

| Preparation | Structure |
|---|---|
| 1r | 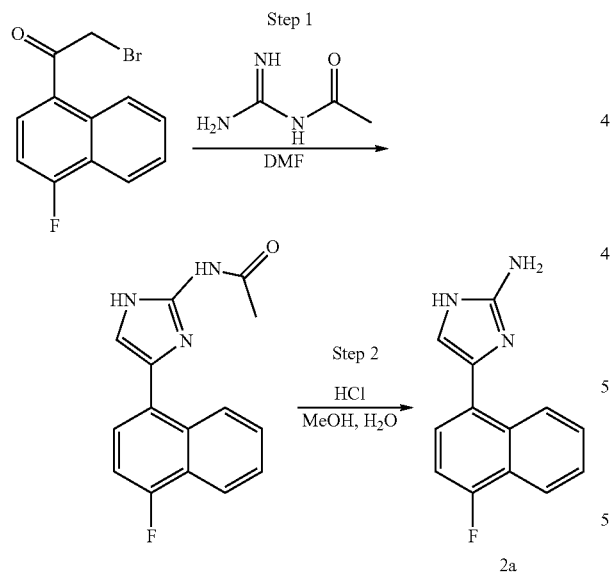 |
| 1t | 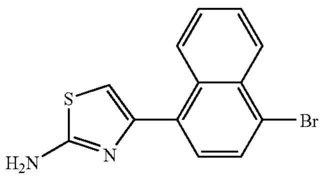 |
| 1w | 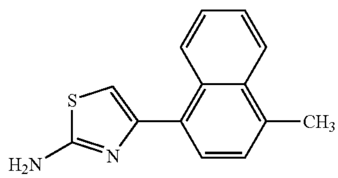 |

Preparation 2

4-[1-(4-Fluoro)naphthyl]aminoimidazole 2a

Step 1

To a solution of the product of preparation 1a, step 1 (18.73 mmol, 5.0 g) in DMF (15 mL) at room temperature was added 1-acetylguanidine (57.43 mmol, 5.80 g). After 5 hours at room temperature, the reaction mixture was diluted with water (100 mL) and extracted with ethyl acetate (3×100 mL). The organic phases were concentrated in vacuo and the residue chromatographed on silica gel (eluted with 5% methanol in dichloromethane) to give 2.0 g (Y: 39%) of the product of step 1. MS (E+) m/z: 270 (MH$^+$).

Step 2

To a solution of the product of step 1 (7.43 mmol, 2.0 g) in methanol (17 mL) was added water (8.5 mL) and 12 N HCl (12.0 mL). After 1 hour at reflux the reaction mixture was concentrated in vacuo to approximately 15 mL. The resulting solution was then purified and neutralized by cation exchange SPE to give 1.66 g (Y: 99%) of the title compound 2a. MS (E+) m/z: 228 (MH$^+$).

In a similar manner the following compounds were prepared from the corresponding ketones.

| Preparation | Structure |
|---|---|
| 2b | 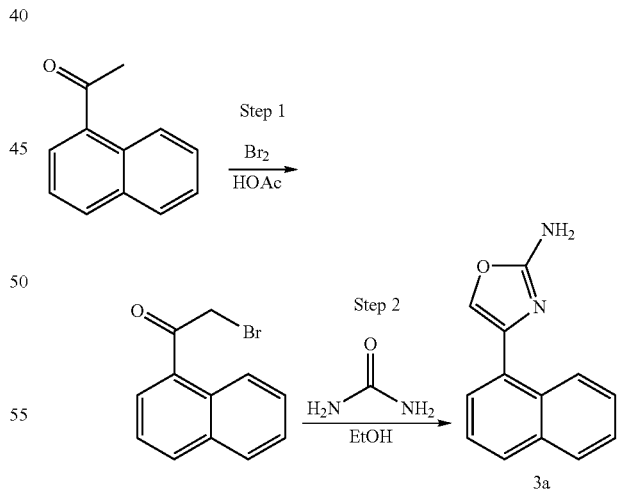 |
| 2e | 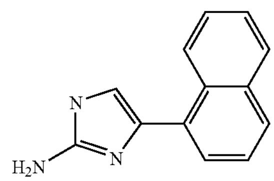 |

Preparation 3

4-(1-naphthyl)aminooxazole 3a

Step 1

To a solution of 1-acetonaphthone (29.38 mmol, 5.0 g) in glacial acetic acid (10.0 mL) at RT was added bromine (30.06 mmol, 4.80 g) in glacial acetic acid (5.0 mL). After 5 minutes the reaction mixture was poured onto crushed ice and extracted with dichloromethane to give 7.31 g (Y: 100%) of the product of step 1. MS (E+) m/z: 250 (MH$^+$).

Step 2

To a solution of the product of step 1 (5.50 mmol, 1.37 g) in ethyl alcohol (10 mL) was added urea (27.50 mmol, 1.65 g). After 2 hours at reflux the reaction mixture was concentrated in vacuo and the residue chromatographed on silica gel (eluted with 30% ethyl acetate in hexane) to give 100 mg (Y: 9%) of the title compound 3a. MS (E+) m/z: 211 (MH$^+$).

Preparation 6

4-[1-(6-Methoxy)naphthyl]-3-aminothiazole 6a

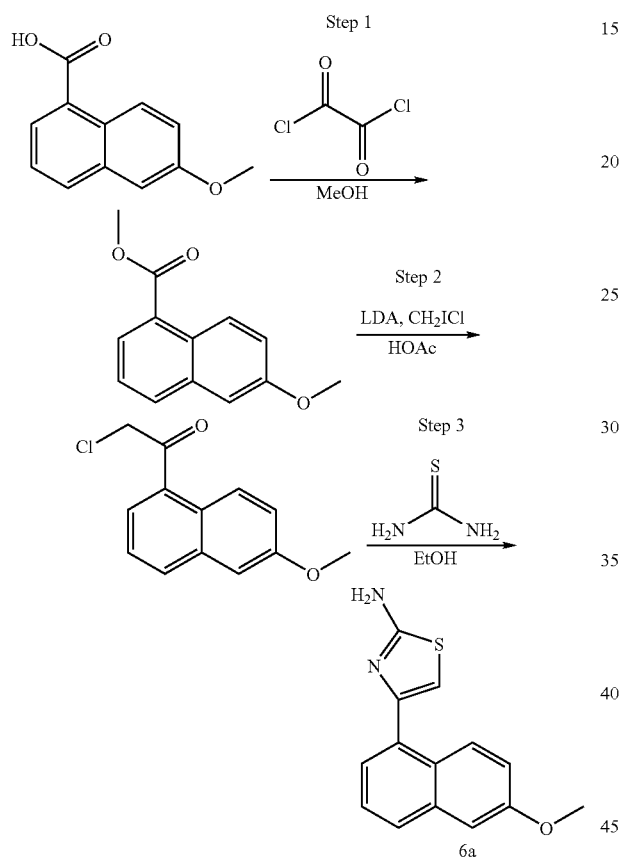

6a

Step 1

To a solution of 6-methoxy-1-naphthoic acid (0.5 g, 2.47 mmol, 1.0 equi.) in dichloromethane (10 mL) at room temperature was added a solution of oxalyl chloride (2M in dichloromethane, 2.5 mL, 5.0 mmol, 2 equi.). The solution was stirred at room temperature for 2 hours, and the excess oxalyl chloride removed in vacuo. The residue was dissolved in methanol and stirred at room temperature for 18 hours. The solvent was removed in vacuo, yielding 0.45 g (84%) of the product of step 1: LC/MS (m/z 217, (M−H)$^+$); $^1$H NMR (CDCl$_3$) δ 8.82 (d, 1H), 8.03 (dd, 1H), 7.90 (d, 1H), 7.44 (t, 1H), 7.26 (dd, 1H), 7.16 (s, 1H), 4.02 (s, 3H), 3.95 (s, 3H).

Step 2

Reference: P. Chen, P. T. Cheng, S. H. Spergel, R. Zahler, X. Wang, J. Thottathil, J. C. Barrish, R. P. Polniaszek, *Tetrahedron Letters*, 38, 3175 (1997).

To a solution of the product of step 1 (0.238 g, 1.1 mmol, 1.0 equi.) and chloroiodomethane (0.32 mL, 4.4 mmol, 4 equi.) in THF (5 mL) was added a solution of LDA (2M, 2.2 mL, 4.0 equi.) in THF (10 mL) dropwise in 30 minutes, while keeping the solution temperature at −78° C. The reaction solution was stirred at −78° C. for 10 minutes. A solution of acetic acid (1.5 mL) in THF (10 mL) was added in dropwise in 10 minutes. After stirring for an additional 10 minutes at −78° C., the solution was quenched with ethyl acetate and saturated sodium chloride solution. The organic phase was washed with saturated sodium bisulfite, saturated sodium chloride, dried with sodium sulfate and concentrated in vacuo. The residue was purified by flash chromatography (10% ethyl acetate in hexane) to yield the 0.23 g (90%) of the product of step 2: LC/MS (m/z 235, (M+H)$^+$); $^1$H NMR (CDCl$_3$) δ 8.82 (d, 1H), 8.03 (dd, 1H), 7.90 (d, 1H), 7.44 (t, 1H), 7.26 (dd, 1H), 7.16 (s, 1H), 4.80 (s, 2H), 3.95 (s, 3H).

Step 3

To a solution of the product of step 2 (0.23 g, 1.0 mm01, 1.0 equi.) in ethanol (5 mL) at room temperature was added thiourea (90 mg, 1.2 mmol, 1.2 equi.). The reaction solution was stirred at room temperature for 2 hours, after which a yellow precipitate was formed. The reaction was quenched by addition of water and ethyl acetate. The aqueous phase was extracted with ethyl acetate (3×). The combined organic phases were dried with sodium sulfate and concentrated in vacuo to yield 200 mg (78%) of the title compound 6a: LC/MS (m/z 235, (M+H)$^+$); $^1$H NMR (CDCl$_3$) δ 8.1 (d, 1H), 7.9 (m, 1H), 7.43 (m, 2H), 7.25 (m, 1H), 7.10 (dd, 1H), 6.65 (s, 1H), 3.95 (s, 3H).

Preparation 7

4-[1-(6-Methoxy)naphthyl]-3-aminoimidazole 7a

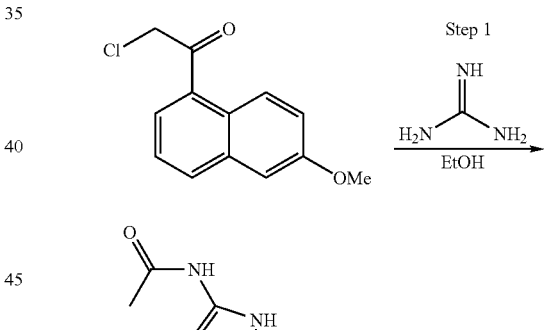

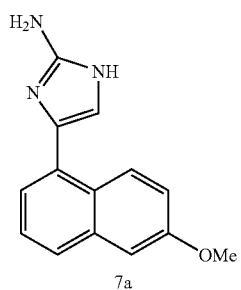

7a

Step 1

To a solution of the product of preparation 6, step 2 (0.5 g, 2.14 mmol, 1.0 equi.), in ethanol (5 mL) at room temperature was added 1-acetylguanidine (650 mg, 6.42 mmol, 3.0 equi.). The reaction solution was stirred at room temperature for 24 hours. The reaction was quenched by addition of water and ethyl acetate. The aqueous phase was extracted with ethyl acetate (3×). The combined organic phases were dried with sodium sulfate and concentrated in vacuo to yield 0.2 g (35%) of the product of step 1: LC/MS (m/z 282, (M+H)$^+$).

Step 2

To a solution of the product of step 1 (0.2 g, 0.7 mmol, 1.0 equi.) in methanol (5 mL) was added water (1.0 mL) and hydrochloric acid (12N, 1.0 mL). The reaction solution was heated to reflux for 1 hour, after which the solvent was removed in vacuo. The crude mixture was purified by cation exchange SPE to give 0.12 g (70%) of the title compound 7a: LC/MS (m/z 240, (M+H)$^+$).

Preparation 14

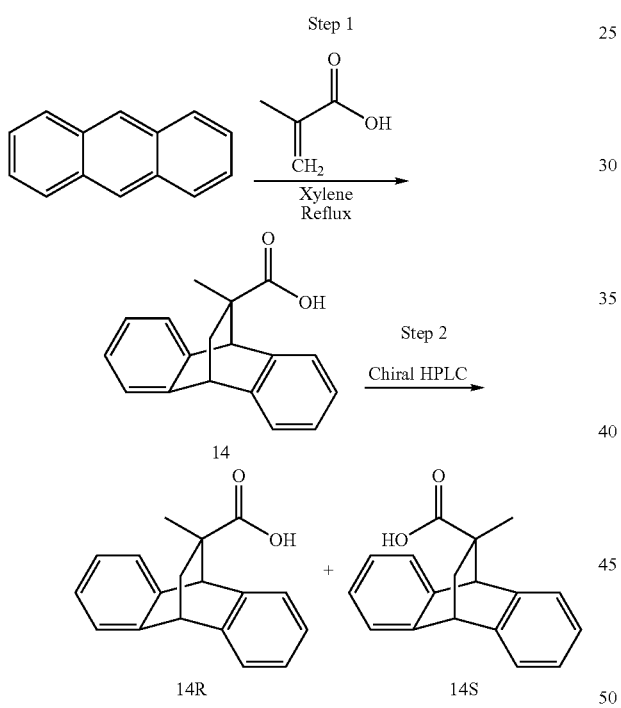

Step 1 Ref: B. Bacle and G. Levesque, *Polymer Communications*, 28, 36 (1987).

A 1L flask was charged with anthracene (14 g, 0.078 mol, 1.0 equi.), hydroquinone (0.8 g, 0.008 mol, 0.1 equi.), methacrylic acid (14 mL, 0.156 mol, 2.0 equi.) and xylene (500 mL). The solution was heated to reflux for 1 day. The solution was cooled and concentrated in vacuo. The residue was dissolved in ethyl acetate and extracted with 1N NaOH (3×). The aqueous phase was acidified with 1N HCl, and the product was extracted with ethyl acetate (3×). The combined organic phases were concentrated in vacuo to give the crude product mixture. Recrystallization with hexane and ethyl acetate to yield 8 g (40%) of step 1, 14:LC/MS (m/z 263 (M−H)$^+$); $^1$H NMR (CDCl$_3$) δ 7.08-7.25 (m, 8H), 4.37 (s, 1H), 4.25(t, 1H), 2.61 (dd, 1H), 1.39 (dd, 1H), 1.07 (s, 3H).

Step 2

The product of step 1, 14 was resolved into its corresponding enantiomers, 14(R) and 14(S) by chiral preparative HPLC with the following conditions, Column: Chiracel®-OJ, 5×50 cm, Mobile phase: trifluroacetic acid/acetonitrile: 1/1000 (vol/vol), Temperature: ambient, Flowrate: 70 mL/min, Injection: 1.5 grams in 50 mL solvent, Detection: UV (250 nm). Retention times for R-enantiomer, 30 min, S-enantiomer, 52 min. Analytical HPLC conditions, Column: Chiracel®-OJ, 4.6×250 cm, Mobile phase: trifluroacetic acid/acetonitrile: 1/1000 (vol/vol), Temperature: ambient, Flowrate: 1.5 mL/min, Detection: UV (250 nm). Retention times: R-enantiomer, 6.5 min, S-enantiomer, 15 min.

In a similar manner the following compounds were prepared from the corresponding 9-nitroanthracene and 9-anthracenecarbonitrile (Reference: P. V. Alston, R. M. Ottenbrite, J. Newby, J. Org. Chem. *J. Org. Chem.* 44, 4939 (1979)) and were resolved to the enantiomers according to the procedure of Step 2.

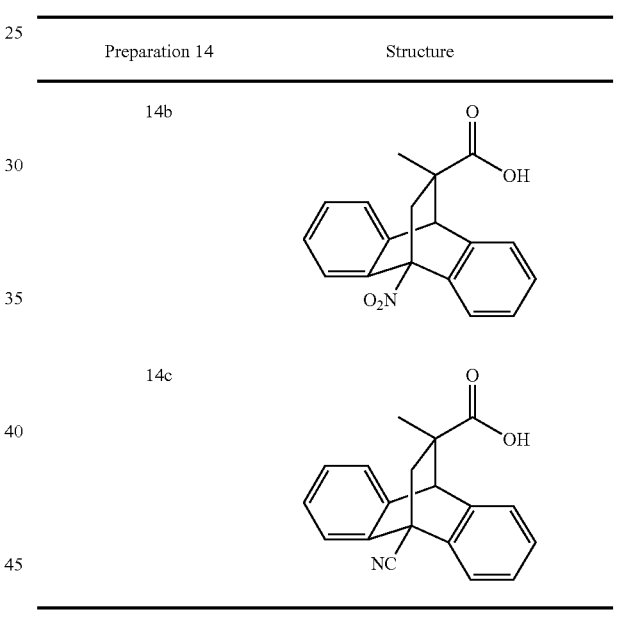

| Preparation 14 | Structure |
|---|---|
| 14b | 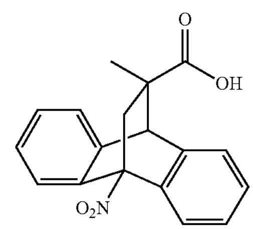 |
| 14c | 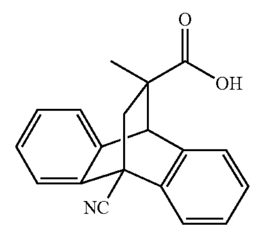 |

EXAMPLES

Example 1

Compound 1

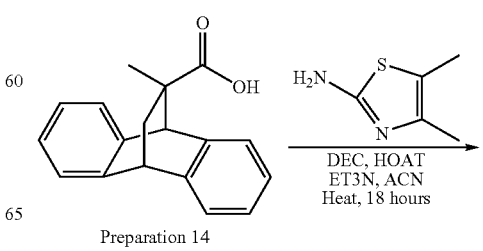

-continued

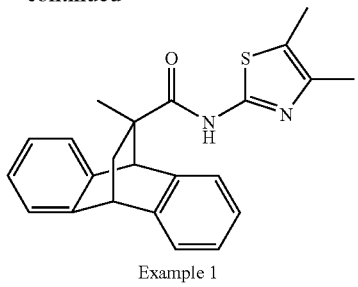

Example 1

To a solution of the product of Preparation 14, step 1 (20 mg, 0.075 mmol, 1.0 equi.) in acetonitrile (2 mL) was added 1-[3-(dimethylamino)propyl]-3-ethylcarbodiimide hydrochloride (DEC) (17 mg, 0.09 mmol, 1.2 equi.), 1-hydroxy-7-azabenzotriazole (HOAt) (12 mg. 0.09 mmol, 1.2 equi.), triethyl amine (0.025 mL, 0.18 mmol, 2.5 equi.), and 2-amino-4,5-dimethylthiazole hydrochloride salt (14.8 mg, 0.09 mmol, 1.2 equi.). The reaction solution was heated to 80° C. for 18 hours. The reaction was then concentrated in vacuo. The product mixture was purified by flash chromatography (20% ethyl acetate in hexane) to yield 19.8 mg (70%) of Example 1. LC/MS (m/z 375, (M+H)+.

In a similar manner Examples 2-51 were prepared from the coupling of the appropriate acids (14, 14R, 14S, 14a, 14aR, 14aS, 14b, 14bR, 14bS)) prepared as described in Preparation 14 and the appropriate amines. Preparations of amines not commercially available are described in the preceding preparations section of this document. All examples in the tables are racemic unless specified otherwise. Examples in the table where one enantiomer predominates or is the sole component, are designated as either R or S.

| Example Number | Compound Number | Chiral Compounds | Structure | MS: (M + H = MW shown +1) |
|---|---|---|---|---|
| 2 | 2 | | 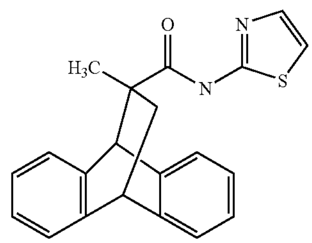 | |
| 3 | 3 | Chiral (R) | 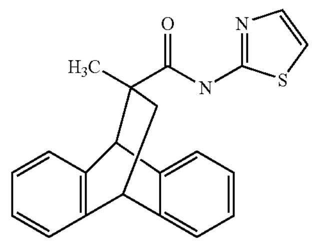 | |
| 4 | 4 | Chiral (S) | 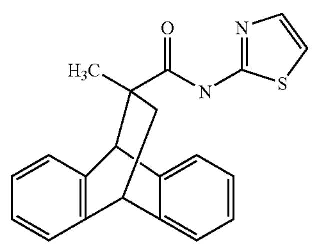 | |
| 5 | 5 | | 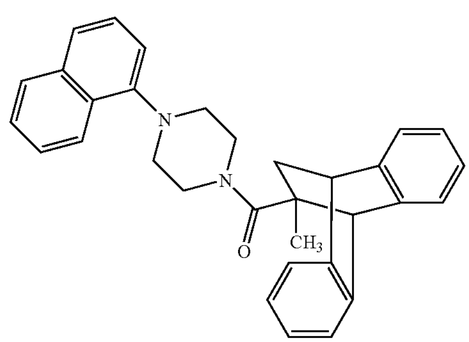 | |

-continued
| Example Number | Compound Number | Chiral Compounds | Structure | MS: (M + H = MW shown +1) |
|---|---|---|---|---|
| 6 | 6 | | 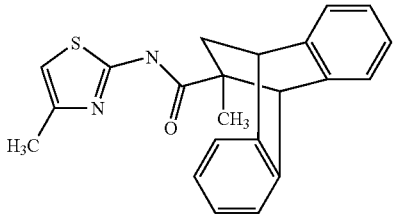 | 360.5 |
| 7 | 7 | | 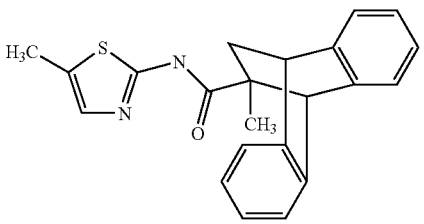 | 360.5 |
| 8 | 8 | | 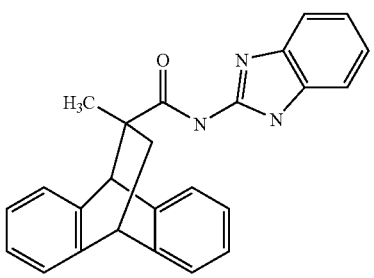 | 379.47 |
| 9 | 9 | | 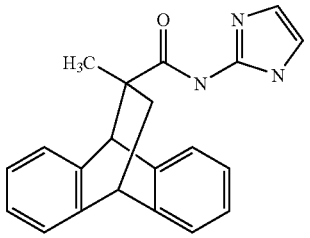 | 329.41 |
| 10 | 10 | | 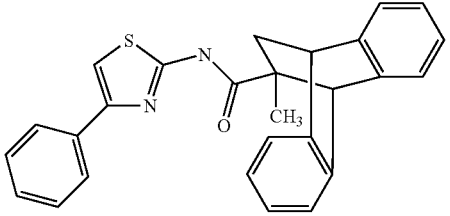 | 422.6 |
| 11 | 11 | | 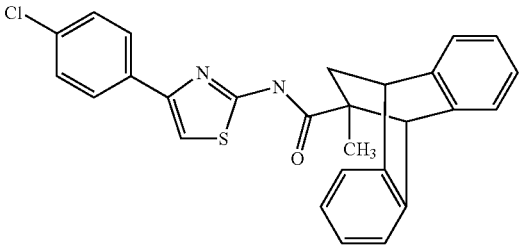 | 457 |

-continued
| Example Number | Compound Number | Chiral Compounds | Structure | MS: (M + H = MW shown +1) |
|---|---|---|---|---|
| 12 | 12 | | 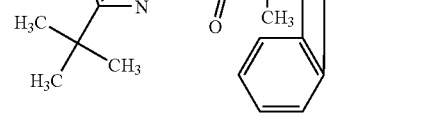 | 402.6 |
| 13 | 13 | | 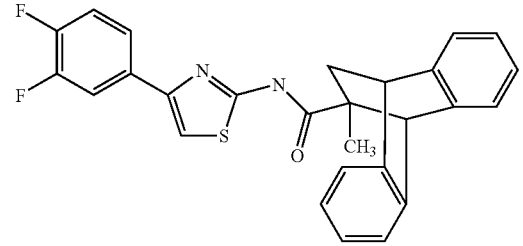 | 458.5 |
| 14 | 14 | | 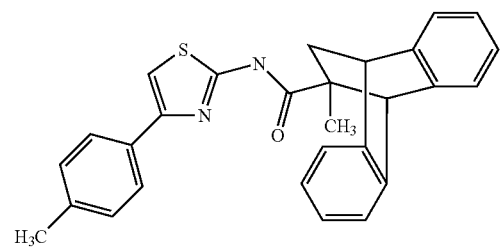 | 436.6 |
| 15 | 15 | | 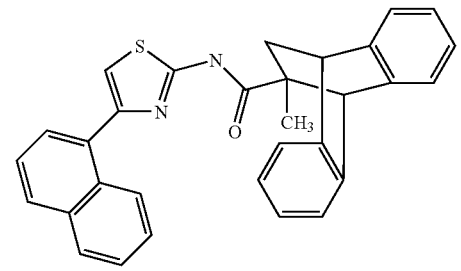 | 472.6 |
| 16 | 16 | | 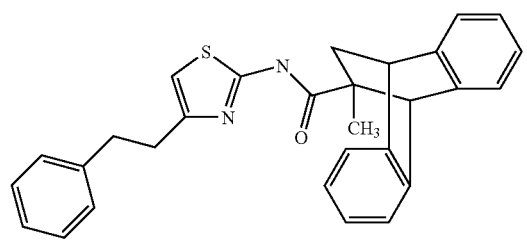 | 450.6 |
| 17 | 17 | Chiral (R) | 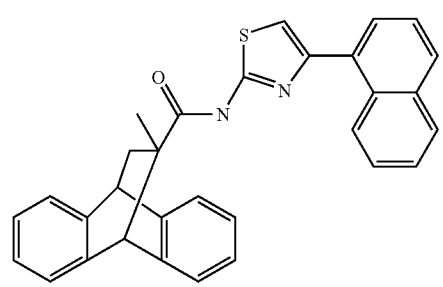 | 472.61 |

-continued
| Example Number | Compound Number | Chiral Compounds | Structure | MS: (M + H = MW shown +1) |
|---|---|---|---|---|
| 18 | 18 | Chiral (S) | 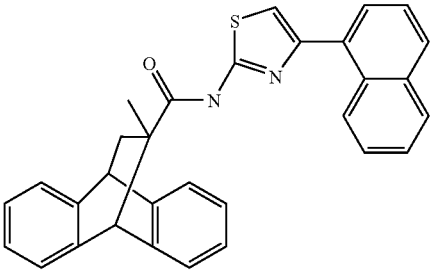 | 472.61 |
| 19 | 19 | | 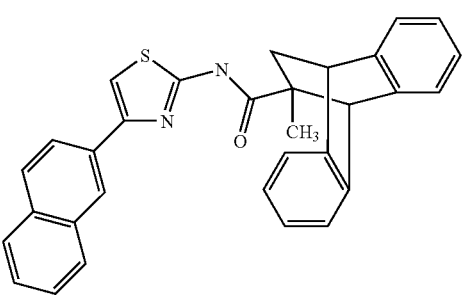 | 472.6 |
| 20 | 20 | | 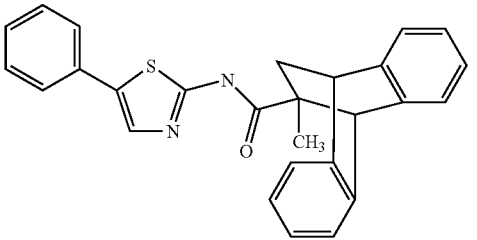 | 422.55 |
| 21 | 21 | | 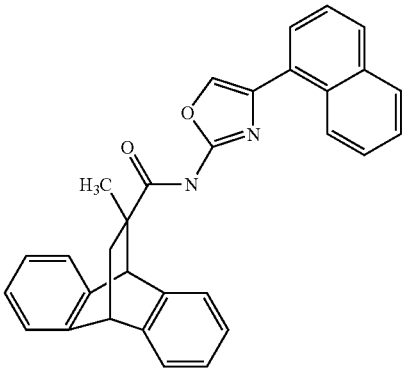 | 456.55 |
| 22 | 22 | | 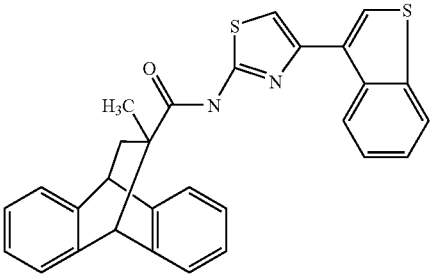 | 478.64 |

-continued

| Example Number | Compound Number | Chiral Compounds | Structure | MS: (M + H = MW shown +1) |
|---|---|---|---|---|
| 23 | 23 | | 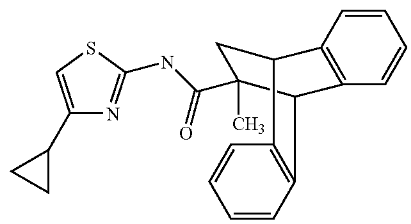 | 386.5 |
| 24 | 24 | | 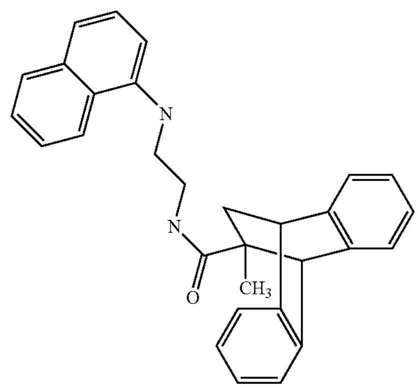 | 432.57 |
| 25 | 25 | | 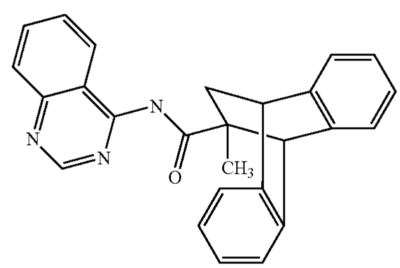 | 391.5 |
| 26 | 26 | | 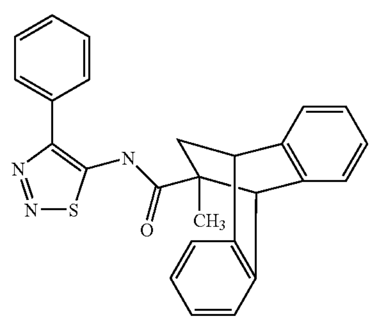 | 423.5 |
| 27 | 27 | | 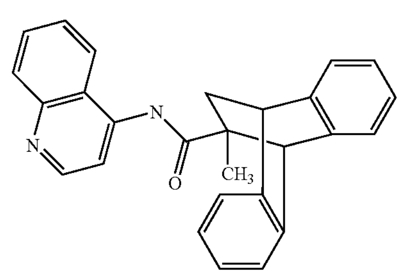 | 390.5 |

-continued

| Example Number | Compound Number | Chiral Compounds | Structure | MS: (M + H = MW shown +1) |
|---|---|---|---|---|
| 28 | 28 | | 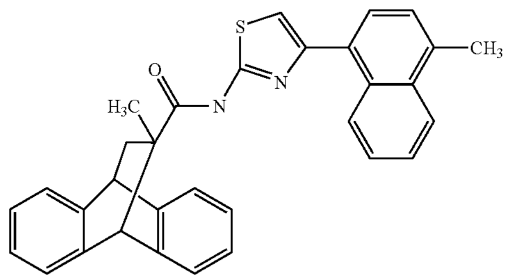 | 486.64 |
| 29 | 29 | | 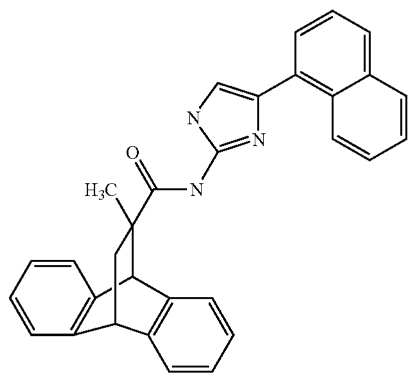 | 455.56 |
| 30 | 30 | | 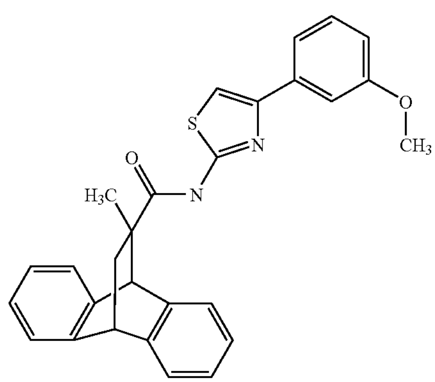 | 452.58 |
| 31 | 31 | | 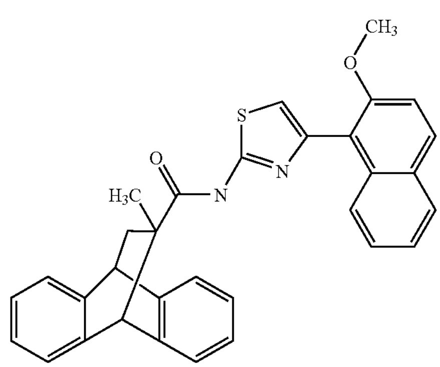 | 502.64 |

-continued
| Example Number | Compound Number | Chiral Compounds | Structure | MS: (M + H = MW shown +1) |
|---|---|---|---|---|
| 32 | 32 | Chiral (R) | 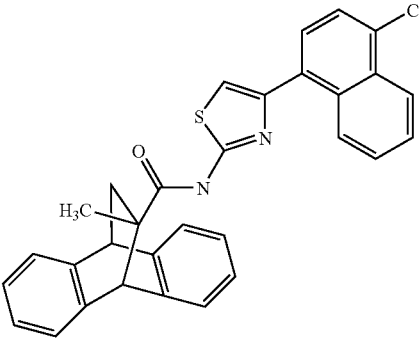 | 486.64 |
| 33 | 33 | Chiral (S) | 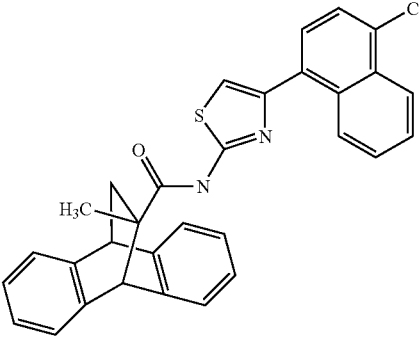 | 486.64 |
| 34 | 34 | Chiral (R) | 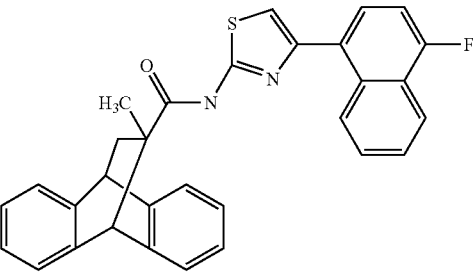 | 490.6 |
| 35 | 35 | Chiral (S) | 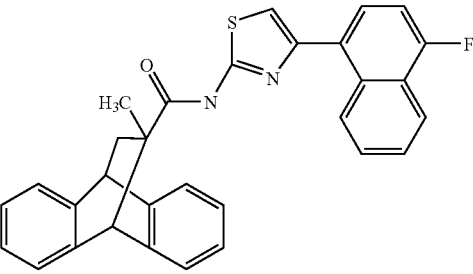 | 490.6 |
| 36 | 36 | Chiral (S) | 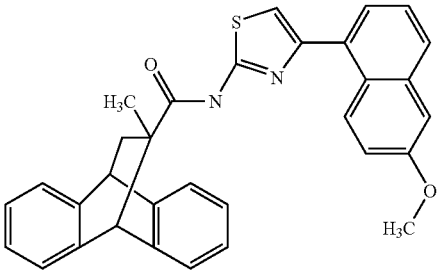 | 502.64 |

-continued
| Example Number | Compound Number | Chiral Compounds | Structure | MS: (M + H = MW shown +1) |
|---|---|---|---|---|
| 37 | 37 | Chiral (R) | 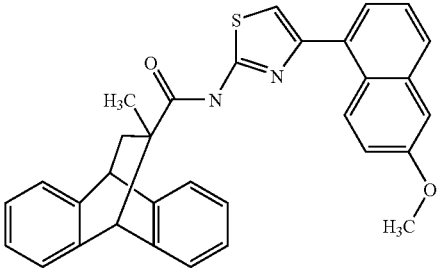 | 502.64 |
| 38 | 38 | Chiral (S) | 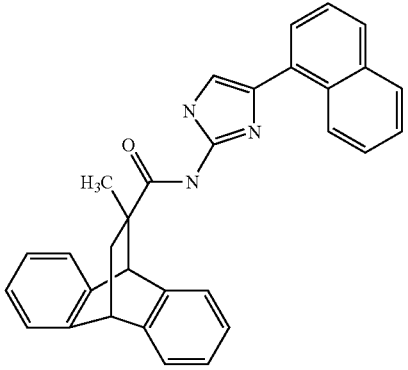 | 455.56 |
| 39 | 39 | Chiral (R) | 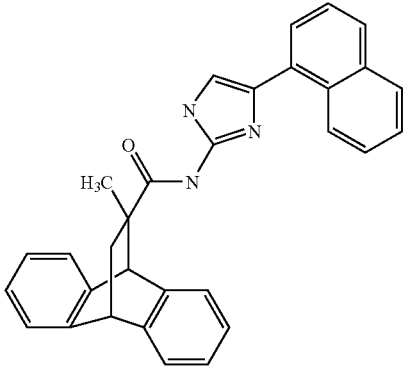 | 455.56 |
| 40 | 40 | Chiral (S) | 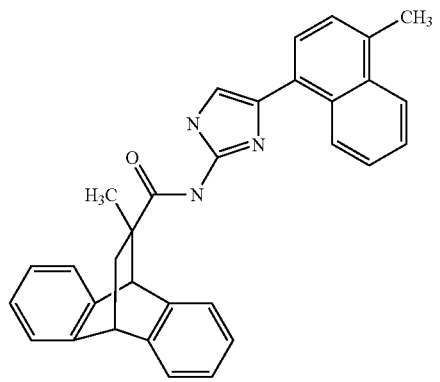 | 469.59 |

-continued

| Example Number | Compound Number | Chiral Compounds | Structure | MS: (M + H = MW shown +1) |
|---|---|---|---|---|
| 41 | 41 | Chiral (R) | 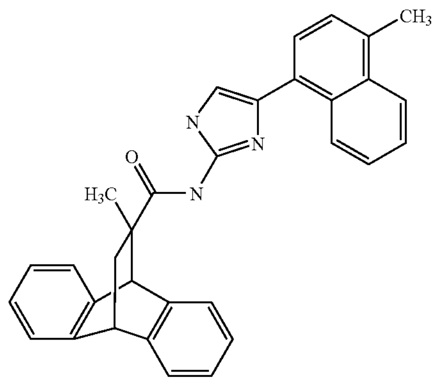 | 469.59 |
| 42 | 42 | Chiral (S) | 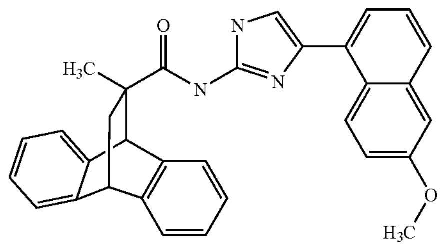 | 485.59 |
| 43 | 43 | Chiral (R) | 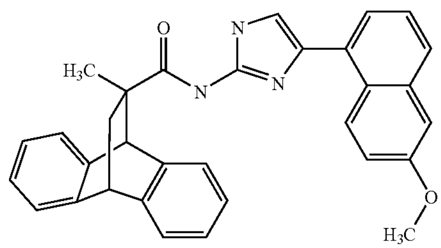 | 485.59 |
| 44 | 44 | Chiral (S) | 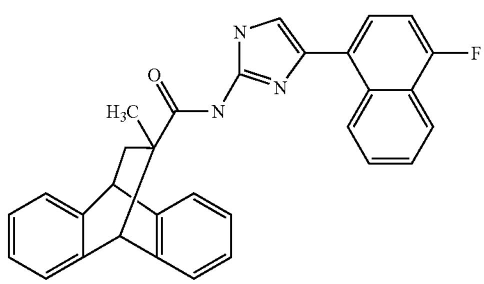 | 473.55 |
| 45 | 45 | Chiral (R) | 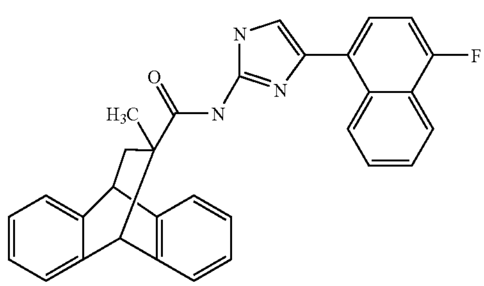 | 473.55 |

-continued

| Example Number | Compound Number | Chiral Compounds | Structure | MS: (M + H = MW shown +1) |
|---|---|---|---|---|
| 46 | 46 | Chiral (R) | 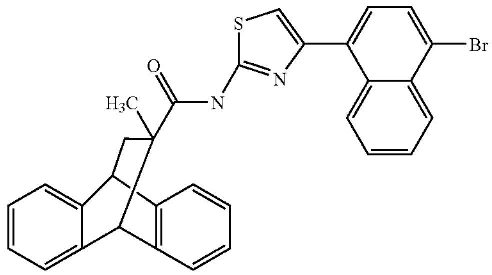 | 551.51 |
| 47 | 47 | Chiral (S) | 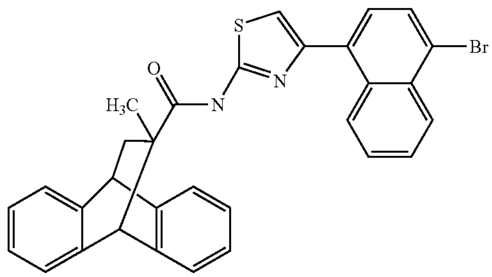 | 551.51 |
| 48 | 48 | Chiral (R) | 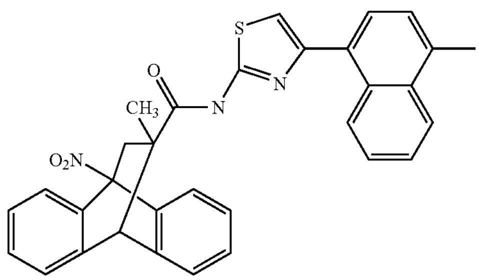 | 532.29 |
| 49 | 49 | Chiral (S) | 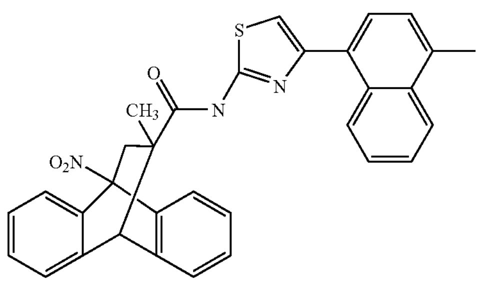 | 532.29 |
| 50 | 50 | Chiral (R) | 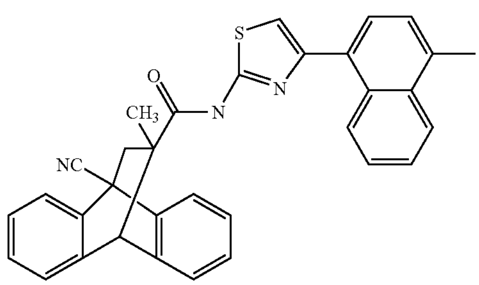 | 512.27 |

-continued

| Example Number | Compound Number | Chiral Compounds | Structure | MS: (M + H = MW shown +1) |
|---|---|---|---|---|
| 51 | 51 | Chiral (S) | 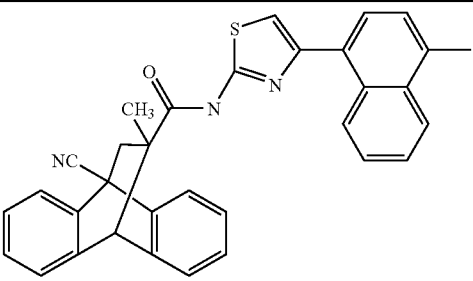 | 512.24 |

Example 2

Site I Binding Assay

In order to measure the binding of compounds to Site I on the glucocorticoid receptor a commercially available kit was used (Glucocorticoid receptor competitor assay kit, Panvera Co., Madison, Wis.). Briefly, a cell lysate containing recombinantly expressed human full-length glucocorticoid receptor was mixed with a fluorescently labeled glucocorticoid (4 nM FITC-dexamethasone) plus or minus test molecule. After one hour at room temperature, the fluorescence polarization (FP) of the samples were measured. The FP of a mixture of receptor, fluorescent probe (i.e. FITC-dexamethasone) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 0.1 nM to 40 μM.

Site I binding assays for any NHR are conducted similarly to the above. An appropriate cell lysate or purified NHR is used as the source of the NHR. The fluorescent probe and unlabeled competitor are appropriate for the specific NHR, i.e. are ligands for the specific NHR.

Example 3

Cellular Transrepressional Assay

To measure the ability of test molecules to inhibit AP-1 induced transcriptional activity we utilized an A549 cell which was stably transfected with a plasmid containing 7xAP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 μM. IC50s were determined by using standard curve fitting methods such as Excel fit (Microsoft Co.). An IC50 is the test molecule concentration which causes a 50% repression of transcription, i.e. a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K., et al., J Biol Chem 1995 Dec. 29;270(52):31315-20 may be used.

The cellular transrepressional assays described above may be used to measure transrepression by any NHR. One of skill in the art will understand that assays may require the addition of components, such as a stimulus (eg. PMA, lipopolysaccharide, TNF-α, etc) which will induce transcription mediated by AP-1 or NF-κB. Additionally, AR mediated transrepression may be measured by the assay described in Palvimo J J, et al. J Biol Chem 1996 Sep. 27;271(39):24151-6, and PR mediated transrepression may be measured by the assay described in Kalkhoven E., et al. J Biol Chem 1996 Mar. 15;271(11): 6217-24.

Example 4

Cellular Transcriptional Assay

In order to measure the ability of compounds to induce DNA binding and transcriptional activation in cells the following assay was performed. A HeLa cell line was stably transfected with a gene expressing a fusion protein consisting of the GAL4 DNA binding domain linked to the ligand binding domain of GR. Also transfected into these cells was a DNA binding site for GAL4 (5 repetitions of a 17-mer GAL4 binding site) linked to the beta-globin reporter in front of the luciferase gene. See Eisenmann, G., Cheynel, and Gronemeyer, H. (1995), Quand les cellules scintillent, Biofutur (Le Technoscope), 151: 8. Cells were incubated for 20 hours with either dexamethasone or test molecule. After 20 hours the level of luciferase activity was measured using a Steady Glo Luciferase assay system (Promega Co., Madison, Wis.). Induction of luciferase activity with 100 nM dexamethasone was considered 100% activation. The activity of test molecules was measured as a percentage of dexamethasone induced DNA binding (transactivation). EC50s were calculated by using standard curve fitting methods such as Excel Fit (Microsoft Co., Redmond, Wash.). An EC50 is the test molecule concentration required to cause a 50% stimulation of transcription.

A second assay which measures the ability of compounds to induce the expression of tyrosine amino transferase mRNA in liver cells was also utilized to determine the ability of compounds to induce DNA binding. In these experiments, an HTC cell line was treated with dexamethasone or test molecules for 20 hours followed by mRNA extraction and analysis by RT-PCR. Again, dexamethasone induction (100 nM) was considered 100% activation. Test molecules were analyzed in the concentration range from 0.1 nM to 40 µM.

Cellular transcription transactivated by any NHR may be measured using an assay similar to the one described above for GR. That is, the NHR (either full length or the ligand binding domain) of interest is overexpressed in a suitable cell line such as COS. A plasmid which contains the DNA binding element specific for the NHR attached to a promoter and linked upstream of a reporter gene (e.g. luciferase), is co-transfected with the NHR. A chimeric NHR—ligand binding domain fused to GAL4, or other transcription factor, could also be used to measure transactivation mediated by ligand binding to the NHR. In this case, the DNA binding element would be specific for the NHR fusion partner. An appropriate nuclear hormone is used for comparison to the test molecule. The cell line is treated with test molecule and reporter gene activity measured.

Example 5

GR Binding Activity AP-1 Inhibitory Activity, and Transactivational Activity of Racemic Mixtures Each of the twenty-seven racemic mixtures described in Example 1 was tested in the GR Site I binding assay, the cellular transrepressional assay, and the cellular transcriptional assay. The results are given in Table II below, in Example 10. GR Site I binding of the compounds ranged from 20.0-99.1% inhibition at 10 µM concentration. AP-1 inhibition in the cellular transrepressional assay ranged from 0.8-82.9% at 10 µM concentration. EC50s for DNA binding in the cellular transcriptional were determined for some of the compounds and were greater than 40 µM for all but one.

The EC50 for dexamethasone induction of tyrosine amino transferase mRNA in the HTC cell line is approximately 50 nM. Two racemic mixtures of Example 1 were analyzed in the tyrosine amino transferase mRNA assay and had EC50s of greater than 40 µM.

Example 6

Enantiomeric Separation of Twelve Racemates

Twelve compounds which were originally synthesized as racemic mixtures were separated into enantiomeric pairs, and the enantiomeric identity of each member of the pair was determined using standard techniques known in the art. These twenty-four enantiomers are among the compounds of Example 1.

Example 7

GR Binding Activity AP-1 Inhibitory Activity, and Transactivational Activity of Twenty-four Enantiomers Each of the twenty-four enantiomers was tested in the cellular transcriptional assay. All but one of the twenty-four enantiomers were tested in the cellular transrepressional assay. Most of the twenty-four enantiomers were tested in the GR Site I binding assay. Two enantiomers (one pair) were tested in the tyrosine amino transferase mRNA assay.

EC50s for DNA binding in the cellular transcriptional assay were greater than 40 µM for all but three of the twelve S enantiomers and for all but two of the twelve R enantiomers. For ten of the S enantiomers, EC50s for DNA binding in the cellular transcriptional assay were greater than 40 µM for all but one. For ten of the R enantiomers, EC50s for DNA binding in the cellular transcriptional assay were greater than 40 µM for all. IC50s for AP-1 inhibition in the cellular transrepressional assay ranged from 15 nM to 11 µM for the twelve S enantiomers, with the range for eleven of the S enantiomers being 15 nM to 275 nM. IC50s for AP-1 inhibition in the cellular transrepressional assay ranged from 33 nM to 11 µM for ten of the S enantiomers, with the range for nine of those S enatiomers being 33 nM to 275 nM. IC50s for AP-1 inhibition in the cellular transrepressional assay ranged from 222 nM to 40 µM for the twelve R enantiomers, with the range for ten of the R enantiomers being 650 nM to 40 µM. GR Site I binding inhibition at 10 µM ranged from 6.1% to 41% for the S enantiomers, and from 51.8% to 99% for the R enantiomers, with the range being 51.8% to 97.9% for ten of the R enantiomers. Both enantiomers of the pair tested had EC50s of greater than 40 µM in the tyrosine amino transferase mRNA assay.

This data clearly shows that the S enantiomers were more potent inhibitors of AP-1 activity relative to the R enantiomers. In contrast, the R enantiomers were more potent inhibitors of dexamethsone binding to GR compared to the S enantiomers.

Example 8

Dissociation of Twenty-four Enantiomers Compounds

The dissociation of the twenty-four enantiomers was calculated by dividing the EC50 from the cellular transcriptional assay by the IC50 from the cellular transrepressional assay. The dissociation constant for the R enantiomers ranged from 62.5 to 1.0. The dissociation value for the S enantiomers ranged from 1000 to 0.91, with the dissociation value for eleven of the S enantiomers ranging from 1000 to 137, and the dissociation value for some of the S enantiomers ranging from 1000 to 167.

Example 9

GR Homology Model

The GR homology model of the ligand binding domain (LBD) was constructed using known methodology. Specifically, the human sequence (QRHUGA obtained from the International Protein Sequence Database, pir.georgetown.edulpirwww), residues 523-777 (SEQ ID NO:1), comprising the LBD was aligned to the human PR sequence (LBD residues 682-932) (SEQ ID NO:2) available as a xray-structure (1A28.pdb obtained from the RCSB, the Research Collaboratory for Structural Bioinformatics using the modeler module within InsightII (Version 2000, MSI/Accelrys).

```
GR:    523 ATLPQLTPTLVSLLEVIEPEVLYAGYDSSVPDSTWRIMTTLNMLGGRQVI  572 (SEQ ID NO:1)
1A28:  682     QLIPPLINLLMSIEPDVIYAGHDNTKPDTSSSLLTSLNQLGERQLL  727 (SEQ ID NO:2)

GR:    573 AAVKWAKAIPGFRNLHLDDQMTLLQYSWMFLMAFALGWRSYRQSSANLLC  622
1A28:  728 SVVKWSKSLPGFRNLHIDDQITLIQYSWMSLMVFGLGWRSYKHVSGQMLY  777

GR:    623 FAPDLIINEQRMTLPCMYDQCKHMLYVSSELHRLQVSYEEYLCMKTLLLL  672
1A28:  778 FAPDLILNEQRMKESSFYSLCLTMWQIPQEFVKLQVSQEEFLCMKVLLLL  827

GR:    673 SSVPKDGLKSQELFDEIRMTYIKELGKAIVKRE-GN-SSQNWQRFYQLTK  720
1A28:  828 NTIPLEGLRSQTQFEEMRSSYIRELIKAIGLRQKGVVSSS--QRFYQLTK  875

GR:    721 LLDSMHEVVENLLNYCFQTFLDKTM-SIEFPEMLAEIITNQIPKYSNGNI  769
1A28:  876 LLDNLHDLVKQLHLYCLNTFIQSRALSVEFPEMMSEVIAAQLPKILAGMV  925

GR:    770 KKLLFHQK (SEQ ID NO:1)                              777
1A28:  926 KPLLFH-K (SEQ ID NO:2)                              932
```

The resulting GR LBD homology model coordinates are provided in Table I, which for convenience is located at the end of this specification under the heading Example 21.

Example 10

Identification of Site II

The classical ligand binding site, i.e. Site I, is defined by the immediate space surrounding progesterone in 1A28.pdb, can be further defined by the amino acid residues in contact with progesterone, and are well known in the art. The analogous GR site I residues were identified as those proximate to a modeled version of dexamethasone in the GR homology model. GR Site I residues in contact with dexamethasone (as found in the GR homology model) are M560, L563, N564, L566, G567, Q570, M601, M604, A605, L608, R611, F623, M639, Q642, M646, L732, Y735, C736, T739 and E748. The present invention is based on the discovery of an alternate binding site, herein known as Site II, present in a number of NHRs (nuclear hormone receptors), in particular in GR, which interacts with small molecule modulators. In the case of GR, a ligand binding to Site II results in a transrepression signaling within cells (inhibition of AP-1 or NF-κB). The location of Site II is defined herein for a number of related NHRs and specifically for GR in FIG. 2. GR Site II residues include the following (using GR numbering): E537-V543, L566, G567, Q570-W577, S599-A607, W610, R611, R614, Q615, P625, Y663, L664 and K667 of SEQ ID NO:13.

The identification of Site II is supported by the three-dimensional complementarity of shape and functional features between the site and ligands having in vivo transrepression activity. An example of such complementarity is shown in FIG. 3, wherein the S-enantiomer of Compound 15 was manually docked into the GR homology model of Site II.

Site I and Site II residues were defined as those capable of van der Waal's contact with a ligand contained by those residues. Using dexamethasone for Site I (bound in a similar manner as that reported for progesterone in PR Site I) and Compound 15 for Site II (manually docked as shown in FIG. 3), all residues capable of vander Waal's contact were listed as site residues. Included as well were those residues not in immediate contact with either ligand, but capable of such contact if the space between ligand and residue was occupied by a small molecule fragment.

In addition, computations of binding energetics for a series of twenty-seven related Site II ligands, which are among the compounds described in Example 1, was found to correlate with the observed in vivo transrepression activities, providing further evidence of the critical role of Site II binding in producing an in vivo transrepression effect. Correlation data are shown in Table II (below) and FIG. 5, and structures are shown in FIG. 4. Although the data reflect the activities of racemates, each individual molecule was modeled as the S-enantiomer for purposes of consistency. These twenty-seven compounds showed % inhibition at 10 μM in the cellular tranrepressional assay ranging from 0.8 to 82.9. The EC50 in the cellular transcriptional assay was greater than 40 μM for twenty-six of the compounds, and was greater than 10 μM for the remaining compound.

Binding energetics were calculated using Flo (Colin McMartin, Thistlesoft, High Meadow, 603 Colebrook Road, Colebrook, Conn. 06021), molecular modeling software which utilizes the Amber molecular mechanics force field to achieve a best fit between ligand and protein binding site. Both the ligand and Site II residues in contact with the ligand are allowed to undergo energy minimization and geometry optimization. The result of these operations provides an optimum ligand binding orientation and a series of calculated energies of interaction. The correlation between observed AP-1 inhibition (percent at 10 uM) and binding energetics is based on the calculated non-bonded contact interactions between ligand and protein residues. This type of calculation generally reflects the degree to which a ligand conforms to the shape of the binding site.

Table II, below, gives correlation data calculated for the analogues of Compound 15 using Flo Contact Energy Scores (Ecnt) after manually docking each analogue into GR Site II (Flo modeling software, Colin McMartin, ThistleSoft). % AP-1 values were determined at an inhibitor concentration of 10 μM. GR binding assay was performed as described in Example 2. DNA binding assay was performed as described in Example 4. AP-1 inhibition assay was performed as described in Example 3.

TABLE II

Correlation Data for Analogues of Compound 15

| Compound | GR Binding (% @ 10 uM) | DNA Binding NP-1 IC50 (uM) | AP-1 (% inh @ 10 uM) | Ecnt (KJ/mol) |
|---|---|---|---|---|
| | 92.1 | | 30.3 | −18.7 |
| | 99.1 | | 24.5 | −15.6 |
| | 97.6 | | 0.8 | −17 |
| | 85.1 | >10 | 29.5 | −16.9 |
| | 92.8 | >40 | 8.7 | −15.1 |
| | 96.0 | | 36.1 | −22.5 |
| | 91.0 | | 15.2 | −19.2 |
| | 84.9 | >40 | 58.6 | −19.4 |

TABLE II-continued

Correlation Data for Analogues of Compound 15

| Compound | GR Binding (% @ 10 uM) | DNA Binding NP-1 IC50 (uM) | AP-1 (% inh @ 10 uM) | Ecnt (KJ/mol) |
|---|---|---|---|---|
| | 92.3 | | 25.1 | −13.3 |
| | 93.2 | | 41.3 | −22.9 |
| | 88.1 | >40 | 61.8 | −28.9 |
| | 88.3 | | 22.5 | −20.2 |
| | 92.2 | | 29.3 | −15.2 |
| | 93.5 | | 33.6 | −18.4 |
| | 65.7 | | 61.8 | −26.3 |
| | 93.8 | | 26.4 | −27.6 |
| | 94.1 | | 23.4 | −16.3 |
| | 94.4 | | 47 | −18.9 |
| | 76.8 | | 7 | −21.9 |
| | 20.0 | | 13.6 | −27.8 |
| | 64.5 | | 32.7 | −18.9 |
| | 45.3 | | 8.6 | −23.3 |
| | 31.9 | | 18.9 | −21.5 |
| | 90.4 | >40 | 82.9 | −29.6 |
| | 56.3 | >40 | 64.2 | −21.2 |
| | 88.7 | | 38.5 | −23.7 |
| | 91.7 | | 43.8 | −25 |

There are a number of published examples wherein the energetics of interaction of docked structures correlated with observed activity; one such example was in the use of AutoDock (Sybyl, Tripos, St. Louis, Mo.) in evaluating 27 HIV-1 Protease inhibitors (Huang, et. al., J. Med. Chem. 45, 333, 2002). Energies of interaction between the HIV-1 protease active site and a series of ligands were calculated using an MM2X force field and found to correlate with observed activities (Holloway and Wai in Computer-Aided Molecular Design, ACS Symposium Series 589, ACS, Washington, D.C. 1995). The solvation contribution to the binding energetics of docked structures was accounted for and provided the means to more accurately predict biological activities (Takamatsu and Itai, Proteins: Structure, Function, and Genetics, 33:62-73, 1998).

Correlating structure with activity is a fundamental criterion in pointing out those aspects of the structure most relevant to activity. When the correlation is carried out with ligands alone, it can demonstrate which properties/features of the ligands are important for activity. When done with a protein binding site acting as a constraint, the correlation provides evidence that certain three-dimensional binding site features are important. Thus, when a correlation exists between AP-1 inhibition data and the calculated binding energetics for a series of molecules, this provides a reasonable certainty that the binding site model is consistent with the observed inhibition data. Therefore, the design of molecules having features complementary to those of the binding site should lead to the effective structure-based design of novel ligands having desired biological activity, in this case, AP-1 inhibition.

A recent publication (Bledsoe, et. al., Cell, online publication by Cell Press, Jul. 1, 2002; DOI: 10.1016/S0092867402008176) describes the successful crystallization and xray structural elucidation of the glucocorticoid receptor LBD as the dimer. Disruption of the dimeric structure was found to occur upon mutation of selected residues at the dimerization interface. These mutants lacked transactivation activity and retained transrepression activity. Interestingly, the dimerization interface and the opening of Site II share the same outer surface (two residues located at the rim of Site II, namely, Q615 and P625, are among several identified by the authors as critical to dimer formation). This observation is consistent with the proposed importance of Site II in modulating dissociated steroid activity.

Example 11

Cellular Transrepressional Assay with Both A Site II Dissociated Compound and Dexamethasone The cellular transrepressional assay was performed by determining the IC50 for transrepression for dexamethasone in the presence or absence of one of the compounds (an S enantiomer) of Example 1. This S enantiomer is hereinafter referred to as Compound A. In the absence of Compound A dexamethasone yielded an IC50 of 3.4 nM with a maximum percent inhibition of 75%, whereas, in the presence of 800 nM of the compound the IC50 decreased to 1.2 nM with 100% inhibition. This showed that there is an additive effect of adding the compound with dexamethasone.

Example 12

Cellular Transcriptional Assay with Both A Site II Dissociated Compound and Dexamethasone For transactivation, the compound used in Example 11, Compound A, was an antagonist of dexamethasone activity. Here, an EC50 was determined in the cellular transcriptional assay for dexamethasone in the presence or absence of the compound. In the absence, the EC50 was 3.4 nM with 100% stimulation, whereas, in the presence of the compound the EC50 shifted to 8.5 nM with 47% stimulation.

Example 13

Overlay of Site II from Various NHRs and Calculation of rms

Consensus alignments were carried out using ICM (Molsoft LLC, La Jolla, Calif.) between human GR LBD and other human NHR LBDs. FIG. 2 shows the alignment, indicating by shading the residues of Site II in each NHR, i.e. residues corresponding to residues of GR Site II. Dots are spaceholders and do not represent amino acids. Numbers refer to the first residue in each line, are specific for each NHR and are based on the full-length NHR. For the NHRs listed below, with the exception of GR and MR, structural data was obtained from the RCSB references listed below, and the numbering system in the RCSB references was used. For GR and MR, structural data was obtained by homology modeling using the literature references below, and the numbering system in those literature references was used. The RCSB references (in parentheses) and literature references for the various NHRs are as follows:

RXRalpha (1lbd) Bourguet, W., Ruff, M., Chambon, P., Gronemeyer, H., Moras, D. Nature 375 pp. 377 (1995); PPAR-gamma (2prg) Nolte, R. T., Wisely, G. B., Westin, S., Cobb, J. E., Lambert, M. H., Kurokawa, R., Rosenfeld, M. G., Willson, T. M., Glass, C. K., Milburn, M. V. Nature 395 pp. 137 (1998); RARgamma (2lbd) Renaud, J. P., Rochel, N., Ruff, M., Vivat, V., Chambon, P., Gronemeyer, H., Moras, D. Nature 378 pp. 681 (1995); PR (1a28) Williams, S. P., Sigler, P. B. Nature 393 pp. 392 (1998); VitDR (1db1) Rochel, N., Wurtz, J. M., Mitschler, A., Klaholz, B., Moras, D. Mol. Cell 5 pp. 173 (2000); AR (1e3g) Matias, P. M., Donner, P., Coelho, R., Thomaz, M., Peixoto, C., Macedo, S., Otto, N., Joschko, S., Scholz, P., Wegg, A., Basler, S., Schafer, M., Egner, U., Carrondo, M. A. J. Biol. Chem. 275 pp. 26164 (2000); ERalpha (1a52) Tanenbaum, D. M., Wang, Y., Williams, S. P., Sigler, P. B. Proc Natl Acad Sci USA 95 pp. 5998 (1998); ERbeta (1l2j) Shiau, A. K., Barstad, D., Radek, J. T., Meyers, M. J., Nettles, K. W., Katzenellenbogen, B. S., Katzenellenbogen, J. A., Agard, D. A., Greene, G. L. Nat. Struct. Biol. 9 pp. 359 (2002); TRbeta (1bsx) Wagner, R. L., Darimont, B. D., Apriletti, J. W., Stallcup, M. R., Kushner, P. J., Baxter, J. D., Fletterick, R. J., Yamamoto, K. R. Genes Dev. 12 pp. 3343 (1998). MR and GR structural data were obtained by homology modeling to PR using the sequences from the following references: GR, PIR Accession Number QRHUGA, Hollenberg, S. M., Weinberger, C., Ong, E. S., Cerelli, G., Oro, A., Leba, R., Thompson, E. B., Rosenfeld, M. G., Evans, R. M., Nature (1985) 318: 635-641; MR, PIR Accession Number A29613, Arriza, J. L.; Weinberger, C., Cerelli, G., Glaser, T. M., Handelin, B. L., Housman, D. E., Evans, R. M., Science (1987) 237: 268-275.

It is understood that FIG. 2 is merely illustrative of the invention and is not intended to be limiting in any manner. Accordingly, it is understood that corresponding amino acid residues of other nuclear receptors such as other estrogen receptors, thyroid receptors, retinoid receptors, glucocorticoid receptors, progestin receptors, mineralocorticoid receptors, androgen receptors, peroxisome receptors and vitamin D receptors may also be used in the methods of the invention.

The structure coordinates of Site II in the NHRs of FIG. 2 are given in Table III, located under the heading for Example 22.

Using structural data described above for several NHR LBDs, rigid fitting operations were conducted between the GR LBD homology model and the following closely-related NHRs: progesterone receptor LBD, androgen receptor LBD, estrogen receptor alpha LBD and estrogen receptor beta LBD. The fitting operation yielded Site II rms deviations in backbone atom comparisons of 0.57-0.71 Å. The fitting operations were carried out using the Match option within InsightII. Backbone atoms of GR Site II were compared to those of the following four NHRs: progesterone receptor (rms=0.57 Å), androgen receptor (rms=0.71 Å), estrogen receptor alpha (rms=0.69 Å), and estrogen receptor beta (rms=0.52 Å).

Example 14

Sequence Alignment of GR Site II from Various Species

Sequence alignments were prepared of the human GR and the GR from various non-human species. The sequence alignments were conducted using the program LOOK (Version 3.5.2 Molecular Applications Group, Palo Alto, Calif.). The alignment is shown in FIG. 6. The sequence for each GR starts at residue 1. Alignments were made based on pair-wise sequence identity. Site II residues are shaded. GR sequences were obtained from the following sources: Squirrel (Saimiri boliviensis boliviensis) (GenBank U87951) Reynolds, P. D., Pittler, S. J. and Scammell, J. G. J. Clin. Endocrinol. Metab. 82 (2), 465-472 (1997); Pig GR (GenBank AF141371) Gutscher, M., Eder, S., Mueller, M. and Claus, R. Submitted to GenBank (08-Apr.-1999) Institut fuer Tierhaltung und Tierzuechtung (470), FG Tierhaltung und Leistungsphysiologie, Universitaet Hohenheim, Garbenstr. 17, Stuttgart 70599, Germany; Guinea Pig (GenBank L13196) Keightley, M. C. and Fuller, P. J. Mol. Endocrinol. 8 (4), 431-439 (1994); Marmoset (GenBank U87953) Reynolds, P. D., Pittler, S. J. and Scammell, J. G. J. Clin. Endocrinol. Metab. 82 (2), 465-472 (1997); Ma'z Monkey (GenBank U87952) Reynolds, P. D., Pittler, S. J. and Scammell, J. G. J. Clin. Endocrinol. Metab. 82 (2), 465-472 (1997); rat (GenBank M14053) Miesfeld, R., Rusconi, S., Godowski, P. J., Maler, B. A., Okret, S., Wikstrom, A. C., Gustafsson, J. A. and Yamamoto, K. R. Cell 46 (3), 389-399 (1986); mouse (GenBank X04435) Danielsen, M., Northrop, J. P. and Ringold, G. M. EMBO J. 5 (10), 2513-2522 (1986); Human (Protein Information Resource QRHUGA) Hollenberg, S. M., Weinberger, C., Ong, E. S., Cerelli, G., Oro, A., Leba, R., Thompson, E. B., Rosenfeld, M. G., Evans, R. M., Nature (1985) 318: 635-641.

Example 15

Site II Binding Assay

In order to measure binding of a test molecule (i.e. a potential ligand) to Site II on GR, a labeled, such as radiolabeled or fluorescently labeled, known ligand of Site II is prepared. Several approaches can be utilized to identify a ligand of Site II that can be used as the labeled known ligand of Site II. All involve analyzing a modulator of GR to determine if it is a ligand of Site II. Three such approaches follow.

The first approach involves making mutations in GR in site II. These Site II mutants are expressed in the transactivation and/or transrepression assays to determine if there is any alteration of the modulator's activity. It would be predicted that those amino acids which are in proximity to the compound, if mutated, should decrease the activity of the modulator in the transrepression assay, whereas, there should be no effect on the activity of dexamethsone mediated tranactivation and/or transrepression. This approach is used in Example 16.

A second approach is to prepare a modulator with a moiety that can be crosslinked to GR, such as dexamethasone mesylate. After crosslinking, the GR is digested with proteases and analyzed by mass spectrometry. The peptide(s) with a covalently attached modulator are identified.

A third approach is to crystallize the GR with the modulator. The structure of the co-crystal complex definitively shows the mode in which the modulator is binding to GR.

Once a ligand is identified, it is labeled and is used in the assay to measure binding of a test molecule to Site II. The test molecule and the labeled ligand are incubated with a cell lysate or purified complex containing GR. The binding of compounds to GR are measured using techniques which are standard in the art such as fluorescence quenching, fluorescence polarization, filter binding, scintillation proximity assay, among others. The readout, such as fluorescence polarization, of a mixture of receptor, labeled ligand and 1 mM unlabeled ligand represents 100% competition, whereas, the readout of the mixture without unlabeled ligand is taken to be 100% binding. The percentage competition of test molecules are then compared to the sample with 1 mM unlabeled ligand and expressed as % relative binding activity with unlabeled ligand being 100% and no competition being 0%. Test molecules are analyzed in the concentration range from 0.1 nM to 40 μM.

To confirm binding of a test molecule to Site II, a GR that has mutations in Site II may be used. It would be expected that a GR with mutations in Site II would have a diminished ability to be modulated by a ligand of Site II. Modulation by the test molecule, i.e. transrepression and transactivation, is compared between the native GR and the mutant GR.

Site II binding may also be confirmed by demonstrating that a steroid known to bind to Site I, such as dexamethasone, does not compete for the binding of the test molecule to Site II.

To determine an IC50, a fixed concentration of labeled ligand is used and a titration with unlabeled test molecule is performed. Test molecules are analyzed in the concentration range from 0.1 nM to 40 µM.

A Site II binding assay may be prepared using any NHR in place of GR as described above. Cross-linking agents and ligands appropriate for the specific NHR are used.

Example 16

Transactivation Studies on GR Site-Directed Mutants

Several mutations in Site II of the human glucocorticoid receptor were made. Two mutations of Alanine 607 to either a valine or phenylalanine were made which were predicted to block the entrance of Site II ligands into the Site II pocket. Valine 543, which is on the interior of the Site II pocket, was mutated to phenylalanine, and this mutation was predicted to disrupt binding of compounds to Site II. A double mutant A607V/V543L was also made. These mutations were made using a commercially available kit, Stratagene Quick Change XL Site Directed Mutagenesis Kit (Stratagene, La Jolla, Calif.).

COS cells were transfected with expression vectors for either the wild type or the various mutants. Cells were also transfected with a highly sensitive, artificial reporter consisting of two glucocorticoid response elements upstream of the gene for luciferase, the GRE2LUC reporter. (PROMEGA steady glo luciferase assay system, Promega, Madison, Wis.). After 24 hours the cells were then treated for an additional 24 hours with either dexamethasone (Dex), or Site II ligands. At the end of the incubation period, luciferase levels were measured using the PROMEGA steady glo luciferase assay system (Promega, Madison, Wis.).

The data is shown in FIG. 8, in which RLU means relative light units. FIG. 8 shows that in the wild type GR, both dexamethasone and Compound A can induce transactivation via the GRE2LUC reporter. However, in the A607F, A607V and V543F mutants, whereas dexamethsone induced transactivation of the reporter, Compound A did not. Compound A is indicated by the left, darker, solid bar in each pair of bars. Dexamethasone is indicated by the right, lighter, hatched bar in each pair of bars. The control is cells transfected with DNA vector alone (no GR) plus the GRE2LUC reporter. These data suggest that either Compound A interacts with amino acids V543 and A607 in Site II or the mutations prevent the interaction of Compound A with GR.

Glucocorticoid receptor transactivation activity is very sensitive to mutations which may alter the conformation of the receptor. As seen in FIG. 8, some point mutations enhance the ability of dexamethasone to induce transactivation. This may occur due to, among other explanations, an increase in the ability of dexamethasone to bind to GR or increased ability to recruit co-activators. The double mutant caused a decrease in the ability of dexamethasone to induce transactivation perhaps due to a more dramatic effect on the conformation of GR and a decreased ability to bind to dexamethasone or recruit co-activators.

Example 17

Effect of Combining BMS Site II Compounds with Dexamethasone or RU486 on AP-1 Mediated Transcription A549 cells stably transfected with an AP-1 reporter with a luciferase readout, as described in Example 3, were treated with various concentrations of compounds. As shown in FIG. 9, a titration of dexamethasone was performed in the presence or absence of Compound A (an S enantiomer) or Compound B (the R enantiomer of Compound A). As seen in FIG. 9, these compounds increase the percentage of inhibition of AP-1 relative to dexamethasone alone, suggesting there is an additive effect between these Site II compounds and dexamethasone. In contrast, RU486 (Hoffmann T G, Hehner S P, Bacher S, Droge W, Schmitz M L. FEBS Lett. 1998 Dec. 28;441(3): 441-6), which is an antagonist of Site I, which is the dexamethasone binding site, inhibits the ability of dexamethasone to repress AP-1 activity. The data taken together demonstrates that Compound A and Compound B act in an additive fashion with compounds which interact with Site I, suggesting they act at an alternative Site II.

Example 18

An Assay to Indirectly Measure the Interaction of Site II Ligands with GR

In order to measure the binding of putative Site II compounds to GR we utilized the Glucocorticoid receptor competitor assay kit (Panvera Co., Madison, Wis.) in a modified version of the FITC-dexamethasone fluorescence polarization assay described in Example 2. In this assay, Compound D was added at a concentration of 200 nM, which yields approximately 50% inhibition of FITC-dexamethasone binding. Compound D (an R enantiomer) is Compound 50 of Example 1. Compound D is a ligand of Site II that inhibits via Site II FITC-dexamethasone binding to GR. To the mixture of cell lysate containing the glucocorticoid receptor, Compound D, and FITC-dexamethasone, various competitor Site II ligands which do not inhibit dexamethasone binding were added and the change in FITC-dexamethasone binding was measured. These competitor Site II ligands, all compounds of Example 1 and all S enantiomers, were: Compound A; Compound C, which is the S enantiomer of Compound D; and Compound E, yet another S enantiomer of Example 1. If the competitor compound binds to Site II and displaces Compound D, then FITC-dexamethasone should rebind to GR. As shown in FIG. 10, the competitor compounds are effective at displacing Compound D and allowing FITC-dexamethasone to rebind to GR. This assay can therefore measure the relative binding of compounds to the Site II on GR.

Example 19

Site II Ligands Act in a GR Dependent Fashion to Repress AP-1 Driven Transcription In order to determine whether the Site II ligands act via GR, COS cells, which do not express GR, were transfected with an AP-1 luciferase reporter (pAP-1-Luc plasmid, Stratagene, La Jolla, Calif.) plus or minus an expression construct for full length human GR. AP-1 activity was measured via luciferase reporter activity as described in Example 3. When GR was not present, neither 1 micromolar dexamethasone nor 40 micromolar Compound A significantly inhibited AP-1 activity. However, when GR was transfected into the cell, both dexamethasone and Compound A suppressed AP-1 activity. These results are shown in FIGS. 11*a* and 11*b*, in which the Y axis is relative light units (RLU). These data show that both of these ligands act in a GR dependent fashion.

Example 20

Provision of GR Site II X-ray Structure Coordinates and Calculations of rms

The GR Site II x-ray structure coordinates were discerned from the disclosure in WO 03/015692 A2, Feb. 27, 2003, Apolito, et. al. and are provided in Table IV under the heading for Example 23. Apolito discloses x-ray structure coordinates of GR LBD, but does not disclose the existence or identity of Site II.

The GR Site II x-ray structure coordinates were discerned from the disclosure in Kauppi et. al., in the Journal of Biological Chemistry Online, JBC Papers In Press as DOI: 10.1074/jbc.M212711200, Apr. 9, 2003, RCSB file: 1nhz.pdb (GR LBD bound to an antagonist, RU 486) and are provided in Table V under the heading for Example 24. Kauppi discloses x-ray structure coordinates of GR LBD, but does not disclose the existence or identity of Site II.

The homology model GR Site II coordinates of Table I were compared to the Site II coordinates available from the disclosures in WO 03/015692 A2, Feb. 27, 2003 Apolito, et. al. and those published by Kauppi et. al., in the Journal of Biological Chemistry Online, JBC Papers In Press as DOI: 10.1074/jbc.M212711200, Apr. 9, 2003, RCSB file: 1nhz.pdb (GR LBD bound to an antagonist, RU 486). When the backbone atoms of the homology model Site II residues, ie, E537-V543, L566, G567, Q570-W577, S599-A607, W610, R611, R614, Q615, P625, Y663, L664 and K667 of SEQ ID NO:13 according to Table I were compared, root mean square deviations (rmsds) of 0.92 and 1.02 Å were obtained between the homology model of Table I Site II residues and the Apolito Site II residues, and between the homology model of Table I Site II residues and the Kauppi Site II residues, respectively. In both instances the Site II residues were first overlaid using the structure overlay option within the ICM (Version 3.0.017, Molsoft. LLC) modeling software. Using the rmslig program within the Flo (Colin McMartin, Thistlesoft) molecular modeling program afforded backbone rmsd calculations. These observations underscore the similarity of the Site II homology model structure to actual crystal structures.

Example 21

Structure Coordinates of GR LBD, Table I

Below is Table I, which gives the three-dimensional structure coordinates of the GR LBD homology model. The format used is based on that commonly used in the RCSB (Research Collaboratory for Structural Bioinformatics, pdb file format), and the fields listed from left to right are defined as follows: record name, atom serial number, atom name, residue name, chain identifier, residue sequence number, orthogonal coordinate for x in Ångstroms, orthogonal cordinate for y in Ångstroms, orthogonal coordinate for z in Ångstroms, occupancy, and temperature factor.

TABLE I

| | | | | | | | | | | |
|---|---|---|---|---|---|---|---|---|---|---|
| | GR Homology Model Coordinates |
| ATOM | 1 | N | ALA | A | 523 | 29.896 | −1.364 | 107.714 | 1.00 | 0.00 |
| ATOM | 5 | CA | ALA | A | 523 | 30.095 | −0.736 | 106.398 | 1.00 | 0.00 |
| ATOM | 6 | CB | ALA | A | 523 | 31.574 | −0.448 | 106.160 | 1.00 | 0.00 |
| ATOM | 7 | C | ALA | A | 523 | 29.565 | −1.627 | 105.280 | 1.00 | 0.00 |
| ATOM | 8 | O | ALA | A | 523 | 29.626 | −2.860 | 105.361 | 1.00 | 0.00 |
| ATOM | 9 | N | THR | A | 524 | 29.027 | −0.987 | 104.257 | 1.00 | 0.00 |
| ATOM | 11 | CA | THR | A | 524 | 28.493 | −1.717 | 103.105 | 1.00 | 0.00 |
| ATOM | 12 | CB | THR | A | 524 | 27.666 | −0.754 | 102.257 | 1.00 | 0.00 |
| ATOM | 13 | OG1 | THR | A | 524 | 27.383 | −1.389 | 101.016 | 1.00 | 0.00 |
| ATOM | 14 | CG2 | THR | A | 524 | 28.428 | 0.532 | 101.951 | 1.00 | 0.00 |
| ATOM | 15 | C | THR | A | 524 | 29.607 | −2.329 | 102.263 | 1.00 | 0.00 |
| ATOM | 16 | O | THR | A | 524 | 30.663 | −1.720 | 102.058 | 1.00 | 0.00 |
| ATOM | 17 | N | LEU | A | 525 | 29.370 | −3.559 | 101.836 | 1.00 | 0.00 |
| ATOM | 19 | CA | LEU | A | 525 | 30.275 | −4.243 | 100.909 | 1.00 | 0.00 |
| ATOM | 20 | CB | LEU | A | 525 | 29.686 | −5.626 | 100.629 | 1.00 | 0.00 |
| ATOM | 21 | CG | LEU | A | 525 | 30.626 | −6.524 | 99.829 | 1.00 | 0.00 |
| ATOM | 22 | CD1 | LEU | A | 525 | 31.867 | −6.870 | 100.645 | 1.00 | 0.00 |
| ATOM | 23 | CD2 | LEU | A | 525 | 29.912 | −7.799 | 99.399 | 1.00 | 0.00 |
| ATOM | 24 | C | LEU | A | 525 | 30.360 | −3.442 | 99.612 | 1.00 | 0.00 |
| ATOM | 25 | O | LEU | A | 525 | 29.329 | −3.065 | 99.040 | 1.00 | 0.00 |
| ATOM | 26 | N | PRO | A | 526 | 31.578 | −3.090 | 99.231 | 1.00 | 0.00 |
| ATOM | 27 | CA | PRO | A | 526 | 31.804 | −2.331 | 98.002 | 1.00 | 0.00 |
| ATOM | 28 | CB | PRO | A | 526 | 33.272 | −2.040 | 97.977 | 1.00 | 0.00 |
| ATOM | 29 | CG | PRO | A | 526 | 33.936 | −2.705 | 99.171 | 1.00 | 0.00 |
| ATOM | 30 | CD | PRO | A | 526 | 32.819 | −3.379 | 99.951 | 1.00 | 0.00 |
| ATOM | 31 | C | PRO | A | 526 | 31.377 | −3.118 | 96.771 | 1.00 | 0.00 |
| ATOM | 32 | O | PRO | A | 526 | 31.487 | −4.348 | 96.713 | 1.00 | 0.00 |
| ATOM | 33 | N | GLN | A | 527 | 30.814 | −2.387 | 95.828 | 1.00 | 0.00 |
| ATOM | 35 | CA | GLN | A | 527 | 30.403 | −2.963 | 94.547 | 1.00 | 0.00 |
| ATOM | 36 | CB | GLN | A | 527 | 29.511 | −1.931 | 93.859 | 1.00 | 0.00 |
| ATOM | 37 | CG | GLN | A | 527 | 28.265 | −2.549 | 93.224 | 1.00 | 0.00 |
| ATOM | 38 | CD | GLN | A | 527 | 28.482 | −2.831 | 91.742 | 1.00 | 0.00 |
| ATOM | 39 | OE1 | GLN | A | 527 | 29.078 | −3.849 | 91.362 | 1.00 | 0.00 |
| ATOM | 40 | NE2 | GLN | A | 527 | 28.005 | −1.911 | 90.924 | 1.00 | 0.00 |
| ATOM | 43 | C | GLN | A | 527 | 31.655 | −3.268 | 93.726 | 1.00 | 0.00 |
| ATOM | 44 | O | GLN | A | 527 | 32.671 | −2.574 | 93.856 | 1.00 | 0.00 |
| ATOM | 45 | N | LEU | A | 528 | 31.578 | −4.294 | 92.894 | 1.00 | 0.00 |
| ATOM | 47 | CA | LEU | A | 528 | 32.746 | −4.723 | 92.118 | 1.00 | 0.00 |
| ATOM | 48 | CB | LEU | A | 528 | 32.560 | −6.180 | 91.716 | 1.00 | 0.00 |
| ATOM | 49 | CG | LEU | A | 528 | 32.452 | −7.090 | 92.933 | 1.00 | 0.00 |
| ATOM | 50 | CD1 | LEU | A | 528 | 32.112 | −8.515 | 92.513 | 1.00 | 0.00 |

TABLE I-continued

GR Homology Model Coordinates

| ATOM | 51 | CD2 | LEU | A | 528 | 33.737 | −7.059 | 93.757 | 1.00 | 0.00 |
|---|---|---|---|---|---|---|---|---|---|---|
| ATOM | 52 | C | LEU | A | 528 | 32.898 | −3.866 | 90.870 | 1.00 | 0.00 |
| ATOM | 53 | O | LEU | A | 528 | 33.997 | −3.721 | 90.325 | 1.00 | 0.00 |
| ATOM | 54 | N | THR | A | 529 | 31.794 | −3.278 | 90.447 | 1.00 | 0.00 |
| ATOM | 56 | CA | THR | A | 529 | 31.839 | −2.254 | 89.408 | 1.00 | 0.00 |
| ATOM | 57 | CB | THR | A | 529 | 30.592 | −2.393 | 88.540 | 1.00 | 0.00 |
| ATOM | 58 | OG1 | THR | A | 529 | 30.607 | −3.688 | 87.958 | 1.00 | 0.00 |
| ATOM | 59 | CG2 | THR | A | 529 | 30.539 | −1.366 | 87.417 | 1.00 | 0.00 |
| ATOM | 60 | C | THR | A | 529 | 31.883 | −0.884 | 90.076 | 1.00 | 0.00 |
| ATOM | 61 | O | THR | A | 529 | 30.909 | −0.470 | 90.718 | 1.00 | 0.00 |
| ATOM | 62 | N | PRO | A | 530 | 32.993 | −0.185 | 89.887 | 1.00 | 0.00 |
| ATOM | 63 | CA | PRO | A | 530 | 33.234 | 1.104 | 90.544 | 1.00 | 0.00 |
| ATOM | 64 | CB | PRO | A | 530 | 34.571 | 1.567 | 90.055 | 1.00 | 0.00 |
| ATOM | 65 | CG | PRO | A | 530 | 35.165 | 0.505 | 89.148 | 1.00 | 0.00 |
| ATOM | 66 | CD | PRO | A | 530 | 34.140 | −0.613 | 89.089 | 1.00 | 0.00 |
| ATOM | 67 | C | PRO | A | 530 | 32.150 | 2.125 | 90.236 | 1.00 | 0.00 |
| ATOM | 68 | O | PRO | A | 530 | 31.449 | 2.042 | 89.216 | 1.00 | 0.00 |
| ATOM | 69 | N | THR | A | 531 | 32.129 | 3.169 | 91.045 | 1.00 | 0.00 |
| ATOM | 71 | CA | THR | A | 531 | 31.052 | 4.162 | 90.968 | 1.00 | 0.00 |
| ATOM | 72 | CB | THR | A | 531 | 31.140 | 5.085 | 92.180 | 1.00 | 0.00 |
| ATOM | 73 | OG1 | THR | A | 531 | 32.362 | 5.809 | 92.114 | 1.00 | 0.00 |
| ATOM | 74 | CG2 | THR | A | 531 | 31.111 | 4.300 | 93.487 | 1.00 | 0.00 |
| ATOM | 75 | C | THR | A | 531 | 31.073 | 5.007 | 89.695 | 1.00 | 0.00 |
| ATOM | 76 | O | THR | A | 531 | 29.993 | 5.350 | 89.210 | 1.00 | 0.00 |
| ATOM | 77 | N | LEU | A | 532 | 32.208 | 5.125 | 89.025 | 1.00 | 0.00 |
| ATOM | 79 | CA | LEU | A | 532 | 32.214 | 5.894 | 87.780 | 1.00 | 0.00 |
| ATOM | 80 | CB | LEU | A | 532 | 33.573 | 6.565 | 87.618 | 1.00 | 0.00 |
| ATOM | 81 | CG | LEU | A | 532 | 33.609 | 7.529 | 86.435 | 1.00 | 0.00 |
| ATOM | 82 | CD1 | LEU | A | 532 | 32.501 | 8.573 | 86.536 | 1.00 | 0.00 |
| ATOM | 83 | CD2 | LEU | A | 532 | 34.970 | 8.206 | 86.334 | 1.00 | 0.00 |
| ATOM | 84 | C | LEU | A | 532 | 31.877 | 5.010 | 86.577 | 1.00 | 0.00 |
| ATOM | 85 | O | LEU | A | 532 | 31.237 | 5.497 | 85.639 | 1.00 | 0.00 |
| ATOM | 86 | N | VAL | A | 533 | 32.020 | 3.701 | 86.726 | 1.00 | 0.00 |
| ATOM | 88 | CA | VAL | A | 533 | 31.635 | 2.801 | 85.633 | 1.00 | 0.00 |
| ATOM | 89 | CB | VAL | A | 533 | 32.392 | 1.482 | 85.741 | 1.00 | 0.00 |
| ATOM | 90 | CG1 | VAL | A | 533 | 31.996 | 0.549 | 84.604 | 1.00 | 0.00 |
| ATOM | 91 | CG2 | VAL | A | 533 | 33.898 | 1.695 | 85.730 | 1.00 | 0.00 |
| ATOM | 92 | C | VAL | A | 533 | 30.137 | 2.530 | 85.710 | 1.00 | 0.00 |
| ATOM | 93 | O | VAL | A | 533 | 29.442 | 2.546 | 84.686 | 1.00 | 0.00 |
| ATOM | 94 | N | SER | A | 534 | 29.623 | 2.561 | 86.929 | 1.00 | 0.00 |
| ATOM | 96 | CA | SER | A | 534 | 28.178 | 2.440 | 87.121 | 1.00 | 0.00 |
| ATOM | 97 | CB | SER | A | 534 | 27.893 | 1.973 | 88.547 | 1.00 | 0.00 |
| ATOM | 98 | OG | SER | A | 534 | 28.439 | 2.917 | 89.458 | 1.00 | 0.00 |
| ATOM | 99 | C | SER | A | 534 | 27.479 | 3.769 | 86.836 | 1.00 | 0.00 |
| ATOM | 100 | O | SER | A | 534 | 26.379 | 3.756 | 86.274 | 1.00 | 0.00 |
| ATOM | 101 | N | LEU | A | 535 | 28.220 | 4.863 | 86.926 | 1.00 | 0.00 |
| ATOM | 103 | CA | LEU | A | 535 | 27.688 | 6.171 | 86.543 | 1.00 | 0.00 |
| ATOM | 104 | CB | LEU | A | 535 | 28.623 | 7.247 | 87.101 | 1.00 | 0.00 |
| ATOM | 105 | CG | LEU | A | 535 | 28.050 | 8.665 | 87.076 | 1.00 | 0.00 |
| ATOM | 106 | CD1 | LEU | A | 535 | 28.691 | 9.518 | 88.164 | 1.00 | 0.00 |
| ATOM | 107 | CD2 | LEU | A | 535 | 28.186 | 9.346 | 85.717 | 1.00 | 0.00 |
| ATOM | 108 | C | LEU | A | 535 | 27.595 | 6.254 | 85.025 | 1.00 | 0.00 |
| ATOM | 109 | O | LEU | A | 535 | 26.532 | 6.638 | 84.525 | 1.00 | 0.00 |
| ATOM | 110 | N | LEU | A | 536 | 28.530 | 5.617 | 84.333 | 1.00 | 0.00 |
| ATOM | 112 | CA | LEU | A | 536 | 28.472 | 5.531 | 82.867 | 1.00 | 0.00 |
| ATOM | 113 | CB | LEU | A | 536 | 29.718 | 4.810 | 82.361 | 1.00 | 0.00 |
| ATOM | 114 | CG | LEU | A | 536 | 30.987 | 5.631 | 82.524 | 1.00 | 0.00 |
| ATOM | 115 | CD1 | LEU | A | 536 | 32.223 | 4.782 | 82.252 | 1.00 | 0.00 |
| ATOM | 116 | CD2 | LEU | A | 536 | 30.958 | 6.847 | 81.611 | 1.00 | 0.00 |
| ATOM | 117 | C | LEU | A | 536 | 27.259 | 4.736 | 82.399 | 1.00 | 0.00 |
| ATOM | 118 | O | LEU | A | 536 | 26.520 | 5.207 | 81.527 | 1.00 | 0.00 |
| ATOM | 119 | N | GLU | A | 537 | 26.914 | 3.696 | 83.143 | 1.00 | 0.00 |
| ATOM | 121 | CA | GLU | A | 537 | 25.777 | 2.858 | 82.762 | 1.00 | 0.00 |
| ATOM | 122 | CB | GLU | A | 537 | 25.977 | 1.487 | 83.413 | 1.00 | 0.00 |
| ATOM | 123 | CG | GLU | A | 537 | 24.963 | 0.430 | 82.969 | 1.00 | 0.00 |
| ATOM | 124 | CD | GLU | A | 537 | 23.742 | 0.407 | 83.887 | 1.00 | 0.00 |
| ATOM | 125 | OE1 | GLU | A | 537 | 23.842 | 1.014 | 84.946 | 1.00 | 0.00 |
| ATOM | 126 | OE2 | GLU | A | 537 | 22.874 | −0.419 | 83.642 | 1.00 | 0.00 |
| ATOM | 127 | C | GLU | A | 537 | 24.435 | 3.482 | 83.158 | 1.00 | 0.00 |
| ATOM | 128 | O | GLU | A | 537 | 23.419 | 3.143 | 82.541 | 1.00 | 0.00 |
| ATOM | 129 | N | VAL | A | 538 | 24.441 | 4.447 | 84.063 | 1.00 | 0.00 |
| ATOM | 131 | CA | VAL | A | 538 | 23.200 | 5.129 | 84.441 | 1.00 | 0.00 |
| ATOM | 132 | CB | VAL | A | 538 | 23.276 | 5.436 | 85.937 | 1.00 | 0.00 |
| ATOM | 133 | CG1 | VAL | A | 538 | 22.137 | 6.333 | 86.412 | 1.00 | 0.00 |
| ATOM | 134 | CG2 | VAL | A | 538 | 23.303 | 4.148 | 86.754 | 1.00 | 0.00 |
| ATOM | 135 | C | VAL | A | 538 | 22.971 | 6.409 | 83.627 | 1.00 | 0.00 |
| ATOM | 136 | O | VAL | A | 538 | 21.821 | 6.826 | 83.441 | 1.00 | 0.00 |

TABLE I-continued

GR Homology Model Coordinates

| ATOM | 137 | N | ILE | A | 539 | 24.032 | 6.969 | 83.066 | 1.00 | 0.00 |
|---|---|---|---|---|---|---|---|---|---|---|
| ATOM | 139 | CA | ILE | A | 539 | 23.872 | 8.155 | 82.212 | 1.00 | 0.00 |
| ATOM | 140 | CB | ILE | A | 539 | 24.957 | 9.187 | 82.534 | 1.00 | 0.00 |
| ATOM | 141 | CG2 | ILE | A | 539 | 24.796 | 9.679 | 83.968 | 1.00 | 0.00 |
| ATOM | 142 | CG1 | ILE | A | 539 | 26.386 | 8.700 | 82.303 | 1.00 | 0.00 |
| ATOM | 143 | CD1 | ILE | A | 539 | 26.921 | 9.060 | 80.923 | 1.00 | 0.00 |
| ATOM | 144 | C | ILE | A | 539 | 23.823 | 7.782 | 80.730 | 1.00 | 0.00 |
| ATOM | 145 | O | ILE | A | 539 | 23.623 | 8.644 | 79.864 | 1.00 | 0.00 |
| ATOM | 146 | N | GLU | A | 540 | 24.011 | 6.501 | 80.459 | 1.00 | 0.00 |
| ATOM | 148 | CA | GLU | A | 540 | 23.833 | 5.941 | 79.118 | 1.00 | 0.00 |
| ATOM | 149 | CB | GLU | A | 540 | 24.149 | 4.449 | 79.241 | 1.00 | 0.00 |
| ATOM | 150 | CG | GLU | A | 540 | 24.286 | 3.751 | 77.894 | 1.00 | 0.00 |
| ATOM | 151 | CD | GLU | A | 540 | 25.492 | 4.312 | 77.147 | 1.00 | 0.00 |
| ATOM | 152 | OE1 | GLU | A | 540 | 26.468 | 4.639 | 77.809 | 1.00 | 0.00 |
| ATOM | 153 | OE2 | GLU | A | 540 | 25.402 | 4.442 | 75.935 | 1.00 | 0.00 |
| ATOM | 154 | C | GLU | A | 540 | 22.386 | 6.135 | 78.651 | 1.00 | 0.00 |
| ATOM | 155 | O | GLU | A | 540 | 21.446 | 5.834 | 79.392 | 1.00 | 0.00 |
| ATOM | 156 | N | PRO | A | 541 | 22.224 | 6.667 | 77.448 | 1.00 | 0.00 |
| ATOM | 157 | CA | PRO | A | 541 | 20.897 | 6.933 | 76.878 | 1.00 | 0.00 |
| ATOM | 158 | CB | PRO | A | 541 | 21.149 | 7.770 | 75.662 | 1.00 | 0.00 |
| ATOM | 159 | CG | PRO | A | 541 | 22.646 | 7.839 | 75.408 | 1.00 | 0.00 |
| ATOM | 160 | CD | PRO | A | 541 | 23.303 | 7.091 | 76.556 | 1.00 | 0.00 |
| ATOM | 161 | C | PRO | A | 541 | 20.126 | 5.663 | 76.507 | 1.00 | 0.00 |
| ATOM | 162 | O | PRO | A | 541 | 20.275 | 4.595 | 77.113 | 1.00 | 0.00 |
| ATOM | 163 | N | GLU | A | 542 | 19.264 | 5.827 | 75.519 | 1.00 | 0.00 |
| ATOM | 165 | CA | GLU | A | 542 | 18.347 | 4.761 | 75.107 | 1.00 | 0.00 |
| ATOM | 166 | CB | GLU | A | 542 | 16.936 | 5.359 | 75.169 | 1.00 | 0.00 |
| ATOM | 167 | CG | GLU | A | 542 | 15.810 | 4.352 | 74.940 | 1.00 | 0.00 |
| ATOM | 168 | CD | GLU | A | 542 | 15.851 | 3.251 | 75.999 | 1.00 | 0.00 |
| ATOM | 169 | OE1 | GLU | A | 542 | 15.282 | 3.461 | 77.059 | 1.00 | 0.00 |
| ATOM | 170 | OE2 | GLU | A | 542 | 16.528 | 2.260 | 75.754 | 1.00 | 0.00 |
| ATOM | 171 | C | GLU | A | 542 | 18.670 | 4.273 | 73.692 | 1.00 | 0.00 |
| ATOM | 172 | O | GLU | A | 542 | 19.133 | 5.060 | 72.858 | 1.00 | 0.00 |
| ATOM | 173 | N | VAL | A | 543 | 18.490 | 2.980 | 73.457 | 1.00 | 0.00 |
| ATOM | 175 | CA | VAL | A | 543 | 18.560 | 2.443 | 72.092 | 1.00 | 0.00 |
| ATOM | 176 | CB | VAL | A | 543 | 18.459 | 0.915 | 72.140 | 1.00 | 0.00 |
| ATOM | 177 | CG1 | VAL | A | 543 | 17.202 | 0.440 | 72.862 | 1.00 | 0.00 |
| ATOM | 178 | CG2 | VAL | A | 543 | 18.554 | 0.286 | 70.753 | 1.00 | 0.00 |
| ATOM | 179 | C | VAL | A | 543 | 17.420 | 3.067 | 71.284 | 1.00 | 0.00 |
| ATOM | 180 | O | VAL | A | 543 | 16.281 | 3.174 | 71.755 | 1.00 | 0.00 |
| ATOM | 181 | N | LEU | A | 544 | 17.781 | 3.629 | 70.145 | 1.00 | 0.00 |
| ATOM | 183 | CA | LEU | A | 544 | 16.825 | 4.430 | 69.382 | 1.00 | 0.00 |
| ATOM | 184 | CB | LEU | A | 544 | 17.562 | 5.656 | 68.864 | 1.00 | 0.00 |
| ATOM | 185 | CG | LEU | A | 544 | 18.042 | 6.512 | 70.029 | 1.00 | 0.00 |
| ATOM | 186 | CD1 | LEU | A | 544 | 19.047 | 7.556 | 69.573 | 1.00 | 0.00 |
| ATOM | 187 | CD2 | LEU | A | 544 | 16.872 | 7.155 | 70.766 | 1.00 | 0.00 |
| ATOM | 188 | C | LEU | A | 544 | 16.180 | 3.683 | 68.227 | 1.00 | 0.00 |
| ATOM | 189 | O | LEU | A | 544 | 16.693 | 2.676 | 67.728 | 1.00 | 0.00 |
| ATOM | 190 | N | TYR | A | 545 | 14.965 | 4.108 | 67.936 | 1.00 | 0.00 |
| ATOM | 192 | CA | TYR | A | 545 | 14.260 | 3.652 | 66.740 | 1.00 | 0.00 |
| ATOM | 193 | CB | TYR | A | 545 | 12.757 | 3.789 | 66.965 | 1.00 | 0.00 |
| ATOM | 194 | CG | TYR | A | 545 | 12.247 | 3.056 | 68.206 | 1.00 | 0.00 |
| ATOM | 195 | CD1 | TYR | A | 545 | 11.731 | 3.778 | 69.276 | 1.00 | 0.00 |
| ATOM | 196 | CE1 | TYR | A | 545 | 11.275 | 3.116 | 70.408 | 1.00 | 0.00 |
| ATOM | 197 | CZ | TYR | A | 545 | 11.333 | 1.730 | 70.467 | 1.00 | 0.00 |
| ATOM | 198 | OH | TYR | A | 545 | 10.913 | 1.073 | 71.603 | 1.00 | 0.00 |
| ATOM | 199 | CE2 | TYR | A | 545 | 11.838 | 1.004 | 69.396 | 1.00 | 0.00 |
| ATOM | 200 | CD2 | TYR | A | 545 | 12.294 | 1.668 | 68.264 | 1.00 | 0.00 |
| ATOM | 201 | C | TYR | A | 545 | 14.710 | 4.509 | 65.561 | 1.00 | 0.00 |
| ATOM | 202 | O | TYR | A | 545 | 14.930 | 5.715 | 65.709 | 1.00 | 0.00 |
| ATOM | 203 | N | ALA | A | 546 | 14.804 | 3.894 | 64.394 | 1.00 | 0.00 |
| ATOM | 205 | CA | ALA | A | 546 | 15.305 | 4.594 | 63.202 | 1.00 | 0.00 |
| ATOM | 206 | CB | ALA | A | 546 | 15.917 | 3.562 | 62.265 | 1.00 | 0.00 |
| ATOM | 207 | C | ALA | A | 546 | 14.225 | 5.362 | 62.447 | 1.00 | 0.00 |
| ATOM | 208 | O | ALA | A | 546 | 14.527 | 6.166 | 61.557 | 1.00 | 0.00 |
| ATOM | 209 | N | GLY | A | 547 | 12.977 | 5.107 | 62.802 | 1.00 | 0.00 |
| ATOM | 211 | CA | GLY | A | 547 | 11.850 | 5.753 | 62.127 | 1.00 | 0.00 |
| ATOM | 212 | C | GLY | A | 547 | 11.509 | 4.995 | 60.851 | 1.00 | 0.00 |
| ATOM | 213 | O | GLY | A | 547 | 11.063 | 5.577 | 59.856 | 1.00 | 0.00 |
| ATOM | 214 | N | TYR | A | 548 | 11.748 | 3.695 | 60.882 | 1.00 | 0.00 |
| ATOM | 216 | CA | TYR | A | 548 | 11.488 | 2.869 | 59.708 | 1.00 | 0.00 |
| ATOM | 217 | CB | TYR | A | 548 | 12.402 | 1.648 | 59.769 | 1.00 | 0.00 |
| ATOM | 218 | CG | TYR | A | 548 | 12.421 | 0.853 | 58.473 | 1.00 | 0.00 |
| ATOM | 219 | CD1 | TYR | A | 548 | 12.358 | 1.532 | 57.263 | 1.00 | 0.00 |
| ATOM | 220 | CE1 | TYR | A | 548 | 12.351 | 0.827 | 56.071 | 1.00 | 0.00 |
| ATOM | 221 | CZ | TYR | A | 548 | 12.421 | −0.558 | 56.092 | 1.00 | 0.00 |
| ATOM | 222 | OH | TYR | A | 548 | 12.386 | −1.249 | 54.905 | 1.00 | 0.00 |

TABLE I-continued

GR Homology Model Coordinates

| | | | | | | | | | | |
|---|---|---|---|---|---|---|---|---|---|---|
| ATOM | 223 | CE2 | TYR | A | 548 | 12.507 | −1.242 | 57.298 | 1.00 | 0.00 |
| ATOM | 224 | CD2 | TYR | A | 548 | 12.509 | −0.533 | 58.493 | 1.00 | 0.00 |
| ATOM | 225 | C | TYR | A | 548 | 10.018 | 2.457 | 59.680 | 1.00 | 0.00 |
| ATOM | 226 | O | TYR | A | 548 | 9.464 | 2.010 | 60.690 | 1.00 | 0.00 |
| ATOM | 227 | N | ASP | A | 549 | 9.403 | 2.586 | 58.512 | 1.00 | 0.00 |
| ATOM | 229 | CA | ASP | A | 549 | 7.982 | 2.238 | 58.349 | 1.00 | 0.00 |
| ATOM | 230 | CB | ASP | A | 549 | 7.420 | 2.999 | 57.152 | 1.00 | 0.00 |
| ATOM | 231 | CG | ASP | A | 549 | 7.556 | 4.508 | 57.353 | 1.00 | 0.00 |
| ATOM | 232 | OD1 | ASP | A | 549 | 6.803 | 5.048 | 58.149 | 1.00 | 0.00 |
| ATOM | 233 | OD2 | ASP | A | 549 | 8.414 | 5.085 | 56.700 | 1.00 | 0.00 |
| ATOM | 234 | C | ASP | A | 549 | 7.753 | 0.735 | 58.152 | 1.00 | 0.00 |
| ATOM | 235 | O | ASP | A | 549 | 6.596 | 0.294 | 58.159 | 1.00 | 0.00 |
| ATOM | 236 | N | SER | A | 550 | 8.824 | 0.003 | 57.862 | 1.00 | 0.00 |
| ATOM | 238 | CA | SER | A | 550 | 8.898 | −1.480 | 57.888 | 1.00 | 0.00 |
| ATOM | 239 | CB | SER | A | 550 | 8.434 | −1.940 | 59.266 | 1.00 | 0.00 |
| ATOM | 240 | OG | SER | A | 550 | 8.472 | −3.360 | 59.288 | 1.00 | 0.00 |
| ATOM | 241 | C | SER | A | 550 | 8.143 | −2.292 | 56.818 | 1.00 | 0.00 |
| ATOM | 242 | O | SER | A | 550 | 8.621 | −3.367 | 56.439 | 1.00 | 0.00 |
| ATOM | 243 | N | SER | A | 551 | 7.012 | −1.814 | 56.330 | 1.00 | 0.00 |
| ATOM | 245 | CA | SER | A | 551 | 6.255 | −2.568 | 55.326 | 1.00 | 0.00 |
| ATOM | 246 | CB | SER | A | 551 | 4.779 | −2.238 | 55.500 | 1.00 | 0.00 |
| ATOM | 247 | OG | SER | A | 551 | 4.424 | −2.568 | 56.836 | 1.00 | 0.00 |
| ATOM | 248 | C | SER | A | 551 | 6.695 | −2.216 | 53.912 | 1.00 | 0.00 |
| ATOM | 249 | O | SER | A | 551 | 6.514 | −3.002 | 52.976 | 1.00 | 0.00 |
| ATOM | 250 | N | VAL | A | 552 | 7.313 | −1.057 | 53.778 | 1.00 | 0.00 |
| ATOM | 252 | CA | VAL | A | 552 | 7.876 | −0.656 | 52.491 | 1.00 | 0.00 |
| ATOM | 253 | CB | VAL | A | 552 | 7.800 | 0.869 | 52.387 | 1.00 | 0.00 |
| ATOM | 254 | CG1 | VAL | A | 552 | 8.416 | 1.566 | 53.596 | 1.00 | 0.00 |
| ATOM | 255 | CG2 | VAL | A | 552 | 8.402 | 1.388 | 51.086 | 1.00 | 0.00 |
| ATOM | 256 | C | VAL | A | 552 | 9.313 | −1.167 | 52.375 | 1.00 | 0.00 |
| ATOM | 257 | O | VAL | A | 552 | 10.136 | −0.946 | 53.272 | 1.00 | 0.00 |
| ATOM | 258 | N | PRO | A | 553 | 9.580 | −1.907 | 51.310 | 1.00 | 0.00 |
| ATOM | 259 | CA | PRO | A | 553 | 10.933 | −2.405 | 51.049 | 1.00 | 0.00 |
| ATOM | 260 | CB | PRO | A | 553 | 10.815 | −3.246 | 49.816 | 1.00 | 0.00 |
| ATOM | 261 | CG | PRO | A | 553 | 9.387 | −3.180 | 49.297 | 1.00 | 0.00 |
| ATOM | 262 | CD | PRO | A | 553 | 8.625 | −2.294 | 50.269 | 1.00 | 0.00 |
| ATOM | 263 | C | PRO | A | 553 | 11.909 | −1.251 | 50.850 | 1.00 | 0.00 |
| ATOM | 264 | O | PRO | A | 553 | 11.602 | −0.258 | 50.179 | 1.00 | 0.00 |
| ATOM | 265 | N | ASP | A | 554 | 13.067 | −1.376 | 51.474 | 1.00 | 0.00 |
| ATOM | 267 | CA | ASP | A | 554 | 14.087 | −0.329 | 51.374 | 1.00 | 0.00 |
| ATOM | 268 | CB | ASP | A | 554 | 15.171 | −0.550 | 52.421 | 1.00 | 0.00 |
| ATOM | 269 | CG | ASP | A | 554 | 14.847 | 0.260 | 53.667 | 1.00 | 0.00 |
| ATOM | 270 | OD1 | ASP | A | 554 | 14.195 | 1.281 | 53.512 | 1.00 | 0.00 |
| ATOM | 271 | OD2 | ASP | A | 554 | 15.249 | −0.162 | 54.740 | 1.00 | 0.00 |
| ATOM | 272 | C | ASP | A | 554 | 14.761 | −0.252 | 50.016 | 1.00 | 0.00 |
| ATOM | 273 | O | ASP | A | 554 | 15.494 | −1.154 | 49.596 | 1.00 | 0.00 |
| ATOM | 274 | N | SER | A | 555 | 14.485 | 0.844 | 49.334 | 1.00 | 0.00 |
| ATOM | 276 | CA | SER | A | 555 | 15.327 | 1.251 | 48.211 | 1.00 | 0.00 |
| ATOM | 277 | CB | SER | A | 555 | 14.626 | 2.330 | 47.398 | 1.00 | 0.00 |
| ATOM | 278 | OG | SER | A | 555 | 14.660 | 3.522 | 48.172 | 1.00 | 0.00 |
| ATOM | 279 | C | SER | A | 555 | 16.577 | 1.853 | 48.831 | 1.00 | 0.00 |
| ATOM | 280 | O | SER | A | 555 | 16.568 | 2.154 | 50.032 | 1.00 | 0.00 |
| ATOM | 281 | N | THR | A | 556 | 17.572 | 2.174 | 48.023 | 1.00 | 0.00 |
| ATOM | 283 | CA | THR | A | 556 | 18.768 | 2.801 | 48.593 | 1.00 | 0.00 |
| ATOM | 284 | CB | THR | A | 556 | 19.911 | 2.769 | 47.583 | 1.00 | 0.00 |
| ATOM | 285 | OG1 | THR | A | 556 | 20.919 | 3.637 | 48.084 | 1.00 | 0.00 |
| ATOM | 286 | CG2 | THR | A | 556 | 19.499 | 3.272 | 46.202 | 1.00 | 0.00 |
| ATOM | 287 | C | THR | A | 556 | 18.499 | 4.234 | 49.061 | 1.00 | 0.00 |
| ATOM | 288 | O | THR | A | 556 | 18.986 | 4.614 | 50.132 | 1.00 | 0.00 |
| ATOM | 289 | N | TRP | A | 557 | 17.501 | 4.873 | 48.472 | 1.00 | 0.00 |
| ATOM | 291 | CA | TRP | A | 557 | 17.101 | 6.209 | 48.911 | 1.00 | 0.00 |
| ATOM | 292 | CB | TRP | A | 557 | 16.147 | 6.804 | 47.878 | 1.00 | 0.00 |
| ATOM | 293 | CG | TRP | A | 557 | 16.685 | 6.926 | 46.461 | 1.00 | 0.00 |
| ATOM | 294 | CD1 | TRP | A | 557 | 18.000 | 6.960 | 46.052 | 1.00 | 0.00 |
| ATOM | 295 | NE1 | TRP | A | 557 | 18.034 | 7.100 | 44.704 | 1.00 | 0.00 |
| ATOM | 297 | CE2 | TRP | A | 557 | 16.792 | 7.152 | 44.193 | 1.00 | 0.00 |
| ATOM | 298 | CZ2 | TRP | A | 557 | 16.313 | 7.298 | 42.899 | 1.00 | 0.00 |
| ATOM | 299 | CH2 | TRP | A | 557 | 14.940 | 7.321 | 42.671 | 1.00 | 0.00 |
| ATOM | 300 | CZ3 | TRP | A | 557 | 14.050 | 7.198 | 43.732 | 1.00 | 0.00 |
| ATOM | 301 | CE3 | TRP | A | 557 | 14.521 | 7.054 | 45.031 | 1.00 | 0.00 |
| ATOM | 302 | CD2 | TRP | A | 557 | 15.887 | 7.032 | 45.261 | 1.00 | 0.00 |
| ATOM | 303 | C | TRP | A | 557 | 16.387 | 6.134 | 50.259 | 1.00 | 0.00 |
| ATOM | 304 | O | TRP | A | 557 | 16.803 | 6.803 | 51.212 | 1.00 | 0.00 |
| ATOM | 305 | N | ARG | A | 558 | 15.517 | 5.145 | 50.411 | 1.00 | 0.00 |
| ATOM | 307 | CA | ARG | A | 558 | 14.791 | 4.994 | 51.677 | 1.00 | 0.00 |
| ATOM | 308 | CB | ARG | A | 558 | 13.663 | 3.993 | 51.479 | 1.00 | 0.00 |
| ATOM | 309 | CG | ARG | A | 558 | 12.693 | 4.469 | 50.410 | 1.00 | 0.00 |

TABLE I-continued

GR Homology Model Coordinates

| ATOM | 310 | CD  | ARG | A | 558 | 11.557 | 3.471  | 50.217 | 1.00 | 0.00 |
|------|-----|-----|-----|---|-----|--------|--------|--------|------|------|
| ATOM | 311 | NE  | ARG | A | 558 | 10.668 | 3.894  | 49.123 | 1.00 | 0.00 |
| ATOM | 312 | CZ  | ARG | A | 558 | 9.544  | 4.594  | 49.306 | 1.00 | 0.00 |
| ATOM | 313 | NH1 | ARG | A | 558 | 9.164  | 4.950  | 50.538 | 1.00 | 0.00 |
| ATOM | 314 | NH2 | ARG | A | 558 | 8.795  | 4.935  | 48.255 | 1.00 | 0.00 |
| ATOM | 315 | C   | ARG | A | 558 | 15.668 | 4.520  | 52.832 | 1.00 | 0.00 |
| ATOM | 316 | O   | ARG | A | 558 | 15.528 | 5.062  | 53.936 | 1.00 | 0.00 |
| ATOM | 317 | N   | ILE | A | 559 | 16.703 | 3.742  | 52.556 | 1.00 | 0.00 |
| ATOM | 319 | CA  | ILE | A | 559 | 17.563 | 3.325  | 53.663 | 1.00 | 0.00 |
| ATOM | 320 | CB  | ILE | A | 559 | 18.271 | 2.004  | 53.340 | 1.00 | 0.00 |
| ATOM | 321 | CG2 | ILE | A | 559 | 19.157 | 2.093  | 52.105 | 1.00 | 0.00 |
| ATOM | 322 | CG1 | ILE | A | 559 | 19.092 | 1.516  | 54.529 | 1.00 | 0.00 |
| ATOM | 323 | CD1 | ILE | A | 559 | 18.210 | 1.234  | 55.740 | 1.00 | 0.00 |
| ATOM | 324 | C   | ILE | A | 559 | 18.542 | 4.439  | 54.047 | 1.00 | 0.00 |
| ATOM | 325 | O   | ILE | A | 559 | 18.731 | 4.655  | 55.250 | 1.00 | 0.00 |
| ATOM | 326 | N   | MET | A | 560 | 18.863 | 5.331  | 53.121 | 1.00 | 0.00 |
| ATOM | 328 | CA  | MET | A | 560 | 19.720 | 6.457  | 53.488 | 1.00 | 0.00 |
| ATOM | 329 | CB  | MET | A | 560 | 20.376 | 7.042  | 52.243 | 1.00 | 0.00 |
| ATOM | 330 | CG  | MET | A | 560 | 21.336 | 6.047  | 51.603 | 1.00 | 0.00 |
| ATOM | 331 | SD  | MET | A | 560 | 22.247 | 6.663  | 50.168 | 1.00 | 0.00 |
| ATOM | 332 | CE  | MET | A | 560 | 20.856 | 7.241  | 49.168 | 1.00 | 0.00 |
| ATOM | 333 | C   | MET | A | 560 | 18.926 | 7.539  | 54.207 | 1.00 | 0.00 |
| ATOM | 334 | O   | MET | A | 560 | 19.406 | 8.049  | 55.224 | 1.00 | 0.00 |
| ATOM | 335 | N   | THR | A | 561 | 17.649 | 7.665  | 53.885 | 1.00 | 0.00 |
| ATOM | 337 | CA  | THR | A | 561 | 16.813 | 8.653  | 54.580 | 1.00 | 0.00 |
| ATOM | 338 | CB  | THR | A | 561 | 15.599 | 9.005  | 53.725 | 1.00 | 0.00 |
| ATOM | 339 | OG1 | THR | A | 561 | 14.891 | 7.812  | 53.416 | 1.00 | 0.00 |
| ATOM | 340 | CG2 | THR | A | 561 | 16.008 | 9.669  | 52.418 | 1.00 | 0.00 |
| ATOM | 341 | C   | THR | A | 561 | 16.358 | 8.187  | 55.966 | 1.00 | 0.00 |
| ATOM | 342 | O   | THR | A | 561 | 16.308 | 9.019  | 56.881 | 1.00 | 0.00 |
| ATOM | 343 | N   | THR | A | 562 | 16.273 | 6.886  | 56.203 | 1.00 | 0.00 |
| ATOM | 345 | CA  | THR | A | 562 | 15.961 | 6.459  | 57.573 | 1.00 | 0.00 |
| ATOM | 346 | CB  | THR | A | 562 | 15.204 | 5.130  | 57.599 | 1.00 | 0.00 |
| ATOM | 347 | OG1 | THR | A | 562 | 14.894 | 4.838  | 58.957 | 1.00 | 0.00 |
| ATOM | 348 | CG2 | THR | A | 562 | 16.002 | 3.962  | 57.033 | 1.00 | 0.00 |
| ATOM | 349 | C   | THR | A | 562 | 17.230 | 6.403  | 58.422 | 1.00 | 0.00 |
| ATOM | 350 | O   | THR | A | 562 | 17.162 | 6.627  | 59.636 | 1.00 | 0.00 |
| ATOM | 351 | N   | LEU | A | 563 | 18.384 | 6.388  | 57.770 | 1.00 | 0.00 |
| ATOM | 353 | CA  | LEU | A | 563 | 19.644 | 6.547  | 58.498 | 1.00 | 0.00 |
| ATOM | 354 | CB  | LEU | A | 563 | 20.762 | 5.840  | 57.741 | 1.00 | 0.00 |
| ATOM | 355 | CG  | LEU | A | 563 | 20.561 | 4.329  | 57.757 | 1.00 | 0.00 |
| ATOM | 356 | CD1 | LEU | A | 563 | 21.617 | 3.623  | 56.914 | 1.00 | 0.00 |
| ATOM | 357 | CD2 | LEU | A | 563 | 20.559 | 3.794  | 59.184 | 1.00 | 0.00 |
| ATOM | 358 | C   | LEU | A | 563 | 19.986 | 8.023  | 58.694 | 1.00 | 0.00 |
| ATOM | 359 | O   | LEU | A | 563 | 20.776 | 8.359  | 59.581 | 1.00 | 0.00 |
| ATOM | 360 | N   | ASN | A | 564 | 19.291 | 8.899  | 57.987 | 1.00 | 0.00 |
| ATOM | 362 | CA  | ASN | A | 564 | 19.408 | 10.340 | 58.231 | 1.00 | 0.00 |
| ATOM | 363 | CB  | ASN | A | 564 | 18.891 | 11.101 | 57.012 | 1.00 | 0.00 |
| ATOM | 364 | CG  | ASN | A | 564 | 19.845 | 11.032 | 55.820 | 1.00 | 0.00 |
| ATOM | 365 | OD1 | ASN | A | 564 | 19.410 | 11.086 | 54.658 | 1.00 | 0.00 |
| ATOM | 366 | ND2 | ASN | A | 564 | 21.132 | 11.072 | 56.120 | 1.00 | 0.00 |
| ATOM | 369 | C   | ASN | A | 564 | 18.562 | 10.738 | 59.432 | 1.00 | 0.00 |
| ATOM | 370 | O   | ASN | A | 564 | 19.003 | 11.535 | 60.274 | 1.00 | 0.00 |
| ATOM | 371 | N   | MET | A | 565 | 17.446 | 10.045 | 59.595 | 1.00 | 0.00 |
| ATOM | 373 | CA  | MET | A | 565 | 16.570 | 10.286 | 60.742 | 1.00 | 0.00 |
| ATOM | 374 | CB  | MET | A | 565 | 15.213 | 9.662  | 60.441 | 1.00 | 0.00 |
| ATOM | 375 | CG  | MET | A | 565 | 14.193 | 10.003 | 61.520 | 1.00 | 0.00 |
| ATOM | 376 | SD  | MET | A | 565 | 13.873 | 11.769 | 61.731 | 1.00 | 0.00 |
| ATOM | 377 | CE  | MET | A | 565 | 13.319 | 12.168 | 60.056 | 1.00 | 0.00 |
| ATOM | 378 | C   | MET | A | 565 | 17.158 | 9.662  | 62.003 | 1.00 | 0.00 |
| ATOM | 379 | O   | MET | A | 565 | 17.307 | 10.352 | 63.021 | 1.00 | 0.00 |
| ATOM | 380 | N   | LEU | A | 566 | 17.734 | 8.481  | 61.847 | 1.00 | 0.00 |
| ATOM | 382 | CA  | LEU | A | 566 | 18.408 | 7.825  | 62.971 | 1.00 | 0.00 |
| ATOM | 383 | CB  | LEU | A | 566 | 18.670 | 6.378  | 62.581 | 1.00 | 0.00 |
| ATOM | 384 | CG  | LEU | A | 566 | 19.330 | 5.598  | 63.709 | 1.00 | 0.00 |
| ATOM | 385 | CD1 | LEU | A | 566 | 18.467 | 5.589  | 64.967 | 1.00 | 0.00 |
| ATOM | 386 | CD2 | LEU | A | 566 | 19.635 | 4.179  | 63.257 | 1.00 | 0.00 |
| ATOM | 387 | C   | LEU | A | 566 | 19.727 | 8.514  | 63.320 | 1.00 | 0.00 |
| ATOM | 388 | O   | LEU | A | 566 | 20.020 | 8.674  | 64.510 | 1.00 | 0.00 |
| ATOM | 389 | N   | GLY | A | 567 | 20.361 | 9.125  | 62.332 | 1.00 | 0.00 |
| ATOM | 391 | CA  | GLY | A | 567 | 21.553 | 9.948  | 62.554 | 1.00 | 0.00 |
| ATOM | 392 | C   | GLY | A | 567 | 21.234 | 11.124 | 63.467 | 1.00 | 0.00 |
| ATOM | 393 | O   | GLY | A | 567 | 21.854 | 11.263 | 64.527 | 1.00 | 0.00 |
| ATOM | 394 | N   | GLY | A | 568 | 20.165 | 11.840 | 63.150 | 1.00 | 0.00 |
| ATOM | 396 | CA  | GLY | A | 568 | 19.707 | 12.956 | 63.986 | 1.00 | 0.00 |
| ATOM | 397 | C   | GLY | A | 568 | 19.314 | 12.517 | 65.396 | 1.00 | 0.00 |
| ATOM | 398 | O   | GLY | A | 568 | 19.749 | 13.140 | 66.375 | 1.00 | 0.00 |

TABLE I-continued

GR Homology Model Coordinates

| ATOM | 399 | N | ARG | A | 569 | 18.646 | 11.378 | 65.501 | 1.00 | 0.00 |
|---|---|---|---|---|---|---|---|---|---|---|
| ATOM | 401 | CA | ARG | A | 569 | 18.287 | 10.823 | 66.814 | 1.00 | 0.00 |
| ATOM | 402 | CB | ARG | A | 569 | 17.431 | 9.576 | 66.607 | 1.00 | 0.00 |
| ATOM | 403 | CG | ARG | A | 569 | 16.096 | 9.914 | 65.955 | 1.00 | 0.00 |
| ATOM | 404 | CD | ARG | A | 569 | 15.301 | 10.883 | 66.824 | 1.00 | 0.00 |
| ATOM | 405 | NE | ARG | A | 569 | 14.045 | 11.279 | 66.170 | 1.00 | 0.00 |
| ATOM | 406 | CZ | ARG | A | 569 | 13.861 | 12.476 | 65.610 | 1.00 | 0.00 |
| ATOM | 407 | NH1 | ARG | A | 569 | 14.862 | 13.359 | 65.576 | 1.00 | 0.00 |
| ATOM | 408 | NH2 | ARG | A | 569 | 12.686 | 12.778 | 65.055 | 1.00 | 0.00 |
| ATOM | 409 | C | ARG | A | 569 | 19.514 | 10.442 | 67.645 | 1.00 | 0.00 |
| ATOM | 410 | O | ARG | A | 569 | 19.581 | 10.806 | 68.826 | 1.00 | 0.00 |
| ATOM | 411 | N | GLN | A | 570 | 20.552 | 9.933 | 67.003 | 1.00 | 0.00 |
| ATOM | 413 | CA | GLN | A | 570 | 21.776 | 9.590 | 67.729 | 1.00 | 0.00 |
| ATOM | 414 | CB | GLN | A | 570 | 22.581 | 8.600 | 66.900 | 1.00 | 0.00 |
| ATOM | 415 | CG | GLN | A | 570 | 21.822 | 7.289 | 66.733 | 1.00 | 0.00 |
| ATOM | 416 | CD | GLN | A | 570 | 22.624 | 6.329 | 65.864 | 1.00 | 0.00 |
| ATOM | 417 | OE1 | GLN | A | 570 | 22.360 | 6.182 | 64.665 | 1.00 | 0.00 |
| ATOM | 418 | NE2 | GLN | A | 570 | 23.624 | 5.716 | 66.473 | 1.00 | 0.00 |
| ATOM | 421 | C | GLN | A | 570 | 22.630 | 10.813 | 68.041 | 1.00 | 0.00 |
| ATOM | 422 | O | GLN | A | 570 | 23.319 | 10.806 | 69.065 | 1.00 | 0.00 |
| ATOM | 423 | N | VAL | A | 571 | 22.418 | 11.909 | 67.331 | 1.00 | 0.00 |
| ATOM | 425 | CA | VAL | A | 571 | 23.112 | 13.154 | 67.664 | 1.00 | 0.00 |
| ATOM | 426 | CB | VAL | A | 571 | 23.083 | 14.085 | 66.455 | 1.00 | 0.00 |
| ATOM | 427 | CG1 | VAL | A | 571 | 23.572 | 15.482 | 66.818 | 1.00 | 0.00 |
| ATOM | 428 | CG2 | VAL | A | 571 | 23.896 | 13.518 | 65.298 | 1.00 | 0.00 |
| ATOM | 429 | C | VAL | A | 571 | 22.462 | 13.844 | 68.858 | 1.00 | 0.00 |
| ATOM | 430 | O | VAL | A | 571 | 23.181 | 14.252 | 69.780 | 1.00 | 0.00 |
| ATOM | 431 | N | ILE | A | 572 | 21.149 | 13.728 | 68.986 | 1.00 | 0.00 |
| ATOM | 433 | CA | ILE | A | 572 | 20.496 | 14.356 | 70.137 | 1.00 | 0.00 |
| ATOM | 434 | CB | ILE | A | 572 | 19.057 | 14.749 | 69.756 | 1.00 | 0.00 |
| ATOM | 435 | CG2 | ILE | A | 572 | 18.171 | 13.538 | 69.493 | 1.00 | 0.00 |
| ATOM | 436 | CG1 | ILE | A | 572 | 18.387 | 15.664 | 70.784 | 1.00 | 0.00 |
| ATOM | 437 | CD1 | ILE | A | 572 | 17.740 | 14.905 | 71.940 | 1.00 | 0.00 |
| ATOM | 438 | C | ILE | A | 572 | 20.613 | 13.460 | 71.378 | 1.00 | 0.00 |
| ATOM | 439 | O | ILE | A | 572 | 20.808 | 13.986 | 72.481 | 1.00 | 0.00 |
| ATOM | 440 | N | ALA | A | 573 | 20.826 | 12.169 | 71.170 | 1.00 | 0.00 |
| ATOM | 442 | CA | ALA | A | 573 | 21.104 | 11.288 | 72.304 | 1.00 | 0.00 |
| ATOM | 443 | CB | ALA | A | 573 | 20.788 | 9.851 | 71.907 | 1.00 | 0.00 |
| ATOM | 444 | C | ALA | A | 573 | 22.564 | 11.389 | 72.735 | 1.00 | 0.00 |
| ATOM | 445 | O | ALA | A | 573 | 22.844 | 11.360 | 73.939 | 1.00 | 0.00 |
| ATOM | 446 | N | ALA | A | 574 | 23.431 | 11.768 | 71.809 | 1.00 | 0.00 |
| ATOM | 448 | CA | ALA | A | 574 | 24.844 | 11.946 | 72.137 | 1.00 | 0.00 |
| ATOM | 449 | CB | ALA | A | 574 | 25.679 | 11.832 | 70.868 | 1.00 | 0.00 |
| ATOM | 450 | C | ALA | A | 574 | 25.115 | 13.288 | 72.800 | 1.00 | 0.00 |
| ATOM | 451 | O | ALA | A | 574 | 25.967 | 13.344 | 73.691 | 1.00 | 0.00 |
| ATOM | 452 | N | VAL | A | 575 | 24.280 | 14.287 | 72.556 | 1.00 | 0.00 |
| ATOM | 454 | CA | VAL | A | 575 | 24.466 | 15.544 | 73.284 | 1.00 | 0.00 |
| ATOM | 455 | CB | VAL | A | 575 | 23.973 | 16.736 | 72.457 | 1.00 | 0.00 |
| ATOM | 456 | CG1 | VAL | A | 575 | 22.492 | 16.662 | 72.109 | 1.00 | 0.00 |
| ATOM | 457 | CG2 | VAL | A | 575 | 24.283 | 18.056 | 73.154 | 1.00 | 0.00 |
| ATOM | 458 | C | VAL | A | 575 | 23.794 | 15.479 | 74.657 | 1.00 | 0.00 |
| ATOM | 459 | O | VAL | A | 575 | 24.335 | 16.042 | 75.617 | 1.00 | 0.00 |
| ATOM | 460 | N | LYS | A | 576 | 22.851 | 14.561 | 74.817 | 1.00 | 0.00 |
| ATOM | 462 | CA | LYS | A | 576 | 22.260 | 14.340 | 76.136 | 1.00 | 0.00 |
| ATOM | 463 | CB | LYS | A | 576 | 20.923 | 13.631 | 75.954 | 1.00 | 0.00 |
| ATOM | 464 | CG | LYS | A | 576 | 20.179 | 13.495 | 77.277 | 1.00 | 0.00 |
| ATOM | 465 | CD | LYS | A | 576 | 19.845 | 14.863 | 77.866 | 1.00 | 0.00 |
| ATOM | 466 | CE | LYS | A | 576 | 18.933 | 15.661 | 76.940 | 1.00 | 0.00 |
| ATOM | 467 | NZ | LYS | A | 576 | 18.649 | 16.992 | 77.502 | 1.00 | 0.00 |
| ATOM | 468 | C | LYS | A | 576 | 23.192 | 13.489 | 76.996 | 1.00 | 0.00 |
| ATOM | 469 | O | LYS | A | 576 | 23.433 | 13.827 | 78.161 | 1.00 | 0.00 |
| ATOM | 470 | N | TRP | A | 577 | 23.921 | 12.600 | 76.341 | 1.00 | 0.00 |
| ATOM | 472 | CA | TRP | A | 577 | 24.933 | 11.783 | 77.016 | 1.00 | 0.00 |
| ATOM | 473 | CB | TRP | A | 577 | 25.275 | 10.636 | 76.070 | 1.00 | 0.00 |
| ATOM | 474 | CG | TRP | A | 577 | 26.408 | 9.734 | 76.514 | 1.00 | 0.00 |
| ATOM | 475 | CD1 | TRP | A | 577 | 26.335 | 8.699 | 77.416 | 1.00 | 0.00 |
| ATOM | 476 | NE1 | TRP | A | 577 | 27.566 | 8.143 | 77.534 | 1.00 | 0.00 |
| ATOM | 478 | CE2 | TRP | A | 577 | 28.459 | 8.765 | 76.744 | 1.00 | 0.00 |
| ATOM | 479 | CZ2 | TRP | A | 577 | 29.818 | 8.580 | 76.527 | 1.00 | 0.00 |
| ATOM | 480 | CH2 | TRP | A | 577 | 30.489 | 9.395 | 75.623 | 1.00 | 0.00 |
| ATOM | 481 | CZ3 | TRP | A | 577 | 29.809 | 10.396 | 74.939 | 1.00 | 0.00 |
| ATOM | 482 | CE3 | TRP | A | 577 | 28.451 | 10.596 | 75.156 | 1.00 | 0.00 |
| ATOM | 483 | CD2 | TRP | A | 577 | 27.778 | 9.786 | 76.059 | 1.00 | 0.00 |
| ATOM | 484 | C | TRP | A | 577 | 26.189 | 12.595 | 77.335 | 1.00 | 0.00 |
| ATOM | 485 | O | TRP | A | 577 | 26.751 | 12.448 | 78.427 | 1.00 | 0.00 |
| ATOM | 486 | N | ALA | A | 578 | 26.443 | 13.617 | 76.534 | 1.00 | 0.00 |
| ATOM | 488 | CA | ALA | A | 578 | 27.569 | 14.521 | 76.777 | 1.00 | 0.00 |

TABLE I-continued

GR Homology Model Coordinates

| ATOM | 489 | CB | ALA | A | 578 | 27.869 | 15.253 | 75.477 | 1.00 | 0.00 |
|---|---|---|---|---|---|---|---|---|---|---|
| ATOM | 490 | C | ALA | A | 578 | 27.265 | 15.526 | 77.887 | 1.00 | 0.00 |
| ATOM | 491 | O | ALA | A | 578 | 28.163 | 15.909 | 78.642 | 1.00 | 0.00 |
| ATOM | 492 | N | LYS | A | 579 | 25.986 | 15.774 | 78.112 | 1.00 | 0.00 |
| ATOM | 494 | CA | LYS | A | 579 | 25.557 | 16.603 | 79.243 | 1.00 | 0.00 |
| ATOM | 495 | CB | LYS | A | 579 | 24.318 | 17.406 | 78.849 | 1.00 | 0.00 |
| ATOM | 496 | CG | LYS | A | 579 | 24.591 | 18.882 | 78.523 | 1.00 | 0.00 |
| ATOM | 497 | CD | LYS | A | 579 | 25.272 | 19.154 | 77.177 | 1.00 | 0.00 |
| ATOM | 498 | CE | LYS | A | 579 | 26.797 | 19.067 | 77.221 | 1.00 | 0.00 |
| ATOM | 499 | NZ | LYS | A | 579 | 27.364 | 20.023 | 78.184 | 1.00 | 0.00 |
| ATOM | 500 | C | LYS | A | 579 | 25.264 | 15.765 | 80.489 | 1.00 | 0.00 |
| ATOM | 501 | O | LYS | A | 579 | 24.777 | 16.293 | 81.496 | 1.00 | 0.00 |
| ATOM | 502 | N | ALA | A | 580 | 25.488 | 14.466 | 80.394 | 1.00 | 0.00 |
| ATOM | 504 | CA | ALA | A | 580 | 25.344 | 13.584 | 81.548 | 1.00 | 0.00 |
| ATOM | 505 | CB | ALA | A | 580 | 24.418 | 12.440 | 81.155 | 1.00 | 0.00 |
| ATOM | 506 | C | ALA | A | 580 | 26.699 | 13.040 | 81.996 | 1.00 | 0.00 |
| ATOM | 507 | O | ALA | A | 580 | 26.812 | 12.466 | 83.087 | 1.00 | 0.00 |
| ATOM | 508 | N | ILE | A | 581 | 27.712 | 13.222 | 81.164 | 1.00 | 0.00 |
| ATOM | 510 | CA | ILE | A | 581 | 29.057 | 12.754 | 81.513 | 1.00 | 0.00 |
| ATOM | 511 | CB | ILE | A | 581 | 29.733 | 12.233 | 80.235 | 1.00 | 0.00 |
| ATOM | 512 | CG2 | ILE | A | 581 | 29.876 | 13.305 | 79.168 | 1.00 | 0.00 |
| ATOM | 513 | CG1 | ILE | A | 581 | 31.085 | 11.594 | 80.507 | 1.00 | 0.00 |
| ATOM | 514 | CD1 | ILE | A | 581 | 30.914 | 10.291 | 81.274 | 1.00 | 0.00 |
| ATOM | 515 | C | ILE | A | 581 | 29.872 | 13.854 | 82.211 | 1.00 | 0.00 |
| ATOM | 516 | O | ILE | A | 581 | 30.131 | 14.936 | 81.664 | 1.00 | 0.00 |
| ATOM | 517 | N | PRO | A | 582 | 30.282 | 13.547 | 83.432 | 1.00 | 0.00 |
| ATOM | 518 | CA | PRO | A | 582 | 31.176 | 14.428 | 84.187 | 1.00 | 0.00 |
| ATOM | 519 | CB | PRO | A | 582 | 31.409 | 13.739 | 85.496 | 1.00 | 0.00 |
| ATOM | 520 | CG | PRO | A | 582 | 30.686 | 12.401 | 85.493 | 1.00 | 0.00 |
| ATOM | 521 | CD | PRO | A | 582 | 29.980 | 12.307 | 84.151 | 1.00 | 0.00 |
| ATOM | 522 | C | PRO | A | 582 | 32.481 | 14.642 | 83.430 | 1.00 | 0.00 |
| ATOM | 523 | O | PRO | A | 582 | 32.879 | 13.809 | 82.607 | 1.00 | 0.00 |
| ATOM | 524 | N | GLY | A | 583 | 33.036 | 15.832 | 83.566 | 1.00 | 0.00 |
| ATOM | 526 | CA | GLY | A | 583 | 34.260 | 16.168 | 82.837 | 1.00 | 0.00 |
| ATOM | 527 | C | GLY | A | 583 | 33.958 | 16.979 | 81.579 | 1.00 | 0.00 |
| ATOM | 528 | O | GLY | A | 583 | 34.499 | 18.078 | 81.396 | 1.00 | 0.00 |
| ATOM | 529 | N | PHE | A | 584 | 33.011 | 16.502 | 80.783 | 1.00 | 0.00 |
| ATOM | 531 | CA | PHE | A | 584 | 32.704 | 17.165 | 79.513 | 1.00 | 0.00 |
| ATOM | 532 | CB | PHE | A | 584 | 31.836 | 16.235 | 78.682 | 1.00 | 0.00 |
| ATOM | 533 | CG | PHE | A | 584 | 31.544 | 16.728 | 77.270 | 1.00 | 0.00 |
| ATOM | 534 | CD1 | PHE | A | 584 | 32.456 | 16.481 | 76.254 | 1.00 | 0.00 |
| ATOM | 535 | CE1 | PHE | A | 584 | 32.187 | 16.910 | 74.962 | 1.00 | 0.00 |
| ATOM | 536 | CZ | PHE | A | 584 | 31.011 | 17.593 | 74.688 | 1.00 | 0.00 |
| ATOM | 537 | CE2 | PHE | A | 584 | 30.109 | 17.860 | 75.708 | 1.00 | 0.00 |
| ATOM | 538 | CD2 | PHE | A | 584 | 30.377 | 17.430 | 77.001 | 1.00 | 0.00 |
| ATOM | 539 | C | PHE | A | 584 | 31.976 | 18.478 | 79.752 | 1.00 | 0.00 |
| ATOM | 540 | O | PHE | A | 584 | 32.399 | 19.506 | 79.207 | 1.00 | 0.00 |
| ATOM | 541 | N | ARG | A | 585 | 31.186 | 18.502 | 80.814 | 1.00 | 0.00 |
| ATOM | 543 | CA | ARG | A | 585 | 30.507 | 19.733 | 81.240 | 1.00 | 0.00 |
| ATOM | 544 | CB | ARG | A | 585 | 29.345 | 19.333 | 82.131 | 1.00 | 0.00 |
| ATOM | 545 | CG | ARG | A | 585 | 28.432 | 18.343 | 81.426 | 1.00 | 0.00 |
| ATOM | 546 | CD | ARG | A | 585 | 27.286 | 17.947 | 82.343 | 1.00 | 0.00 |
| ATOM | 547 | NE | ARG | A | 585 | 27.795 | 17.323 | 83.574 | 1.00 | 0.00 |
| ATOM | 548 | CZ | ARG | A | 585 | 27.390 | 17.697 | 84.789 | 1.00 | 0.00 |
| ATOM | 549 | NH1 | ARG | A | 585 | 26.498 | 18.681 | 84.920 | 1.00 | 0.00 |
| ATOM | 550 | NH2 | ARG | A | 585 | 27.886 | 17.096 | 85.873 | 1.00 | 0.00 |
| ATOM | 551 | C | ARG | A | 585 | 31.414 | 20.686 | 82.026 | 1.00 | 0.00 |
| ATOM | 552 | O | ARG | A | 585 | 30.976 | 21.769 | 82.426 | 1.00 | 0.00 |
| ATOM | 553 | N | ASN | A | 586 | 32.657 | 20.285 | 82.241 | 1.00 | 0.00 |
| ATOM | 555 | CA | ASN | A | 586 | 33.616 | 21.107 | 82.973 | 1.00 | 0.00 |
| ATOM | 556 | CB | ASN | A | 586 | 34.311 | 20.210 | 83.992 | 1.00 | 0.00 |
| ATOM | 557 | CG | ASN | A | 586 | 33.266 | 19.620 | 84.938 | 1.00 | 0.00 |
| ATOM | 558 | OD1 | ASN | A | 586 | 32.806 | 18.480 | 84.772 | 1.00 | 0.00 |
| ATOM | 559 | ND2 | ASN | A | 586 | 32.846 | 20.442 | 85.882 | 1.00 | 0.00 |
| ATOM | 562 | C | ASN | A | 586 | 34.619 | 21.717 | 81.997 | 1.00 | 0.00 |
| ATOM | 563 | O | ASN | A | 586 | 35.348 | 22.658 | 82.337 | 1.00 | 0.00 |
| ATOM | 564 | N | LEU | A | 587 | 34.618 | 21.187 | 80.783 | 1.00 | 0.00 |
| ATOM | 566 | CA | LEU | A | 587 | 35.398 | 21.759 | 79.679 | 1.00 | 0.00 |
| ATOM | 567 | CB | LEU | A | 587 | 35.372 | 20.789 | 78.503 | 1.00 | 0.00 |
| ATOM | 568 | CG | LEU | A | 587 | 36.045 | 19.467 | 78.838 | 1.00 | 0.00 |
| ATOM | 569 | CD1 | LEU | A | 587 | 35.842 | 18.453 | 77.720 | 1.00 | 0.00 |
| ATOM | 570 | CD2 | LEU | A | 587 | 37.526 | 19.678 | 79.110 | 1.00 | 0.00 |
| ATOM | 571 | C | LEU | A | 587 | 34.792 | 23.075 | 79.216 | 1.00 | 0.00 |
| ATOM | 572 | O | LEU | A | 587 | 33.635 | 23.381 | 79.521 | 1.00 | 0.00 |
| ATOM | 573 | N | HIS | A | 588 | 35.584 | 23.846 | 78.490 | 1.00 | 0.00 |
| ATOM | 575 | CA | HIS | A | 588 | 35.078 | 25.082 | 77.877 | 1.00 | 0.00 |
| ATOM | 576 | CB | HIS | A | 588 | 36.258 | 25.795 | 77.222 | 1.00 | 0.00 |

TABLE I-continued

GR Homology Model Coordinates

| ATOM | 577 | CG | HIS | A | 588 | 35.913 | 27.059 | 76.463 | 1.00 | 0.00 |
|---|---|---|---|---|---|---|---|---|---|---|
| ATOM | 578 | ND1 | HIS | A | 588 | 36.161 | 27.298 | 75.163 | 1.00 | 0.00 |
| ATOM | 580 | CE1 | HIS | A | 588 | 35.694 | 28.526 | 74.849 | 1.00 | 0.00 |
| ATOM | 581 | NE2 | HIS | A | 588 | 35.158 | 29.064 | 75.965 | 1.00 | 0.00 |
| ATOM | 582 | CD2 | HIS | A | 588 | 35.292 | 28.175 | 76.973 | 1.00 | 0.00 |
| ATOM | 583 | C | HIS | A | 588 | 33.995 | 24.730 | 76.853 | 1.00 | 0.00 |
| ATOM | 584 | O | HIS | A | 588 | 34.136 | 23.734 | 76.133 | 1.00 | 0.00 |
| ATOM | 585 | N | LEU | A | 589 | 32.998 | 25.592 | 76.706 | 1.00 | 0.00 |
| ATOM | 587 | CA | LEU | A | 589 | 31.819 | 25.293 | 75.877 | 1.00 | 0.00 |
| ATOM | 588 | CB | LEU | A | 589 | 30.798 | 26.405 | 76.119 | 1.00 | 0.00 |
| ATOM | 589 | CG | LEU | A | 589 | 29.468 | 26.173 | 75.404 | 1.00 | 0.00 |
| ATOM | 590 | CD1 | LEU | A | 589 | 28.292 | 26.500 | 76.318 | 1.00 | 0.00 |
| ATOM | 591 | CD2 | LEU | A | 589 | 29.373 | 26.957 | 74.097 | 1.00 | 0.00 |
| ATOM | 592 | C | LEU | A | 589 | 32.119 | 25.144 | 74.382 | 1.00 | 0.00 |
| ATOM | 593 | O | LEU | A | 589 | 31.635 | 24.185 | 73.770 | 1.00 | 0.00 |
| ATOM | 594 | N | ASP | A | 590 | 33.128 | 25.841 | 73.881 | 1.00 | 0.00 |
| ATOM | 596 | CA | ASP | A | 590 | 33.489 | 25.662 | 72.466 | 1.00 | 0.00 |
| ATOM | 597 | CB | ASP | A | 590 | 34.272 | 26.871 | 71.966 | 1.00 | 0.00 |
| ATOM | 598 | CG | ASP | A | 590 | 33.418 | 28.137 | 72.020 | 1.00 | 0.00 |
| ATOM | 599 | OD1 | ASP | A | 590 | 32.206 | 28.017 | 71.906 | 1.00 | 0.00 |
| ATOM | 600 | OD2 | ASP | A | 590 | 33.989 | 29.191 | 72.256 | 1.00 | 0.00 |
| ATOM | 601 | C | ASP | A | 590 | 34.313 | 24.390 | 72.254 | 1.00 | 0.00 |
| ATOM | 602 | O | ASP | A | 590 | 34.208 | 23.760 | 71.194 | 1.00 | 0.00 |
| ATOM | 603 | N | ASP | A | 591 | 34.855 | 23.863 | 73.341 | 1.00 | 0.00 |
| ATOM | 605 | CA | ASP | A | 591 | 35.599 | 22.607 | 73.273 | 1.00 | 0.00 |
| ATOM | 606 | CB | ASP | A | 591 | 36.581 | 22.508 | 74.432 | 1.00 | 0.00 |
| ATOM | 607 | CG | ASP | A | 591 | 37.570 | 23.665 | 74.440 | 1.00 | 0.00 |
| ATOM | 608 | OD1 | ASP | A | 591 | 37.852 | 24.229 | 73.392 | 1.00 | 0.00 |
| ATOM | 609 | OD2 | ASP | A | 591 | 38.072 | 23.970 | 75.512 | 1.00 | 0.00 |
| ATOM | 610 | C | ASP | A | 591 | 34.624 | 21.448 | 73.385 | 1.00 | 0.00 |
| ATOM | 611 | O | ASP | A | 591 | 34.844 | 20.408 | 72.759 | 1.00 | 0.00 |
| ATOM | 612 | N | GLN | A | 592 | 33.473 | 21.710 | 73.984 | 1.00 | 0.00 |
| ATOM | 614 | CA | GLN | A | 592 | 32.406 | 20.714 | 74.060 | 1.00 | 0.00 |
| ATOM | 615 | CB | GLN | A | 592 | 31.336 | 21.222 | 75.015 | 1.00 | 0.00 |
| ATOM | 616 | CG | GLN | A | 592 | 31.875 | 21.427 | 76.421 | 1.00 | 0.00 |
| ATOM | 617 | CD | GLN | A | 592 | 30.825 | 22.143 | 77.264 | 1.00 | 0.00 |
| ATOM | 618 | OE1 | GLN | A | 592 | 29.914 | 22.790 | 76.735 | 1.00 | 0.00 |
| ATOM | 619 | NE2 | GLN | A | 592 | 30.989 | 22.043 | 78.568 | 1.00 | 0.00 |
| ATOM | 622 | C | GLN | A | 592 | 31.776 | 20.539 | 72.690 | 1.00 | 0.00 |
| ATOM | 623 | O | GLN | A | 592 | 31.686 | 19.408 | 72.189 | 1.00 | 0.00 |
| ATOM | 624 | N | MET | A | 593 | 31.592 | 21.662 | 72.013 | 1.00 | 0.00 |
| ATOM | 626 | CA | MET | A | 593 | 31.067 | 21.654 | 70.647 | 1.00 | 0.00 |
| ATOM | 627 | CB | MET | A | 593 | 30.972 | 23.090 | 70.151 | 1.00 | 0.00 |
| ATOM | 628 | CG | MET | A | 593 | 29.986 | 23.908 | 70.975 | 1.00 | 0.00 |
| ATOM | 629 | SD | MET | A | 593 | 29.862 | 25.647 | 70.499 | 1.00 | 0.00 |
| ATOM | 630 | CE | MET | A | 593 | 29.469 | 25.427 | 68.748 | 1.00 | 0.00 |
| ATOM | 631 | C | MET | A | 593 | 31.986 | 20.873 | 69.722 | 1.00 | 0.00 |
| ATOM | 632 | O | MET | A | 593 | 31.611 | 19.767 | 69.308 | 1.00 | 0.00 |
| ATOM | 633 | N | THR | A | 594 | 33.252 | 21.260 | 69.701 | 1.00 | 0.00 |
| ATOM | 635 | CA | THR | A | 594 | 34.221 | 20.615 | 68.803 | 1.00 | 0.00 |
| ATOM | 636 | CB | THR | A | 594 | 35.519 | 21.417 | 68.818 | 1.00 | 0.00 |
| ATOM | 637 | OG1 | THR | A | 594 | 35.986 | 21.505 | 70.160 | 1.00 | 0.00 |
| ATOM | 638 | CG2 | THR | A | 594 | 35.308 | 22.832 | 68.291 | 1.00 | 0.00 |
| ATOM | 639 | C | THR | A | 594 | 34.532 | 19.161 | 69.161 | 1.00 | 0.00 |
| ATOM | 640 | O | THR | A | 594 | 34.664 | 18.345 | 68.243 | 1.00 | 0.00 |
| ATOM | 641 | N | LEU | A | 595 | 34.388 | 18.783 | 70.419 | 1.00 | 0.00 |
| ATOM | 643 | CA | LEU | A | 595 | 34.655 | 17.401 | 70.820 | 1.00 | 0.00 |
| ATOM | 644 | CB | LEU | A | 595 | 34.707 | 17.349 | 72.337 | 1.00 | 0.00 |
| ATOM | 645 | CG | LEU | A | 595 | 36.035 | 16.810 | 72.841 | 1.00 | 0.00 |
| ATOM | 646 | CD1 | LEU | A | 595 | 37.207 | 17.620 | 72.297 | 1.00 | 0.00 |
| ATOM | 647 | CD2 | LEU | A | 595 | 36.047 | 16.782 | 74.363 | 1.00 | 0.00 |
| ATOM | 648 | C | LEU | A | 595 | 33.548 | 16.476 | 70.345 | 1.00 | 0.00 |
| ATOM | 649 | O | LEU | A | 595 | 33.821 | 15.528 | 69.594 | 1.00 | 0.00 |
| ATOM | 650 | N | LEU | A | 596 | 32.317 | 16.934 | 70.504 | 1.00 | 0.00 |
| ATOM | 652 | CA | LEU | A | 596 | 31.168 | 16.125 | 70.099 | 1.00 | 0.00 |
| ATOM | 653 | CB | LEU | A | 596 | 29.917 | 16.724 | 70.731 | 1.00 | 0.00 |
| ATOM | 654 | CG | LEU | A | 596 | 28.678 | 15.888 | 70.432 | 1.00 | 0.00 |
| ATOM | 655 | CD1 | LEU | A | 596 | 28.811 | 14.485 | 71.015 | 1.00 | 0.00 |
| ATOM | 656 | CD2 | LEU | A | 596 | 27.427 | 16.570 | 70.970 | 1.00 | 0.00 |
| ATOM | 657 | C | LEU | A | 596 | 31.020 | 16.111 | 68.582 | 1.00 | 0.00 |
| ATOM | 658 | O | LEU | A | 596 | 30.764 | 15.046 | 68.007 | 1.00 | 0.00 |
| ATOM | 659 | N | GLN | A | 597 | 31.458 | 17.181 | 67.940 | 1.00 | 0.00 |
| ATOM | 661 | CA | GLN | A | 597 | 31.401 | 17.246 | 66.482 | 1.00 | 0.00 |
| ATOM | 662 | CB | GLN | A | 597 | 31.509 | 18.709 | 66.071 | 1.00 | 0.00 |
| ATOM | 663 | CG | GLN | A | 597 | 30.300 | 19.504 | 66.547 | 1.00 | 0.00 |
| ATOM | 664 | CD | GLN | A | 597 | 30.469 | 20.978 | 66.197 | 1.00 | 0.00 |
| ATOM | 665 | OE1 | GLN | A | 597 | 31.241 | 21.709 | 66.833 | 1.00 | 0.00 |

TABLE I-continued

GR Homology Model Coordinates

| ATOM | 666 | NE2 | GLN | A | 597 | 29.741 | 21.399 | 65.177 | 1.00 | 0.00 |
|---|---|---|---|---|---|---|---|---|---|---|
| ATOM | 669 | C | GLN | A | 597 | 32.514 | 16.446 | 65.808 | 1.00 | 0.00 |
| ATOM | 670 | O | GLN | A | 597 | 32.279 | 15.884 | 64.735 | 1.00 | 0.00 |
| ATOM | 671 | N | TYR | A | 598 | 33.628 | 16.229 | 66.483 | 1.00 | 0.00 |
| ATOM | 673 | CA | TYR | A | 598 | 34.695 | 15.440 | 65.861 | 1.00 | 0.00 |
| ATOM | 674 | CB | TYR | A | 598 | 36.050 | 15.808 | 66.465 | 1.00 | 0.00 |
| ATOM | 675 | CG | TYR | A | 598 | 36.616 | 17.205 | 66.194 | 1.00 | 0.00 |
| ATOM | 676 | CD1 | TYR | A | 598 | 35.993 | 18.095 | 65.326 | 1.00 | 0.00 |
| ATOM | 677 | CE1 | TYR | A | 598 | 36.538 | 19.353 | 65.107 | 1.00 | 0.00 |
| ATOM | 678 | CZ | TYR | A | 598 | 37.709 | 19.718 | 65.755 | 1.00 | 0.00 |
| ATOM | 679 | OH | TYR | A | 598 | 38.266 | 20.957 | 65.529 | 1.00 | 0.00 |
| ATOM | 680 | CE2 | TYR | A | 598 | 38.333 | 18.834 | 66.622 | 1.00 | 0.00 |
| ATOM | 681 | CD2 | TYR | A | 598 | 37.786 | 17.578 | 66.841 | 1.00 | 0.00 |
| ATOM | 682 | C | TYR | A | 598 | 34.467 | 13.954 | 66.103 | 1.00 | 0.00 |
| ATOM | 683 | O | TYR | A | 598 | 34.723 | 13.121 | 65.224 | 1.00 | 0.00 |
| ATOM | 684 | N | SER | A | 599 | 33.841 | 13.653 | 67.227 | 1.00 | 0.00 |
| ATOM | 686 | CA | SER | A | 599 | 33.624 | 12.259 | 67.620 | 1.00 | 0.00 |
| ATOM | 687 | CB | SER | A | 599 | 33.723 | 12.174 | 69.136 | 1.00 | 0.00 |
| ATOM | 688 | OG | SER | A | 599 | 32.627 | 12.901 | 69.675 | 1.00 | 0.00 |
| ATOM | 689 | C | SER | A | 599 | 32.271 | 11.690 | 67.204 | 1.00 | 0.00 |
| ATOM | 690 | O | SER | A | 599 | 32.081 | 10.475 | 67.351 | 1.00 | 0.00 |
| ATOM | 691 | N | TRP | A | 600 | 31.435 | 12.468 | 66.531 | 1.00 | 0.00 |
| ATOM | 693 | CA | TRP | A | 600 | 30.040 | 12.049 | 66.305 | 1.00 | 0.00 |
| ATOM | 694 | CB | TRP | A | 600 | 29.232 | 13.214 | 65.714 | 1.00 | 0.00 |
| ATOM | 695 | CG | TRP | A | 600 | 29.398 | 13.482 | 64.224 | 1.00 | 0.00 |
| ATOM | 696 | CD1 | TRP | A | 600 | 30.539 | 13.900 | 63.574 | 1.00 | 0.00 |
| ATOM | 697 | NE1 | TRP | A | 600 | 30.273 | 14.004 | 62.250 | 1.00 | 0.00 |
| ATOM | 699 | CE2 | TRP | A | 600 | 28.996 | 13.673 | 61.983 | 1.00 | 0.00 |
| ATOM | 700 | CZ2 | TRP | A | 600 | 28.262 | 13.629 | 60.808 | 1.00 | 0.00 |
| ATOM | 701 | CH2 | TRP | A | 600 | 26.927 | 13.240 | 60.843 | 1.00 | 0.00 |
| ATOM | 702 | CZ3 | TRP | A | 600 | 26.327 | 12.899 | 62.052 | 1.00 | 0.00 |
| ATOM | 703 | CE3 | TRP | A | 600 | 27.054 | 12.944 | 63.234 | 1.00 | 0.00 |
| ATOM | 704 | CD2 | TRP | A | 600 | 28.386 | 13.332 | 63.204 | 1.00 | 0.00 |
| ATOM | 705 | C | TRP | A | 600 | 29.909 | 10.820 | 65.402 | 1.00 | 0.00 |
| ATOM | 706 | O | TRP | A | 600 | 29.151 | 9.910 | 65.763 | 1.00 | 0.00 |
| ATOM | 707 | N | MET | A | 601 | 30.850 | 10.632 | 64.487 | 1.00 | 0.00 |
| ATOM | 709 | CA | MET | A | 601 | 30.744 | 9.511 | 63.559 | 1.00 | 0.00 |
| ATOM | 710 | CB | MET | A | 601 | 31.575 | 9.809 | 62.319 | 1.00 | 0.00 |
| ATOM | 711 | CG | MET | A | 601 | 30.690 | 9.840 | 61.079 | 1.00 | 0.00 |
| ATOM | 712 | SD | MET | A | 601 | 29.759 | 8.325 | 60.753 | 1.00 | 0.00 |
| ATOM | 713 | CE | MET | A | 601 | 28.886 | 8.842 | 59.258 | 1.00 | 0.00 |
| ATOM | 714 | C | MET | A | 601 | 31.206 | 8.206 | 64.187 | 1.00 | 0.00 |
| ATOM | 715 | O | MET | A | 601 | 30.581 | 7.168 | 63.946 | 1.00 | 0.00 |
| ATOM | 716 | N | PHE | A | 602 | 32.096 | 8.276 | 65.162 | 1.00 | 0.00 |
| ATOM | 718 | CA | PHE | A | 602 | 32.505 | 7.022 | 65.779 | 1.00 | 0.00 |
| ATOM | 719 | CB | PHE | A | 602 | 33.998 | 6.996 | 66.065 | 1.00 | 0.00 |
| ATOM | 720 | CG | PHE | A | 602 | 34.476 | 5.568 | 66.316 | 1.00 | 0.00 |
| ATOM | 721 | CD1 | PHE | A | 602 | 33.801 | 4.508 | 65.720 | 1.00 | 0.00 |
| ATOM | 722 | CE1 | PHE | A | 602 | 34.205 | 3.202 | 65.957 | 1.00 | 0.00 |
| ATOM | 723 | CZ | PHE | A | 602 | 35.293 | 2.956 | 66.780 | 1.00 | 0.00 |
| ATOM | 724 | CE2 | PHE | A | 602 | 35.988 | 4.014 | 67.350 | 1.00 | 0.00 |
| ATOM | 725 | CD2 | PHE | A | 602 | 35.583 | 5.322 | 67.114 | 1.00 | 0.00 |
| ATOM | 726 | C | PHE | A | 602 | 31.693 | 6.751 | 67.040 | 1.00 | 0.00 |
| ATOM | 727 | O | PHE | A | 602 | 31.553 | 5.587 | 67.425 | 1.00 | 0.00 |
| ATOM | 728 | N | LEU | A | 603 | 30.974 | 7.744 | 67.531 | 1.00 | 0.00 |
| ATOM | 730 | CA | LEU | A | 603 | 30.038 | 7.458 | 68.617 | 1.00 | 0.00 |
| ATOM | 731 | CB | LEU | A | 603 | 29.579 | 8.757 | 69.271 | 1.00 | 0.00 |
| ATOM | 732 | CG | LEU | A | 603 | 30.709 | 9.450 | 70.024 | 1.00 | 0.00 |
| ATOM | 733 | CD1 | LEU | A | 603 | 30.235 | 10.779 | 70.601 | 1.00 | 0.00 |
| ATOM | 734 | CD2 | LEU | A | 603 | 31.272 | 8.559 | 71.126 | 1.00 | 0.00 |
| ATOM | 735 | C | LEU | A | 603 | 28.837 | 6.696 | 68.069 | 1.00 | 0.00 |
| ATOM | 736 | O | LEU | A | 603 | 28.516 | 5.617 | 68.589 | 1.00 | 0.00 |
| ATOM | 737 | N | MET | A | 604 | 28.399 | 7.068 | 66.876 | 1.00 | 0.00 |
| ATOM | 739 | CA | MET | A | 604 | 27.269 | 6.355 | 66.278 | 1.00 | 0.00 |
| ATOM | 740 | CB | MET | A | 604 | 26.546 | 7.278 | 65.295 | 1.00 | 0.00 |
| ATOM | 741 | CG | MET | A | 604 | 27.430 | 7.788 | 64.164 | 1.00 | 0.00 |
| ATOM | 742 | SD | MET | A | 604 | 26.649 | 8.960 | 63.033 | 1.00 | 0.00 |
| ATOM | 743 | CE | MET | A | 604 | 25.297 | 7.919 | 62.439 | 1.00 | 0.00 |
| ATOM | 744 | C | MET | A | 604 | 27.687 | 5.039 | 65.612 | 1.00 | 0.00 |
| ATOM | 745 | O | MET | A | 604 | 26.922 | 4.069 | 65.699 | 1.00 | 0.00 |
| ATOM | 746 | N | ALA | A | 605 | 28.948 | 4.916 | 65.223 | 1.00 | 0.00 |
| ATOM | 748 | CA | ALA | A | 605 | 29.417 | 3.659 | 64.631 | 1.00 | 0.00 |
| ATOM | 749 | CB | ALA | A | 605 | 30.571 | 3.954 | 63.682 | 1.00 | 0.00 |
| ATOM | 750 | C | ALA | A | 605 | 29.864 | 2.639 | 65.675 | 1.00 | 0.00 |
| ATOM | 751 | O | ALA | A | 605 | 29.707 | 1.434 | 65.448 | 1.00 | 0.00 |
| ATOM | 752 | N | PHE | A | 606 | 30.208 | 3.099 | 66.867 | 1.00 | 0.00 |
| ATOM | 754 | CA | PHE | A | 606 | 30.563 | 2.168 | 67.938 | 1.00 | 0.00 |

TABLE I-continued

GR Homology Model Coordinates

| ATOM | 755 | CB | PHE | A | 606 | 31.488 | 2.877 | 68.920 | 1.00 | 0.00 |
|------|-----|-----|-----|---|-----|--------|-------|--------|------|------|
| ATOM | 756 | CG | PHE | A | 606 | 32.423 | 1.957 | 69.697 | 1.00 | 0.00 |
| ATOM | 757 | CD1 | PHE | A | 606 | 32.882 | 0.782 | 69.115 | 1.00 | 0.00 |
| ATOM | 758 | CE1 | PHE | A | 606 | 33.747 | −0.048 | 69.816 | 1.00 | 0.00 |
| ATOM | 759 | CZ | PHE | A | 606 | 34.155 | 0.297 | 71.098 | 1.00 | 0.00 |
| ATOM | 760 | CE2 | PHE | A | 606 | 33.697 | 1.472 | 71.680 | 1.00 | 0.00 |
| ATOM | 761 | CD2 | PHE | A | 606 | 32.830 | 2.300 | 70.980 | 1.00 | 0.00 |
| ATOM | 762 | C | PHE | A | 606 | 29.292 | 1.717 | 68.645 | 1.00 | 0.00 |
| ATOM | 763 | O | PHE | A | 606 | 29.201 | 0.564 | 69.090 | 1.00 | 0.00 |
| ATOM | 764 | N | ALA | A | 607 | 28.256 | 2.536 | 68.531 | 1.00 | 0.00 |
| ATOM | 766 | CA | ALA | A | 607 | 26.931 | 2.134 | 68.999 | 1.00 | 0.00 |
| ATOM | 767 | CB | ALA | A | 607 | 26.015 | 3.353 | 69.019 | 1.00 | 0.00 |
| ATOM | 768 | C | ALA | A | 607 | 26.358 | 1.075 | 68.068 | 1.00 | 0.00 |
| ATOM | 769 | O | ALA | A | 607 | 25.956 | 0.011 | 68.549 | 1.00 | 0.00 |
| ATOM | 770 | N | LEU | A | 608 | 26.588 | 1.243 | 66.774 | 1.00 | 0.00 |
| ATOM | 772 | CA | LEU | A | 608 | 26.178 | 0.243 | 65.778 | 1.00 | 0.00 |
| ATOM | 773 | CB | LEU | A | 608 | 26.480 | 0.825 | 64.402 | 1.00 | 0.00 |
| ATOM | 774 | CG | LEU | A | 608 | 26.293 | −0.194 | 63.284 | 1.00 | 0.00 |
| ATOM | 775 | CD1 | LEU | A | 608 | 24.846 | −0.648 | 63.180 | 1.00 | 0.00 |
| ATOM | 776 | CD2 | LEU | A | 608 | 26.758 | 0.383 | 61.957 | 1.00 | 0.00 |
| ATOM | 777 | C | LEU | A | 608 | 26.943 | −1.067 | 65.949 | 1.00 | 0.00 |
| ATOM | 778 | O | LEU | A | 608 | 26.328 | −2.141 | 65.989 | 1.00 | 0.00 |
| ATOM | 779 | N | GLY | A | 609 | 28.229 | −0.952 | 66.243 | 1.00 | 0.00 |
| ATOM | 781 | CA | GLY | A | 609 | 29.068 | −2.113 | 66.542 | 1.00 | 0.00 |
| ATOM | 782 | C | GLY | A | 609 | 28.504 | −2.934 | 67.694 | 1.00 | 0.00 |
| ATOM | 783 | O | GLY | A | 609 | 28.122 | −4.094 | 67.488 | 1.00 | 0.00 |
| ATOM | 784 | N | TRP | A | 610 | 28.237 | −2.271 | 68.808 | 1.00 | 0.00 |
| ATOM | 786 | CA | TRP | A | 610 | 27.778 | −2.964 | 70.012 | 1.00 | 0.00 |
| ATOM | 787 | CB | TRP | A | 610 | 27.928 | −1.998 | 71.173 | 1.00 | 0.00 |
| ATOM | 788 | CG | TRP | A | 610 | 27.755 | −2.641 | 72.528 | 1.00 | 0.00 |
| ATOM | 789 | CD1 | TRP | A | 610 | 26.658 | −2.568 | 73.358 | 1.00 | 0.00 |
| ATOM | 790 | NE1 | TRP | A | 610 | 26.925 | −3.278 | 74.483 | 1.00 | 0.00 |
| ATOM | 792 | CE2 | TRP | A | 610 | 28.158 | −3.820 | 74.436 | 1.00 | 0.00 |
| ATOM | 793 | CZ2 | TRP | A | 610 | 28.880 | −4.593 | 75.328 | 1.00 | 0.00 |
| ATOM | 794 | CH2 | TRP | A | 610 | 30.164 | −5.012 | 74.995 | 1.00 | 0.00 |
| ATOM | 795 | CZ3 | TRP | A | 610 | 30.726 | −4.656 | 73.774 | 1.00 | 0.00 |
| ATOM | 796 | CE3 | TRP | A | 610 | 30.011 | −3.878 | 72.876 | 1.00 | 0.00 |
| ATOM | 797 | CD2 | TRP | A | 610 | 28.730 | −3.457 | 73.206 | 1.00 | 0.00 |
| ATOM | 798 | C | TRP | A | 610 | 26.323 | −3.424 | 69.949 | 1.00 | 0.00 |
| ATOM | 799 | O | TRP | A | 610 | 26.014 | −4.495 | 70.485 | 1.00 | 0.00 |
| ATOM | 800 | N | ARG | A | 611 | 25.492 | −2.762 | 69.162 | 1.00 | 0.00 |
| ATOM | 802 | CA | ARG | A | 611 | 24.107 | −3.219 | 69.027 | 1.00 | 0.00 |
| ATOM | 803 | CB | ARG | A | 611 | 23.235 | −2.083 | 68.512 | 1.00 | 0.00 |
| ATOM | 804 | CG | ARG | A | 611 | 23.117 | −0.950 | 69.523 | 1.00 | 0.00 |
| ATOM | 805 | CD | ARG | A | 611 | 22.226 | 0.158 | 68.981 | 1.00 | 0.00 |
| ATOM | 806 | NE | ARG | A | 611 | 22.725 | 0.624 | 67.678 | 1.00 | 0.00 |
| ATOM | 807 | CZ | ARG | A | 611 | 22.559 | 1.868 | 67.227 | 1.00 | 0.00 |
| ATOM | 808 | NH1 | ARG | A | 611 | 21.888 | 2.760 | 67.961 | 1.00 | 0.00 |
| ATOM | 809 | NH2 | ARG | A | 611 | 23.050 | 2.216 | 66.036 | 1.00 | 0.00 |
| ATOM | 810 | C | ARG | A | 611 | 24.014 | −4.402 | 68.074 | 1.00 | 0.00 |
| ATOM | 811 | O | ARG | A | 611 | 23.218 | −5.317 | 68.315 | 1.00 | 0.00 |
| ATOM | 812 | N | SER | A | 612 | 24.963 | −4.499 | 67.159 | 1.00 | 0.00 |
| ATOM | 814 | CA | SER | A | 612 | 25.031 | −5.671 | 66.291 | 1.00 | 0.00 |
| ATOM | 815 | CB | SER | A | 612 | 25.949 | −5.357 | 65.123 | 1.00 | 0.00 |
| ATOM | 816 | OG | SER | A | 612 | 25.359 | −4.282 | 64.414 | 1.00 | 0.00 |
| ATOM | 817 | C | SER | A | 612 | 25.595 | −6.845 | 67.066 | 1.00 | 0.00 |
| ATOM | 818 | O | SER | A | 612 | 24.998 | −7.932 | 67.061 | 1.00 | 0.00 |
| ATOM | 819 | N | TYR | A | 613 | 26.556 | −6.544 | 67.924 | 1.00 | 0.00 |
| ATOM | 821 | CA | TYR | A | 613 | 27.149 | −7.554 | 68.799 | 1.00 | 0.00 |
| ATOM | 822 | CB | TYR | A | 613 | 28.266 | −6.892 | 69.600 | 1.00 | 0.00 |
| ATOM | 823 | CG | TYR | A | 613 | 29.046 | −7.820 | 70.528 | 1.00 | 0.00 |
| ATOM | 824 | CD1 | TYR | A | 613 | 29.154 | −9.176 | 70.243 | 1.00 | 0.00 |
| ATOM | 825 | CE1 | TYR | A | 613 | 29.872 | −10.007 | 71.092 | 1.00 | 0.00 |
| ATOM | 826 | CZ | TYR | A | 613 | 30.487 | −9.480 | 72.219 | 1.00 | 0.00 |
| ATOM | 827 | OH | TYR | A | 613 | 31.350 | −10.262 | 72.951 | 1.00 | 0.00 |
| ATOM | 828 | CE2 | TYR | A | 613 | 30.369 | −8.129 | 72.513 | 1.00 | 0.00 |
| ATOM | 829 | CD2 | TYR | A | 613 | 29.646 | −7.300 | 71.667 | 1.00 | 0.00 |
| ATOM | 830 | C | TYR | A | 613 | 26.098 | −8.149 | 69.732 | 1.00 | 0.00 |
| ATOM | 831 | O | TYR | A | 613 | 25.861 | −9.360 | 69.661 | 1.00 | 0.00 |
| ATOM | 832 | N | ARG | A | 614 | 25.301 | −7.297 | 70.352 | 1.00 | 0.00 |
| ATOM | 834 | CA | ARG | A | 614 | 24.261 | −7.779 | 71.260 | 1.00 | 0.00 |
| ATOM | 835 | CB | ARG | A | 614 | 23.755 | −6.602 | 72.083 | 1.00 | 0.00 |
| ATOM | 836 | CG | ARG | A | 614 | 24.793 | −6.158 | 73.104 | 1.00 | 0.00 |
| ATOM | 837 | CD | ARG | A | 614 | 25.104 | −7.292 | 74.075 | 1.00 | 0.00 |
| ATOM | 838 | NE | ARG | A | 614 | 26.038 | −6.865 | 75.129 | 1.00 | 0.00 |
| ATOM | 839 | CZ | ARG | A | 614 | 25.667 | −6.698 | 76.401 | 1.00 | 0.00 |
| ATOM | 840 | NH1 | ARG | A | 614 | 24.396 | −6.898 | 76.758 | 1.00 | 0.00 |
| ATOM | 841 | NH2 | ARG | A | 614 | 26.563 | −6.319 | 77.315 | 1.00 | 0.00 |

TABLE I-continued

GR Homology Model Coordinates

| ATOM | 842 | C | ARG | A | 614 | 23.083 | −8.445 | 70.553 | 1.00 | 0.00 |
|---|---|---|---|---|---|---|---|---|---|---|
| ATOM | 843 | O | ARG | A | 614 | 22.912 | −9.662 | 70.685 | 1.00 | 0.00 |
| ATOM | 844 | N | GLN | A | 615 | 22.409 | −7.721 | 69.674 | 1.00 | 0.00 |
| ATOM | 846 | CA | GLN | A | 615 | 21.115 | −8.198 | 69.168 | 1.00 | 0.00 |
| ATOM | 847 | CB | GLN | A | 615 | 20.284 | −6.973 | 68.777 | 1.00 | 0.00 |
| ATOM | 848 | CG | GLN | A | 615 | 18.816 | −7.326 | 68.538 | 1.00 | 0.00 |
| ATOM | 849 | CD | GLN | A | 615 | 17.992 | −6.089 | 68.185 | 1.00 | 0.00 |
| ATOM | 850 | OE1 | GLN | A | 615 | 18.283 | −4.972 | 68.631 | 1.00 | 0.00 |
| ATOM | 851 | NE2 | GLN | A | 615 | 16.941 | −6.320 | 67.419 | 1.00 | 0.00 |
| ATOM | 854 | C | GLN | A | 615 | 21.214 | −9.180 | 67.993 | 1.00 | 0.00 |
| ATOM | 855 | O | GLN | A | 615 | 20.241 | −9.893 | 67.722 | 1.00 | 0.00 |
| ATOM | 856 | N | SER | A | 616 | 22.363 | −9.283 | 67.345 | 1.00 | 0.00 |
| ATOM | 858 | CA | SER | A | 616 | 22.472 | −10.273 | 66.267 | 1.00 | 0.00 |
| ATOM | 859 | CB | SER | A | 616 | 22.640 | −9.570 | 64.925 | 1.00 | 0.00 |
| ATOM | 860 | OG | SER | A | 616 | 24.018 | −9.260 | 64.758 | 1.00 | 0.00 |
| ATOM | 861 | C | SER | A | 616 | 23.648 | −11.225 | 66.457 | 1.00 | 0.00 |
| ATOM | 862 | O | SER | A | 616 | 23.869 | −12.079 | 65.593 | 1.00 | 0.00 |
| ATOM | 863 | N | SER | A | 617 | 24.401 | −11.069 | 67.537 | 1.00 | 0.00 |
| ATOM | 865 | CA | SER | A | 617 | 25.662 | −11.813 | 67.737 | 1.00 | 0.00 |
| ATOM | 866 | CB | SER | A | 617 | 25.405 | −13.317 | 67.801 | 1.00 | 0.00 |
| ATOM | 867 | OG | SER | A | 617 | 26.636 | −13.965 | 68.091 | 1.00 | 0.00 |
| ATOM | 868 | C | SER | A | 617 | 26.655 | −11.458 | 66.629 | 1.00 | 0.00 |
| ATOM | 869 | O | SER | A | 617 | 27.124 | −12.313 | 65.866 | 1.00 | 0.00 |
| ATOM | 870 | N | ALA | A | 618 | 26.799 | −10.151 | 66.470 | 1.00 | 0.00 |
| ATOM | 872 | CA | ALA | A | 618 | 27.716 | −9.457 | 65.542 | 1.00 | 0.00 |
| ATOM | 873 | CB | ALA | A | 618 | 29.126 | −9.555 | 66.103 | 1.00 | 0.00 |
| ATOM | 874 | C | ALA | A | 618 | 27.743 | −9.869 | 64.067 | 1.00 | 0.00 |
| ATOM | 875 | O | ALA | A | 618 | 28.769 | −9.651 | 63.412 | 1.00 | 0.00 |
| ATOM | 876 | N | ASN | A | 619 | 26.663 | −10.413 | 63.531 | 1.00 | 0.00 |
| ATOM | 878 | CA | ASN | A | 619 | 26.655 | −10.707 | 62.098 | 1.00 | 0.00 |
| ATOM | 879 | CB | ASN | A | 619 | 26.274 | −12.171 | 61.876 | 1.00 | 0.00 |
| ATOM | 880 | CG | ASN | A | 619 | 25.046 | −12.570 | 62.689 | 1.00 | 0.00 |
| ATOM | 881 | OD1 | ASN | A | 619 | 23.958 | −12.001 | 62.539 | 1.00 | 0.00 |
| ATOM | 882 | ND2 | ASN | A | 619 | 25.238 | −13.565 | 63.536 | 1.00 | 0.00 |
| ATOM | 885 | C | ASN | A | 619 | 25.759 | −9.779 | 61.276 | 1.00 | 0.00 |
| ATOM | 886 | O | ASN | A | 619 | 25.995 | −9.640 | 60.070 | 1.00 | 0.00 |
| ATOM | 887 | N | LEU | A | 620 | 24.789 | −9.111 | 61.885 | 1.00 | 0.00 |
| ATOM | 889 | CA | LEU | A | 620 | 23.941 | −8.201 | 61.109 | 1.00 | 0.00 |
| ATOM | 890 | CB | LEU | A | 620 | 22.482 | −8.648 | 61.178 | 1.00 | 0.00 |
| ATOM | 891 | CG | LEU | A | 620 | 22.267 | −10.064 | 60.651 | 1.00 | 0.00 |
| ATOM | 892 | CD1 | LEU | A | 620 | 20.812 | −10.490 | 60.813 | 1.00 | 0.00 |
| ATOM | 893 | CD2 | LEU | A | 620 | 22.709 | −10.203 | 59.198 | 1.00 | 0.00 |
| ATOM | 894 | C | LEU | A | 620 | 24.061 | −6.803 | 61.686 | 1.00 | 0.00 |
| ATOM | 895 | O | LEU | A | 620 | 24.332 | −6.640 | 62.882 | 1.00 | 0.00 |
| ATOM | 896 | N | LEU | A | 621 | 23.840 | −5.806 | 60.848 | 1.00 | 0.00 |
| ATOM | 898 | CA | LEU | A | 621 | 23.954 | −4.420 | 61.305 | 1.00 | 0.00 |
| ATOM | 899 | CB | LEU | A | 621 | 24.308 | −3.512 | 60.139 | 1.00 | 0.00 |
| ATOM | 900 | CG | LEU | A | 621 | 25.760 | −3.705 | 59.726 | 1.00 | 0.00 |
| ATOM | 901 | CD1 | LEU | A | 621 | 26.101 | −2.813 | 58.543 | 1.00 | 0.00 |
| ATOM | 902 | CD2 | LEU | A | 621 | 26.699 | −3.420 | 60.895 | 1.00 | 0.00 |
| ATOM | 903 | C | LEU | A | 621 | 22.681 | −3.941 | 61.984 | 1.00 | 0.00 |
| ATOM | 904 | O | LEU | A | 621 | 21.679 | −3.588 | 61.349 | 1.00 | 0.00 |
| ATOM | 905 | N | CYS | A | 622 | 22.786 | −3.844 | 63.293 | 1.00 | 0.00 |
| ATOM | 907 | CA | CYS | A | 622 | 21.660 | −3.399 | 64.108 | 1.00 | 0.00 |
| ATOM | 908 | CB | CYS | A | 622 | 21.679 | −4.108 | 65.452 | 1.00 | 0.00 |
| ATOM | 909 | SG | CYS | A | 622 | 20.424 | −3.549 | 66.627 | 1.00 | 0.00 |
| ATOM | 910 | C | CYS | A | 622 | 21.738 | −1.900 | 64.321 | 1.00 | 0.00 |
| ATOM | 911 | O | CYS | A | 622 | 22.496 | −1.408 | 65.164 | 1.00 | 0.00 |
| ATOM | 912 | N | PHE | A | 623 | 20.958 | −1.181 | 63.533 | 1.00 | 0.00 |
| ATOM | 914 | CA | PHE | A | 623 | 20.917 | 0.275 | 63.655 | 1.00 | 0.00 |
| ATOM | 915 | CB | PHE | A | 623 | 20.624 | 0.882 | 62.287 | 1.00 | 0.00 |
| ATOM | 916 | CG | PHE | A | 623 | 21.739 | 0.764 | 61.252 | 1.00 | 0.00 |
| ATOM | 917 | CD1 | PHE | A | 623 | 22.768 | 1.697 | 61.241 | 1.00 | 0.00 |
| ATOM | 918 | CE1 | PHE | A | 623 | 23.780 | 1.604 | 60.295 | 1.00 | 0.00 |
| ATOM | 919 | CZ | PHE | A | 623 | 23.763 | 0.580 | 59.357 | 1.00 | 0.00 |
| ATOM | 920 | CE2 | PHE | A | 623 | 22.733 | −0.350 | 59.366 | 1.00 | 0.00 |
| ATOM | 921 | CD2 | PHE | A | 623 | 21.720 | −0.257 | 60.311 | 1.00 | 0.00 |
| ATOM | 922 | C | PHE | A | 623 | 19.809 | 0.658 | 64.622 | 1.00 | 0.00 |
| ATOM | 923 | O | PHE | A | 623 | 19.852 | 1.699 | 65.286 | 1.00 | 0.00 |
| ATOM | 924 | N | ALA | A | 624 | 18.868 | −0.256 | 64.749 | 1.00 | 0.00 |
| ATOM | 926 | CA | ALA | A | 624 | 17.746 | −0.077 | 65.665 | 1.00 | 0.00 |
| ATOM | 927 | CB | ALA | A | 624 | 16.787 | 0.909 | 65.009 | 1.00 | 0.00 |
| ATOM | 928 | C | ALA | A | 624 | 17.065 | −1.423 | 65.853 | 1.00 | 0.00 |
| ATOM | 929 | O | ALA | A | 624 | 17.204 | −2.292 | 64.984 | 1.00 | 0.00 |
| ATOM | 930 | N | PRO | A | 625 | 16.223 | −1.562 | 66.867 | 1.00 | 0.00 |
| ATOM | 931 | CA | PRO | A | 625 | 15.400 | −2.777 | 66.970 | 1.00 | 0.00 |
| ATOM | 932 | CB | PRO | A | 625 | 14.682 | −2.644 | 68.279 | 1.00 | 0.00 |

TABLE I-continued

GR Homology Model Coordinates

| ATOM | 933 | CG | PRO | A | 625 | 14.985 | −1.282 | 68.887 | 1.00 | 0.00 |
|---|---|---|---|---|---|---|---|---|---|---|
| ATOM | 934 | CD | PRO | A | 625 | 15.945 | −0.593 | 67.932 | 1.00 | 0.00 |
| ATOM | 935 | C | PRO | A | 625 | 14.407 | −2.928 | 65.803 | 1.00 | 0.00 |
| ATOM | 936 | O | PRO | A | 625 | 14.127 | −4.055 | 65.379 | 1.00 | 0.00 |
| ATOM | 937 | N | ASP | A | 626 | 14.030 | −1.813 | 65.189 | 1.00 | 0.00 |
| ATOM | 939 | CA | ASP | A | 626 | 13.174 | −1.813 | 63.994 | 1.00 | 0.00 |
| ATOM | 940 | CB | ASP | A | 626 | 12.237 | −0.598 | 64.034 | 1.00 | 0.00 |
| ATOM | 941 | CG | ASP | A | 626 | 12.982 | 0.736 | 63.929 | 1.00 | 0.00 |
| ATOM | 942 | OD1 | ASP | A | 626 | 13.627 | 1.110 | 64.901 | 1.00 | 0.00 |
| ATOM | 943 | OD2 | ASP | A | 626 | 12.763 | 1.458 | 62.963 | 1.00 | 0.00 |
| ATOM | 944 | C | ASP | A | 626 | 13.974 | −1.790 | 62.686 | 1.00 | 0.00 |
| ATOM | 945 | O | ASP | A | 626 | 13.374 | −1.775 | 61.605 | 1.00 | 0.00 |
| ATOM | 946 | N | LEU | A | 627 | 15.297 | −1.811 | 62.774 | 1.00 | 0.00 |
| ATOM | 948 | CA | LEU | A | 627 | 16.135 | −1.725 | 61.571 | 1.00 | 0.00 |
| ATOM | 949 | CB | LEU | A | 627 | 16.541 | −0.272 | 61.354 | 1.00 | 0.00 |
| ATOM | 950 | CG | LEU | A | 627 | 17.229 | −0.082 | 60.006 | 1.00 | 0.00 |
| ATOM | 951 | CD1 | LEU | A | 627 | 16.321 | −0.525 | 58.863 | 1.00 | 0.00 |
| ATOM | 952 | CD2 | LEU | A | 627 | 17.659 | 1.367 | 59.815 | 1.00 | 0.00 |
| ATOM | 953 | C | LEU | A | 627 | 17.379 | −2.609 | 61.697 | 1.00 | 0.00 |
| ATOM | 954 | O | LEU | A | 627 | 18.441 | −2.175 | 62.175 | 1.00 | 0.00 |
| ATOM | 955 | N | ILE | A | 628 | 17.212 | −3.854 | 61.282 | 1.00 | 0.00 |
| ATOM | 957 | CA | ILE | A | 628 | 18.310 | −4.831 | 61.278 | 1.00 | 0.00 |
| ATOM | 958 | CB | ILE | A | 628 | 17.836 | −6.121 | 61.943 | 1.00 | 0.00 |
| ATOM | 959 | CG2 | ILE | A | 628 | 18.979 | −7.131 | 62.016 | 1.00 | 0.00 |
| ATOM | 960 | CG1 | ILE | A | 628 | 17.292 | −5.862 | 63.342 | 1.00 | 0.00 |
| ATOM | 961 | CD1 | ILE | A | 628 | 18.399 | −5.394 | 64.274 | 1.00 | 0.00 |
| ATOM | 962 | C | ILE | A | 628 | 18.721 | −5.133 | 59.841 | 1.00 | 0.00 |
| ATOM | 963 | O | ILE | A | 628 | 18.089 | −5.945 | 59.150 | 1.00 | 0.00 |
| ATOM | 964 | N | ILE | A | 629 | 19.800 | −4.504 | 59.417 | 1.00 | 0.00 |
| ATOM | 966 | CA | ILE | A | 629 | 20.255 | −4.648 | 58.035 | 1.00 | 0.00 |
| ATOM | 967 | CB | ILE | A | 629 | 21.033 | −3.398 | 57.642 | 1.00 | 0.00 |
| ATOM | 968 | CG2 | ILE | A | 629 | 21.708 | −3.589 | 56.288 | 1.00 | 0.00 |
| ATOM | 969 | CG1 | ILE | A | 629 | 20.113 | −2.184 | 57.608 | 1.00 | 0.00 |
| ATOM | 970 | CD1 | ILE | A | 629 | 19.048 | −2.326 | 56.527 | 1.00 | 0.00 |
| ATOM | 971 | C | ILE | A | 629 | 21.113 | −5.891 | 57.843 | 1.00 | 0.00 |
| ATOM | 972 | O | ILE | A | 629 | 22.222 | −6.019 | 58.379 | 1.00 | 0.00 |
| ATOM | 973 | N | ASN | A | 630 | 20.530 | −6.847 | 57.143 | 1.00 | 0.00 |
| ATOM | 975 | CA | ASN | A | 630 | 21.286 | −8.016 | 56.703 | 1.00 | 0.00 |
| ATOM | 976 | CB | ASN | A | 630 | 20.371 | −9.236 | 56.584 | 1.00 | 0.00 |
| ATOM | 977 | CG | ASN | A | 630 | 19.231 | −9.020 | 55.595 | 1.00 | 0.00 |
| ATOM | 978 | OD1 | ASN | A | 630 | 19.454 | −8.971 | 54.379 | 1.00 | 0.00 |
| ATOM | 979 | ND2 | ASN | A | 630 | 18.016 | −9.001 | 56.117 | 1.00 | 0.00 |
| ATOM | 982 | C | ASN | A | 630 | 21.984 | −7.690 | 55.387 | 1.00 | 0.00 |
| ATOM | 983 | O | ASN | A | 630 | 21.666 | −6.685 | 54.735 | 1.00 | 0.00 |
| ATOM | 984 | N | GLU | A | 631 | 22.800 | −8.618 | 54.919 | 1.00 | 0.00 |
| ATOM | 986 | CA | GLU | A | 631 | 23.664 | −8.354 | 53.757 | 1.00 | 0.00 |
| ATOM | 987 | CB | GLU | A | 631 | 24.838 | −9.345 | 53.721 | 1.00 | 0.00 |
| ATOM | 988 | CG | GLU | A | 631 | 24.486 | −10.782 | 53.317 | 1.00 | 0.00 |
| ATOM | 989 | CD | GLU | A | 631 | 24.159 | −11.676 | 54.514 | 1.00 | 0.00 |
| ATOM | 990 | OE1 | GLU | A | 631 | 25.048 | −12.398 | 54.937 | 1.00 | 0.00 |
| ATOM | 991 | OE2 | GLU | A | 631 | 23.111 | −11.453 | 55.121 | 1.00 | 0.00 |
| ATOM | 992 | C | GLU | A | 631 | 22.919 | −8.369 | 52.414 | 1.00 | 0.00 |
| ATOM | 993 | O | GLU | A | 631 | 23.433 | −7.814 | 51.438 | 1.00 | 0.00 |
| ATOM | 994 | N | GLN | A | 632 | 21.658 | −8.773 | 52.419 | 1.00 | 0.00 |
| ATOM | 996 | CA | GLN | A | 632 | 20.849 | −8.769 | 51.199 | 1.00 | 0.00 |
| ATOM | 997 | CB | GLN | A | 632 | 19.841 | −9.923 | 51.219 | 1.00 | 0.00 |
| ATOM | 998 | CG | GLN | A | 632 | 20.456 | −11.308 | 50.997 | 1.00 | 0.00 |
| ATOM | 999 | CD | GLN | A | 632 | 20.990 | −11.938 | 52.284 | 1.00 | 0.00 |
| ATOM | 1000 | OE1 | GLN | A | 632 | 22.124 | −12.427 | 52.327 | 1.00 | 0.00 |
| ATOM | 1001 | NE2 | GLN | A | 632 | 20.203 | −11.842 | 53.342 | 1.00 | 0.00 |
| ATOM | 1004 | C | GLN | A | 632 | 20.083 | −7.455 | 51.042 | 1.00 | 0.00 |
| ATOM | 1005 | O | GLN | A | 632 | 19.446 | −7.237 | 50.005 | 1.00 | 0.00 |
| ATOM | 1006 | N | ARG | A | 633 | 20.146 | −6.586 | 52.041 | 1.00 | 0.00 |
| ATOM | 1008 | CA | ARG | A | 633 | 19.444 | −5.304 | 51.928 | 1.00 | 0.00 |
| ATOM | 1009 | CB | ARG | A | 633 | 18.962 | −4.865 | 53.303 | 1.00 | 0.00 |
| ATOM | 1010 | CG | ARG | A | 633 | 18.282 | −6.014 | 54.029 | 1.00 | 0.00 |
| ATOM | 1011 | CD | ARG | A | 633 | 17.471 | −5.518 | 55.213 | 1.00 | 0.00 |
| ATOM | 1012 | NE | ARG | A | 633 | 16.273 | −4.832 | 54.715 | 1.00 | 0.00 |
| ATOM | 1013 | CZ | ARG | A | 633 | 15.417 | −4.165 | 55.490 | 1.00 | 0.00 |
| ATOM | 1014 | NH1 | ARG | A | 633 | 15.680 | −3.992 | 56.788 | 1.00 | 0.00 |
| ATOM | 1015 | NH2 | ARG | A | 633 | 14.332 | −3.614 | 54.946 | 1.00 | 0.00 |
| ATOM | 1016 | C | ARG | A | 633 | 20.350 | −4.223 | 51.358 | 1.00 | 0.00 |
| ATOM | 1017 | O | ARG | A | 633 | 19.866 | −3.225 | 50.808 | 1.00 | 0.00 |
| ATOM | 1018 | N | MET | A | 634 | 21.649 | −4.463 | 51.388 | 1.00 | 0.00 |
| ATOM | 1020 | CA | MET | A | 634 | 22.582 | −3.481 | 50.832 | 1.00 | 0.00 |
| ATOM | 1021 | CB | MET | A | 634 | 23.781 | −3.338 | 51.755 | 1.00 | 0.00 |
| ATOM | 1022 | CG | MET | A | 634 | 23.365 | −2.639 | 53.042 | 1.00 | 0.00 |

TABLE I-continued

GR Homology Model Coordinates

| | | | | | | | | | |
|---|---|---|---|---|---|---|---|---|---|
| ATOM | 1023 | SD | MET | A | 634 | 22.588 | −1.024 | 52.799 | 1.00 | 0.00 |
| ATOM | 1024 | CE | MET | A | 634 | 22.391 | −0.515 | 54.522 | 1.00 | 0.00 |
| ATOM | 1025 | C | MET | A | 634 | 23.013 | −3.864 | 49.424 | 1.00 | 0.00 |
| ATOM | 1026 | O | MET | A | 634 | 24.138 | −4.318 | 49.189 | 1.00 | 0.00 |
| ATOM | 1027 | N | THR | A | 635 | 22.134 | −3.554 | 48.485 | 1.00 | 0.00 |
| ATOM | 1029 | CA | THR | A | 635 | 22.369 | −3.888 | 47.078 | 1.00 | 0.00 |
| ATOM | 1030 | CB | THR | A | 635 | 21.008 | −4.091 | 46.411 | 1.00 | 0.00 |
| ATOM | 1031 | OG1 | THR | A | 635 | 21.211 | −4.321 | 45.024 | 1.00 | 0.00 |
| ATOM | 1032 | CG2 | THR | A | 635 | 20.096 | −2.877 | 46.566 | 1.00 | 0.00 |
| ATOM | 1033 | C | THR | A | 635 | 23.194 | −2.824 | 46.345 | 1.00 | 0.00 |
| ATOM | 1034 | O | THR | A | 635 | 23.726 | −3.090 | 45.261 | 1.00 | 0.00 |
| ATOM | 1035 | N | LEU | A | 636 | 23.365 | −1.664 | 46.958 | 1.00 | 0.00 |
| ATOM | 1037 | CA | LEU | A | 636 | 24.251 | −0.649 | 46.383 | 1.00 | 0.00 |
| ATOM | 1038 | CB | LEU | A | 636 | 23.785 | 0.731 | 46.860 | 1.00 | 0.00 |
| ATOM | 1039 | CG | LEU | A | 636 | 24.373 | 1.897 | 46.057 | 1.00 | 0.00 |
| ATOM | 1040 | CD1 | LEU | A | 636 | 23.423 | 3.086 | 46.029 | 1.00 | 0.00 |
| ATOM | 1041 | CD2 | LEU | A | 636 | 25.753 | 2.332 | 46.541 | 1.00 | 0.00 |
| ATOM | 1042 | C | LEU | A | 636 | 25.670 | −0.967 | 46.844 | 1.00 | 0.00 |
| ATOM | 1043 | O | LEU | A | 636 | 25.964 | −0.877 | 48.042 | 1.00 | 0.00 |
| ATOM | 1044 | N | PRO | A | 637 | 26.561 | −1.189 | 45.889 | 1.00 | 0.00 |
| ATOM | 1045 | CA | PRO | A | 637 | 27.835 | −1.858 | 46.181 | 1.00 | 0.00 |
| ATOM | 1046 | CB | PRO | A | 637 | 28.485 | −2.063 | 44.846 | 1.00 | 0.00 |
| ATOM | 1047 | CG | PRO | A | 637 | 27.568 | −1.545 | 43.748 | 1.00 | 0.00 |
| ATOM | 1048 | CD | PRO | A | 637 | 26.323 | −1.032 | 44.450 | 1.00 | 0.00 |
| ATOM | 1049 | C | PRO | A | 637 | 28.749 | −1.069 | 47.119 | 1.00 | 0.00 |
| ATOM | 1050 | O | PRO | A | 637 | 29.155 | −1.622 | 48.146 | 1.00 | 0.00 |
| ATOM | 1051 | N | CYS | A | 638 | 28.778 | 0.247 | 46.973 | 1.00 | 0.00 |
| ATOM | 1053 | CA | CYS | A | 638 | 29.640 | 1.074 | 47.829 | 1.00 | 0.00 |
| ATOM | 1054 | CB | CYS | A | 638 | 29.791 | 2.441 | 47.175 | 1.00 | 0.00 |
| ATOM | 1055 | SG | CYS | A | 638 | 30.496 | 2.427 | 45.511 | 1.00 | 0.00 |
| ATOM | 1056 | C | CYS | A | 638 | 29.076 | 1.242 | 49.241 | 1.00 | 0.00 |
| ATOM | 1057 | O | CYS | A | 638 | 29.847 | 1.199 | 50.209 | 1.00 | 0.00 |
| ATOM | 1058 | N | MET | A | 639 | 27.769 | 1.080 | 49.370 | 1.00 | 0.00 |
| ATOM | 1060 | CA | MET | A | 639 | 27.129 | 1.175 | 50.677 | 1.00 | 0.00 |
| ATOM | 1061 | CB | MET | A | 639 | 25.646 | 1.457 | 50.467 | 1.00 | 0.00 |
| ATOM | 1062 | CG | MET | A | 639 | 24.918 | 1.641 | 51.792 | 1.00 | 0.00 |
| ATOM | 1063 | SD | MET | A | 639 | 25.516 | 2.998 | 52.822 | 1.00 | 0.00 |
| ATOM | 1064 | CE | MET | A | 639 | 24.392 | 2.809 | 54.225 | 1.00 | 0.00 |
| ATOM | 1065 | C | MET | A | 639 | 27.313 | −0.136 | 51.428 | 1.00 | 0.00 |
| ATOM | 1066 | O | MET | A | 639 | 27.702 | −0.104 | 52.601 | 1.00 | 0.00 |
| ATOM | 1067 | N | TYR | A | 640 | 27.376 | −1.226 | 50.678 | 1.00 | 0.00 |
| ATOM | 1069 | CA | TYR | A | 640 | 27.632 | −2.544 | 51.264 | 1.00 | 0.00 |
| ATOM | 1070 | CB | TYR | A | 640 | 27.194 | −3.604 | 50.263 | 1.00 | 0.00 |
| ATOM | 1071 | CG | TYR | A | 640 | 27.344 | −5.031 | 50.776 | 1.00 | 0.00 |
| ATOM | 1072 | CD1 | TYR | A | 640 | 26.853 | −5.370 | 52.031 | 1.00 | 0.00 |
| ATOM | 1073 | CE1 | TYR | A | 640 | 26.992 | −6.668 | 52.503 | 1.00 | 0.00 |
| ATOM | 1074 | CZ | TYR | A | 640 | 27.620 | −7.624 | 51.716 | 1.00 | 0.00 |
| ATOM | 1075 | OH | TYR | A | 640 | 27.774 | −8.907 | 52.191 | 1.00 | 0.00 |
| ATOM | 1076 | CE2 | TYR | A | 640 | 28.107 | −7.290 | 50.460 | 1.00 | 0.00 |
| ATOM | 1077 | CD2 | TYR | A | 640 | 27.968 | −5.991 | 49.989 | 1.00 | 0.00 |
| ATOM | 1078 | C | TYR | A | 640 | 29.114 | −2.737 | 51.587 | 1.00 | 0.00 |
| ATOM | 1079 | O | TYR | A | 640 | 29.441 | −3.369 | 52.598 | 1.00 | 0.00 |
| ATOM | 1080 | N | ASP | A | 641 | 29.970 | −1.993 | 50.906 | 1.00 | 0.00 |
| ATOM | 1082 | CA | ASP | A | 641 | 31.403 | −2.022 | 51.212 | 1.00 | 0.00 |
| ATOM | 1083 | CB | ASP | A | 641 | 32.174 | −1.359 | 50.073 | 1.00 | 0.00 |
| ATOM | 1084 | CG | ASP | A | 641 | 31.985 | −2.107 | 48.754 | 1.00 | 0.00 |
| ATOM | 1085 | OD1 | ASP | A | 641 | 31.899 | −3.328 | 48.792 | 1.00 | 0.00 |
| ATOM | 1086 | OD2 | ASP | A | 641 | 32.034 | −1.450 | 47.721 | 1.00 | 0.00 |
| ATOM | 1087 | C | ASP | A | 641 | 31.680 | −1.266 | 52.507 | 1.00 | 0.00 |
| ATOM | 1088 | O | ASP | A | 641 | 32.427 | −1.759 | 53.361 | 1.00 | 0.00 |
| ATOM | 1089 | N | GLN | A | 642 | 30.885 | −0.239 | 52.763 | 1.00 | 0.00 |
| ATOM | 1091 | CA | GLN | A | 642 | 30.995 | 0.486 | 54.028 | 1.00 | 0.00 |
| ATOM | 1092 | CB | GLN | A | 642 | 30.375 | 1.863 | 53.850 | 1.00 | 0.00 |
| ATOM | 1093 | CG | GLN | A | 642 | 30.481 | 2.664 | 55.138 | 1.00 | 0.00 |
| ATOM | 1094 | CD | GLN | A | 642 | 29.900 | 4.054 | 54.938 | 1.00 | 0.00 |
| ATOM | 1095 | OE1 | GLN | A | 642 | 30.613 | 5.055 | 55.070 | 1.00 | 0.00 |
| ATOM | 1096 | NE2 | GLN | A | 642 | 28.615 | 4.098 | 54.636 | 1.00 | 0.00 |
| ATOM | 1099 | C | GLN | A | 642 | 30.292 | −0.260 | 55.162 | 1.00 | 0.00 |
| ATOM | 1100 | O | GLN | A | 642 | 30.757 | −0.219 | 56.308 | 1.00 | 0.00 |
| ATOM | 1101 | N | CYS | A | 643 | 29.367 | −1.135 | 54.805 | 1.00 | 0.00 |
| ATOM | 1103 | CA | CYS | A | 643 | 28.738 | −2.009 | 55.795 | 1.00 | 0.00 |
| ATOM | 1104 | CB | CYS | A | 643 | 27.440 | −2.559 | 55.219 | 1.00 | 0.00 |
| ATOM | 1105 | SG | CYS | A | 643 | 26.127 | −1.339 | 54.997 | 1.00 | 0.00 |
| ATOM | 1106 | C | CYS | A | 643 | 29.655 | −3.156 | 56.201 | 1.00 | 0.00 |
| ATOM | 1107 | O | CYS | A | 643 | 29.618 | −3.566 | 57.365 | 1.00 | 0.00 |
| ATOM | 1108 | N | LYS | A | 644 | 30.634 | −3.471 | 55.367 | 1.00 | 0.00 |
| ATOM | 1110 | CA | LYS | A | 644 | 31.654 | −4.447 | 55.759 | 1.00 | 0.00 |

TABLE I-continued

GR Homology Model Coordinates

| ATOM | 1111 | CB | LYS | A | 644 | 32.305 | −5.027 | 54.507 | 1.00 | 0.00 |
|---|---|---|---|---|---|---|---|---|---|---|
| ATOM | 1112 | CG | LYS | A | 644 | 31.338 | −5.789 | 53.595 | 1.00 | 0.00 |
| ATOM | 1113 | CD | LYS | A | 644 | 30.873 | −7.138 | 54.153 | 1.00 | 0.00 |
| ATOM | 1114 | CE | LYS | A | 644 | 29.694 | −7.035 | 55.121 | 1.00 | 0.00 |
| ATOM | 1115 | NZ | LYS | A | 644 | 29.317 | −8.358 | 55.640 | 1.00 | 0.00 |
| ATOM | 1116 | C | LYS | A | 644 | 32.715 | −3.800 | 56.645 | 1.00 | 0.00 |
| ATOM | 1117 | O | LYS | A | 644 | 33.216 | −4.451 | 57.568 | 1.00 | 0.00 |
| ATOM | 1118 | N | HIS | A | 645 | 32.825 | −2.484 | 56.555 | 1.00 | 0.00 |
| ATOM | 1120 | CA | HIS | A | 645 | 33.718 | −1.738 | 57.445 | 1.00 | 0.00 |
| ATOM | 1121 | CB | HIS | A | 645 | 33.965 | −0.352 | 56.860 | 1.00 | 0.00 |
| ATOM | 1122 | CG | HIS | A | 645 | 35.017 | −0.284 | 55.773 | 1.00 | 0.00 |
| ATOM | 1123 | ND1 | HIS | A | 645 | 34.846 | −0.527 | 54.460 | 1.00 | 0.00 |
| ATOM | 1125 | CE1 | HIS | A | 645 | 36.020 | −0.349 | 53.819 | 1.00 | 0.00 |
| ATOM | 1126 | NE2 | HIS | A | 645 | 36.942 | 0.002 | 54.743 | 1.00 | 0.00 |
| ATOM | 1127 | CD2 | HIS | A | 645 | 36.341 | 0.042 | 55.952 | 1.00 | 0.00 |
| ATOM | 1128 | C | HIS | A | 645 | 33.109 | −1.592 | 58.835 | 1.00 | 0.00 |
| ATOM | 1129 | O | HIS | A | 645 | 33.808 | −1.785 | 59.837 | 1.00 | 0.00 |
| ATOM | 1130 | N | MET | A | 646 | 31.790 | −1.510 | 58.889 | 1.00 | 0.00 |
| ATOM | 1132 | CA | MET | A | 646 | 31.101 | −1.452 | 60.182 | 1.00 | 0.00 |
| ATOM | 1133 | CB | MET | A | 646 | 29.788 | −0.706 | 59.981 | 1.00 | 0.00 |
| ATOM | 1134 | CG | MET | A | 646 | 30.071 | 0.699 | 59.456 | 1.00 | 0.00 |
| ATOM | 1135 | SD | MET | A | 646 | 28.641 | 1.774 | 59.196 | 1.00 | 0.00 |
| ATOM | 1136 | CE | MET | A | 646 | 27.754 | 0.800 | 57.960 | 1.00 | 0.00 |
| ATOM | 1137 | C | MET | A | 646 | 30.871 | −2.850 | 60.763 | 1.00 | 0.00 |
| ATOM | 1138 | O | MET | A | 646 | 30.815 | −3.016 | 61.990 | 1.00 | 0.00 |
| ATOM | 1139 | N | LEU | A | 647 | 31.021 | −3.852 | 59.910 | 1.00 | 0.00 |
| ATOM | 1141 | CA | LEU | A | 647 | 31.002 | −5.246 | 60.351 | 1.00 | 0.00 |
| ATOM | 1142 | CB | LEU | A | 647 | 30.748 | −6.136 | 59.136 | 1.00 | 0.00 |
| ATOM | 1143 | CG | LEU | A | 647 | 29.661 | −7.185 | 59.372 | 1.00 | 0.00 |
| ATOM | 1144 | CD1 | LEU | A | 647 | 30.022 | −8.157 | 60.490 | 1.00 | 0.00 |
| ATOM | 1145 | CD2 | LEU | A | 647 | 28.310 | −6.535 | 59.645 | 1.00 | 0.00 |
| ATOM | 1146 | C | LEU | A | 647 | 32.347 | −5.613 | 60.976 | 1.00 | 0.00 |
| ATOM | 1147 | O | LEU | A | 647 | 32.373 | −6.428 | 61.904 | 1.00 | 0.00 |
| ATOM | 1148 | N | TYR | A | 648 | 33.385 | −4.847 | 60.671 | 1.00 | 0.00 |
| ATOM | 1150 | CA | TYR | A | 648 | 34.680 | −5.063 | 61.324 | 1.00 | 0.00 |
| ATOM | 1151 | CB | TYR | A | 648 | 35.785 | −4.317 | 60.579 | 1.00 | 0.00 |
| ATOM | 1152 | CG | TYR | A | 648 | 36.029 | −4.744 | 59.134 | 1.00 | 0.00 |
| ATOM | 1153 | CD1 | TYR | A | 648 | 36.440 | −3.796 | 58.205 | 1.00 | 0.00 |
| ATOM | 1154 | CE1 | TYR | A | 648 | 36.659 | −4.164 | 56.884 | 1.00 | 0.00 |
| ATOM | 1155 | CZ | TYR | A | 648 | 36.475 | −5.484 | 56.499 | 1.00 | 0.00 |
| ATOM | 1156 | OH | TYR | A | 648 | 36.636 | −5.838 | 55.177 | 1.00 | 0.00 |
| ATOM | 1157 | CE2 | TYR | A | 648 | 36.086 | −6.440 | 57.428 | 1.00 | 0.00 |
| ATOM | 1158 | CD2 | TYR | A | 648 | 35.868 | −6.070 | 58.749 | 1.00 | 0.00 |
| ATOM | 1159 | C | TYR | A | 648 | 34.644 | −4.554 | 62.760 | 1.00 | 0.00 |
| ATOM | 1160 | O | TYR | A | 648 | 35.165 | −5.231 | 63.652 | 1.00 | 0.00 |
| ATOM | 1161 | N | VAL | A | 649 | 33.814 | −3.556 | 63.019 | 1.00 | 0.00 |
| ATOM | 1163 | CA | VAL | A | 649 | 33.677 | −3.041 | 64.383 | 1.00 | 0.00 |
| ATOM | 1164 | CB | VAL | A | 649 | 32.892 | −1.733 | 64.329 | 1.00 | 0.00 |
| ATOM | 1165 | CG1 | VAL | A | 649 | 32.756 | −1.115 | 65.717 | 1.00 | 0.00 |
| ATOM | 1166 | CG2 | VAL | A | 649 | 33.541 | −0.745 | 63.366 | 1.00 | 0.00 |
| ATOM | 1167 | C | VAL | A | 649 | 32.930 | −4.047 | 65.254 | 1.00 | 0.00 |
| ATOM | 1168 | O | VAL | A | 649 | 33.470 | −4.481 | 66.282 | 1.00 | 0.00 |
| ATOM | 1169 | N | SER | A | 650 | 31.895 | −4.640 | 64.676 | 1.00 | 0.00 |
| ATOM | 1171 | CA | SER | A | 650 | 31.086 | −5.614 | 65.412 | 1.00 | 0.00 |
| ATOM | 1172 | CB | SER | A | 650 | 29.793 | −5.857 | 64.640 | 1.00 | 0.00 |
| ATOM | 1173 | OG | SER | A | 650 | 29.095 | −4.622 | 64.547 | 1.00 | 0.00 |
| ATOM | 1174 | C | SER | A | 650 | 31.823 | −6.938 | 65.594 | 1.00 | 0.00 |
| ATOM | 1175 | O | SER | A | 650 | 31.846 | −7.458 | 66.716 | 1.00 | 0.00 |
| ATOM | 1176 | N | SER | A | 651 | 32.650 | −7.298 | 64.625 | 1.00 | 0.00 |
| ATOM | 1178 | CA | SER | A | 651 | 33.413 | −8.544 | 64.722 | 1.00 | 0.00 |
| ATOM | 1179 | CB | SER | A | 651 | 33.898 | −8.952 | 63.334 | 1.00 | 0.00 |
| ATOM | 1180 | OG | SER | A | 651 | 34.821 | −7.972 | 62.876 | 1.00 | 0.00 |
| ATOM | 1181 | C | SER | A | 651 | 34.616 | −8.432 | 65.654 | 1.00 | 0.00 |
| ATOM | 1182 | O | SER | A | 651 | 34.940 | −9.426 | 66.312 | 1.00 | 0.00 |
| ATOM | 1183 | N | GLU | A | 652 | 35.105 | −7.229 | 65.915 | 1.00 | 0.00 |
| ATOM | 1185 | CA | GLU | A | 652 | 36.214 | −7.121 | 66.865 | 1.00 | 0.00 |
| ATOM | 1186 | CB | GLU | A | 652 | 37.029 | −5.854 | 66.628 | 1.00 | 0.00 |
| ATOM | 1187 | CG | GLU | A | 652 | 37.621 | −5.783 | 65.223 | 1.00 | 0.00 |
| ATOM | 1188 | CD | GLU | A | 652 | 38.337 | −7.074 | 64.835 | 1.00 | 0.00 |
| ATOM | 1189 | OE1 | GLU | A | 652 | 39.488 | −7.223 | 65.220 | 1.00 | 0.00 |
| ATOM | 1190 | OE2 | GLU | A | 652 | 37.768 | −7.812 | 64.039 | 1.00 | 0.00 |
| ATOM | 1191 | C | GLU | A | 652 | 35.681 | −7.130 | 68.289 | 1.00 | 0.00 |
| ATOM | 1192 | O | GLU | A | 652 | 36.244 | −7.836 | 69.133 | 1.00 | 0.00 |
| ATOM | 1193 | N | LEU | A | 653 | 34.457 | −6.653 | 68.455 | 1.00 | 0.00 |
| ATOM | 1195 | CA | LEU | A | 653 | 33.820 | −6.700 | 69.773 | 1.00 | 0.00 |
| ATOM | 1196 | CB | LEU | A | 653 | 32.614 | −5.767 | 69.769 | 1.00 | 0.00 |
| ATOM | 1197 | CG | LEU | A | 653 | 33.009 | −4.322 | 69.486 | 1.00 | 0.00 |

TABLE I-continued

GR Homology Model Coordinates

| ATOM | 1198 | CD1 | LEU | A | 653 | 31.778 | −3.450 | 69.281 | 1.00 | 0.00 |
|---|---|---|---|---|---|---|---|---|---|---|
| ATOM | 1199 | CD2 | LEU | A | 653 | 33.893 | −3.754 | 70.591 | 1.00 | 0.00 |
| ATOM | 1200 | C | LEU | A | 653 | 33.358 | −8.119 | 70.093 | 1.00 | 0.00 |
| ATOM | 1201 | O | LEU | A | 653 | 33.492 | −8.571 | 71.239 | 1.00 | 0.00 |
| ATOM | 1202 | N | HIS | A | 654 | 33.064 | −8.866 | 69.042 | 1.00 | 0.00 |
| ATOM | 1204 | CA | HIS | A | 654 | 32.661 | −10.264 | 69.169 | 1.00 | 0.00 |
| ATOM | 1205 | CB | HIS | A | 654 | 32.058 | −10.685 | 67.835 | 1.00 | 0.00 |
| ATOM | 1206 | CG | HIS | A | 654 | 31.437 | −12.066 | 67.819 | 1.00 | 0.00 |
| ATOM | 1207 | ND1 | HIS | A | 654 | 32.011 | −13.208 | 67.394 | 1.00 | 0.00 |
| ATOM | 1209 | CE1 | HIS | A | 654 | 31.136 | −14.224 | 67.531 | 1.00 | 0.00 |
| ATOM | 1210 | NE2 | HIS | A | 654 | 29.994 | −13.716 | 68.046 | 1.00 | 0.00 |
| ATOM | 1211 | CD2 | HIS | A | 654 | 30.163 | −12.386 | 68.227 | 1.00 | 0.00 |
| ATOM | 1212 | C | HIS | A | 654 | 33.837 | −11.173 | 69.496 | 1.00 | 0.00 |
| ATOM | 1213 | O | HIS | A | 654 | 33.816 | −11.838 | 70.538 | 1.00 | 0.00 |
| ATOM | 1214 | N | ARG | A | 655 | 34.924 | −11.030 | 68.754 | 1.00 | 0.00 |
| ATOM | 1216 | CA | ARG | A | 655 | 36.068 | −11.938 | 68.910 | 1.00 | 0.00 |
| ATOM | 1217 | CB | ARG | A | 655 | 36.914 | −11.868 | 67.647 | 1.00 | 0.00 |
| ATOM | 1218 | CG | ARG | A | 655 | 36.146 | −12.351 | 66.425 | 1.00 | 0.00 |
| ATOM | 1219 | CD | ARG | A | 655 | 37.008 | −12.253 | 65.172 | 1.00 | 0.00 |
| ATOM | 1220 | NE | ARG | A | 655 | 38.220 | −13.079 | 65.312 | 1.00 | 0.00 |
| ATOM | 1221 | CZ | ARG | A | 655 | 39.459 | −12.590 | 65.223 | 1.00 | 0.00 |
| ATOM | 1222 | NH1 | ARG | A | 655 | 39.649 | −11.286 | 65.012 | 1.00 | 0.00 |
| ATOM | 1223 | NH2 | ARG | A | 655 | 40.509 | −13.403 | 65.365 | 1.00 | 0.00 |
| ATOM | 1224 | C | ARG | A | 655 | 36.955 | −11.605 | 70.105 | 1.00 | 0.00 |
| ATOM | 1225 | O | ARG | A | 655 | 37.716 | −12.464 | 70.563 | 1.00 | 0.00 |
| ATOM | 1226 | N | LEU | A | 656 | 36.832 | −10.398 | 70.628 | 1.00 | 0.00 |
| ATOM | 1228 | CA | LEU | A | 656 | 37.541 | −10.057 | 71.861 | 1.00 | 0.00 |
| ATOM | 1229 | CB | LEU | A | 656 | 38.003 | −8.609 | 71.766 | 1.00 | 0.00 |
| ATOM | 1230 | CG | LEU | A | 656 | 38.995 | −8.397 | 70.626 | 1.00 | 0.00 |
| ATOM | 1231 | CD1 | LEU | A | 656 | 39.336 | −6.918 | 70.473 | 1.00 | 0.00 |
| ATOM | 1232 | CD2 | LEU | A | 656 | 40.259 | −9.226 | 70.826 | 1.00 | 0.00 |
| ATOM | 1233 | C | LEU | A | 656 | 36.642 | −10.241 | 73.084 | 1.00 | 0.00 |
| ATOM | 1234 | O | LEU | A | 656 | 37.136 | −10.227 | 74.220 | 1.00 | 0.00 |
| ATOM | 1235 | N | GLN | A | 657 | 35.374 | −10.533 | 72.827 | 1.00 | 0.00 |
| ATOM | 1237 | CA | GLN | A | 657 | 34.333 | −10.652 | 73.855 | 1.00 | 0.00 |
| ATOM | 1238 | CB | GLN | A | 657 | 34.489 | −11.972 | 74.598 | 1.00 | 0.00 |
| ATOM | 1239 | CG | GLN | A | 657 | 34.336 | −13.153 | 73.649 | 1.00 | 0.00 |
| ATOM | 1240 | CD | GLN | A | 657 | 34.338 | −14.447 | 74.451 | 1.00 | 0.00 |
| ATOM | 1241 | OE1 | GLN | A | 657 | 34.424 | −15.547 | 73.892 | 1.00 | 0.00 |
| ATOM | 1242 | NE2 | GLN | A | 657 | 34.208 | −14.295 | 75.758 | 1.00 | 0.00 |
| ATOM | 1245 | C | GLN | A | 657 | 34.383 | −9.490 | 74.831 | 1.00 | 0.00 |
| ATOM | 1246 | O | GLN | A | 657 | 34.536 | −9.690 | 76.041 | 1.00 | 0.00 |
| ATOM | 1247 | N | VAL | A | 658 | 34.190 | −8.295 | 74.298 | 1.00 | 0.00 |
| ATOM | 1249 | CA | VAL | A | 658 | 34.338 | −7.073 | 75.095 | 1.00 | 0.00 |
| ATOM | 1250 | CB | VAL | A | 658 | 34.309 | −5.890 | 74.127 | 1.00 | 0.00 |
| ATOM | 1251 | CG1 | VAL | A | 658 | 34.573 | −4.560 | 74.828 | 1.00 | 0.00 |
| ATOM | 1252 | CG2 | VAL | A | 658 | 35.324 | −6.094 | 73.011 | 1.00 | 0.00 |
| ATOM | 1253 | C | VAL | A | 658 | 33.219 | −6.953 | 76.125 | 1.00 | 0.00 |
| ATOM | 1254 | O | VAL | A | 658 | 32.049 | −7.210 | 75.818 | 1.00 | 0.00 |
| ATOM | 1255 | N | SER | A | 659 | 33.592 | −6.660 | 77.360 | 1.00 | 0.00 |
| ATOM | 1257 | CA | SER | A | 659 | 32.586 | −6.398 | 78.394 | 1.00 | 0.00 |
| ATOM | 1258 | CB | SER | A | 659 | 33.231 | −6.381 | 79.775 | 1.00 | 0.00 |
| ATOM | 1259 | OG | SER | A | 659 | 33.860 | −5.116 | 79.950 | 1.00 | 0.00 |
| ATOM | 1260 | C | SER | A | 659 | 31.954 | −5.036 | 78.149 | 1.00 | 0.00 |
| ATOM | 1261 | O | SER | A | 659 | 32.594 | −4.138 | 77.585 | 1.00 | 0.00 |
| ATOM | 1262 | N | TYR | A | 660 | 30.798 | −4.820 | 78.754 | 1.00 | 0.00 |
| ATOM | 1264 | CA | TYR | A | 660 | 30.094 | −3.536 | 78.604 | 1.00 | 0.00 |
| ATOM | 1265 | CB | TYR | A | 660 | 28.631 | −3.697 | 79.031 | 1.00 | 0.00 |
| ATOM | 1266 | CG | TYR | A | 660 | 28.387 | −4.075 | 80.495 | 1.00 | 0.00 |
| ATOM | 1267 | CD1 | TYR | A | 660 | 28.328 | −5.412 | 80.874 | 1.00 | 0.00 |
| ATOM | 1268 | CE1 | TYR | A | 660 | 28.124 | −5.750 | 82.205 | 1.00 | 0.00 |
| ATOM | 1269 | CZ | TYR | A | 660 | 27.962 | −4.749 | 83.154 | 1.00 | 0.00 |
| ATOM | 1270 | OH | TYR | A | 660 | 27.954 | −5.075 | 84.492 | 1.00 | 0.00 |
| ATOM | 1271 | CE2 | TYR | A | 660 | 27.981 | −3.414 | 82.774 | 1.00 | 0.00 |
| ATOM | 1272 | CD2 | TYR | A | 660 | 28.186 | −3.078 | 81.443 | 1.00 | 0.00 |
| ATOM | 1273 | C | TYR | A | 660 | 30.769 | −2.427 | 79.414 | 1.00 | 0.00 |
| ATOM | 1274 | O | TYR | A | 660 | 30.727 | −1.258 | 79.014 | 1.00 | 0.00 |
| ATOM | 1275 | N | GLU | A | 661 | 31.580 | −2.821 | 80.382 | 1.00 | 0.00 |
| ATOM | 1277 | CA | GLU | A | 661 | 32.356 | −1.863 | 81.164 | 1.00 | 0.00 |
| ATOM | 1278 | CB | GLU | A | 661 | 32.890 | −2.538 | 82.428 | 1.00 | 0.00 |
| ATOM | 1279 | CG | GLU | A | 661 | 31.786 | −2.930 | 83.412 | 1.00 | 0.00 |
| ATOM | 1280 | CD | GLU | A | 661 | 31.495 | −4.430 | 83.375 | 1.00 | 0.00 |
| ATOM | 1281 | OE1 | GLU | A | 661 | 31.605 | −5.001 | 82.294 | 1.00 | 0.00 |
| ATOM | 1282 | OE2 | GLU | A | 661 | 31.047 | −4.947 | 84.388 | 1.00 | 0.00 |
| ATOM | 1283 | C | GLU | A | 661 | 33.516 | −1.338 | 80.328 | 1.00 | 0.00 |
| ATOM | 1284 | O | GLU | A | 661 | 33.669 | −0.116 | 80.202 | 1.00 | 0.00 |
| ATOM | 1285 | N | GLU | A | 662 | 34.168 | −2.226 | 79.589 | 1.00 | 0.00 |

TABLE I-continued

GR Homology Model Coordinates

| ATOM | 1287 | CA | GLU | A | 662 | 35.237 | −1.783 | 78.694 | 1.00 | 0.00 |
|---|---|---|---|---|---|---|---|---|---|---|
| ATOM | 1288 | CB | GLU | A | 662 | 35.978 | −3.010 | 78.183 | 1.00 | 0.00 |
| ATOM | 1289 | CG | GLU | A | 662 | 36.714 | −3.716 | 79.313 | 1.00 | 0.00 |
| ATOM | 1290 | CD | GLU | A | 662 | 37.161 | −5.095 | 78.849 | 1.00 | 0.00 |
| ATOM | 1291 | OE1 | GLU | A | 662 | 36.307 | −5.800 | 78.324 | 1.00 | 0.00 |
| ATOM | 1292 | OE2 | GLU | A | 662 | 38.346 | −5.380 | 78.933 | 1.00 | 0.00 |
| ATOM | 1293 | C | GLU | A | 662 | 34.684 | −0.993 | 77.516 | 1.00 | 0.00 |
| ATOM | 1294 | O | GLU | A | 662 | 35.196 | 0.101 | 77.254 | 1.00 | 0.00 |
| ATOM | 1295 | N | TYR | A | 663 | 33.509 | −1.369 | 77.035 | 1.00 | 0.00 |
| ATOM | 1297 | CA | TYR | A | 663 | 32.888 | −0.642 | 75.925 | 1.00 | 0.00 |
| ATOM | 1298 | CB | TYR | A | 663 | 31.658 | −1.414 | 75.460 | 1.00 | 0.00 |
| ATOM | 1299 | CG | TYR | A | 663 | 30.799 | −0.633 | 74.468 | 1.00 | 0.00 |
| ATOM | 1300 | CD1 | TYR | A | 663 | 31.220 | −0.482 | 73.154 | 1.00 | 0.00 |
| ATOM | 1301 | CE1 | TYR | A | 663 | 30.448 | 0.246 | 72.259 | 1.00 | 0.00 |
| ATOM | 1302 | CZ | TYR | A | 663 | 29.258 | 0.822 | 72.680 | 1.00 | 0.00 |
| ATOM | 1303 | OH | TYR | A | 663 | 28.502 | 1.554 | 71.793 | 1.00 | 0.00 |
| ATOM | 1304 | CE2 | TYR | A | 663 | 28.828 | 0.664 | 73.990 | 1.00 | 0.00 |
| ATOM | 1305 | CD2 | TYR | A | 663 | 29.599 | −0.067 | 74.883 | 1.00 | 0.00 |
| ATOM | 1306 | C | TYR | A | 663 | 32.464 | 0.772 | 76.312 | 1.00 | 0.00 |
| ATOM | 1307 | O | TYR | A | 663 | 32.767 | 1.712 | 75.568 | 1.00 | 0.00 |
| ATOM | 1308 | N | LEU | A | 664 | 32.006 | 0.957 | 77.539 | 1.00 | 0.00 |
| ATOM | 1310 | CA | LEU | A | 664 | 31.543 | 2.281 | 77.966 | 1.00 | 0.00 |
| ATOM | 1311 | CB | LEU | A | 664 | 30.705 | 2.125 | 79.234 | 1.00 | 0.00 |
| ATOM | 1312 | CG | LEU | A | 664 | 29.195 | 2.219 | 78.995 | 1.00 | 0.00 |
| ATOM | 1313 | CD1 | LEU | A | 664 | 28.682 | 1.260 | 77.927 | 1.00 | 0.00 |
| ATOM | 1314 | CD2 | LEU | A | 664 | 28.439 | 1.986 | 80.294 | 1.00 | 0.00 |
| ATOM | 1315 | C | LEU | A | 664 | 32.712 | 3.222 | 78.235 | 1.00 | 0.00 |
| ATOM | 1316 | O | LEU | A | 664 | 32.674 | 4.380 | 77.794 | 1.00 | 0.00 |
| ATOM | 1317 | N | CYS | A | 665 | 33.828 | 2.665 | 78.677 | 1.00 | 0.00 |
| ATOM | 1319 | CA | CYS | A | 665 | 35.008 | 3.493 | 78.920 | 1.00 | 0.00 |
| ATOM | 1320 | CB | CYS | A | 665 | 35.919 | 2.760 | 79.890 | 1.00 | 0.00 |
| ATOM | 1321 | SG | CYS | A | 665 | 35.186 | 2.404 | 81.503 | 1.00 | 0.00 |
| ATOM | 1322 | C | CYS | A | 665 | 35.751 | 3.812 | 77.623 | 1.00 | 0.00 |
| ATOM | 1323 | O | CYS | A | 665 | 36.166 | 4.962 | 77.434 | 1.00 | 0.00 |
| ATOM | 1324 | N | MET | A | 666 | 35.649 | 2.927 | 76.644 | 1.00 | 0.00 |
| ATOM | 1326 | CA | MET | A | 666 | 36.238 | 3.199 | 75.329 | 1.00 | 0.00 |
| ATOM | 1327 | CB | MET | A | 666 | 36.305 | 1.897 | 74.543 | 1.00 | 0.00 |
| ATOM | 1328 | CG | MET | A | 666 | 37.277 | 0.904 | 75.160 | 1.00 | 0.00 |
| ATOM | 1329 | SD | MET | A | 666 | 37.151 | −0.776 | 74.512 | 1.00 | 0.00 |
| ATOM | 1330 | CE | MET | A | 666 | 37.494 | −0.446 | 72.770 | 1.00 | 0.00 |
| ATOM | 1331 | C | MET | A | 666 | 35.396 | 4.188 | 74.536 | 1.00 | 0.00 |
| ATOM | 1332 | O | MET | A | 666 | 35.958 | 5.085 | 73.902 | 1.00 | 0.00 |
| ATOM | 1333 | N | LYS | A | 667 | 34.097 | 4.188 | 74.779 | 1.00 | 0.00 |
| ATOM | 1335 | CA | LYS | A | 667 | 33.199 | 5.094 | 74.067 | 1.00 | 0.00 |
| ATOM | 1336 | CB | LYS | A | 667 | 31.787 | 4.547 | 74.215 | 1.00 | 0.00 |
| ATOM | 1337 | CG | LYS | A | 667 | 30.755 | 5.383 | 73.466 | 1.00 | 0.00 |
| ATOM | 1338 | CD | LYS | A | 667 | 29.323 | 4.883 | 73.671 | 1.00 | 0.00 |
| ATOM | 1339 | CE | LYS | A | 667 | 28.649 | 5.412 | 74.942 | 1.00 | 0.00 |
| ATOM | 1340 | NZ | LYS | A | 667 | 29.218 | 4.876 | 76.192 | 1.00 | 0.00 |
| ATOM | 1341 | C | LYS | A | 667 | 33.283 | 6.519 | 74.609 | 1.00 | 0.00 |
| ATOM | 1342 | O | LYS | A | 667 | 33.311 | 7.464 | 73.811 | 1.00 | 0.00 |
| ATOM | 1343 | N | THR | A | 668 | 33.599 | 6.665 | 75.888 | 1.00 | 0.00 |
| ATOM | 1345 | CA | THR | A | 668 | 33.818 | 8.020 | 76.403 | 1.00 | 0.00 |
| ATOM | 1346 | CB | THR | A | 668 | 33.497 | 8.105 | 77.895 | 1.00 | 0.00 |
| ATOM | 1347 | OG1 | THR | A | 668 | 33.777 | 9.433 | 78.313 | 1.00 | 0.00 |
| ATOM | 1348 | CG2 | THR | A | 668 | 34.321 | 7.157 | 78.755 | 1.00 | 0.00 |
| ATOM | 1349 | C | THR | A | 668 | 35.238 | 8.501 | 76.095 | 1.00 | 0.00 |
| ATOM | 1350 | O | THR | A | 668 | 35.429 | 9.701 | 75.866 | 1.00 | 0.00 |
| ATOM | 1351 | N | LEU | A | 669 | 36.125 | 7.567 | 75.784 | 1.00 | 0.00 |
| ATOM | 1353 | CA | LEU | A | 669 | 37.451 | 7.923 | 75.277 | 1.00 | 0.00 |
| ATOM | 1354 | CB | LEU | A | 669 | 38.407 | 6.756 | 75.489 | 1.00 | 0.00 |
| ATOM | 1355 | CG | LEU | A | 669 | 38.838 | 6.653 | 76.945 | 1.00 | 0.00 |
| ATOM | 1356 | CD1 | LEU | A | 669 | 39.642 | 5.381 | 77.188 | 1.00 | 0.00 |
| ATOM | 1357 | CD2 | LEU | A | 669 | 39.635 | 7.888 | 77.348 | 1.00 | 0.00 |
| ATOM | 1358 | C | LEU | A | 669 | 37.419 | 8.286 | 73.796 | 1.00 | 0.00 |
| ATOM | 1359 | O | LEU | A | 669 | 38.247 | 9.098 | 73.378 | 1.00 | 0.00 |
| ATOM | 1360 | N | LEU | A | 670 | 36.348 | 7.935 | 73.096 | 1.00 | 0.00 |
| ATOM | 1362 | CA | LEU | A | 670 | 36.198 | 8.327 | 71.687 | 1.00 | 0.00 |
| ATOM | 1363 | CB | LEU | A | 670 | 35.195 | 7.409 | 71.015 | 1.00 | 0.00 |
| ATOM | 1364 | CG | LEU | A | 670 | 35.713 | 5.986 | 71.005 | 1.00 | 0.00 |
| ATOM | 1365 | CD1 | LEU | A | 670 | 34.660 | 5.048 | 70.441 | 1.00 | 0.00 |
| ATOM | 1366 | CD2 | LEU | A | 670 | 37.025 | 5.893 | 70.234 | 1.00 | 0.00 |
| ATOM | 1367 | C | LEU | A | 670 | 35.704 | 9.756 | 71.560 | 1.00 | 0.00 |
| ATOM | 1368 | O | LEU | A | 670 | 36.144 | 10.482 | 70.659 | 1.00 | 0.00 |
| ATOM | 1369 | N | LEU | A | 671 | 35.085 | 10.230 | 72.629 | 1.00 | 0.00 |
| ATOM | 1371 | CA | LEU | A | 671 | 34.688 | 11.635 | 72.724 | 1.00 | 0.00 |
| ATOM | 1372 | CB | LEU | A | 671 | 33.669 | 11.721 | 73.857 | 1.00 | 0.00 |

TABLE I-continued

GR Homology Model Coordinates

| | | | | | | | | | | |
|---|---|---|---|---|---|---|---|---|---|---|
| ATOM | 1373 | CG | LEU | A | 671 | 33.128 | 13.127 | 74.083 | 1.00 | 0.00 |
| ATOM | 1374 | CD1 | LEU | A | 671 | 32.411 | 13.648 | 72.844 | 1.00 | 0.00 |
| ATOM | 1375 | CD2 | LEU | A | 671 | 32.189 | 13.138 | 75.283 | 1.00 | 0.00 |
| ATOM | 1376 | C | LEU | A | 671 | 35.912 | 12.500 | 73.040 | 1.00 | 0.00 |
| ATOM | 1377 | O | LEU | A | 671 | 35.968 | 13.679 | 72.676 | 1.00 | 0.00 |
| ATOM | 1378 | N | LEU | A | 672 | 36.949 | 11.845 | 73.534 | 1.00 | 0.00 |
| ATOM | 1380 | CA | LEU | A | 672 | 38.228 | 12.482 | 73.844 | 1.00 | 0.00 |
| ATOM | 1381 | CB | LEU | A | 672 | 38.642 | 11.993 | 75.228 | 1.00 | 0.00 |
| ATOM | 1382 | CG | LEU | A | 672 | 37.539 | 12.238 | 76.254 | 1.00 | 0.00 |
| ATOM | 1383 | CD1 | LEU | A | 672 | 37.761 | 11.428 | 77.524 | 1.00 | 0.00 |
| ATOM | 1384 | CD2 | LEU | A | 672 | 37.371 | 13.720 | 76.568 | 1.00 | 0.00 |
| ATOM | 1385 | C | LEU | A | 672 | 39.321 | 12.121 | 72.826 | 1.00 | 0.00 |
| ATOM | 1386 | O | LEU | A | 672 | 40.502 | 12.367 | 73.092 | 1.00 | 0.00 |
| ATOM | 1387 | N | SER | A | 673 | 38.950 | 11.557 | 71.684 | 1.00 | 0.00 |
| ATOM | 1389 | CA | SER | A | 673 | 39.957 | 11.067 | 70.725 | 1.00 | 0.00 |
| ATOM | 1390 | CB | SER | A | 673 | 39.403 | 9.861 | 69.974 | 1.00 | 0.00 |
| ATOM | 1391 | OG | SER | A | 673 | 39.316 | 8.768 | 70.872 | 1.00 | 0.00 |
| ATOM | 1392 | C | SER | A | 673 | 40.419 | 12.074 | 69.675 | 1.00 | 0.00 |
| ATOM | 1393 | O | SER | A | 673 | 41.293 | 11.728 | 68.869 | 1.00 | 0.00 |
| ATOM | 1394 | N | SER | A | 674 | 39.854 | 13.269 | 69.632 | 1.00 | 0.00 |
| ATOM | 1396 | CA | SER | A | 674 | 40.263 | 14.210 | 68.577 | 1.00 | 0.00 |
| ATOM | 1397 | CB | SER | A | 674 | 39.311 | 14.072 | 67.394 | 1.00 | 0.00 |
| ATOM | 1398 | OG | SER | A | 674 | 39.394 | 12.744 | 66.897 | 1.00 | 0.00 |
| ATOM | 1399 | C | SER | A | 674 | 40.258 | 15.664 | 69.030 | 1.00 | 0.00 |
| ATOM | 1400 | O | SER | A | 674 | 39.212 | 16.210 | 69.399 | 1.00 | 0.00 |
| ATOM | 1401 | N | VAL | A | 675 | 41.422 | 16.286 | 68.964 | 1.00 | 0.00 |
| ATOM | 1403 | CA | VAL | A | 675 | 41.522 | 17.728 | 69.218 | 1.00 | 0.00 |
| ATOM | 1404 | CB | VAL | A | 675 | 42.703 | 17.996 | 70.152 | 1.00 | 0.00 |
| ATOM | 1405 | CG1 | VAL | A | 675 | 42.400 | 17.553 | 71.576 | 1.00 | 0.00 |
| ATOM | 1406 | CG2 | VAL | A | 675 | 43.990 | 17.360 | 69.644 | 1.00 | 0.00 |
| ATOM | 1407 | C | VAL | A | 675 | 41.698 | 18.466 | 67.892 | 1.00 | 0.00 |
| ATOM | 1408 | O | VAL | A | 675 | 41.985 | 17.835 | 66.870 | 1.00 | 0.00 |
| ATOM | 1409 | N | PRO | A | 676 | 41.413 | 19.756 | 67.863 | 1.00 | 0.00 |
| ATOM | 1410 | CA | PRO | A | 676 | 41.889 | 20.576 | 66.750 | 1.00 | 0.00 |
| ATOM | 1411 | CB | PRO | A | 676 | 41.325 | 21.942 | 66.995 | 1.00 | 0.00 |
| ATOM | 1412 | CG | PRO | A | 676 | 40.664 | 21.967 | 68.366 | 1.00 | 0.00 |
| ATOM | 1413 | CD | PRO | A | 676 | 40.797 | 20.558 | 68.922 | 1.00 | 0.00 |
| ATOM | 1414 | C | PRO | A | 676 | 43.411 | 20.598 | 66.756 | 1.00 | 0.00 |
| ATOM | 1415 | O | PRO | A | 676 | 44.029 | 20.390 | 67.807 | 1.00 | 0.00 |
| ATOM | 1416 | N | LYS | A | 677 | 44.010 | 20.965 | 65.635 | 1.00 | 0.00 |
| ATOM | 1418 | CA | LYS | A | 677 | 45.478 | 21.035 | 65.565 | 1.00 | 0.00 |
| ATOM | 1419 | CB | LYS | A | 677 | 45.874 | 21.122 | 64.094 | 1.00 | 0.00 |
| ATOM | 1420 | CG | LYS | A | 677 | 47.359 | 20.847 | 63.896 | 1.00 | 0.00 |
| ATOM | 1421 | CD | LYS | A | 677 | 47.714 | 19.452 | 64.398 | 1.00 | 0.00 |
| ATOM | 1422 | CE | LYS | A | 677 | 49.199 | 19.161 | 64.234 | 1.00 | 0.00 |
| ATOM | 1423 | NZ | LYS | A | 677 | 49.523 | 17.811 | 64.721 | 1.00 | 0.00 |
| ATOM | 1424 | C | LYS | A | 677 | 46.051 | 22.238 | 66.336 | 1.00 | 0.00 |
| ATOM | 1425 | O | LYS | A | 677 | 47.238 | 22.253 | 66.680 | 1.00 | 0.00 |
| ATOM | 1426 | N | ASP | A | 678 | 45.185 | 23.159 | 66.730 | 1.00 | 0.00 |
| ATOM | 1428 | CA | ASP | A | 678 | 45.584 | 24.288 | 67.577 | 1.00 | 0.00 |
| ATOM | 1429 | CB | ASP | A | 678 | 44.738 | 25.503 | 67.209 | 1.00 | 0.00 |
| ATOM | 1430 | CG | ASP | A | 678 | 44.931 | 25.879 | 65.742 | 1.00 | 0.00 |
| ATOM | 1431 | OD1 | ASP | A | 678 | 44.166 | 25.385 | 64.922 | 1.00 | 0.00 |
| ATOM | 1432 | OD2 | ASP | A | 678 | 45.846 | 26.640 | 65.465 | 1.00 | 0.00 |
| ATOM | 1433 | C | ASP | A | 678 | 45.381 | 23.999 | 69.069 | 1.00 | 0.00 |
| ATOM | 1434 | O | ASP | A | 678 | 45.724 | 24.842 | 69.905 | 1.00 | 0.00 |
| ATOM | 1435 | N | GLY | A | 679 | 44.829 | 22.840 | 69.400 | 1.00 | 0.00 |
| ATOM | 1437 | CA | GLY | A | 679 | 44.537 | 22.520 | 70.801 | 1.00 | 0.00 |
| ATOM | 1438 | C | GLY | A | 679 | 43.230 | 23.158 | 71.271 | 1.00 | 0.00 |
| ATOM | 1439 | O | GLY | A | 679 | 42.640 | 24.000 | 70.582 | 1.00 | 0.00 |
| ATOM | 1440 | N | LEU | A | 680 | 42.752 | 22.677 | 72.406 | 1.00 | 0.00 |
| ATOM | 1442 | CA | LEU | A | 680 | 41.547 | 23.224 | 73.039 | 1.00 | 0.00 |
| ATOM | 1443 | CB | LEU | A | 680 | 40.853 | 22.116 | 73.820 | 1.00 | 0.00 |
| ATOM | 1444 | CG | LEU | A | 680 | 40.336 | 21.013 | 72.907 | 1.00 | 0.00 |
| ATOM | 1445 | CD1 | LEU | A | 680 | 39.795 | 19.854 | 73.729 | 1.00 | 0.00 |
| ATOM | 1446 | CD2 | LEU | A | 680 | 39.263 | 21.541 | 71.961 | 1.00 | 0.00 |
| ATOM | 1447 | C | LEU | A | 680 | 41.896 | 24.355 | 73.999 | 1.00 | 0.00 |
| ATOM | 1448 | O | LEU | A | 680 | 43.008 | 24.412 | 74.539 | 1.00 | 0.00 |
| ATOM | 1449 | N | LYS | A | 681 | 40.907 | 25.182 | 74.296 | 1.00 | 0.00 |
| ATOM | 1451 | CA | LYS | A | 681 | 41.126 | 26.285 | 75.241 | 1.00 | 0.00 |
| ATOM | 1452 | CB | LYS | A | 681 | 39.953 | 27.253 | 75.161 | 1.00 | 0.00 |
| ATOM | 1453 | CG | LYS | A | 681 | 40.145 | 28.427 | 76.116 | 1.00 | 0.00 |
| ATOM | 1454 | CD | LYS | A | 681 | 39.004 | 29.427 | 75.994 | 1.00 | 0.00 |
| ATOM | 1455 | CE | LYS | A | 681 | 39.141 | 30.567 | 76.995 | 1.00 | 0.00 |
| ATOM | 1456 | NZ | LYS | A | 681 | 38.007 | 31.499 | 76.875 | 1.00 | 0.00 |
| ATOM | 1457 | C | LYS | A | 681 | 41.271 | 25.748 | 76.663 | 1.00 | 0.00 |
| ATOM | 1458 | O | LYS | A | 681 | 42.271 | 26.031 | 77.333 | 1.00 | 0.00 |

TABLE I-continued

GR Homology Model Coordinates

| ATOM | 1459 | N | SER | A | 682 | 40.419 | 24.800 | 77.017 | 1.00 | 0.00 |
|---|---|---|---|---|---|---|---|---|---|---|
| ATOM | 1461 | CA | SER | A | 682 | 40.578 | 24.096 | 78.295 | 1.00 | 0.00 |
| ATOM | 1462 | CB | SER | A | 682 | 39.226 | 23.905 | 78.985 | 1.00 | 0.00 |
| ATOM | 1463 | OG | SER | A | 682 | 38.369 | 23.114 | 78.171 | 1.00 | 0.00 |
| ATOM | 1464 | C | SER | A | 682 | 41.279 | 22.758 | 78.070 | 1.00 | 0.00 |
| ATOM | 1465 | O | SER | A | 682 | 40.849 | 21.718 | 78.590 | 1.00 | 0.00 |
| ATOM | 1466 | N | GLN | A | 683 | 42.462 | 22.836 | 77.476 | 1.00 | 0.00 |
| ATOM | 1468 | CA | GLN | A | 683 | 43.238 | 21.646 | 77.107 | 1.00 | 0.00 |
| ATOM | 1469 | CB | GLN | A | 683 | 44.399 | 22.101 | 76.227 | 1.00 | 0.00 |
| ATOM | 1470 | CG | GLN | A | 683 | 45.280 | 20.941 | 75.774 | 1.00 | 0.00 |
| ATOM | 1471 | CD | GLN | A | 683 | 44.511 | 20.017 | 74.835 | 1.00 | 0.00 |
| ATOM | 1472 | OE1 | GLN | A | 683 | 43.908 | 20.471 | 73.854 | 1.00 | 0.00 |
| ATOM | 1473 | NE2 | GLN | A | 683 | 44.543 | 18.734 | 75.143 | 1.00 | 0.00 |
| ATOM | 1476 | C | GLN | A | 683 | 43.800 | 20.911 | 78.320 | 1.00 | 0.00 |
| ATOM | 1477 | O | GLN | A | 683 | 43.781 | 19.675 | 78.332 | 1.00 | 0.00 |
| ATOM | 1478 | N | GLU | A | 684 | 43.994 | 21.625 | 79.418 | 1.00 | 0.00 |
| ATOM | 1480 | CA | GLU | A | 684 | 44.466 | 20.976 | 80.645 | 1.00 | 0.00 |
| ATOM | 1481 | CB | GLU | A | 684 | 44.894 | 22.049 | 81.636 | 1.00 | 0.00 |
| ATOM | 1482 | CG | GLU | A | 684 | 45.348 | 21.434 | 82.957 | 1.00 | 0.00 |
| ATOM | 1483 | CD | GLU | A | 684 | 45.646 | 22.541 | 83.962 | 1.00 | 0.00 |
| ATOM | 1484 | OE1 | GLU | A | 684 | 45.187 | 23.649 | 83.718 | 1.00 | 0.00 |
| ATOM | 1485 | OE2 | GLU | A | 684 | 46.415 | 22.292 | 84.879 | 1.00 | 0.00 |
| ATOM | 1486 | C | GLU | A | 684 | 43.365 | 20.129 | 81.277 | 1.00 | 0.00 |
| ATOM | 1487 | O | GLU | A | 684 | 43.616 | 18.957 | 81.592 | 1.00 | 0.00 |
| ATOM | 1488 | N | LEU | A | 685 | 42.130 | 20.576 | 81.116 | 1.00 | 0.00 |
| ATOM | 1490 | CA | LEU | A | 685 | 40.990 | 19.852 | 81.678 | 1.00 | 0.00 |
| ATOM | 1491 | CB | LEU | A | 685 | 39.778 | 20.773 | 81.840 | 1.00 | 0.00 |
| ATOM | 1492 | CG | LEU | A | 685 | 39.888 | 21.764 | 83.001 | 1.00 | 0.00 |
| ATOM | 1493 | CD1 | LEU | A | 685 | 40.555 | 23.076 | 82.590 | 1.00 | 0.00 |
| ATOM | 1494 | CD2 | LEU | A | 685 | 38.498 | 22.074 | 83.546 | 1.00 | 0.00 |
| ATOM | 1495 | C | LEU | A | 685 | 40.624 | 18.688 | 80.771 | 1.00 | 0.00 |
| ATOM | 1496 | O | LEU | A | 685 | 40.301 | 17.605 | 81.275 | 1.00 | 0.00 |
| ATOM | 1497 | N | PHE | A | 686 | 40.980 | 18.815 | 79.503 | 1.00 | 0.00 |
| ATOM | 1499 | CA | PHE | A | 686 | 40.797 | 17.720 | 78.552 | 1.00 | 0.00 |
| ATOM | 1500 | CB | PHE | A | 686 | 40.929 | 18.281 | 77.144 | 1.00 | 0.00 |
| ATOM | 1501 | CG | PHE | A | 686 | 40.810 | 17.222 | 76.056 | 1.00 | 0.00 |
| ATOM | 1502 | CD1 | PHE | A | 686 | 39.556 | 16.827 | 75.612 | 1.00 | 0.00 |
| ATOM | 1503 | CE1 | PHE | A | 686 | 39.448 | 15.864 | 74.617 | 1.00 | 0.00 |
| ATOM | 1504 | CZ | PHE | A | 686 | 40.590 | 15.293 | 74.075 | 1.00 | 0.00 |
| ATOM | 1505 | CE2 | PHE | A | 686 | 41.842 | 15.681 | 74.528 | 1.00 | 0.00 |
| ATOM | 1506 | CD2 | PHE | A | 686 | 41.951 | 16.644 | 75.518 | 1.00 | 0.00 |
| ATOM | 1507 | C | PHE | A | 686 | 41.834 | 16.622 | 78.764 | 1.00 | 0.00 |
| ATOM | 1508 | O | PHE | A | 686 | 41.484 | 15.435 | 78.734 | 1.00 | 0.00 |
| ATOM | 1509 | N | ASP | A | 687 | 43.009 | 17.009 | 79.235 | 1.00 | 0.00 |
| ATOM | 1511 | CA | ASP | A | 687 | 44.052 | 16.032 | 79.554 | 1.00 | 0.00 |
| ATOM | 1512 | CB | ASP | A | 687 | 45.367 | 16.760 | 79.832 | 1.00 | 0.00 |
| ATOM | 1513 | CG | ASP | A | 687 | 45.820 | 17.617 | 78.652 | 1.00 | 0.00 |
| ATOM | 1514 | OD1 | ASP | A | 687 | 45.576 | 17.223 | 77.517 | 1.00 | 0.00 |
| ATOM | 1515 | OD2 | ASP | A | 687 | 46.465 | 18.627 | 78.900 | 1.00 | 0.00 |
| ATOM | 1516 | C | ASP | A | 687 | 43.666 | 15.261 | 80.809 | 1.00 | 0.00 |
| ATOM | 1517 | O | ASP | A | 687 | 43.729 | 14.025 | 80.821 | 1.00 | 0.00 |
| ATOM | 1518 | N | GLU | A | 688 | 43.004 | 15.955 | 81.719 | 1.00 | 0.00 |
| ATOM | 1520 | CA | GLU | A | 688 | 42.563 | 15.337 | 82.968 | 1.00 | 0.00 |
| ATOM | 1521 | CB | GLU | A | 688 | 42.176 | 16.455 | 83.929 | 1.00 | 0.00 |
| ATOM | 1522 | CG | GLU | A | 688 | 43.381 | 17.329 | 84.258 | 1.00 | 0.00 |
| ATOM | 1523 | CD | GLU | A | 688 | 42.945 | 18.576 | 85.021 | 1.00 | 0.00 |
| ATOM | 1524 | OE1 | GLU | A | 688 | 42.967 | 19.647 | 84.424 | 1.00 | 0.00 |
| ATOM | 1525 | OE2 | GLU | A | 688 | 42.663 | 18.453 | 86.203 | 1.00 | 0.00 |
| ATOM | 1526 | C | GLU | A | 688 | 41.374 | 14.400 | 82.764 | 1.00 | 0.00 |
| ATOM | 1527 | O | GLU | A | 688 | 41.423 | 13.265 | 83.256 | 1.00 | 0.00 |
| ATOM | 1528 | N | ILE | A | 689 | 40.464 | 14.748 | 81.867 | 1.00 | 0.00 |
| ATOM | 1530 | CA | ILE | A | 689 | 39.301 | 13.881 | 81.659 | 1.00 | 0.00 |
| ATOM | 1531 | CB | ILE | A | 689 | 38.126 | 14.675 | 81.078 | 1.00 | 0.00 |
| ATOM | 1532 | CG2 | ILE | A | 689 | 38.474 | 15.414 | 79.794 | 1.00 | 0.00 |
| ATOM | 1533 | CG1 | ILE | A | 689 | 36.936 | 13.762 | 80.833 | 1.00 | 0.00 |
| ATOM | 1534 | CD1 | ILE | A | 689 | 35.876 | 14.443 | 79.978 | 1.00 | 0.00 |
| ATOM | 1535 | C | ILE | A | 689 | 39.631 | 12.667 | 80.789 | 1.00 | 0.00 |
| ATOM | 1536 | O | ILE | A | 689 | 39.161 | 11.566 | 81.112 | 1.00 | 0.00 |
| ATOM | 1537 | N | ARG | A | 690 | 40.623 | 12.770 | 79.917 | 1.00 | 0.00 |
| ATOM | 1539 | CA | ARG | A | 690 | 40.971 | 11.579 | 79.148 | 1.00 | 0.00 |
| ATOM | 1540 | CB | ARG | A | 690 | 41.551 | 11.949 | 77.783 | 1.00 | 0.00 |
| ATOM | 1541 | CG | ARG | A | 690 | 42.895 | 12.665 | 77.836 | 1.00 | 0.00 |
| ATOM | 1542 | CD | ARG | A | 690 | 43.397 | 12.919 | 76.422 | 1.00 | 0.00 |
| ATOM | 1543 | NE | ARG | A | 690 | 43.374 | 11.661 | 75.656 | 1.00 | 0.00 |
| ATOM | 1544 | CZ | ARG | A | 690 | 44.370 | 11.256 | 74.865 | 1.00 | 0.00 |
| ATOM | 1545 | NH1 | ARG | A | 690 | 45.445 | 12.029 | 74.694 | 1.00 | 0.00 |
| ATOM | 1546 | NH2 | ARG | A | 690 | 44.276 | 10.090 | 74.220 | 1.00 | 0.00 |

TABLE I-continued

GR Homology Model Coordinates

| ATOM | 1547 | C   | ARG | A | 690 | 41.909 | 10.679 | 79.944 | 1.00 | 0.00 |
|------|------|-----|-----|---|-----|--------|--------|--------|------|------|
| ATOM | 1548 | O   | ARG | A | 690 | 41.750 | 9.456  | 79.873 | 1.00 | 0.00 |
| ATOM | 1549 | N   | MET | A | 691 | 42.589 | 11.250 | 80.927 | 1.00 | 0.00 |
| ATOM | 1551 | CA  | MET | A | 691 | 43.444 | 10.447 | 81.793 | 1.00 | 0.00 |
| ATOM | 1552 | CB  | MET | A | 691 | 44.382 | 11.378 | 82.550 | 1.00 | 0.00 |
| ATOM | 1553 | CG  | MET | A | 691 | 45.336 | 10.604 | 83.450 | 1.00 | 0.00 |
| ATOM | 1554 | SD  | MET | A | 691 | 46.473 | 11.625 | 84.412 | 1.00 | 0.00 |
| ATOM | 1555 | CE  | MET | A | 691 | 47.263 | 12.517 | 83.052 | 1.00 | 0.00 |
| ATOM | 1556 | C   | MET | A | 691 | 42.608 | 9.650  | 82.784 | 1.00 | 0.00 |
| ATOM | 1557 | O   | MET | A | 691 | 42.790 | 8.429  | 82.870 | 1.00 | 0.00 |
| ATOM | 1558 | N   | THR | A | 692 | 41.532 | 10.242 | 83.281 | 1.00 | 0.00 |
| ATOM | 1560 | CA  | THR | A | 692 | 40.697 | 9.504  | 84.231 | 1.00 | 0.00 |
| ATOM | 1561 | CB  | THR | A | 692 | 39.910 | 10.464 | 85.122 | 1.00 | 0.00 |
| ATOM | 1562 | OG1 | THR | A | 692 | 39.130 | 9.675  | 86.010 | 1.00 | 0.00 |
| ATOM | 1563 | CG2 | THR | A | 692 | 38.960 | 11.372 | 84.350 | 1.00 | 0.00 |
| ATOM | 1564 | C   | THR | A | 692 | 39.759 | 8.512  | 83.544 | 1.00 | 0.00 |
| ATOM | 1565 | O   | THR | A | 692 | 39.461 | 7.473  | 84.142 | 1.00 | 0.00 |
| ATOM | 1566 | N   | TYR | A | 693 | 39.505 | 8.671  | 82.254 | 1.00 | 0.00 |
| ATOM | 1568 | CA  | TYR | A | 693 | 38.719 | 7.647  | 81.564 | 1.00 | 0.00 |
| ATOM | 1569 | CB  | TYR | A | 693 | 37.835 | 8.284  | 80.503 | 1.00 | 0.00 |
| ATOM | 1570 | CG  | TYR | A | 693 | 36.652 | 9.014  | 81.130 | 1.00 | 0.00 |
| ATOM | 1571 | CD1 | TYR | A | 693 | 36.047 | 8.482  | 82.262 | 1.00 | 0.00 |
| ATOM | 1572 | CE1 | TYR | A | 693 | 34.978 | 9.139  | 82.855 | 1.00 | 0.00 |
| ATOM | 1573 | CZ  | TYR | A | 693 | 34.511 | 10.325 | 82.309 | 1.00 | 0.00 |
| ATOM | 1574 | OH  | TYR | A | 693 | 33.531 | 11.038 | 82.965 | 1.00 | 0.00 |
| ATOM | 1575 | CE2 | TYR | A | 693 | 35.096 | 10.847 | 81.164 | 1.00 | 0.00 |
| ATOM | 1576 | CD2 | TYR | A | 693 | 36.167 | 10.189 | 80.572 | 1.00 | 0.00 |
| ATOM | 1577 | C   | TYR | A | 693 | 39.602 | 6.536  | 81.004 | 1.00 | 0.00 |
| ATOM | 1578 | O   | TYR | A | 693 | 39.139 | 5.395  | 80.894 | 1.00 | 0.00 |
| ATOM | 1579 | N   | ILE | A | 694 | 40.900 | 6.789  | 80.936 | 1.00 | 0.00 |
| ATOM | 1581 | CA  | ILE | A | 694 | 41.857 | 5.715  | 80.653 | 1.00 | 0.00 |
| ATOM | 1582 | CB  | ILE | A | 694 | 43.156 | 6.329  | 80.133 | 1.00 | 0.00 |
| ATOM | 1583 | CG2 | ILE | A | 694 | 44.301 | 5.323  | 80.167 | 1.00 | 0.00 |
| ATOM | 1584 | CG1 | ILE | A | 694 | 42.973 | 6.874  | 78.722 | 1.00 | 0.00 |
| ATOM | 1585 | CD1 | ILE | A | 694 | 44.247 | 7.534  | 78.205 | 1.00 | 0.00 |
| ATOM | 1586 | C   | ILE | A | 694 | 42.122 | 4.900  | 81.918 | 1.00 | 0.00 |
| ATOM | 1587 | O   | ILE | A | 694 | 42.183 | 3.666  | 81.846 | 1.00 | 0.00 |
| ATOM | 1588 | N   | LYS | A | 695 | 41.981 | 5.540  | 83.070 | 1.00 | 0.00 |
| ATOM | 1590 | CA  | LYS | A | 695 | 42.095 | 4.818  | 84.344 | 1.00 | 0.00 |
| ATOM | 1591 | CB  | LYS | A | 695 | 42.345 | 5.819  | 85.467 | 1.00 | 0.00 |
| ATOM | 1592 | CG  | LYS | A | 695 | 43.629 | 6.610  | 85.248 | 1.00 | 0.00 |
| ATOM | 1593 | CD  | LYS | A | 695 | 44.860 | 5.711  | 85.232 | 1.00 | 0.00 |
| ATOM | 1594 | CE  | LYS | A | 695 | 46.114 | 6.518  | 84.918 | 1.00 | 0.00 |
| ATOM | 1595 | NZ  | LYS | A | 695 | 46.295 | 7.604  | 85.894 | 1.00 | 0.00 |
| ATOM | 1596 | C   | LYS | A | 695 | 40.816 | 4.045  | 84.646 | 1.00 | 0.00 |
| ATOM | 1597 | O   | LYS | A | 695 | 40.882 | 2.914  | 85.143 | 1.00 | 0.00 |
| ATOM | 1598 | N   | GLU | A | 696 | 39.703 | 4.536  | 84.126 | 1.00 | 0.00 |
| ATOM | 1600 | CA  | GLU | A | 696 | 38.431 | 3.831  | 84.276 | 1.00 | 0.00 |
| ATOM | 1601 | CB  | GLU | A | 696 | 37.310 | 4.828  | 84.007 | 1.00 | 0.00 |
| ATOM | 1602 | CG  | GLU | A | 696 | 36.035 | 4.466  | 84.758 | 1.00 | 0.00 |
| ATOM | 1603 | CD  | GLU | A | 696 | 36.250 | 4.648  | 86.260 | 1.00 | 0.00 |
| ATOM | 1604 | OE1 | GLU | A | 696 | 37.071 | 5.483  | 86.614 | 1.00 | 0.00 |
| ATOM | 1605 | OE2 | GLU | A | 696 | 35.496 | 4.061  | 87.028 | 1.00 | 0.00 |
| ATOM | 1606 | C   | GLU | A | 696 | 38.336 | 2.661  | 83.296 | 1.00 | 0.00 |
| ATOM | 1607 | O   | GLU | A | 696 | 37.782 | 1.615  | 83.655 | 1.00 | 0.00 |
| ATOM | 1608 | N   | LEU | A | 697 | 39.057 | 2.754  | 82.188 | 1.00 | 0.00 |
| ATOM | 1610 | CA  | LEU | A | 697 | 39.173 | 1.624  | 81.262 | 1.00 | 0.00 |
| ATOM | 1611 | CB  | LEU | A | 697 | 39.714 | 2.132  | 79.929 | 1.00 | 0.00 |
| ATOM | 1612 | CG  | LEU | A | 697 | 39.845 | 1.007  | 78.906 | 1.00 | 0.00 |
| ATOM | 1613 | CD1 | LEU | A | 697 | 38.505 | 0.324  | 78.662 | 1.00 | 0.00 |
| ATOM | 1614 | CD2 | LEU | A | 697 | 40.432 | 1.521  | 77.596 | 1.00 | 0.00 |
| ATOM | 1615 | C   | LEU | A | 697 | 40.118 | 0.578  | 81.843 | 1.00 | 0.00 |
| ATOM | 1616 | O   | LEU | A | 697 | 39.818 | −0.618 | 81.777 | 1.00 | 0.00 |
| ATOM | 1617 | N   | GLY | A | 698 | 41.099 | 1.042  | 82.599 | 1.00 | 0.00 |
| ATOM | 1619 | CA  | GLY | A | 698 | 41.971 | 0.162  | 83.383 | 1.00 | 0.00 |
| ATOM | 1620 | C   | GLY | A | 698 | 41.155 | −0.699 | 84.343 | 1.00 | 0.00 |
| ATOM | 1621 | O   | GLY | A | 698 | 41.166 | −1.928 | 84.213 | 1.00 | 0.00 |
| ATOM | 1622 | N   | LYS | A | 699 | 40.282 | −0.063 | 85.112 | 1.00 | 0.00 |
| ATOM | 1624 | CA  | LYS | A | 699 | 39.420 | −0.783 | 86.065 | 1.00 | 0.00 |
| ATOM | 1625 | CB  | LYS | A | 699 | 38.610 | 0.252  | 86.837 | 1.00 | 0.00 |
| ATOM | 1626 | CG  | LYS | A | 699 | 39.505 | 1.316  | 87.455 | 1.00 | 0.00 |
| ATOM | 1627 | CD  | LYS | A | 699 | 38.683 | 2.417  | 88.113 | 1.00 | 0.00 |
| ATOM | 1628 | CE  | LYS | A | 699 | 39.575 | 3.563  | 88.575 | 1.00 | 0.00 |
| ATOM | 1629 | NZ  | LYS | A | 699 | 40.615 | 3.081  | 89.497 | 1.00 | 0.00 |
| ATOM | 1630 | C   | LYS | A | 699 | 38.433 | −1.730 | 85.378 | 1.00 | 0.00 |
| ATOM | 1631 | O   | LYS | A | 699 | 38.276 | −2.873 | 85.826 | 1.00 | 0.00 |
| ATOM | 1632 | N   | ALA | A | 700 | 37.986 | −1.357 | 84.188 | 1.00 | 0.00 |

TABLE I-continued

GR Homology Model Coordinates

| ATOM | 1634 | CA | ALA | A | 700 | 37.053 | −2.183 | 83.417 | 1.00 | 0.00 |
|------|------|-----|-----|---|-----|--------|--------|--------|------|------|
| ATOM | 1635 | CB | ALA | A | 700 | 36.418 | −1.286 | 82.365 | 1.00 | 0.00 |
| ATOM | 1636 | C | ALA | A | 700 | 37.713 | −3.382 | 82.735 | 1.00 | 0.00 |
| ATOM | 1637 | O | ALA | A | 700 | 37.030 | −4.363 | 82.412 | 1.00 | 0.00 |
| ATOM | 1638 | N | ILE | A | 701 | 39.028 | −3.347 | 82.617 | 1.00 | 0.00 |
| ATOM | 1640 | CA | ILE | A | 701 | 39.787 | −4.479 | 82.091 | 1.00 | 0.00 |
| ATOM | 1641 | CB | ILE | A | 701 | 40.988 | −3.906 | 81.354 | 1.00 | 0.00 |
| ATOM | 1642 | CG2 | ILE | A | 701 | 41.973 | −4.994 | 80.961 | 1.00 | 0.00 |
| ATOM | 1643 | CG1 | ILE | A | 701 | 40.524 | −3.137 | 80.126 | 1.00 | 0.00 |
| ATOM | 1644 | CD1 | ILE | A | 701 | 41.686 | −2.439 | 79.438 | 1.00 | 0.00 |
| ATOM | 1645 | C | ILE | A | 701 | 40.232 | −5.396 | 83.224 | 1.00 | 0.00 |
| ATOM | 1646 | O | ILE | A | 701 | 40.054 | −6.618 | 83.111 | 1.00 | 0.00 |
| ATOM | 1647 | N | VAL | A | 702 | 40.413 | −4.802 | 84.395 | 1.00 | 0.00 |
| ATOM | 1649 | CA | VAL | A | 702 | 40.795 | −5.550 | 85.605 | 1.00 | 0.00 |
| ATOM | 1650 | CB | VAL | A | 702 | 41.270 | −4.545 | 86.659 | 1.00 | 0.00 |
| ATOM | 1651 | CG1 | VAL | A | 702 | 41.485 | −5.186 | 88.025 | 1.00 | 0.00 |
| ATOM | 1652 | CG2 | VAL | A | 702 | 42.541 | −3.832 | 86.217 | 1.00 | 0.00 |
| ATOM | 1653 | C | VAL | A | 702 | 39.641 | −6.385 | 86.170 | 1.00 | 0.00 |
| ATOM | 1654 | O | VAL | A | 702 | 39.893 | −7.418 | 86.804 | 1.00 | 0.00 |
| ATOM | 1655 | N | LYS | A | 703 | 38.422 | −6.100 | 85.736 | 1.00 | 0.00 |
| ATOM | 1657 | CA | LYS | A | 703 | 37.280 | −6.927 | 86.141 | 1.00 | 0.00 |
| ATOM | 1658 | CB | LYS | A | 703 | 35.990 | −6.279 | 85.657 | 1.00 | 0.00 |
| ATOM | 1659 | CG | LYS | A | 703 | 35.699 | −4.935 | 86.305 | 1.00 | 0.00 |
| ATOM | 1660 | CD | LYS | A | 703 | 34.310 | −4.472 | 85.883 | 1.00 | 0.00 |
| ATOM | 1661 | CE | LYS | A | 703 | 33.924 | −3.141 | 86.508 | 1.00 | 0.00 |
| ATOM | 1662 | NZ | LYS | A | 703 | 34.768 | −2.050 | 86.006 | 1.00 | 0.00 |
| ATOM | 1663 | C | LYS | A | 703 | 37.316 | −8.335 | 85.543 | 1.00 | 0.00 |
| ATOM | 1664 | O | LYS | A | 703 | 36.806 | −9.271 | 86.170 | 1.00 | 0.00 |
| ATOM | 1665 | N | ARG | A | 704 | 37.927 | −8.503 | 84.380 | 1.00 | 0.00 |
| ATOM | 1667 | CA | ARG | A | 704 | 37.996 | −9.844 | 83.793 | 1.00 | 0.00 |
| ATOM | 1668 | CB | ARG | A | 704 | 37.374 | −9.815 | 82.402 | 1.00 | 0.00 |
| ATOM | 1669 | CG | ARG | A | 704 | 35.948 | −9.277 | 82.435 | 1.00 | 0.00 |
| ATOM | 1670 | CD | ARG | A | 704 | 35.251 | −9.473 | 81.093 | 1.00 | 0.00 |
| ATOM | 1671 | NE | ARG | A | 704 | 36.041 | −8.896 | 79.994 | 1.00 | 0.00 |
| ATOM | 1672 | CZ | ARG | A | 704 | 36.356 | −9.590 | 78.899 | 1.00 | 0.00 |
| ATOM | 1673 | NH1 | ARG | A | 704 | 35.981 | −10.866 | 78.786 | 1.00 | 0.00 |
| ATOM | 1674 | NH2 | ARG | A | 704 | 37.070 | −9.018 | 77.929 | 1.00 | 0.00 |
| ATOM | 1675 | C | ARG | A | 704 | 39.432 | −10.344 | 83.692 | 1.00 | 0.00 |
| ATOM | 1676 | O | ARG | A | 704 | 39.682 | −11.556 | 83.660 | 1.00 | 0.00 |
| ATOM | 1677 | N | GLU | A | 705 | 40.375 | −9.420 | 83.679 | 1.00 | 0.00 |
| ATOM | 1679 | CA | GLU | A | 705 | 41.780 | −9.806 | 83.537 | 1.00 | 0.00 |
| ATOM | 1680 | CB | GLU | A | 705 | 42.485 | −8.792 | 82.649 | 1.00 | 0.00 |
| ATOM | 1681 | CG | GLU | A | 705 | 41.793 | −8.633 | 81.298 | 1.00 | 0.00 |
| ATOM | 1682 | CD | GLU | A | 705 | 41.769 | −9.943 | 80.515 | 1.00 | 0.00 |
| ATOM | 1683 | OE1 | GLU | A | 705 | 42.762 | −10.659 | 80.548 | 1.00 | 0.00 |
| ATOM | 1684 | OE2 | GLU | A | 705 | 40.754 | −10.202 | 79.886 | 1.00 | 0.00 |
| ATOM | 1685 | C | GLU | A | 705 | 42.469 | −9.883 | 84.892 | 1.00 | 0.00 |
| ATOM | 1686 | O | GLU | A | 705 | 43.165 | −8.952 | 85.313 | 1.00 | 0.00 |
| ATOM | 1687 | N | GLY | A | 706 | 42.318 | −11.041 | 85.516 | 1.00 | 0.00 |
| ATOM | 1689 | CA | GLY | A | 706 | 42.921 | −11.312 | 86.826 | 1.00 | 0.00 |
| ATOM | 1690 | C | GLY | A | 706 | 44.444 | −11.303 | 86.755 | 1.00 | 0.00 |
| ATOM | 1691 | O | GLY | A | 706 | 45.105 | −10.616 | 87.544 | 1.00 | 0.00 |
| ATOM | 1692 | N | ASN | A | 707 | 44.985 | −12.073 | 85.825 | 1.00 | 0.00 |
| ATOM | 1694 | CA | ASN | A | 707 | 46.434 | −12.072 | 85.604 | 1.00 | 0.00 |
| ATOM | 1695 | CB | ASN | A | 707 | 46.780 | −13.096 | 84.526 | 1.00 | 0.00 |
| ATOM | 1696 | CG | ASN | A | 707 | 46.228 | −14.477 | 84.870 | 1.00 | 0.00 |
| ATOM | 1697 | OD1 | ASN | A | 707 | 46.198 | −14.886 | 86.036 | 1.00 | 0.00 |
| ATOM | 1698 | ND2 | ASN | A | 707 | 45.814 | −15.189 | 83.836 | 1.00 | 0.00 |
| ATOM | 1701 | C | ASN | A | 707 | 46.866 | −10.691 | 85.129 | 1.00 | 0.00 |
| ATOM | 1702 | O | ASN | A | 707 | 46.345 | −10.190 | 84.126 | 1.00 | 0.00 |
| ATOM | 1703 | N | SER | A | 708 | 47.929 | −10.173 | 85.722 | 1.00 | 0.00 |
| ATOM | 1705 | CA | SER | A | 708 | 48.365 | −8.802 | 85.408 | 1.00 | 0.00 |
| ATOM | 1706 | CB | SER | A | 708 | 49.375 | −8.343 | 86.456 | 1.00 | 0.00 |
| ATOM | 1707 | OG | SER | A | 708 | 50.518 | −9.187 | 86.383 | 1.00 | 0.00 |
| ATOM | 1708 | C | SER | A | 708 | 48.977 | −8.664 | 84.014 | 1.00 | 0.00 |
| ATOM | 1709 | O | SER | A | 708 | 48.712 | −7.657 | 83.348 | 1.00 | 0.00 |
| ATOM | 1710 | N | SER | A | 709 | 49.487 | −9.759 | 83.468 | 1.00 | 0.00 |
| ATOM | 1712 | CA | SER | A | 709 | 50.000 | −9.724 | 82.096 | 1.00 | 0.00 |
| ATOM | 1713 | CB | SER | A | 709 | 50.898 | −10.929 | 81.864 | 1.00 | 0.00 |
| ATOM | 1714 | OG | SER | A | 709 | 51.288 | −10.898 | 80.498 | 1.00 | 0.00 |
| ATOM | 1715 | C | SER | A | 709 | 48.860 | −9.753 | 81.087 | 1.00 | 0.00 |
| ATOM | 1716 | O | SER | A | 709 | 48.912 | −9.013 | 80.099 | 1.00 | 0.00 |
| ATOM | 1717 | N | GLN | A | 710 | 47.734 | −10.302 | 81.514 | 1.00 | 0.00 |
| ATOM | 1719 | CA | GLN | A | 710 | 46.533 | −10.337 | 80.686 | 1.00 | 0.00 |
| ATOM | 1720 | CB | GLN | A | 710 | 45.613 | −11.429 | 81.217 | 1.00 | 0.00 |
| ATOM | 1721 | CG | GLN | A | 710 | 46.048 | −12.826 | 80.804 | 1.00 | 0.00 |
| ATOM | 1722 | CD | GLN | A | 710 | 45.774 | −13.048 | 79.319 | 1.00 | 0.00 |

TABLE I-continued

GR Homology Model Coordinates

| ATOM | 1723 | OE1 | GLN | A | 710 | 46.534 | −13.753 | 78.645 | 1.00 | 0.00 |
|---|---|---|---|---|---|---|---|---|---|---|
| ATOM | 1724 | NE2 | GLN | A | 710 | 44.669 | −12.497 | 78.843 | 1.00 | 0.00 |
| ATOM | 1727 | C | GLN | A | 710 | 45.794 | −9.011 | 80.750 | 1.00 | 0.00 |
| ATOM | 1728 | O | GLN | A | 710 | 45.195 | −8.591 | 79.753 | 1.00 | 0.00 |
| ATOM | 1729 | N | ASN | A | 711 | 46.017 | −8.276 | 81.826 | 1.00 | 0.00 |
| ATOM | 1731 | CA | ASN | A | 711 | 45.452 | −6.938 | 81.954 | 1.00 | 0.00 |
| ATOM | 1732 | CB | ASN | A | 711 | 45.583 | −6.508 | 83.411 | 1.00 | 0.00 |
| ATOM | 1733 | CG | ASN | A | 711 | 45.045 | −5.095 | 83.598 | 1.00 | 0.00 |
| ATOM | 1734 | OD1 | ASN | A | 711 | 43.838 | −4.853 | 83.497 | 1.00 | 0.00 |
| ATOM | 1735 | ND2 | ASN | A | 711 | 45.952 | −4.167 | 83.859 | 1.00 | 0.00 |
| ATOM | 1738 | C | ASN | A | 711 | 46.196 | −5.965 | 81.050 | 1.00 | 0.00 |
| ATOM | 1739 | O | ASN | A | 711 | 45.553 | −5.246 | 80.273 | 1.00 | 0.00 |
| ATOM | 1740 | N | TRP | A | 712 | 47.503 | −6.147 | 80.941 | 1.00 | 0.00 |
| ATOM | 1742 | CA | TRP | A | 712 | 48.293 | −5.279 | 80.063 | 1.00 | 0.00 |
| ATOM | 1743 | CB | TRP | A | 712 | 49.760 | −5.349 | 80.469 | 1.00 | 0.00 |
| ATOM | 1744 | CG | TRP | A | 712 | 50.062 | −4.651 | 81.780 | 1.00 | 0.00 |
| ATOM | 1745 | CD1 | TRP | A | 712 | 50.445 | −5.237 | 82.965 | 1.00 | 0.00 |
| ATOM | 1746 | NE1 | TRP | A | 712 | 50.616 | −4.263 | 83.892 | 1.00 | 0.00 |
| ATOM | 1748 | CE2 | TRP | A | 712 | 50.371 | −3.047 | 83.372 | 1.00 | 0.00 |
| ATOM | 1749 | CZ2 | TRP | A | 712 | 50.416 | −1.767 | 83.905 | 1.00 | 0.00 |
| ATOM | 1750 | CH2 | TRP | A | 712 | 50.108 | −0.674 | 83.103 | 1.00 | 0.00 |
| ATOM | 1751 | CZ3 | TRP | A | 712 | 49.757 | −0.857 | 81.769 | 1.00 | 0.00 |
| ATOM | 1752 | CE3 | TRP | A | 712 | 49.710 | −2.135 | 81.226 | 1.00 | 0.00 |
| ATOM | 1753 | CD2 | TRP | A | 712 | 50.016 | −3.228 | 82.022 | 1.00 | 0.00 |
| ATOM | 1754 | C | TRP | A | 712 | 48.150 | −5.650 | 78.591 | 1.00 | 0.00 |
| ATOM | 1755 | O | TRP | A | 712 | 48.091 | −4.747 | 77.745 | 1.00 | 0.00 |
| ATOM | 1756 | N | GLN | A | 713 | 47.865 | −6.913 | 78.312 | 1.00 | 0.00 |
| ATOM | 1758 | CA | GLN | A | 713 | 47.625 | −7.321 | 76.926 | 1.00 | 0.00 |
| ATOM | 1759 | CB | GLN | A | 713 | 47.658 | −8.842 | 76.819 | 1.00 | 0.00 |
| ATOM | 1760 | CG | GLN | A | 713 | 49.051 | −9.411 | 77.069 | 1.00 | 0.00 |
| ATOM | 1761 | CD | GLN | A | 713 | 50.036 | −8.933 | 76.005 | 1.00 | 0.00 |
| ATOM | 1762 | OE1 | GLN | A | 713 | 49.954 | −9.335 | 74.839 | 1.00 | 0.00 |
| ATOM | 1763 | NE2 | GLN | A | 713 | 50.996 | −8.130 | 76.433 | 1.00 | 0.00 |
| ATOM | 1766 | C | GLN | A | 713 | 46.275 | −6.813 | 76.456 | 1.00 | 0.00 |
| ATOM | 1767 | O | GLN | A | 713 | 46.233 | −6.074 | 75.466 | 1.00 | 0.00 |
| ATOM | 1768 | N | ARG | A | 714 | 45.304 | −6.867 | 77.352 | 1.00 | 0.00 |
| ATOM | 1770 | CA | ARG | A | 714 | 43.946 | −6.435 | 77.035 | 1.00 | 0.00 |
| ATOM | 1771 | CB | ARG | A | 714 | 43.065 | −6.919 | 78.173 | 1.00 | 0.00 |
| ATOM | 1772 | CG | ARG | A | 714 | 41.592 | −6.780 | 77.843 | 1.00 | 0.00 |
| ATOM | 1773 | CD | ARG | A | 714 | 41.216 | −7.730 | 76.722 | 1.00 | 0.00 |
| ATOM | 1774 | NE | ARG | A | 714 | 39.804 | −7.551 | 76.386 | 1.00 | 0.00 |
| ATOM | 1775 | CZ | ARG | A | 714 | 39.396 | −7.227 | 75.162 | 1.00 | 0.00 |
| ATOM | 1776 | NH1 | ARG | A | 714 | 40.287 | −7.095 | 74.177 | 1.00 | 0.00 |
| ATOM | 1777 | NH2 | ARG | A | 714 | 38.096 | −7.050 | 74.925 | 1.00 | 0.00 |
| ATOM | 1778 | C | ARG | A | 714 | 43.837 | −4.916 | 76.921 | 1.00 | 0.00 |
| ATOM | 1779 | O | ARG | A | 714 | 43.162 | −4.416 | 76.011 | 1.00 | 0.00 |
| ATOM | 1780 | N | PHE | A | 715 | 44.666 | −4.204 | 77.668 | 1.00 | 0.00 |
| ATOM | 1782 | CA | PHE | A | 715 | 44.694 | −2.744 | 77.557 | 1.00 | 0.00 |
| ATOM | 1783 | CB | PHE | A | 715 | 45.456 | −2.173 | 78.747 | 1.00 | 0.00 |
| ATOM | 1784 | CG | PHE | A | 715 | 45.507 | −0.648 | 78.774 | 1.00 | 0.00 |
| ATOM | 1785 | CD1 | PHE | A | 715 | 44.386 | 0.074 | 79.162 | 1.00 | 0.00 |
| ATOM | 1786 | CE1 | PHE | A | 715 | 44.426 | 1.462 | 79.184 | 1.00 | 0.00 |
| ATOM | 1787 | CZ | PHE | A | 715 | 45.589 | 2.127 | 78.817 | 1.00 | 0.00 |
| ATOM | 1788 | CE2 | PHE | A | 715 | 46.710 | 1.406 | 78.429 | 1.00 | 0.00 |
| ATOM | 1789 | CD2 | PHE | A | 715 | 46.669 | 0.018 | 78.407 | 1.00 | 0.00 |
| ATOM | 1790 | C | PHE | A | 715 | 45.358 | −2.305 | 76.257 | 1.00 | 0.00 |
| ATOM | 1791 | O | PHE | A | 715 | 44.796 | −1.461 | 75.544 | 1.00 | 0.00 |
| ATOM | 1792 | N | TYR | A | 716 | 46.358 | −3.055 | 75.824 | 1.00 | 0.00 |
| ATOM | 1794 | CA | TYR | A | 716 | 47.011 | −2.746 | 74.553 | 1.00 | 0.00 |
| ATOM | 1795 | CB | TYR | A | 716 | 48.307 | −3.542 | 74.446 | 1.00 | 0.00 |
| ATOM | 1796 | CG | TYR | A | 716 | 49.046 | −3.324 | 73.128 | 1.00 | 0.00 |
| ATOM | 1797 | CD1 | TYR | A | 716 | 49.801 | −2.173 | 72.944 | 1.00 | 0.00 |
| ATOM | 1798 | CE1 | TYR | A | 716 | 50.465 | −1.963 | 71.743 | 1.00 | 0.00 |
| ATOM | 1799 | CZ | TYR | A | 716 | 50.370 | −2.905 | 70.728 | 1.00 | 0.00 |
| ATOM | 1800 | OH | TYR | A | 716 | 50.984 | −2.671 | 69.518 | 1.00 | 0.00 |
| ATOM | 1801 | CE2 | TYR | A | 716 | 49.621 | −4.060 | 70.910 | 1.00 | 0.00 |
| ATOM | 1802 | CD2 | TYR | A | 716 | 48.959 | −4.270 | 72.112 | 1.00 | 0.00 |
| ATOM | 1803 | C | TYR | A | 716 | 46.101 | −3.094 | 73.381 | 1.00 | 0.00 |
| ATOM | 1804 | O | TYR | A | 716 | 45.947 | −2.262 | 72.480 | 1.00 | 0.00 |
| ATOM | 1805 | N | GLN | A | 717 | 45.312 | −4.145 | 73.533 | 1.00 | 0.00 |
| ATOM | 1807 | CA | GLN | A | 717 | 44.381 | −4.561 | 72.482 | 1.00 | 0.00 |
| ATOM | 1808 | CB | GLN | A | 717 | 43.806 | −5.917 | 72.864 | 1.00 | 0.00 |
| ATOM | 1809 | CG | GLN | A | 717 | 44.881 | −6.993 | 72.925 | 1.00 | 0.00 |
| ATOM | 1810 | CD | GLN | A | 717 | 44.287 | −8.261 | 73.526 | 1.00 | 0.00 |
| ATOM | 1811 | OE1 | GLN | A | 717 | 44.686 | −8.711 | 74.609 | 1.00 | 0.00 |
| ATOM | 1812 | NE2 | GLN | A | 717 | 43.299 | −8.796 | 72.832 | 1.00 | 0.00 |
| ATOM | 1815 | C | GLN | A | 717 | 43.227 | −3.581 | 72.311 | 1.00 | 0.00 |

TABLE I-continued

GR Homology Model Coordinates

| ATOM | 1816 | O   | GLN | A | 717 | 42.932 | −3.196 | 71.174 | 1.00 | 0.00 |
|------|------|-----|-----|---|-----|--------|--------|--------|------|------|
| ATOM | 1817 | N   | LEU | A | 718 | 42.745 | −3.011 | 73.402 | 1.00 | 0.00 |
| ATOM | 1819 | CA  | LEU | A | 718 | 41.625 | −2.072 | 73.293 | 1.00 | 0.00 |
| ATOM | 1820 | CB  | LEU | A | 718 | 40.925 | −1.980 | 74.640 | 1.00 | 0.00 |
| ATOM | 1821 | CG  | LEU | A | 718 | 40.260 | −3.307 | 74.984 | 1.00 | 0.00 |
| ATOM | 1822 | CD1 | LEU | A | 718 | 39.617 | −3.258 | 76.364 | 1.00 | 0.00 |
| ATOM | 1823 | CD2 | LEU | A | 718 | 39.239 | −3.689 | 73.919 | 1.00 | 0.00 |
| ATOM | 1824 | C   | LEU | A | 718 | 42.065 | −0.690 | 72.834 | 1.00 | 0.00 |
| ATOM | 1825 | O   | LEU | A | 718 | 41.383 | −0.090 | 71.994 | 1.00 | 0.00 |
| ATOM | 1826 | N   | THR | A | 719 | 43.294 | −0.319 | 73.150 | 1.00 | 0.00 |
| ATOM | 1828 | CA  | THR | A | 719 | 43.803 | 0.973  | 72.678 | 1.00 | 0.00 |
| ATOM | 1829 | CB  | THR | A | 719 | 44.932 | 1.455  | 73.583 | 1.00 | 0.00 |
| ATOM | 1830 | OG1 | THR | A | 719 | 45.962 | 0.476  | 73.610 | 1.00 | 0.00 |
| ATOM | 1831 | CG2 | THR | A | 719 | 44.443 | 1.695  | 75.006 | 1.00 | 0.00 |
| ATOM | 1832 | C   | THR | A | 719 | 44.285 | 0.896  | 71.231 | 1.00 | 0.00 |
| ATOM | 1833 | O   | THR | A | 719 | 44.076 | 1.847  | 70.466 | 1.00 | 0.00 |
| ATOM | 1834 | N   | LYS | A | 720 | 44.662 | −0.295 | 70.796 | 1.00 | 0.00 |
| ATOM | 1836 | CA  | LYS | A | 720 | 45.050 | −0.483 | 69.400 | 1.00 | 0.00 |
| ATOM | 1837 | CB  | LYS | A | 720 | 45.947 | −1.711 | 69.304 | 1.00 | 0.00 |
| ATOM | 1838 | CG  | LYS | A | 720 | 46.557 | −1.838 | 67.917 | 1.00 | 0.00 |
| ATOM | 1839 | CD  | LYS | A | 720 | 47.389 | −0.605 | 67.580 | 1.00 | 0.00 |
| ATOM | 1840 | CE  | LYS | A | 720 | 47.988 | −0.717 | 66.186 | 1.00 | 0.00 |
| ATOM | 1841 | NZ  | LYS | A | 720 | 48.859 | −1.900 | 66.083 | 1.00 | 0.00 |
| ATOM | 1842 | C   | LYS | A | 720 | 43.814 | −0.663 | 68.524 | 1.00 | 0.00 |
| ATOM | 1843 | O   | LYS | A | 720 | 43.795 | −0.186 | 67.381 | 1.00 | 0.00 |
| ATOM | 1844 | N   | LEU | A | 721 | 42.727 | −1.092 | 69.143 | 1.00 | 0.00 |
| ATOM | 1846 | CA  | LEU | A | 721 | 41.447 | −1.157 | 68.445 | 1.00 | 0.00 |
| ATOM | 1847 | CB  | LEU | A | 721 | 40.451 | −1.930 | 69.304 | 1.00 | 0.00 |
| ATOM | 1848 | CG  | LEU | A | 721 | 39.100 | −2.072 | 68.610 | 1.00 | 0.00 |
| ATOM | 1849 | CD1 | LEU | A | 721 | 39.251 | −2.767 | 67.260 | 1.00 | 0.00 |
| ATOM | 1850 | CD2 | LEU | A | 721 | 38.111 | −2.824 | 69.493 | 1.00 | 0.00 |
| ATOM | 1851 | C   | LEU | A | 721 | 40.925 | 0.250  | 68.195 | 1.00 | 0.00 |
| ATOM | 1852 | O   | LEU | A | 721 | 40.699 | 0.591  | 67.029 | 1.00 | 0.00 |
| ATOM | 1853 | N   | LEU | A | 722 | 41.072 | 1.123  | 69.181 | 1.00 | 0.00 |
| ATOM | 1855 | CA  | LEU | A | 722 | 40.635 | 2.514  | 69.010 | 1.00 | 0.00 |
| ATOM | 1856 | CB  | LEU | A | 722 | 40.666 | 3.213  | 70.366 | 1.00 | 0.00 |
| ATOM | 1857 | CG  | LEU | A | 722 | 39.721 | 2.552  | 71.362 | 1.00 | 0.00 |
| ATOM | 1858 | CD1 | LEU | A | 722 | 39.850 | 3.185  | 72.743 | 1.00 | 0.00 |
| ATOM | 1859 | CD2 | LEU | A | 722 | 38.276 | 2.602  | 70.876 | 1.00 | 0.00 |
| ATOM | 1860 | C   | LEU | A | 722 | 41.535 | 3.267  | 68.033 | 1.00 | 0.00 |
| ATOM | 1861 | O   | LEU | A | 722 | 41.022 | 3.962  | 67.146 | 1.00 | 0.00 |
| ATOM | 1862 | N   | ASP | A | 723 | 42.808 | 2.903  | 68.008 | 1.00 | 0.00 |
| ATOM | 1864 | CA  | ASP | A | 723 | 43.753 | 3.502  | 67.059 | 1.00 | 0.00 |
| ATOM | 1865 | CB  | ASP | A | 723 | 45.157 | 3.007  | 67.384 | 1.00 | 0.00 |
| ATOM | 1866 | CG  | ASP | A | 723 | 45.766 | 3.774  | 68.552 | 1.00 | 0.00 |
| ATOM | 1867 | OD1 | ASP | A | 723 | 45.032 | 4.465  | 69.245 | 1.00 | 0.00 |
| ATOM | 1868 | OD2 | ASP | A | 723 | 46.979 | 3.922  | 68.525 | 1.00 | 0.00 |
| ATOM | 1869 | C   | ASP | A | 723 | 43.437 | 3.124  | 65.616 | 1.00 | 0.00 |
| ATOM | 1870 | O   | ASP | A | 723 | 43.224 | 4.020  | 64.786 | 1.00 | 0.00 |
| ATOM | 1871 | N   | SER | A | 724 | 43.128 | 1.855  | 65.402 | 1.00 | 0.00 |
| ATOM | 1873 | CA  | SER | A | 724 | 42.847 | 1.355  | 64.051 | 1.00 | 0.00 |
| ATOM | 1874 | CB  | SER | A | 724 | 43.057 | −0.155 | 64.032 | 1.00 | 0.00 |
| ATOM | 1875 | OG  | SER | A | 724 | 42.110 | −0.747 | 64.913 | 1.00 | 0.00 |
| ATOM | 1876 | C   | SER | A | 724 | 41.427 | 1.668  | 63.583 | 1.00 | 0.00 |
| ATOM | 1877 | O   | SER | A | 724 | 41.164 | 1.639  | 62.375 | 1.00 | 0.00 |
| ATOM | 1878 | N   | MET | A | 725 | 40.578 | 2.143  | 64.478 | 1.00 | 0.00 |
| ATOM | 1880 | CA  | MET | A | 725 | 39.226 | 2.522  | 64.079 | 1.00 | 0.00 |
| ATOM | 1881 | CB  | MET | A | 725 | 38.302 | 2.427  | 65.279 | 1.00 | 0.00 |
| ATOM | 1882 | CG  | MET | A | 725 | 38.024 | 0.986  | 65.707 | 1.00 | 0.00 |
| ATOM | 1883 | SD  | MET | A | 725 | 37.134 | −0.071 | 64.538 | 1.00 | 0.00 |
| ATOM | 1884 | CE  | MET | A | 725 | 38.513 | −0.893 | 63.704 | 1.00 | 0.00 |
| ATOM | 1885 | C   | MET | A | 725 | 39.156 | 3.918  | 63.468 | 1.00 | 0.00 |
| ATOM | 1886 | O   | MET | A | 725 | 38.213 | 4.182  | 62.711 | 1.00 | 0.00 |
| ATOM | 1887 | N   | HIS | A | 726 | 40.243 | 4.672  | 63.521 | 1.00 | 0.00 |
| ATOM | 1889 | CA  | HIS | A | 726 | 40.255 | 5.971  | 62.835 | 1.00 | 0.00 |
| ATOM | 1890 | CB  | HIS | A | 726 | 41.453 | 6.792  | 63.301 | 1.00 | 0.00 |
| ATOM | 1891 | CG  | HIS | A | 726 | 41.413 | 7.237  | 64.751 | 1.00 | 0.00 |
| ATOM | 1892 | ND1 | HIS | A | 726 | 42.077 | 6.678  | 65.778 | 1.00 | 0.00 |
| ATOM | 1894 | CE1 | HIS | A | 726 | 41.801 | 7.352  | 66.912 | 1.00 | 0.00 |
| ATOM | 1895 | NE2 | HIS | A | 726 | 40.951 | 8.354  | 66.594 | 1.00 | 0.00 |
| ATOM | 1896 | CD2 | HIS | A | 726 | 40.703 | 8.296  | 65.265 | 1.00 | 0.00 |
| ATOM | 1897 | C   | HIS | A | 726 | 40.328 | 5.806  | 61.313 | 1.00 | 0.00 |
| ATOM | 1898 | O   | HIS | A | 726 | 39.691 | 6.590  | 60.596 | 1.00 | 0.00 |
| ATOM | 1899 | N   | GLU | A | 727 | 40.784 | 4.645  | 60.861 | 1.00 | 0.00 |
| ATOM | 1901 | CA  | GLU | A | 727 | 40.862 | 4.406  | 59.420 | 1.00 | 0.00 |
| ATOM | 1902 | CB  | GLU | A | 727 | 41.940 | 3.360  | 59.128 | 1.00 | 0.00 |
| ATOM | 1903 | CG  | GLU | A | 727 | 41.508 | 1.935  | 59.457 | 1.00 | 0.00 |

TABLE I-continued

GR Homology Model Coordinates

| ATOM | 1904 | CD | GLU | A | 727 | 42.735 | 1.062 | 59.699 | 1.00 | 0.00 |
|---|---|---|---|---|---|---|---|---|---|---|
| ATOM | 1905 | OE1 | GLU | A | 727 | 43.667 | 1.562 | 60.314 | 1.00 | 0.00 |
| ATOM | 1906 | OE2 | GLU | A | 727 | 42.694 | −0.104 | 59.329 | 1.00 | 0.00 |
| ATOM | 1907 | C | GLU | A | 727 | 39.510 | 3.996 | 58.827 | 1.00 | 0.00 |
| ATOM | 1908 | O | GLU | A | 727 | 39.299 | 4.245 | 57.637 | 1.00 | 0.00 |
| ATOM | 1909 | N | VAL | A | 728 | 38.551 | 3.604 | 59.657 | 1.00 | 0.00 |
| ATOM | 1911 | CA | VAL | A | 728 | 37.213 | 3.338 | 59.131 | 1.00 | 0.00 |
| ATOM | 1912 | CB | VAL | A | 728 | 36.630 | 2.052 | 59.725 | 1.00 | 0.00 |
| ATOM | 1913 | CG1 | VAL | A | 728 | 36.806 | 1.943 | 61.232 | 1.00 | 0.00 |
| ATOM | 1914 | CG2 | VAL | A | 728 | 35.167 | 1.866 | 59.344 | 1.00 | 0.00 |
| ATOM | 1915 | C | VAL | A | 728 | 36.312 | 4.549 | 59.359 | 1.00 | 0.00 |
| ATOM | 1916 | O | VAL | A | 728 | 35.470 | 4.864 | 58.506 | 1.00 | 0.00 |
| ATOM | 1917 | N | VAL | A | 729 | 36.704 | 5.392 | 60.302 | 1.00 | 0.00 |
| ATOM | 1919 | CA | VAL | A | 729 | 35.952 | 6.625 | 60.544 | 1.00 | 0.00 |
| ATOM | 1920 | CB | VAL | A | 729 | 36.318 | 7.170 | 61.921 | 1.00 | 0.00 |
| ATOM | 1921 | CG1 | VAL | A | 729 | 35.681 | 8.532 | 62.178 | 1.00 | 0.00 |
| ATOM | 1922 | CG2 | VAL | A | 729 | 35.909 | 6.187 | 63.006 | 1.00 | 0.00 |
| ATOM | 1923 | C | VAL | A | 729 | 36.240 | 7.665 | 59.467 | 1.00 | 0.00 |
| ATOM | 1924 | O | VAL | A | 729 | 35.314 | 8.371 | 59.048 | 1.00 | 0.00 |
| ATOM | 1925 | N | GLU | A | 730 | 37.387 | 7.547 | 58.817 | 1.00 | 0.00 |
| ATOM | 1927 | CA | GLU | A | 730 | 37.669 | 8.451 | 57.702 | 1.00 | 0.00 |
| ATOM | 1928 | CB | GLU | A | 730 | 39.179 | 8.568 | 57.497 | 1.00 | 0.00 |
| ATOM | 1929 | CG | GLU | A | 730 | 39.825 | 7.247 | 57.100 | 1.00 | 0.00 |
| ATOM | 1930 | CD | GLU | A | 730 | 41.345 | 7.378 | 57.066 | 1.00 | 0.00 |
| ATOM | 1931 | OE1 | GLU | A | 730 | 41.868 | 7.723 | 56.017 | 1.00 | 0.00 |
| ATOM | 1932 | OE2 | GLU | A | 730 | 41.955 | 7.126 | 58.097 | 1.00 | 0.00 |
| ATOM | 1933 | C | GLU | A | 730 | 36.962 | 8.028 | 56.408 | 1.00 | 0.00 |
| ATOM | 1934 | O | GLU | A | 730 | 36.682 | 8.908 | 55.584 | 1.00 | 0.00 |
| ATOM | 1935 | N | ASN | A | 731 | 36.484 | 6.794 | 56.300 | 1.00 | 0.00 |
| ATOM | 1937 | CA | ASN | A | 731 | 35.678 | 6.471 | 55.120 | 1.00 | 0.00 |
| ATOM | 1938 | CB | ASN | A | 731 | 35.961 | 5.068 | 54.567 | 1.00 | 0.00 |
| ATOM | 1939 | CG | ASN | A | 731 | 35.700 | 3.917 | 55.540 | 1.00 | 0.00 |
| ATOM | 1940 | OD1 | ASN | A | 731 | 36.640 | 3.383 | 56.136 | 1.00 | 0.00 |
| ATOM | 1941 | ND2 | ASN | A | 731 | 34.461 | 3.453 | 55.575 | 1.00 | 0.00 |
| ATOM | 1944 | C | ASN | A | 731 | 34.201 | 6.685 | 55.429 | 1.00 | 0.00 |
| ATOM | 1945 | O | ASN | A | 731 | 33.451 | 7.073 | 54.525 | 1.00 | 0.00 |
| ATOM | 1946 | N | LEU | A | 732 | 33.871 | 6.721 | 56.712 | 1.00 | 0.00 |
| ATOM | 1948 | CA | LEU | A | 732 | 32.508 | 7.055 | 57.132 | 1.00 | 0.00 |
| ATOM | 1949 | CB | LEU | A | 732 | 32.348 | 6.743 | 58.617 | 1.00 | 0.00 |
| ATOM | 1950 | CG | LEU | A | 732 | 32.443 | 5.254 | 58.924 | 1.00 | 0.00 |
| ATOM | 1951 | CD1 | LEU | A | 732 | 32.476 | 5.011 | 60.429 | 1.00 | 0.00 |
| ATOM | 1952 | CD2 | LEU | A | 732 | 31.300 | 4.481 | 58.283 | 1.00 | 0.00 |
| ATOM | 1953 | C | LEU | A | 732 | 32.250 | 8.539 | 56.917 | 1.00 | 0.00 |
| ATOM | 1954 | O | LEU | A | 732 | 31.232 | 8.906 | 56.320 | 1.00 | 0.00 |
| ATOM | 1955 | N | LEU | A | 733 | 33.270 | 9.346 | 57.162 | 1.00 | 0.00 |
| ATOM | 1957 | CA | LEU | A | 733 | 33.158 | 10.786 | 56.917 | 1.00 | 0.00 |
| ATOM | 1958 | CB | LEU | A | 733 | 34.283 | 11.487 | 57.664 | 1.00 | 0.00 |
| ATOM | 1959 | CG | LEU | A | 733 | 34.013 | 11.480 | 59.164 | 1.00 | 0.00 |
| ATOM | 1960 | CD1 | LEU | A | 733 | 35.251 | 11.870 | 59.959 | 1.00 | 0.00 |
| ATOM | 1961 | CD2 | LEU | A | 733 | 32.837 | 12.389 | 59.502 | 1.00 | 0.00 |
| ATOM | 1962 | C | LEU | A | 733 | 33.222 | 11.133 | 55.433 | 1.00 | 0.00 |
| ATOM | 1963 | O | LEU | A | 733 | 32.441 | 11.983 | 54.989 | 1.00 | 0.00 |
| ATOM | 1964 | N | ASN | A | 734 | 33.921 | 10.327 | 54.649 | 1.00 | 0.00 |
| ATOM | 1966 | CA | ASN | A | 734 | 33.948 | 10.554 | 53.202 | 1.00 | 0.00 |
| ATOM | 1967 | CB | ASN | A | 734 | 35.056 | 9.724 | 52.564 | 1.00 | 0.00 |
| ATOM | 1968 | CG | ASN | A | 734 | 36.277 | 10.603 | 52.322 | 1.00 | 0.00 |
| ATOM | 1969 | OD1 | ASN | A | 734 | 36.316 | 11.379 | 51.356 | 1.00 | 0.00 |
| ATOM | 1970 | ND2 | ASN | A | 734 | 37.239 | 10.513 | 53.222 | 1.00 | 0.00 |
| ATOM | 1973 | C | ASN | A | 734 | 32.621 | 10.201 | 52.550 | 1.00 | 0.00 |
| ATOM | 1974 | O | ASN | A | 734 | 32.024 | 11.078 | 51.910 | 1.00 | 0.00 |
| ATOM | 1975 | N | TYR | A | 735 | 32.033 | 9.089 | 52.962 | 1.00 | 0.00 |
| ATOM | 1977 | CA | TYR | A | 735 | 30.776 | 8.654 | 52.354 | 1.00 | 0.00 |
| ATOM | 1978 | CB | TYR | A | 735 | 30.563 | 7.180 | 52.673 | 1.00 | 0.00 |
| ATOM | 1979 | CG | TYR | A | 735 | 29.561 | 6.466 | 51.767 | 1.00 | 0.00 |
| ATOM | 1980 | CD1 | TYR | A | 735 | 30.027 | 5.739 | 50.680 | 1.00 | 0.00 |
| ATOM | 1981 | CE1 | TYR | A | 735 | 29.133 | 5.077 | 49.850 | 1.00 | 0.00 |
| ATOM | 1982 | CZ | TYR | A | 735 | 27.772 | 5.144 | 50.110 | 1.00 | 0.00 |
| ATOM | 1983 | OH | TYR | A | 735 | 26.888 | 4.463 | 49.302 | 1.00 | 0.00 |
| ATOM | 1984 | CE2 | TYR | A | 735 | 27.300 | 5.869 | 51.196 | 1.00 | 0.00 |
| ATOM | 1985 | CD2 | TYR | A | 735 | 28.197 | 6.530 | 52.027 | 1.00 | 0.00 |
| ATOM | 1986 | C | TYR | A | 735 | 29.597 | 9.475 | 52.867 | 1.00 | 0.00 |
| ATOM | 1987 | O | TYR | A | 735 | 28.729 | 9.847 | 52.067 | 1.00 | 0.00 |
| ATOM | 1988 | N | CYS | A | 736 | 29.696 | 9.977 | 54.086 | 1.00 | 0.00 |
| ATOM | 1990 | CA | CYS | A | 736 | 28.640 | 10.843 | 54.608 | 1.00 | 0.00 |
| ATOM | 1991 | CB | CYS | A | 736 | 28.826 | 11.008 | 56.111 | 1.00 | 0.00 |
| ATOM | 1992 | SG | CYS | A | 736 | 27.633 | 12.095 | 56.926 | 1.00 | 0.00 |
| ATOM | 1993 | C | CYS | A | 736 | 28.678 | 12.217 | 53.952 | 1.00 | 0.00 |

TABLE I-continued

GR Homology Model Coordinates

| ATOM | 1994 | O   | CYS | A | 736 | 27.638 | 12.677 | 53.463 | 1.00 | 0.00 |
| ---- | ---- | --- | --- | - | --- | ------ | ------ | ------ | ---- | ---- |
| ATOM | 1995 | N   | PHE | A | 737 | 29.874 | 12.713 | 53.681 | 1.00 | 0.00 |
| ATOM | 1997 | CA  | PHE | A | 737 | 30.000 | 14.042 | 53.085 | 1.00 | 0.00 |
| ATOM | 1998 | CB  | PHE | A | 737 | 31.431 | 14.524 | 53.302 | 1.00 | 0.00 |
| ATOM | 1999 | CG  | PHE | A | 737 | 31.671 | 15.997 | 52.981 | 1.00 | 0.00 |
| ATOM | 2000 | CD1 | PHE | A | 737 | 32.188 | 16.373 | 51.749 | 1.00 | 0.00 |
| ATOM | 2001 | CE1 | PHE | A | 737 | 32.408 | 17.715 | 51.468 | 1.00 | 0.00 |
| ATOM | 2002 | CZ  | PHE | A | 737 | 32.115 | 18.681 | 52.422 | 1.00 | 0.00 |
| ATOM | 2003 | CE2 | PHE | A | 737 | 31.605 | 18.305 | 53.658 | 1.00 | 0.00 |
| ATOM | 2004 | CD2 | PHE | A | 737 | 31.385 | 16.963 | 53.938 | 1.00 | 0.00 |
| ATOM | 2005 | C   | PHE | A | 737 | 29.667 | 14.017 | 51.595 | 1.00 | 0.00 |
| ATOM | 2006 | O   | PHE | A | 737 | 28.942 | 14.905 | 51.128 | 1.00 | 0.00 |
| ATOM | 2007 | N   | GLN | A | 738 | 29.943 | 12.909 | 50.926 | 1.00 | 0.00 |
| ATOM | 2009 | CA  | GLN | A | 738 | 29.590 | 12.836 | 49.508 | 1.00 | 0.00 |
| ATOM | 2010 | CB  | GLN | A | 738 | 30.484 | 11.829 | 48.788 | 1.00 | 0.00 |
| ATOM | 2011 | CG  | GLN | A | 738 | 30.307 | 10.413 | 49.320 | 1.00 | 0.00 |
| ATOM | 2012 | CD  | GLN | A | 738 | 31.187 | 9.439  | 48.556 | 1.00 | 0.00 |
| ATOM | 2013 | OE1 | GLN | A | 738 | 32.012 | 8.728  | 49.143 | 1.00 | 0.00 |
| ATOM | 2014 | NE2 | GLN | A | 738 | 30.969 | 9.395  | 47.253 | 1.00 | 0.00 |
| ATOM | 2017 | C   | GLN | A | 738 | 28.117 | 12.485 | 49.304 | 1.00 | 0.00 |
| ATOM | 2018 | O   | GLN | A | 738 | 27.521 | 13.009 | 48.357 | 1.00 | 0.00 |
| ATOM | 2019 | N   | THR | A | 739 | 27.470 | 11.882 | 50.290 | 1.00 | 0.00 |
| ATOM | 2021 | CA  | THR | A | 739 | 26.043 | 11.590 | 50.149 | 1.00 | 0.00 |
| ATOM | 2022 | CB  | THR | A | 739 | 25.707 | 10.354 | 50.976 | 1.00 | 0.00 |
| ATOM | 2023 | OG1 | THR | A | 739 | 26.490 | 9.280  | 50.474 | 1.00 | 0.00 |
| ATOM | 2024 | CG2 | THR | A | 739 | 24.244 | 9.956  | 50.836 | 1.00 | 0.00 |
| ATOM | 2025 | C   | THR | A | 739 | 25.210 | 12.791 | 50.584 | 1.00 | 0.00 |
| ATOM | 2026 | O   | THR | A | 739 | 24.126 | 13.016 | 50.036 | 1.00 | 0.00 |
| ATOM | 2027 | N   | PHE | A | 740 | 25.831 | 13.668 | 51.357 | 1.00 | 0.00 |
| ATOM | 2029 | CA  | PHE | A | 740 | 25.223 | 14.951 | 51.711 | 1.00 | 0.00 |
| ATOM | 2030 | CB  | PHE | A | 740 | 25.918 | 15.449 | 52.977 | 1.00 | 0.00 |
| ATOM | 2031 | CG  | PHE | A | 740 | 25.552 | 16.861 | 53.426 | 1.00 | 0.00 |
| ATOM | 2032 | CD1 | PHE | A | 740 | 24.342 | 17.098 | 54.065 | 1.00 | 0.00 |
| ATOM | 2033 | CE1 | PHE | A | 740 | 24.014 | 18.385 | 54.476 | 1.00 | 0.00 |
| ATOM | 2034 | CZ  | PHE | A | 740 | 24.897 | 19.433 | 54.249 | 1.00 | 0.00 |
| ATOM | 2035 | CE2 | PHE | A | 740 | 26.108 | 19.195 | 53.613 | 1.00 | 0.00 |
| ATOM | 2036 | CD2 | PHE | A | 740 | 26.435 | 17.910 | 53.202 | 1.00 | 0.00 |
| ATOM | 2037 | C   | PHE | A | 740 | 25.395 | 15.974 | 50.589 | 1.00 | 0.00 |
| ATOM | 2038 | O   | PHE | A | 740 | 24.533 | 16.840 | 50.406 | 1.00 | 0.00 |
| ATOM | 2039 | N   | LEU | A | 741 | 26.410 | 15.794 | 49.761 | 1.00 | 0.00 |
| ATOM | 2041 | CA  | LEU | A | 741 | 26.590 | 16.683 | 48.610 | 1.00 | 0.00 |
| ATOM | 2042 | CB  | LEU | A | 741 | 28.076 | 16.651 | 48.237 | 1.00 | 0.00 |
| ATOM | 2043 | CG  | LEU | A | 741 | 28.511 | 17.759 | 47.275 | 1.00 | 0.00 |
| ATOM | 2044 | CD1 | LEU | A | 741 | 28.244 | 17.441 | 45.806 | 1.00 | 0.00 |
| ATOM | 2045 | CD2 | LEU | A | 741 | 27.939 | 19.115 | 47.679 | 1.00 | 0.00 |
| ATOM | 2046 | C   | LEU | A | 741 | 25.716 | 16.199 | 47.454 | 1.00 | 0.00 |
| ATOM | 2047 | O   | LEU | A | 741 | 24.995 | 16.990 | 46.834 | 1.00 | 0.00 |
| ATOM | 2048 | N   | ASP | A | 742 | 25.600 | 14.886 | 47.350 | 1.00 | 0.00 |
| ATOM | 2050 | CA  | ASP | A | 742 | 24.803 | 14.248 | 46.298 | 1.00 | 0.00 |
| ATOM | 2051 | CB  | ASP | A | 742 | 25.404 | 12.878 | 45.973 | 1.00 | 0.00 |
| ATOM | 2052 | CG  | ASP | A | 742 | 26.853 | 12.975 | 45.486 | 1.00 | 0.00 |
| ATOM | 2053 | OD1 | ASP | A | 742 | 27.193 | 13.990 | 44.894 | 1.00 | 0.00 |
| ATOM | 2054 | OD2 | ASP | A | 742 | 27.564 | 11.985 | 45.621 | 1.00 | 0.00 |
| ATOM | 2055 | C   | ASP | A | 742 | 23.342 | 14.041 | 46.697 | 1.00 | 0.00 |
| ATOM | 2056 | O   | ASP | A | 742 | 22.604 | 13.408 | 45.930 | 1.00 | 0.00 |
| ATOM | 2057 | N   | LYS | A | 743 | 22.876 | 14.718 | 47.737 | 1.00 | 0.00 |
| ATOM | 2059 | CA  | LYS | A | 743 | 21.573 | 14.391 | 48.333 | 1.00 | 0.00 |
| ATOM | 2060 | CB  | LYS | A | 743 | 21.478 | 15.004 | 49.738 | 1.00 | 0.00 |
| ATOM | 2061 | CG  | LYS | A | 743 | 20.899 | 16.419 | 49.850 | 1.00 | 0.00 |
| ATOM | 2062 | CD  | LYS | A | 743 | 21.811 | 17.518 | 49.317 | 1.00 | 0.00 |
| ATOM | 2063 | CE  | LYS | A | 743 | 21.271 | 18.900 | 49.659 | 1.00 | 0.00 |
| ATOM | 2064 | NZ  | LYS | A | 743 | 21.189 | 19.068 | 51.120 | 1.00 | 0.00 |
| ATOM | 2065 | C   | LYS | A | 743 | 20.366 | 14.786 | 47.477 | 1.00 | 0.00 |
| ATOM | 2066 | O   | LYS | A | 743 | 19.344 | 14.092 | 47.546 | 1.00 | 0.00 |
| ATOM | 2067 | N   | THR | A | 744 | 20.570 | 15.639 | 46.484 | 1.00 | 0.00 |
| ATOM | 2069 | CA  | THR | A | 744 | 19.469 | 15.997 | 45.582 | 1.00 | 0.00 |
| ATOM | 2070 | CB  | THR | A | 744 | 19.745 | 17.370 | 44.978 | 1.00 | 0.00 |
| ATOM | 2071 | OG1 | THR | A | 744 | 20.919 | 17.288 | 44.180 | 1.00 | 0.00 |
| ATOM | 2072 | CG2 | THR | A | 744 | 19.958 | 18.433 | 46.048 | 1.00 | 0.00 |
| ATOM | 2073 | C   | THR | A | 744 | 19.299 | 14.988 | 44.445 | 1.00 | 0.00 |
| ATOM | 2074 | O   | THR | A | 744 | 18.212 | 14.896 | 43.869 | 1.00 | 0.00 |
| ATOM | 2075 | N   | MET | A | 745 | 20.311 | 14.168 | 44.209 | 1.00 | 0.00 |
| ATOM | 2077 | CA  | MET | A | 745 | 20.236 | 13.170 | 43.139 | 1.00 | 0.00 |
| ATOM | 2078 | CB  | MET | A | 745 | 21.533 | 13.239 | 42.344 | 1.00 | 0.00 |
| ATOM | 2079 | CG  | MET | A | 745 | 21.761 | 14.636 | 41.776 | 1.00 | 0.00 |
| ATOM | 2080 | SD  | MET | A | 745 | 23.344 | 14.883 | 40.942 | 1.00 | 0.00 |
| ATOM | 2081 | CE  | MET | A | 745 | 24.446 | 14.543 | 42.335 | 1.00 | 0.00 |

TABLE I-continued

GR Homology Model Coordinates

| ATOM | 2082 | C | MET | A | 745 | 20.077 | 11.775 | 43.729 | 1.00 | 0.00 |
|---|---|---|---|---|---|---|---|---|---|---|
| ATOM | 2083 | O | MET | A | 745 | 19.551 | 10.856 | 43.091 | 1.00 | 0.00 |
| ATOM | 2084 | N | SER | A | 746 | 20.503 | 11.654 | 44.975 | 1.00 | 0.00 |
| ATOM | 2086 | CA | SER | A | 746 | 20.402 | 10.392 | 45.711 | 1.00 | 0.00 |
| ATOM | 2087 | CB | SER | A | 746 | 21.629 | 10.242 | 46.602 | 1.00 | 0.00 |
| ATOM | 2088 | OG | SER | A | 746 | 21.556 | 11.239 | 47.615 | 1.00 | 0.00 |
| ATOM | 2089 | C | SER | A | 746 | 19.158 | 10.337 | 46.590 | 1.00 | 0.00 |
| ATOM | 2090 | O | SER | A | 746 | 19.008 | 9.374 | 47.348 | 1.00 | 0.00 |
| ATOM | 2091 | N | ILE | A | 747 | 18.336 | 11.377 | 46.524 | 1.00 | 0.00 |
| ATOM | 2093 | CA | ILE | A | 747 | 17.112 | 11.507 | 47.332 | 1.00 | 0.00 |
| ATOM | 2094 | CB | ILE | A | 747 | 16.026 | 10.602 | 46.752 | 1.00 | 0.00 |
| ATOM | 2095 | CG2 | ILE | A | 747 | 14.708 | 10.772 | 47.504 | 1.00 | 0.00 |
| ATOM | 2096 | CG1 | ILE | A | 747 | 15.805 | 10.913 | 45.273 | 1.00 | 0.00 |
| ATOM | 2097 | CD1 | ILE | A | 747 | 15.255 | 12.322 | 45.067 | 1.00 | 0.00 |
| ATOM | 2098 | C | ILE | A | 747 | 17.419 | 11.188 | 48.795 | 1.00 | 0.00 |
| ATOM | 2099 | O | ILE | A | 747 | 17.033 | 10.149 | 49.343 | 1.00 | 0.00 |
| ATOM | 2100 | N | GLU | A | 748 | 18.256 | 12.039 | 49.358 | 1.00 | 0.00 |
| ATOM | 2102 | CA | GLU | A | 748 | 18.735 | 11.844 | 50.721 | 1.00 | 0.00 |
| ATOM | 2103 | CB | GLU | A | 748 | 20.233 | 11.562 | 50.637 | 1.00 | 0.00 |
| ATOM | 2104 | CG | GLU | A | 748 | 20.802 | 10.962 | 51.916 | 1.00 | 0.00 |
| ATOM | 2105 | CD | GLU | A | 748 | 21.747 | 11.941 | 52.609 | 1.00 | 0.00 |
| ATOM | 2106 | OE1 | GLU | A | 748 | 21.634 | 13.127 | 52.348 | 1.00 | 0.00 |
| ATOM | 2107 | OE2 | GLU | A | 748 | 22.562 | 11.485 | 53.405 | 1.00 | 0.00 |
| ATOM | 2108 | C | GLU | A | 748 | 18.430 | 13.109 | 51.510 | 1.00 | 0.00 |
| ATOM | 2109 | O | GLU | A | 748 | 18.682 | 14.219 | 51.032 | 1.00 | 0.00 |
| ATOM | 2110 | N | PHE | A | 749 | 17.851 | 12.949 | 52.686 | 1.00 | 0.00 |
| ATOM | 2112 | CA | PHE | A | 749 | 17.424 | 14.129 | 53.448 | 1.00 | 0.00 |
| ATOM | 2113 | CB | PHE | A | 749 | 15.901 | 14.222 | 53.402 | 1.00 | 0.00 |
| ATOM | 2114 | CG | PHE | A | 749 | 15.320 | 14.358 | 51.997 | 1.00 | 0.00 |
| ATOM | 2115 | CD1 | PHE | A | 749 | 14.561 | 13.327 | 51.454 | 1.00 | 0.00 |
| ATOM | 2116 | CE1 | PHE | A | 749 | 14.039 | 13.450 | 50.173 | 1.00 | 0.00 |
| ATOM | 2117 | CZ | PHE | A | 749 | 14.272 | 14.603 | 49.436 | 1.00 | 0.00 |
| ATOM | 2118 | CE2 | PHE | A | 749 | 15.024 | 15.635 | 49.982 | 1.00 | 0.00 |
| ATOM | 2119 | CD2 | PHE | A | 749 | 15.546 | 15.514 | 51.262 | 1.00 | 0.00 |
| ATOM | 2120 | C | PHE | A | 749 | 17.880 | 14.066 | 54.900 | 1.00 | 0.00 |
| ATOM | 2121 | O | PHE | A | 749 | 17.137 | 13.594 | 55.768 | 1.00 | 0.00 |
| ATOM | 2122 | N | PRO | A | 750 | 19.079 | 14.561 | 55.161 | 1.00 | 0.00 |
| ATOM | 2123 | CA | PRO | A | 750 | 19.544 | 14.689 | 56.537 | 1.00 | 0.00 |
| ATOM | 2124 | CB | PRO | A | 750 | 21.007 | 14.988 | 56.426 | 1.00 | 0.00 |
| ATOM | 2125 | CG | PRO | A | 750 | 21.327 | 15.328 | 54.979 | 1.00 | 0.00 |
| ATOM | 2126 | CD | PRO | A | 750 | 20.030 | 15.135 | 54.206 | 1.00 | 0.00 |
| ATOM | 2127 | C | PRO | A | 750 | 18.805 | 15.823 | 57.230 | 1.00 | 0.00 |
| ATOM | 2128 | O | PRO | A | 750 | 18.674 | 16.918 | 56.677 | 1.00 | 0.00 |
| ATOM | 2129 | N | GLU | A | 751 | 18.336 | 15.561 | 58.436 | 1.00 | 0.00 |
| ATOM | 2131 | CA | GLU | A | 751 | 17.700 | 16.620 | 59.228 | 1.00 | 0.00 |
| ATOM | 2132 | CB | GLU | A | 751 | 17.037 | 16.006 | 60.451 | 1.00 | 0.00 |
| ATOM | 2133 | CG | GLU | A | 751 | 18.001 | 15.153 | 61.262 | 1.00 | 0.00 |
| ATOM | 2134 | CD | GLU | A | 751 | 17.227 | 14.486 | 62.389 | 1.00 | 0.00 |
| ATOM | 2135 | OE1 | GLU | A | 751 | 16.771 | 13.371 | 62.177 | 1.00 | 0.00 |
| ATOM | 2136 | OE2 | GLU | A | 751 | 17.033 | 15.143 | 63.401 | 1.00 | 0.00 |
| ATOM | 2137 | C | GLU | A | 751 | 18.728 | 17.681 | 59.613 | 1.00 | 0.00 |
| ATOM | 2138 | O | GLU | A | 751 | 19.938 | 17.437 | 59.505 | 1.00 | 0.00 |
| ATOM | 2139 | N | MET | A | 752 | 18.259 | 18.788 | 60.168 | 1.00 | 0.00 |
| ATOM | 2141 | CA | MET | A | 752 | 19.114 | 19.968 | 60.399 | 1.00 | 0.00 |
| ATOM | 2142 | CB | MET | A | 752 | 18.222 | 21.088 | 60.916 | 1.00 | 0.00 |
| ATOM | 2143 | CG | MET | A | 752 | 17.132 | 21.422 | 59.904 | 1.00 | 0.00 |
| ATOM | 2144 | SD | MET | A | 752 | 15.961 | 22.698 | 60.419 | 1.00 | 0.00 |
| ATOM | 2145 | CE | MET | A | 752 | 15.283 | 21.876 | 61.879 | 1.00 | 0.00 |
| ATOM | 2146 | C | MET | A | 752 | 20.269 | 19.758 | 61.379 | 1.00 | 0.00 |
| ATOM | 2147 | O | MET | A | 752 | 21.357 | 20.290 | 61.125 | 1.00 | 0.00 |
| ATOM | 2148 | N | LEU | A | 753 | 20.133 | 18.792 | 62.277 | 1.00 | 0.00 |
| ATOM | 2150 | CA | LEU | A | 753 | 21.222 | 18.440 | 63.198 | 1.00 | 0.00 |
| ATOM | 2151 | CB | LEU | A | 753 | 20.765 | 17.356 | 64.185 | 1.00 | 0.00 |
| ATOM | 2152 | CG | LEU | A | 753 | 19.913 | 17.851 | 65.360 | 1.00 | 0.00 |
| ATOM | 2153 | CD1 | LEU | A | 753 | 18.445 | 18.058 | 64.991 | 1.00 | 0.00 |
| ATOM | 2154 | CD2 | LEU | A | 753 | 19.987 | 16.848 | 66.506 | 1.00 | 0.00 |
| ATOM | 2155 | C | LEU | A | 753 | 22.425 | 17.898 | 62.427 | 1.00 | 0.00 |
| ATOM | 2156 | O | LEU | A | 753 | 23.505 | 18.500 | 62.473 | 1.00 | 0.00 |
| ATOM | 2157 | N | ALA | A | 754 | 22.143 | 17.013 | 61.485 | 1.00 | 0.00 |
| ATOM | 2159 | CA | ALA | A | 754 | 23.213 | 16.380 | 60.719 | 1.00 | 0.00 |
| ATOM | 2160 | CB | ALA | A | 754 | 22.696 | 15.058 | 60.163 | 1.00 | 0.00 |
| ATOM | 2161 | C | ALA | A | 754 | 23.677 | 17.276 | 59.578 | 1.00 | 0.00 |
| ATOM | 2162 | O | ALA | A | 754 | 24.878 | 17.302 | 59.286 | 1.00 | 0.00 |
| ATOM | 2163 | N | GLU | A | 755 | 22.814 | 18.182 | 59.145 | 1.00 | 0.00 |
| ATOM | 2165 | CA | GLU | A | 755 | 23.193 | 19.116 | 58.085 | 1.00 | 0.00 |
| ATOM | 2166 | CB | GLU | A | 755 | 21.960 | 19.852 | 57.575 | 1.00 | 0.00 |
| ATOM | 2167 | CG | GLU | A | 755 | 21.023 | 18.913 | 56.829 | 1.00 | 0.00 |

TABLE I-continued

GR Homology Model Coordinates

| ATOM | 2168 | CD | GLU | A | 755 | 19.798 | 19.674 | 56.332 | 1.00 | 0.00 |
|---|---|---|---|---|---|---|---|---|---|---|
| ATOM | 2169 | OE1 | GLU | A | 755 | 18.961 | 20.000 | 57.165 | 1.00 | 0.00 |
| ATOM | 2170 | OE2 | GLU | A | 755 | 19.799 | 20.053 | 55.169 | 1.00 | 0.00 |
| ATOM | 2171 | C | GLU | A | 755 | 24.214 | 20.130 | 58.576 | 1.00 | 0.00 |
| ATOM | 2172 | O | GLU | A | 755 | 25.291 | 20.222 | 57.973 | 1.00 | 0.00 |
| ATOM | 2173 | N | ILE | A | 756 | 24.028 | 20.653 | 59.779 | 1.00 | 0.00 |
| ATOM | 2175 | CA | ILE | A | 756 | 24.983 | 21.654 | 60.260 | 1.00 | 0.00 |
| ATOM | 2176 | CB | ILE | A | 756 | 24.322 | 22.545 | 61.318 | 1.00 | 0.00 |
| ATOM | 2177 | CG2 | ILE | A | 756 | 23.817 | 21.752 | 62.519 | 1.00 | 0.00 |
| ATOM | 2178 | CG1 | ILE | A | 756 | 25.268 | 23.650 | 61.779 | 1.00 | 0.00 |
| ATOM | 2179 | CD1 | ILE | A | 756 | 25.661 | 24.571 | 60.627 | 1.00 | 0.00 |
| ATOM | 2180 | C | ILE | A | 756 | 26.272 | 21.011 | 60.780 | 1.00 | 0.00 |
| ATOM | 2181 | O | ILE | A | 756 | 27.349 | 21.570 | 60.541 | 1.00 | 0.00 |
| ATOM | 2182 | N | ILE | A | 757 | 26.217 | 19.749 | 61.176 | 1.00 | 0.00 |
| ATOM | 2184 | CA | ILE | A | 757 | 27.444 | 19.091 | 61.625 | 1.00 | 0.00 |
| ATOM | 2185 | CB | ILE | A | 757 | 27.065 | 17.921 | 62.521 | 1.00 | 0.00 |
| ATOM | 2186 | CG2 | ILE | A | 757 | 28.286 | 17.096 | 62.897 | 1.00 | 0.00 |
| ATOM | 2187 | CG1 | ILE | A | 757 | 26.378 | 18.436 | 63.778 | 1.00 | 0.00 |
| ATOM | 2188 | CD1 | ILE | A | 757 | 25.992 | 17.291 | 64.706 | 1.00 | 0.00 |
| ATOM | 2189 | C | ILE | A | 757 | 28.295 | 18.633 | 60.441 | 1.00 | 0.00 |
| ATOM | 2190 | O | ILE | A | 757 | 29.513 | 18.862 | 60.459 | 1.00 | 0.00 |
| ATOM | 2191 | N | THR | A | 758 | 27.641 | 18.331 | 59.328 | 1.00 | 0.00 |
| ATOM | 2193 | CA | THR | A | 758 | 28.359 | 17.931 | 58.112 | 1.00 | 0.00 |
| ATOM | 2194 | CB | THR | A | 758 | 27.449 | 17.028 | 57.282 | 1.00 | 0.00 |
| ATOM | 2195 | OG1 | THR | A | 758 | 27.057 | 15.934 | 58.101 | 1.00 | 0.00 |
| ATOM | 2196 | CG2 | THR | A | 758 | 28.160 | 16.456 | 56.060 | 1.00 | 0.00 |
| ATOM | 2197 | C | THR | A | 758 | 28.812 | 19.148 | 57.299 | 1.00 | 0.00 |
| ATOM | 2198 | O | THR | A | 758 | 29.766 | 19.061 | 56.517 | 1.00 | 0.00 |
| ATOM | 2199 | N | ASN | A | 759 | 28.256 | 20.302 | 57.631 | 1.00 | 0.00 |
| ATOM | 2201 | CA | ASN | A | 759 | 28.694 | 21.564 | 57.032 | 1.00 | 0.00 |
| ATOM | 2202 | CB | ASN | A | 759 | 27.521 | 22.538 | 57.142 | 1.00 | 0.00 |
| ATOM | 2203 | CG | ASN | A | 759 | 27.446 | 23.525 | 55.975 | 1.00 | 0.00 |
| ATOM | 2204 | OD1 | ASN | A | 759 | 26.357 | 23.772 | 55.443 | 1.00 | 0.00 |
| ATOM | 2205 | ND2 | ASN | A | 759 | 28.582 | 24.076 | 55.582 | 1.00 | 0.00 |
| ATOM | 2208 | C | ASN | A | 759 | 29.900 | 22.120 | 57.796 | 1.00 | 0.00 |
| ATOM | 2209 | O | ASN | A | 759 | 30.681 | 22.906 | 57.241 | 1.00 | 0.00 |
| ATOM | 2210 | N | GLN | A | 760 | 30.106 | 21.637 | 59.008 | 1.00 | 0.00 |
| ATOM | 2212 | CA | GLN | A | 760 | 31.236 | 22.099 | 59.810 | 1.00 | 0.00 |
| ATOM | 2213 | CB | GLN | A | 760 | 30.869 | 22.018 | 61.291 | 1.00 | 0.00 |
| ATOM | 2214 | CG | GLN | A | 760 | 29.783 | 23.005 | 61.703 | 1.00 | 0.00 |
| ATOM | 2215 | CD | GLN | A | 760 | 30.279 | 24.443 | 61.609 | 1.00 | 0.00 |
| ATOM | 2216 | OE1 | GLN | A | 760 | 29.595 | 25.307 | 61.051 | 1.00 | 0.00 |
| ATOM | 2217 | NE2 | GLN | A | 760 | 31.420 | 24.701 | 62.228 | 1.00 | 0.00 |
| ATOM | 2220 | C | GLN | A | 760 | 32.486 | 21.256 | 59.594 | 1.00 | 0.00 |
| ATOM | 2221 | O | GLN | A | 760 | 33.313 | 21.514 | 58.711 | 1.00 | 0.00 |
| ATOM | 2222 | N | ILE | A | 761 | 32.583 | 20.215 | 60.399 | 1.00 | 0.00 |
| ATOM | 2224 | CA | ILE | A | 761 | 33.856 | 19.496 | 60.557 | 1.00 | 0.00 |
| ATOM | 2225 | CB | ILE | A | 761 | 33.966 | 18.975 | 61.994 | 1.00 | 0.00 |
| ATOM | 2226 | CG2 | ILE | A | 761 | 33.612 | 20.082 | 62.981 | 1.00 | 0.00 |
| ATOM | 2227 | CG1 | ILE | A | 761 | 33.122 | 17.730 | 62.279 | 1.00 | 0.00 |
| ATOM | 2228 | CD1 | ILE | A | 761 | 31.655 | 18.019 | 62.571 | 1.00 | 0.00 |
| ATOM | 2229 | C | ILE | A | 761 | 34.255 | 18.353 | 59.592 | 1.00 | 0.00 |
| ATOM | 2230 | O | ILE | A | 761 | 35.470 | 18.128 | 59.556 | 1.00 | 0.00 |
| ATOM | 2231 | N | PRO | A | 762 | 33.423 | 17.684 | 58.786 | 1.00 | 0.00 |
| ATOM | 2232 | CA | PRO | A | 762 | 33.990 | 16.587 | 57.981 | 1.00 | 0.00 |
| ATOM | 2233 | CB | PRO | A | 762 | 32.826 | 15.811 | 57.454 | 1.00 | 0.00 |
| ATOM | 2234 | CG | PRO | A | 762 | 31.549 | 16.541 | 57.811 | 1.00 | 0.00 |
| ATOM | 2235 | CD | PRO | A | 762 | 31.969 | 17.768 | 58.599 | 1.00 | 0.00 |
| ATOM | 2236 | C | PRO | A | 762 | 34.895 | 17.045 | 56.832 | 1.00 | 0.00 |
| ATOM | 2237 | O | PRO | A | 762 | 35.794 | 16.284 | 56.452 | 1.00 | 0.00 |
| ATOM | 2238 | N | LYS | A | 763 | 34.858 | 18.322 | 56.481 | 1.00 | 0.00 |
| ATOM | 2240 | CA | LYS | A | 763 | 35.800 | 18.836 | 55.488 | 1.00 | 0.00 |
| ATOM | 2241 | CB | LYS | A | 763 | 35.284 | 20.178 | 54.987 | 1.00 | 0.00 |
| ATOM | 2242 | CG | LYS | A | 763 | 36.216 | 20.769 | 53.937 | 1.00 | 0.00 |
| ATOM | 2243 | CD | LYS | A | 763 | 35.715 | 22.129 | 53.471 | 1.00 | 0.00 |
| ATOM | 2244 | CE | LYS | A | 763 | 35.608 | 23.099 | 54.641 | 1.00 | 0.00 |
| ATOM | 2245 | NZ | LYS | A | 763 | 35.122 | 24.413 | 54.193 | 1.00 | 0.00 |
| ATOM | 2246 | C | LYS | A | 763 | 37.186 | 19.017 | 56.108 | 1.00 | 0.00 |
| ATOM | 2247 | O | LYS | A | 763 | 38.180 | 18.599 | 55.500 | 1.00 | 0.00 |
| ATOM | 2248 | N | TYR | A | 764 | 37.208 | 19.290 | 57.403 | 1.00 | 0.00 |
| ATOM | 2250 | CA | TYR | A | 764 | 38.473 | 19.445 | 58.126 | 1.00 | 0.00 |
| ATOM | 2251 | CB | TYR | A | 764 | 38.246 | 20.377 | 59.309 | 1.00 | 0.00 |
| ATOM | 2252 | CG | TYR | A | 764 | 37.765 | 21.762 | 58.892 | 1.00 | 0.00 |
| ATOM | 2253 | CD1 | TYR | A | 764 | 38.571 | 22.563 | 58.091 | 1.00 | 0.00 |
| ATOM | 2254 | CE1 | TYR | A | 764 | 38.132 | 23.822 | 57.703 | 1.00 | 0.00 |
| ATOM | 2255 | CZ | TYR | A | 764 | 36.887 | 24.275 | 58.118 | 1.00 | 0.00 |
| ATOM | 2256 | OH | TYR | A | 764 | 36.439 | 25.514 | 57.714 | 1.00 | 0.00 |

TABLE I-continued

GR Homology Model Coordinates

| ATOM | 2257 | CE2 | TYR | A | 764 | 36.081 | 23.479 | 58.921 | 1.00 | 0.00 |
|---|---|---|---|---|---|---|---|---|---|---|
| ATOM | 2258 | CD2 | TYR | A | 764 | 36.521 | 22.221 | 59.308 | 1.00 | 0.00 |
| ATOM | 2259 | C | TYR | A | 764 | 39.005 | 18.100 | 58.610 | 1.00 | 0.00 |
| ATOM | 2260 | O | TYR | A | 764 | 40.201 | 17.963 | 58.894 | 1.00 | 0.00 |
| ATOM | 2261 | N | SER | A | 765 | 38.160 | 17.085 | 58.583 | 1.00 | 0.00 |
| ATOM | 2263 | CA | SER | A | 765 | 38.642 | 15.731 | 58.841 | 1.00 | 0.00 |
| ATOM | 2264 | CB | SER | A | 765 | 37.476 | 14.854 | 59.262 | 1.00 | 0.00 |
| ATOM | 2265 | OG | SER | A | 765 | 37.996 | 13.542 | 59.423 | 1.00 | 0.00 |
| ATOM | 2266 | C | SER | A | 765 | 39.243 | 15.129 | 57.583 | 1.00 | 0.00 |
| ATOM | 2267 | O | SER | A | 765 | 40.322 | 14.528 | 57.647 | 1.00 | 0.00 |
| ATOM | 2268 | N | ASN | A | 766 | 38.692 | 15.522 | 56.446 | 1.00 | 0.00 |
| ATOM | 2270 | CA | ASN | A | 766 | 39.144 | 15.001 | 55.156 | 1.00 | 0.00 |
| ATOM | 2271 | CB | ASN | A | 766 | 37.997 | 15.175 | 54.170 | 1.00 | 0.00 |
| ATOM | 2272 | CG | ASN | A | 766 | 37.991 | 14.009 | 53.192 | 1.00 | 0.00 |
| ATOM | 2273 | OD1 | ASN | A | 766 | 38.705 | 13.017 | 53.392 | 1.00 | 0.00 |
| ATOM | 2274 | ND2 | ASN | A | 766 | 37.139 | 14.107 | 52.187 | 1.00 | 0.00 |
| ATOM | 2277 | C | ASN | A | 766 | 40.386 | 15.734 | 54.649 | 1.00 | 0.00 |
| ATOM | 2278 | O | ASN | A | 766 | 41.107 | 15.219 | 53.788 | 1.00 | 0.00 |
| ATOM | 2279 | N | GLY | A | 767 | 40.683 | 16.872 | 55.256 | 1.00 | 0.00 |
| ATOM | 2281 | CA | GLY | A | 767 | 41.940 | 17.575 | 54.985 | 1.00 | 0.00 |
| ATOM | 2282 | C | GLY | A | 767 | 42.836 | 17.626 | 56.225 | 1.00 | 0.00 |
| ATOM | 2283 | O | GLY | A | 767 | 43.666 | 18.537 | 56.347 | 1.00 | 0.00 |
| ATOM | 2284 | N | ASN | A | 768 | 42.705 | 16.611 | 57.075 | 1.00 | 0.00 |
| ATOM | 2286 | CA | ASN | A | 768 | 43.451 | 16.447 | 58.347 | 1.00 | 0.00 |
| ATOM | 2287 | CB | ASN | A | 768 | 44.624 | 15.474 | 58.159 | 1.00 | 0.00 |
| ATOM | 2288 | CG | ASN | A | 768 | 45.422 | 15.672 | 56.865 | 1.00 | 0.00 |
| ATOM | 2289 | OD1 | ASN | A | 768 | 45.237 | 14.929 | 55.895 | 1.00 | 0.00 |
| ATOM | 2290 | ND2 | ASN | A | 768 | 46.277 | 16.679 | 56.856 | 1.00 | 0.00 |
| ATOM | 2293 | C | ASN | A | 768 | 43.890 | 17.736 | 59.057 | 1.00 | 0.00 |
| ATOM | 2294 | O | ASN | A | 768 | 45.074 | 18.098 | 59.107 | 1.00 | 0.00 |
| ATOM | 2295 | N | ILE | A | 769 | 42.901 | 18.422 | 59.604 | 1.00 | 0.00 |
| ATOM | 2297 | CA | ILE | A | 769 | 43.129 | 19.606 | 60.441 | 1.00 | 0.00 |
| ATOM | 2298 | CB | ILE | A | 769 | 42.150 | 20.697 | 59.998 | 1.00 | 0.00 |
| ATOM | 2299 | CG2 | ILE | A | 769 | 42.373 | 21.997 | 60.764 | 1.00 | 0.00 |
| ATOM | 2300 | CG1 | ILE | A | 769 | 42.273 | 20.969 | 58.501 | 1.00 | 0.00 |
| ATOM | 2301 | CD1 | ILE | A | 769 | 43.632 | 21.569 | 58.146 | 1.00 | 0.00 |
| ATOM | 2302 | C | ILE | A | 769 | 42.904 | 19.214 | 61.905 | 1.00 | 0.00 |
| ATOM | 2303 | O | ILE | A | 769 | 43.157 | 19.978 | 62.848 | 1.00 | 0.00 |
| ATOM | 2304 | N | LYS | A | 770 | 42.384 | 18.009 | 62.067 | 1.00 | 0.00 |
| ATOM | 2306 | CA | LYS | A | 770 | 42.197 | 17.426 | 63.396 | 1.00 | 0.00 |
| ATOM | 2307 | CB | LYS | A | 770 | 40.980 | 16.514 | 63.367 | 1.00 | 0.00 |
| ATOM | 2308 | CG | LYS | A | 770 | 39.732 | 17.226 | 62.870 | 1.00 | 0.00 |
| ATOM | 2309 | CD | LYS | A | 770 | 38.559 | 16.256 | 62.860 | 1.00 | 0.00 |
| ATOM | 2310 | CE | LYS | A | 770 | 37.295 | 16.905 | 62.317 | 1.00 | 0.00 |
| ATOM | 2311 | NZ | LYS | A | 770 | 36.176 | 15.951 | 62.360 | 1.00 | 0.00 |
| ATOM | 2312 | C | LYS | A | 770 | 43.402 | 16.583 | 63.790 | 1.00 | 0.00 |
| ATOM | 2313 | O | LYS | A | 770 | 43.904 | 15.779 | 62.995 | 1.00 | 0.00 |
| ATOM | 2314 | N | LYS | A | 771 | 43.789 | 16.704 | 65.044 | 1.00 | 0.00 |
| ATOM | 2316 | CA | LYS | A | 771 | 44.871 | 15.890 | 65.589 | 1.00 | 0.00 |
| ATOM | 2317 | CB | LYS | A | 771 | 45.718 | 16.747 | 66.522 | 1.00 | 0.00 |
| ATOM | 2318 | CG | LYS | A | 771 | 46.919 | 15.970 | 67.046 | 1.00 | 0.00 |
| ATOM | 2319 | CD | LYS | A | 771 | 47.746 | 16.808 | 68.012 | 1.00 | 0.00 |
| ATOM | 2320 | CE | LYS | A | 771 | 48.978 | 16.044 | 68.482 | 1.00 | 0.00 |
| ATOM | 2321 | NZ | LYS | A | 771 | 48.595 | 14.773 | 69.117 | 1.00 | 0.00 |
| ATOM | 2322 | C | LYS | A | 771 | 44.279 | 14.701 | 66.341 | 1.00 | 0.00 |
| ATOM | 2323 | O | LYS | A | 771 | 43.718 | 14.839 | 67.439 | 1.00 | 0.00 |
| ATOM | 2324 | N | LEU | A | 772 | 44.328 | 13.556 | 65.681 | 1.00 | 0.00 |
| ATOM | 2326 | CA | LEU | A | 772 | 43.820 | 12.312 | 66.269 | 1.00 | 0.00 |
| ATOM | 2327 | CB | LEU | A | 772 | 43.750 | 11.239 | 65.190 | 1.00 | 0.00 |
| ATOM | 2328 | CG | LEU | A | 772 | 42.857 | 11.660 | 64.027 | 1.00 | 0.00 |
| ATOM | 2329 | CD1 | LEU | A | 772 | 42.936 | 10.647 | 62.891 | 1.00 | 0.00 |
| ATOM | 2330 | CD2 | LEU | A | 772 | 41.412 | 11.858 | 64.474 | 1.00 | 0.00 |
| ATOM | 2331 | C | LEU | A | 772 | 44.735 | 11.847 | 67.392 | 1.00 | 0.00 |
| ATOM | 2332 | O | LEU | A | 772 | 45.962 | 11.777 | 67.243 | 1.00 | 0.00 |
| ATOM | 2333 | N | LEU | A | 773 | 44.121 | 11.518 | 68.511 | 1.00 | 0.00 |
| ATOM | 2335 | CA | LEU | A | 773 | 44.879 | 11.136 | 69.702 | 1.00 | 0.00 |
| ATOM | 2336 | CB | LEU | A | 773 | 44.153 | 11.686 | 70.918 | 1.00 | 0.00 |
| ATOM | 2337 | CG | LEU | A | 773 | 44.107 | 13.209 | 70.874 | 1.00 | 0.00 |
| ATOM | 2338 | CD1 | LEU | A | 773 | 43.185 | 13.758 | 71.949 | 1.00 | 0.00 |
| ATOM | 2339 | CD2 | LEU | A | 773 | 45.502 | 13.813 | 71.000 | 1.00 | 0.00 |
| ATOM | 2340 | C | LEU | A | 773 | 45.049 | 9.627 | 69.811 | 1.00 | 0.00 |
| ATOM | 2341 | O | LEU | A | 773 | 44.270 | 8.925 | 70.468 | 1.00 | 0.00 |
| ATOM | 2342 | N | PHE | A | 774 | 46.102 | 9.152 | 69.171 | 1.00 | 0.00 |
| ATOM | 2344 | CA | PHE | A | 774 | 46.446 | 7.730 | 69.206 | 1.00 | 0.00 |
| ATOM | 2345 | CB | PHE | A | 774 | 47.402 | 7.415 | 68.061 | 1.00 | 0.00 |
| ATOM | 2346 | CG | PHE | A | 774 | 46.818 | 7.588 | 66.661 | 1.00 | 0.00 |
| ATOM | 2347 | CD1 | PHE | A | 774 | 46.000 | 6.601 | 66.129 | 1.00 | 0.00 |

TABLE I-continued

GR Homology Model Coordinates

| ATOM | 2348 | CE1 | PHE | A | 774 | 45.469 | 6.750 | 64.855 | 1.00 | 0.00 |
|------|------|-----|-----|---|-----|--------|-------|--------|------|------|
| ATOM | 2349 | CZ  | PHE | A | 774 | 45.756 | 7.886 | 64.111 | 1.00 | 0.00 |
| ATOM | 2350 | CE2 | PHE | A | 774 | 46.580 | 8.872 | 64.639 | 1.00 | 0.00 |
| ATOM | 2351 | CD2 | PHE | A | 774 | 47.113 | 8.722 | 65.913 | 1.00 | 0.00 |
| ATOM | 2352 | C   | PHE | A | 774 | 47.098 | 7.359 | 70.533 | 1.00 | 0.00 |
| ATOM | 2353 | O   | PHE | A | 774 | 47.703 | 8.196 | 71.214 | 1.00 | 0.00 |
| ATOM | 2354 | N   | HIS | A | 775 | 46.872 | 6.123 | 70.935 | 1.00 | 0.00 |
| ATOM | 2356 | CA  | HIS | A | 775 | 47.477 | 5.606 | 72.164 | 1.00 | 0.00 |
| ATOM | 2357 | CB  | HIS | A | 775 | 46.495 | 4.641 | 72.813 | 1.00 | 0.00 |
| ATOM | 2358 | CG  | HIS | A | 775 | 45.110 | 5.223 | 73.015 | 1.00 | 0.00 |
| ATOM | 2359 | ND1 | HIS | A | 775 | 44.779 | 6.249 | 73.822 | 1.00 | 0.00 |
| ATOM | 2361 | CE1 | HIS | A | 775 | 43.452 | 6.474 | 73.733 | 1.00 | 0.00 |
| ATOM | 2362 | NE2 | HIS | A | 775 | 42.943 | 5.584 | 72.852 | 1.00 | 0.00 |
| ATOM | 2363 | CD2 | HIS | A | 775 | 43.953 | 4.808 | 72.399 | 1.00 | 0.00 |
| ATOM | 2364 | C   | HIS | A | 775 | 48.783 | 4.881 | 71.850 | 1.00 | 0.00 |
| ATOM | 2365 | O   | HIS | A | 775 | 49.606 | 4.626 | 72.738 | 1.00 | 0.00 |
| ATOM | 2366 | N   | GLN | A | 776 | 48.938 | 4.524 | 70.587 | 1.00 | 0.00 |
| ATOM | 2368 | CA  | GLN | A | 776 | 50.184 | 3.948 | 70.082 | 1.00 | 0.00 |
| ATOM | 2369 | CB  | GLN | A | 776 | 49.907 | 2.620 | 69.368 | 1.00 | 0.00 |
| ATOM | 2370 | CG  | GLN | A | 776 | 49.722 | 1.423 | 70.301 | 1.00 | 0.00 |
| ATOM | 2371 | CD  | GLN | A | 776 | 48.349 | 1.388 | 70.971 | 1.00 | 0.00 |
| ATOM | 2372 | OE1 | GLN | A | 776 | 47.317 | 1.635 | 70.338 | 1.00 | 0.00 |
| ATOM | 2373 | NE2 | GLN | A | 776 | 48.366 | 1.169 | 72.273 | 1.00 | 0.00 |
| ATOM | 2376 | C   | GLN | A | 776 | 50.844 | 4.920 | 69.109 | 1.00 | 0.00 |
| ATOM | 2377 | O   | GLN | A | 776 | 50.191 | 5.805 | 68.543 | 1.00 | 0.00 |
| ATOM | 2378 | N   | LYS | A | 777 | 52.144 | 4.759 | 68.938 | 1.00 | 0.00 |
| ATOM | 2380 | CA  | LYS | A | 777 | 52.889 | 5.591 | 67.988 | 1.00 | 0.00 |
| ATOM | 2381 | CB  | LYS | A | 777 | 54.380 | 5.448 | 68.265 | 1.00 | 0.00 |
| ATOM | 2382 | CG  | LYS | A | 777 | 55.198 | 6.329 | 67.324 | 1.00 | 0.00 |
| ATOM | 2383 | CD  | LYS | A | 777 | 56.692 | 6.164 | 67.572 | 1.00 | 0.00 |
| ATOM | 2384 | CE  | LYS | A | 777 | 57.512 | 7.038 | 66.629 | 1.00 | 0.00 |
| ATOM | 2385 | NZ  | LYS | A | 777 | 58.955 | 6.873 | 66.868 | 1.00 | 0.00 |
| ATOM | 2386 | C   | LYS | A | 777 | 52.585 | 5.164 | 66.560 | 1.00 | 0.00 |
| ATOM | 2387 | O   | LYS | A | 777 | 51.832 | 5.875 | 65.904 | 1.00 | 0.00 |
| ATOM | 2388 | OXT | LYS | A | 777 | 53.080 | 4.119 | 66.149 | 1.00 | 0.00 |

Example 22

Structure Coordinates of Site II in Various NHRs, Table III

Below is Table III, which gives the structure coordinates for Site II in various NHRs based on the consensus alignments in FIG. 2. The format used is based on that commonly used in the RCSB (Research Collaboratory for Structural Bioinformatics, pdb file format), and the fields listed from left to right are defined as follows: record name, atom serial number, atom name, residue name, chain identifier, residue sequence number, orthogonal coordinate for x in Ångstroms, orthogonal cordinate for y in Ångstroms, orthogonal coordinate for z in Ångstroms, occupancy, and temperature factor.

TABLE III

Structure Coordinates for Site II in Various NHRs
Based on the Consensus Alignments in FIG.2

AR Site II Residues (ref. 1E3G.pdb) (highlighted residues of SEQ ID NO:6)

| ATOM | 73 | N   | GLU | A | 678 | 9.927  | 12.170 | 14.764 | 1.00 | 34.27 |
|------|----|-----|-----|---|-----|--------|--------|--------|------|-------|
| ATOM | 74 | CA  | GLU | A | 678 | 9.788  | 11.576 | 13.433 | 1.00 | 33.68 |
| ATOM | 75 | C   | GLU | A | 678 | 8.502  | 10.791 | 13.361 | 1.00 | 31.24 |
| ATOM | 76 | O   | GLU | A | 678 | 7.837  | 10.730 | 12.318 | 1.00 | 29.04 |
| ATOM | 77 | CB  | GLU | A | 678 | 10.972 | 10.692 | 13.139 | 1.00 | 41.54 |
| ATOM | 78 | CG  | GLU | A | 678 | 12.250 | 11.475 | 13.231 | 1.00 | 62.50 |
| ATOM | 79 | CD  | GLU | A | 678 | 13.492 | 10.632 | 13.140 | 1.00 | 75.90 |
| ATOM | 80 | OE1 | GLU | A | 678 | 13.382 | 9.393  | 13.275 | 1.00 | 81.73 |
| ATOM | 81 | OE2 | GLU | A | 678 | 14.581 | 11.222 | 12.946 | 1.00 | 77.79 |
| ATOM | 82 | N   | ALA | A | 679 | 8.118  | 10.229 | 14.496 | 1.00 | 27.29 |
| ATOM | 83 | CA  | ALA | A | 679 | 6.878  | 9.486  | 14.561 | 1.00 | 31.51 |
| ATOM | 84 | C   | ALA | A | 679 | 5.658  | 10.400 | 14.416 | 1.00 | 37.88 |
| ATOM | 85 | O   | ALA | A | 679 | 4.657  | 10.013 | 13.784 | 1.00 | 39.80 |
| ATOM | 86 | CB  | ALA | A | 679 | 6.807  | 8.699  | 15.862 | 1.00 | 32.16 |
| ATOM | 87 | N   | ILE | A | 680 | 5.748  | 11.621 | 14.958 | 1.00 | 36.75 |
| ATOM | 88 | CA  | ILE | A | 680 | 4.623  | 12.567 | 14.893 | 1.00 | 33.51 |
| ATOM | 89 | C   | ILE | A | 680 | 4.603  | 13.553 | 13.732 | 1.00 | 29.78 |
| ATOM | 90 | O   | ILE | A | 680 | 3.560  | 14.137 | 13.425 | 1.00 | 35.01 |
| ATOM | 91 | CB  | ILE | A | 680 | 4.445  | 13.322 | 16.204 | 1.00 | 36.86 |
| ATOM | 92 | CG1 | ILE | A | 680 | 5.672  | 14.178 | 16.493 | 1.00 | 39.01 |

TABLE III-continued

Structure Coordinates for Site II in Various NHRs
Based on the Consensus Alignments in FIG.2

| ATOM | 93 | CG2 | ILE | A | 680 | 4.222 | 12.324 | 17.343 | 1.00 | 34.87 |
|---|---|---|---|---|---|---|---|---|---|---|
| ATOM | 94 | CD1 | ILE | A | 680 | 5.503 | 15.046 | 17.719 | 1.00 | 38.54 |
| ATOM | 95 | N | GLU | A | 681 | 5.732 | 13.677 | 13.044 | 1.00 | 31.29 |
| ATOM | 96 | CA | GLU | A | 681 | 5.833 | 14.570 | 11.904 | 1.00 | 36.50 |
| ATOM | 97 | C | GLU | A | 681 | 4.638 | 14.373 | 11.013 | 1.00 | 38.74 |
| ATOM | 98 | O | GLU | A | 681 | 4.348 | 13.251 | 10.596 | 1.00 | 46.06 |
| ATOM | 99 | CB | GLU | A | 681 | 7.101 | 14.285 | 11.106 | 1.00 | 33.49 |
| ATOM | 100 | CG | GLU | A | 681 | 7.361 | 15.322 | 10.028 | 1.00 | 41.42 |
| ATOM | 101 | CD | GLU | A | 681 | 7.500 | 16.742 | 10.581 | 1.00 | 49.46 |
| ATOM | 102 | OE1 | GLU | A | 681 | 7.569 | 16.924 | 11.824 | 1.00 | 44.22 |
| ATOM | 103 | OE2 | GLU | A | 681 | 7.527 | 17.687 | 9.759 | 1.00 | 52.12 |
| ATOM | 104 | N | PRO | A | 682 | 3.892 | 15.446 | 10.751 | 1.00 | 41.06 |
| ATOM | 105 | CA | PRO | A | 682 | 2.695 | 15.422 | 9.904 | 1.00 | 41.12 |
| ATOM | 106 | C | PRO | A | 682 | 2.968 | 14.980 | 8.444 | 1.00 | 44.28 |
| ATOM | 107 | O | PRO | A | 682 | 4.076 | 15.133 | 7.920 | 1.00 | 36.92 |
| ATOM | 108 | CB | PRO | A | 682 | 2.214 | 16.870 | 9.965 | 1.00 | 43.30 |
| ATOM | 109 | CG | PRO | A | 682 | 2.800 | 17.399 | 11.250 | 1.00 | 38.89 |
| ATOM | 110 | CD | PRO | A | 682 | 4.159 | 16.800 | 11.261 | 1.00 | 39.59 |
| ATOM | 111 | N | GLY | A | 683 | 1.943 | 14.446 | 7.788 | 1.00 | 48.21 |
| ATOM | 112 | CA | GLY | A | 683 | 2.103 | 13.990 | 6.416 | 1.00 | 51.13 |
| ATOM | 113 | C | GLY | A | 683 | 1.905 | 15.043 | 5.334 | 1.00 | 54.68 |
| ATOM | 114 | O | GLY | A | 683 | 1.817 | 16.226 | 5.629 | 1.00 | 63.53 |
| ATOM | 115 | N | VAL | A | 684 | 1.729 | 14.601 | 4.089 | 1.00 | 57.20 |
| ATOM | 116 | CA | VAL | A | 684 | 1.544 | 15.505 | 2.959 | 1.00 | 54.91 |
| ATOM | 117 | C | VAL | A | 684 | 0.123 | 16.048 | 2.952 | 1.00 | 54.45 |
| ATOM | 118 | O | VAL | A | 684 | −0.828 | 15.287 | 2.775 | 1.00 | 57.51 |
| ATOM | 119 | CB | VAL | A | 684 | 1.805 | 14.792 | 1.625 | 1.00 | 51.72 |
| ATOM | 120 | CG1 | VAL | A | 684 | 1.618 | 15.769 | 0.487 | 1.00 | 53.17 |
| ATOM | 121 | CG2 | VAL | A | 684 | 3.222 | 14.212 | 1.591 | 1.00 | 53.92 |
| ATOM | 282 | N | LEU | A | 707 | −5.307 | 26.167 | 2.636 | 1.00 | 38.31 |
| ATOM | 283 | CA | LEU | A | 707 | −4.152 | 25.342 | 2.982 | 1.00 | 37.96 |
| ATOM | 284 | C | LEU | A | 707 | −3.767 | 25.654 | 4.431 | 1.00 | 44.27 |
| ATOM | 285 | O | LEU | A | 707 | −3.464 | 24.747 | 5.211 | 1.00 | 51.41 |
| ATOM | 286 | CB | LEU | A | 707 | −2.958 | 25.608 | 2.046 | 1.00 | 35.41 |
| ATOM | 287 | CG | LEU | A | 707 | −1.651 | 24.872 | 2.392 | 1.00 | 35.71 |
| ATOM | 288 | CD1 | LEU | A | 707 | −1.895 | 23.385 | 2.326 | 1.00 | 38.82 |
| ATOM | 289 | CD2 | LEU | A | 707 | −0.518 | 25.239 | 1.459 | 1.00 | 33.25 |
| ATOM | 290 | N | GLY | A | 708 | −3.782 | 26.938 | 4.787 | 1.00 | 45.88 |
| ATOM | 291 | CA | GLY | A | 708 | −3.463 | 27.344 | 6.144 | 1.00 | 40.92 |
| ATOM | 292 | C | GLY | A | 708 | −4.386 | 26.618 | 7.096 | 1.00 | 39.05 |
| ATOM | 293 | O | GLY | A | 708 | −3.937 | 25.851 | 7.924 | 1.00 | 45.81 |
| ATOM | 314 | N | GLN | A | 711 | −3.596 | 22.939 | 7.556 | 1.00 | 40.11 |
| ATOM | 315 | CA | GLN | A | 711 | −2.310 | 22.685 | 8.189 | 1.00 | 34.69 |
| ATOM | 316 | C | GLN | A | 711 | −2.355 | 23.007 | 9.653 | 1.00 | 36.60 |
| ATOM | 317 | O | GLN | A | 711 | −1.501 | 22.557 | 10.408 | 1.00 | 40.79 |
| ATOM | 318 | CB | GLN | A | 711 | −1.194 | 23.478 | 7.542 | 1.00 | 42.15 |
| ATOM | 319 | CG | GLN | A | 711 | −0.753 | 22.877 | 6.244 | 1.00 | 43.03 |
| ATOM | 320 | CD | GLN | A | 711 | 0.553 | 23.442 | 5.779 | 1.00 | 44.24 |
| ATOM | 321 | OE1 | GLN | A | 711 | 1.321 | 23.988 | 6.567 | 1.00 | 54.32 |
| ATOM | 322 | NE2 | GLN | A | 711 | 0.828 | 23.305 | 4.496 | 1.00 | 52.33 |
| ATOM | 323 | N | LEU | A | 712 | −3.361 | 23.778 | 10.054 | 1.00 | 41.25 |
| ATOM | 324 | CA | LEU | A | 712 | −3.561 | 24.163 | 11.457 | 1.00 | 43.47 |
| ATOM | 325 | C | LEU | A | 712 | −4.061 | 22.938 | 12.222 | 1.00 | 45.20 |
| ATOM | 326 | O | LEU | A | 712 | −3.595 | 22.628 | 13.320 | 1.00 | 46.51 |
| ATOM | 327 | CB | LEU | A | 712 | −4.585 | 25.295 | 11.550 | 1.00 | 42.08 |
| ATOM | 328 | CG | LEU | A | 712 | −4.829 | 25.943 | 12.905 | 1.00 | 45.04 |
| ATOM | 329 | CD1 | LEU | A | 712 | −3.489 | 26.199 | 13.594 | 1.00 | 48.18 |
| ATOM | 330 | CD2 | LEU | A | 712 | −5.610 | 27.248 | 12.711 | 1.00 | 44.32 |
| ATOM | 331 | N | VAL | A | 713 | −5.014 | 22.240 | 11.623 | 1.00 | 42.76 |
| ATOM | 332 | CA | VAL | A | 713 | −5.555 | 21.026 | 12.198 | 1.00 | 41.99 |
| ATOM | 333 | C | VAL | A | 713 | −4.383 | 20.100 | 12.562 | 1.00 | 45.10 |
| ATOM | 334 | O | VAL | A | 713 | −4.275 | 19.646 | 13.703 | 1.00 | 45.64 |
| ATOM | 335 | CB | VAL | A | 713 | −6.480 | 20.348 | 11.170 | 1.00 | 43.85 |
| ATOM | 336 | CG1 | VAL | A | 713 | −6.887 | 18.953 | 11.628 | 1.00 | 52.59 |
| ATOM | 337 | CG2 | VAL | A | 713 | −7.708 | 21.203 | 10.966 | 1.00 | 42.38 |
| ATOM | 338 | N | HIS | A | 714 | −3.471 | 19.905 | 11.604 | 1.00 | 46.35 |
| ATOM | 339 | CA | HIS | A | 714 | −2.286 | 19.044 | 11.767 | 1.00 | 45.95 |
| ATOM | 340 | C | HIS | A | 714 | −1.379 | 19.495 | 12.857 | 1.00 | 43.82 |
| ATOM | 341 | O | HIS | A | 714 | −0.798 | 18.674 | 13.571 | 1.00 | 48.61 |
| ATOM | 342 | CB | HIS | A | 714 | −1.458 | 18.971 | 10.487 | 1.00 | 49.61 |
| ATOM | 343 | CG | HIS | A | 714 | −1.950 | 17.947 | 9.519 | 1.00 | 62.09 |
| ATOM | 344 | ND1 | HIS | A | 714 | −3.157 | 18.058 | 8.873 | 1.00 | 63.02 |
| ATOM | 345 | CD2 | HIS | A | 714 | −1.404 | 16.778 | 9.108 | 1.00 | 64.82 |
| ATOM | 346 | CE1 | HIS | A | 714 | −3.340 | 17.005 | 8.100 | 1.00 | 70.96 |
| ATOM | 347 | NE2 | HIS | A | 714 | −2.291 | 16.211 | 8.219 | 1.00 | 70.54 |
| ATOM | 348 | N | VAL | A | 715 | −1.172 | 20.803 | 12.898 | 1.00 | 40.29 |

TABLE III-continued

Structure Coordinates for Site II in Various NHRs
Based on the Consensus Alignments in FIG.2

| ATOM | 349 | CA | VAL | A | 715 | −0.326 | 21.415 | 13.908 | 1.00 | 39.63 |
|---|---|---|---|---|---|---|---|---|---|---|
| ATOM | 350 | C | VAL | A | 715 | −0.962 | 21.201 | 15.273 | 1.00 | 36.62 |
| ATOM | 351 | O | VAL | A | 715 | −0.266 | 20.874 | 16.244 | 1.00 | 30.18 |
| ATOM | 352 | CB | VAL | A | 715 | −0.101 | 22.918 | 13.620 | 1.00 | 38.77 |
| ATOM | 353 | CG1 | VAL | A | 715 | 0.500 | 23.617 | 14.820 | 1.00 | 30.17 |
| ATOM | 354 | CG2 | VAL | A | 715 | 0.857 | 23.048 | 12.463 | 1.00 | 40.69 |
| ATOM | 355 | N | VAL | A | 716 | −2.286 | 21.329 | 15.331 | 1.00 | 28.64 |
| ATOM | 356 | CA | VAL | A | 716 | −2.994 | 21.113 | 16.570 | 1.00 | 28.84 |
| ATOM | 357 | C | VAL | A | 716 | −2.687 | 19.683 | 17.037 | 1.00 | 36.83 |
| ATOM | 358 | O | VAL | A | 716 | −2.078 | 19.485 | 18.092 | 1.00 | 36.70 |
| ATOM | 359 | CB | VAL | A | 716 | −4.508 | 21.331 | 16.403 | 1.00 | 34.61 |
| ATOM | 360 | CG1 | VAL | A | 716 | −5.239 | 20.839 | 17.647 | 1.00 | 29.84 |
| ATOM | 361 | CG2 | VAL | A | 716 | −4.805 | 22.811 | 16.185 | 1.00 | 32.32 |
| ATOM | 362 | N | LYS | A | 717 | −2.972 | 18.709 | 16.179 | 1.00 | 38.71 |
| ATOM | 363 | CA | LYS | A | 717 | −2.737 | 17.313 | 16.505 | 1.00 | 32.14 |
| ATOM | 364 | C | LYS | A | 717 | −1.263 | 16.990 | 16.699 | 1.00 | 32.82 |
| ATOM | 365 | O | LYS | A | 717 | −0.920 | 16.262 | 17.631 | 1.00 | 34.86 |
| ATOM | 366 | CB | LYS | A | 717 | −3.370 | 16.410 | 15.450 | 1.00 | 32.30 |
| ATOM | 367 | CG | LYS | A | 717 | −4.890 | 16.352 | 15.569 | 1.00 | 38.88 |
| ATOM | 368 | CD | LYS | A | 717 | −5.538 | 15.584 | 14.436 | 1.00 | 36.05 |
| ATOM | 369 | CE | LYS | A | 717 | −7.009 | 15.353 | 14.736 | 1.00 | 36.14 |
| ATOM | 370 | NZ | LYS | A | 717 | −7.739 | 14.704 | 13.619 | 1.00 | 35.32 |
| ATOM | 371 | N | TRP | A | 718 | −0.383 | 17.589 | 15.893 | 1.00 | 31.69 |
| ATOM | 372 | CA | TRP | A | 718 | 1.058 | 17.319 | 16.010 | 1.00 | 34.84 |
| ATOM | 373 | C | TRP | A | 718 | 1.604 | 17.753 | 17.367 | 1.00 | 44.15 |
| ATOM | 374 | O | TRP | A | 718 | 2.347 | 17.014 | 18.020 | 1.00 | 48.94 |
| ATOM | 375 | CB | TRP | A | 718 | 1.850 | 17.995 | 14.883 | 1.00 | 25.87 |
| ATOM | 376 | CG | TRP | A | 718 | 3.343 | 18.092 | 15.136 | 1.00 | 25.59 |
| ATOM | 377 | CD1 | TRP | A | 718 | 4.279 | 17.133 | 14.909 | 1.00 | 35.87 |
| ATOM | 378 | CD2 | TRP | A | 718 | 4.055 | 19.232 | 15.641 | 1.00 | 30.45 |
| ATOM | 379 | NE1 | TRP | A | 718 | 5.533 | 17.598 | 15.237 | 1.00 | 32.13 |
| ATOM | 380 | CE2 | TRP | A | 718 | 5.419 | 18.889 | 15.689 | 1.00 | 30.51 |
| ATOM | 381 | CE3 | TRP | A | 718 | 3.672 | 20.519 | 16.046 | 1.00 | 32.20 |
| ATOM | 382 | CZ2 | TRP | A | 718 | 6.403 | 19.782 | 16.119 | 1.00 | 32.90 |
| ATOM | 383 | CZ3 | TRP | A | 718 | 4.650 | 21.408 | 16.468 | 1.00 | 25.41 |
| ATOM | 384 | CH2 | TRP | A | 718 | 5.997 | 21.036 | 16.503 | 1.00 | 28.69 |
| ATOM | 552 | N | SER | A | 740 | 2.351 | 30.606 | 17.674 | 1.00 | 36.52 |
| ATOM | 553 | CA | SER | A | 740 | 3.459 | 30.114 | 16.875 | 1.00 | 38.17 |
| ATOM | 554 | C | SER | A | 740 | 3.129 | 29.453 | 15.535 | 1.00 | 38.14 |
| ATOM | 555 | O | SER | A | 740 | 4.024 | 29.259 | 14.706 | 1.00 | 41.67 |
| ATOM | 556 | CB | SER | A | 740 | 4.390 | 29.231 | 17.727 | 1.00 | 42.37 |
| ATOM | 557 | OG | SER | A | 740 | 3.756 | 28.053 | 18.200 | 1.00 | 39.05 |
| ATOM | 558 | N | TRP | A | 741 | 1.851 | 29.268 | 15.236 | 1.00 | 32.00 |
| ATOM | 559 | CA | TRP | A | 741 | 1.482 | 28.588 | 14.004 | 1.00 | 32.79 |
| ATOM | 560 | C | TRP | A | 741 | 2.099 | 29.060 | 12.681 | 1.00 | 34.24 |
| ATOM | 561 | O | TRP | A | 741 | 2.578 | 28.250 | 11.891 | 1.00 | 34.43 |
| ATOM | 562 | CB | TRP | A | 741 | −0.034 | 28.446 | 13.918 | 1.00 | 44.21 |
| ATOM | 563 | CG | TRP | A | 741 | −0.733 | 29.487 | 13.136 | 1.00 | 58.12 |
| ATOM | 564 | CD1 | TRP | A | 741 | −0.889 | 30.806 | 13.458 | 1.00 | 64.16 |
| ATOM | 565 | CD2 | TRP | A | 741 | −1.365 | 29.303 | 11.870 | 1.00 | 63.13 |
| ATOM | 566 | NE1 | TRP | A | 741 | −1.574 | 31.462 | 12.462 | 1.00 | 67.31 |
| ATOM | 567 | CE2 | TRP | A | 741 | −1.882 | 30.562 | 11.473 | 1.00 | 67.95 |
| ATOM | 568 | CE3 | TRP | A | 741 | −1.558 | 28.194 | 11.031 | 1.00 | 57.71 |
| ATOM | 569 | CZ2 | TRP | A | 741 | −2.561 | 30.747 | 10.260 | 1.00 | 70.02 |
| ATOM | 570 | CZ3 | TRP | A | 741 | −2.232 | 28.373 | 9.831 | 1.00 | 59.16 |
| ATOM | 571 | CH2 | TRP | A | 741 | −2.731 | 29.642 | 9.458 | 1.00 | 65.30 |
| ATOM | 572 | N | MET | A | 742 | 2.184 | 30.370 | 12.489 | 1.00 | 41.58 |
| ATOM | 573 | CA | MET | A | 742 | 2.749 | 30.945 | 11.265 | 1.00 | 39.13 |
| ATOM | 574 | C | MET | A | 742 | 4.193 | 30.537 | 11.090 | 1.00 | 30.85 |
| ATOM | 575 | O | MET | A | 742 | 4.602 | 30.115 | 10.017 | 1.00 | 34.78 |
| ATOM | 576 | CB | MET | A | 742 | 2.689 | 32.476 | 11.309 | 1.00 | 42.39 |
| ATOM | 577 | CG | MET | A | 742 | 3.147 | 33.177 | 10.032 | 1.00 | 43.70 |
| ATOM | 578 | SD | MET | A | 742 | 1.988 | 32.993 | 8.658 | 1.00 | 45.17 |
| ATOM | 579 | CE | MET | A | 742 | 0.678 | 34.132 | 9.133 | 1.00 | 22.14 |
| ATOM | 580 | N | GLY | A | 743 | 4.954 | 30.648 | 12.165 | 1.00 | 24.94 |
| ATOM | 581 | CA | GLY | A | 743 | 6.367 | 30.312 | 12.117 | 1.00 | 27.24 |
| ATOM | 582 | C | GLY | A | 743 | 6.630 | 28.836 | 11.886 | 1.00 | 27.21 |
| ATOM | 583 | O | GLY | A | 743 | 7.660 | 28.461 | 11.322 | 1.00 | 27.69 |
| ATOM | 584 | N | LEU | A | 744 | 5.734 | 27.983 | 12.372 | 1.00 | 25.91 |
| ATOM | 585 | CA | LEU | A | 744 | 5.895 | 26.550 | 12.172 | 1.00 | 26.90 |
| ATOM | 586 | C | LEU | A | 744 | 5.632 | 26.287 | 10.708 | 1.00 | 27.04 |
| ATOM | 587 | O | LEU | A | 744 | 6.375 | 25.574 | 10.048 | 1.00 | 31.01 |
| ATOM | 588 | CB | LEU | A | 744 | 4.899 | 25.755 | 13.018 | 1.00 | 25.72 |
| ATOM | 589 | CG | LEU | A | 744 | 5.234 | 25.626 | 14.514 | 1.00 | 29.11 |
| ATOM | 590 | CD1 | LEU | A | 744 | 4.063 | 25.022 | 15.275 | 1.00 | 23.25 |
| ATOM | 591 | CD2 | LEU | A | 744 | 6.484 | 24.771 | 14.689 | 1.00 | 24.15 |

TABLE III-continued

Structure Coordinates for Site II in Various NHRs
Based on the Consensus Alignments in FIG.2

| ATOM | 592 | N | MET | A | 745 | 4.566 | 26.886 | 10.200 | 1.00 | 25.67 |
|---|---|---|---|---|---|---|---|---|---|---|
| ATOM | 593 | CA | MET | A | 745 | 4.188 | 26.725 | 8.803 | 1.00 | 23.96 |
| ATOM | 594 | C | MET | A | 745 | 5.254 | 27.179 | 7.822 | 1.00 | 29.61 |
| ATOM | 595 | O | MET | A | 745 | 5.550 | 26.480 | 6.857 | 1.00 | 34.60 |
| ATOM | 596 | CB | MET | A | 745 | 2.895 | 27.454 | 8.534 | 1.00 | 20.46 |
| ATOM | 597 | CG | MET | A | 745 | 1.730 | 26.888 | 9.310 | 1.00 | 19.98 |
| ATOM | 598 | SD | MET | A | 745 | 0.297 | 27.272 | 8.341 | 1.00 | 43.15 |
| ATOM | 599 | CE | MET | A | 745 | 0.642 | 29.041 | 8.042 | 1.00 | 44.27 |
| ATOM | 600 | N | VAL | A | 746 | 5.830 | 28.341 | 8.095 | 1.00 | 27.98 |
| ATOM | 601 | CA | VAL | A | 746 | 6.876 | 28.924 | 7.288 | 1.00 | 24.84 |
| ATOM | 602 | C | VAL | A | 746 | 8.107 | 28.051 | 7.345 | 1.00 | 28.42 |
| ATOM | 603 | O | VAL | A | 746 | 8.749 | 27.786 | 6.333 | 1.00 | 37.05 |
| ATOM | 604 | CB | VAL | A | 746 | 7.248 | 30.304 | 7.835 | 1.00 | 31.98 |
| ATOM | 605 | CG1 | VAL | A | 746 | 8.423 | 30.888 | 7.073 | 1.00 | 29.03 |
| ATOM | 606 | CG2 | VAL | A | 746 | 6.066 | 31.196 | 7.737 | 1.00 | 32.19 |
| ATOM | 607 | N | PHE | A | 747 | 8.439 | 27.607 | 8.541 | 1.00 | 31.29 |
| ATOM | 608 | CA | PHE | A | 747 | 9.605 | 26.765 | 8.736 | 1.00 | 32.19 |
| ATOM | 609 | C | PHE | A | 747 | 9.468 | 25.401 | 8.030 | 1.00 | 35.99 |
| ATOM | 610 | O | PHE | A | 747 | 10.398 | 24.916 | 7.384 | 1.00 | 34.95 |
| ATOM | 611 | CB | PHE | A | 747 | 9.820 | 26.536 | 10.224 | 1.00 | 27.90 |
| ATOM | 612 | CG | PHE | A | 747 | 11.209 | 26.082 | 10.573 | 1.00 | 26.00 |
| ATOM | 613 | CD1 | PHE | A | 747 | 12.293 | 26.915 | 10.343 | 1.00 | 24.54 |
| ATOM | 614 | CD2 | PHE | A | 747 | 11.428 | 24.846 | 11.166 | 1.00 | 27.23 |
| ATOM | 615 | CE1 | PHE | A | 747 | 13.571 | 26.532 | 10.699 | 1.00 | 25.88 |
| ATOM | 616 | CE2 | PHE | A | 747 | 12.711 | 24.451 | 11.528 | 1.00 | 25.61 |
| ATOM | 617 | CZ | PHE | A | 747 | 13.785 | 25.297 | 11.293 | 1.00 | 28.75 |
| ATOM | 618 | N | ALA | A | 748 | 8.309 | 24.774 | 8.171 | 1.00 | 35.11 |
| ATOM | 619 | CA | ALA | A | 748 | 8.096 | 23.483 | 7.561 | 1.00 | 34.00 |
| ATOM | 620 | C | ALA | A | 748 | 8.114 | 23.683 | 6.054 | 1.00 | 37.26 |
| ATOM | 621 | O | ALA | A | 748 | 8.831 | 22.973 | 5.344 | 1.00 | 35.87 |
| ATOM | 622 | CB | ALA | A | 748 | 6.773 | 22.896 | 8.022 | 1.00 | 29.48 |
| ATOM | 635 | N | TRP | A | 751 | 11.304 | 23.876 | 4.581 | 1.00 | 45.43 |
| ATOM | 636 | CA | TRP | A | 751 | 11.976 | 22.588 | 4.528 | 1.00 | 42.53 |
| ATOM | 637 | C | TRP | A | 751 | 11.519 | 21.806 | 3.294 | 1.00 | 43.17 |
| ATOM | 638 | O | TRP | A | 751 | 12.336 | 21.207 | 2.596 | 1.00 | 40.24 |
| ATOM | 639 | CB | TRP | A | 751 | 11.717 | 21.776 | 5.787 | 1.00 | 39.21 |
| ATOM | 640 | CG | TRP | A | 751 | 12.359 | 20.401 | 5.737 | 1.00 | 41.85 |
| ATOM | 641 | CD1 | TRP | A | 751 | 11.736 | 19.213 | 5.461 | 1.00 | 39.44 |
| ATOM | 642 | CD2 | TRP | A | 751 | 13.743 | 20.085 | 5.968 | 1.00 | 37.37 |
| ATOM | 643 | NE1 | TRP | A | 751 | 12.645 | 18.186 | 5.516 | 1.00 | 42.23 |
| ATOM | 644 | CE2 | TRP | A | 751 | 13.878 | 18.692 | 5.821 | 1.00 | 41.26 |
| ATOM | 645 | CE3 | TRP | A | 751 | 14.877 | 20.841 | 6.275 | 1.00 | 41.35 |
| ATOM | 646 | CZ2 | TRP | A | 751 | 15.110 | 18.046 | 5.978 | 1.00 | 48.39 |
| ATOM | 647 | CZ3 | TRP | A | 751 | 16.104 | 20.195 | 6.431 | 1.00 | 39.62 |
| ATOM | 648 | CH2 | TRP | A | 751 | 16.208 | 18.817 | 6.280 | 1.00 | 43.38 |
| ATOM | 649 | N | ARG | A | 752 | 10.214 | 21.792 | 3.037 | 1.00 | 42.27 |
| ATOM | 650 | CA | ARG | A | 752 | 9.683 | 21.100 | 1.862 | 1.00 | 41.53 |
| ATOM | 651 | C | ARG | A | 752 | 10.257 | 21.740 | 0.602 | 1.00 | 44.18 |
| ATOM | 652 | O | ARG | A | 752 | 10.522 | 21.048 | −0.380 | 1.00 | 43.20 |
| ATOM | 653 | CB | ARG | A | 752 | 8.163 | 21.186 | 1.800 | 1.00 | 42.14 |
| ATOM | 654 | CG | ARG | A | 752 | 7.441 | 20.465 | 2.920 | 1.00 | 49.76 |
| ATOM | 655 | CD | ARG | A | 752 | 5.938 | 20.434 | 2.649 | 1.00 | 48.23 |
| ATOM | 656 | NE | ARG | A | 752 | 5.382 | 21.773 | 2.483 | 1.00 | 45.23 |
| ATOM | 657 | CZ | ARG | A | 752 | 5.013 | 22.572 | 3.490 | 1.00 | 52.17 |
| ATOM | 658 | NH1 | ARG | A | 752 | 5.131 | 22.175 | 4.764 | 1.00 | 33.80 |
| ATOM | 659 | NH2 | ARG | A | 752 | 4.536 | 23.785 | 3.223 | 1.00 | 49.84 |
| ATOM | 677 | N | THR | A | 755 | 13.948 | 20.208 | 0.225 | 1.00 | 53.24 |
| ATOM | 678 | CA | THR | A | 755 | 14.053 | 18.818 | −0.197 | 1.00 | 53.33 |
| ATOM | 679 | C | THR | A | 755 | 13.287 | 18.474 | −1.478 | 1.00 | 54.87 |
| ATOM | 680 | O | THR | A | 755 | 13.554 | 17.431 | −2.068 | 1.00 | 57.41 |
| ATOM | 681 | CB | THR | A | 755 | 13.596 | 17.830 | 0.934 | 1.00 | 45.98 |
| ATOM | 682 | OG1 | THR | A | 755 | 12.221 | 18.055 | 1.245 | 1.00 | 49.35 |
| ATOM | 683 | CG2 | THR | A | 755 | 14.405 | 18.033 | 2.190 | 1.00 | 40.03 |
| ATOM | 684 | N | ASN | A | 756 | 12.360 | 19.336 | −1.911 | 1.00 | 52.97 |
| ATOM | 685 | CA | ASN | A | 756 | 11.539 | 19.044 | −3.097 | 1.00 | 56.15 |
| ATOM | 686 | C | ASN | A | 756 | 11.821 | 19.826 | −4.394 | 1.00 | 55.33 |
| ATOM | 687 | O | ASN | A | 756 | 11.705 | 19.257 | −5.481 | 1.00 | 54.81 |
| ATOM | 688 | CB | ASN | A | 756 | 10.019 | 19.124 | −2.769 | 1.00 | 60.43 |
| ATOM | 689 | CG | ASN | A | 756 | 9.504 | 17.959 | −1.869 | 1.00 | 57.82 |
| ATOM | 690 | OD1 | ASN | A | 756 | 10.123 | 16.909 | −1.763 | 1.00 | 55.71 |
| ATOM | 691 | ND2 | ASN | A | 756 | 8.354 | 18.169 | −1.234 | 1.00 | 56.46 |
| ATOM | 768 | N | PRO | A | 766 | 1.766 | 20.021 | −2.533 | 1.00 | 52.86 |
| ATOM | 769 | CA | PRO | A | 766 | 2.120 | 19.407 | −3.813 | 1.00 | 50.96 |
| ATOM | 770 | C | PRO | A | 766 | 1.359 | 20.040 | −4.970 | 1.00 | 48.25 |
| ATOM | 771 | O | PRO | A | 766 | 1.893 | 20.144 | −6.082 | 1.00 | 44.31 |
| ATOM | 772 | CB | PRO | A | 766 | 1.721 | 17.949 | −3.604 | 1.00 | 57.00 |

TABLE III-continued

Structure Coordinates for Site II in Various NHRs
Based on the Consensus Alignments in FIG.2

| ATOM | 773 | CG | PRO | A | 766 | 1.899 | 17.761 | −2.133 | 1.00 | 58.08 |
|---|---|---|---|---|---|---|---|---|---|---|
| ATOM | 774 | CD | PRO | A | 766 | 1.237 | 19.002 | −1.617 | 1.00 | 57.23 |
| ATOM | 1099 | N | PHE | A | 804 | 16.541 | 19.584 | 11.932 | 1.00 | 32.10 |
| ATOM | 1100 | CA | PHE | A | 804 | 15.286 | 20.166 | 11.519 | 1.00 | 26.58 |
| ATOM | 1101 | C | PHE | A | 804 | 14.157 | 19.876 | 12.497 | 1.00 | 29.08 |
| ATOM | 1102 | O | PHE | A | 804 | 13.528 | 20.793 | 13.024 | 1.00 | 38.23 |
| ATOM | 1103 | CB | PHE | A | 804 | 14.872 | 19.663 | 10.142 | 1.00 | 24.46 |
| ATOM | 1104 | CG | PHE | A | 804 | 13.445 | 20.032 | 9.767 | 1.00 | 35.13 |
| ATOM | 1105 | CD1 | PHE | A | 804 | 13.091 | 21.361 | 9.540 | 1.00 | 36.25 |
| ATOM | 1106 | CD2 | PHE | A | 804 | 12.468 | 19.048 | 9.617 | 1.00 | 38.14 |
| ATOM | 1107 | CE1 | PHE | A | 804 | 11.795 | 21.712 | 9.164 | 1.00 | 27.83 |
| ATOM | 1108 | CE2 | PHE | A | 804 | 11.163 | 19.385 | 9.238 | 1.00 | 39.32 |
| ATOM | 1109 | CZ | PHE | A | 804 | 10.826 | 20.723 | 9.011 | 1.00 | 38.61 |
| ATOM | 1110 | N | LEU | A | 805 | 13.887 | 18.600 | 12.728 | 1.00 | 30.73 |
| ATOM | 1111 | CA | LEU | A | 805 | 12.784 | 18.215 | 13.586 | 1.00 | 28.43 |
| ATOM | 1112 | C | LEU | A | 805 | 12.880 | 18.799 | 14.946 | 1.00 | 26.10 |
| ATOM | 1113 | O | LEU | A | 805 | 11.881 | 19.243 | 15.493 | 1.00 | 34.14 |
| ATOM | 1114 | CB | LEU | A | 805 | 12.648 | 16.702 | 13.661 | 1.00 | 34.10 |
| ATOM | 1115 | CG | LEU | A | 805 | 12.000 | 16.079 | 12.423 | 1.00 | 43.20 |
| ATOM | 1116 | CD1 | LEU | A | 805 | 12.046 | 14.617 | 12.600 | 1.00 | 36.94 |
| ATOM | 1117 | CD2 | LEU | A | 805 | 10.549 | 16.523 | 12.252 | 1.00 | 44.97 |
| ATOM | 1132 | N | LYS | A | 808 | 12.006 | 22.545 | 14.617 | 1.00 | 27.59 |
| ATOM | 1133 | CA | LYS | A | 808 | 10.597 | 22.787 | 14.378 | 1.00 | 27.15 |
| ATOM | 1134 | C | LYS | A | 808 | 9.841 | 22.681 | 15.686 | 1.00 | 29.83 |
| ATOM | 1135 | O | LYS | A | 808 | 8.954 | 23.486 | 15.952 | 1.00 | 35.67 |
| ATOM | 1136 | CB | LYS | A | 808 | 10.029 | 21.837 | 13.313 | 1.00 | 24.49 |
| ATOM | 1137 | CG | LYS | A | 808 | 8.598 | 22.158 | 12.811 | 1.00 | 23.62 |
| ATOM | 1138 | CD | LYS | A | 808 | 8.148 | 21.143 | 11.740 | 1.00 | 24.64 |
| ATOM | 1139 | CE | LYS | A | 808 | 7.157 | 20.101 | 12.280 | 1.00 | 29.39 |
| ATOM | 1140 | NZ | LYS | A | 808 | 5.683 | 20.529 | 12.198 | 1.00 | 36.92 |
| | | | ERalpha Site II Residues (ref. 1A52.pdb) | | | | | | | |
| ATOM | 99 | N | LEU | A | 320 | 99.203 | 35.236 | 105.992 | 1.00 | 52.59 |
| ATOM | 100 | CA | LEU | A | 320 | 100.556 | 35.138 | 106.514 | 1.00 | 52.15 |
| ATOM | 101 | C | LEU | A | 320 | 100.597 | 34.433 | 107.854 | 1.00 | 52.92 |
| ATOM | 102 | O | LEU | A | 320 | 101.488 | 33.625 | 108.100 | 1.00 | 53.52 |
| ATOM | 103 | CB | LEU | A | 320 | 101.202 | 36.518 | 106.612 | 1.00 | 51.20 |
| ATOM | 104 | CG | LEU | A | 320 | 101.704 | 37.051 | 105.270 | 1.00 | 50.53 |
| ATOM | 105 | CD1 | LEU | A | 320 | 102.077 | 38.500 | 105.353 | 1.00 | 50.26 |
| ATOM | 106 | CD2 | LEU | A | 320 | 102.898 | 36.232 | 104.860 | 1.00 | 51.08 |
| ATOM | 107 | N | ASP | A | 321 | 99.629 | 34.697 | 108.718 | 1.00 | 53.43 |
| ATOM | 108 | CA | ASP | A | 321 | 99.645 | 34.048 | 110.015 | 1.00 | 54.53 |
| ATOM | 109 | C | ASP | A | 321 | 99.250 | 32.587 | 109.939 | 1.00 | 54.61 |
| ATOM | 110 | O | ASP | A | 321 | 99.661 | 31.777 | 110.769 | 1.00 | 54.98 |
| ATOM | 111 | CB | ASP | A | 321 | 98.731 | 34.785 | 110.993 | 1.00 | 56.68 |
| ATOM | 112 | CG | ASP | A | 321 | 99.259 | 36.183 | 111.361 | 1.00 | 57.98 |
| ATOM | 113 | OD1 | ASP | A | 321 | 100.332 | 36.589 | 110.852 | 1.00 | 58.21 |
| ATOM | 114 | OD2 | ASP | A | 321 | 98.594 | 36.878 | 112.165 | 1.00 | 59.27 |
| ATOM | 115 | N | ALA | A | 322 | 98.460 | 32.240 | 108.936 | 1.00 | 54.13 |
| ATOM | 116 | CA | ALA | A | 322 | 98.014 | 30.865 | 108.787 | 1.00 | 53.35 |
| ATOM | 117 | C | ALA | A | 322 | 99.151 | 29.943 | 108.300 | 1.00 | 52.94 |
| ATOM | 118 | O | ALA | A | 322 | 99.020 | 28.702 | 108.340 | 1.00 | 52.54 |
| ATOM | 119 | CB | ALA | A | 322 | 96.825 | 30.821 | 107.812 | 1.00 | 54.16 |
| ATOM | 120 | N | GLU | A | 323 | 100.259 | 30.544 | 107.850 | 1.00 | 52.13 |
| ATOM | 121 | CA | GLU | A | 323 | 101.393 | 29.774 | 107.338 | 1.00 | 51.75 |
| ATOM | 122 | C | GLU | A | 323 | 101.839 | 28.683 | 108.270 | 1.00 | 52.28 |
| ATOM | 123 | O | GLU | A | 323 | 102.104 | 28.912 | 109.443 | 1.00 | 51.95 |
| ATOM | 124 | CB | GLU | A | 323 | 102.551 | 30.690 | 107.007 | 1.00 | 51.77 |
| ATOM | 125 | CG | GLU | A | 323 | 102.353 | 31.385 | 105.703 | 1.00 | 52.53 |
| ATOM | 126 | CD | GLU | A | 323 | 102.333 | 30.394 | 104.540 | 1.00 | 53.56 |
| ATOM | 127 | OE1 | GLU | A | 323 | 103.433 | 29.960 | 104.114 | 1.00 | 54.59 |
| ATOM | 128 | OE2 | GLU | A | 323 | 101.227 | 30.031 | 104.065 | 1.00 | 52.74 |
| ATOM | 129 | N | PRO | A | 324 | 101.964 | 27.468 | 107.743 | 1.00 | 53.31 |
| ATOM | 130 | CA | PRO | A | 324 | 102.372 | 26.301 | 108.525 | 1.00 | 54.25 |
| ATOM | 131 | C | PRO | A | 324 | 103.845 | 26.353 | 108.943 | 1.00 | 54.72 |
| ATOM | 132 | O | PRO | A | 324 | 104.663 | 27.053 | 108.319 | 1.00 | 54.54 |
| ATOM | 133 | CB | PRO | A | 324 | 102.068 | 25.147 | 107.565 | 1.00 | 53.80 |
| ATOM | 134 | CG | PRO | A | 324 | 102.536 | 25.776 | 106.251 | 1.00 | 52.98 |
| ATOM | 135 | CD | PRO | A | 324 | 101.762 | 27.082 | 106.335 | 1.00 | 53.61 |
| ATOM | 136 | N | PRO | A | 325 | 104.208 | 25.577 | 109.983 | 1.00 | 55.14 |
| ATOM | 137 | CA | PRO | A | 325 | 105.593 | 25.547 | 110.469 | 1.00 | 54.70 |
| ATOM | 138 | C | PRO | A | 325 | 106.379 | 24.848 | 109.385 | 1.00 | 54.48 |
| ATOM | 139 | O | PRO | A | 325 | 105.787 | 24.056 | 108.642 | 1.00 | 55.54 |
| ATOM | 140 | CB | PRO | A | 325 | 105.498 | 24.655 | 111.705 | 1.00 | 54.34 |
| ATOM | 141 | CG | PRO | A | 325 | 104.000 | 24.741 | 112.096 | 1.00 | 55.28 |
| ATOM | 142 | CD | PRO | A | 325 | 103.384 | 24.614 | 110.742 | 1.00 | 55.43 |

TABLE III-continued

Structure Coordinates for Site II in Various NHRs
Based on the Consensus Alignments in FIG.2

| ATOM | 143 | N | ILE | A | 326 | 107.669 | 25.137 | 109.238 | 1.00 | 53.52 |
|------|-----|------|-----|---|-----|---------|--------|---------|------|-------|
| ATOM | 144 | CA | ILE | A | 326 | 108.431 | 24.363 | 108.257 | 1.00 | 53.10 |
| ATOM | 145 | C | ILE | A | 326 | 108.947 | 23.151 | 109.046 | 1.00 | 53.30 |
| ATOM | 146 | O | ILE | A | 326 | 109.625 | 23.300 | 110.060 | 1.00 | 53.12 |
| ATOM | 147 | CB | ILE | A | 326 | 109.607 | 25.120 | 107.663 | 1.00 | 52.50 |
| ATOM | 148 | CG1 | ILE | A | 326 | 109.084 | 26.335 | 106.902 | 1.00 | 52.50 |
| ATOM | 149 | CG2 | ILE | A | 326 | 110.397 | 24.196 | 106.754 | 1.00 | 50.93 |
| ATOM | 150 | CD1 | ILE | A | 326 | 110.123 | 27.100 | 106.106 | 1.00 | 52.06 |
| ATOM | 335 | N | LEU | A | 349 | 107.683 | 12.917 | 105.119 | 1.00 | 58.44 |
| ATOM | 336 | CA | LEU | A | 349 | 107.691 | 14.379 | 105.202 | 1.00 | 56.38 |
| ATOM | 337 | C | LEU | A | 349 | 106.356 | 14.884 | 104.687 | 1.00 | 56.04 |
| ATOM | 338 | O | LEU | A | 349 | 105.738 | 15.751 | 105.278 | 1.00 | 56.02 |
| ATOM | 339 | CB | LEU | A | 349 | 108.809 | 14.943 | 104.334 | 1.00 | 55.75 |
| ATOM | 340 | CG | LEU | A | 349 | 108.897 | 16.461 | 104.251 | 1.00 | 55.07 |
| ATOM | 341 | CD1 | LEU | A | 349 | 109.007 | 16.966 | 105.652 | 1.00 | 55.38 |
| ATOM | 342 | CD2 | LEU | A | 349 | 110.093 | 16.927 | 103.420 | 1.00 | 54.73 |
| ATOM | 343 | N | ALA | A | 350 | 105.905 | 14.318 | 103.577 | 1.00 | 55.56 |
| ATOM | 344 | CA | ALA | A | 350 | 104.634 | 14.712 | 103.008 | 1.00 | 55.49 |
| ATOM | 345 | C | ALA | A | 350 | 103.449 | 14.347 | 103.908 | 1.00 | 56.16 |
| ATOM | 346 | O | ALA | A | 350 | 102.596 | 15.203 | 104.190 | 1.00 | 56.22 |
| ATOM | 347 | CB | ALA | A | 350 | 104.464 | 14.076 | 101.649 | 1.00 | 55.28 |
| ATOM | 367 | N | GLU | A | 353 | 103.417 | 16.944 | 106.610 | 1.00 | 56.06 |
| ATOM | 368 | CA | GLU | A | 353 | 103.047 | 18.295 | 106.162 | 1.00 | 54.56 |
| ATOM | 369 | C | GLU | A | 353 | 101.569 | 18.318 | 105.901 | 1.00 | 54.44 |
| ATOM | 370 | O | GLU | A | 353 | 100.910 | 19.359 | 106.000 | 1.00 | 53.15 |
| ATOM | 371 | CB | GLU | A | 353 | 103.727 | 18.642 | 104.868 | 1.00 | 53.28 |
| ATOM | 372 | CG | GLU | A | 353 | 105.109 | 19.058 | 105.045 | 1.00 | 53.60 |
| ATOM | 373 | CD | GLU | A | 353 | 105.702 | 19.417 | 103.747 | 1.00 | 54.14 |
| ATOM | 374 | OE1 | GLU | A | 353 | 105.891 | 18.500 | 102.923 | 1.00 | 53.79 |
| ATOM | 375 | OE2 | GLU | A | 353 | 105.955 | 20.618 | 103.544 | 1.00 | 55.37 |
| ATOM | 376 | N | LEU | A | 354 | 101.068 | 17.136 | 105.553 | 1.00 | 54.59 |
| ATOM | 377 | CA | LEU | A | 354 | 99.684 | 16.970 | 105.247 | 1.00 | 55.05 |
| ATOM | 378 | C | LEU | A | 354 | 98.899 | 17.390 | 106.452 | 1.00 | 55.83 |
| ATOM | 379 | O | LEU | A | 354 | 98.064 | 18.289 | 106.369 | 1.00 | 56.40 |
| ATOM | 380 | CB | LEU | A | 354 | 99.415 | 15.525 | 104.904 | 1.00 | 55.25 |
| ATOM | 381 | CG | LEU | A | 354 | 98.027 | 15.235 | 104.327 | 1.00 | 55.93 |
| ATOM | 382 | CD1 | LEU | A | 354 | 97.723 | 16.127 | 103.112 | 1.00 | 55.51 |
| ATOM | 383 | CD2 | LEU | A | 354 | 98.005 | 13.772 | 103.920 | 1.00 | 56.20 |
| ATOM | 384 | N | VAL | A | 355 | 99.198 | 16.758 | 107.584 | 1.00 | 56.64 |
| ATOM | 385 | CA | VAL | A | 355 | 98.517 | 17.047 | 108.854 | 1.00 | 56.37 |
| ATOM | 386 | C | VAL | A | 355 | 98.478 | 18.566 | 109.086 | 1.00 | 56.20 |
| ATOM | 387 | O | VAL | A | 355 | 97.429 | 19.123 | 109.399 | 1.00 | 55.29 |
| ATOM | 388 | CB | VAL | A | 355 | 99.243 | 16.309 | 110.047 | 1.00 | 56.40 |
| ATOM | 389 | CG1 | VAL | A | 355 | 98.476 | 16.491 | 111.354 | 1.00 | 55.19 |
| ATOM | 390 | CG2 | VAL | A | 355 | 99.383 | 14.813 | 109.719 | 1.00 | 55.99 |
| ATOM | 391 | N | HIS | A | 356 | 99.616 | 19.234 | 108.914 | 1.00 | 56.56 |
| ATOM | 392 | CA | HIS | A | 356 | 99.668 | 20.689 | 109.087 | 1.00 | 57.22 |
| ATOM | 393 | C | HIS | A | 356 | 98.862 | 21.449 | 108.039 | 1.00 | 57.46 |
| ATOM | 394 | O | HIS | A | 356 | 98.374 | 22.554 | 108.309 | 1.00 | 57.24 |
| ATOM | 395 | CB | HIS | A | 356 | 101.119 | 21.167 | 109.071 | 1.00 | 57.78 |
| ATOM | 396 | CG | HIS | A | 356 | 101.864 | 20.809 | 110.316 | 1.00 | 58.97 |
| ATOM | 397 | ND1 | HIS | A | 356 | 101.689 | 21.487 | 111.507 | 1.00 | 57.69 |
| ATOM | 398 | CD2 | HIS | A | 356 | 102.697 | 19.774 | 110.586 | 1.00 | 59.14 |
| ATOM | 399 | CE1 | HIS | A | 356 | 102.381 | 20.882 | 112.454 | 1.00 | 58.77 |
| ATOM | 400 | NE2 | HIS | A | 356 | 103.001 | 19.841 | 111.922 | 1.00 | 59.96 |
| ATOM | 401 | N | MET | A | 357 | 98.730 | 20.853 | 106.846 | 1.00 | 57.44 |
| ATOM | 402 | CA | MET | A | 357 | 97.969 | 21.458 | 105.766 | 1.00 | 56.62 |
| ATOM | 403 | C | MET | A | 357 | 96.513 | 21.540 | 106.169 | 1.00 | 57.20 |
| ATOM | 404 | O | MET | A | 357 | 95.855 | 22.535 | 105.872 | 1.00 | 57.88 |
| ATOM | 405 | CB | MET | A | 357 | 98.074 | 20.644 | 104.497 | 1.00 | 56.36 |
| ATOM | 406 | CG | MET | A | 357 | 97.404 | 21.316 | 103.317 | 1.00 | 55.15 |
| ATOM | 407 | SD | MET | A | 357 | 97.619 | 20.356 | 101.830 | 1.00 | 54.74 |
| ATOM | 408 | CE | MET | A | 357 | 99.420 | 20.228 | 101.751 | 1.00 | 52.92 |
| ATOM | 409 | N | ILE | A | 358 | 95.995 | 20.505 | 106.827 | 1.00 | 56.60 |
| ATOM | 410 | CA | ILE | A | 358 | 94.614 | 20.556 | 107.282 | 1.00 | 56.75 |
| ATOM | 411 | C | ILE | A | 358 | 94.424 | 21.724 | 108.270 | 1.00 | 57.56 |
| ATOM | 412 | O | ILE | A | 358 | 93.376 | 22.355 | 108.292 | 1.00 | 57.84 |
| ATOM | 413 | CB | ILE | A | 358 | 94.217 | 19.299 | 108.025 | 1.00 | 56.52 |
| ATOM | 414 | CG1 | ILE | A | 358 | 94.325 | 18.071 | 107.119 | 1.00 | 56.72 |
| ATOM | 415 | CG2 | ILE | A | 358 | 92.819 | 19.475 | 108.563 | 1.00 | 55.68 |
| ATOM | 416 | CD1 | ILE | A | 358 | 93.270 | 17.991 | 106.063 | 1.00 | 57.04 |
| ATOM | 417 | N | ASN | A | 359 | 95.428 | 22.001 | 109.102 | 1.00 | 58.53 |
| ATOM | 418 | CA | ASN | A | 359 | 95.328 | 23.101 | 110.087 | 1.00 | 59.39 |
| ATOM | 419 | C | ASN | A | 359 | 95.343 | 24.434 | 109.366 | 1.00 | 59.28 |
| ATOM | 420 | O | ASN | A | 359 | 94.671 | 25.393 | 109.757 | 1.00 | 59.79 |
| ATOM | 421 | CB | ASN | A | 359 | 96.503 | 23.094 | 111.093 | 1.00 | 59.23 |

TABLE III-continued

Structure Coordinates for Site II in Various NHRs
Based on the Consensus Alignments in FIG.2

| ATOM | 422 | CG | ASN | A | 359 | 96.406 | 21.977 | 112.137 | 1.00 | 58.85 |
|---|---|---|---|---|---|---|---|---|---|---|
| ATOM | 423 | OD1 | ASN | A | 359 | 97.357 | 21.766 | 112.883 | 1.00 | 58.21 |
| ATOM | 424 | ND2 | ASN | A | 359 | 95.259 | 21.280 | 112.207 | 1.00 | 58.60 |
| ATOM | 425 | N | TRP | A | 360 | 96.143 | 24.485 | 108.316 | 1.00 | 59.09 |
| ATOM | 426 | CA | TRP | A | 360 | 96.273 | 25.691 | 107.511 | 1.00 | 58.86 |
| ATOM | 427 | C | TRP | A | 360 | 94.979 | 25.972 | 106.752 | 1.00 | 59.22 |
| ATOM | 428 | O | TRP | A | 360 | 94.404 | 27.049 | 106.907 | 1.00 | 59.55 |
| ATOM | 429 | CB | TRP | A | 360 | 97.433 | 25.524 | 106.539 | 1.00 | 57.75 |
| ATOM | 430 | CG | TRP | A | 360 | 97.432 | 26.496 | 105.428 | 1.00 | 55.96 |
| ATOM | 431 | CD1 | TRP | A | 360 | 97.898 | 27.775 | 105.448 | 1.00 | 55.46 |
| ATOM | 432 | CD2 | TRP | A | 360 | 96.932 | 26.269 | 104.117 | 1.00 | 54.62 |
| ATOM | 433 | NE1 | TRP | A | 360 | 97.723 | 28.360 | 104.223 | 1.00 | 53.87 |
| ATOM | 434 | CE2 | TRP | A | 360 | 97.128 | 27.456 | 103.387 | 1.00 | 53.93 |
| ATOM | 435 | CE3 | TRP | A | 360 | 96.336 | 25.172 | 103.486 | 1.00 | 54.51 |
| ATOM | 436 | CZ2 | TRP | A | 360 | 96.751 | 27.583 | 102.062 | 1.00 | 54.47 |
| ATOM | 437 | CZ3 | TRP | A | 360 | 95.956 | 25.293 | 102.159 | 1.00 | 54.55 |
| ATOM | 438 | CH2 | TRP | A | 360 | 96.164 | 26.491 | 101.461 | 1.00 | 55.14 |
| ATOM | 606 | N | ALA | A | 382 | 93.720 | 19.091 | 95.631 | 1.00 | 48.18 |
| ATOM | 607 | CA | ALA | A | 382 | 94.850 | 20.021 | 95.659 | 1.00 | 46.44 |
| ATOM | 608 | C | ALA | A | 382 | 96.066 | 19.788 | 96.546 | 1.00 | 45.10 |
| ATOM | 609 | O | ALA | A | 382 | 97.059 | 20.502 | 96.421 | 1.00 | 44.69 |
| ATOM | 610 | CB | ALA | A | 382 | 94.313 | 21.418 | 95.944 | 1.00 | 46.52 |
| ATOM | 611 | N | TRP | A | 383 | 96.023 | 18.796 | 97.417 | 1.00 | 43.80 |
| ATOM | 612 | CA | TRP | A | 383 | 97.132 | 18.602 | 98.333 | 1.00 | 42.62 |
| ATOM | 613 | C | TRP | A | 383 | 98.512 | 18.580 | 97.713 | 1.00 | 42.80 |
| ATOM | 614 | O | TRP | A | 383 | 99.418 | 19.269 | 98.192 | 1.00 | 42.64 |
| ATOM | 615 | CB | TRP | A | 383 | 96.935 | 17.356 | 99.180 | 1.00 | 41.81 |
| ATOM | 616 | CG | TRP | A | 383 | 97.078 | 16.095 | 98.441 | 1.00 | 42.13 |
| ATOM | 617 | CD1 | TRP | A | 383 | 96.121 | 15.443 | 97.699 | 1.00 | 41.98 |
| ATOM | 618 | CD2 | TRP | A | 383 | 98.280 | 15.329 | 98.310 | 1.00 | 42.10 |
| ATOM | 619 | NE1 | TRP | A | 383 | 96.664 | 14.313 | 97.114 | 1.00 | 41.37 |
| ATOM | 620 | CE2 | TRP | A | 383 | 97.984 | 14.219 | 97.472 | 1.00 | 41.64 |
| ATOM | 621 | CE3 | TRP | A | 383 | 99.582 | 15.472 | 98.815 | 1.00 | 41.02 |
| ATOM | 622 | CZ2 | TRP | A | 383 | 98.942 | 13.264 | 97.132 | 1.00 | 41.39 |
| ATOM | 623 | CZ3 | TRP | A | 383 | 100.529 | 14.525 | 98.475 | 1.00 | 40.98 |
| ATOM | 624 | CH2 | TRP | A | 383 | 100.205 | 13.430 | 97.639 | 1.00 | 41.01 |
| ATOM | 625 | N | LEU | A | 384 | 98.700 | 17.823 | 96.644 | 1.00 | 42.54 |
| ATOM | 626 | CA | LEU | A | 384 | 100.031 | 17.787 | 96.049 | 1.00 | 42.84 |
| ATOM | 627 | C | LEU | A | 384 | 100.438 | 19.088 | 95.346 | 1.00 | 43.49 |
| ATOM | 628 | O | LEU | A | 384 | 101.630 | 19.377 | 95.233 | 1.00 | 44.08 |
| ATOM | 629 | CB | LEU | A | 384 | 100.172 | 16.594 | 95.094 | 1.00 | 41.56 |
| ATOM | 630 | CG | LEU | A | 384 | 101.523 | 16.480 | 94.387 | 1.00 | 41.31 |
| ATOM | 631 | CD1 | LEU | A | 384 | 102.679 | 16.449 | 95.405 | 1.00 | 41.62 |
| ATOM | 632 | CD2 | LEU | A | 384 | 101.520 | 15.229 | 93.530 | 1.00 | 40.95 |
| ATOM | 633 | N | GLU | A | 385 | 99.476 | 19.869 | 94.842 | 1.00 | 44.36 |
| ATOM | 634 | CA | GLU | A | 385 | 99.859 | 21.138 | 94.202 | 1.00 | 44.04 |
| ATOM | 635 | C | GLU | A | 385 | 100.354 | 21.981 | 95.349 | 1.00 | 43.68 |
| ATOM | 636 | O | GLU | A | 385 | 101.436 | 22.569 | 95.280 | 1.00 | 44.08 |
| ATOM | 637 | CB | GLU | A | 385 | 98.682 | 21.871 | 93.532 | 1.00 | 44.27 |
| ATOM | 638 | CG | GLU | A | 385 | 98.129 | 21.194 | 92.295 | 1.00 | 45.37 |
| ATOM | 639 | CD | GLU | A | 385 | 97.018 | 21.989 | 91.622 | 1.00 | 45.49 |
| ATOM | 640 | OE1 | GLU | A | 385 | 97.298 | 23.003 | 90.937 | 1.00 | 47.13 |
| ATOM | 641 | OE2 | GLU | A | 385 | 95.852 | 21.600 | 91.785 | 1.00 | 45.12 |
| ATOM | 642 | N | ILE | A | 386 | 99.566 | 22.011 | 96.423 | 1.00 | 42.40 |
| ATOM | 643 | CA | ILE | A | 386 | 99.931 | 22.805 | 97.584 | 1.00 | 41.27 |
| ATOM | 644 | C | ILE | A | 386 | 101.317 | 22.465 | 98.129 | 1.00 | 41.05 |
| ATOM | 645 | O | ILE | A | 386 | 102.083 | 23.374 | 98.426 | 1.00 | 41.04 |
| ATOM | 646 | CB | ILE | A | 386 | 98.857 | 22.694 | 98.682 | 1.00 | 41.25 |
| ATOM | 647 | CG1 | ILE | A | 386 | 97.560 | 23.323 | 98.161 | 1.00 | 41.02 |
| ATOM | 648 | CG2 | ILE | A | 386 | 99.318 | 23.391 | 99.969 | 1.00 | 40.11 |
| ATOM | 649 | CD1 | ILE | A | 386 | 96.406 | 23.327 | 99.158 | 1.00 | 41.13 |
| ATOM | 650 | N | LEU | A | 387 | 101.667 | 21.179 | 98.251 | 1.00 | 40.50 |
| ATOM | 651 | CA | LEU | A | 387 | 103.012 | 20.854 | 98.734 | 1.00 | 38.67 |
| ATOM | 652 | C | LEU | A | 387 | 104.012 | 21.352 | 97.729 | 1.00 | 37.88 |
| ATOM | 653 | O | LEU | A | 387 | 104.989 | 21.978 | 98.081 | 1.00 | 38.53 |
| ATOM | 654 | CB | LEU | A | 387 | 103.241 | 19.361 | 98.888 | 1.00 | 38.37 |
| ATOM | 655 | CG | LEU | A | 387 | 102.483 | 18.607 | 99.963 | 1.00 | 38.32 |
| ATOM | 656 | CD1 | LEU | A | 387 | 102.980 | 17.207 | 99.926 | 1.00 | 38.21 |
| ATOM | 657 | CD2 | LEU | A | 387 | 102.688 | 19.217 | 101.331 | 1.00 | 38.68 |
| ATOM | 658 | N | MET | A | 388 | 103.767 | 21.085 | 96.464 | 1.00 | 36.94 |
| ATOM | 659 | CA | MET | A | 388 | 104.704 | 21.522 | 95.468 | 1.00 | 37.35 |
| ATOM | 660 | C | MET | A | 388 | 105.013 | 23.017 | 95.449 | 1.00 | 37.65 |
| ATOM | 661 | O | MET | A | 388 | 106.181 | 23.403 | 95.272 | 1.00 | 37.12 |
| ATOM | 662 | CB | MET | A | 388 | 104.247 | 21.039 | 94.100 | 1.00 | 38.12 |
| ATOM | 663 | CG | MET | A | 388 | 104.336 | 19.543 | 94.010 | 1.00 | 39.96 |
| ATOM | 664 | SD | MET | A | 388 | 104.131 | 18.976 | 92.374 | 1.00 | 43.43 |

TABLE III-continued

Structure Coordinates for Site II in Various NHRs
Based on the Consensus Alignments in FIG.2

| ATOM | 665 | CE | MET | A | 388 | 104.602 | 17.301 | 92.499 | 1.00 | 42.19 |
|---|---|---|---|---|---|---|---|---|---|---|
| ATOM | 666 | N | ILE | A | 389 | 104.000 | 23.864 | 95.652 | 1.00 | 37.61 |
| ATOM | 667 | CA | ILE | A | 389 | 104.260 | 25.297 | 95.592 | 1.00 | 37.05 |
| ATOM | 668 | C | ILE | A | 389 | 105.089 | 25.716 | 96.800 | 1.00 | 37.88 |
| ATOM | 669 | O | ILE | A | 389 | 105.971 | 26.595 | 96.702 | 1.00 | 36.98 |
| ATOM | 670 | CB | ILE | A | 389 | 102.953 | 26.125 | 95.495 | 1.00 | 35.49 |
| ATOM | 671 | CG1 | ILE | A | 389 | 103.300 | 27.514 | 94.961 | 1.00 | 34.22 |
| ATOM | 672 | CG2 | ILE | A | 389 | 102.285 | 26.217 | 96.822 | 1.00 | 33.85 |
| ATOM | 673 | CD1 | ILE | A | 389 | 102.156 | 28.318 | 94.504 | 1.00 | 33.77 |
| ATOM | 674 | N | GLY | A | 390 | 104.823 | 25.059 | 97.933 | 1.00 | 38.26 |
| ATOM | 675 | CA | GLY | A | 390 | 105.579 | 25.348 | 99.144 | 1.00 | 39.15 |
| ATOM | 676 | C | GLY | A | 390 | 107.045 | 24.961 | 98.905 | 1.00 | 39.94 |
| ATOM | 677 | O | GLY | A | 390 | 107.952 | 25.778 | 99.094 | 1.00 | 39.41 |
| ATOM | 693 | N | TRP | A | 393 | 108.644 | 27.458 | 96.768 | 1.00 | 46.72 |
| ATOM | 694 | CA | TRP | A | 393 | 108.925 | 28.703 | 97.470 | 1.00 | 48.60 |
| ATOM | 695 | C | TRP | A | 393 | 110.211 | 28.586 | 98.301 | 1.00 | 49.48 |
| ATOM | 696 | O | TRP | A | 393 | 111.101 | 29.434 | 98.214 | 1.00 | 49.93 |
| ATOM | 697 | CB | TRP | A | 393 | 107.737 | 29.024 | 98.368 | 1.00 | 48.90 |
| ATOM | 698 | CG | TRP | A | 393 | 107.887 | 30.184 | 99.292 | 1.00 | 48.84 |
| ATOM | 699 | CD1 | TRP | A | 393 | 107.712 | 30.170 | 100.653 | 1.00 | 49.55 |
| ATOM | 700 | CD2 | TRP | A | 393 | 108.060 | 31.550 | 98.930 | 1.00 | 49.05 |
| ATOM | 701 | NE1 | TRP | A | 393 | 107.755 | 31.455 | 101.162 | 1.00 | 49.29 |
| ATOM | 702 | CE2 | TRP | A | 393 | 107.965 | 32.321 | 100.124 | 1.00 | 48.99 |
| ATOM | 703 | CE3 | TRP | A | 393 | 108.278 | 32.208 | 97.712 | 1.00 | 50.02 |
| ATOM | 704 | CZ2 | TRP | A | 393 | 108.082 | 33.712 | 100.134 | 1.00 | 49.14 |
| ATOM | 705 | CZ3 | TRP | A | 393 | 108.393 | 33.614 | 97.718 | 1.00 | 50.46 |
| ATOM | 706 | CH2 | TRP | A | 393 | 108.293 | 34.344 | 98.927 | 1.00 | 49.90 |
| ATOM | 707 | N | ARG | A | 394 | 110.295 | 27.531 | 99.105 | 1.00 | 50.21 |
| ATOM | 708 | CA | ARG | A | 394 | 111.461 | 27.274 | 99.960 | 1.00 | 50.94 |
| ATOM | 709 | C | ARG | A | 394 | 112.756 | 27.068 | 99.155 | 1.00 | 52.04 |
| ATOM | 710 | O | ARG | A | 394 | 113.844 | 27.404 | 99.643 | 1.00 | 52.38 |
| ATOM | 711 | CB | ARG | A | 394 | 111.262 | 26.006 | 100.809 | 1.00 | 50.31 |
| ATOM | 712 | CG | ARG | A | 394 | 110.034 | 25.974 | 101.674 | 1.00 | 50.30 |
| ATOM | 713 | CD | ARG | A | 394 | 110.153 | 24.878 | 102.698 | 1.00 | 49.88 |
| ATOM | 714 | NE | ARG | A | 394 | 109.924 | 23.537 | 102.187 | 1.00 | 49.74 |
| ATOM | 715 | CZ | ARG | A | 394 | 108.716 | 23.038 | 101.973 | 1.00 | 50.74 |
| ATOM | 716 | NH1 | ARG | A | 394 | 107.641 | 23.780 | 102.224 | 1.00 | 51.52 |
| ATOM | 717 | NH2 | ARG | A | 394 | 108.572 | 21.792 | 101.552 | 1.00 | 50.41 |
| ATOM | 732 | N | GLU | A | 397 | 115.749 | 30.358 | 97.413 | 1.00 | 59.67 |
| ATOM | 733 | CA | GLU | A | 397 | 117.049 | 30.786 | 97.986 | 1.00 | 60.86 |
| ATOM | 734 | C | GLU | A | 397 | 118.156 | 29.784 | 97.665 | 1.00 | 60.54 |
| ATOM | 735 | O | GLU | A | 397 | 119.328 | 30.062 | 97.922 | 1.00 | 61.19 |
| ATOM | 736 | CB | GLU | A | 397 | 116.974 | 30.899 | 99.534 | 1.00 | 62.68 |
| ATOM | 737 | CG | GLU | A | 397 | 116.006 | 31.953 | 100.067 | 1.00 | 65.83 |
| ATOM | 738 | CD | GLU | A | 397 | 116.522 | 33.384 | 99.863 | 1.00 | 67.85 |
| ATOM | 739 | OE1 | GLU | A | 397 | 117.298 | 33.861 | 100.728 | 1.00 | 68.99 |
| ATOM | 740 | OE2 | GLU | A | 397 | 116.177 | 34.021 | 98.830 | 1.00 | 68.91 |
| ATOM | 803 | N | PRO | A | 406 | 114.567 | 21.882 | 106.062 | 1.00 | 52.84 |
| ATOM | 804 | CA | PRO | A | 406 | 115.835 | 22.473 | 106.457 | 1.00 | 53.87 |
| ATOM | 805 | C | PRO | A | 406 | 116.961 | 21.462 | 106.436 | 1.00 | 55.27 |
| ATOM | 806 | O | PRO | A | 406 | 118.046 | 21.757 | 105.935 | 1.00 | 55.84 |
| ATOM | 807 | CB | PRO | A | 406 | 115.533 | 22.985 | 107.848 | 1.00 | 53.50 |
| ATOM | 808 | CG | PRO | A | 406 | 114.115 | 23.420 | 107.694 | 1.00 | 53.44 |
| ATOM | 809 | CD | PRO | A | 406 | 113.558 | 22.158 | 107.092 | 1.00 | 52.74 |
| ATOM | 1112 | N | PHE | A | 445 | 102.932 | 34.883 | 97.394 | 1.00 | 40.62 |
| ATOM | 1113 | CA | PHE | A | 445 | 102.968 | 33.433 | 97.569 | 1.00 | 39.52 |
| ATOM | 1114 | C | PHE | A | 445 | 101.768 | 32.864 | 98.288 | 1.00 | 39.48 |
| ATOM | 1115 | O | PHE | A | 445 | 101.164 | 31.903 | 97.814 | 1.00 | 40.17 |
| ATOM | 1116 | CB | PHE | A | 445 | 104.236 | 33.044 | 98.341 | 1.00 | 38.13 |
| ATOM | 1117 | CG | PHE | A | 445 | 104.251 | 31.623 | 98.840 | 1.00 | 36.69 |
| ATOM | 1118 | CD1 | PHE | A | 445 | 104.293 | 30.555 | 97.960 | 1.00 | 35.89 |
| ATOM | 1119 | CD2 | PHE | A | 445 | 104.261 | 31.360 | 100.212 | 1.00 | 36.19 |
| ATOM | 1120 | CE1 | PHE | A | 445 | 104.350 | 29.242 | 98.442 | 1.00 | 35.78 |
| ATOM | 1121 | CE2 | PHE | A | 445 | 104.319 | 30.065 | 100.693 | 1.00 | 35.05 |
| ATOM | 1122 | CZ | PHE | A | 445 | 104.364 | 29.003 | 99.808 | 1.00 | 35.27 |
| ATOM | 1123 | N | VAL | A | 446 | 101.418 | 33.438 | 99.430 | 1.00 | 39.54 |
| ATOM | 1124 | CA | VAL | A | 446 | 100.298 | 32.912 | 100.190 | 1.00 | 40.25 |
| ATOM | 1125 | C | VAL | A | 446 | 98.963 | 33.084 | 99.460 | 1.00 | 41.56 |
| ATOM | 1126 | O | VAL | A | 446 | 98.039 | 32.272 | 99.652 | 1.00 | 42.13 |
| ATOM | 1127 | CB | VAL | A | 446 | 100.236 | 33.551 | 101.578 | 1.00 | 39.66 |
| ATOM | 1128 | CG1 | VAL | A | 446 | 101.518 | 33.255 | 102.312 | 1.00 | 39.41 |
| ATOM | 1129 | CG2 | VAL | A | 446 | 100.035 | 35.041 | 101.452 | 1.00 | 39.84 |
| ATOM | 1144 | N | LYS | A | 449 | 98.826 | 30.117 | 97.098 | 1.00 | 40.49 |
| ATOM | 1145 | CA | LYS | A | 449 | 98.582 | 28.832 | 97.766 | 1.00 | 40.08 |
| ATOM | 1146 | C | LYS | A | 449 | 97.065 | 28.707 | 98.033 | 1.00 | 39.21 |
| ATOM | 1147 | O | LYS | A | 449 | 96.463 | 27.681 | 97.721 | 1.00 | 38.04 |

TABLE III-continued

Structure Coordinates for Site II in Various NHRs
Based on the Consensus Alignments in FIG.2

| ATOM | 1148 | CB | LYS | A | 449 | 99.418 | 28.783 | 99.070 | 1.00 | 42.46 |
|---|---|---|---|---|---|---|---|---|---|---|
| ATOM | 1149 | CG | LYS | A | 449 | 99.578 | 27.462 | 99.940 | 1.00 | 42.75 |
| ATOM | 1150 | CD | LYS | A | 449 | 100.593 | 27.825 | 101.073 | 1.00 | 43.32 |
| ATOM | 1151 | CE | LYS | A | 449 | 100.997 | 26.726 | 102.078 | 1.00 | 45.38 |
| ATOM | 1152 | NZ | LYS | A | 449 | 100.059 | 26.334 | 103.235 | 1.00 | 45.31 |
| | | | ERbeta Site II Residues (ref. 1L2J.pdb) | | | | | | | |
| ATOM | 84 | N | LEU | A | 273 | 25.561 | 69.746 | 8.280 | 1.00 | 29.28 |
| ATOM | 85 | CA | LEU | A | 273 | 24.842 | 68.816 | 7.428 | 1.00 | 30.73 |
| ATOM | 86 | C | LEU | A | 273 | 23.457 | 69.322 | 7.107 | 1.00 | 32.14 |
| ATOM | 87 | O | LEU | A | 273 | 23.002 | 69.256 | 5.967 | 1.00 | 31.30 |
| ATOM | 88 | CB | LEU | A | 273 | 24.733 | 67.449 | 8.102 | 1.00 | 30.00 |
| ATOM | 89 | CG | LEU | A | 273 | 25.927 | 66.508 | 7.951 | 1.00 | 31.09 |
| ATOM | 90 | CD1 | LEU | A | 273 | 25.722 | 65.262 | 8.804 | 1.00 | 29.29 |
| ATOM | 91 | CD2 | LEU | A | 273 | 26.090 | 66.130 | 6.472 | 1.00 | 33.12 |
| ATOM | 92 | N | GLU | A | 274 | 22.799 | 69.848 | 8.130 | 1.00 | 34.03 |
| ATOM | 93 | CA | GLU | A | 274 | 21.446 | 70.334 | 7.965 | 1.00 | 37.36 |
| ATOM | 94 | C | GLU | A | 274 | 21.402 | 71.743 | 7.419 | 1.00 | 37.99 |
| ATOM | 95 | O | GLU | A | 274 | 20.411 | 72.152 | 6.825 | 1.00 | 38.85 |
| ATOM | 96 | CB | GLU | A | 274 | 20.712 | 70.268 | 9.297 | 1.00 | 38.49 |
| ATOM | 97 | N | ALA | A | 275 | 22.490 | 72.475 | 7.606 | 1.00 | 38.21 |
| ATOM | 98 | CA | ALA | A | 275 | 22.562 | 73.860 | 7.168 | 1.00 | 37.18 |
| ATOM | 99 | C | ALA | A | 275 | 22.827 | 73.954 | 5.675 | 1.00 | 36.12 |
| ATOM | 100 | O | ALA | A | 275 | 22.533 | 74.959 | 5.038 | 1.00 | 36.11 |
| ATOM | 101 | CB | ALA | A | 275 | 23.645 | 74.578 | 7.943 | 1.00 | 35.11 |
| ATOM | 102 | N | GLU | A | 276 | 23.338 | 72.873 | 5.115 | 1.00 | 37.82 |
| ATOM | 103 | CA | GLU | A | 276 | 23.639 | 72.836 | 3.691 | 1.00 | 40.70 |
| ATOM | 104 | C | GLU | A | 276 | 22.412 | 73.106 | 2.854 | 1.00 | 41.89 |
| ATOM | 105 | O | GLU | A | 276 | 21.405 | 72.425 | 2.974 | 1.00 | 44.28 |
| ATOM | 106 | CB | GLU | A | 276 | 24.204 | 71.470 | 3.289 | 1.00 | 40.51 |
| ATOM | 107 | CG | GLU | A | 276 | 25.707 | 71.443 | 3.107 | 1.00 | 41.75 |
| ATOM | 108 | CD | GLU | A | 276 | 26.158 | 72.093 | 1.824 | 1.00 | 41.08 |
| ATOM | 109 | OE1 | GLU | A | 276 | 25.914 | 71.528 | 0.732 | 1.00 | 42.10 |
| ATOM | 110 | OE2 | GLU | A | 276 | 26.762 | 73.175 | 1.913 | 1.00 | 41.89 |
| ATOM | 111 | N | PRO | A | 277 | 22.477 | 74.110 | 1.991 | 1.00 | 43.10 |
| ATOM | 112 | CA | PRO | A | 277 | 21.323 | 74.417 | 1.139 | 1.00 | 45.04 |
| ATOM | 113 | C | PRO | A | 277 | 21.232 | 73.506 | −0.074 | 1.00 | 47.07 |
| ATOM | 114 | O | PRO | A | 277 | 22.234 | 72.937 | −0.494 | 1.00 | 48.36 |
| ATOM | 115 | CB | PRO | A | 277 | 21.573 | 75.861 | 0.745 | 1.00 | 45.33 |
| ATOM | 116 | CG | PRO | A | 277 | 23.045 | 75.885 | 0.600 | 1.00 | 44.31 |
| ATOM | 117 | CD | PRO | A | 277 | 23.528 | 75.128 | 1.822 | 1.00 | 43.44 |
| ATOM | 118 | N | PRO | A | 278 | 20.028 | 73.356 | −0.657 | 1.00 | 49.65 |
| ATOM | 119 | CA | PRO | A | 278 | 19.860 | 72.488 | −1.833 | 1.00 | 50.10 |
| ATOM | 120 | C | PRO | A | 278 | 20.412 | 73.155 | −3.085 | 1.00 | 49.50 |
| ATOM | 121 | O | PRO | A | 278 | 20.314 | 74.367 | −3.246 | 1.00 | 49.29 |
| ATOM | 122 | CB | PRO | A | 278 | 18.346 | 72.282 | −1.908 | 1.00 | 51.43 |
| ATOM | 123 | CG | PRO | A | 278 | 17.870 | 72.581 | −0.487 | 1.00 | 51.67 |
| ATOM | 124 | CD | PRO | A | 278 | 18.715 | 73.778 | −0.141 | 1.00 | 50.69 |
| ATOM | 125 | N | HIS | A | 279 | 20.988 | 72.360 | −3.972 | 1.00 | 49.61 |
| ATOM | 126 | CA | HIS | A | 279 | 21.572 | 72.901 | −5.187 | 1.00 | 49.19 |
| ATOM | 127 | C | HIS | A | 279 | 20.548 | 73.722 | −5.941 | 1.00 | 47.98 |
| ATOM | 128 | O | HIS | A | 279 | 19.384 | 73.357 | −6.022 | 1.00 | 46.87 |
| ATOM | 129 | CB | HIS | A | 279 | 22.109 | 71.769 | −6.070 | 1.00 | 48.45 |
| ATOM | 235 | N | LEU | A | 301 | 23.142 | 82.321 | −11.653 | 1.00 | 39.42 |
| ATOM | 236 | CA | LEU | A | 301 | 23.297 | 81.248 | −10.678 | 1.00 | 38.51 |
| ATOM | 237 | C | LEU | A | 301 | 24.074 | 81.762 | −9.477 | 1.00 | 36.22 |
| ATOM | 238 | O | LEU | A | 301 | 23.680 | 81.564 | −8.335 | 1.00 | 35.05 |
| ATOM | 239 | CB | LEU | A | 301 | 24.040 | 80.071 | −11.309 | 1.00 | 41.75 |
| ATOM | 240 | CG | LEU | A | 301 | 24.287 | 78.874 | −10.391 | 1.00 | 43.32 |
| ATOM | 241 | CD1 | LEU | A | 301 | 22.964 | 78.215 | −10.003 | 1.00 | 43.90 |
| ATOM | 242 | CD2 | LEU | A | 301 | 25.196 | 77.887 | −11.100 | 1.00 | 44.77 |
| ATOM | 243 | N | ALA | A | 302 | 25.181 | 82.433 | −9.756 | 1.00 | 35.01 |
| ATOM | 244 | CA | ALA | A | 302 | 26.024 | 82.999 | −8.719 | 1.00 | 37.36 |
| ATOM | 245 | C | ALA | A | 302 | 25.196 | 83.771 | −7.705 | 1.00 | 38.89 |
| ATOM | 246 | O | ALA | A | 302 | 25.316 | 83.560 | −6.498 | 1.00 | 39.07 |
| ATOM | 247 | CB | ALA | A | 302 | 27.061 | 83.915 | −9.345 | 1.00 | 36.91 |
| ATOM | 265 | N | GLU | A | 305 | 23.169 | 81.589 | −5.589 | 1.00 | 42.82 |
| ATOM | 266 | CA | GLU | A | 305 | 23.951 | 80.823 | −4.627 | 1.00 | 42.67 |
| ATOM | 267 | C | GLU | A | 305 | 24.482 | 81.691 | −3.495 | 1.00 | 41.23 |
| ATOM | 268 | O | GLU | A | 305 | 24.567 | 81.235 | −2.351 | 1.00 | 40.16 |
| ATOM | 269 | CB | GLU | A | 305 | 25.106 | 80.126 | −5.330 | 1.00 | 44.09 |
| ATOM | 270 | CG | GLU | A | 305 | 24.645 | 78.970 | −6.160 | 1.00 | 44.66 |
| ATOM | 271 | CD | GLU | A | 305 | 25.782 | 78.274 | −6.843 | 1.00 | 45.46 |
| ATOM | 272 | OE1 | GLU | A | 305 | 26.524 | 78.938 | −7.599 | 1.00 | 43.22 |
| ATOM | 273 | OE2 | GLU | A | 305 | 25.931 | 77.056 | −6.623 | 1.00 | 49.46 |
| ATOM | 274 | N | LEU | A | 306 | 24.840 | 82.935 | −3.816 | 1.00 | 38.20 |

TABLE III-continued

Structure Coordinates for Site II in Various NHRs
Based on the Consensus Alignments in FIG.2

| ATOM | 275 | CA | LEU | A | 306 | 25.341 | 83.853 | −2.810 | 1.00 | 36.32 |
|---|---|---|---|---|---|---|---|---|---|---|
| ATOM | 276 | C | LEU | A | 306 | 24.295 | 84.071 | −1.710 | 1.00 | 36.84 |
| ATOM | 277 | O | LEU | A | 306 | 24.637 | 84.147 | −0.527 | 1.00 | 39.11 |
| ATOM | 278 | CB | LEU | A | 306 | 25.746 | 85.173 | −3.460 | 1.00 | 30.89 |
| ATOM | 279 | CG | LEU | A | 306 | 27.024 | 85.078 | −4.296 | 1.00 | 29.12 |
| ATOM | 280 | CD1 | LEU | A | 306 | 27.244 | 86.344 | −5.055 | 1.00 | 28.99 |
| ATOM | 281 | CD2 | LEU | A | 306 | 28.213 | 84.831 | −3.411 | 1.00 | 31.75 |
| ATOM | 282 | N | VAL | A | 307 | 23.024 | 84.144 | −2.093 | 1.00 | 35.35 |
| ATOM | 283 | CA | VAL | A | 307 | 21.943 | 84.325 | −1.121 | 1.00 | 35.56 |
| ATOM | 284 | C | VAL | A | 307 | 21.963 | 83.154 | −0.143 | 1.00 | 35.53 |
| ATOM | 285 | O | VAL | A | 307 | 21.982 | 83.334 | 1.078 | 1.00 | 36.47 |
| ATOM | 286 | CB | VAL | A | 307 | 20.561 | 84.367 | −1.821 | 1.00 | 35.38 |
| ATOM | 287 | CG1 | VAL | A | 307 | 19.464 | 84.541 | −0.812 | 1.00 | 35.78 |
| ATOM | 288 | CG2 | VAL | A | 307 | 20.516 | 85.504 | −2.806 | 1.00 | 37.25 |
| ATOM | 289 | N | HIS | A | 308 | 21.954 | 81.949 | −0.699 | 1.00 | 35.96 |
| ATOM | 290 | CA | HIS | A | 308 | 21.996 | 80.722 | 0.085 | 1.00 | 35.90 |
| ATOM | 291 | C | HIS | A | 308 | 23.221 | 80.708 | 0.983 | 1.00 | 32.55 |
| ATOM | 292 | O | HIS | A | 308 | 23.175 | 80.248 | 2.122 | 1.00 | 30.70 |
| ATOM | 293 | CB | HIS | A | 308 | 22.065 | 79.517 | −0.850 | 1.00 | 42.30 |
| ATOM | 294 | CG | HIS | A | 308 | 20.738 | 79.096 | −1.395 | 1.00 | 50.05 |
| ATOM | 295 | ND1 | HIS | A | 308 | 19.727 | 78.607 | −0.593 | 1.00 | 55.44 |
| ATOM | 296 | CD2 | HIS | A | 308 | 20.253 | 79.087 | −2.659 | 1.00 | 52.89 |
| ATOM | 297 | CE1 | HIS | A | 308 | 18.678 | 78.315 | −1.340 | 1.00 | 56.67 |
| ATOM | 298 | NE2 | HIS | A | 308 | 18.970 | 78.597 | −2.598 | 1.00 | 56.96 |
| ATOM | 299 | N | MET | A | 309 | 24.323 | 81.214 | 0.448 | 1.00 | 28.95 |
| ATOM | 300 | CA | MET | A | 309 | 25.571 | 81.247 | 1.178 | 1.00 | 27.16 |
| ATOM | 301 | C | MET | A | 309 | 25.441 | 82.032 | 2.469 | 1.00 | 24.47 |
| ATOM | 302 | O | MET | A | 309 | 25.939 | 81.613 | 3.503 | 1.00 | 24.53 |
| ATOM | 303 | CB | MET | A | 309 | 26.669 | 81.852 | 0.313 | 1.00 | 25.50 |
| ATOM | 304 | CG | MET | A | 309 | 28.026 | 81.510 | 0.830 | 1.00 | 26.26 |
| ATOM | 305 | SD | MET | A | 309 | 29.265 | 82.251 | −0.145 | 1.00 | 30.35 |
| ATOM | 306 | CE | MET | A | 309 | 29.366 | 83.764 | 0.675 | 1.00 | 29.47 |
| ATOM | 307 | N | ILE | A | 310 | 24.767 | 83.171 | 2.404 | 1.00 | 19.70 |
| ATOM | 308 | CA | ILE | A | 310 | 24.577 | 83.993 | 3.576 | 1.00 | 19.52 |
| ATOM | 309 | C | ILE | A | 310 | 23.701 | 83.289 | 4.623 | 1.00 | 21.07 |
| ATOM | 310 | O | ILE | A | 310 | 23.959 | 83.390 | 5.818 | 1.00 | 21.03 |
| ATOM | 311 | CB | ILE | A | 310 | 23.972 | 85.345 | 3.169 | 1.00 | 18.29 |
| ATOM | 312 | CG1 | ILE | A | 310 | 24.925 | 86.021 | 2.176 | 1.00 | 16.69 |
| ATOM | 313 | CG2 | ILE | A | 310 | 23.728 | 86.209 | 4.403 | 1.00 | 16.22 |
| ATOM | 314 | CD1 | ILE | A | 310 | 24.556 | 87.408 | 1.758 | 1.00 | 17.44 |
| ATOM | 315 | N | SER | A | 311 | 22.673 | 82.572 | 4.176 | 1.00 | 21.38 |
| ATOM | 316 | CA | SER | A | 311 | 21.814 | 81.838 | 5.091 | 1.00 | 21.32 |
| ATOM | 317 | C | SER | A | 311 | 22.670 | 80.769 | 5.732 | 1.00 | 22.38 |
| ATOM | 318 | O | SER | A | 311 | 22.623 | 80.552 | 6.940 | 1.00 | 27.93 |
| ATOM | 319 | CB | SER | A | 311 | 20.668 | 81.173 | 4.344 | 1.00 | 19.97 |
| ATOM | 320 | OG | SER | A | 311 | 19.790 | 82.141 | 3.825 | 1.00 | 29.81 |
| ATOM | 321 | N | TRP | A | 312 | 23.451 | 80.103 | 4.893 | 1.00 | 18.68 |
| ATOM | 322 | CA | TRP | A | 312 | 24.347 | 79.055 | 5.328 | 1.00 | 16.46 |
| ATOM | 323 | C | TRP | A | 312 | 25.280 | 79.582 | 6.420 | 1.00 | 17.03 |
| ATOM | 324 | O | TRP | A | 312 | 25.408 | 78.979 | 7.485 | 1.00 | 18.99 |
| ATOM | 325 | CB | TRP | A | 312 | 25.147 | 78.551 | 4.120 | 1.00 | 14.40 |
| ATOM | 326 | CG | TRP | A | 312 | 26.278 | 77.658 | 4.485 | 1.00 | 12.23 |
| ATOM | 327 | CD1 | TRP | A | 312 | 26.195 | 76.379 | 4.934 | 1.00 | 11.53 |
| ATOM | 328 | CD2 | TRP | A | 312 | 27.673 | 77.999 | 4.478 | 1.00 | 12.83 |
| ATOM | 329 | NE1 | TRP | A | 312 | 27.456 | 75.894 | 5.222 | 1.00 | 15.57 |
| ATOM | 330 | CE2 | TRP | A | 312 | 28.379 | 76.869 | 4.955 | 1.00 | 13.92 |
| ATOM | 331 | CE3 | TRP | A | 312 | 28.391 | 79.150 | 4.137 | 1.00 | 11.91 |
| ATOM | 332 | CZ2 | TRP | A | 312 | 29.775 | 76.856 | 5.075 | 1.00 | 13.72 |
| ATOM | 333 | CZ3 | TRP | A | 312 | 29.790 | 79.142 | 4.261 | 1.00 | 11.65 |
| ATOM | 334 | CH2 | TRP | A | 312 | 30.460 | 78.006 | 4.736 | 1.00 | 15.65 |
| ATOM | 498 | N | CYS | A | 334 | 35.346 | 85.584 | 1.011 | 1.00 | 10.61 |
| ATOM | 499 | CA | CYS | A | 334 | 35.360 | 84.154 | 0.704 | 1.00 | 8.93 |
| ATOM | 500 | C | CYS | A | 334 | 34.348 | 83.651 | −0.307 | 1.00 | 10.23 |
| ATOM | 501 | O | CYS | A | 334 | 34.330 | 82.462 | −0.629 | 1.00 | 6.33 |
| ATOM | 502 | CB | CYS | A | 334 | 35.138 | 83.351 | 1.984 | 1.00 | 13.63 |
| ATOM | 503 | SG | CYS | A | 334 | 33.388 | 83.352 | 2.564 | 1.00 | 15.47 |
| ATOM | 504 | N | TRP | A | 335 | 33.494 | 84.530 | −0.802 | 1.00 | 11.06 |
| ATOM | 505 | CA | TRP | A | 335 | 32.467 | 84.074 | −1.718 | 1.00 | 15.96 |
| ATOM | 506 | C | TRP | A | 335 | 33.009 | 83.334 | −2.963 | 1.00 | 18.59 |
| ATOM | 507 | O | TRP | A | 335 | 32.468 | 82.297 | −3.360 | 1.00 | 20.05 |
| ATOM | 508 | CB | TRP | A | 335 | 31.554 | 85.252 | −2.108 | 1.00 | 15.63 |
| ATOM | 509 | CG | TRP | A | 335 | 32.165 | 86.212 | −3.056 | 1.00 | 13.54 |
| ATOM | 510 | CD1 | TRP | A | 335 | 32.908 | 87.306 | −2.753 | 1.00 | 11.75 |
| ATOM | 511 | CD2 | TRP | A | 335 | 32.175 | 86.098 | −4.486 | 1.00 | 15.51 |
| ATOM | 512 | NE1 | TRP | A | 335 | 33.389 | 87.876 | −3.900 | 1.00 | 13.51 |
| ATOM | 513 | CE2 | TRP | A | 335 | 32.953 | 87.147 | −4.983 | 1.00 | 16.55 |

TABLE III-continued

Structure Coordinates for Site II in Various NHRs
Based on the Consensus Alignments in FIG.2

| ATOM | 514 | CE3 | TRP | A | 335 | 31.592 | 85.196 | −5.395 | 1.00 | 15.54 |
|---|---|---|---|---|---|---|---|---|---|---|
| ATOM | 515 | CZ2 | TRP | A | 335 | 33.184 | 87.330 | −6.357 | 1.00 | 16.36 |
| ATOM | 516 | CZ3 | TRP | A | 335 | 31.817 | 85.376 | −6.758 | 1.00 | 13.43 |
| ATOM | 517 | CH2 | TRP | A | 335 | 32.604 | 86.433 | −7.222 | 1.00 | 15.29 |
| ATOM | 518 | N | MET | A | 336 | 34.084 | 83.850 | −3.564 | 1.00 | 19.76 |
| ATOM | 519 | CA | MET | A | 336 | 34.680 | 83.226 | −4.746 | 1.00 | 18.53 |
| ATOM | 520 | C | MET | A | 336 | 35.102 | 81.806 | −4.427 | 1.00 | 16.57 |
| ATOM | 521 | O | MET | A | 336 | 34.711 | 80.840 | −5.084 | 1.00 | 13.78 |
| ATOM | 522 | CB | MET | A | 336 | 35.898 | 84.018 | −5.183 | 1.00 | 25.38 |
| ATOM | 523 | CG | MET | A | 336 | 36.622 | 83.455 | −6.405 | 1.00 | 32.05 |
| ATOM | 524 | SD | MET | A | 336 | 35.649 | 83.602 | −7.882 | 1.00 | 40.49 |
| ATOM | 525 | CE | MET | A | 336 | 36.142 | 85.307 | −8.404 | 1.00 | 37.86 |
| ATOM | 526 | N | GLU | A | 337 | 35.915 | 81.695 | −3.390 | 1.00 | 14.84 |
| ATOM | 527 | CA | GLU | A | 337 | 36.403 | 80.413 | −2.964 | 1.00 | 12.50 |
| ATOM | 528 | C | GLU | A | 337 | 35.278 | 79.455 | −2.578 | 1.00 | 12.56 |
| ATOM | 529 | O | GLU | A | 337 | 35.328 | 78.295 | −2.922 | 1.00 | 13.22 |
| ATOM | 530 | CB | GLU | A | 337 | 37.372 | 80.604 | −1.810 | 1.00 | 8.55 |
| ATOM | 531 | CG | GLU | A | 337 | 38.383 | 79.505 | −1.706 | 1.00 | 14.40 |
| ATOM | 532 | CD | GLU | A | 337 | 39.372 | 79.719 | −0.553 | 1.00 | 18.30 |
| ATOM | 533 | OE1 | GLU | A | 337 | 39.685 | 80.890 | −0.242 | 1.00 | 18.01 |
| ATOM | 534 | OE2 | GLU | A | 337 | 39.845 | 78.720 | 0.038 | 1.00 | 15.07 |
| ATOM | 535 | N | VAL | A | 338 | 34.256 | 79.935 | −1.877 | 1.00 | 12.46 |
| ATOM | 536 | CA | VAL | A | 338 | 33.161 | 79.069 | −1.464 | 1.00 | 11.85 |
| ATOM | 537 | C | VAL | A | 338 | 32.382 | 78.626 | −2.699 | 1.00 | 13.28 |
| ATOM | 538 | O | VAL | A | 338 | 31.961 | 77.470 | −2.799 | 1.00 | 10.19 |
| ATOM | 539 | CB | VAL | A | 338 | 32.254 | 79.802 | −0.408 | 1.00 | 15.77 |
| ATOM | 540 | CG1 | VAL | A | 338 | 30.938 | 79.099 | −0.206 | 1.00 | 16.03 |
| ATOM | 541 | CG2 | VAL | A | 338 | 32.973 | 79.849 | 0.922 | 1.00 | 15.48 |
| ATOM | 542 | N | LEU | A | 339 | 32.211 | 79.522 | −3.669 | 1.00 | 15.67 |
| ATOM | 543 | CA | LEU | A | 339 | 31.494 | 79.131 | −4.876 | 1.00 | 17.55 |
| ATOM | 544 | C | LEU | A | 339 | 32.298 | 78.064 | −5.590 | 1.00 | 18.67 |
| ATOM | 545 | O | LEU | A | 339 | 31.751 | 77.065 | −6.047 | 1.00 | 18.92 |
| ATOM | 546 | CB | LEU | A | 339 | 31.275 | 80.324 | −5.809 | 1.00 | 20.11 |
| ATOM | 547 | CG | LEU | A | 339 | 30.055 | 81.239 | −5.647 | 1.00 | 19.03 |
| ATOM | 548 | CD1 | LEU | A | 339 | 30.110 | 82.244 | −6.767 | 1.00 | 19.53 |
| ATOM | 549 | CD2 | LEU | A | 339 | 28.753 | 80.479 | −5.709 | 1.00 | 17.35 |
| ATOM | 550 | N | MET | A | 340 | 33.607 | 78.276 | −5.679 | 1.00 | 17.94 |
| ATOM | 551 | CA | MET | A | 340 | 34.473 | 77.305 | −6.328 | 1.00 | 20.80 |
| ATOM | 552 | C | MET | A | 340 | 34.399 | 75.930 | −5.664 | 1.00 | 22.16 |
| ATOM | 553 | O | MET | A | 340 | 34.195 | 74.927 | −6.343 | 1.00 | 25.64 |
| ATOM | 554 | CB | MET | A | 340 | 35.907 | 77.825 | −6.350 | 1.00 | 21.88 |
| ATOM | 555 | CG | MET | A | 340 | 36.054 | 79.100 | −7.160 | 1.00 | 22.21 |
| ATOM | 556 | SD | MET | A | 340 | 37.744 | 79.436 | −7.509 | 1.00 | 22.03 |
| ATOM | 557 | CE | MET | A | 340 | 37.603 | 80.420 | −8.952 | 1.00 | 22.39 |
| ATOM | 558 | N | MET | A | 341 | 34.554 | 75.883 | −4.345 | 1.00 | 21.23 |
| ATOM | 559 | CA | MET | A | 341 | 34.469 | 74.623 | −3.609 | 1.00 | 22.72 |
| ATOM | 560 | C | MET | A | 341 | 33.159 | 73.900 | −3.928 | 1.00 | 25.03 |
| ATOM | 561 | O | MET | A | 341 | 33.131 | 72.683 | −4.124 | 1.00 | 26.27 |
| ATOM | 562 | CB | MET | A | 341 | 34.524 | 74.870 | −2.104 | 1.00 | 20.25 |
| ATOM | 563 | CG | MET | A | 341 | 35.901 | 75.000 | −1.516 | 1.00 | 20.06 |
| ATOM | 564 | SD | MET | A | 341 | 36.855 | 73.482 | −1.656 | 1.00 | 27.93 |
| ATOM | 565 | CE | MET | A | 341 | 35.893 | 72.410 | −0.741 | 1.00 | 20.39 |
| ATOM | 566 | N | GLY | A | 342 | 32.069 | 74.655 | −3.974 | 1.00 | 26.08 |
| ATOM | 567 | CA | GLY | A | 342 | 30.776 | 74.061 | −4.252 | 1.00 | 25.83 |
| ATOM | 568 | C | GLY | A | 342 | 30.671 | 73.519 | −5.663 | 1.00 | 25.47 |
| ATOM | 569 | O | GLY | A | 342 | 30.003 | 72.519 | −5.907 | 1.00 | 24.31 |
| ATOM | 586 | N | TRP | A | 345 | 32.604 | 70.110 | −5.820 | 1.00 | 31.56 |
| ATOM | 587 | CA | TRP | A | 345 | 31.935 | 68.990 | −5.176 | 1.00 | 31.51 |
| ATOM | 588 | C | TRP | A | 345 | 30.811 | 68.380 | −6.031 | 1.00 | 34.86 |
| ATOM | 589 | O | TRP | A | 345 | 30.627 | 67.151 | −6.056 | 1.00 | 34.73 |
| ATOM | 590 | CB | TRP | A | 345 | 31.419 | 69.408 | −3.800 | 1.00 | 24.78 |
| ATOM | 591 | CG | TRP | A | 345 | 30.665 | 68.349 | −3.123 | 1.00 | 21.06 |
| ATOM | 592 | CD1 | TRP | A | 345 | 29.319 | 68.289 | −2.975 | 1.00 | 21.80 |
| ATOM | 593 | CD2 | TRP | A | 345 | 31.191 | 67.164 | −2.503 | 1.00 | 22.45 |
| ATOM | 594 | NE1 | TRP | A | 345 | 28.964 | 67.138 | −2.297 | 1.00 | 23.41 |
| ATOM | 595 | CE2 | TRP | A | 345 | 30.099 | 66.429 | −1.997 | 1.00 | 22.74 |
| ATOM | 596 | CE3 | TRP | A | 345 | 32.478 | 66.645 | −2.328 | 1.00 | 23.11 |
| ATOM | 597 | CZ2 | TRP | A | 345 | 30.254 | 65.205 | −1.329 | 1.00 | 21.55 |
| ATOM | 598 | CZ3 | TRP | A | 345 | 32.629 | 65.422 | −1.663 | 1.00 | 22.09 |
| ATOM | 599 | CH2 | TRP | A | 345 | 31.520 | 64.722 | −1.175 | 1.00 | 21.02 |
| ATOM | 600 | N | ARG | A | 346 | 30.075 | 69.235 | −6.741 | 1.00 | 36.80 |
| ATOM | 601 | CA | ARG | A | 346 | 28.987 | 68.780 | −7.601 | 1.00 | 37.33 |
| ATOM | 602 | C | ARG | A | 346 | 29.578 | 68.037 | −8.797 | 1.00 | 39.47 |
| ATOM | 603 | O | ARG | A | 346 | 29.037 | 67.033 | −9.270 | 1.00 | 39.87 |
| ATOM | 604 | CB | ARG | A | 346 | 28.168 | 69.979 | −8.100 | 1.00 | 35.61 |
| ATOM | 605 | CG | ARG | A | 346 | 27.515 | 70.790 | −6.996 | 1.00 | 35.27 |

TABLE III-continued

Structure Coordinates for Site II in Various NHRs
Based on the Consensus Alignments in FIG.2

| ATOM | 606 | CD | ARG | A | 346 | 26.483 | 71.733 | −7.560 | 1.00 | 32.82 |
| ATOM | 607 | NE | ARG | A | 346 | 27.065 | 72.830 | −8.323 | 1.00 | 29.79 |
| ATOM | 608 | CZ | ARG | A | 346 | 27.472 | 73.975 | −7.788 | 1.00 | 27.93 |
| ATOM | 609 | NH1 | ARG | A | 346 | 27.362 | 74.176 | −6.487 | 1.00 | 26.25 |
| ATOM | 610 | NH2 | ARG | A | 346 | 27.974 | 74.924 | −8.558 | 1.00 | 27.25 |
| ATOM | 625 | N | ASP | A | 349 | 32.433 | 63.755 | −9.263 | 1.00 | 48.72 |
| ATOM | 626 | CA | ASP | A | 349 | 32.284 | 62.462 | −9.916 | 1.00 | 49.63 |
| ATOM | 627 | C | ASP | A | 349 | 32.051 | 62.517 | −11.430 | 1.00 | 50.48 |
| ATOM | 628 | O | ASP | A | 349 | 31.770 | 61.496 | −12.047 | 1.00 | 52.40 |
| ATOM | 629 | CB | ASP | A | 349 | 31.145 | 61.681 | −9.247 | 1.00 | 50.96 |
| ATOM | 630 | CG | ASP | A | 349 | 31.397 | 61.433 | −7.762 | 1.00 | 54.14 |
| ATOM | 631 | OD1 | ASP | A | 349 | 32.563 | 61.178 | −7.397 | 1.00 | 57.25 |
| ATOM | 632 | OD2 | ASP | A | 349 | 30.437 | 61.476 | −6.960 | 1.00 | 54.83 |
| ATOM | 695 | N | PRO | A | 358 | 22.357 | 71.048 | −12.407 | 1.00 | 51.18 |
| ATOM | 696 | CA | PRO | A | 358 | 21.930 | 69.832 | −13.105 | 1.00 | 52.77 |
| ATOM | 697 | C | PRO | A | 358 | 21.782 | 70.051 | −14.600 | 1.00 | 54.38 |
| ATOM | 698 | O | PRO | A | 358 | 22.245 | 69.241 | −15.402 | 1.00 | 56.29 |
| ATOM | 699 | CB | PRO | A | 358 | 20.612 | 69.487 | −12.420 | 1.00 | 51.61 |
| ATOM | 700 | CG | PRO | A | 358 | 20.875 | 69.898 | −11.008 | 1.00 | 51.81 |
| ATOM | 701 | CD | PRO | A | 358 | 21.546 | 71.259 | −11.195 | 1.00 | 52.76 |
| ATOM | 996 | N | TYR | A | 397 | 34.120 | 67.559 | 3.349 | 1.00 | 24.82 |
| ATOM | 997 | CA | TYR | A | 397 | 33.800 | 68.689 | 2.487 | 1.00 | 23.38 |
| ATOM | 998 | C | TYR | A | 397 | 33.126 | 69.782 | 3.289 | 1.00 | 22.45 |
| ATOM | 999 | O | TYR | A | 397 | 33.530 | 70.937 | 3.245 | 1.00 | 23.10 |
| ATOM | 1000 | CB | TYR | A | 397 | 32.879 | 68.208 | 1.359 | 1.00 | 25.09 |
| ATOM | 1001 | CG | TYR | A | 397 | 32.138 | 69.291 | 0.571 | 1.00 | 25.87 |
| ATOM | 1002 | CD1 | TYR | A | 397 | 32.822 | 70.219 | −0.213 | 1.00 | 24.58 |
| ATOM | 1003 | CD2 | TYR | A | 397 | 30.744 | 69.374 | 0.609 | 1.00 | 24.99 |
| ATOM | 1004 | CE1 | TYR | A | 397 | 32.136 | 71.204 | −0.939 | 1.00 | 24.05 |
| ATOM | 1005 | CE2 | TYR | A | 397 | 30.050 | 70.349 | −0.109 | 1.00 | 24.00 |
| ATOM | 1006 | CZ | TYR | A | 397 | 30.746 | 71.261 | −0.878 | 1.00 | 26.24 |
| ATOM | 1007 | OH | TYR | A | 397 | 30.034 | 72.230 | −1.569 | 1.00 | 29.36 |
| ATOM | 1008 | N | LEU | A | 398 | 32.110 | 69.411 | 4.049 | 1.00 | 22.21 |
| ATOM | 1009 | CA | LEU | A | 398 | 31.397 | 70.397 | 4.835 | 1.00 | 22.58 |
| ATOM | 1010 | C | LEU | A | 398 | 32.272 | 71.129 | 5.849 | 1.00 | 22.08 |
| ATOM | 1011 | O | LEU | A | 398 | 32.127 | 72.339 | 6.027 | 1.00 | 22.04 |
| ATOM | 1012 | CB | LEU | A | 398 | 30.195 | 69.757 | 5.539 | 1.00 | 23.08 |
| ATOM | 1013 | CG | LEU | A | 398 | 29.100 | 69.090 | 4.679 | 1.00 | 24.43 |
| ATOM | 1014 | CD1 | LEU | A | 398 | 27.860 | 68.904 | 5.536 | 1.00 | 23.58 |
| ATOM | 1015 | CD2 | LEU | A | 398 | 28.740 | 69.931 | 3.465 | 1.00 | 23.50 |
| ATOM | 1029 | N | LYS | A | 401 | 34.605 | 73.520 | 4.066 | 1.00 | 17.69 |
| ATOM | 1030 | CA | LYS | A | 401 | 33.897 | 74.681 | 3.542 | 1.00 | 17.79 |
| ATOM | 1031 | C | LYS | A | 401 | 33.763 | 75.765 | 4.575 | 1.00 | 17.99 |
| ATOM | 1032 | O | LYS | A | 401 | 34.004 | 76.930 | 4.301 | 1.00 | 19.98 |
| ATOM | 1033 | CB | LYS | A | 401 | 32.510 | 74.284 | 3.068 | 1.00 | 19.62 |
| ATOM | 1034 | CG | LYS | A | 401 | 31.907 | 75.273 | 2.112 | 1.00 | 22.29 |
| ATOM | 1035 | CD | LYS | A | 401 | 30.912 | 74.581 | 1.156 | 1.00 | 24.70 |
| ATOM | 1036 | CE | LYS | A | 401 | 29.552 | 74.361 | 1.798 | 1.00 | 24.63 |
| ATOM | 1037 | NZ | LYS | A | 401 | 28.970 | 75.682 | 2.242 | 1.00 | 28.13 |

GR Homology Model Site II Residues (ref. GR_icm_aligned.pdb)
(highlighted residues of SEQ ID NO:13)

| ATOM | 103 | N | GLU | A | 537 | −11.080 | 4.969 | −10.004 | 1.00 | 20.00 |
| ATOM | 104 | CA | GLU | A | 537 | −10.913 | 3.599 | −10.490 | 1.00 | 20.00 |
| ATOM | 105 | C | GLU | A | 537 | −10.384 | 3.551 | −11.927 | 1.00 | 20.00 |
| ATOM | 106 | O | GLU | A | 537 | −9.790 | 2.536 | −12.306 | 1.00 | 20.00 |
| ATOM | 107 | CB | GLU | A | 537 | −12.267 | 2.897 | −10.362 | 1.00 | 20.00 |
| ATOM | 108 | CG | GLU | A | 537 | −12.225 | 1.397 | −10.662 | 1.00 | 20.00 |
| ATOM | 109 | CD | GLU | A | 537 | −12.502 | 1.114 | −12.138 | 1.00 | 20.00 |
| ATOM | 110 | OE1 | GLU | A | 537 | −12.954 | 2.042 | −12.797 | 1.00 | 20.00 |
| ATOM | 111 | OE2 | GLU | A | 537 | −12.518 | −0.057 | −12.489 | 1.00 | 20.00 |
| ATOM | 112 | N | VAL | A | 538 | −10.481 | 4.647 | −12.662 | 1.00 | 20.00 |
| ATOM | 113 | CA | VAL | A | 538 | −9.938 | 4.688 | −14.022 | 1.00 | 20.00 |
| ATOM | 114 | C | VAL | A | 538 | −8.508 | 5.243 | −14.060 | 1.00 | 20.00 |
| ATOM | 115 | O | VAL | A | 538 | −7.739 | 4.908 | −14.969 | 1.00 | 20.00 |
| ATOM | 116 | CB | VAL | A | 538 | −10.880 | 5.542 | −14.872 | 1.00 | 20.00 |
| ATOM | 117 | CG1 | VAL | A | 538 | −10.316 | 5.838 | −16.259 | 1.00 | 20.00 |
| ATOM | 118 | CG2 | VAL | A | 538 | −12.249 | 4.880 | −14.995 | 1.00 | 20.00 |
| ATOM | 119 | N | ILE | A | 539 | −8.123 | 5.996 | −13.041 | 1.00 | 20.00 |
| ATOM | 120 | CA | ILE | A | 539 | −6.742 | 6.497 | −12.978 | 1.00 | 20.00 |
| ATOM | 121 | C | ILE | A | 539 | −5.858 | 5.612 | −12.099 | 1.00 | 20.00 |
| ATOM | 122 | O | ILE | A | 539 | −4.647 | 5.839 | −11.983 | 1.00 | 20.00 |
| ATOM | 123 | CB | ILE | A | 539 | −6.734 | 7.967 | −12.548 | 1.00 | 20.00 |
| ATOM | 124 | CG1 | ILE | A | 539 | −7.332 | 8.228 | −11.167 | 1.00 | 20.00 |
| ATOM | 125 | CG2 | ILE | A | 539 | −7.441 | 8.818 | −13.596 | 1.00 | 20.00 |
| ATOM | 126 | CD1 | ILE | A | 539 | −6.287 | 8.243 | −10.060 | 1.00 | 20.00 |

TABLE III-continued

Structure Coordinates for Site II in Various NHRs
Based on the Consensus Alignments in FIG.2

| ATOM | 127 | N | GLU | A | 540 | −6.479 | 4.616 | −11.488 | 1.00 | 20.00 |
|---|---|---|---|---|---|---|---|---|---|---|
| ATOM | 128 | CA | GLU | A | 540 | −5.766 | 3.576 | −10.744 | 1.00 | 20.00 |
| ATOM | 129 | C | GLU | A | 540 | −4.822 | 2.810 | −11.678 | 1.00 | 20.00 |
| ATOM | 130 | O | GLU | A | 540 | −5.227 | 2.388 | −12.765 | 1.00 | 20.00 |
| ATOM | 131 | CB | GLU | A | 540 | −6.843 | 2.636 | −10.200 | 1.00 | 20.00 |
| ATOM | 132 | CG | GLU | A | 540 | −6.313 | 1.647 | −9.170 | 1.00 | 20.00 |
| ATOM | 133 | CD | GLU | A | 540 | −5.839 | 2.402 | −7.932 | 1.00 | 20.00 |
| ATOM | 134 | OE1 | GLU | A | 540 | −6.459 | 3.406 | −7.607 | 1.00 | 20.00 |
| ATOM | 135 | OE2 | GLU | A | 540 | −4.842 | 1.988 | −7.358 | 1.00 | 20.00 |
| ATOM | 136 | N | PRO | A | 541 | −3.571 | 2.672 | −11.264 | 1.00 | 20.00 |
| ATOM | 137 | CA | PRO | A | 541 | −2.549 | 1.983 | −12.062 | 1.00 | 20.00 |
| ATOM | 138 | C | PRO | A | 541 | −2.768 | 0.470 | −12.159 | 1.00 | 20.00 |
| ATOM | 139 | O | PRO | A | 541 | −3.893 | −0.042 | −12.120 | 1.00 | 20.00 |
| ATOM | 140 | CB | PRO | A | 541 | −1.247 | 2.285 | −11.386 | 1.00 | 20.00 |
| ATOM | 141 | CG | PRO | A | 541 | −1.524 | 3.000 | −10.074 | 1.00 | 20.00 |
| ATOM | 142 | CD | PRO | A | 541 | −3.028 | 3.202 | −10.012 | 1.00 | 20.00 |
| ATOM | 143 | N | GLU | A | 542 | −1.656 | −0.223 | −12.330 | 1.00 | 20.00 |
| ATOM | 144 | CA | GLU | A | 542 | −1.675 | −1.669 | −12.569 | 1.00 | 20.00 |
| ATOM | 145 | C | GLU | A | 542 | −1.033 | −2.428 | −11.404 | 1.00 | 20.00 |
| ATOM | 146 | O | GLU | A | 542 | −0.112 | −1.909 | −10.762 | 1.00 | 20.00 |
| ATOM | 147 | CB | GLU | A | 542 | −0.893 | −1.901 | −13.868 | 1.00 | 20.00 |
| ATOM | 148 | CG | GLU | A | 542 | −0.941 | −3.337 | −14.389 | 1.00 | 20.00 |
| ATOM | 149 | CD | GLU | A | 542 | −2.382 | −3.754 | −14.681 | 1.00 | 20.00 |
| ATOM | 150 | OE1 | GLU | A | 542 | −2.844 | −3.471 | −15.775 | 1.00 | 20.00 |
| ATOM | 151 | OE2 | GLU | A | 542 | −3.015 | −4.268 | −13.766 | 1.00 | 20.00 |
| ATOM | 152 | N | VAL | A | 543 | −1.564 | −3.605 | −11.102 | 1.00 | 20.00 |
| ATOM | 153 | CA | VAL | A | 543 | −0.902 | −4.511 | −10.154 | 1.00 | 20.00 |
| ATOM | 154 | C | VAL | A | 543 | 0.442 | −4.922 | −10.758 | 1.00 | 20.00 |
| ATOM | 155 | O | VAL | A | 543 | 0.543 | −5.236 | −11.950 | 1.00 | 20.00 |
| ATOM | 156 | CB | VAL | A | 543 | −1.806 | −5.720 | −9.890 | 1.00 | 20.00 |
| ATOM | 157 | CG1 | VAL | A | 543 | −2.193 | −6.445 | −11.175 | 1.00 | 20.00 |
| ATOM | 158 | CG2 | VAL | A | 543 | −1.191 | −6.692 | −8.887 | 1.00 | 20.00 |
| ATOM | 334 | N | LEU | A | 566 | 10.458 | −4.244 | −6.551 | 1.00 | 20.00 |
| ATOM | 335 | CA | LEU | A | 566 | 9.019 | −3.973 | −6.485 | 1.00 | 20.00 |
| ATOM | 336 | C | LEU | A | 566 | 8.726 | −2.637 | −5.801 | 1.00 | 20.00 |
| ATOM | 337 | O | LEU | A | 566 | 7.849 | −1.905 | −6.272 | 1.00 | 20.00 |
| ATOM | 338 | CB | LEU | A | 566 | 8.363 | −5.104 | −5.708 | 1.00 | 20.00 |
| ATOM | 339 | CG | LEU | A | 566 | 6.853 | −4.933 | −5.626 | 1.00 | 20.00 |
| ATOM | 340 | CD1 | LEU | A | 566 | 6.214 | −4.892 | −7.011 | 1.00 | 20.00 |
| ATOM | 341 | CD2 | LEU | A | 566 | 6.244 | −6.046 | −4.787 | 1.00 | 20.00 |
| ATOM | 361 | N | GLN | A | 570 | 6.584 | 0.298 | −7.548 | 1.00 | 20.00 |
| ATOM | 362 | CA | GLN | A | 570 | 5.437 | 0.936 | −6.899 | 1.00 | 20.00 |
| ATOM | 363 | C | GLN | A | 570 | 5.643 | 2.432 | −6.693 | 1.00 | 20.00 |
| ATOM | 364 | O | GLN | A | 570 | 4.656 | 3.173 | −6.717 | 1.00 | 20.00 |
| ATOM | 365 | CB | GLN | A | 570 | 5.191 | 0.262 | −5.558 | 1.00 | 20.00 |
| ATOM | 366 | CG | GLN | A | 570 | 4.794 | −1.197 | −5.748 | 1.00 | 20.00 |
| ATOM | 367 | CD | GLN | A | 570 | 4.596 | −1.865 | −4.394 | 1.00 | 20.00 |
| ATOM | 368 | OE1 | GLN | A | 570 | 5.477 | −2.575 | −3.898 | 1.00 | 20.00 |
| ATOM | 369 | NE2 | GLN | A | 570 | 3.451 | −1.593 | −3.792 | 1.00 | 20.00 |
| ATOM | 370 | N | VAL | A | 571 | 6.883 | 2.894 | −6.730 | 1.00 | 20.00 |
| ATOM | 371 | CA | VAL | A | 571 | 7.140 | 4.333 | −6.668 | 1.00 | 20.00 |
| ATOM | 372 | C | VAL | A | 571 | 6.890 | 4.996 | −8.018 | 1.00 | 20.00 |
| ATOM | 373 | O | VAL | A | 571 | 6.212 | 6.032 | −8.062 | 1.00 | 20.00 |
| ATOM | 374 | CB | VAL | A | 571 | 8.587 | 4.568 | −6.242 | 1.00 | 20.00 |
| ATOM | 375 | CG1 | VAL | A | 571 | 8.981 | 6.032 | −6.395 | 1.00 | 20.00 |
| ATOM | 376 | CG2 | VAL | A | 571 | 8.828 | 4.097 | −4.813 | 1.00 | 20.00 |
| ATOM | 377 | N | ILE | A | 572 | 7.169 | 4.290 | −9.103 | 1.00 | 20.00 |
| ATOM | 378 | CA | ILE | A | 572 | 6.914 | 4.887 | −10.416 | 1.00 | 20.00 |
| ATOM | 379 | C | ILE | A | 572 | 5.436 | 4.736 | −10.799 | 1.00 | 20.00 |
| ATOM | 380 | O | ILE | A | 572 | 4.871 | 5.667 | −11.388 | 1.00 | 20.00 |
| ATOM | 381 | CB | ILE | A | 572 | 7.910 | 4.311 | −11.440 | 1.00 | 20.00 |
| ATOM | 382 | CG1 | ILE | A | 572 | 7.921 | 5.073 | −12.768 | 1.00 | 20.00 |
| ATOM | 383 | CG2 | ILE | A | 572 | 7.686 | 2.827 | −11.702 | 1.00 | 20.00 |
| ATOM | 384 | CD1 | ILE | A | 572 | 6.842 | 4.607 | −13.742 | 1.00 | 20.00 |
| ATOM | 385 | N | ALA | A | 573 | 4.754 | 3.770 | −10.201 | 1.00 | 20.00 |
| ATOM | 386 | CA | ALA | A | 573 | 3.309 | 3.672 | −10.400 | 1.00 | 20.00 |
| ATOM | 387 | C | ALA | A | 573 | 2.561 | 4.657 | −9.507 | 1.00 | 20.00 |
| ATOM | 388 | O | ALA | A | 573 | 1.566 | 5.243 | −9.950 | 1.00 | 20.00 |
| ATOM | 389 | CB | ALA | A | 573 | 2.858 | 2.251 | −10.080 | 1.00 | 20.00 |
| ATOM | 390 | N | ALA | A | 574 | 3.173 | 5.031 | −8.394 | 1.00 | 20.00 |
| ATOM | 391 | CA | ALA | A | 574 | 2.562 | 6.013 | −7.500 | 1.00 | 20.00 |
| ATOM | 392 | C | ALA | A | 574 | 2.777 | 7.440 | −7.981 | 1.00 | 20.00 |
| ATOM | 393 | O | ALA | A | 574 | 1.870 | 8.260 | −7.816 | 1.00 | 20.00 |
| ATOM | 394 | CB | ALA | A | 574 | 3.146 | 5.858 | −6.101 | 1.00 | 20.00 |
| ATOM | 395 | N | VAL | A | 575 | 3.827 | 7.690 | −8.749 | 1.00 | 20.00 |
| ATOM | 396 | CA | VAL | A | 575 | 3.972 | 9.034 | −9.313 | 1.00 | 20.00 |

TABLE III-continued

Structure Coordinates for Site II in Various NHRs
Based on the Consensus Alignments in FIG.2

| ATOM | 397 | C   | VAL | A | 575 | 3.152  | 9.174  | -10.597 | 1.00 | 20.00 |
|------|-----|-----|-----|---|-----|--------|--------|---------|------|-------|
| ATOM | 398 | O   | VAL | A | 575 | 2.598  | 10.253 | -10.841 | 1.00 | 20.00 |
| ATOM | 399 | CB  | VAL | A | 575 | 5.448  | 9.381  | -9.531  | 1.00 | 20.00 |
| ATOM | 400 | CG1 | VAL | A | 575 | 6.158  | 8.438  | -10.494 | 1.00 | 20.00 |
| ATOM | 401 | CG2 | VAL | A | 575 | 5.612  | 10.825 | -9.995  | 1.00 | 20.00 |
| ATOM | 402 | N   | LYS | A | 576 | 2.810  | 8.050  | -11.212 | 1.00 | 20.00 |
| ATOM | 403 | CA  | LYS | A | 576 | 1.910  | 8.090  | -12.364 | 1.00 | 20.00 |
| ATOM | 404 | C   | LYS | A | 576 | 0.463  | 8.241  | -11.898 | 1.00 | 20.00 |
| ATOM | 405 | O   | LYS | A | 576 | -0.273 | 9.074  | -12.440 | 1.00 | 20.00 |
| ATOM | 406 | CB  | LYS | A | 576 | 2.074  | 6.795  | -13.151 | 1.00 | 20.00 |
| ATOM | 407 | CG  | LYS | A | 576 | 1.273  | 6.824  | -14.447 | 1.00 | 20.00 |
| ATOM | 408 | CD  | LYS | A | 576 | 1.761  | 7.935  | -15.372 | 1.00 | 20.00 |
| ATOM | 409 | CE  | LYS | A | 576 | 3.218  | 7.728  | -15.772 | 1.00 | 20.00 |
| ATOM | 410 | NZ  | LYS | A | 576 | 3.687  | 8.826  | -16.634 | 1.00 | 20.00 |
| ATOM | 411 | N   | TRP | A | 577 | 0.174  | 7.673  | -10.739 | 1.00 | 20.00 |
| ATOM | 412 | CA  | TRP | A | 577 | -1.144 | 7.819  | -10.115 | 1.00 | 20.00 |
| ATOM | 413 | C   | TRP | A | 577 | -1.321 | 9.205  | -9.494  | 1.00 | 20.00 |
| ATOM | 414 | O   | TRP | A | 577 | -2.398 | 9.800  | -9.622  | 1.00 | 20.00 |
| ATOM | 415 | CB  | TRP | A | 577 | -1.242 | 6.744  | -9.037  | 1.00 | 20.00 |
| ATOM | 416 | CG  | TRP | A | 577 | -2.481 | 6.797  | -8.167  | 1.00 | 20.00 |
| ATOM | 417 | CD1 | TRP | A | 577 | -3.729 | 6.312  | -8.478  | 1.00 | 20.00 |
| ATOM | 418 | CD2 | TRP | A | 577 | -2.577 | 7.356  | -6.839  | 1.00 | 20.00 |
| ATOM | 419 | NE1 | TRP | A | 577 | -4.558 | 6.554  | -7.433  | 1.00 | 20.00 |
| ATOM | 420 | CE2 | TRP | A | 577 | -3.911 | 7.181  | -6.434  | 1.00 | 20.00 |
| ATOM | 421 | CE3 | TRP | A | 577 | -1.662 | 7.973  | -5.997  | 1.00 | 20.00 |
| ATOM | 422 | CZ2 | TRP | A | 577 | -4.318 | 7.645  | -5.190  | 1.00 | 20.00 |
| ATOM | 423 | CZ3 | TRP | A | 577 | -2.078 | 8.424  | -4.751  | 1.00 | 20.00 |
| ATOM | 424 | CH2 | TRP | A | 577 | -3.399 | 8.263  | -4.350  | 1.00 | 20.00 |
| ATOM | 596 | N   | SER | A | 599 | 4.149  | 9.996  | 1.965   | 1.00 | 20.00 |
| ATOM | 597 | CA  | SER | A | 599 | 3.110  | 8.965  | 1.912   | 1.00 | 20.00 |
| ATOM | 598 | C   | SER | A | 599 | 3.534  | 7.679  | 1.209   | 1.00 | 20.00 |
| ATOM | 599 | O   | SER | A | 599 | 2.773  | 6.704  | 1.271   | 1.00 | 20.00 |
| ATOM | 600 | CB  | SER | A | 599 | 1.914  | 9.536  | 1.164   | 1.00 | 20.00 |
| ATOM | 601 | OG  | SER | A | 599 | 2.316  | 9.748  | -0.183  | 1.00 | 20.00 |
| ATOM | 602 | N   | TRP | A | 600 | 4.769  | 7.593  | 0.733   | 1.00 | 20.00 |
| ATOM | 603 | CA  | TRP | A | 600 | 5.156  | 6.475  | -0.146  | 1.00 | 20.00 |
| ATOM | 604 | C   | TRP | A | 600 | 5.137  | 5.113  | 0.553   | 1.00 | 20.00 |
| ATOM | 605 | O   | TRP | A | 600 | 4.590  | 4.167  | -0.029  | 1.00 | 20.00 |
| ATOM | 606 | CB  | TRP | A | 600 | 6.549  | 6.733  | -0.739  | 1.00 | 20.00 |
| ATOM | 607 | CG  | TRP | A | 600 | 7.745  | 6.447  | 0.160   | 1.00 | 20.00 |
| ATOM | 608 | CD1 | TRP | A | 600 | 8.085  | 7.097  | 1.327   | 1.00 | 20.00 |
| ATOM | 609 | CD2 | TRP | A | 600 | 8.745  | 5.424  | -0.037  | 1.00 | 20.00 |
| ATOM | 610 | NE1 | TRP | A | 600 | 9.207  | 6.530  | 1.830   | 1.00 | 20.00 |
| ATOM | 611 | CE2 | TRP | A | 600 | 9.637  | 5.524  | 1.046   | 1.00 | 20.00 |
| ATOM | 612 | CE3 | TRP | A | 600 | 8.942  | 4.460  | -1.016  | 1.00 | 20.00 |
| ATOM | 613 | CZ2 | TRP | A | 600 | 10.720 | 4.663  | 1.131   | 1.00 | 20.00 |
| ATOM | 614 | CZ3 | TRP | A | 600 | 10.027 | 3.599  | -0.921  | 1.00 | 20.00 |
| ATOM | 615 | CH2 | TRP | A | 600 | 10.914 | 3.699  | 0.147   | 1.00 | 20.00 |
| ATOM | 616 | N   | MET | A | 601 | 5.381  | 5.092  | 1.856   | 1.00 | 20.00 |
| ATOM | 617 | CA  | MET | A | 601 | 5.436  | 3.817  | 2.562   | 1.00 | 20.00 |
| ATOM | 618 | C   | MET | A | 601 | 4.049  | 3.290  | 2.895   | 1.00 | 20.00 |
| ATOM | 619 | O   | MET | A | 601 | 3.823  | 2.080  | 2.785   | 1.00 | 20.00 |
| ATOM | 620 | CB  | MET | A | 601 | 6.242  | 3.989  | 3.842   | 1.00 | 20.00 |
| ATOM | 621 | CG  | MET | A | 601 | 7.468  | 3.084  | 3.825   | 1.00 | 20.00 |
| ATOM | 622 | SD  | MET | A | 601 | 7.126  | 1.318  | 3.636   | 1.00 | 20.00 |
| ATOM | 623 | CE  | MET | A | 601 | 8.822  | 0.695  | 3.653   | 1.00 | 20.00 |
| ATOM | 624 | N   | PHE | A | 602 | 3.076  | 4.172  | 3.039   | 1.00 | 20.00 |
| ATOM | 625 | CA  | PHE | A | 602 | 1.745  | 3.653  | 3.323   | 1.00 | 20.00 |
| ATOM | 626 | C   | PHE | A | 602 | 0.933  | 3.520  | 2.040   | 1.00 | 20.00 |
| ATOM | 627 | O   | PHE | A | 602 | 0.010  | 2.702  | 1.997   | 1.00 | 20.00 |
| ATOM | 628 | CB  | PHE | A | 602 | 1.018  | 4.502  | 4.354   | 1.00 | 20.00 |
| ATOM | 629 | CG  | PHE | A | 602 | -0.170 | 3.743  | 4.939   | 1.00 | 20.00 |
| ATOM | 630 | CD1 | PHE | A | 602 | -0.131 | 2.353  | 4.994   | 1.00 | 20.00 |
| ATOM | 631 | CD2 | PHE | A | 602 | -1.273 | 4.424  | 5.431   | 1.00 | 20.00 |
| ATOM | 632 | CE1 | PHE | A | 602 | -1.212 | 1.645  | 5.499   | 1.00 | 20.00 |
| ATOM | 633 | CE2 | PHE | A | 602 | -2.354 | 3.714  | 5.938   | 1.00 | 20.00 |
| ATOM | 634 | CZ  | PHE | A | 602 | -2.327 | 2.326  | 5.962   | 1.00 | 20.00 |
| ATOM | 635 | N   | LEU | A | 603 | 1.401  | 4.109  | 0.955   | 1.00 | 20.00 |
| ATOM | 636 | CA  | LEU | A | 603 | 0.750  | 3.834  | -0.325  | 1.00 | 20.00 |
| ATOM | 637 | C   | LEU | A | 603 | 1.106  | 2.426  | -0.787  | 1.00 | 20.00 |
| ATOM | 638 | O   | LEU | A | 603 | 0.195  | 1.633  | -1.070  | 1.00 | 20.00 |
| ATOM | 639 | CB  | LEU | A | 603 | 1.191  | 4.854  | -1.369  | 1.00 | 20.00 |
| ATOM | 640 | CG  | LEU | A | 603 | 0.668  | 6.252  | -1.062  | 1.00 | 20.00 |
| ATOM | 641 | CD1 | LEU | A | 603 | 1.188  | 7.258  | -2.083  | 1.00 | 20.00 |
| ATOM | 642 | CD2 | LEU | A | 603 | -0.856 | 6.278  | -1.015  | 1.00 | 20.00 |
| ATOM | 643 | N   | MET | A | 604 | 2.348  | 2.028  | -0.558  | 1.00 | 20.00 |

TABLE III-continued

Structure Coordinates for Site II in Various NHRs
Based on the Consensus Alignments in FIG.2

| ATOM | 644 | CA | MET | A | 604 | 2.746 | 0.674 | −0.947 | 1.00 | 20.00 |
|---|---|---|---|---|---|---|---|---|---|---|
| ATOM | 645 | C | MET | A | 604 | 2.317 | −0.384 | 0.076 | 1.00 | 20.00 |
| ATOM | 646 | O | MET | A | 604 | 1.938 | −1.486 | −0.344 | 1.00 | 20.00 |
| ATOM | 647 | CB | MET | A | 604 | 4.255 | 0.637 | −1.195 | 1.00 | 20.00 |
| ATOM | 648 | CG | MET | A | 604 | 5.089 | 1.042 | 0.014 | 1.00 | 20.00 |
| ATOM | 649 | SD | MET | A | 604 | 6.873 | 1.110 | −0.258 | 1.00 | 20.00 |
| ATOM | 650 | CE | MET | A | 604 | 7.149 | −0.608 | −0.746 | 1.00 | 20.00 |
| ATOM | 651 | N | ALA | A | 605 | 2.106 | 0.011 | 1.323 | 1.00 | 20.00 |
| ATOM | 652 | CA | ALA | A | 605 | 1.640 | −0.947 | 2.331 | 1.00 | 20.00 |
| ATOM | 653 | C | ALA | A | 605 | 0.122 | −1.102 | 2.349 | 1.00 | 20.00 |
| ATOM | 654 | O | ALA | A | 605 | −0.370 | −2.197 | 2.644 | 1.00 | 20.00 |
| ATOM | 655 | CB | ALA | A | 605 | 2.123 | −0.501 | 3.704 | 1.00 | 20.00 |
| ATOM | 656 | N | PHE | A | 606 | −0.597 | −0.112 | 1.845 | 1.00 | 20.00 |
| ATOM | 657 | CA | PHE | A | 606 | −2.052 | −0.234 | 1.754 | 1.00 | 20.00 |
| ATOM | 658 | C | PHE | A | 606 | −2.409 | −0.954 | 0.461 | 1.00 | 20.00 |
| ATOM | 659 | O | PHE | A | 606 | −3.386 | −1.715 | 0.419 | 1.00 | 20.00 |
| ATOM | 660 | CB | PHE | A | 606 | −2.665 | 1.161 | 1.767 | 1.00 | 20.00 |
| ATOM | 661 | CG | PHE | A | 606 | −4.092 | 1.228 | 2.298 | 1.00 | 20.00 |
| ATOM | 662 | CD1 | PHE | A | 606 | −4.513 | 0.331 | 3.272 | 1.00 | 20.00 |
| ATOM | 663 | CD2 | PHE | A | 606 | −4.968 | 2.195 | 1.821 | 1.00 | 20.00 |
| ATOM | 664 | CE1 | PHE | A | 606 | −5.808 | 0.403 | 3.768 | 1.00 | 20.00 |
| ATOM | 665 | CE2 | PHE | A | 606 | −6.262 | 2.268 | 2.319 | 1.00 | 20.00 |
| ATOM | 666 | CZ | PHE | A | 606 | −6.683 | 1.371 | 3.292 | 1.00 | 20.00 |
| ATOM | 667 | N | ALA | A | 607 | −1.494 | −0.893 | −0.496 | 1.00 | 20.00 |
| ATOM | 668 | CA | ALA | A | 607 | −1.629 | −1.694 | −1.711 | 1.00 | 20.00 |
| ATOM | 669 | C | ALA | A | 607 | −1.379 | −3.161 | −1.389 | 1.00 | 20.00 |
| ATOM | 670 | O | ALA | A | 607 | −2.225 | −3.998 | −1.718 | 1.00 | 20.00 |
| ATOM | 671 | CB | ALA | A | 607 | −0.616 | −1.213 | −2.745 | 1.00 | 20.00 |
| ATOM | 684 | N | TRP | A | 610 | −4.529 | −4.496 | 0.500 | 1.00 | 20.00 |
| ATOM | 685 | CA | TRP | A | 610 | −5.667 | −4.797 | −0.368 | 1.00 | 20.00 |
| ATOM | 686 | C | TRP | A | 610 | −5.403 | −5.914 | −1.376 | 1.00 | 20.00 |
| ATOM | 687 | O | TRP | A | 610 | −6.325 | −6.688 | −1.660 | 1.00 | 20.00 |
| ATOM | 688 | CB | TRP | A | 610 | −5.999 | −3.528 | −1.132 | 1.00 | 20.00 |
| ATOM | 689 | CG | TRP | A | 610 | −7.315 | −3.587 | −1.870 | 1.00 | 20.00 |
| ATOM | 690 | CD1 | TRP | A | 610 | −7.512 | −3.767 | −3.222 | 1.00 | 20.00 |
| ATOM | 691 | CD2 | TRP | A | 610 | −8.622 | −3.458 | −1.278 | 1.00 | 20.00 |
| ATOM | 692 | NE1 | TRP | A | 610 | −8.847 | −3.743 | −3.466 | 1.00 | 20.00 |
| ATOM | 693 | CE2 | TRP | A | 610 | −9.547 | −3.552 | −2.330 | 1.00 | 20.00 |
| ATOM | 694 | CE3 | TRP | A | 610 | −9.059 | −3.259 | 0.025 | 1.00 | 20.00 |
| ATOM | 695 | CZ2 | TRP | A | 610 | −10.900 | −3.436 | −2.068 | 1.00 | 20.00 |
| ATOM | 696 | CZ3 | TRP | A | 610 | −10.418 | −3.148 | 0.279 | 1.00 | 20.00 |
| ATOM | 697 | CH2 | TRP | A | 610 | −11.335 | −3.235 | −0.762 | 1.00 | 20.00 |
| ATOM | 698 | N | ARG | A | 611 | −4.156 | −6.131 | −1.756 | 1.00 | 20.00 |
| ATOM | 699 | CA | ARG | A | 611 | −3.861 | −7.238 | −2.668 | 1.00 | 20.00 |
| ATOM | 700 | C | ARG | A | 611 | −3.829 | −8.565 | −1.923 | 1.00 | 20.00 |
| ATOM | 701 | O | ARG | A | 611 | −4.278 | −9.580 | −2.467 | 1.00 | 20.00 |
| ATOM | 702 | CB | ARG | A | 611 | −2.519 | −7.006 | −3.348 | 1.00 | 20.00 |
| ATOM | 703 | CG | ARG | A | 611 | −2.552 | −5.803 | −4.281 | 1.00 | 20.00 |
| ATOM | 704 | CD | ARG | A | 611 | −1.201 | −5.612 | −4.954 | 1.00 | 20.00 |
| ATOM | 705 | NE | ARG | A | 611 | −0.138 | −5.503 | −3.943 | 1.00 | 20.00 |
| ATOM | 706 | CZ | ARG | A | 611 | 0.984 | −4.805 | −4.125 | 1.00 | 20.00 |
| ATOM | 707 | NH1 | ARG | A | 611 | 1.197 | −4.175 | −5.283 | 1.00 | 20.00 |
| ATOM | 708 | NH2 | ARG | A | 611 | 1.898 | −4.748 | −3.154 | 1.00 | 20.00 |
| ATOM | 727 | N | ARG | A | 614 | −7.642 | −9.259 | −1.472 | 1.00 | 20.00 |
| ATOM | 728 | CA | ARG | A | 614 | −8.243 | −9.807 | −2.687 | 1.00 | 20.00 |
| ATOM | 729 | C | ARG | A | 614 | −7.722 | −11.191 | −3.065 | 1.00 | 20.00 |
| ATOM | 730 | O | ARG | A | 614 | −8.480 | −12.164 | −2.979 | 1.00 | 20.00 |
| ATOM | 731 | CB | ARG | A | 614 | −7.982 | −8.840 | −3.834 | 1.00 | 20.00 |
| ATOM | 732 | CG | ARG | A | 614 | −8.818 | −7.576 | −3.688 | 1.00 | 20.00 |
| ATOM | 733 | CD | ARG | A | 614 | −10.305 | −7.915 | −3.709 | 1.00 | 20.00 |
| ATOM | 734 | NE | ARG | A | 614 | −11.140 | −6.705 | −3.660 | 1.00 | 20.00 |
| ATOM | 735 | CZ | ARG | A | 614 | −11.850 | −6.273 | −4.706 | 1.00 | 20.00 |
| ATOM | 736 | NH1 | ARG | A | 614 | −11.803 | −6.934 | −5.865 | 1.00 | 20.00 |
| ATOM | 737 | NH2 | ARG | A | 614 | −12.598 | −5.173 | −4.597 | 1.00 | 20.00 |
| ATOM | 738 | N | GLN | A | 615 | −6.423 | −11.316 | −3.284 | 1.00 | 20.00 |
| ATOM | 739 | CA | GLN | A | 615 | −5.898 | −12.536 | −3.912 | 1.00 | 20.00 |
| ATOM | 740 | C | GLN | A | 615 | −5.649 | −13.696 | −2.939 | 1.00 | 20.00 |
| ATOM | 741 | O | GLN | A | 615 | −5.544 | −14.844 | −3.387 | 1.00 | 20.00 |
| ATOM | 742 | CB | GLN | A | 615 | −4.608 | −12.166 | −4.650 | 1.00 | 20.00 |
| ATOM | 743 | CG | GLN | A | 615 | −4.148 | −13.276 | −5.595 | 1.00 | 20.00 |
| ATOM | 744 | CD | GLN | A | 615 | −2.882 | −12.878 | −6.352 | 1.00 | 20.00 |
| ATOM | 745 | OE1 | GLN | A | 615 | −2.647 | −11.698 | −6.641 | 1.00 | 20.00 |
| ATOM | 746 | NE2 | GLN | A | 615 | −2.103 | −13.886 | −6.702 | 1.00 | 20.00 |
| ATOM | 810 | N | PRO | A | 625 | 1.353 | −10.802 | −8.117 | 1.00 | 20.00 |
| ATOM | 811 | CA | PRO | A | 625 | 0.837 | −12.115 | −8.533 | 1.00 | 20.00 |
| ATOM | 812 | C | PRO | A | 625 | 1.938 | −13.187 | −8.632 | 1.00 | 20.00 |

TABLE III-continued

Structure Coordinates for Site II in Various NHRs
Based on the Consensus Alignments in FIG.2

| | | | | | | | | | | |
|---|---|---|---|---|---|---|---|---|---|---|
| ATOM | 813 | O | PRO | A | 625 | 1.677 | −14.360 | −8.344 | 1.00 | 20.00 |
| ATOM | 814 | CB | PRO | A | 625 | 0.196 | −11.871 | −9.866 | 1.00 | 20.00 |
| ATOM | 815 | CG | PRO | A | 625 | 0.452 | −10.433 | −10.295 | 1.00 | 20.00 |
| ATOM | 816 | CD | PRO | A | 625 | 1.237 | −9.785 | −9.168 | 1.00 | 20.00 |
| ATOM | 1129 | N | TYR | A | 663 | −11.805 | 2.057 | −0.132 | 1.00 | 20.00 |
| ATOM | 1130 | CA | TYR | A | 663 | −10.353 | 1.872 | −0.181 | 1.00 | 20.00 |
| ATOM | 1131 | C | TYR | A | 663 | −9.660 | 2.895 | −1.077 | 1.00 | 20.00 |
| ATOM | 1132 | O | TYR | A | 663 | −8.661 | 3.484 | −0.649 | 1.00 | 20.00 |
| ATOM | 1133 | CB | TYR | A | 663 | −10.054 | 0.473 | −0.710 | 1.00 | 20.00 |
| ATOM | 1134 | CG | TYR | A | 663 | −8.576 | 0.255 | −1.027 | 1.00 | 20.00 |
| ATOM | 1135 | CD1 | TYR | A | 663 | −7.664 | 0.076 | 0.005 | 1.00 | 20.00 |
| ATOM | 1136 | CD2 | TYR | A | 663 | −8.143 | 0.241 | −2.348 | 1.00 | 20.00 |
| ATOM | 1137 | CE1 | TYR | A | 663 | −6.318 | −0.101 | −0.284 | 1.00 | 20.00 |
| ATOM | 1138 | CE2 | TYR | A | 663 | −6.797 | 0.067 | −2.638 | 1.00 | 20.00 |
| ATOM | 1139 | CZ | TYR | A | 663 | −5.887 | −0.099 | −1.603 | 1.00 | 20.00 |
| ATOM | 1140 | OH | TYR | A | 663 | −4.550 | −0.263 | −1.885 | 1.00 | 20.00 |
| ATOM | 1141 | N | LEU | A | 664 | −10.297 | 3.279 | −2.170 | 1.00 | 20.00 |
| ATOM | 1142 | CA | LEU | A | 664 | −9.673 | 4.228 | −3.097 | 1.00 | 20.00 |
| ATOM | 1143 | C | LEU | A | 664 | −9.708 | 5.650 | −2.549 | 1.00 | 20.00 |
| ATOM | 1144 | O | LEU | A | 664 | −8.688 | 6.352 | −2.613 | 1.00 | 20.00 |
| ATOM | 1145 | CB | LEU | A | 664 | −10.414 | 4.173 | −4.432 | 1.00 | 20.00 |
| ATOM | 1146 | CG | LEU | A | 664 | −9.675 | 3.386 | −5.519 | 1.00 | 20.00 |
| ATOM | 1147 | CD1 | LEU | A | 664 | −9.285 | 1.975 | −5.097 | 1.00 | 20.00 |
| ATOM | 1148 | CD2 | LEU | A | 664 | −10.512 | 3.325 | −6.788 | 1.00 | 20.00 |
| ATOM | 1163 | N | LYS | A | 667 | −7.067 | 5.761 | 0.246 | 1.00 | 20.00 |
| ATOM | 1164 | CA | LYS | A | 667 | −5.708 | 5.727 | −0.288 | 1.00 | 20.00 |
| ATOM | 1165 | C | LYS | A | 667 | −5.292 | 7.076 | −0.870 | 1.00 | 20.00 |
| ATOM | 1166 | O | LYS | A | 667 | −4.158 | 7.509 | −0.631 | 1.00 | 20.00 |
| ATOM | 1167 | CB | LYS | A | 667 | −5.665 | 4.646 | −1.358 | 1.00 | 20.00 |
| ATOM | 1168 | CG | LYS | A | 667 | −4.275 | 4.476 | −1.961 | 1.00 | 20.00 |
| ATOM | 1169 | CD | LYS | A | 667 | −4.239 | 3.443 | −3.090 | 1.00 | 20.00 |
| ATOM | 1170 | CE | LYS | A | 667 | −4.633 | 4.000 | −4.463 | 1.00 | 20.00 |
| ATOM | 1171 | NZ | LYS | A | 667 | −6.057 | 4.359 | −4.580 | 1.00 | 20.00 |
| MR Homology Model Site II Residues (ref. MR_homo.pdb) (highlighted residues of SEQ ID NO:11) | | | | | | | | | | |
| ATOM | 88 | N | GLU | | 13 | 50.931 | 27.871 | 20.999 | 1.00 | 0.00 |
| ATOM | 89 | CA | GLU | | 13 | 50.817 | 29.290 | 20.819 | 1.00 | 0.00 |
| ATOM | 90 | CB | GLU | | 13 | 52.092 | 29.933 | 20.251 | 1.00 | 0.00 |
| ATOM | 91 | CG | GLU | | 13 | 52.003 | 31.458 | 20.153 | 1.00 | 0.00 |
| ATOM | 92 | CD | GLU | | 13 | 53.314 | 31.973 | 19.577 | 1.00 | 0.00 |
| ATOM | 93 | OE1 | GLU | | 13 | 54.151 | 31.126 | 19.165 | 1.00 | 0.00 |
| ATOM | 94 | OE2 | GLU | | 13 | 53.496 | 33.219 | 19.541 | 1.00 | 0.00 |
| ATOM | 95 | C | GLU | | 13 | 49.713 | 29.586 | 19.852 | 1.00 | 0.00 |
| ATOM | 96 | O | GLU | | 13 | 48.968 | 30.550 | 20.026 | 1.00 | 0.00 |
| ATOM | 97 | N | ASN | | 14 | 49.577 | 28.760 | 18.799 | 1.00 | 0.00 |
| ATOM | 98 | CA | ASN | | 14 | 48.615 | 29.036 | 17.770 | 1.00 | 0.00 |
| ATOM | 99 | CB | ASN | | 14 | 48.697 | 28.039 | 16.602 | 1.00 | 0.00 |
| ATOM | 100 | CG | ASN | | 14 | 47.913 | 28.622 | 15.435 | 1.00 | 0.00 |
| ATOM | 101 | OD1 | ASN | | 14 | 47.172 | 29.591 | 15.587 | 1.00 | 0.00 |
| ATOM | 102 | ND2 | ASN | | 14 | 48.079 | 28.011 | 14.231 | 1.00 | 0.00 |
| ATOM | 103 | C | ASN | | 14 | 47.213 | 28.992 | 18.312 | 1.00 | 0.00 |
| ATOM | 104 | O | ASN | | 14 | 46.392 | 29.849 | 17.996 | 1.00 | 0.00 |
| ATOM | 105 | N | ILE | | 15 | 46.916 | 27.976 | 19.141 | 1.00 | 0.00 |
| ATOM | 106 | CA | ILE | | 15 | 45.633 | 27.682 | 19.725 | 1.00 | 0.00 |
| ATOM | 107 | CB | ILE | | 15 | 45.577 | 26.305 | 20.331 | 1.00 | 0.00 |
| ATOM | 108 | CG2 | ILE | | 15 | 45.787 | 25.295 | 19.190 | 1.00 | 0.00 |
| ATOM | 109 | CG1 | ILE | | 15 | 46.580 | 26.147 | 21.485 | 1.00 | 0.00 |
| ATOM | 110 | CD1 | ILE | | 15 | 46.397 | 24.849 | 22.273 | 1.00 | 0.00 |
| ATOM | 111 | C | ILE | | 15 | 45.189 | 28.695 | 20.741 | 1.00 | 0.00 |
| ATOM | 112 | O | ILE | | 15 | 43.985 | 28.817 | 20.968 | 1.00 | 0.00 |
| ATOM | 113 | N | GLU | | 16 | 46.132 | 29.383 | 21.429 | 1.00 | 0.00 |
| ATOM | 114 | CA | GLU | | 16 | 45.791 | 30.312 | 22.480 | 1.00 | 0.00 |
| ATOM | 115 | CB | GLU | | 16 | 46.950 | 31.203 | 22.966 | 1.00 | 0.00 |
| ATOM | 116 | CG | GLU | | 16 | 47.969 | 30.501 | 23.864 | 1.00 | 0.00 |
| ATOM | 117 | CD | GLU | | 16 | 47.425 | 30.438 | 25.288 | 1.00 | 0.00 |
| ATOM | 118 | OE1 | GLU | | 16 | 47.568 | 31.446 | 26.032 | 1.00 | 0.00 |
| ATOM | 119 | OE2 | GLU | | 16 | 46.859 | 29.373 | 25.652 | 1.00 | 0.00 |
| ATOM | 120 | C | GLU | | 16 | 44.714 | 31.238 | 22.012 | 1.00 | 0.00 |
| ATOM | 121 | O | GLU | | 16 | 44.677 | 31.697 | 20.871 | 1.00 | 0.00 |
| ATOM | 122 | N | PRO | | 17 | 43.806 | 31.494 | 22.913 | 1.00 | 0.00 |
| ATOM | 123 | CA | PRO | | 17 | 42.694 | 32.337 | 22.590 | 1.00 | 0.00 |
| ATOM | 124 | CD | PRO | | 17 | 43.472 | 30.530 | 23.945 | 1.00 | 0.00 |
| ATOM | 125 | CB | PRO | | 17 | 41.611 | 32.034 | 23.608 | 1.00 | 0.00 |
| ATOM | 126 | CG | PRO | | 17 | 42.309 | 31.194 | 24.693 | 1.00 | 0.00 |
| ATOM | 127 | C | PRO | | 17 | 43.075 | 33.773 | 22.516 | 1.00 | 0.00 |

TABLE III-continued

Structure Coordinates for Site II in Various NHRs
Based on the Consensus Alignments in FIG.2

| ATOM | 128 | O | PRO | 17 | 44.063 | 34.167 | 23.133 | 1.00 | 0.00 |
|---|---|---|---|---|---|---|---|---|---|
| ATOM | 129 | N | GLU | 18 | 42.299 | 34.566 | 21.753 | 1.00 | 0.00 |
| ATOM | 130 | CA | GLU | 18 | 42.588 | 35.960 | 21.624 | 1.00 | 0.00 |
| ATOM | 131 | CB | GLU | 18 | 42.033 | 36.612 | 20.340 | 1.00 | 0.00 |
| ATOM | 132 | CG | GLU | 18 | 40.509 | 36.606 | 20.224 | 1.00 | 0.00 |
| ATOM | 133 | CD | GLU | 18 | 40.113 | 37.261 | 18.904 | 1.00 | 0.00 |
| ATOM | 134 | OE1 | GLU | 18 | 40.910 | 38.078 | 18.369 | 1.00 | 0.00 |
| ATOM | 135 | OE2 | GLU | 18 | 38.998 | 36.945 | 18.411 | 1.00 | 0.00 |
| ATOM | 136 | C | GLU | 18 | 42.029 | 36.646 | 22.830 | 1.00 | 0.00 |
| ATOM | 137 | O | GLU | 18 | 41.272 | 36.057 | 23.599 | 1.00 | 0.00 |
| ATOM | 138 | N | ILE | 19 | 42.420 | 37.916 | 23.039 | 1.00 | 0.00 |
| ATOM | 139 | CA | ILE | 19 | 41.997 | 38.627 | 24.209 | 1.00 | 0.00 |
| ATOM | 140 | CB | ILE | 19 | 42.419 | 40.062 | 24.273 | 1.00 | 0.00 |
| ATOM | 141 | CG2 | ILE | 19 | 41.512 | 40.845 | 23.311 | 1.00 | 0.00 |
| ATOM | 142 | CG1 | ILE | 19 | 42.331 | 40.567 | 25.722 | 1.00 | 0.00 |
| ATOM | 143 | CD1 | ILE | 19 | 43.339 | 39.889 | 26.650 | 1.00 | 0.00 |
| ATOM | 144 | C | ILE | 19 | 40.510 | 38.630 | 24.271 | 1.00 | 0.00 |
| ATOM | 145 | O | ILE | 19 | 39.822 | 38.676 | 23.253 | 1.00 | 0.00 |
| ATOM | 315 | N | LEU | 42 | 33.148 | 37.906 | 32.521 | 1.00 | 0.00 |
| ATOM | 316 | CA | LEU | 42 | 34.407 | 37.687 | 31.875 | 1.00 | 0.00 |
| ATOM | 317 | CB | LEU | 42 | 35.532 | 38.502 | 32.546 | 1.00 | 0.00 |
| ATOM | 318 | CG | LEU | 42 | 36.931 | 38.342 | 31.921 | 1.00 | 0.00 |
| ATOM | 319 | CD2 | LEU | 42 | 38.021 | 38.928 | 32.836 | 1.00 | 0.00 |
| ATOM | 320 | CD1 | LEU | 42 | 36.974 | 38.932 | 30.502 | 1.00 | 0.00 |
| ATOM | 321 | C | LEU | 42 | 34.735 | 36.234 | 32.024 | 1.00 | 0.00 |
| ATOM | 322 | O | LEU | 42 | 35.168 | 35.574 | 31.081 | 1.00 | 0.00 |
| ATOM | 323 | N | ALA | 43 | 34.488 | 35.691 | 33.229 | 1.00 | 0.00 |
| ATOM | 324 | CA | ALA | 43 | 34.795 | 34.322 | 33.518 | 1.00 | 0.00 |
| ATOM | 325 | CB | ALA | 43 | 34.435 | 33.917 | 34.957 | 1.00 | 0.00 |
| ATOM | 326 | C | ALA | 43 | 34.012 | 33.442 | 32.593 | 1.00 | 0.00 |
| ATOM | 327 | O | ALA | 43 | 34.530 | 32.444 | 32.096 | 1.00 | 0.00 |
| ATOM | 341 | N | GLN | 46 | 35.564 | 33.506 | 29.250 | 1.00 | 0.00 |
| ATOM | 342 | CA | GLN | 46 | 36.820 | 32.822 | 29.264 | 1.00 | 0.00 |
| ATOM | 343 | CB | GLN | 46 | 37.738 | 33.286 | 30.411 | 1.00 | 0.00 |
| ATOM | 344 | CG | GLN | 46 | 38.134 | 34.757 | 30.230 | 1.00 | 0.00 |
| ATOM | 345 | CD | GLN | 46 | 39.055 | 35.221 | 31.353 | 1.00 | 0.00 |
| ATOM | 346 | OE1 | GLN | 46 | 38.899 | 34.870 | 32.521 | 1.00 | 0.00 |
| ATOM | 347 | NE2 | GLN | 46 | 40.057 | 36.060 | 30.978 | 1.00 | 0.00 |
| ATOM | 348 | C | GLN | 46 | 36.587 | 31.343 | 29.341 | 1.00 | 0.00 |
| ATOM | 349 | O | GLN | 46 | 37.340 | 30.564 | 28.760 | 1.00 | 0.00 |
| ATOM | 350 | N | MET | 47 | 35.544 | 30.909 | 30.075 | 1.00 | 0.00 |
| ATOM | 351 | CA | MET | 47 | 35.276 | 29.502 | 30.196 | 1.00 | 0.00 |
| ATOM | 352 | CB | MET | 47 | 34.190 | 29.155 | 31.227 | 1.00 | 0.00 |
| ATOM | 353 | CG | MET | 47 | 34.688 | 29.305 | 32.667 | 1.00 | 0.00 |
| ATOM | 354 | SD | MET | 47 | 33.526 | 28.732 | 33.942 | 1.00 | 0.00 |
| ATOM | 355 | CE | MET | 47 | 32.462 | 30.200 | 33.859 | 1.00 | 0.00 |
| ATOM | 356 | C | MET | 47 | 34.895 | 28.928 | 28.863 | 1.00 | 0.00 |
| ATOM | 357 | O | MET | 47 | 35.288 | 27.809 | 28.537 | 1.00 | 0.00 |
| ATOM | 358 | N | ILE | 48 | 34.124 | 29.669 | 28.045 | 1.00 | 0.00 |
| ATOM | 359 | CA | ILE | 48 | 33.739 | 29.134 | 26.768 | 1.00 | 0.00 |
| ATOM | 360 | CB | ILE | 48 | 32.787 | 30.022 | 25.996 | 1.00 | 0.00 |
| ATOM | 361 | CG2 | ILE | 48 | 33.553 | 31.222 | 25.419 | 1.00 | 0.00 |
| ATOM | 362 | CG1 | ILE | 48 | 32.045 | 29.216 | 24.915 | 1.00 | 0.00 |
| ATOM | 363 | CD1 | ILE | 48 | 32.950 | 28.621 | 23.839 | 1.00 | 0.00 |
| ATOM | 364 | C | ILE | 48 | 35.001 | 28.931 | 25.985 | 1.00 | 0.00 |
| ATOM | 365 | O | ILE | 48 | 35.171 | 27.932 | 25.288 | 1.00 | 0.00 |
| ATOM | 366 | N | GLN | 49 | 35.934 | 29.887 | 26.124 | 1.00 | 0.00 |
| ATOM | 367 | CA | GLN | 49 | 37.205 | 29.941 | 25.465 | 1.00 | 0.00 |
| ATOM | 368 | CB | GLN | 49 | 37.951 | 31.181 | 25.969 | 1.00 | 0.00 |
| ATOM | 369 | CG | GLN | 49 | 39.382 | 31.319 | 25.491 | 1.00 | 0.00 |
| ATOM | 370 | CD | GLN | 49 | 39.948 | 32.566 | 26.158 | 1.00 | 0.00 |
| ATOM | 371 | OE1 | GLN | 49 | 40.213 | 33.581 | 25.516 | 1.00 | 0.00 |
| ATOM | 372 | NE2 | GLN | 49 | 40.130 | 32.488 | 27.504 | 1.00 | 0.00 |
| ATOM | 373 | C | GLN | 49 | 38.023 | 28.742 | 25.840 | 1.00 | 0.00 |
| ATOM | 374 | O | GLN | 49 | 38.668 | 28.133 | 24.987 | 1.00 | 0.00 |
| ATOM | 375 | N | VAL | 50 | 38.021 | 28.376 | 27.136 | 1.00 | 0.00 |
| ATOM | 376 | CA | VAL | 50 | 38.816 | 27.273 | 27.593 | 1.00 | 0.00 |
| ATOM | 377 | CB | VAL | 50 | 38.842 | 27.108 | 29.089 | 1.00 | 0.00 |
| ATOM | 378 | CG1 | VAL | 50 | 37.495 | 26.564 | 29.581 | 1.00 | 0.00 |
| ATOM | 379 | CG2 | VAL | 50 | 40.035 | 26.208 | 29.442 | 1.00 | 0.00 |
| ATOM | 380 | C | VAL | 50 | 38.308 | 26.008 | 26.980 | 1.00 | 0.00 |
| ATOM | 381 | O | VAL | 50 | 39.088 | 25.128 | 26.622 | 1.00 | 0.00 |
| ATOM | 382 | N | VAL | 51 | 36.976 | 25.875 | 26.849 | 1.00 | 0.00 |
| ATOM | 383 | CA | VAL | 51 | 36.414 | 24.678 | 26.294 | 1.00 | 0.00 |
| ATOM | 384 | CB | VAL | 51 | 34.912 | 24.692 | 26.305 | 1.00 | 0.00 |
| ATOM | 385 | CG1 | VAL | 51 | 34.404 | 23.377 | 25.692 | 1.00 | 0.00 |

TABLE III-continued

Structure Coordinates for Site II in Various NHRs
Based on the Consensus Alignments in FIG.2

| ATOM | 386 | CG2 | VAL | 51 | 34.430 | 24.941 | 27.746 | 1.00 | 0.00 |
|---|---|---|---|---|---|---|---|---|---|
| ATOM | 387 | C | VAL | 51 | 36.876 | 24.541 | 24.873 | 1.00 | 0.00 |
| ATOM | 388 | O | VAL | 51 | 37.293 | 23.464 | 24.449 | 1.00 | 0.00 |
| ATOM | 389 | N | LYS | 52 | 36.835 | 25.647 | 24.103 | 1.00 | 0.00 |
| ATOM | 390 | CA | LYS | 52 | 37.212 | 25.627 | 22.715 | 1.00 | 0.00 |
| ATOM | 391 | CB | LYS | 52 | 37.071 | 27.003 | 22.044 | 1.00 | 0.00 |
| ATOM | 392 | CG | LYS | 52 | 35.621 | 27.463 | 21.919 | 1.00 | 0.00 |
| ATOM | 393 | CD | LYS | 52 | 34.766 | 26.499 | 21.096 | 1.00 | 0.00 |
| ATOM | 394 | CE | LYS | 52 | 33.303 | 26.924 | 20.964 | 1.00 | 0.00 |
| ATOM | 395 | NZ | LYS | 52 | 32.566 | 25.933 | 20.150 | 1.00 | 0.00 |
| ATOM | 396 | C | LYS | 52 | 38.653 | 25.243 | 22.614 | 1.00 | 0.00 |
| ATOM | 397 | O | LYS | 52 | 39.040 | 24.430 | 21.776 | 1.00 | 0.00 |
| ATOM | 398 | N | TRP | 53 | 39.475 | 25.822 | 23.501 | 1.00 | 0.00 |
| ATOM | 399 | CA | TRP | 53 | 40.895 | 25.630 | 23.554 | 1.00 | 0.00 |
| ATOM | 400 | CB | TRP | 53 | 41.475 | 26.501 | 24.686 | 1.00 | 0.00 |
| ATOM | 401 | CG | TRP | 53 | 42.945 | 26.376 | 25.000 | 1.00 | 0.00 |
| ATOM | 402 | CD2 | TRP | 53 | 43.439 | 25.944 | 26.277 | 1.00 | 0.00 |
| ATOM | 403 | CD1 | TRP | 53 | 44.038 | 26.694 | 24.249 | 1.00 | 0.00 |
| ATOM | 404 | NE1 | TRP | 53 | 45.184 | 26.480 | 24.978 | 1.00 | 0.00 |
| ATOM | 405 | CE2 | TRP | 53 | 44.830 | 26.022 | 26.229 | 1.00 | 0.00 |
| ATOM | 406 | CE3 | TRP | 53 | 42.784 | 25.529 | 27.401 | 1.00 | 0.00 |
| ATOM | 407 | CZ2 | TRP | 53 | 45.593 | 25.682 | 27.310 | 1.00 | 0.00 |
| ATOM | 408 | CZ3 | TRP | 53 | 43.556 | 25.176 | 28.485 | 1.00 | 0.00 |
| ATOM | 409 | CH2 | TRP | 53 | 44.934 | 25.251 | 28.440 | 1.00 | 0.00 |
| ATOM | 410 | C | TRP | 53 | 41.189 | 24.182 | 23.822 | 1.00 | 0.00 |
| ATOM | 411 | O | TRP | 53 | 42.059 | 23.580 | 23.197 | 1.00 | 0.00 |
| ATOM | 581 | N | SER | 75 | 39.887 | 22.457 | 37.038 | 1.00 | 0.00 |
| ATOM | 582 | CA | SER | 75 | 40.947 | 23.398 | 36.753 | 1.00 | 0.00 |
| ATOM | 583 | CB | SER | 75 | 41.896 | 22.887 | 35.651 | 1.00 | 0.00 |
| ATOM | 584 | OG | SER | 75 | 41.214 | 22.807 | 34.408 | 1.00 | 0.00 |
| ATOM | 585 | C | SER | 75 | 40.579 | 24.808 | 36.360 | 1.00 | 0.00 |
| ATOM | 586 | O | SER | 75 | 41.475 | 25.646 | 36.275 | 1.00 | 0.00 |
| ATOM | 587 | N | TRP | 76 | 39.302 | 25.147 | 36.119 | 1.00 | 0.00 |
| ATOM | 588 | CA | TRP | 76 | 39.003 | 26.424 | 35.509 | 1.00 | 0.00 |
| ATOM | 589 | CB | TRP | 76 | 37.491 | 26.643 | 35.310 | 1.00 | 0.00 |
| ATOM | 590 | CG | TRP | 76 | 36.673 | 26.648 | 36.581 | 1.00 | 0.00 |
| ATOM | 591 | CD2 | TRP | 76 | 36.356 | 27.830 | 37.333 | 1.00 | 0.00 |
| ATOM | 592 | CD1 | TRP | 76 | 36.081 | 25.605 | 37.232 | 1.00 | 0.00 |
| ATOM | 593 | NE1 | TRP | 76 | 35.419 | 26.063 | 38.347 | 1.00 | 0.00 |
| ATOM | 594 | CE2 | TRP | 76 | 35.579 | 27.431 | 38.420 | 1.00 | 0.00 |
| ATOM | 595 | CE3 | TRP | 76 | 36.683 | 29.140 | 37.132 | 1.00 | 0.00 |
| ATOM | 596 | CZ2 | TRP | 76 | 35.116 | 28.340 | 39.328 | 1.00 | 0.00 |
| ATOM | 597 | CZ3 | TRP | 76 | 36.216 | 30.055 | 38.051 | 1.00 | 0.00 |
| ATOM | 598 | CH2 | TRP | 76 | 35.448 | 29.662 | 39.127 | 1.00 | 0.00 |
| ATOM | 599 | C | TRP | 76 | 39.550 | 27.596 | 36.285 | 1.00 | 0.00 |
| ATOM | 600 | O | TRP | 76 | 40.098 | 28.524 | 35.690 | 1.00 | 0.00 |
| ATOM | 601 | N | MET | 77 | 39.427 | 27.603 | 37.623 | 1.00 | 0.00 |
| ATOM | 602 | CA | MET | 77 | 39.884 | 28.723 | 38.406 | 1.00 | 0.00 |
| ATOM | 603 | CB | MET | 77 | 39.653 | 28.497 | 39.912 | 1.00 | 0.00 |
| ATOM | 604 | CG | MET | 77 | 39.840 | 29.734 | 40.795 | 1.00 | 0.00 |
| ATOM | 605 | SD | MET | 77 | 38.411 | 30.858 | 40.857 | 1.00 | 0.00 |
| ATOM | 606 | CE | MET | 77 | 38.558 | 31.470 | 39.157 | 1.00 | 0.00 |
| ATOM | 607 | C | MET | 77 | 41.366 | 28.887 | 38.235 | 1.00 | 0.00 |
| ATOM | 608 | O | MET | 77 | 41.867 | 30.002 | 38.088 | 1.00 | 0.00 |
| ATOM | 609 | N | CYS | 78 | 42.110 | 27.767 | 38.260 | 1.00 | 0.00 |
| ATOM | 610 | CA | CYS | 78 | 43.542 | 27.811 | 38.167 | 1.00 | 0.00 |
| ATOM | 611 | CB | CYS | 78 | 44.185 | 26.422 | 38.317 | 1.00 | 0.00 |
| ATOM | 612 | SG | CYS | 78 | 43.910 | 25.711 | 39.967 | 1.00 | 0.00 |
| ATOM | 613 | C | CYS | 78 | 43.946 | 28.365 | 36.836 | 1.00 | 0.00 |
| ATOM | 614 | O | CYS | 78 | 44.834 | 29.211 | 36.751 | 1.00 | 0.00 |
| ATOM | 615 | N | LEU | 79 | 43.293 | 27.914 | 35.752 | 1.00 | 0.00 |
| ATOM | 616 | CA | LEU | 79 | 43.663 | 28.371 | 34.443 | 1.00 | 0.00 |
| ATOM | 617 | CB | LEU | 79 | 42.854 | 27.695 | 33.325 | 1.00 | 0.00 |
| ATOM | 618 | CG | LEU | 79 | 43.171 | 26.200 | 33.156 | 1.00 | 0.00 |
| ATOM | 619 | CD2 | LEU | 79 | 44.680 | 25.969 | 32.963 | 1.00 | 0.00 |
| ATOM | 620 | CD1 | LEU | 79 | 42.332 | 25.587 | 32.025 | 1.00 | 0.00 |
| ATOM | 621 | C | LEU | 79 | 43.427 | 29.848 | 34.334 | 1.00 | 0.00 |
| ATOM | 622 | O | LEU | 79 | 44.252 | 30.571 | 33.778 | 1.00 | 0.00 |
| ATOM | 623 | N | SER | 80 | 42.289 | 30.340 | 34.856 | 1.00 | 0.00 |
| ATOM | 624 | CA | SER | 80 | 41.946 | 31.730 | 34.721 | 1.00 | 0.00 |
| ATOM | 625 | CB | SER | 80 | 40.522 | 32.041 | 35.214 | 1.00 | 0.00 |
| ATOM | 626 | OG | SER | 80 | 39.568 | 31.365 | 34.408 | 1.00 | 0.00 |
| ATOM | 627 | C | SER | 80 | 42.881 | 32.614 | 35.489 | 1.00 | 0.00 |
| ATOM | 628 | O | SER | 80 | 43.304 | 33.653 | 34.986 | 1.00 | 0.00 |
| ATOM | 629 | N | SER | 81 | 43.217 | 32.241 | 36.737 | 1.00 | 0.00 |
| ATOM | 630 | CA | SER | 81 | 44.062 | 33.086 | 37.536 | 1.00 | 0.00 |

TABLE III-continued

Structure Coordinates for Site II in Various NHRs
Based on the Consensus Alignments in FIG.2

| ATOM | 631 | CB | SER | 81 | 44.198 | 32.596 | 38.989 | 1.00 | 0.00 |
|---|---|---|---|---|---|---|---|---|---|
| ATOM | 632 | OG | SER | 81 | 45.043 | 33.471 | 39.720 | 1.00 | 0.00 |
| ATOM | 633 | C | SER | 81 | 45.428 | 33.117 | 36.926 | 1.00 | 0.00 |
| ATOM | 634 | O | SER | 81 | 46.124 | 34.129 | 36.980 | 1.00 | 0.00 |
| ATOM | 635 | N | PHE | 82 | 45.847 | 31.986 | 36.334 | 1.00 | 0.00 |
| ATOM | 636 | CA | PHE | 82 | 47.141 | 31.861 | 35.731 | 1.00 | 0.00 |
| ATOM | 637 | CB | PHE | 82 | 47.375 | 30.406 | 35.273 | 1.00 | 0.00 |
| ATOM | 638 | CG | PHE | 82 | 48.827 | 30.155 | 35.056 | 1.00 | 0.00 |
| ATOM | 639 | CD1 | PHE | 82 | 49.665 | 29.989 | 36.135 | 1.00 | 0.00 |
| ATOM | 640 | CD2 | PHE | 82 | 49.346 | 30.051 | 33.788 | 1.00 | 0.00 |
| ATOM | 641 | CE1 | PHE | 82 | 51.006 | 29.745 | 35.955 | 1.00 | 0.00 |
| ATOM | 642 | CE2 | PHE | 82 | 50.686 | 29.807 | 33.601 | 1.00 | 0.00 |
| ATOM | 643 | CZ | PHE | 82 | 51.518 | 29.656 | 34.684 | 1.00 | 0.00 |
| ATOM | 644 | C | PHE | 82 | 47.185 | 32.781 | 34.545 | 1.00 | 0.00 |
| ATOM | 645 | O | PHE | 82 | 48.177 | 33.473 | 34.316 | 1.00 | 0.00 |
| ATOM | 646 | N | ALA | 83 | 46.092 | 32.801 | 33.755 | 1.00 | 0.00 |
| ATOM | 647 | CA | ALA | 83 | 45.988 | 33.623 | 32.580 | 1.00 | 0.00 |
| ATOM | 648 | CB | ALA | 83 | 44.678 | 33.392 | 31.807 | 1.00 | 0.00 |
| ATOM | 649 | C | ALA | 83 | 46.026 | 35.065 | 32.978 | 1.00 | 0.00 |
| ATOM | 650 | O | ALA | 83 | 46.677 | 35.883 | 32.329 | 1.00 | 0.00 |
| ATOM | 665 | N | TRP | 86 | 49.445 | 36.147 | 33.580 | 1.00 | 0.00 |
| ATOM | 666 | CA | TRP | 86 | 50.241 | 36.360 | 32.408 | 1.00 | 0.00 |
| ATOM | 667 | CB | TRP | 86 | 50.115 | 35.246 | 31.363 | 1.00 | 0.00 |
| ATOM | 668 | CG | TRP | 86 | 51.048 | 35.483 | 30.206 | 1.00 | 0.00 |
| ATOM | 669 | CD2 | TRP | 86 | 52.475 | 35.422 | 30.336 | 1.00 | 0.00 |
| ATOM | 670 | CD1 | TRP | 86 | 50.790 | 35.860 | 28.920 | 1.00 | 0.00 |
| ATOM | 671 | NE1 | TRP | 86 | 51.972 | 36.024 | 28.236 | 1.00 | 0.00 |
| ATOM | 672 | CE2 | TRP | 86 | 53.017 | 35.763 | 29.098 | 1.00 | 0.00 |
| ATOM | 673 | CE3 | TRP | 86 | 53.268 | 35.120 | 31.407 | 1.00 | 0.00 |
| ATOM | 674 | CZ2 | TRP | 86 | 54.369 | 35.806 | 28.910 | 1.00 | 0.00 |
| ATOM | 675 | CZ3 | TRP | 86 | 54.629 | 35.153 | 31.211 | 1.00 | 0.00 |
| ATOM | 676 | CH2 | TRP | 86 | 55.169 | 35.489 | 29.986 | 1.00 | 0.00 |
| ATOM | 677 | C | TRP | 86 | 49.916 | 37.667 | 31.747 | 1.00 | 0.00 |
| ATOM | 678 | O | TRP | 86 | 50.815 | 38.401 | 31.343 | 1.00 | 0.00 |
| ATOM | 679 | N | ARG | 87 | 48.619 | 37.999 | 31.615 | 1.00 | 0.00 |
| ATOM | 680 | CA | ARG | 87 | 48.224 | 39.208 | 30.946 | 1.00 | 0.00 |
| ATOM | 681 | CB | ARG | 87 | 46.697 | 39.320 | 30.782 | 1.00 | 0.00 |
| ATOM | 682 | CG | ARG | 87 | 46.177 | 38.518 | 29.583 | 1.00 | 0.00 |
| ATOM | 683 | CD | ARG | 87 | 44.654 | 38.499 | 29.424 | 1.00 | 0.00 |
| ATOM | 684 | NE | ARG | 87 | 44.130 | 37.261 | 30.072 | 1.00 | 0.00 |
| ATOM | 685 | CZ | ARG | 87 | 43.828 | 37.222 | 31.403 | 1.00 | 0.00 |
| ATOM | 686 | NH1 | ARG | 87 | 44.048 | 38.310 | 32.193 | 1.00 | 0.00 |
| ATOM | 687 | NH2 | ARG | 87 | 43.301 | 36.089 | 31.951 | 1.00 | 0.00 |
| ATOM | 688 | C | ARG | 87 | 48.734 | 40.396 | 31.700 | 1.00 | 0.00 |
| ATOM | 689 | O | ARG | 87 | 49.153 | 41.387 | 31.106 | 1.00 | 0.00 |
| ATOM | 708 | N | LYS | 90 | 52.507 | 40.704 | 31.086 | 1.00 | 0.00 |
| ATOM | 709 | CA | LYS | 90 | 52.874 | 41.161 | 29.777 | 1.00 | 0.00 |
| ATOM | 710 | CB | LYS | 90 | 52.219 | 40.305 | 28.682 | 1.00 | 0.00 |
| ATOM | 711 | CG | LYS | 90 | 52.843 | 40.475 | 27.298 | 1.00 | 0.00 |
| ATOM | 712 | CD | LYS | 90 | 52.458 | 39.344 | 26.345 | 1.00 | 0.00 |
| ATOM | 713 | CE | LYS | 90 | 53.062 | 39.476 | 24.949 | 1.00 | 0.00 |
| ATOM | 714 | NZ | LYS | 90 | 52.710 | 38.287 | 24.142 | 1.00 | 0.00 |
| ATOM | 715 | C | LYS | 90 | 52.528 | 42.598 | 29.508 | 1.00 | 0.00 |
| ATOM | 716 | O | LYS | 90 | 53.366 | 43.358 | 29.023 | 1.00 | 0.00 |
| ATOM | 717 | N | HIS | 91 | 51.258 | 42.989 | 29.744 | 1.00 | 0.00 |
| ATOM | 718 | CA | HIS | 91 | 50.834 | 44.320 | 29.395 | 1.00 | 0.00 |
| ATOM | 719 | ND1 | HIS | 91 | 49.206 | 43.769 | 26.718 | 1.00 | 0.00 |
| ATOM | 720 | CG | HIS | 91 | 48.929 | 43.494 | 28.039 | 1.00 | 0.00 |
| ATOM | 721 | NE2 | HIS | 91 | 48.198 | 41.788 | 26.757 | 1.00 | 0.00 |
| ATOM | 722 | CD2 | HIS | 91 | 48.311 | 42.282 | 28.045 | 1.00 | 0.00 |
| ATOM | 723 | CE1 | HIS | 91 | 48.749 | 42.716 | 25.996 | 1.00 | 0.00 |
| ATOM | 724 | CB | HIS | 91 | 49.316 | 44.393 | 29.172 | 1.00 | 0.00 |
| ATOM | 725 | C | HIS | 91 | 51.233 | 45.390 | 30.369 | 1.00 | 0.00 |
| ATOM | 726 | O | HIS | 91 | 51.759 | 46.435 | 29.998 | 1.00 | 0.00 |
| ATOM | 804 | N | PRO | 101 | 41.024 | 44.104 | 28.674 | 1.00 | 0.00 |
| ATOM | 805 | CA | PRO | 101 | 41.382 | 45.430 | 28.240 | 1.00 | 0.00 |
| ATOM | 806 | CD | PRO | 101 | 40.297 | 43.370 | 27.648 | 1.00 | 0.00 |
| ATOM | 807 | CB | PRO | 101 | 41.182 | 45.423 | 26.725 | 1.00 | 0.00 |
| ATOM | 808 | CG | PRO | 101 | 40.064 | 44.385 | 26.520 | 1.00 | 0.00 |
| ATOM | 809 | C | PRO | 101 | 40.491 | 46.456 | 28.882 | 1.00 | 0.00 |
| ATOM | 810 | O | PRO | 101 | 40.960 | 47.552 | 29.183 | 1.00 | 0.00 |
| ATOM | 1122 | N | TYR | 139 | 55.206 | 29.212 | 29.912 | 1.00 | 0.00 |
| ATOM | 1123 | CA | TYR | 139 | 53.880 | 29.563 | 30.334 | 1.00 | 0.00 |
| ATOM | 1124 | CB | TYR | 139 | 53.601 | 31.034 | 29.953 | 1.00 | 0.00 |
| ATOM | 1125 | CG | TYR | 139 | 52.188 | 31.433 | 30.200 | 1.00 | 0.00 |
| ATOM | 1126 | CD1 | TYR | 139 | 51.726 | 31.666 | 31.474 | 1.00 | 0.00 |

TABLE III-continued

Structure Coordinates for Site II in Various NHRs
Based on the Consensus Alignments in FIG.2

| ATOM | 1127 | CD2 | TYR | | 139 | 51.332 | 31.609 | 29.138 | 1.00 | 0.00 |
|---|---|---|---|---|---|---|---|---|---|---|
| ATOM | 1128 | CE1 | TYR | | 139 | 50.420 | 32.046 | 31.682 | 1.00 | 0.00 |
| ATOM | 1129 | CE2 | TYR | | 139 | 50.027 | 31.990 | 29.338 | 1.00 | 0.00 |
| ATOM | 1130 | CZ | TYR | | 139 | 49.569 | 32.207 | 30.614 | 1.00 | 0.00 |
| ATOM | 1131 | OH | TYR | | 139 | 48.230 | 32.597 | 30.829 | 1.00 | 0.00 |
| ATOM | 1132 | C | TYR | | 139 | 52.877 | 28.666 | 29.665 | 1.00 | 0.00 |
| ATOM | 1133 | O | TYR | | 139 | 51.978 | 28.133 | 30.316 | 1.00 | 0.00 |
| ATOM | 1134 | N | THR | | 140 | 53.023 | 28.451 | 28.344 | 1.00 | 0.00 |
| ATOM | 1135 | CA | THR | | 140 | 52.065 | 27.679 | 27.603 | 1.00 | 0.00 |
| ATOM | 1136 | CB | THR | | 140 | 52.355 | 27.654 | 26.126 | 1.00 | 0.00 |
| ATOM | 1137 | OG1 | THR | | 140 | 51.289 | 27.029 | 25.427 | 1.00 | 0.00 |
| ATOM | 1138 | CG2 | THR | | 140 | 53.675 | 26.906 | 25.874 | 1.00 | 0.00 |
| ATOM | 1139 | C | THR | | 140 | 52.015 | 26.271 | 28.099 | 1.00 | 0.00 |
| ATOM | 1140 | O | THR | | 140 | 50.942 | 25.684 | 28.227 | 1.00 | 0.00 |
| ATOM | 1157 | N | LYS | | 143 | 50.485 | 26.019 | 31.567 | 1.00 | 0.00 |
| ATOM | 1158 | CA | LYS | | 143 | 49.063 | 26.209 | 31.513 | 1.00 | 0.00 |
| ATOM | 1159 | CB | LYS | | 143 | 48.652 | 27.022 | 30.271 | 1.00 | 0.00 |
| ATOM | 1160 | CG | LYS | | 143 | 48.857 | 28.531 | 30.349 | 1.00 | 0.00 |
| ATOM | 1161 | CD | LYS | | 143 | 47.776 | 29.256 | 31.147 | 1.00 | 0.00 |
| ATOM | 1162 | CE | LYS | | 143 | 46.693 | 29.859 | 30.247 | 1.00 | 0.00 |
| ATOM | 1163 | NZ | LYS | | 143 | 46.140 | 28.822 | 29.343 | 1.00 | 0.00 |
| ATOM | 1164 | C | LYS | | 143 | 48.410 | 24.876 | 31.309 | 1.00 | 0.00 |
| ATOM | 1165 | O | LYS | | 143 | 47.403 | 24.565 | 31.944 | 1.00 | 0.00 |

PPARgamma Site II Residues (ref. 2PRG.pdb)
(highlighted residues of SEQ ID NO:10)

| ATOM | 93 | N | TYR | A | 219 | 49.317 | −20.485 | 0.542 | 1.00 | 26.16 |
|---|---|---|---|---|---|---|---|---|---|---|
| ATOM | 94 | CA | TYR | A | 219 | 48.188 | −21.396 | 0.545 | 1.00 | 27.09 |
| ATOM | 95 | C | TYR | A | 219 | 48.474 | −22.592 | −0.357 | 1.00 | 28.21 |
| ATOM | 96 | O | TYR | A | 219 | 48.164 | −23.724 | 0.008 | 1.00 | 27.53 |
| ATOM | 97 | CB | TYR | A | 219 | 46.909 | −20.661 | 0.113 | 1.00 | 31.07 |
| ATOM | 98 | CG | TYR | A | 219 | 45.667 | −21.528 | 0.102 | 1.00 | 34.26 |
| ATOM | 99 | CD1 | TYR | A | 219 | 45.415 | −22.424 | 1.135 | 1.00 | 30.92 |
| ATOM | 100 | CD2 | TYR | A | 219 | 44.724 | −21.417 | −0.912 | 1.00 | 37.77 |
| ATOM | 101 | CE1 | TYR | A | 219 | 44.256 | −23.191 | 1.161 | 1.00 | 35.65 |
| ATOM | 102 | CE2 | TYR | A | 219 | 43.550 | −22.181 | −0.898 | 1.00 | 41.57 |
| ATOM | 103 | CZ | TYR | A | 219 | 43.328 | −23.066 | 0.144 | 1.00 | 38.33 |
| ATOM | 104 | OH | TYR | A | 219 | 42.188 | −23.837 | 0.171 | 1.00 | 42.57 |
| ATOM | 105 | N | ASP | A | 220 | 49.086 | −22.357 | −1.519 | 1.00 | 30.62 |
| ATOM | 106 | CA | ASP | A | 220 | 49.409 | −23.473 | −2.412 | 1.00 | 32.11 |
| ATOM | 107 | C | ASP | A | 220 | 50.414 | −24.436 | −1.797 | 1.00 | 28.77 |
| ATOM | 108 | O | ASP | A | 220 | 50.240 | −25.652 | −1.888 | 1.00 | 30.81 |
| ATOM | 109 | CB | ASP | A | 220 | 49.983 | −23.010 | −3.758 | 1.00 | 31.77 |
| ATOM | 110 | CG | ASP | A | 220 | 48.984 | −22.238 | −4.593 | 1.00 | 33.82 |
| ATOM | 111 | OD1 | ASP | A | 220 | 47.784 | −22.586 | −4.572 | 1.00 | 33.95 |
| ATOM | 112 | OD2 | ASP | A | 220 | 49.409 | −21.301 | −5.293 | 1.00 | 39.99 |
| ATOM | 113 | N | SER | A | 221 | 51.466 | −23.911 | −1.175 | 1.00 | 29.83 |
| ATOM | 114 | CA | SER | A | 221 | 52.467 | −24.800 | −0.597 | 1.00 | 32.70 |
| ATOM | 115 | C | SER | A | 221 | 51.877 | −25.501 | 0.616 | 1.00 | 28.79 |
| ATOM | 116 | O | SER | A | 221 | 52.251 | −26.623 | 0.938 | 1.00 | 31.65 |
| ATOM | 117 | CB | SER | A | 221 | 53.743 | −24.033 | −0.231 | 1.00 | 33.22 |
| ATOM | 118 | OG | SER | A | 221 | 53.502 | −23.093 | 0.784 | 1.00 | 42.80 |
| ATOM | 119 | N | TYR | A | 222 | 50.936 | −24.834 | 1.275 | 1.00 | 32.44 |
| ATOM | 120 | CA | TYR | A | 222 | 50.259 | −25.415 | 2.424 | 1.00 | 29.27 |
| ATOM | 121 | C | TYR | A | 222 | 49.438 | −26.592 | 1.910 | 1.00 | 31.32 |
| ATOM | 122 | O | TYR | A | 222 | 49.440 | −27.661 | 2.517 | 1.00 | 33.08 |
| ATOM | 123 | CB | TYR | A | 222 | 49.383 | −24.347 | 3.091 | 1.00 | 29.11 |
| ATOM | 124 | CG | TYR | A | 222 | 48.384 | −24.814 | 4.128 | 1.00 | 23.58 |
| ATOM | 125 | CD1 | TYR | A | 222 | 47.233 | −25.521 | 3.754 | 1.00 | 25.68 |
| ATOM | 126 | CD2 | TYR | A | 222 | 48.526 | −24.449 | 5.471 | 1.00 | 27.50 |
| ATOM | 127 | CE1 | TYR | A | 222 | 46.240 | −25.839 | 4.690 | 1.00 | 31.92 |
| ATOM | 128 | CE2 | TYR | A | 222 | 47.536 | −24.762 | 6.422 | 1.00 | 24.65 |
| ATOM | 129 | CZ | TYR | A | 222 | 46.394 | −25.452 | 6.022 | 1.00 | 30.90 |
| ATOM | 130 | OH | TYR | A | 222 | 45.392 | −25.716 | 6.937 | 1.00 | 31.36 |
| ATOM | 131 | N | ILE | A | 223 | 48.751 | −26.409 | 0.781 | 1.00 | 34.58 |
| ATOM | 132 | CA | ILE | A | 223 | 47.963 | −27.502 | 0.208 | 1.00 | 34.35 |
| ATOM | 133 | C | ILE | A | 223 | 48.866 | −28.678 | −0.144 | 1.00 | 35.22 |
| ATOM | 134 | O | ILE | A | 223 | 48.477 | −29.832 | 0.005 | 1.00 | 36.41 |
| ATOM | 135 | CB | ILE | A | 223 | 47.216 | −27.088 | −1.085 | 1.00 | 34.59 |
| ATOM | 136 | CG1 | ILE | A | 223 | 46.071 | −26.134 | −0.754 | 1.00 | 35.22 |
| ATOM | 137 | CG2 | ILE | A | 223 | 46.683 | −28.340 | −1.803 | 1.00 | 32.70 |
| ATOM | 138 | CD1 | ILE | A | 223 | 45.010 | −26.742 | 0.136 | 1.00 | 39.33 |
| ATOM | 139 | N | LYS | A | 224 | 50.073 | −28.380 | −0.619 | 1.00 | 36.65 |
| ATOM | 140 | CA | LYS | A | 224 | 51.011 | −29.434 | −0.989 | 1.00 | 38.16 |
| ATOM | 141 | C | LYS | A | 224 | 51.738 | −30.133 | 0.144 | 1.00 | 34.79 |
| ATOM | 142 | O | LYS | A | 224 | 52.132 | −31.284 | −0.013 | 1.00 | 35.05 |

TABLE III-continued

Structure Coordinates for Site II in Various NHRs
Based on the Consensus Alignments in FIG.2

| ATOM | 143 | CB | LYS | A | 224 | 52.058 | −28.914 | −1.974 | 1.00 | 40.32 |
|---|---|---|---|---|---|---|---|---|---|---|
| ATOM | 144 | CG | LYS | A | 224 | 51.555 | −28.828 | −3.407 | 1.00 | 50.64 |
| ATOM | 145 | CD | LYS | A | 224 | 52.713 | −28.647 | −4.382 | 1.00 | 58.74 |
| ATOM | 146 | CE | LYS | A | 224 | 52.248 | −28.792 | −5.826 | 1.00 | 58.38 |
| ATOM | 147 | NZ | LYS | A | 224 | 53.382 | −28.721 | −6.790 | 1.00 | 62.48 |
| ATOM | 148 | N | SER | A | 225 | 51.893 | −29.457 | 1.281 | 1.00 | 32.90 |
| ATOM | 149 | CA | SER | A | 225 | 52.631 | −30.012 | 2.416 | 1.00 | 32.12 |
| ATOM | 150 | C | SER | A | 225 | 51.796 | −30.776 | 3.433 | 1.00 | 33.07 |
| ATOM | 151 | O | SER | A | 225 | 52.283 | −31.713 | 4.066 | 1.00 | 34.52 |
| ATOM | 152 | CB | SER | A | 225 | 53.380 | −28.888 | 3.153 | 1.00 | 29.50 |
| ATOM | 153 | OG | SER | A | 225 | 54.250 | −28.179 | 2.287 | 1.00 | 36.10 |
| ATOM | 154 | N | PHE | A | 226 | 50.540 | −30.375 | 3.589 | 1.00 | 32.08 |
| ATOM | 155 | CA | PHE | A | 226 | 49.664 | −30.994 | 4.565 | 1.00 | 34.40 |
| ATOM | 156 | C | PHE | A | 226 | 48.522 | −31.784 | 3.935 | 1.00 | 39.63 |
| ATOM | 157 | O | PHE | A | 226 | 47.620 | −31.215 | 3.326 | 1.00 | 41.93 |
| ATOM | 158 | CB | PHE | A | 226 | 49.106 | −29.911 | 5.482 | 1.00 | 30.58 |
| ATOM | 159 | CG | PHE | A | 226 | 50.167 | −29.043 | 6.108 | 1.00 | 30.45 |
| ATOM | 160 | CD1 | PHE | A | 226 | 51.124 | −29.591 | 6.958 | 1.00 | 26.08 |
| ATOM | 161 | CD2 | PHE | A | 226 | 50.211 | −27.674 | 5.844 | 1.00 | 32.25 |
| ATOM | 162 | CE1 | PHE | A | 226 | 52.110 | −28.790 | 7.535 | 1.00 | 26.05 |
| ATOM | 163 | CE2 | PHE | A | 226 | 51.190 | −26.864 | 6.415 | 1.00 | 31.29 |
| ATOM | 164 | CZ | PHE | A | 226 | 52.141 | −27.423 | 7.261 | 1.00 | 33.33 |
| ATOM | 165 | N | PRO | A | 227 | 48.535 | −33.113 | 4.107 | 1.00 | 44.70 |
| ATOM | 166 | CA | PRO | A | 227 | 47.529 | −34.040 | 3.578 | 1.00 | 46.95 |
| ATOM | 167 | C | PRO | A | 227 | 46.124 | −33.753 | 4.093 | 1.00 | 45.50 |
| ATOM | 168 | O | PRO | A | 227 | 45.189 | −33.532 | 3.315 | 1.00 | 45.30 |
| ATOM | 169 | CB | PRO | A | 227 | 48.041 | −35.398 | 4.062 | 1.00 | 46.06 |
| ATOM | 170 | CG | PRO | A | 227 | 49.531 | −35.177 | 4.132 | 1.00 | 50.39 |
| ATOM | 171 | CD | PRO | A | 227 | 49.535 | −33.868 | 4.879 | 1.00 | 47.37 |
| ATOM | 650 | N | ARG | A | 288 | 53.071 | −39.607 | 15.013 | 1.00 | 47.42 |
| ATOM | 651 | CA | ARG | A | 288 | 52.383 | −38.698 | 14.108 | 1.00 | 46.07 |
| ATOM | 652 | C | ARG | A | 288 | 53.036 | −37.325 | 14.091 | 1.00 | 41.26 |
| ATOM | 653 | O | ARG | A | 288 | 52.933 | −36.595 | 13.111 | 1.00 | 39.85 |
| ATOM | 654 | CB | ARG | A | 288 | 50.905 | −38.573 | 14.496 | 1.00 | 50.86 |
| ATOM | 655 | CG | ARG | A | 288 | 50.176 | −37.445 | 13.773 | 1.00 | 59.11 |
| ATOM | 656 | CD | ARG | A | 288 | 50.362 | −37.533 | 12.261 | 1.00 | 65.80 |
| ATOM | 657 | NE | ARG | A | 288 | 50.009 | −36.275 | 11.608 | 1.00 | 71.79 |
| ATOM | 658 | CZ | ARG | A | 288 | 50.278 | −35.987 | 10.339 | 1.00 | 72.53 |
| ATOM | 659 | NH1 | ARG | A | 288 | 50.905 | −36.867 | 9.575 | 1.00 | 72.45 |
| ATOM | 660 | NH2 | ARG | A | 288 | 49.931 | −34.811 | 9.835 | 1.00 | 76.74 |
| ATOM | 661 | N | SER | A | 289 | 53.717 | −36.986 | 15.180 | 1.00 | 41.14 |
| ATOM | 662 | CA | SER | A | 289 | 54.394 | −35.702 | 15.296 | 1.00 | 38.47 |
| ATOM | 663 | C | SER | A | 289 | 55.675 | −35.710 | 14.463 | 1.00 | 38.98 |
| ATOM | 664 | O | SER | A | 289 | 56.054 | −34.694 | 13.884 | 1.00 | 38.45 |
| ATOM | 665 | CB | SER | A | 289 | 54.713 | −35.416 | 16.764 | 1.00 | 39.42 |
| ATOM | 666 | OG | SER | A | 289 | 55.352 | −34.163 | 16.909 | 1.00 | 46.15 |
| ATOM | 683 | N | ALA | A | 292 | 54.638 | −34.991 | 11.179 | 1.00 | 42.33 |
| ATOM | 684 | CA | ALA | A | 292 | 54.244 | −33.586 | 11.135 | 1.00 | 37.96 |
| ATOM | 685 | C | ALA | A | 292 | 55.461 | −32.669 | 10.999 | 1.00 | 36.30 |
| ATOM | 686 | O | ALA | A | 292 | 55.425 | −31.684 | 10.265 | 1.00 | 37.45 |
| ATOM | 687 | CB | ALA | A | 292 | 53.444 | −33.229 | 12.386 | 1.00 | 31.14 |
| ATOM | 688 | N | VAL | A | 293 | 56.541 | −32.993 | 11.703 | 1.00 | 37.86 |
| ATOM | 689 | CA | VAL | A | 293 | 57.759 | −32.189 | 11.631 | 1.00 | 35.96 |
| ATOM | 690 | C | VAL | A | 293 | 58.276 | −32.092 | 10.193 | 1.00 | 37.16 |
| ATOM | 691 | O | VAL | A | 293 | 58.750 | −31.044 | 9.753 | 1.00 | 39.01 |
| ATOM | 692 | CB | VAL | A | 293 | 58.875 | −32.795 | 12.503 | 1.00 | 32.38 |
| ATOM | 693 | CG1 | VAL | A | 293 | 60.176 | −32.003 | 12.320 | 1.00 | 30.77 |
| ATOM | 694 | CG2 | VAL | A | 293 | 58.447 | −32.798 | 13.951 | 1.00 | 32.30 |
| ATOM | 695 | N | GLN | A | 294 | 58.180 | −33.198 | 9.467 | 1.00 | 36.25 |
| ATOM | 696 | CA | GLN | A | 294 | 58.649 | −33.264 | 8.092 | 1.00 | 32.53 |
| ATOM | 697 | C | GLN | A | 294 | 57.780 | −32.457 | 7.133 | 1.00 | 29.89 |
| ATOM | 698 | O | GLN | A | 294 | 58.289 | −31.799 | 6.226 | 1.00 | 28.01 |
| ATOM | 699 | CB | GLN | A | 294 | 58.721 | −34.730 | 7.673 | 1.00 | 36.86 |
| ATOM | 700 | CG | GLN | A | 294 | 59.677 | −35.533 | 8.566 | 1.00 | 41.69 |
| ATOM | 701 | CD | GLN | A | 294 | 59.618 | −37.028 | 8.318 | 1.00 | 49.48 |
| ATOM | 702 | OE1 | GLN | A | 294 | 59.878 | −37.503 | 7.210 | 1.00 | 52.48 |
| ATOM | 703 | NE2 | GLN | A | 294 | 59.276 | −37.781 | 9.355 | 1.00 | 51.85 |
| ATOM | 704 | N | GLU | A | 295 | 56.473 | −32.495 | 7.342 | 1.00 | 26.58 |
| ATOM | 705 | CA | GLU | A | 295 | 55.545 | −31.756 | 6.498 | 1.00 | 29.65 |
| ATOM | 706 | C | GLU | A | 295 | 55.713 | −30.266 | 6.765 | 1.00 | 27.31 |
| ATOM | 707 | O | GLU | A | 295 | 55.750 | −29.461 | 5.834 | 1.00 | 28.65 |
| ATOM | 708 | CB | GLU | A | 295 | 54.105 | −32.164 | 6.816 | 1.00 | 31.76 |
| ATOM | 709 | CG | GLU | A | 295 | 53.894 | −33.662 | 6.874 | 1.00 | 41.29 |
| ATOM | 710 | CD | GLU | A | 295 | 52.489 | −34.037 | 7.311 | 1.00 | 43.08 |
| ATOM | 711 | OE1 | GLU | A | 295 | 51.992 | −33.456 | 8.296 | 1.00 | 49.49 |
| ATOM | 712 | OE2 | GLU | A | 295 | 51.888 | −34.931 | 6.685 | 1.00 | 52.62 |

TABLE III-continued

Structure Coordinates for Site II in Various NHRs
Based on the Consensus Alignments in FIG.2

| ATOM | 713 | N | ILE | A | 296 | 55.815 | −29.917 | 8.050 | 1.00 | 28.18 |
|---|---|---|---|---|---|---|---|---|---|---|
| ATOM | 714 | CA | ILE | A | 296 | 55.973 | −28.532 | 8.492 | 1.00 | 29.14 |
| ATOM | 715 | C | ILE | A | 296 | 57.293 | −27.927 | 8.036 | 1.00 | 30.82 |
| ATOM | 716 | O | ILE | A | 296 | 57.362 | −26.746 | 7.683 | 1.00 | 30.56 |
| ATOM | 717 | CB | ILE | A | 296 | 55.890 | −28.429 | 10.037 | 1.00 | 31.25 |
| ATOM | 718 | CG1 | ILE | A | 296 | 54.514 | −28.906 | 10.508 | 1.00 | 33.48 |
| ATOM | 719 | CG2 | ILE | A | 296 | 56.121 | −26.985 | 10.493 | 1.00 | 24.18 |
| ATOM | 720 | CD1 | ILE | A | 296 | 54.348 | −28.908 | 12.015 | 1.00 | 34.47 |
| ATOM | 721 | N | THR | A | 297 | 58.347 | −28.731 | 8.056 | 1.00 | 32.77 |
| ATOM | 722 | CA | THR | A | 297 | 59.648 | −28.249 | 7.625 | 1.00 | 29.52 |
| ATOM | 723 | C | THR | A | 297 | 59.612 | −27.944 | 6.136 | 1.00 | 29.40 |
| ATOM | 724 | O | THR | A | 297 | 60.193 | −26.961 | 5.679 | 1.00 | 27.20 |
| ATOM | 725 | CB | THR | A | 297 | 60.743 | −29.282 | 7.902 | 1.00 | 30.55 |
| ATOM | 726 | OG1 | THR | A | 297 | 60.900 | −29.435 | 9.321 | 1.00 | 31.64 |
| ATOM | 727 | CG2 | THR | A | 297 | 62.058 | −28.841 | 7.261 | 1.00 | 29.15 |
| ATOM | 728 | N | GLU | A | 298 | 58.926 | −28.792 | 5.381 | 1.00 | 31.50 |
| ATOM | 729 | CA | GLU | A | 298 | 58.810 | −28.571 | 3.950 | 1.00 | 34.95 |
| ATOM | 730 | C | GLU | A | 298 | 58.034 | −27.268 | 3.735 | 1.00 | 32.29 |
| ATOM | 731 | O | GLU | A | 298 | 58.417 | −26.426 | 2.927 | 1.00 | 33.09 |
| ATOM | 732 | CB | GLU | A | 298 | 58.079 | −29.735 | 3.287 | 1.00 | 37.99 |
| ATOM | 733 | CG | GLU | A | 298 | 58.301 | −29.782 | 1.791 | 1.00 | 53.91 |
| ATOM | 734 | CD | GLU | A | 298 | 59.779 | −29.915 | 1.438 | 1.00 | 58.00 |
| ATOM | 735 | OE1 | GLU | A | 298 | 60.409 | −30.919 | 1.837 | 1.00 | 66.07 |
| ATOM | 736 | OE2 | GLU | A | 298 | 60.312 | −29.006 | 0.766 | 1.00 | 65.07 |
| ATOM | 737 | N | TYR | A | 299 | 56.942 | −27.095 | 4.468 | 1.00 | 31.49 |
| ATOM | 738 | CA | TYR | A | 299 | 56.167 | −25.872 | 4.346 | 1.00 | 26.31 |
| ATOM | 739 | C | TYR | A | 299 | 57.009 | −24.654 | 4.704 | 1.00 | 27.39 |
| ATOM | 740 | O | TYR | A | 299 | 56.949 | −23.632 | 4.029 | 1.00 | 26.41 |
| ATOM | 741 | CB | TYR | A | 299 | 54.961 | −25.895 | 5.276 | 1.00 | 25.28 |
| ATOM | 742 | CG | TYR | A | 299 | 54.183 | −24.609 | 5.242 | 1.00 | 23.43 |
| ATOM | 743 | CD1 | TYR | A | 299 | 53.431 | −24.262 | 4.117 | 1.00 | 24.14 |
| ATOM | 744 | CD2 | TYR | A | 299 | 54.232 | −23.716 | 6.311 | 1.00 | 23.27 |
| ATOM | 745 | CE1 | TYR | A | 299 | 52.741 | −23.054 | 4.052 | 1.00 | 24.89 |
| ATOM | 746 | CE2 | TYR | A | 299 | 53.548 | −22.503 | 6.261 | 1.00 | 25.45 |
| ATOM | 747 | CZ | TYR | A | 299 | 52.806 | −22.183 | 5.126 | 1.00 | 25.47 |
| ATOM | 748 | OH | TYR | A | 299 | 52.139 | −20.991 | 5.058 | 1.00 | 29.93 |
| ATOM | 914 | N | GLY | A | 321 | 58.998 | −23.431 | 16.750 | 1.00 | 35.39 |
| ATOM | 915 | CA | GLY | A | 321 | 57.701 | −23.228 | 16.129 | 1.00 | 35.61 |
| ATOM | 916 | C | GLY | A | 321 | 56.938 | −24.471 | 15.728 | 1.00 | 33.20 |
| ATOM | 917 | O | GLY | A | 321 | 55.727 | −24.409 | 15.520 | 1.00 | 36.84 |
| ATOM | 918 | N | VAL | A | 322 | 57.620 | −25.604 | 15.623 | 1.00 | 32.05 |
| ATOM | 919 | CA | VAL | A | 322 | 56.942 | −26.823 | 15.208 | 1.00 | 32.49 |
| ATOM | 920 | C | VAL | A | 322 | 55.750 | −27.232 | 16.070 | 1.00 | 31.08 |
| ATOM | 921 | O | VAL | A | 322 | 54.695 | −27.574 | 15.536 | 1.00 | 36.08 |
| ATOM | 922 | CB | VAL | A | 322 | 57.929 | −28.011 | 15.101 | 1.00 | 37.63 |
| ATOM | 923 | CG1 | VAL | A | 322 | 57.163 | −29.314 | 14.889 | 1.00 | 42.68 |
| ATOM | 924 | CG2 | VAL | A | 322 | 58.851 | −27.796 | 13.912 | 1.00 | 38.13 |
| ATOM | 925 | N | HIS | A | 323 | 55.891 | −27.207 | 17.389 | 1.00 | 30.11 |
| ATOM | 926 | CA | HIS | A | 323 | 54.754 | −27.604 | 18.207 | 1.00 | 31.92 |
| ATOM | 927 | C | HIS | A | 323 | 53.594 | −26.624 | 18.194 | 1.00 | 29.54 |
| ATOM | 928 | O | HIS | A | 323 | 52.441 | −27.041 | 18.240 | 1.00 | 27.50 |
| ATOM | 929 | CB | HIS | A | 323 | 55.172 | −27.914 | 19.647 | 1.00 | 30.61 |
| ATOM | 930 | CG | HIS | A | 323 | 55.918 | −29.203 | 19.778 | 1.00 | 34.26 |
| ATOM | 931 | ND1 | HIS | A | 323 | 57.291 | −29.267 | 19.870 | 1.00 | 37.08 |
| ATOM | 932 | CD2 | HIS | A | 323 | 55.481 | −30.487 | 19.767 | 1.00 | 36.78 |
| ATOM | 933 | CE1 | HIS | A | 323 | 57.669 | −30.533 | 19.909 | 1.00 | 37.36 |
| ATOM | 934 | NE2 | HIS | A | 323 | 56.590 | −31.293 | 19.847 | 1.00 | 34.75 |
| ATOM | 935 | N | GLU | A | 324 | 53.888 | −25.329 | 18.119 | 1.00 | 30.21 |
| ATOM | 936 | CA | GLU | A | 324 | 52.819 | −24.340 | 18.084 | 1.00 | 27.19 |
| ATOM | 937 | C | GLU | A | 324 | 51.993 | −24.567 | 16.818 | 1.00 | 28.15 |
| ATOM | 938 | O | GLU | A | 324 | 50.788 | −24.324 | 16.797 | 1.00 | 28.90 |
| ATOM | 939 | CB | GLU | A | 324 | 53.397 | −22.923 | 18.099 | 1.00 | 24.17 |
| ATOM | 940 | CG | GLU | A | 324 | 54.104 | −22.559 | 19.399 | 1.00 | 26.67 |
| ATOM | 941 | CD | GLU | A | 324 | 54.720 | −21.166 | 19.374 | 1.00 | 29.48 |
| ATOM | 942 | OE1 | GLU | A | 324 | 54.533 | −20.423 | 18.386 | 1.00 | 32.08 |
| ATOM | 943 | OE2 | GLU | A | 324 | 55.401 | −20.808 | 20.353 | 1.00 | 29.74 |
| ATOM | 944 | N | ILE | A | 325 | 52.650 | −25.040 | 15.764 | 1.00 | 29.34 |
| ATOM | 945 | CA | ILE | A | 325 | 51.969 | −25.305 | 14.505 | 1.00 | 27.95 |
| ATOM | 946 | C | ILE | A | 325 | 51.235 | −26.637 | 14.552 | 1.00 | 27.21 |
| ATOM | 947 | O | ILE | A | 325 | 50.156 | −26.777 | 13.980 | 1.00 | 26.67 |
| ATOM | 948 | CB | ILE | A | 325 | 52.963 | −25.308 | 13.319 | 1.00 | 29.47 |
| ATOM | 949 | CG1 | ILE | A | 325 | 53.570 | −23.910 | 13.169 | 1.00 | 31.96 |
| ATOM | 950 | CG2 | ILE | A | 325 | 52.259 | −25.746 | 12.023 | 1.00 | 26.17 |
| ATOM | 951 | CD1 | ILE | A | 325 | 54.519 | −23.798 | 12.016 | 1.00 | 36.43 |
| ATOM | 952 | N | ILE | A | 326 | 51.814 | −27.620 | 15.236 | 1.00 | 26.54 |
| ATOM | 953 | CA | ILE | A | 326 | 51.157 | −28.914 | 15.339 | 1.00 | 28.11 |

TABLE III-continued

Structure Coordinates for Site II in Various NHRs
Based on the Consensus Alignments in FIG. 2

| ATOM | 954 | C | ILE | A | 326 | 49.825 | −28.743 | 16.057 | 1.00 | 29.17 |
|---|---|---|---|---|---|---|---|---|---|---|
| ATOM | 955 | O | ILE | A | 326 | 48.798 | −29.274 | 15.626 | 1.00 | 29.80 |
| ATOM | 956 | CB | ILE | A | 326 | 52.015 | −29.929 | 16.118 | 1.00 | 33.05 |
| ATOM | 957 | CG1 | ILE | A | 326 | 53.267 | −30.281 | 15.306 | 1.00 | 31.62 |
| ATOM | 958 | CG2 | ILE | A | 326 | 51.185 | −31.184 | 16.445 | 1.00 | 27.50 |
| ATOM | 959 | CD1 | ILE | A | 326 | 54.192 | −31.278 | 15.993 | 1.00 | 29.00 |
| ATOM | 960 | N | TYR | A | 327 | 49.836 | −27.981 | 17.145 | 1.00 | 29.50 |
| ATOM | 961 | CA | TYR | A | 327 | 48.620 | −27.779 | 17.918 | 1.00 | 30.34 |
| ATOM | 962 | C | TYR | A | 327 | 47.612 | −26.890 | 17.221 | 1.00 | 32.40 |
| ATOM | 963 | O | TYR | A | 327 | 46.413 | −26.984 | 17.487 | 1.00 | 32.56 |
| ATOM | 964 | CB | TYR | A | 327 | 48.967 | −27.246 | 19.310 | 1.00 | 29.71 |
| ATOM | 965 | CG | TYR | A | 327 | 49.845 | −28.208 | 20.082 | 1.00 | 27.91 |
| ATOM | 966 | CD1 | TYR | A | 327 | 49.495 | −29.554 | 20.202 | 1.00 | 36.87 |
| ATOM | 967 | CD2 | TYR | A | 327 | 51.028 | −27.786 | 20.673 | 1.00 | 34.57 |
| ATOM | 968 | CE1 | TYR | A | 327 | 50.312 | −30.457 | 20.896 | 1.00 | 39.01 |
| ATOM | 969 | CE2 | TYR | A | 327 | 51.850 | −28.677 | 21.369 | 1.00 | 35.00 |
| ATOM | 970 | CZ | TYR | A | 327 | 51.488 | −30.007 | 21.476 | 1.00 | 37.53 |
| ATOM | 971 | OH | TYR | A | 327 | 52.289 | −30.885 | 22.176 | 1.00 | 43.90 |
| ATOM | 972 | N | THR | A | 328 | 48.097 | −26.033 | 16.321 | 1.00 | 33.44 |
| ATOM | 973 | CA | THR | A | 328 | 47.217 | −25.159 | 15.556 | 1.00 | 27.97 |
| ATOM | 974 | C | THR | A | 328 | 46.500 | −26.030 | 14.526 | 1.00 | 28.13 |
| ATOM | 975 | O | THR | A | 328 | 45.289 | −25.925 | 14.341 | 1.00 | 28.36 |
| ATOM | 976 | CB | THR | A | 328 | 48.015 | −24.062 | 14.803 | 1.00 | 31.65 |
| ATOM | 977 | OG1 | THR | A | 328 | 48.614 | −23.166 | 15.749 | 1.00 | 34.24 |
| ATOM | 978 | CG2 | THR | A | 328 | 47.100 | −23.279 | 13.857 | 1.00 | 28.42 |
| ATOM | 979 | N | MET | A | 329 | 47.268 | −26.894 | 13.866 | 1.00 | 26.24 |
| ATOM | 980 | CA | MET | A | 329 | 46.740 | −27.792 | 12.841 | 1.00 | 28.47 |
| ATOM | 981 | C | MET | A | 329 | 45.831 | −28.853 | 13.461 | 1.00 | 30.21 |
| ATOM | 982 | O | MET | A | 329 | 44.822 | −29.251 | 12.867 | 1.00 | 29.30 |
| ATOM | 983 | CB | MET | A | 329 | 47.893 | −28.484 | 12.097 | 1.00 | 31.16 |
| ATOM | 984 | CG | MET | A | 329 | 48.870 | −27.530 | 11.390 | 1.00 | 40.71 |
| ATOM | 985 | SD | MET | A | 329 | 48.138 | −26.605 | 10.026 | 1.00 | 47.88 |
| ATOM | 986 | CE | MET | A | 329 | 47.820 | −27.914 | 8.823 | 1.00 | 46.75 |
| ATOM | 1000 | N | SER | A | 332 | 42.137 | −28.210 | 13.823 | 1.00 | 33.69 |
| ATOM | 1001 | CA | SER | A | 332 | 41.327 | −28.455 | 12.634 | 1.00 | 31.46 |
| ATOM | 1002 | C | SER | A | 332 | 40.688 | −29.850 | 12.678 | 1.00 | 34.05 |
| ATOM | 1003 | O | SER | A | 332 | 39.633 | −30.071 | 12.093 | 1.00 | 36.02 |
| ATOM | 1004 | CB | SER | A | 332 | 42.180 | −28.342 | 11.355 | 1.00 | 32.80 |
| ATOM | 1005 | OG | SER | A | 332 | 42.678 | −27.026 | 11.143 | 1.00 | 34.02 |
| ATOM | 1006 | N | LEU | A | 333 | 41.326 | −30.786 | 13.375 | 1.00 | 31.60 |
| ATOM | 1007 | CA | LEU | A | 333 | 40.827 | −32.157 | 13.445 | 1.00 | 35.66 |
| ATOM | 1008 | C | LEU | A | 333 | 39.978 | −32.399 | 14.688 | 1.00 | 33.42 |
| ATOM | 1009 | O | LEU | A | 333 | 39.483 | −33.504 | 14.909 | 1.00 | 38.08 |
| ATOM | 1010 | CB | LEU | A | 333 | 42.009 | −33.136 | 13.436 | 1.00 | 33.49 |
| ATOM | 1011 | CG | LEU | A | 333 | 43.111 | −32.826 | 12.407 | 1.00 | 39.04 |
| ATOM | 1012 | CD1 | LEU | A | 333 | 44.221 | −33.875 | 12.471 | 1.00 | 30.81 |
| ATOM | 1013 | CD2 | LEU | A | 333 | 42.513 | −32.777 | 11.024 | 1.00 | 34.79 |
| ATOM | 1022 | N | ASN | A | 335 | 36.759 | −31.278 | 17.509 | 1.00 | 37.06 |
| ATOM | 1023 | CA | ASN | A | 335 | 35.499 | −30.613 | 17.799 | 1.00 | 34.66 |
| ATOM | 1024 | C | ASN | A | 335 | 35.479 | −30.749 | 19.317 | 1.00 | 37.43 |
| ATOM | 1025 | O | ASN | A | 335 | 36.424 | −31.309 | 19.896 | 1.00 | 36.55 |
| ATOM | 1026 | CB | ASN | A | 335 | 34.268 | −31.269 | 17.141 | 1.00 | 36.33 |
| ATOM | 1027 | CG | ASN | A | 335 | 34.033 | −32.694 | 17.578 | 1.00 | 33.81 |
| ATOM | 1028 | OD1 | ASN | A | 335 | 34.175 | −33.041 | 18.750 | 1.00 | 39.06 |
| ATOM | 1029 | ND2 | ASN | A | 335 | 33.625 | −33.526 | 16.635 | 1.00 | 41.11 |
| ATOM | 1030 | N | LYS | A | 336 | 34.438 | −30.251 | 19.973 | 1.00 | 40.23 |
| ATOM | 1031 | CA | LYS | A | 336 | 34.385 | −30.315 | 21.431 | 1.00 | 43.15 |
| ATOM | 1032 | C | LYS | A | 336 | 34.401 | −31.726 | 22.021 | 1.00 | 43.02 |
| ATOM | 1033 | O | LYS | A | 336 | 34.794 | −31.908 | 23.177 | 1.00 | 44.52 |
| ATOM | 1034 | CB | LYS | A | 336 | 33.144 | −29.579 | 21.951 | 1.00 | 49.47 |
| ATOM | 1035 | CG | LYS | A | 336 | 31.832 | −30.233 | 21.565 | 1.00 | 56.12 |
| ATOM | 1036 | CD | LYS | A | 336 | 30.654 | −29.497 | 22.174 | 1.00 | 63.31 |
| ATOM | 1037 | CE | LYS | A | 336 | 29.347 | −30.208 | 21.859 | 1.00 | 68.69 |
| ATOM | 1038 | NZ | LYS | A | 336 | 28.183 | −29.551 | 22.517 | 1.00 | 72.75 |
| ATOM | 1080 | N | GLU | A | 343 | 44.675 | −40.220 | 9.810 | 1.00 | 50.51 |
| ATOM | 1081 | CA | GLU | A | 343 | 44.295 | −39.491 | 8.604 | 1.00 | 51.89 |
| ATOM | 1082 | C | GLU | A | 343 | 42.791 | −39.468 | 8.328 | 1.00 | 50.95 |
| ATOM | 1083 | O | GLU | A | 343 | 42.363 | −39.622 | 7.184 | 1.00 | 50.39 |
| ATOM | 1084 | CB | GLU | A | 343 | 45.027 | −40.082 | 7.397 | 1.00 | 59.73 |
| ATOM | 1085 | CG | GLU | A | 343 | 46.541 | −40.019 | 7.508 | 1.00 | 68.39 |
| ATOM | 1086 | CD | GLU | A | 343 | 47.240 | −40.616 | 6.302 | 1.00 | 76.46 |
| ATOM | 1087 | OE1 | GLU | A | 343 | 47.070 | −41.832 | 6.049 | 1.00 | 78.36 |
| ATOM | 1088 | OE2 | GLU | A | 343 | 47.959 | −39.865 | 5.605 | 1.00 | 79.29 |
| ATOM | 1419 | N | LEU | A | 384 | 44.818 | −20.042 | 7.630 | 1.00 | 27.46 |
| ATOM | 1420 | CA | LEU | A | 384 | 45.776 | −20.800 | 8.417 | 1.00 | 27.85 |
| ATOM | 1421 | C | LEU | A | 384 | 47.169 | −20.825 | 7.787 | 1.00 | 28.31 |

TABLE III-continued

Structure Coordinates for Site II in Various NHRs
Based on the Consensus Alignments in FIG.2

| ATOM | 1422 | O | LEU | A | 384 | 48.173 | −20.663 | 8.478 | 1.00 | 27.17 |
|---|---|---|---|---|---|---|---|---|---|---|
| ATOM | 1423 | CB | LEU | A | 384 | 45.259 | −22.228 | 8.617 | 1.00 | 25.10 |
| ATOM | 1424 | CG | LEU | A | 384 | 43.996 | −22.358 | 9.483 | 1.00 | 28.35 |
| ATOM | 1425 | CD1 | LEU | A | 384 | 43.482 | −23.776 | 9.427 | 1.00 | 25.74 |
| ATOM | 1426 | CD2 | LEU | A | 384 | 44.306 | −21.947 | 10.934 | 1.00 | 24.70 |
| ATOM | 1427 | N | ALA | A | 385 | 47.237 | −21.012 | 6.474 | 1.00 | 28.77 |
| ATOM | 1428 | CA | ALA | A | 385 | 48.541 | −21.054 | 5.815 | 1.00 | 28.21 |
| ATOM | 1429 | C | ALA | A | 385 | 49.392 | −19.832 | 6.154 | 1.00 | 23.50 |
| ATOM | 1430 | O | ALA | A | 385 | 50.584 | −19.968 | 6.393 | 1.00 | 28.41 |
| ATOM | 1431 | CB | ALA | A | 385 | 48.373 | −21.184 | 4.316 | 1.00 | 22.62 |
| ATOM | 1451 | N | ILE | A | 388 | 50.323 | −19.739 | 10.091 | 1.00 | 25.45 |
| ATOM | 1452 | CA | ILE | A | 388 | 51.389 | −20.683 | 10.388 | 1.00 | 25.58 |
| ATOM | 1453 | C | ILE | A | 388 | 52.741 | −20.079 | 10.026 | 1.00 | 23.26 |
| ATOM | 1454 | O | ILE | A | 388 | 53.724 | −20.295 | 10.720 | 1.00 | 30.01 |
| ATOM | 1455 | CB | ILE | A | 388 | 51.169 | −22.004 | 9.601 | 1.00 | 29.97 |
| ATOM | 1456 | CG1 | ILE | A | 388 | 49.853 | −22.647 | 10.042 | 1.00 | 38.36 |
| ATOM | 1457 | CG2 | ILE | A | 388 | 52.316 | −22.947 | 9.804 | 1.00 | 36.50 |
| ATOM | 1458 | CD1 | ILE | A | 388 | 49.736 | −22.823 | 11.518 | 1.00 | 31.88 |
| | | | PR Site II Residues (ref. 1A28.pdb) | | | | | | | |
| | | | (highlighted residues of SEQ ID NO:5) | | | | | | | |
| ATOM | 76 | N | MET | A | 692 | 27.562 | 5.259 | 83.253 | 1.00 | 24.62 |
| ATOM | 77 | CA | MET | A | 692 | 26.351 | 4.476 | 83.019 | 1.00 | 27.60 |
| ATOM | 78 | C | MET | A | 692 | 25.156 | 5.337 | 83.440 | 1.00 | 27.94 |
| ATOM | 79 | O | MET | A | 692 | 24.145 | 5.416 | 82.745 | 1.00 | 25.86 |
| ATOM | 80 | CB | MET | A | 692 | 26.385 | 3.195 | 83.860 | 1.00 | 27.45 |
| ATOM | 81 | CG | MET | A | 692 | 25.197 | 2.289 | 83.686 | 1.00 | 39.52 |
| ATOM | 82 | SD | MET | A | 692 | 25.017 | 1.642 | 82.004 | 1.00 | 51.06 |
| ATOM | 83 | CE | MET | A | 692 | 24.268 | 3.029 | 81.134 | 1.00 | 52.36 |
| ATOM | 84 | N | SER | A | 693 | 25.296 | 6.010 | 84.574 | 1.00 | 25.24 |
| ATOM | 85 | CA | SER | A | 693 | 24.216 | 6.835 | 85.083 | 1.00 | 31.97 |
| ATOM | 86 | C | SER | A | 693 | 23.878 | 8.044 | 84.219 | 1.00 | 29.88 |
| ATOM | 87 | O | SER | A | 693 | 22.719 | 8.455 | 84.157 | 1.00 | 28.14 |
| ATOM | 88 | CB | SER | A | 693 | 24.531 | 7.313 | 86.508 | 1.00 | 38.05 |
| ATOM | 89 | OG | SER | A | 693 | 25.623 | 8.222 | 86.526 | 1.00 | 43.01 |
| ATOM | 90 | N | ILE | A | 694 | 24.865 | 8.625 | 83.547 | 1.00 | 25.23 |
| ATOM | 91 | CA | ILE | A | 694 | 24.553 | 9.808 | 82.741 | 1.00 | 26.22 |
| ATOM | 92 | C | ILE | A | 694 | 24.257 | 9.520 | 81.279 | 1.00 | 23.06 |
| ATOM | 93 | O | ILE | A | 694 | 24.031 | 10.442 | 80.504 | 1.00 | 24.41 |
| ATOM | 94 | CB | ILE | A | 694 | 25.669 | 10.875 | 82.813 | 1.00 | 22.83 |
| ATOM | 95 | CG1 | ILE | A | 694 | 26.984 | 10.307 | 82.265 | 1.00 | 22.20 |
| ATOM | 96 | CG2 | ILE | A | 694 | 25.849 | 11.338 | 84.270 | 1.00 | 28.20 |
| ATOM | 97 | CD1 | ILE | A | 694 | 28.060 | 11.373 | 82.014 | 1.00 | 22.62 |
| ATOM | 98 | N | GLU | A | 695 | 24.257 | 8.242 | 80.899 | 1.00 | 26.89 |
| ATOM | 99 | CA | GLU | A | 695 | 23.969 | 7.876 | 79.517 | 1.00 | 21.93 |
| ATOM | 100 | C | GLU | A | 695 | 22.511 | 8.296 | 79.289 | 1.00 | 28.96 |
| ATOM | 101 | O | GLU | A | 695 | 21.632 | 7.992 | 80.087 | 1.00 | 29.21 |
| ATOM | 102 | CB | GLU | A | 695 | 24.150 | 6.362 | 79.338 | 1.00 | 34.17 |
| ATOM | 103 | CG | GLU | A | 695 | 24.063 | 5.848 | 77.911 | 1.00 | 34.86 |
| ATOM | 104 | CD | GLU | A | 695 | 25.240 | 6.232 | 77.021 | 1.00 | 45.46 |
| ATOM | 105 | OE1 | GLU | A | 695 | 26.126 | 7.019 | 77.436 | 1.00 | 31.19 |
| ATOM | 106 | OE2 | GLU | A | 695 | 25.275 | 5.730 | 75.873 | 1.00 | 49.30 |
| ATOM | 107 | N | PRO | A | 696 | 22.242 | 9.037 | 78.215 | 1.00 | 32.33 |
| ATOM | 108 | CA | PRO | A | 696 | 20.865 | 9.469 | 77.961 | 1.00 | 34.70 |
| ATOM | 109 | C | PRO | A | 696 | 19.862 | 8.330 | 77.764 | 1.00 | 30.39 |
| ATOM | 110 | O | PRO | A | 696 | 20.232 | 7.235 | 77.371 | 1.00 | 27.63 |
| ATOM | 111 | CB | PRO | A | 696 | 21.020 | 10.333 | 76.710 | 1.00 | 38.27 |
| ATOM | 112 | CG | PRO | A | 696 | 22.198 | 9.652 | 75.997 | 1.00 | 40.07 |
| ATOM | 113 | CD | PRO | A | 696 | 23.141 | 9.561 | 77.173 | 1.00 | 34.72 |
| ATOM | 114 | N | ASP | A | 697 | 18.588 | 8.613 | 78.037 | 1.00 | 38.27 |
| ATOM | 115 | CA | ASP | A | 697 | 17.516 | 7.632 | 77.863 | 1.00 | 35.46 |
| ATOM | 116 | C | ASP | A | 697 | 17.341 | 7.513 | 76.340 | 1.00 | 35.96 |
| ATOM | 117 | O | ASP | A | 697 | 17.600 | 8.468 | 75.620 | 1.00 | 30.43 |
| ATOM | 118 | CB | ASP | A | 697 | 16.238 | 8.147 | 78.523 | 1.00 | 44.25 |
| ATOM | 119 | CG | ASP | A | 697 | 15.176 | 7.069 | 78.683 | 1.00 | 53.62 |
| ATOM | 120 | OD1 | ASP | A | 697 | 15.420 | 5.901 | 78.302 | 1.00 | 57.04 |
| ATOM | 121 | OD2 | ASP | A | 697 | 14.085 | 7.398 | 79.203 | 1.00 | 61.97 |
| ATOM | 122 | N | VAL | A | 698 | 16.909 | 6.359 | 75.841 | 1.00 | 32.80 |
| ATOM | 123 | CA | VAL | A | 698 | 16.766 | 6.195 | 74.393 | 1.00 | 34.66 |
| ATOM | 124 | C | VAL | A | 698 | 15.941 | 7.312 | 73.736 | 1.00 | 28.44 |
| ATOM | 125 | O | VAL | A | 698 | 14.937 | 7.775 | 74.266 | 1.00 | 30.11 |
| ATOM | 126 | CB | VAL | A | 698 | 16.153 | 4.813 | 74.026 | 1.00 | 41.68 |
| ATOM | 127 | CG1 | VAL | A | 698 | 14.649 | 4.830 | 74.237 | 1.00 | 38.06 |
| ATOM | 128 | CG2 | VAL | A | 698 | 16.517 | 4.451 | 72.586 | 1.00 | 45.80 |
| ATOM | 282 | N | LEU | A | 721 | 16.006 | 12.741 | 63.995 | 1.00 | 19.58 |
| ATOM | 283 | CA | LEU | A | 721 | 16.568 | 11.942 | 65.084 | 1.00 | 17.13 |

TABLE III-continued

Structure Coordinates for Site II in Various NHRs
Based on the Consensus Alignments in FIG.2

| ATOM | 284 | C | LEU | A | 721 | 17.924 | 12.545 | 65.476 | 1.00 | 16.29 |
|------|-----|-----|-----|---|-----|--------|--------|--------|------|-------|
| ATOM | 285 | O | LEU | A | 721 | 18.228 | 12.690 | 66.662 | 1.00 | 19.55 |
| ATOM | 286 | CB | LEU | A | 721 | 16.742 | 10.479 | 64.638 | 1.00 | 17.00 |
| ATOM | 287 | CG | LEU | A | 721 | 17.378 | 9.549 | 65.673 | 1.00 | 19.10 |
| ATOM | 288 | CD1 | LEU | A | 721 | 16.508 | 9.497 | 66.942 | 1.00 | 18.65 |
| ATOM | 289 | CD2 | LEU | A | 721 | 17.536 | 8.145 | 65.037 | 1.00 | 17.08 |
| ATOM | 290 | N | GLY | A | 722 | 18.724 | 12.896 | 64.476 | 1.00 | 16.83 |
| ATOM | 291 | CA | GLY | A | 722 | 20.036 | 13.486 | 64.710 | 1.00 | 17.42 |
| ATOM | 292 | C | GLY | A | 722 | 19.929 | 14.774 | 65.516 | 1.00 | 24.76 |
| ATOM | 293 | O | GLY | A | 722 | 20.749 | 15.038 | 66.402 | 1.00 | 19.56 |
| ATOM | 314 | N | GLN | A | 725 | 19.296 | 13.770 | 69.009 | 1.00 | 19.77 |
| ATOM | 315 | CA | GLN | A | 725 | 20.474 | 13.188 | 69.634 | 1.00 | 19.30 |
| ATOM | 316 | C | GLN | A | 725 | 21.545 | 14.239 | 69.906 | 1.00 | 21.49 |
| ATOM | 317 | O | GLN | A | 725 | 22.309 | 14.113 | 70.855 | 1.00 | 21.43 |
| ATOM | 318 | CB | GLN | A | 725 | 21.055 | 12.063 | 68.771 | 1.00 | 19.47 |
| ATOM | 319 | CG | GLN | A | 725 | 20.135 | 10.843 | 68.774 | 1.00 | 22.41 |
| ATOM | 320 | CD | GLN | A | 725 | 20.746 | 9.633 | 68.092 | 1.00 | 30.53 |
| ATOM | 321 | OE1 | GLN | A | 725 | 20.104 | 8.578 | 67.970 | 1.00 | 32.93 |
| ATOM | 322 | NE2 | GLN | A | 725 | 21.987 | 9.770 | 67.647 | 1.00 | 27.09 |
| ATOM | 323 | N | LEU | A | 726 | 21.592 | 15.284 | 69.085 | 1.00 | 21.82 |
| ATOM | 324 | CA | LEU | A | 726 | 22.573 | 16.347 | 69.288 | 1.00 | 22.79 |
| ATOM | 325 | C | LEU | A | 726 | 22.284 | 17.027 | 70.624 | 1.00 | 21.40 |
| ATOM | 326 | O | LEU | A | 726 | 23.207 | 17.293 | 71.406 | 1.00 | 23.41 |
| ATOM | 327 | CB | LEU | A | 726 | 22.526 | 17.367 | 68.135 | 1.00 | 19.53 |
| ATOM | 328 | CG | LEU | A | 726 | 23.533 | 18.531 | 68.138 | 1.00 | 24.90 |
| ATOM | 329 | CD1 | LEU | A | 726 | 24.948 | 18.005 | 68.300 | 1.00 | 22.88 |
| ATOM | 330 | CD2 | LEU | A | 726 | 23.421 | 19.325 | 66.812 | 1.00 | 20.28 |
| ATOM | 331 | N | LEU | A | 727 | 21.007 | 17.301 | 70.890 | 1.00 | 18.00 |
| ATOM | 332 | CA | LEU | A | 727 | 20.623 | 17.906 | 72.156 | 1.00 | 19.91 |
| ATOM | 333 | C | LEU | A | 727 | 21.078 | 16.978 | 73.281 | 1.00 | 24.23 |
| ATOM | 334 | O | LEU | A | 727 | 21.678 | 17.402 | 74.274 | 1.00 | 19.07 |
| ATOM | 335 | CB | LEU | A | 727 | 19.105 | 18.065 | 72.247 | 1.00 | 21.64 |
| ATOM | 336 | CG | LEU | A | 727 | 18.591 | 18.563 | 73.594 | 1.00 | 21.40 |
| ATOM | 337 | CD1 | LEU | A | 727 | 19.256 | 19.906 | 73.912 | 1.00 | 26.36 |
| ATOM | 338 | CD2 | LEU | A | 727 | 17.082 | 18.699 | 73.546 | 1.00 | 28.00 |
| ATOM | 339 | N | SER | A | 728 | 20.783 | 15.695 | 73.106 | 1.00 | 21.94 |
| ATOM | 340 | CA | SER | A | 728 | 21.131 | 14.690 | 74.097 | 1.00 | 21.38 |
| ATOM | 341 | C | SER | A | 728 | 22.637 | 14.682 | 74.355 | 1.00 | 20.10 |
| ATOM | 342 | O | SER | A | 728 | 23.066 | 14.611 | 75.512 | 1.00 | 22.32 |
| ATOM | 343 | CB | SER | A | 728 | 20.645 | 13.310 | 73.630 | 1.00 | 24.08 |
| ATOM | 344 | OG | SER | A | 728 | 20.719 | 12.380 | 74.689 | 1.00 | 30.43 |
| ATOM | 345 | N | VAL | A | 729 | 23.433 | 14.741 | 73.297 | 1.00 | 18.72 |
| ATOM | 346 | CA | VAL | A | 729 | 24.891 | 14.781 | 73.415 | 1.00 | 20.27 |
| ATOM | 347 | C | VAL | A | 729 | 25.388 | 15.988 | 74.203 | 1.00 | 18.31 |
| ATOM | 348 | O | VAL | A | 729 | 26.274 | 15.860 | 75.049 | 1.00 | 19.16 |
| ATOM | 349 | CB | VAL | A | 729 | 25.574 | 14.796 | 72.034 | 1.00 | 17.15 |
| ATOM | 350 | CG1 | VAL | A | 729 | 27.060 | 15.147 | 72.164 | 1.00 | 20.31 |
| ATOM | 351 | CG2 | VAL | A | 729 | 25.453 | 13.395 | 71.407 | 1.00 | 21.83 |
| ATOM | 352 | N | VAL | A | 730 | 24.830 | 17.159 | 73.937 | 1.00 | 17.43 |
| ATOM | 353 | CA | VAL | A | 730 | 25.282 | 18.333 | 74.660 | 1.00 | 21.44 |
| ATOM | 354 | C | VAL | A | 730 | 24.888 | 18.225 | 76.132 | 1.00 | 19.86 |
| ATOM | 355 | O | VAL | A | 730 | 25.678 | 18.584 | 76.993 | 1.00 | 21.47 |
| ATOM | 356 | CB | VAL | A | 730 | 24.725 | 19.630 | 74.038 | 1.00 | 20.22 |
| ATOM | 357 | CG1 | VAL | A | 730 | 25.210 | 20.849 | 74.834 | 1.00 | 21.24 |
| ATOM | 358 | CG2 | VAL | A | 730 | 25.178 | 19.734 | 72.596 | 1.00 | 19.32 |
| ATOM | 359 | N | LYS | A | 731 | 23.686 | 17.727 | 76.427 | 1.00 | 17.73 |
| ATOM | 360 | CA | LYS | A | 731 | 23.275 | 17.552 | 77.817 | 1.00 | 22.58 |
| ATOM | 361 | C | LYS | A | 731 | 24.186 | 16.546 | 78.517 | 1.00 | 23.23 |
| ATOM | 362 | O | LYS | A | 731 | 24.613 | 16.757 | 79.659 | 1.00 | 20.64 |
| ATOM | 363 | CB | LYS | A | 731 | 21.808 | 17.121 | 77.911 | 1.00 | 23.07 |
| ATOM | 364 | CG | LYS | A | 731 | 20.850 | 18.296 | 77.646 | 1.00 | 25.92 |
| ATOM | 365 | CD | LYS | A | 731 | 19.388 | 18.009 | 78.016 | 1.00 | 37.08 |
| ATOM | 366 | CE | LYS | A | 731 | 18.717 | 17.034 | 77.063 | 1.00 | 48.50 |
| ATOM | 367 | NZ | LYS | A | 731 | 17.247 | 16.901 | 77.346 | 1.00 | 49.18 |
| ATOM | 368 | N | TRP | A | 732 | 24.486 | 15.452 | 77.828 | 1.00 | 18.73 |
| ATOM | 369 | CA | TRP | A | 732 | 25.383 | 14.437 | 78.364 | 1.00 | 21.37 |
| ATOM | 370 | C | TRP | A | 732 | 26.743 | 15.038 | 78.703 | 1.00 | 22.20 |
| ATOM | 371 | O | TRP | A | 732 | 27.293 | 14.772 | 79.770 | 1.00 | 23.93 |
| ATOM | 372 | CB | TRP | A | 732 | 25.552 | 13.321 | 77.334 | 1.00 | 21.47 |
| ATOM | 373 | CG | TRP | A | 732 | 26.674 | 12.347 | 77.582 | 1.00 | 17.78 |
| ATOM | 374 | CD1 | TRP | A | 732 | 26.728 | 11.348 | 78.528 | 1.00 | 20.71 |
| ATOM | 375 | CD2 | TRP | A | 732 | 27.861 | 12.225 | 76.806 | 1.00 | 17.23 |
| ATOM | 376 | NE1 | TRP | A | 732 | 27.879 | 10.613 | 78.370 | 1.00 | 19.88 |
| ATOM | 377 | CE2 | TRP | A | 732 | 28.593 | 11.130 | 77.318 | 1.00 | 19.41 |
| ATOM | 378 | CE3 | TRP | A | 732 | 28.383 | 12.938 | 75.713 | 1.00 | 19.83 |
| ATOM | 379 | CZ2 | TRP | A | 732 | 29.824 | 10.726 | 76.771 | 1.00 | 18.15 |

TABLE III-continued

Structure Coordinates for Site II in Various NHRs
Based on the Consensus Alignments in FIG.2

| ATOM | 380 | CZ3 | TRP | A | 732 | 29.612 | 12.533 | 75.165 | 1.00 | 20.23 |
|------|-----|-----|-----|---|-----|--------|--------|--------|------|-------|
| ATOM | 381 | CH2 | TRP | A | 732 | 30.314 | 11.435 | 75.701 | 1.00 | 22.27 |
| ATOM | 382 | N | SER | A | 733 | 27.274 | 15.872 | 77.811 | 1.00 | 20.68 |
| ATOM | 555 | N | SER | A | 754 | 33.038 | 15.988 | 66.904 | 1.00 | 19.69 |
| ATOM | 556 | CA | SER | A | 754 | 32.699 | 14.594 | 67.147 | 1.00 | 21.05 |
| ATOM | 557 | C | SER | A | 754 | 31.265 | 14.109 | 67.119 | 1.00 | 20.67 |
| ATOM | 558 | O | SER | A | 754 | 31.042 | 12.893 | 67.259 | 1.00 | 17.40 |
| ATOM | 559 | CB | SER | A | 754 | 33.288 | 14.196 | 68.498 | 1.00 | 24.21 |
| ATOM | 560 | OG | SER | A | 754 | 32.556 | 14.827 | 69.535 | 1.00 | 27.35 |
| ATOM | 561 | N | TRP | A | 755 | 30.300 | 14.998 | 66.911 | 1.00 | 17.55 |
| ATOM | 562 | CA | TRP | A | 755 | 28.912 | 14.547 | 66.960 | 1.00 | 21.93 |
| ATOM | 563 | C | TRP | A | 755 | 28.620 | 13.345 | 66.055 | 1.00 | 18.91 |
| ATOM | 564 | O | TRP | A | 755 | 27.956 | 12.409 | 66.486 | 1.00 | 20.07 |
| ATOM | 565 | CB | TRP | A | 755 | 27.925 | 15.684 | 66.647 | 1.00 | 22.52 |
| ATOM | 566 | CG | TRP | A | 755 | 28.003 | 16.222 | 65.257 | 1.00 | 23.08 |
| ATOM | 567 | CD1 | TRP | A | 755 | 28.859 | 17.175 | 64.791 | 1.00 | 28.21 |
| ATOM | 568 | CD2 | TRP | A | 755 | 27.217 | 15.803 | 64.141 | 1.00 | 24.51 |
| ATOM | 569 | NE1 | TRP | A | 755 | 28.655 | 17.379 | 63.445 | 1.00 | 25.19 |
| ATOM | 570 | CE2 | TRP | A | 755 | 27.651 | 16.548 | 63.022 | 1.00 | 26.64 |
| ATOM | 571 | CE3 | TRP | A | 755 | 26.189 | 14.869 | 63.979 | 1.00 | 25.75 |
| ATOM | 572 | CZ2 | TRP | A | 755 | 27.089 | 16.388 | 61.743 | 1.00 | 29.86 |
| ATOM | 573 | CZ3 | TRP | A | 755 | 25.630 | 14.707 | 62.707 | 1.00 | 32.59 |
| ATOM | 574 | CH2 | TRP | A | 755 | 26.083 | 15.465 | 61.608 | 1.00 | 30.85 |
| ATOM | 575 | N | MET | A | 756 | 29.114 | 13.357 | 64.820 | 1.00 | 21.38 |
| ATOM | 576 | CA | MET | A | 756 | 28.848 | 12.243 | 63.896 | 1.00 | 18.69 |
| ATOM | 577 | C | MET | A | 756 | 29.439 | 10.939 | 64.415 | 1.00 | 23.20 |
| ATOM | 578 | O | MET | A | 756 | 28.794 | 9.878 | 64.350 | 1.00 | 21.19 |
| ATOM | 579 | CB | MET | A | 756 | 29.432 | 12.529 | 62.511 | 1.00 | 21.49 |
| ATOM | 580 | CG | MET | A | 756 | 29.112 | 11.430 | 61.496 | 1.00 | 22.22 |
| ATOM | 581 | SD | MET | A | 756 | 27.367 | 11.449 | 60.920 | 1.00 | 27.03 |
| ATOM | 582 | CE | MET | A | 756 | 27.451 | 12.902 | 59.772 | 1.00 | 26.64 |
| ATOM | 583 | N | SER | A | 757 | 30.675 | 11.013 | 64.899 | 1.00 | 19.23 |
| ATOM | 584 | CA | SER | A | 757 | 31.344 | 9.845 | 65.451 | 1.00 | 22.32 |
| ATOM | 585 | C | SER | A | 757 | 30.575 | 9.283 | 66.631 | 1.00 | 20.68 |
| ATOM | 586 | O | SER | A | 757 | 30.376 | 8.078 | 66.718 | 1.00 | 21.09 |
| ATOM | 587 | CB | SER | A | 757 | 32.759 | 10.190 | 65.911 | 1.00 | 23.54 |
| ATOM | 588 | OG | SER | A | 757 | 33.562 | 10.611 | 64.826 | 1.00 | 31.88 |
| ATOM | 589 | N | LEU | A | 758 | 30.150 | 10.149 | 67.548 | 1.00 | 20.06 |
| ATOM | 590 | CA | LEU | A | 758 | 29.430 | 9.698 | 68.735 | 1.00 | 16.39 |
| ATOM | 591 | C | LEU | A | 758 | 28.105 | 9.061 | 68.355 | 1.00 | 18.68 |
| ATOM | 592 | O | LEU | A | 758 | 27.709 | 8.038 | 68.918 | 1.00 | 18.94 |
| ATOM | 593 | CB | LEU | A | 758 | 29.147 | 10.880 | 69.675 | 1.00 | 14.15 |
| ATOM | 594 | CG | LEU | A | 758 | 30.373 | 11.599 | 70.232 | 1.00 | 20.53 |
| ATOM | 595 | CD1 | LEU | A | 758 | 29.919 | 12.855 | 70.981 | 1.00 | 20.07 |
| ATOM | 596 | CD2 | LEU | A | 758 | 31.121 | 10.656 | 71.186 | 1.00 | 24.11 |
| ATOM | 597 | N | MET | A | 759 | 27.410 | 9.674 | 67.404 | 1.00 | 18.42 |
| ATOM | 598 | CA | MET | A | 759 | 26.125 | 9.149 | 67.001 | 1.00 | 19.21 |
| ATOM | 599 | C | MET | A | 759 | 26.209 | 7.828 | 66.242 | 1.00 | 19.93 |
| ATOM | 600 | O | MET | A | 759 | 25.363 | 6.949 | 66.456 | 1.00 | 23.09 |
| ATOM | 601 | CB | MET | A | 759 | 25.364 | 10.197 | 66.193 | 1.00 | 21.20 |
| ATOM | 602 | CG | MET | A | 759 | 24.937 | 11.397 | 67.065 | 1.00 | 21.45 |
| ATOM | 603 | SD | MET | A | 759 | 23.950 | 12.587 | 66.168 | 1.00 | 25.97 |
| ATOM | 604 | CE | MET | A | 759 | 23.941 | 13.961 | 67.348 | 1.00 | 26.52 |
| ATOM | 605 | N | VAL | A | 760 | 27.193 | 7.673 | 65.365 | 1.00 | 18.66 |
| ATOM | 606 | CA | VAL | A | 760 | 27.300 | 6.397 | 64.638 | 1.00 | 19.71 |
| ATOM | 607 | C | VAL | A | 760 | 27.779 | 5.292 | 65.596 | 1.00 | 22.38 |
| ATOM | 608 | O | VAL | A | 760 | 27.409 | 4.127 | 65.448 | 1.00 | 18.63 |
| ATOM | 609 | CB | VAL | A | 760 | 28.262 | 6.492 | 63.417 | 1.00 | 20.60 |
| ATOM | 610 | CG1 | VAL | A | 760 | 29.708 | 6.659 | 63.860 | 1.00 | 22.90 |
| ATOM | 611 | CG2 | VAL | A | 760 | 28.129 | 5.226 | 62.559 | 1.00 | 22.05 |
| ATOM | 612 | N | PHE | A | 761 | 28.597 | 5.672 | 66.572 | 1.00 | 18.16 |
| ATOM | 613 | CA | PHE | A | 761 | 29.107 | 4.729 | 67.579 | 1.00 | 20.65 |
| ATOM | 614 | C | PHE | A | 761 | 27.907 | 4.256 | 68.419 | 1.00 | 21.25 |
| ATOM | 615 | O | PHE | A | 761 | 27.773 | 3.058 | 68.717 | 1.00 | 23.39 |
| ATOM | 616 | CB | PHE | A | 761 | 30.166 | 5.441 | 68.447 | 1.00 | 19.84 |
| ATOM | 617 | CG | PHE | A | 761 | 31.100 | 4.502 | 69.206 | 1.00 | 22.22 |
| ATOM | 618 | CD1 | PHE | A | 761 | 31.944 | 3.631 | 68.520 | 1.00 | 22.72 |
| ATOM | 619 | CD2 | PHE | A | 761 | 31.158 | 4.529 | 70.597 | 1.00 | 23.08 |
| ATOM | 620 | CE1 | PHE | A | 761 | 32.834 | 2.802 | 69.200 | 1.00 | 23.74 |
| ATOM | 621 | CE2 | PHE | A | 761 | 32.044 | 3.706 | 71.297 | 1.00 | 24.95 |
| ATOM | 622 | CZ | PHE | A | 761 | 32.880 | 2.842 | 70.602 | 1.00 | 22.67 |
| ATOM | 623 | N | GLY | A | 762 | 27.041 | 5.196 | 68.803 | 1.00 | 18.00 |
| ATOM | 624 | CA | GLY | A | 762 | 25.851 | 4.861 | 69.564 | 1.00 | 19.15 |
| ATOM | 625 | C | GLY | A | 762 | 24.928 | 3.957 | 68.761 | 1.00 | 19.60 |
| ATOM | 626 | O | GLY | A | 762 | 24.304 | 3.038 | 69.306 | 1.00 | 17.94 |
| ATOM | 639 | N | TRP | A | 765 | 26.279 | 0.520 | 68.998 | 1.00 | 18.65 |

TABLE III-continued

Structure Coordinates for Site II in Various NHRs
Based on the Consensus Alignments in FIG.2

| ATOM | 640 | CA | TRP | A | 765 | 25.954 | −0.118 | 70.265 | 1.00 | 21.70 |
|------|-----|-----|-----|---|-----|--------|--------|--------|------|-------|
| ATOM | 641 | C | TRP | A | 765 | 24.485 | −0.582 | 70.330 | 1.00 | 20.69 |
| ATOM | 642 | O | TRP | A | 765 | 24.202 | −1.710 | 70.730 | 1.00 | 20.73 |
| ATOM | 643 | CB | TRP | A | 765 | 26.275 | 0.832 | 71.426 | 1.00 | 19.80 |
| ATOM | 644 | CG | TRP | A | 765 | 25.985 | 0.232 | 72.766 | 1.00 | 20.60 |
| ATOM | 645 | CD1 | TRP | A | 765 | 24.895 | 0.450 | 73.543 | 1.00 | 26.35 |
| ATOM | 646 | CD2 | TRP | A | 765 | 26.765 | −0.770 | 73.435 | 1.00 | 22.75 |
| ATOM | 647 | NE1 | TRP | A | 765 | 24.936 | −0.354 | 74.660 | 1.00 | 25.80 |
| ATOM | 648 | CE2 | TRP | A | 765 | 26.076 | −1.114 | 74.618 | 1.00 | 27.72 |
| ATOM | 649 | CE3 | TRP | A | 765 | 27.974 | −1.408 | 73.145 | 1.00 | 24.76 |
| ATOM | 650 | CZ2 | TRP | A | 765 | 26.558 | −2.080 | 75.522 | 1.00 | 28.33 |
| ATOM | 651 | CZ3 | TRP | A | 765 | 28.461 | −2.372 | 74.045 | 1.00 | 25.79 |
| ATOM | 652 | CH2 | TRP | A | 765 | 27.747 | −2.692 | 75.217 | 1.00 | 23.99 |
| ATOM | 653 | N | ARG | A | 766 | 23.544 | 0.273 | 69.936 | 1.00 | 20.81 |
| ATOM | 654 | CA | ARG | A | 766 | 22.136 | −0.116 | 69.987 | 1.00 | 18.86 |
| ATOM | 655 | C | ARG | A | 766 | 21.844 | −1.288 | 69.048 | 1.00 | 18.44 |
| ATOM | 656 | O | ARG | A | 766 | 21.066 | −2.185 | 69.381 | 1.00 | 20.30 |
| ATOM | 657 | CB | ARG | A | 766 | 21.223 | 1.061 | 69.624 | 1.00 | 18.28 |
| ATOM | 658 | CG | ARG | A | 766 | 21.246 | 2.229 | 70.632 | 1.00 | 20.05 |
| ATOM | 659 | CD | ARG | A | 766 | 20.179 | 3.260 | 70.256 | 1.00 | 25.08 |
| ATOM | 660 | NE | ARG | A | 766 | 20.413 | 3.889 | 68.956 | 1.00 | 20.13 |
| ATOM | 661 | CZ | ARG | A | 766 | 21.239 | 4.908 | 68.742 | 1.00 | 22.33 |
| ATOM | 662 | NH1 | ARG | A | 766 | 21.909 | 5.442 | 69.754 | 1.00 | 22.73 |
| ATOM | 663 | NH2 | ARG | A | 766 | 21.380 | 5.412 | 67.519 | 1.00 | 19.31 |
| ATOM | 682 | N | LYS | A | 769 | 23.313 | −4.427 | 70.751 | 1.00 | 19.61 |
| ATOM | 683 | CA | LYS | A | 769 | 22.500 | −4.833 | 71.899 | 1.00 | 20.88 |
| ATOM | 684 | C | LYS | A | 769 | 21.090 | −5.323 | 71.636 | 1.00 | 25.83 |
| ATOM | 685 | O | LYS | A | 769 | 20.661 | −6.320 | 72.222 | 1.00 | 23.20 |
| ATOM | 686 | CB | LYS | A | 769 | 22.402 | −3.682 | 72.904 | 1.00 | 26.26 |
| ATOM | 687 | CG | LYS | A | 769 | 23.682 | −3.356 | 73.623 | 1.00 | 29.74 |
| ATOM | 688 | CD | LYS | A | 769 | 23.998 | −4.345 | 74.756 | 1.00 | 34.33 |
| ATOM | 689 | CE | LYS | A | 769 | 23.010 | −4.251 | 75.914 | 1.00 | 31.35 |
| ATOM | 690 | NZ | LYS | A | 769 | 23.424 | −5.118 | 77.078 | 1.00 | 27.64 |
| ATOM | 691 | N | HIS | A | 770 | 20.372 | −4.627 | 70.762 | 1.00 | 20.34 |
| ATOM | 692 | CA | HIS | A | 770 | 18.968 | −4.935 | 70.496 | 1.00 | 25.32 |
| ATOM | 693 | C | HIS | A | 770 | 18.652 | −5.887 | 69.353 | 1.00 | 24.30 |
| ATOM | 694 | O | HIS | A | 770 | 17.631 | −6.572 | 69.382 | 1.00 | 23.64 |
| ATOM | 695 | CB | HIS | A | 770 | 18.204 | −3.622 | 70.246 | 1.00 | 25.43 |
| ATOM | 696 | CG | HIS | A | 770 | 18.239 | −2.672 | 71.397 | 1.00 | 32.32 |
| ATOM | 697 | ND1 | HIS | A | 770 | 17.517 | −2.879 | 72.554 | 1.00 | 34.84 |
| ATOM | 698 | CD2 | HIS | A | 770 | 18.920 | −1.516 | 71.581 | 1.00 | 28.95 |
| ATOM | 699 | CE1 | HIS | A | 770 | 17.751 | −1.889 | 73.398 | 1.00 | 36.65 |
| ATOM | 700 | NE2 | HIS | A | 770 | 18.598 | −1.049 | 72.833 | 1.00 | 35.04 |
| ATOM | 771 | N | PRO | A | 780 | 14.074 | 3.224 | 68.501 | 1.00 | 24.08 |
| ATOM | 772 | CA | PRO | A | 780 | 13.061 | 2.176 | 68.645 | 1.00 | 22.75 |
| ATOM | 773 | C | PRO | A | 780 | 11.985 | 2.260 | 67.551 | 1.00 | 31.17 |
| ATOM | 774 | O | PRO | A | 780 | 11.405 | 1.242 | 67.163 | 1.00 | 27.19 |
| ATOM | 775 | CB | PRO | A | 780 | 12.506 | 2.451 | 70.039 | 1.00 | 23.42 |
| ATOM | 776 | CG | PRO | A | 780 | 13.723 | 3.011 | 70.760 | 1.00 | 29.68 |
| ATOM | 777 | CD | PRO | A | 780 | 14.122 | 4.036 | 69.731 | 1.00 | 19.66 |
| ATOM | 1091 | N | PHE | A | 818 | 32.469 | 0.119 | 76.224 | 1.00 | 21.31 |
| ATOM | 1092 | CA | PHE | A | 818 | 31.805 | 1.043 | 75.304 | 1.00 | 22.08 |
| ATOM | 1093 | C | PHE | A | 818 | 31.696 | 2.467 | 75.884 | 1.00 | 21.29 |
| ATOM | 1094 | O | PHE | A | 818 | 31.920 | 3.460 | 75.180 | 1.00 | 20.03 |
| ATOM | 1095 | CB | PHE | A | 818 | 30.406 | 0.528 | 75.002 | 1.00 | 23.06 |
| ATOM | 1096 | CG | PHE | A | 818 | 29.513 | 1.549 | 74.373 | 1.00 | 22.01 |
| ATOM | 1097 | CD1 | PHE | A | 818 | 29.678 | 1.914 | 73.040 | 1.00 | 22.32 |
| ATOM | 1098 | CD2 | PHE | A | 818 | 28.514 | 2.156 | 75.124 | 1.00 | 23.62 |
| ATOM | 1099 | CE1 | PHE | A | 818 | 28.852 | 2.869 | 72.467 | 1.00 | 27.65 |
| ATOM | 1100 | CE2 | PHE | A | 818 | 27.681 | 3.116 | 74.558 | 1.00 | 28.88 |
| ATOM | 1101 | CZ | PHE | A | 818 | 27.852 | 3.471 | 73.231 | 1.00 | 22.16 |
| ATOM | 1102 | N | LEU | A | 819 | 31.323 | 2.556 | 77.154 | 1.00 | 21.31 |
| ATOM | 1103 | CA | LEU | A | 819 | 31.164 | 3.857 | 77.812 | 1.00 | 23.49 |
| ATOM | 1104 | C | LEU | A | 819 | 32.445 | 4.699 | 77.808 | 1.00 | 26.91 |
| ATOM | 1105 | O | LEU | A | 819 | 32.394 | 5.907 | 77.557 | 1.00 | 20.81 |
| ATOM | 1106 | CB | LEU | A | 819 | 30.640 | 3.655 | 79.238 | 1.00 | 24.50 |
| ATOM | 1107 | CG | LEU | A | 819 | 29.199 | 3.116 | 79.294 | 1.00 | 23.57 |
| ATOM | 1108 | CD1 | LEU | A | 819 | 28.780 | 2.812 | 80.728 | 1.00 | 22.54 |
| ATOM | 1109 | CD2 | LEU | A | 819 | 28.256 | 4.174 | 78.693 | 1.00 | 27.51 |
| ATOM | 1124 | N | LYS | A | 822 | 33.403 | 5.748 | 74.210 | 1.00 | 22.26 |
| ATOM | 1125 | CA | LYS | A | 822 | 32.595 | 6.856 | 73.684 | 1.00 | 21.99 |
| ATOM | 1126 | C | LYS | A | 822 | 33.157 | 8.208 | 74.120 | 1.00 | 23.71 |
| ATOM | 1127 | O | LYS | A | 822 | 33.125 | 9.182 | 73.359 | 1.00 | 20.06 |
| ATOM | 1128 | CB | LYS | A | 822 | 31.123 | 6.713 | 74.115 | 1.00 | 24.02 |
| ATOM | 1129 | CG | LYS | A | 822 | 30.164 | 7.608 | 73.337 | 1.00 | 31.07 |
| ATOM | 1130 | CD | LYS | A | 822 | 28.727 | 7.077 | 73.410 | 1.00 | 38.28 |

TABLE III-continued

Structure Coordinates for Site II in Various NHRs
Based on the Consensus Alignments in FIG.2

| | | | | | | | | | |
|---|---|---|---|---|---|---|---|---|---|
| ATOM | 1131 | CE | LYS | A | 822 | 28.155 | 7.091 | 74.822 | 1.00 39.48 |
| ATOM | 1132 | NZ | LYS | A | 822 | 27.958 | 8.479 | 75.331 | 1.00 42.42 |

RARgamma Site II Residues (ref. 2LBD.pdb)
(highlighted residues of SEQ ID NO:4)

| | | | | | | | | |
|---|---|---|---|---|---|---|---|---|
| ATOM | 110 | N | SER | 194 | 33.462 | 12.139 | 105.047 | 1.00 21.53 |
| ATOM | 111 | CA | SER | 194 | 32.239 | 12.265 | 104.247 | 1.00 21.04 |
| ATOM | 112 | C | SER | 194 | 31.924 | 13.712 | 103.899 | 1.00 21.80 |
| ATOM | 113 | O | SER | 194 | 31.727 | 14.047 | 102.732 | 1.00 21.17 |
| ATOM | 114 | CB | SER | 194 | 31.059 | 11.646 | 104.989 | 1.00 19.63 |
| ATOM | 115 | OG | SER | 194 | 29.904 | 11.654 | 104.183 | 1.00 19.69 |
| ATOM | 116 | H | SER | 194 | 33.433 | 11.608 | 105.870 | 1.00 13.44 |
| ATOM | 117 | HG | SER | 194 | 29.696 | 12.575 | 103.994 | 1.00 16.06 |
| ATOM | 118 | N | LYS | 195 | 31.894 | 14.557 | 104.925 | 1.00 22.99 |
| ATOM | 119 | CA | LYS | 195 | 31.614 | 15.981 | 104.797 | 1.00 22.87 |
| ATOM | 120 | C | LYS | 195 | 32.642 | 16.707 | 103.958 | 1.00 22.28 |
| ATOM | 121 | O | LYS | 195 | 32.278 | 17.511 | 103.124 | 1.00 23.38 |
| ATOM | 122 | CB | LYS | 195 | 31.496 | 16.626 | 106.180 | 1.00 23.64 |
| ATOM | 123 | CG | LYS | 195 | 30.078 | 16.572 | 106.747 | 1.00 28.29 |
| ATOM | 124 | CD | LYS | 195 | 29.209 | 15.582 | 105.952 | 1.00 30.25 |
| ATOM | 125 | CE | LYS | 195 | 27.736 | 15.623 | 106.362 | 1.00 32.32 |
| ATOM | 126 | NZ | LYS | 195 | 27.053 | 16.905 | 105.983 | 1.00 33.22 |
| ATOM | 127 | H | LYS | 195 | 32.099 | 14.210 | 105.821 | 1.00 12.80 |
| ATOM | 128 | 1 HZ | LYS | 195 | 27.088 | 17.060 | 104.958 | 1.00 15.82 |
| ATOM | 129 | 2 HZ | LYS | 195 | 26.063 | 16.878 | 106.305 | 1.00 15.26 |
| ATOM | 130 | 3 HZ | LYS | 195 | 27.530 | 17.695 | 106.469 | 1.00 11.80 |
| ATOM | 131 | N | ALA | 196 | 33.923 | 16.430 | 104.165 | 1.00 21.84 |
| ATOM | 132 | CA | ALA | 196 | 34.952 | 17.086 | 103.377 | 1.00 21.79 |
| ATOM | 133 | C | ALA | 196 | 34.725 | 16.717 | 101.913 | 1.00 21.34 |
| ATOM | 134 | O | ALA | 196 | 34.829 | 17.563 | 101.024 | 1.00 23.62 |
| ATOM | 135 | CB | ALA | 196 | 36.347 | 16.659 | 103.841 | 1.00 20.88 |
| ATOM | 136 | H | ALA | 196 | 34.178 | 15.781 | 104.855 | 1.00 21.01 |
| ATOM | 137 | N | HIS | 197 | 34.378 | 15.465 | 101.645 | 1.00 20.81 |
| ATOM | 138 | CA | HIS | 197 | 34.128 | 15.073 | 100.265 | 1.00 20.38 |
| ATOM | 139 | C | HIS | 197 | 32.896 | 15.796 | 99.701 | 1.00 21.21 |
| ATOM | 140 | O | HIS | 197 | 32.952 | 16.388 | 98.621 | 1.00 22.59 |
| ATOM | 141 | CB | HIS | 197 | 33.968 | 13.568 | 100.113 | 1.00 18.26 |
| ATOM | 142 | CG | HIS | 197 | 33.600 | 13.156 | 98.727 | 1.00 19.16 |
| ATOM | 143 | ND1 | HIS | 197 | 34.524 | 13.060 | 97.706 | 1.00 19.65 |
| ATOM | 144 | CD2 | HIS | 197 | 32.406 | 12.825 | 98.183 | 1.00 17.84 |
| ATOM | 145 | CE1 | HIS | 197 | 33.917 | 12.682 | 96.598 | 1.00 18.43 |
| ATOM | 146 | NE2 | HIS | 197 | 32.633 | 12.531 | 96.862 | 1.00 20.25 |
| ATOM | 147 | H | HIS | 197 | 34.300 | 14.821 | 102.382 | 1.00 16.92 |
| ATOM | 148 | HD1 | HIS | 197 | 35.497 | 13.235 | 97.727 | 1.00 15.58 |
| ATOM | 149 | HE2 | HIS | 197 | 31.936 | 12.266 | 96.223 | 1.00 12.28 |
| ATOM | 150 | N | GLN | 198 | 31.791 | 15.775 | 100.427 | 1.00 21.25 |
| ATOM | 151 | CA | GLN | 198 | 30.600 | 16.434 | 99.941 | 1.00 23.59 |
| ATOM | 152 | C | GLN | 198 | 30.828 | 17.916 | 99.658 | 1.00 24.07 |
| ATOM | 153 | O | GLN | 198 | 30.421 | 18.441 | 98.617 | 1.00 25.03 |
| ATOM | 154 | CB | GLN | 198 | 29.500 | 16.304 | 100.961 | 1.00 26.42 |
| ATOM | 155 | CG | GLN | 198 | 28.782 | 14.985 | 100.984 | 1.00 29.27 |
| ATOM | 156 | CD | GLN | 198 | 27.891 | 14.931 | 102.190 | 1.00 30.05 |
| ATOM | 157 | OE1 | GLN | 198 | 27.411 | 15.972 | 102.653 | 1.00 31.98 |
| ATOM | 158 | NE2 | GLN | 198 | 27.736 | 13.745 | 102.771 | 1.00 31.27 |
| ATOM | 159 | H | GLN | 198 | 31.789 | 15.330 | 101.298 | 1.00 16.00 |
| ATOM | 160 | 1HE2 | GLN | 198 | 27.144 | 13.729 | 103.551 | 1.00 15.85 |
| ATOM | 161 | 2HE2 | GLN | 198 | 28.203 | 12.971 | 102.398 | 1.00 16.16 |
| ATOM | 162 | N | GLU | 199 | 31.470 | 18.584 | 100.606 | 1.00 25.01 |
| ATOM | 163 | CA | GLU | 199 | 31.773 | 20.002 | 100.512 | 1.00 24.53 |
| ATOM | 164 | C | GLU | 199 | 32.720 | 20.377 | 99.400 | 1.00 23.37 |
| ATOM | 165 | O | GLU | 199 | 32.675 | 21.495 | 98.934 | 1.00 24.39 |
| ATOM | 166 | CB | GLU | 199 | 32.301 | 20.506 | 101.837 | 1.00 24.38 |
| ATOM | 167 | CG | GLU | 199 | 31.213 | 20.542 | 102.874 | 1.00 27.91 |
| ATOM | 168 | CD | GLU | 199 | 31.673 | 21.119 | 104.186 | 1.00 29.06 |
| ATOM | 169 | OE1 | GLU | 199 | 32.496 | 22.065 | 104.169 | 1.00 30.26 |
| ATOM | 170 | OE2 | GLU | 199 | 31.194 | 20.639 | 105.238 | 1.00 32.53 |
| ATOM | 171 | H | GLU | 199 | 31.753 | 18.106 | 101.411 | 1.00 12.27 |
| ATOM | 172 | N | THR | 200 | 33.561 | 19.449 | 98.960 | 1.00 21.99 |
| ATOM | 173 | CA | THR | 200 | 34.505 | 19.726 | 97.877 | 1.00 20.58 |
| ATOM | 174 | C | THR | 200 | 34.103 | 19.054 | 96.553 | 1.00 19.62 |
| ATOM | 175 | O | THR | 200 | 34.807 | 19.163 | 95.548 | 1.00 17.71 |
| ATOM | 176 | CB | THR | 200 | 35.934 | 19.275 | 98.260 | 1.00 20.42 |
| ATOM | 177 | OG1 | THR | 200 | 36.007 | 17.835 | 98.247 | 1.00 17.20 |
| ATOM | 178 | CG2 | THR | 200 | 36.299 | 19.831 | 99.658 | 1.00 18.24 |
| ATOM | 179 | H | THR | 200 | 33.574 | 18.555 | 99.363 | 1.00 15.26 |
| ATOM | 180 | HG1 | THR | 200 | 35.526 | 17.536 | 99.027 | 1.00 18.31 |

TABLE III-continued

Structure Coordinates for Site II in Various NHRs
Based on the Consensus Alignments in FIG.2

| ATOM | 181 | N | PHE | 201 | 32.993 | 18.328 | 96.561 | 1.00 | 20.00 |
|---|---|---|---|---|---|---|---|---|---|
| ATOM | 182 | CA | PHE | 201 | 32.535 | 17.665 | 95.354 | 1.00 | 21.05 |
| ATOM | 183 | C | PHE | 201 | 31.047 | 17.393 | 95.340 | 1.00 | 21.47 |
| ATOM | 184 | O | PHE | 201 | 30.604 | 16.377 | 95.848 | 1.00 | 22.07 |
| ATOM | 185 | CB | PHE | 201 | 33.245 | 16.338 | 95.183 | 1.00 | 22.20 |
| ATOM | 186 | CG | PHE | 201 | 33.122 | 15.769 | 93.814 | 1.00 | 21.15 |
| ATOM | 187 | CD1 | PHE | 201 | 33.696 | 16.424 | 92.727 | 1.00 | 24.07 |
| ATOM | 188 | CD2 | PHE | 201 | 32.499 | 14.558 | 93.610 | 1.00 | 23.24 |
| ATOM | 189 | CE1 | PHE | 201 | 33.660 | 15.871 | 91.458 | 1.00 | 23.53 |
| ATOM | 190 | CE2 | PHE | 201 | 32.454 | 13.993 | 92.347 | 1.00 | 21.82 |
| ATOM | 191 | CZ | PHE | 201 | 33.041 | 14.655 | 91.268 | 1.00 | 22.68 |
| ATOM | 192 | H | PHE | 201 | 32.482 | 18.197 | 97.386 | 1.00 | 15.60 |
| ATOM | 193 | N | PRO | 202 | 30.269 | 18.256 | 94.680 | 1.00 | 23.56 |
| ATOM | 194 | CA | PRO | 202 | 28.812 | 18.163 | 94.548 | 1.00 | 23.81 |
| ATOM | 195 | C | PRO | 202 | 28.400 | 16.880 | 93.861 | 1.00 | 24.15 |
| ATOM | 196 | O | PRO | 202 | 29.039 | 16.462 | 92.888 | 1.00 | 23.02 |
| ATOM | 197 | CB | PRO | 202 | 28.485 | 19.348 | 93.655 | 1.00 | 23.88 |
| ATOM | 198 | CG | PRO | 202 | 29.475 | 20.339 | 94.055 | 1.00 | 25.50 |
| ATOM | 199 | CD | PRO | 202 | 30.750 | 19.528 | 94.119 | 1.00 | 24.92 |
| ATOM | 496 | N | LEU | 233 | 38.159 | 23.558 | 84.412 | 1.00 | 13.93 |
| ATOM | 497 | CA | LEU | 233 | 37.402 | 22.729 | 85.345 | 1.00 | 13.81 |
| ATOM | 498 | C | LEU | 233 | 38.315 | 21.721 | 86.032 | 1.00 | 13.48 |
| ATOM | 499 | O | LEU | 233 | 38.108 | 21.387 | 87.192 | 1.00 | 15.95 |
| ATOM | 500 | CB | LEU | 233 | 36.250 | 22.001 | 84.634 | 1.00 | 12.25 |
| ATOM | 501 | CG | LEU | 233 | 35.083 | 22.858 | 84.105 | 1.00 | 12.32 |
| ATOM | 502 | CD1 | LEU | 233 | 34.147 | 21.981 | 83.337 | 1.00 | 12.38 |
| ATOM | 503 | CD2 | LEU | 233 | 34.336 | 23.557 | 85.223 | 1.00 | 13.65 |
| ATOM | 504 | H | LEU | 233 | 37.941 | 23.494 | 83.454 | 1.00 | 14.66 |
| ATOM | 505 | N | ALA | 234 | 39.324 | 21.233 | 85.327 | 1.00 | 12.52 |
| ATOM | 506 | CA | ALA | 234 | 40.243 | 20.291 | 85.935 | 1.00 | 14.87 |
| ATOM | 507 | C | ALA | 234 | 41.085 | 21.048 | 86.995 | 1.00 | 16.06 |
| ATOM | 508 | O | ALA | 234 | 41.209 | 20.596 | 88.141 | 1.00 | 15.82 |
| ATOM | 509 | CB | ALA | 234 | 41.133 | 19.635 | 84.876 | 1.00 | 13.08 |
| ATOM | 510 | H | ALA | 234 | 39.421 | 21.484 | 84.388 | 1.00 | 18.02 |
| ATOM | 546 | N | CYS | 237 | 39.285 | 21.662 | 90.004 | 1.00 | 14.60 |
| ATOM | 547 | CA | CYS | 237 | 39.063 | 20.411 | 90.679 | 1.00 | 16.39 |
| ATOM | 548 | C | CYS | 237 | 40.287 | 20.070 | 91.534 | 1.00 | 16.47 |
| ATOM | 549 | O | CYS | 237 | 40.160 | 19.703 | 92.703 | 1.00 | 17.24 |
| ATOM | 550 | CB | CYS | 237 | 38.720 | 19.278 | 89.708 | 1.00 | 14.97 |
| ATOM | 551 | SG | CYS | 237 | 37.905 | 17.917 | 90.622 | 1.00 | 17.49 |
| ATOM | 552 | H | CYS | 237 | 39.424 | 21.679 | 89.042 | 1.00 | 13.36 |
| ATOM | 553 | N | ILE | 238 | 41.477 | 20.237 | 90.969 | 1.00 | 15.33 |
| ATOM | 554 | CA | ILE | 238 | 42.705 | 19.945 | 91.699 | 1.00 | 13.85 |
| ATOM | 555 | C | ILE | 238 | 42.774 | 20.741 | 93.007 | 1.00 | 14.22 |
| ATOM | 556 | O | ILE | 238 | 43.224 | 20.252 | 94.044 | 1.00 | 14.79 |
| ATOM | 557 | CB | ILE | 238 | 43.889 | 20.245 | 90.810 | 1.00 | 13.01 |
| ATOM | 558 | CG1 | ILE | 238 | 43.899 | 19.259 | 89.634 | 1.00 | 12.70 |
| ATOM | 559 | CG2 | ILE | 238 | 45.188 | 20.219 | 91.616 | 1.00 | 14.88 |
| ATOM | 560 | CD1 | ILE | 238 | 44.860 | 19.636 | 88.559 | 1.00 | 10.75 |
| ATOM | 561 | H | ILE | 238 | 41.538 | 20.554 | 90.045 | 1.00 | 16.76 |
| ATOM | 562 | N | ILE | 239 | 42.358 | 21.990 | 92.940 | 1.00 | 14.17 |
| ATOM | 563 | CA | ILE | 239 | 42.329 | 22.858 | 94.107 | 1.00 | 14.19 |
| ATOM | 564 | C | ILE | 239 | 41.325 | 22.268 | 95.102 | 1.00 | 14.54 |
| ATOM | 565 | O | ILE | 239 | 41.582 | 22.238 | 96.299 | 1.00 | 14.16 |
| ATOM | 566 | CB | ILE | 239 | 41.910 | 24.293 | 93.703 | 1.00 | 14.59 |
| ATOM | 567 | CG1 | ILE | 239 | 43.095 | 25.050 | 93.099 | 1.00 | 13.80 |
| ATOM | 568 | CG2 | ILE | 239 | 41.339 | 25.024 | 94.871 | 1.00 | 15.96 |
| ATOM | 569 | CD1 | ILE | 239 | 42.680 | 26.334 | 92.386 | 1.00 | 13.34 |
| ATOM | 570 | H | ILE | 239 | 42.056 | 22.353 | 92.079 | 1.00 | 18.53 |
| ATOM | 571 | N | LYS | 240 | 40.201 | 21.764 | 94.615 | 1.00 | 15.39 |
| ATOM | 572 | CA | LYS | 240 | 39.220 | 21.175 | 95.515 | 1.00 | 15.53 |
| ATOM | 573 | C | LYS | 240 | 39.718 | 19.879 | 96.140 | 1.00 | 15.65 |
| ATOM | 574 | O | LYS | 240 | 39.295 | 19.531 | 97.244 | 1.00 | 13.48 |
| ATOM | 575 | CB | LYS | 240 | 37.885 | 20.951 | 94.810 | 1.00 | 18.27 |
| ATOM | 576 | CG | LYS | 240 | 37.099 | 22.226 | 94.594 | 1.00 | 21.05 |
| ATOM | 577 | CD | LYS | 240 | 36.331 | 22.615 | 95.838 | 1.00 | 23.72 |
| ATOM | 578 | CE | LYS | 240 | 36.215 | 24.137 | 96.000 | 1.00 | 27.33 |
| ATOM | 579 | NZ | LYS | 240 | 37.448 | 24.762 | 96.648 | 1.00 | 30.09 |
| ATOM | 580 | H | LYS | 240 | 39.995 | 21.825 | 93.653 | 1.00 | 14.20 |
| ATOM | 581 | 1HZ | LYS | 240 | 37.590 | 24.341 | 97.587 | 1.00 | 18.02 |
| ATOM | 582 | 2HZ | LYS | 240 | 38.287 | 24.568 | 96.066 | 1.00 | 14.97 |
| ATOM | 583 | 3HZ | LYS | 240 | 37.322 | 25.789 | 96.751 | 1.00 | 16.98 |
| ATOM | 584 | N | ILE | 241 | 40.619 | 19.179 | 95.447 | 1.00 | 14.37 |
| ATOM | 585 | CA | ILE | 241 | 41.183 | 17.934 | 95.962 | 1.00 | 15.71 |
| ATOM | 586 | C | ILE | 241 | 42.175 | 18.268 | 97.083 | 1.00 | 16.21 |
| ATOM | 587 | O | ILE | 241 | 42.213 | 17.598 | 98.123 | 1.00 | 15.85 |

TABLE III-continued

Structure Coordinates for Site II in Various NHRs
Based on the Consensus Alignments in FIG.2

| ATOM | 588 | CB | ILE | 241 | 41.852 | 17.092 | 94.849 | 1.00 | 15.46 |
|------|-----|-----|-----|-----|--------|--------|--------|------|-------|
| ATOM | 589 | CG1 | ILE | 241 | 40.770 | 16.452 | 93.981 | 1.00 | 16.06 |
| ATOM | 590 | CG2 | ILE | 241 | 42.699 | 15.981 | 95.448 | 1.00 | 17.68 |
| ATOM | 591 | CD1 | ILE | 241 | 41.249 | 15.771 | 92.705 | 1.00 | 17.03 |
| ATOM | 592 | H | ILE | 241 | 40.882 | 19.507 | 94.561 | 1.00 | 16.01 |
| ATOM | 593 | N | VAL | 242 | 42.955 | 19.330 | 96.874 | 1.00 | 17.19 |
| ATOM | 594 | CA | VAL | 242 | 43.919 | 19.797 | 97.869 | 1.00 | 16.87 |
| ATOM | 595 | C | VAL | 242 | 43.155 | 20.219 | 99.116 | 1.00 | 16.56 |
| ATOM | 596 | O | VAL | 242 | 43.539 | 19.863 | 100.225 | 1.00 | 16.69 |
| ATOM | 597 | CB | VAL | 242 | 44.756 | 20.963 | 97.348 | 1.00 | 15.52 |
| ATOM | 598 | CG1 | VAL | 242 | 45.481 | 21.614 | 98.481 | 1.00 | 15.69 |
| ATOM | 599 | CG2 | VAL | 242 | 45.739 | 20.461 | 96.299 | 1.00 | 16.20 |
| ATOM | 600 | H | VAL | 242 | 42.885 | 19.801 | 96.014 | 1.00 | 17.48 |
| ATOM | 601 | N | GLU | 243 | 42.046 | 20.930 | 98.929 | 1.00 | 16.45 |
| ATOM | 602 | CA | GLU | 243 | 41.213 | 21.338 | 100.062 | 1.00 | 19.31 |
| ATOM | 603 | C | GLU | 243 | 40.680 | 20.112 | 100.818 | 1.00 | 17.64 |
| ATOM | 604 | O | GLU | 243 | 40.579 | 20.125 | 102.024 | 1.00 | 14.49 |
| ATOM | 605 | CB | GLU | 243 | 40.013 | 22.160 | 99.601 | 1.00 | 22.56 |
| ATOM | 606 | CG | GLU | 243 | 39.152 | 22.517 | 100.780 | 1.00 | 27.44 |
| ATOM | 607 | CD | GLU | 243 | 37.781 | 23.001 | 100.416 | 1.00 | 31.18 |
| ATOM | 608 | OE1 | GLU | 243 | 37.679 | 23.810 | 99.463 | 1.00 | 33.07 |
| ATOM | 609 | OE2 | GLU | 243 | 36.810 | 22.586 | 101.109 | 1.00 | 33.67 |
| ATOM | 610 | H | GLU | 243 | 41.792 | 21.201 | 98.022 | 1.00 | 15.45 |
| ATOM | 611 | N | PHE | 244 | 40.256 | 19.100 | 100.064 | 1.00 | 18.29 |
| ATOM | 612 | CA | PHE | 244 | 39.743 | 17.837 | 100.600 | 1.00 | 16.37 |
| ATOM | 613 | C | PHE | 244 | 40.842 | 17.147 | 101.406 | 1.00 | 15.24 |
| ATOM | 614 | O | PHE | 244 | 40.595 | 16.721 | 102.531 | 1.00 | 15.07 |
| ATOM | 615 | CB | PHE | 244 | 39.277 | 16.927 | 99.452 | 1.00 | 17.51 |
| ATOM | 616 | CG | PHE | 244 | 38.981 | 15.503 | 99.858 | 1.00 | 14.72 |
| ATOM | 617 | CD1 | PHE | 244 | 37.831 | 15.187 | 100.549 | 1.00 | 15.04 |
| ATOM | 618 | CD2 | PHE | 244 | 39.845 | 14.479 | 99.500 | 1.00 | 15.96 |
| ATOM | 619 | CE1 | PHE | 244 | 37.540 | 13.862 | 100.880 | 1.00 | 16.72 |
| ATOM | 620 | CE2 | PHE | 244 | 39.565 | 13.154 | 99.823 | 1.00 | 16.27 |
| ATOM | 621 | CZ | PHE | 244 | 38.405 | 12.845 | 100.518 | 1.00 | 14.78 |
| ATOM | 622 | H | PHE | 244 | 40.258 | 19.205 | 99.089 | 1.00 | 13.23 |
| ATOM | 814 | N | ALA | 266 | 48.576 | 10.971 | 93.812 | 1.00 | 15.90 |
| ATOM | 815 | CA | ALA | 266 | 47.182 | 10.496 | 93.792 | 1.00 | 17.39 |
| ATOM | 816 | C | ALA | 266 | 46.167 | 11.428 | 93.127 | 1.00 | 17.22 |
| ATOM | 817 | O | ALA | 266 | 45.012 | 11.043 | 92.903 | 1.00 | 16.41 |
| ATOM | 818 | CB | ALA | 266 | 46.722 | 10.185 | 95.222 | 1.00 | 16.38 |
| ATOM | 819 | H | ALA | 266 | 48.811 | 11.745 | 94.370 | 1.00 | 15.48 |
| ATOM | 820 | N | CYS | 267 | 46.597 | 12.643 | 92.802 | 1.00 | 15.91 |
| ATOM | 821 | CA | CYS | 267 | 45.700 | 13.622 | 92.214 | 1.00 | 17.69 |
| ATOM | 822 | C | CYS | 267 | 44.940 | 13.171 | 90.958 | 1.00 | 16.15 |
| ATOM | 823 | O | CYS | 267 | 43.718 | 13.343 | 90.888 | 1.00 | 14.43 |
| ATOM | 824 | CB | CYS | 267 | 46.438 | 14.920 | 91.951 | 1.00 | 18.90 |
| ATOM | 825 | SG | CYS | 267 | 45.310 | 16.241 | 91.678 | 1.00 | 23.66 |
| ATOM | 826 | H | CYS | 267 | 47.530 | 12.902 | 92.957 | 1.00 | 11.70 |
| ATOM | 827 | N | LEU | 268 | 45.650 | 12.573 | 89.999 | 1.00 | 14.38 |
| ATOM | 828 | CA | LEU | 268 | 45.009 | 12.091 | 88.787 | 1.00 | 15.09 |
| ATOM | 829 | C | LEU | 268 | 44.049 | 10.961 | 89.129 | 1.00 | 15.22 |
| ATOM | 830 | O | LEU | 268 | 42.932 | 10.926 | 88.602 | 1.00 | 15.41 |
| ATOM | 831 | CB | LEU | 268 | 46.037 | 11.609 | 87.758 | 1.00 | 14.82 |
| ATOM | 832 | CG | LEU | 268 | 45.922 | 12.104 | 86.291 | 1.00 | 16.13 |
| ATOM | 833 | CD1 | LEU | 268 | 46.809 | 11.216 | 85.363 | 1.00 | 13.28 |
| ATOM | 834 | CD2 | LEU | 268 | 44.465 | 12.106 | 85.808 | 1.00 | 13.62 |
| ATOM | 835 | H | LEU | 268 | 46.624 | 12.472 | 90.107 | 1.00 | 11.61 |
| ATOM | 836 | N | ASP | 269 | 44.475 | 10.032 | 89.989 | 1.00 | 14.39 |
| ATOM | 837 | CA | ASP | 269 | 43.610 | 8.927 | 90.390 | 1.00 | 14.73 |
| ATOM | 838 | C | ASP | 269 | 42.264 | 9.494 | 90.826 | 1.00 | 16.42 |
| ATOM | 839 | O | ASP | 269 | 41.214 | 9.159 | 90.250 | 1.00 | 17.01 |
| ATOM | 840 | CB | ASP | 269 | 44.193 | 8.164 | 91.583 | 1.00 | 16.26 |
| ATOM | 841 | CG | ASP | 269 | 45.461 | 7.396 | 91.251 | 1.00 | 16.52 |
| ATOM | 842 | OD1 | ASP | 269 | 46.050 | 7.627 | 90.207 | 1.00 | 18.78 |
| ATOM | 843 | OD2 | ASP | 269 | 45.887 | 6.548 | 92.057 | 1.00 | 19.84 |
| ATOM | 844 | H | ASP | 269 | 45.390 | 10.079 | 90.347 | 1.00 | 13.22 |
| ATOM | 845 | N | ILE | 270 | 42.299 | 10.400 | 91.809 | 1.00 | 16.86 |
| ATOM | 846 | CA | ILE | 270 | 41.069 | 10.996 | 92.356 | 1.00 | 16.75 |
| ATOM | 847 | C | ILE | 270 | 40.260 | 11.805 | 91.336 | 1.00 | 15.88 |
| ATOM | 848 | O | ILE | 270 | 39.035 | 11.758 | 91.345 | 1.00 | 16.48 |
| ATOM | 849 | CB | ILE | 270 | 41.351 | 11.838 | 93.625 | 1.00 | 16.55 |
| ATOM | 850 | CG1 | ILE | 270 | 42.034 | 10.972 | 94.680 | 1.00 | 15.45 |
| ATOM | 851 | CG2 | ILE | 270 | 40.046 | 12.388 | 94.221 | 1.00 | 16.85 |
| ATOM | 852 | CD1 | ILE | 270 | 42.364 | 11.741 | 95.933 | 1.00 | 18.34 |
| ATOM | 853 | H | ILE | 270 | 43.171 | 10.675 | 92.167 | 1.00 | 13.31 |
| ATOM | 854 | N | LEU | 271 | 40.932 | 12.535 | 90.458 | 1.00 | 15.65 |

TABLE III-continued

Structure Coordinates for Site II in Various NHRs
Based on the Consensus Alignments in FIG. 2

| ATOM | 855 | CA | LEU | 271 | 40.246 | 13.308 | 89.430 | 1.00 | 16.49 |
|---|---|---|---|---|---|---|---|---|---|
| ATOM | 856 | C | LEU | 271 | 39.456 | 12.294 | 88.580 | 1.00 | 16.41 |
| ATOM | 857 | O | LEU | 271 | 38.294 | 12.530 | 88.244 | 1.00 | 17.42 |
| ATOM | 858 | CB | LEU | 271 | 41.297 | 14.038 | 88.597 | 1.00 | 16.24 |
| ATOM | 859 | CG | LEU | 271 | 41.309 | 15.557 | 88.415 | 1.00 | 17.43 |
| ATOM | 860 | CD1 | LEU | 271 | 40.654 | 16.308 | 89.533 | 1.00 | 14.58 |
| ATOM | 861 | CD2 | LEU | 271 | 42.735 | 16.005 | 88.203 | 1.00 | 16.24 |
| ATOM | 862 | H | LEU | 271 | 41.910 | 12.566 | 90.512 | 1.00 | 15.08 |
| ATOM | 863 | N | MET | 272 | 40.060 | 11.131 | 88.316 | 1.00 | 16.60 |
| ATOM | 864 | CA | MET | 272 | 39.418 | 10.073 | 87.528 | 1.00 | 16.79 |
| ATOM | 865 | C | MET | 272 | 38.250 | 9.441 | 88.300 | 1.00 | 17.44 |
| ATOM | 866 | O | MET | 272 | 37.176 | 9.161 | 87.733 | 1.00 | 19.90 |
| ATOM | 867 | CB | MET | 272 | 40.420 | 8.978 | 87.127 | 1.00 | 17.65 |
| ATOM | 868 | CG | MET | 272 | 41.448 | 9.392 | 86.102 | 1.00 | 18.79 |
| ATOM | 869 | SD | MET | 272 | 40.799 | 9.486 | 84.419 | 1.00 | 22.97 |
| ATOM | 870 | CE | MET | 272 | 42.292 | 9.289 | 83.461 | 1.00 | 19.64 |
| ATOM | 871 | H | MET | 272 | 40.964 | 10.976 | 88.662 | 1.00 | 18.75 |
| ATOM | 872 | N | LEU | 273 | 38.441 | 9.179 | 89.581 | 1.00 | 14.90 |
| ATOM | 873 | CA | LEU | 273 | 37.356 | 8.606 | 90.339 | 1.00 | 14.87 |
| ATOM | 874 | C | LEU | 273 | 36.185 | 9.588 | 90.339 | 1.00 | 15.34 |
| ATOM | 875 | O | LEU | 273 | 35.037 | 9.194 | 90.129 | 1.00 | 15.36 |
| ATOM | 876 | CB | LEU | 273 | 37.809 | 8.343 | 91.761 | 1.00 | 15.48 |
| ATOM | 877 | CG | LEU | 273 | 36.730 | 7.760 | 92.651 | 1.00 | 16.54 |
| ATOM | 878 | CD1 | LEU | 273 | 36.312 | 6.404 | 92.086 | 1.00 | 17.29 |
| ATOM | 879 | CD2 | LEU | 273 | 37.282 | 7.620 | 94.064 | 1.00 | 15.37 |
| ATOM | 880 | H | LEU | 273 | 39.308 | 9.367 | 89.992 | 1.00 | 16.64 |
| ATOM | 881 | N | ARG | 274 | 36.494 | 10.873 | 90.528 | 1.00 | 15.34 |
| ATOM | 882 | CA | ARG | 274 | 35.486 | 11.919 | 90.572 | 1.00 | 15.78 |
| ATOM | 883 | C | ARG | 274 | 34.629 | 12.006 | 89.328 | 1.00 | 17.06 |
| ATOM | 884 | O | ARG | 274 | 33.434 | 11.812 | 89.437 | 1.00 | 18.66 |
| ATOM | 885 | CB | ARG | 274 | 36.095 | 13.267 | 90.936 | 1.00 | 16.75 |
| ATOM | 886 | CG | ARG | 274 | 36.461 | 13.333 | 92.429 | 1.00 | 17.30 |
| ATOM | 887 | CD | ARG | 274 | 36.835 | 14.716 | 92.892 | 1.00 | 17.86 |
| ATOM | 888 | NE | ARG | 274 | 36.951 | 14.740 | 94.351 | 1.00 | 21.93 |
| ATOM | 889 | CZ | ARG | 274 | 37.027 | 15.844 | 95.093 | 1.00 | 22.23 |
| ATOM | 890 | NH1 | ARG | 274 | 36.998 | 17.045 | 94.520 | 1.00 | 21.99 |
| ATOM | 891 | NH2 | ARG | 274 | 37.115 | 15.745 | 96.413 | 1.00 | 20.01 |
| ATOM | 892 | H | ARG | 274 | 37.434 | 11.117 | 90.631 | 1.00 | 16.07 |
| ATOM | 893 | HE | ARG | 274 | 36.978 | 13.875 | 94.802 | 1.00 | 14.88 |
| ATOM | 894 | 1HH1 | ARG | 274 | 36.923 | 17.134 | 93.527 | 1.00 | 14.06 |
| ATOM | 895 | 2HH1 | ARG | 274 | 37.061 | 17.866 | 95.089 | 1.00 | 14.03 |
| ATOM | 896 | 1HH2 | ARG | 274 | 37.122 | 14.847 | 96.850 | 1.00 | 17.31 |
| ATOM | 897 | 2HH2 | ARG | 274 | 37.173 | 16.572 | 96.971 | 1.00 | 14.92 |
| ATOM | 914 | N | THR | 277 | 32.271 | 9.023 | 88.779 | 1.00 | 13.95 |
| ATOM | 915 | CA | THR | 277 | 31.115 | 8.905 | 89.661 | 1.00 | 15.92 |
| ATOM | 916 | C | THR | 277 | 30.004 | 9.856 | 89.186 | 1.00 | 17.31 |
| ATOM | 917 | O | THR | 277 | 28.859 | 9.761 | 89.626 | 1.00 | 19.20 |
| ATOM | 918 | CB | THR | 277 | 31.471 | 9.205 | 91.138 | 1.00 | 18.17 |
| ATOM | 919 | OG1 | THR | 277 | 31.879 | 10.567 | 91.267 | 1.00 | 20.50 |
| ATOM | 920 | CG2 | THR | 277 | 32.613 | 8.315 | 91.605 | 1.00 | 19.00 |
| ATOM | 921 | H | THR | 277 | 33.002 | 9.624 | 89.038 | 1.00 | 16.11 |
| ATOM | 922 | HG1 | THR | 277 | 32.699 | 10.722 | 90.788 | 1.00 | 14.03 |
| ATOM | 923 | N | ARG | 278 | 30.352 | 10.756 | 88.266 | 1.00 | 17.51 |
| ATOM | 924 | CA | ARG | 278 | 29.428 | 11.741 | 87.669 | 1.00 | 17.48 |
| ATOM | 925 | C | ARG | 278 | 28.907 | 11.260 | 86.280 | 1.00 | 16.92 |
| ATOM | 926 | O | ARG | 278 | 28.552 | 12.046 | 85.396 | 1.00 | 16.64 |
| ATOM | 927 | CB | ARG | 278 | 30.176 | 13.060 | 87.508 | 1.00 | 17.18 |
| ATOM | 928 | CG | ARG | 278 | 30.446 | 13.774 | 88.808 | 1.00 | 16.64 |
| ATOM | 929 | CD | ARG | 278 | 29.338 | 14.762 | 89.057 | 1.00 | 17.73 |
| ATOM | 930 | NE | ARG | 278 | 29.640 | 15.725 | 90.108 | 1.00 | 17.21 |
| ATOM | 931 | CZ | ARG | 278 | 30.658 | 16.570 | 90.085 | 1.00 | 19.13 |
| ATOM | 932 | NH1 | ARG | 278 | 31.499 | 16.576 | 89.060 | 1.00 | 20.62 |
| ATOM | 933 | NH2 | ARG | 278 | 30.816 | 17.433 | 91.081 | 1.00 | 20.16 |
| ATOM | 934 | H | ARG | 278 | 31.277 | 10.787 | 87.949 | 1.00 | 13.43 |
| ATOM | 935 | HE | ARG | 278 | 29.047 | 15.731 | 90.894 | 1.00 | 15.33 |
| ATOM | 936 | 1HH1 | ARG | 278 | 31.378 | 15.948 | 88.280 | 1.00 | 16.80 |
| ATOM | 937 | 2HH1 | ARG | 278 | 32.325 | 17.162 | 89.023 | 1.00 | 14.95 |
| ATOM | 938 | 1HH2 | ARG | 278 | 30.169 | 17.426 | 91.850 | 1.00 | 14.24 |
| ATOM | 939 | 2HH2 | ARG | 278 | 31.583 | 18.098 | 91.094 | 1.00 | 15.16 |
| ATOM | 954 | N | THR | 280 | 26.282 | 9.265 | 83.776 | 1.00 | 17.68 |
| ATOM | 955 | CA | THR | 280 | 24.869 | 8.925 | 83.581 | 1.00 | 18.60 |
| ATOM | 956 | C | THR | 280 | 24.815 | 7.906 | 82.476 | 1.00 | 18.63 |
| ATOM | 957 | O | THR | 280 | 25.028 | 8.237 | 81.316 | 1.00 | 19.24 |
| ATOM | 958 | CB | THR | 280 | 24.038 | 10.130 | 83.148 | 1.00 | 18.35 |
| ATOM | 959 | OG1 | THR | 280 | 24.226 | 11.205 | 84.076 | 1.00 | 19.23 |
| ATOM | 960 | CG2 | THR | 280 | 22.590 | 9.770 | 83.156 | 1.00 | 19.36 |

TABLE III-continued

Structure Coordinates for Site II in Various NHRs
Based on the Consensus Alignments in FIG.2

| ATOM | 961 | H | THR | 280 | 26.736 | 9.748 | 83.057 | 1.00 | 16.32 |
|------|-----|-----|-----|-----|--------|-------|--------|------|-------|
| ATOM | 962 | HG1 | THR | 280 | 25.144 | 11.476 | 84.000 | 1.00 | 9.92 |
| ATOM | 963 | N | PRO | 281 | 24.538 | 6.648 | 82.822 | 1.00 | 19.26 |
| ATOM | 964 | CA | PRO | 281 | 24.470 | 5.596 | 81.828 | 1.00 | 23.13 |
| ATOM | 965 | C | PRO | 281 | 23.422 | 5.934 | 80.771 | 1.00 | 27.05 |
| ATOM | 966 | O | PRO | 281 | 23.723 | 5.886 | 79.589 | 1.00 | 29.83 |
| ATOM | 967 | CB | PRO | 281 | 24.055 | 4.378 | 82.659 | 1.00 | 21.19 |
| ATOM | 968 | CG | PRO | 281 | 24.526 | 4.683 | 83.975 | 1.00 | 19.03 |
| ATOM | 969 | CD | PRO | 281 | 24.140 | 6.111 | 84.126 | 1.00 | 19.67 |
| ATOM | 970 | N | GLU | 282 | 22.225 | 6.347 | 81.201 | 1.00 | 29.52 |
| ATOM | 971 | CA | GLU | 282 | 21.114 | 6.686 | 80.289 | 1.00 | 30.92 |
| ATOM | 972 | C | GLU | 282 | 21.496 | 7.566 | 79.079 | 1.00 | 29.16 |
| ATOM | 973 | O | GLU | 282 | 21.189 | 7.244 | 77.923 | 1.00 | 29.44 |
| ATOM | 974 | CB | GLU | 282 | 19.949 | 7.342 | 81.083 | 1.00 | 34.18 |
| ATOM | 975 | CG | GLU | 282 | 18.596 | 6.561 | 81.059 | 1.00 | 37.63 |
| ATOM | 976 | CD | GLU | 282 | 17.598 | 7.038 | 79.975 | 1.00 | 39.35 |
| ATOM | 977 | OE1 | GLU | 282 | 17.763 | 6.709 | 78.769 | 1.00 | 39.81 |
| ATOM | 978 | OE2 | GLU | 282 | 16.628 | 7.737 | 80.345 | 1.00 | 40.91 |
| ATOM | 979 | H | GLU | 282 | 22.043 | 6.390 | 82.163 | 1.00 | 14.17 |
| ATOM | 1048 | N | ASP | 290 | 30.544 | 22.243 | 87.680 | 1.00 | 18.56 |
| ATOM | 1049 | CA | ASP | 290 | 29.751 | 23.433 | 87.443 | 1.00 | 16.64 |
| ATOM | 1050 | C | ASP | 290 | 28.396 | 23.055 | 86.781 | 1.00 | 16.67 |
| ATOM | 1051 | O | ASP | 290 | 27.492 | 23.889 | 86.648 | 1.00 | 16.11 |
| ATOM | 1052 | CB | ASP | 290 | 30.547 | 24.465 | 86.627 | 1.00 | 19.14 |
| ATOM | 1053 | CG | ASP | 290 | 30.679 | 24.105 | 85.162 | 1.00 | 17.90 |
| ATOM | 1054 | OD1 | ASP | 290 | 30.715 | 22.918 | 84.812 | 1.00 | 19.78 |
| ATOM | 1055 | OD2 | ASP | 290 | 30.765 | 25.038 | 84.360 | 1.00 | 17.99 |
| ATOM | 1056 | H | ASP | 290 | 31.098 | 21.861 | 86.974 | 1.00 | 13.42 |
| ATOM | 1393 | N | THR | 328 | 32.657 | 6.889 | 98.484 | 1.00 | 12.39 |
| ATOM | 1394 | CA | THR | 328 | 33.499 | 7.531 | 97.480 | 1.00 | 14.32 |
| ATOM | 1395 | C | THR | 328 | 34.507 | 8.459 | 98.191 | 1.00 | 13.38 |
| ATOM | 1396 | O | THR | 328 | 35.684 | 8.521 | 97.820 | 1.00 | 12.40 |
| ATOM | 1397 | CB | THR | 328 | 32.650 | 8.351 | 96.491 | 1.00 | 12.84 |
| ATOM | 1398 | OG1 | THR | 328 | 31.708 | 7.492 | 95.841 | 1.00 | 14.19 |
| ATOM | 1399 | CG2 | THR | 328 | 33.517 | 8.994 | 95.486 | 1.00 | 12.73 |
| ATOM | 1400 | H | THR | 328 | 31.697 | 7.093 | 98.476 | 1.00 | 17.66 |
| ATOM | 1401 | HG1 | THR | 328 | 32.184 | 6.794 | 95.373 | 1.00 | 15.73 |
| ATOM | 1402 | N | GLY | 329 | 34.037 | 9.169 | 99.218 | 1.00 | 14.14 |
| ATOM | 1403 | CA | GLY | 329 | 34.898 | 10.063 | 99.963 | 1.00 | 10.87 |
| ATOM | 1404 | C | GLY | 329 | 35.973 | 9.248 | 100.634 | 1.00 | 11.08 |
| ATOM | 1405 | O | GLY | 329 | 37.146 | 9.586 | 100.525 | 1.00 | 11.93 |
| ATOM | 1406 | H | GLY | 329 | 33.106 | 9.075 | 99.503 | 1.00 | 18.91 |
| ATOM | 1425 | N | SER | 332 | 38.488 | 7.748 | 98.210 | 1.00 | 12.43 |
| ATOM | 1426 | CA | SER | 332 | 39.440 | 8.792 | 97.800 | 1.00 | 12.96 |
| ATOM | 1427 | C | SER | 332 | 40.505 | 9.050 | 98.856 | 1.00 | 12.57 |
| ATOM | 1428 | O | SER | 332 | 41.677 | 9.204 | 98.527 | 1.00 | 11.85 |
| ATOM | 1429 | CB | SER | 332 | 38.720 | 10.109 | 97.515 | 1.00 | 12.28 |
| ATOM | 1430 | OG | SER | 332 | 37.815 | 9.953 | 96.454 | 1.00 | 15.83 |
| ATOM | 1431 | H | SER | 332 | 37.552 | 7.988 | 98.365 | 1.00 | 18.36 |
| ATOM | 1432 | HG | SER | 332 | 37.203 | 9.240 | 96.682 | 1.00 | 17.36 |

RXRalpha Site II Residues (ref. 1LBD.pdb)
(highlighted residues of SEQ ID NO:3)

| ATOM | 87 | N | LEU | 236 | 30.657 | 84.317 | 63.377 | 1.00 | 35.43 |
|------|-----|-----|-----|-----|--------|--------|--------|------|-------|
| ATOM | 88 | CA | LEU | 236 | 29.844 | 85.467 | 63.046 | 1.00 | 35.76 |
| ATOM | 89 | C | LEU | 236 | 29.344 | 85.142 | 61.634 | 1.00 | 36.91 |
| ATOM | 90 | O | LEU | 236 | 28.157 | 85.245 | 61.327 | 1.00 | 37.85 |
| ATOM | 91 | CB | LEU | 236 | 30.713 | 86.718 | 62.998 | 1.00 | 34.14 |
| ATOM | 92 | CG | LEU | 236 | 30.091 | 88.105 | 63.184 | 1.00 | 35.41 |
| ATOM | 93 | CD1 | LEU | 236 | 31.028 | 89.058 | 62.487 | 1.00 | 38.27 |
| ATOM | 94 | CD2 | LEU | 236 | 28.654 | 88.262 | 62.637 | 1.00 | 36.08 |
| ATOM | 95 | N | GLU | 237 | 30.280 | 84.697 | 60.804 | 1.00 | 37.85 |
| ATOM | 96 | CA | GLU | 237 | 30.055 | 84.311 | 59.414 | 1.00 | 37.03 |
| ATOM | 97 | C | GLU | 237 | 28.875 | 83.317 | 59.253 | 1.00 | 36.46 |
| ATOM | 98 | O | GLU | 237 | 27.977 | 83.527 | 58.431 | 1.00 | 33.55 |
| ATOM | 99 | CB | GLU | 237 | 31.365 | 83.701 | 58.898 | 1.00 | 39.91 |
| ATOM | 100 | CG | GLU | 237 | 31.585 | 83.796 | 57.431 | 1.00 | 42.42 |
| ATOM | 101 | CD | GLU | 237 | 30.519 | 83.050 | 56.702 | 1.00 | 49.05 |
| ATOM | 102 | OE1 | GLU | 237 | 30.598 | 81.800 | 56.680 | 1.00 | 52.01 |
| ATOM | 103 | OE2 | GLU | 237 | 29.567 | 83.707 | 56.208 | 1.00 | 53.07 |
| ATOM | 104 | N | ALA | 238 | 28.854 | 82.285 | 60.096 | 1.00 | 39.98 |
| ATOM | 105 | CA | ALA | 238 | 27.821 | 81.232 | 60.093 | 1.00 | 37.99 |
| ATOM | 106 | C | ALA | 238 | 26.415 | 81.715 | 60.408 | 1.00 | 35.29 |
| ATOM | 107 | O | ALA | 238 | 25.458 | 81.248 | 59.801 | 1.00 | 34.55 |
| ATOM | 108 | CB | ALA | 238 | 28.221 | 80.063 | 61.066 | 1.00 | 33.06 |
| ATOM | 109 | N | GLU | 239 | 26.286 | 82.615 | 61.380 | 1.00 | 35.97 |

TABLE III-continued

Structure Coordinates for Site II in Various NHRs
Based on the Consensus Alignments in FIG.2

| ATOM | 110 | CA | GLU | 239 | 24.967 | 83.135 | 61.755 | 1.00 | 38.46 |
|---|---|---|---|---|---|---|---|---|---|
| ATOM | 111 | C | GLU | 239 | 24.490 | 83.961 | 60.599 | 1.00 | 39.38 |
| ATOM | 112 | O | GLU | 239 | 23.401 | 83.752 | 60.096 | 1.00 | 42.38 |
| ATOM | 113 | CB | GLU | 239 | 25.002 | 84.017 | 63.031 | 1.00 | 38.94 |
| ATOM | 114 | CG | GLU | 239 | 25.017 | 83.277 | 64.403 | 1.00 | 37.77 |
| ATOM | 115 | CD | GLU | 239 | 23.716 | 82.538 | 64.709 | 1.00 | 34.29 |
| ATOM | 116 | OE1 | GLU | 239 | 22.637 | 83.173 | 64.751 | 1.00 | 34.87 |
| ATOM | 117 | OE2 | GLU | 239 | 23.777 | 81.307 | 64.903 | 1.00 | 28.74 |
| ATOM | 118 | N | LEU | 240 | 25.342 | 84.884 | 60.164 | 1.00 | 40.88 |
| ATOM | 119 | CA | LEU | 240 | 25.042 | 85.771 | 59.043 | 1.00 | 36.87 |
| ATOM | 120 | C | LEU | 240 | 24.747 | 84.943 | 57.829 | 1.00 | 35.24 |
| ATOM | 121 | O | LEU | 240 | 23.789 | 85.202 | 57.109 | 1.00 | 34.29 |
| ATOM | 122 | CB | LEU | 240 | 26.201 | 86.733 | 58.777 | 1.00 | 34.15 |
| ATOM | 123 | CG | LEU | 240 | 26.032 | 87.969 | 59.663 | 1.00 | 36.58 |
| ATOM | 124 | CD1 | LEU | 240 | 27.280 | 88.842 | 59.591 | 1.00 | 40.07 |
| ATOM | 125 | CD2 | LEU | 240 | 24.745 | 88.728 | 59.280 | 1.00 | 32.86 |
| ATOM | 126 | N | ALA | 241 | 25.492 | 83.868 | 57.668 | 1.00 | 33.12 |
| ATOM | 127 | CA | ALA | 241 | 25.266 | 82.987 | 56.544 | 1.00 | 32.07 |
| ATOM | 128 | C | ALA | 241 | 23.882 | 82.367 | 56.562 | 1.00 | 28.57 |
| ATOM | 129 | O | ALA | 241 | 23.554 | 81.610 | 55.664 | 1.00 | 30.72 |
| ATOM | 130 | CB | ALA | 241 | 26.291 | 81.900 | 56.537 | 1.00 | 34.96 |
| ATOM | 131 | N | VAL | 242 | 23.051 | 82.725 | 57.533 | 1.00 | 28.22 |
| ATOM | 132 | CA | VAL | 242 | 21.738 | 82.120 | 57.636 | 1.00 | 25.21 |
| ATOM | 133 | C | VAL | 242 | 20.623 | 83.069 | 58.183 | 1.00 | 25.77 |
| ATOM | 134 | O | VAL | 242 | 19.550 | 82.653 | 58.631 | 1.00 | 23.41 |
| ATOM | 135 | CB | VAL | 242 | 21.899 | 80.842 | 58.444 | 1.00 | 22.99 |
| ATOM | 136 | CG1 | VAL | 242 | 21.975 | 81.138 | 59.916 | 1.00 | 21.73 |
| ATOM | 137 | CG2 | VAL | 242 | 20.846 | 79.898 | 58.098 | 1.00 | 23.34 |
| ATOM | 138 | N | GLU | 243 | 20.873 | 84.366 | 58.050 | 1.00 | 29.04 |
| ATOM | 139 | CA | GLU | 243 | 19.955 | 85.420 | 58.485 | 1.00 | 31.55 |
| ATOM | 140 | C | GLU | 243 | 18.790 | 85.495 | 57.515 | 1.00 | 32.99 |
| ATOM | 141 | O | GLU | 243 | 19.016 | 85.500 | 56.315 | 1.00 | 36.40 |
| ATOM | 142 | CB | GLU | 243 | 20.697 | 86.738 | 58.401 | 1.00 | 33.53 |
| ATOM | 143 | CG | GLU | 243 | 19.950 | 87.907 | 58.936 | 1.00 | 38.25 |
| ATOM | 144 | CD | GLU | 243 | 20.565 | 88.357 | 60.224 | 1.00 | 42.27 |
| ATOM | 145 | OE1 | GLU | 243 | 21.818 | 88.544 | 60.242 | 1.00 | 36.36 |
| ATOM | 146 | OE2 | GLU | 243 | 19.800 | 88.483 | 61.221 | 1.00 | 49.21 |
| ATOM | 147 | N | PRO | 244 | 17.555 | 85.687 | 58.001 | 1.00 | 33.30 |
| ATOM | 148 | CA | PRO | 244 | 16.452 | 85.759 | 57.055 | 1.00 | 36.93 |
| ATOM | 149 | C | PRO | 244 | 16.587 | 87.115 | 56.376 | 1.00 | 42.25 |
| ATOM | 150 | O | PRO | 244 | 16.983 | 88.088 | 57.009 | 1.00 | 44.70 |
| ATOM | 151 | CB | PRO | 244 | 15.215 | 85.718 | 57.947 | 1.00 | 39.57 |
| ATOM | 152 | CG | PRO | 244 | 15.726 | 85.581 | 59.340 | 1.00 | 35.65 |
| ATOM | 153 | CD | PRO | 244 | 17.100 | 86.165 | 59.302 | 1.00 | 36.07 |
| ATOM | 349 | N | ALA | 271 | 7.191 | 76.115 | 57.199 | 1.00 | 29.50 |
| ATOM | 350 | CA | ALA | 271 | 7.966 | 76.681 | 58.300 | 1.00 | 27.28 |
| ATOM | 351 | C | ALA | 271 | 8.794 | 75.692 | 59.151 | 1.00 | 26.76 |
| ATOM | 352 | O | ALA | 271 | 9.872 | 76.064 | 59.652 | 1.00 | 27.26 |
| ATOM | 353 | CB | ALA | 271 | 7.083 | 77.497 | 59.168 | 1.00 | 23.29 |
| ATOM | 354 | N | ALA | 272 | 8.287 | 74.476 | 59.382 | 1.00 | 27.64 |
| ATOM | 355 | CA | ALA | 272 | 9.036 | 73.462 | 60.144 | 1.00 | 26.95 |
| ATOM | 356 | C | ALA | 272 | 10.327 | 73.296 | 59.374 | 1.00 | 29.21 |
| ATOM | 357 | O | ALA | 272 | 11.440 | 73.568 | 59.824 | 1.00 | 30.82 |
| ATOM | 358 | CB | ALA | 272 | 8.287 | 72.166 | 60.096 | 1.00 | 24.06 |
| ATOM | 376 | N | GLN | 275 | 12.864 | 76.169 | 59.278 | 1.00 | 28.33 |
| ATOM | 377 | CA | GLN | 275 | 13.609 | 76.269 | 60.539 | 1.00 | 26.75 |
| ATOM | 378 | C | GLN | 275 | 14.692 | 75.203 | 60.489 | 1.00 | 29.14 |
| ATOM | 379 | O | GLN | 275 | 15.879 | 75.506 | 60.635 | 1.00 | 30.79 |
| ATOM | 380 | CB | GLN | 275 | 12.723 | 76.046 | 61.766 | 1.00 | 20.91 |
| ATOM | 381 | CG | GLN | 275 | 11.564 | 76.979 | 61.849 | 1.00 | 21.96 |
| ATOM | 382 | CD | GLN | 275 | 10.817 | 76.871 | 63.163 | 1.00 | 22.43 |
| ATOM | 383 | OE1 | GLN | 275 | 10.539 | 75.781 | 63.664 | 1.00 | 24.91 |
| ATOM | 384 | NE2 | GLN | 275 | 10.445 | 78.011 | 63.705 | 1.00 | 20.62 |
| ATOM | 385 | N | LEU | 276 | 14.304 | 73.979 | 60.158 | 1.00 | 28.84 |
| ATOM | 386 | CA | LEU | 276 | 15.288 | 72.913 | 60.115 | 1.00 | 32.72 |
| ATOM | 387 | C | LEU | 276 | 16.523 | 73.357 | 59.349 | 1.00 | 33.75 |
| ATOM | 388 | O | LEU | 276 | 17.640 | 73.252 | 59.856 | 1.00 | 33.64 |
| ATOM | 389 | CB | LEU | 276 | 14.702 | 71.633 | 59.489 | 1.00 | 33.19 |
| ATOM | 390 | CG | LEU | 276 | 15.702 | 70.508 | 59.214 | 1.00 | 32.49 |
| ATOM | 391 | CD1 | LEU | 276 | 16.333 | 70.081 | 60.488 | 1.00 | 30.89 |
| ATOM | 392 | CD2 | LEU | 276 | 15.037 | 69.353 | 58.554 | 1.00 | 33.68 |
| ATOM | 393 | N | PHE | 277 | 16.320 | 73.920 | 58.158 | 1.00 | 32.96 |
| ATOM | 394 | CA | PHE | 277 | 17.466 | 74.336 | 57.359 | 1.00 | 33.52 |
| ATOM | 395 | C | PHE | 277 | 18.235 | 75.463 | 57.943 | 1.00 | 32.72 |
| ATOM | 396 | O | PHE | 277 | 19.473 | 75.425 | 57.951 | 1.00 | 34.61 |
| ATOM | 397 | CB | PHE | 277 | 17.148 | 74.608 | 55.892 | 1.00 | 38.91 |

TABLE III-continued

Structure Coordinates for Site II in Various NHRs
Based on the Consensus Alignments in FIG.2

| ATOM | 398 | CG | PHE | 277 | 17.934 | 73.734 | 54.955 | 1.00 | 46.04 |
|---|---|---|---|---|---|---|---|---|---|
| ATOM | 399 | CD1 | PHE | 277 | 18.866 | 72.821 | 55.465 | 1.00 | 49.86 |
| ATOM | 400 | CD2 | PHE | 277 | 17.733 | 73.786 | 53.588 | 1.00 | 46.15 |
| ATOM | 401 | CE1 | PHE | 277 | 19.584 | 71.970 | 54.633 | 1.00 | 48.96 |
| ATOM | 402 | CE2 | PHE | 277 | 18.450 | 72.931 | 52.738 | 1.00 | 51.33 |
| ATOM | 403 | CZ | PHE | 277 | 19.383 | 72.017 | 53.277 | 1.00 | 51.91 |
| ATOM | 404 | N | THR | 278 | 17.537 | 76.410 | 58.546 | 1.00 | 30.83 |
| ATOM | 405 | CA | THR | 278 | 18.263 | 77.507 | 59.141 | 1.00 | 29.49 |
| ATOM | 406 | C | THR | 278 | 19.159 | 76.951 | 60.228 | 1.00 | 30.33 |
| ATOM | 407 | O | THR | 278 | 20.045 | 77.647 | 60.721 | 1.00 | 32.94 |
| ATOM | 408 | CB | THR | 278 | 17.315 | 78.536 | 59.675 | 1.00 | 27.12 |
| ATOM | 409 | OG1 | THR | 278 | 16.012 | 78.272 | 59.136 | 1.00 | 30.31 |
| ATOM | 410 | CG2 | THR | 278 | 17.732 | 79.913 | 59.181 | 1.00 | 25.40 |
| ATOM | 411 | N | LEU | 279 | 18.987 | 75.647 | 60.491 | 1.00 | 29.99 |
| ATOM | 412 | CA | LEU | 279 | 19.702 | 74.886 | 61.510 | 1.00 | 31.31 |
| ATOM | 413 | C | LEU | 279 | 20.905 | 74.100 | 61.030 | 1.00 | 33.54 |
| ATOM | 414 | O | LEU | 279 | 22.025 | 74.363 | 61.505 | 1.00 | 38.01 |
| ATOM | 415 | CB | LEU | 279 | 18.734 | 73.930 | 62.206 | 1.00 | 33.42 |
| ATOM | 416 | CG | LEU | 279 | 18.683 | 73.794 | 63.722 | 1.00 | 28.79 |
| ATOM | 417 | CD1 | LEU | 279 | 18.067 | 75.049 | 64.376 | 1.00 | 23.73 |
| ATOM | 418 | CD2 | LEU | 279 | 17.859 | 72.574 | 63.990 | 1.00 | 27.75 |
| ATOM | 419 | N | VAL | 280 | 20.720 | 73.111 | 60.146 | 1.00 | 32.77 |
| ATOM | 420 | CA | VAL | 280 | 21.916 | 72.371 | 59.693 | 1.00 | 34.18 |
| ATOM | 421 | C | VAL | 280 | 22.902 | 73.298 | 58.968 | 1.00 | 34.17 |
| ATOM | 422 | O | VAL | 280 | 24.092 | 73.324 | 59.278 | 1.00 | 33.48 |
| ATOM | 423 | CB | VAL | 280 | 21.627 | 71.065 | 58.868 | 1.00 | 30.97 |
| ATOM | 424 | CG1 | VAL | 280 | 20.352 | 70.358 | 59.369 | 1.00 | 31.67 |
| ATOM | 425 | CG2 | VAL | 280 | 21.619 | 71.325 | 57.402 | 1.00 | 33.04 |
| ATOM | 426 | N | GLU | 281 | 22.383 | 74.162 | 58.109 | 1.00 | 31.06 |
| ATOM | 427 | CA | GLU | 281 | 23.273 | 75.071 | 57.406 | 1.00 | 31.66 |
| ATOM | 428 | C | GLU | 281 | 24.099 | 75.925 | 58.364 | 1.00 | 30.93 |
| ATOM | 429 | O | GLU | 281 | 25.203 | 76.339 | 58.016 | 1.00 | 31.16 |
| ATOM | 430 | CB | GLU | 281 | 22.536 | 75.961 | 56.385 | 1.00 | 35.28 |
| ATOM | 431 | CG | GLU | 281 | 21.923 | 75.246 | 55.168 | 1.00 | 34.78 |
| ATOM | 432 | CD | GLU | 281 | 22.864 | 74.267 | 54.486 | 1.00 | 32.73 |
| ATOM | 433 | OE1 | GLU | 281 | 24.087 | 74.529 | 54.427 | 1.00 | 19.72 |
| ATOM | 434 | OE2 | GLU | 281 | 22.351 | 73.222 | 54.004 | 1.00 | 32.69 |
| ATOM | 435 | N | TRP | 282 | 23.577 | 76.199 | 59.553 | 1.00 | 28.28 |
| ATOM | 436 | CA | TRP | 282 | 24.341 | 77.002 | 60.510 | 1.00 | 30.40 |
| ATOM | 437 | C | TRP | 282 | 25.429 | 76.091 | 61.158 | 1.00 | 35.40 |
| ATOM | 438 | O | TRP | 282 | 26.597 | 76.495 | 61.323 | 1.00 | 36.16 |
| ATOM | 439 | CB | TRP | 282 | 23.394 | 77.659 | 61.559 | 1.00 | 24.73 |
| ATOM | 440 | CG | TRP | 282 | 24.075 | 78.176 | 62.841 | 1.00 | 20.02 |
| ATOM | 441 | CD1 | TRP | 282 | 24.751 | 79.359 | 63.006 | 1.00 | 19.84 |
| ATOM | 442 | CD2 | TRP | 282 | 24.284 | 77.437 | 64.046 | 1.00 | 23.23 |
| ATOM | 443 | NE1 | TRP | 282 | 25.410 | 79.380 | 64.213 | 1.00 | 16.40 |
| ATOM | 444 | CE2 | TRP | 282 | 25.144 | 78.213 | 64.873 | 1.00 | 21.68 |
| ATOM | 445 | CE3 | TRP | 282 | 23.843 | 76.185 | 64.507 | 1.00 | 20.19 |
| ATOM | 446 | CZ2 | TRP | 282 | 25.579 | 77.772 | 66.120 | 1.00 | 19.31 |
| ATOM | 447 | CZ3 | TRP | 282 | 24.275 | 75.748 | 65.747 | 1.00 | 22.95 |
| ATOM | 448 | CH2 | TRP | 282 | 25.136 | 76.536 | 66.541 | 1.00 | 20.41 |
| ATOM | 620 | N | GLY | 304 | 20.287 | 69.044 | 70.953 | 1.00 | 29.43 |
| ATOM | 621 | CA | GLY | 304 | 20.094 | 70.450 | 71.256 | 1.00 | 29.15 |
| ATOM | 622 | C | GLY | 304 | 19.355 | 71.333 | 70.270 | 1.00 | 25.88 |
| ATOM | 623 | O | GLY | 304 | 19.573 | 72.527 | 70.332 | 1.00 | 29.72 |
| ATOM | 624 | N | TRP | 305 | 18.476 | 70.792 | 69.417 | 1.00 | 25.81 |
| ATOM | 625 | CA | TRP | 305 | 17.688 | 71.571 | 68.426 | 1.00 | 28.27 |
| ATOM | 626 | C | TRP | 305 | 16.862 | 72.793 | 68.914 | 1.00 | 31.21 |
| ATOM | 627 | O | TRP | 305 | 16.762 | 73.828 | 68.242 | 1.00 | 30.23 |
| ATOM | 628 | CB | TRP | 305 | 16.704 | 70.630 | 67.708 | 1.00 | 26.86 |
| ATOM | 629 | CG | TRP | 305 | 15.237 | 71.110 | 67.705 | 1.00 | 33.15 |
| ATOM | 630 | CD1 | TRP | 305 | 14.740 | 72.346 | 67.290 | 1.00 | 36.35 |
| ATOM | 631 | CD2 | TRP | 305 | 14.116 | 70.409 | 68.228 | 1.00 | 34.91 |
| ATOM | 632 | NE1 | TRP | 305 | 13.396 | 72.446 | 67.562 | 1.00 | 32.18 |
| ATOM | 633 | CE2 | TRP | 305 | 12.985 | 71.278 | 68.123 | 1.00 | 33.00 |
| ATOM | 634 | CE3 | TRP | 305 | 13.960 | 69.140 | 68.776 | 1.00 | 32.73 |
| ATOM | 635 | CZ2 | TRP | 305 | 11.732 | 70.909 | 68.545 | 1.00 | 33.45 |
| ATOM | 636 | CZ3 | TRP | 305 | 12.711 | 68.776 | 69.195 | 1.00 | 42.77 |
| ATOM | 637 | CH2 | TRP | 305 | 11.603 | 69.659 | 69.078 | 1.00 | 43.63 |
| ATOM | 638 | N | ASN | 306 | 16.035 | 72.530 | 69.918 | 1.00 | 33.01 |
| ATOM | 639 | CA | ASN | 306 | 15.130 | 73.503 | 70.502 | 1.00 | 33.62 |
| ATOM | 640 | C | ASN | 306 | 15.843 | 74.691 | 71.167 | 1.00 | 34.24 |
| ATOM | 641 | O | ASN | 306 | 15.381 | 75.822 | 71.143 | 1.00 | 35.65 |
| ATOM | 642 | CB | ASN | 306 | 14.244 | 72.755 | 71.505 | 1.00 | 35.17 |
| ATOM | 643 | CG | ASN | 306 | 15.028 | 72.250 | 72.740 | 1.00 | 39.33 |
| ATOM | 644 | OD1 | ASN | 306 | 16.144 | 71.695 | 72.626 | 1.00 | 33.48 |

TABLE III-continued

Structure Coordinates for Site II in Various NHRs
Based on the Consensus Alignments in FIG.2

| ATOM | 645 | ND2 | ASN | 306 | 14.441 | 72.464 | 73.939 | 1.00 | 39.83 |
|---|---|---|---|---|---|---|---|---|---|
| ATOM | 646 | N | GLU | 307 | 16.957 | 74.436 | 71.809 | 1.00 | 28.91 |
| ATOM | 647 | CA | GLU | 307 | 17.662 | 75.516 | 72.434 | 1.00 | 24.93 |
| ATOM | 648 | C | GLU | 307 | 18.318 | 76.379 | 71.384 | 1.00 | 22.24 |
| ATOM | 649 | O | GLU | 307 | 18.376 | 77.581 | 71.551 | 1.00 | 19.58 |
| ATOM | 650 | CB | GLU | 307 | 18.696 | 74.946 | 73.399 | 1.00 | 30.44 |
| ATOM | 651 | CG | GLU | 307 | 18.149 | 74.781 | 74.809 | 1.00 | 29.85 |
| ATOM | 652 | CD | GLU | 307 | 19.079 | 74.010 | 75.689 | 1.00 | 28.89 |
| ATOM | 653 | OE1 | GLU | 307 | 19.983 | 74.601 | 76.331 | 1.00 | 28.55 |
| ATOM | 654 | OE2 | GLU | 307 | 18.876 | 72.790 | 75.745 | 1.00 | 35.64 |
| ATOM | 655 | N | LEU | 308 | 18.814 | 75.758 | 70.306 | 1.00 | 24.10 |
| ATOM | 656 | CA | LEU | 308 | 19.482 | 76.450 | 69.185 | 1.00 | 23.45 |
| ATOM | 657 | C | LEU | 308 | 18.415 | 77.274 | 68.460 | 1.00 | 22.44 |
| ATOM | 658 | O | LEU | 308 | 18.652 | 78.424 | 68.085 | 1.00 | 24.47 |
| ATOM | 659 | CB | LEU | 308 | 20.165 | 75.436 | 68.228 | 1.00 | 19.67 |
| ATOM | 660 | CG | LEU | 308 | 21.367 | 74.560 | 68.688 | 1.00 | 19.56 |
| ATOM | 661 | CD1 | LEU | 308 | 21.596 | 73.356 | 67.810 | 1.00 | 9.80 |
| ATOM | 662 | CD2 | LEU | 308 | 22.642 | 75.355 | 68.781 | 1.00 | 18.92 |
| ATOM | 663 | N | LEU | 309 | 17.217 | 76.702 | 68.360 | 1.00 | 23.04 |
| ATOM | 664 | CA | LEU | 309 | 16.031 | 77.317 | 67.740 | 1.00 | 22.80 |
| ATOM | 665 | C | LEU | 309 | 15.537 | 78.579 | 68.499 | 1.00 | 28.05 |
| ATOM | 666 | O | LEU | 309 | 15.164 | 79.590 | 67.894 | 1.00 | 28.58 |
| ATOM | 667 | CB | LEU | 309 | 14.937 | 76.271 | 67.725 | 1.00 | 22.01 |
| ATOM | 668 | CG | LEU | 309 | 14.086 | 76.188 | 66.490 | 1.00 | 23.94 |
| ATOM | 669 | CD1 | LEU | 309 | 13.043 | 77.266 | 66.523 | 1.00 | 27.11 |
| ATOM | 670 | CD2 | LEU | 309 | 14.986 | 76.295 | 65.297 | 1.00 | 30.77 |
| ATOM | 671 | N | ILE | 310 | 15.543 | 78.503 | 69.833 | 1.00 | 32.40 |
| ATOM | 672 | CA | ILE | 310 | 15.141 | 79.589 | 70.745 | 1.00 | 28.14 |
| ATOM | 673 | C | ILE | 310 | 16.216 | 80.687 | 70.789 | 1.00 | 26.11 |
| ATOM | 674 | O | ILE | 310 | 15.914 | 81.862 | 70.668 | 1.00 | 23.24 |
| ATOM | 675 | CB | ILE | 310 | 14.926 | 79.021 | 72.201 | 1.00 | 31.03 |
| ATOM | 676 | CG1 | ILE | 310 | 13.656 | 78.177 | 72.263 | 1.00 | 26.74 |
| ATOM | 677 | CG2 | ILE | 310 | 14.828 | 80.140 | 73.253 | 1.00 | 34.33 |
| ATOM | 678 | CD1 | ILE | 310 | 13.456 | 77.576 | 73.588 | 1.00 | 25.96 |
| ATOM | 679 | N | ALA | 311 | 17.474 | 80.291 | 70.942 | 1.00 | 27.15 |
| ATOM | 680 | CA | ALA | 311 | 18.563 | 81.255 | 71.023 | 1.00 | 28.97 |
| ATOM | 681 | C | ALA | 311 | 18.447 | 82.140 | 69.833 | 1.00 | 30.48 |
| ATOM | 682 | O | ALA | 311 | 18.723 | 83.330 | 69.917 | 1.00 | 36.17 |
| ATOM | 683 | CB | ALA | 311 | 19.899 | 80.565 | 71.033 | 1.00 | 29.09 |
| ATOM | 684 | N | SER | 312 | 17.968 | 81.554 | 68.736 | 1.00 | 30.86 |
| ATOM | 685 | CA | SER | 312 | 17.777 | 82.279 | 67.494 | 1.00 | 29.77 |
| ATOM | 686 | C | SER | 312 | 16.489 | 83.060 | 67.431 | 1.00 | 28.46 |
| ATOM | 687 | O | SER | 312 | 16.566 | 84.285 | 67.376 | 1.00 | 26.28 |
| ATOM | 688 | CB | SER | 312 | 17.900 | 81.363 | 66.288 | 1.00 | 32.52 |
| ATOM | 689 | OG | SER | 312 | 18.879 | 81.890 | 65.410 | 1.00 | 38.04 |
| ATOM | 707 | N | HIS | 315 | 16.912 | 86.232 | 69.632 | 1.00 | 31.29 |
| ATOM | 708 | CA | HIS | 315 | 17.794 | 87.294 | 69.157 | 1.00 | 29.26 |
| ATOM | 709 | C | HIS | 315 | 17.124 | 88.248 | 68.188 | 1.00 | 28.74 |
| ATOM | 710 | O | HIS | 315 | 16.855 | 89.395 | 68.551 | 1.00 | 27.46 |
| ATOM | 711 | CB | HIS | 315 | 19.072 | 86.763 | 68.525 | 1.00 | 31.22 |
| ATOM | 712 | CG | HIS | 315 | 20.217 | 87.709 | 68.665 | 1.00 | 31.31 |
| ATOM | 713 | ND1 | HIS | 315 | 20.069 | 88.950 | 69.246 | 1.00 | 32.38 |
| ATOM | 714 | CD2 | HIS | 315 | 21.536 | 87.565 | 68.422 | 1.00 | 32.42 |
| ATOM | 715 | CE1 | HIS | 315 | 21.252 | 89.524 | 69.371 | 1.00 | 30.07 |
| ATOM | 716 | NE2 | HIS | 315 | 22.161 | 88.704 | 68.878 | 1.00 | 33.09 |
| ATOM | 717 | N | ARG | 316 | 16.783 | 87.749 | 67.000 | 1.00 | 27.07 |
| ATOM | 718 | CA | ARG | 316 | 16.130 | 88.551 | 65.979 | 1.00 | 29.67 |
| ATOM | 719 | C | ARG | 316 | 14.912 | 89.275 | 66.509 | 1.00 | 29.29 |
| ATOM | 720 | O | ARG | 316 | 14.552 | 90.351 | 66.018 | 1.00 | 34.98 |
| ATOM | 721 | CB | ARG | 316 | 15.779 | 87.678 | 64.783 | 1.00 | 31.58 |
| ATOM | 722 | CG | ARG | 316 | 14.818 | 88.255 | 63.768 | 1.00 | 39.55 |
| ATOM | 723 | CD | ARG | 316 | 15.004 | 89.756 | 63.448 | 1.00 | 48.73 |
| ATOM | 724 | NE | ARG | 316 | 16.369 | 90.243 | 63.586 | 1.00 | 52.32 |
| ATOM | 725 | CZ | ARG | 316 | 16.998 | 90.978 | 62.676 | 1.00 | 54.42 |
| ATOM | 726 | NH1 | ARG | 316 | 16.394 | 91.330 | 61.541 | 1.00 | 50.05 |
| ATOM | 727 | NH2 | ARG | 316 | 18.259 | 91.322 | 62.894 | 1.00 | 58.94 |
| ATOM | 742 | N | ALA | 319 | 14.883 | 93.183 | 67.782 | 1.00 | 38.65 |
| ATOM | 743 | CA | ALA | 319 | 14.456 | 94.164 | 66.784 | 1.00 | 37.22 |
| ATOM | 744 | C | ALA | 319 | 13.032 | 94.659 | 67.106 | 1.00 | 39.05 |
| ATOM | 745 | O | ALA | 319 | 12.794 | 95.870 | 67.190 | 1.00 | 39.00 |
| ATOM | 746 | CB | ALA | 319 | 14.501 | 93.511 | 65.386 | 1.00 | 32.02 |
| ATOM | 747 | N | VAL | 320 | 12.136 | 93.697 | 67.349 | 1.00 | 38.72 |
| ATOM | 748 | CA | VAL | 320 | 10.729 | 93.930 | 67.668 | 1.00 | 36.93 |
| ATOM | 749 | C | VAL | 320 | 10.454 | 94.147 | 69.180 | 1.00 | 35.57 |
| ATOM | 750 | O | VAL | 320 | 11.296 | 93.850 | 70.048 | 1.00 | 34.97 |
| ATOM | 751 | CB | VAL | 320 | 9.889 | 92.710 | 67.153 | 1.00 | 36.85 |

TABLE III-continued

Structure Coordinates for Site II in Various NHRs
Based on the Consensus Alignments in FIG. 2

| ATOM | 752 | CG1 | VAL | | 320 | 8.391 | 92.969 | 67.218 | 1.00 | 36.58 |
|---|---|---|---|---|---|---|---|---|---|---|
| ATOM | 753 | CG2 | VAL | | 320 | 10.290 | 92.405 | 65.769 | 1.00 | 30.70 |
| ATOM | 804 | N | THR | | 328 | 10.898 | 82.215 | 58.897 | 1.00 | 32.35 |
| ATOM | 805 | CA | THR | | 328 | 9.845 | 82.464 | 57.948 | 1.00 | 31.40 |
| ATOM | 806 | C | THR | | 328 | 9.676 | 84.002 | 57.703 | 1.00 | 33.59 |
| ATOM | 807 | O | THR | | 328 | 9.033 | 84.413 | 56.733 | 1.00 | 35.22 |
| ATOM | 808 | CB | THR | | 328 | 8.589 | 81.753 | 58.558 | 1.00 | 32.98 |
| ATOM | 809 | OG1 | THR | | 328 | 8.351 | 80.528 | 57.867 | 1.00 | 36.33 |
| ATOM | 810 | CG2 | THR | | 328 | 7.338 | 82.602 | 58.627 | 1.00 | 25.48 |
| ATOM | 1105 | N | LEU | | 367 | 26.072 | 85.794 | 70.190 | 1.00 | 29.24 |
| ATOM | 1106 | CA | LEU | | 367 | 24.948 | 84.884 | 69.994 | 1.00 | 25.60 |
| ATOM | 1107 | C | LEU | | 367 | 25.327 | 83.579 | 69.317 | 1.00 | 25.61 |
| ATOM | 1108 | O | LEU | | 367 | 24.886 | 82.513 | 69.740 | 1.00 | 28.03 |
| ATOM | 1109 | CB | LEU | | 367 | 23.859 | 85.522 | 69.186 | 1.00 | 20.56 |
| ATOM | 1110 | CG | LEU | | 367 | 22.788 | 84.450 | 69.066 | 1.00 | 23.00 |
| ATOM | 1111 | CD1 | LEU | | 367 | 21.733 | 84.549 | 70.133 | 1.00 | 15.44 |
| ATOM | 1112 | CD2 | LEU | | 367 | 22.171 | 84.596 | 67.721 | 1.00 | 30.25 |
| ATOM | 1113 | N | GLY | | 368 | 26.089 | 83.666 | 68.236 | 1.00 | 22.75 |
| ATOM | 1114 | CA | GLY | | 368 | 26.500 | 82.469 | 67.527 | 1.00 | 22.27 |
| ATOM | 1115 | C | GLY | | 368 | 27.456 | 81.654 | 68.379 | 1.00 | 25.34 |
| ATOM | 1116 | O | GLY | | 368 | 27.631 | 80.443 | 68.181 | 1.00 | 24.00 |
| ATOM | 1131 | N | ARG | | 371 | 25.241 | 79.722 | 71.035 | 1.00 | 29.43 |
| ATOM | 1132 | CA | ARG | | 371 | 24.712 | 78.642 | 70.217 | 1.00 | 26.92 |
| ATOM | 1133 | C | ARG | | 371 | 25.781 | 77.585 | 69.780 | 1.00 | 26.81 |
| ATOM | 1134 | O | ARG | | 371 | 25.428 | 76.471 | 69.408 | 1.00 | 30.58 |
| ATOM | 1135 | CB | ARG | | 371 | 24.030 | 79.225 | 68.995 | 1.00 | 26.56 |
| ATOM | 1136 | CG | ARG | | 371 | 22.802 | 80.020 | 69.279 | 1.00 | 22.05 |
| ATOM | 1137 | CD | ARG | | 371 | 22.202 | 80.545 | 67.941 | 1.00 | 26.82 |
| ATOM | 1138 | NE | ARG | | 371 | 21.109 | 79.777 | 67.318 | 1.00 | 24.69 |
| ATOM | 1139 | CZ | ARG | | 371 | 21.216 | 79.073 | 66.183 | 1.00 | 26.53 |
| ATOM | 1140 | NH1 | ARG | | 371 | 22.380 | 78.996 | 65.522 | 1.00 | 18.75 |
| ATOM | 1141 | NH2 | ARG | | 371 | 20.123 | 78.507 | 65.645 | 1.00 | 23.91 |
| | | | TRbeta Site II Residues (ref. 1BSX.pdb) (highlighted residues of SEQ ID NO:12) | | | | | | | |
| ATOM | 120 | N | THR | A | 226 | 30.851 | 22.267 | 38.045 | 1.00 | 49.68 |
| ATOM | 121 | CA | THR | A | 226 | 30.531 | 21.932 | 36.661 | 1.00 | 49.68 |
| ATOM | 122 | C | THR | A | 226 | 29.159 | 21.297 | 36.533 | 1.00 | 49.68 |
| ATOM | 123 | O | THR | A | 226 | 28.301 | 21.819 | 35.826 | 1.00 | 49.68 |
| ATOM | 124 | CB | THR | A | 226 | 31.553 | 20.961 | 36.055 | 1.00 | 41.41 |
| ATOM | 125 | OG1 | THR | A | 226 | 32.808 | 21.630 | 35.883 | 1.00 | 41.41 |
| ATOM | 126 | CG2 | THR | A | 226 | 31.059 | 20.454 | 34.711 | 1.00 | 41.41 |
| ATOM | 127 | N | GLU | A | 227 | 28.955 | 20.163 | 37.198 | 1.00 | 52.18 |
| ATOM | 128 | CA | GLU | A | 227 | 27.657 | 19.492 | 37.138 | 1.00 | 52.18 |
| ATOM | 129 | C | GLU | A | 227 | 26.572 | 20.555 | 37.274 | 1.00 | 52.18 |
| ATOM | 130 | O | GLU | A | 227 | 25.504 | 20.453 | 36.666 | 1.00 | 52.18 |
| ATOM | 131 | CB | GLU | A | 227 | 27.531 | 18.460 | 38.266 | 1.00 | 51.55 |
| ATOM | 132 | N | ALA | A | 228 | 26.867 | 21.584 | 38.065 | 1.00 | 48.32 |
| ATOM | 133 | CA | ALA | A | 228 | 25.931 | 22.674 | 38.278 | 1.00 | 48.32 |
| ATOM | 134 | C | ALA | A | 228 | 25.789 | 23.508 | 37.019 | 1.00 | 48.32 |
| ATOM | 135 | O | ALA | A | 228 | 24.795 | 23.399 | 36.306 | 1.00 | 48.32 |
| ATOM | 136 | CB | ALA | A | 228 | 26.399 | 23.543 | 39.421 | 1.00 | 41.74 |
| ATOM | 137 | N | HIS | A | 229 | 26.788 | 24.332 | 36.732 | 1.00 | 50.10 |
| ATOM | 138 | CA | HIS | A | 229 | 26.723 | 25.177 | 35.548 | 1.00 | 50.10 |
| ATOM | 139 | C | HIS | A | 229 | 26.203 | 24.491 | 34.305 | 1.00 | 50.10 |
| ATOM | 140 | O | HIS | A | 229 | 25.567 | 25.131 | 33.479 | 1.00 | 50.10 |
| ATOM | 141 | CB | HIS | A | 229 | 28.087 | 25.785 | 35.210 | 1.00 | 43.42 |
| ATOM | 142 | CG | HIS | A | 229 | 28.138 | 26.393 | 33.838 | 1.00 | 43.42 |
| ATOM | 143 | ND1 | HIS | A | 229 | 27.215 | 27.315 | 33.403 | 1.00 | 43.42 |
| ATOM | 144 | CD2 | HIS | A | 229 | 28.981 | 26.180 | 32.800 | 1.00 | 43.42 |
| ATOM | 145 | CE1 | HIS | A | 229 | 27.485 | 27.645 | 32.150 | 1.00 | 43.42 |
| ATOM | 146 | NE2 | HIS | A | 229 | 28.551 | 26.971 | 31.762 | 1.00 | 43.42 |
| ATOM | 147 | N | VAL | A | 230 | 26.475 | 23.201 | 34.162 | 1.00 | 55.78 |
| ATOM | 148 | CA | VAL | A | 230 | 26.036 | 22.498 | 32.969 | 1.00 | 55.78 |
| ATOM | 149 | C | VAL | A | 230 | 24.555 | 22.163 | 32.958 | 1.00 | 55.78 |
| ATOM | 150 | O | VAL | A | 230 | 23.905 | 22.238 | 31.914 | 1.00 | 55.78 |
| ATOM | 151 | CB | VAL | A | 230 | 26.812 | 21.196 | 32.761 | 1.00 | 55.57 |
| ATOM | 152 | CG1 | VAL | A | 230 | 26.472 | 20.625 | 31.395 | 1.00 | 55.57 |
| ATOM | 153 | CG2 | VAL | A | 230 | 28.295 | 21.453 | 32.874 | 1.00 | 55.57 |
| ATOM | 154 | N | ALA | A | 231 | 24.023 | 21.785 | 34.112 | 1.00 | 61.34 |
| ATOM | 155 | CA | ALA | A | 231 | 22.614 | 21.450 | 34.198 | 1.00 | 61.34 |
| ATOM | 156 | C | ALA | A | 231 | 21.787 | 22.725 | 34.312 | 1.00 | 61.34 |
| ATOM | 157 | O | ALA | A | 231 | 20.560 | 22.675 | 34.303 | 1.00 | 61.34 |
| ATOM | 158 | CB | ALA | A | 231 | 22.368 | 20.557 | 35.394 | 1.00 | 58.57 |
| ATOM | 159 | N | THR | A | 232 | 22.463 | 23.866 | 34.408 | 1.00 | 57.34 |
| ATOM | 160 | CA | THR | A | 232 | 21.773 | 25.145 | 34.532 | 1.00 | 57.34 |

TABLE III-continued

Structure Coordinates for Site II in Various NHRs
Based on the Consensus Alignments in FIG.2

| ATOM | 161 | C | THR | A | 232 | 22.150 | 26.114 | 33.426 | 1.00 | 57.34 |
|---|---|---|---|---|---|---|---|---|---|---|
| ATOM | 162 | O | THR | A | 232 | 21.941 | 27.315 | 33.561 | 1.00 | 57.34 |
| ATOM | 163 | CB | THR | A | 232 | 22.099 | 25.859 | 35.854 | 1.00 | 50.43 |
| ATOM | 164 | OG1 | THR | A | 232 | 23.454 | 26.318 | 35.822 | 1.00 | 50.43 |
| ATOM | 165 | CG2 | THR | A | 232 | 21.927 | 24.918 | 37.026 | 1.00 | 50.43 |
| ATOM | 166 | N | ASN | A | 233 | 22.727 | 25.604 | 32.347 | 1.00 | 73.93 |
| ATOM | 167 | CA | ASN | A | 233 | 23.115 | 26.458 | 31.234 | 1.00 | 73.93 |
| ATOM | 168 | C | ASN | A | 233 | 22.217 | 26.033 | 30.085 | 1.00 | 73.93 |
| ATOM | 169 | O | ASN | A | 233 | 22.240 | 24.876 | 29.673 | 1.00 | 73.93 |
| ATOM | 170 | CB | ASN | A | 233 | 24.593 | 26.254 | 30.897 | 1.00 | 81.13 |
| ATOM | 171 | CG | ASN | A | 233 | 25.110 | 27.263 | 29.895 | 1.00 | 81.13 |
| ATOM | 172 | OD1 | ASN | A | 233 | 24.893 | 28.463 | 30.034 | 1.00 | 81.13 |
| ATOM | 173 | ND2 | ASN | A | 233 | 25.822 | 26.779 | 28.888 | 1.00 | 81.13 |
| ATOM | 174 | N | ALA | A | 234 | 21.423 | 26.971 | 29.584 | 1.00 | 85.48 |
| ATOM | 175 | CA | ALA | A | 234 | 20.464 | 26.693 | 28.526 | 1.00 | 85.48 |
| ATOM | 176 | C | ALA | A | 234 | 20.981 | 26.046 | 27.264 | 1.00 | 85.48 |
| ATOM | 177 | O | ALA | A | 234 | 21.988 | 26.456 | 26.703 | 1.00 | 85.48 |
| ATOM | 178 | CB | ALA | A | 234 | 19.718 | 27.958 | 28.161 | 1.00 | 84.92 |
| ATOM | 179 | N | GLN | A | 235 | 20.249 | 25.029 | 26.827 | 1.00 | 89.64 |
| ATOM | 180 | CA | GLN | A | 235 | 20.566 | 24.303 | 25.612 | 1.00 | 89.64 |
| ATOM | 181 | C | GLN | A | 235 | 21.961 | 23.679 | 25.535 | 1.00 | 89.64 |
| ATOM | 182 | O | GLN | A | 235 | 22.338 | 23.154 | 24.489 | 1.00 | 89.64 |
| ATOM | 183 | CB | GLN | A | 235 | 20.336 | 25.224 | 24.399 | 1.00 | 92.63 |
| ATOM | 184 | CG | GLN | A | 235 | 18.884 | 25.361 | 23.918 | 1.00 | 92.63 |
| ATOM | 185 | CD | GLN | A | 235 | 17.879 | 25.531 | 25.043 | 1.00 | 92.63 |
| ATOM | 186 | OE1 | GLN | A | 235 | 17.649 | 24.611 | 25.825 | 1.00 | 92.63 |
| ATOM | 187 | NE2 | GLN | A | 235 | 17.274 | 26.712 | 25.128 | 1.00 | 92.63 |
| ATOM | 429 | N | ILE | A | 275 | 11.867 | 37.044 | 28.524 | 1.00 | 66.16 |
| ATOM | 430 | CA | ILE | A | 275 | 12.617 | 35.819 | 28.794 | 1.00 | 66.16 |
| ATOM | 431 | C | ILE | A | 275 | 13.556 | 35.932 | 29.996 | 1.00 | 66.16 |
| ATOM | 432 | O | ILE | A | 275 | 14.025 | 34.929 | 30.527 | 1.00 | 66.16 |
| ATOM | 433 | CB | ILE | A | 275 | 13.441 | 35.398 | 27.562 | 1.00 | 58.27 |
| ATOM | 434 | CG1 | ILE | A | 275 | 14.324 | 36.551 | 27.107 | 1.00 | 58.27 |
| ATOM | 435 | CG2 | ILE | A | 275 | 12.519 | 34.972 | 26.444 | 1.00 | 58.27 |
| ATOM | 436 | CD1 | ILE | A | 275 | 15.091 | 36.244 | 25.857 | 1.00 | 58.27 |
| ATOM | 437 | N | ILE | A | 276 | 13.815 | 37.158 | 30.429 | 1.00 | 66.14 |
| ATOM | 438 | CA | ILE | A | 276 | 14.706 | 37.417 | 31.553 | 1.00 | 66.14 |
| ATOM | 439 | C | ILE | A | 276 | 14.296 | 36.685 | 32.827 | 1.00 | 66.14 |
| ATOM | 440 | O | ILE | A | 276 | 15.089 | 36.539 | 33.750 | 1.00 | 66.14 |
| ATOM | 441 | CB | ILE | A | 276 | 14.737 | 38.915 | 31.859 | 1.00 | 69.98 |
| ATOM | 442 | CG1 | ILE | A | 276 | 15.765 | 39.220 | 32.948 | 1.00 | 69.98 |
| ATOM | 443 | CG2 | ILE | A | 276 | 13.369 | 39.364 | 32.318 | 1.00 | 69.98 |
| ATOM | 444 | CD1 | ILE | A | 276 | 17.177 | 38.987 | 32.517 | 1.00 | 69.98 |
| ATOM | 459 | N | ALA | A | 279 | 15.631 | 33.064 | 33.124 | 1.00 | 47.85 |
| ATOM | 460 | CA | ALA | A | 279 | 17.065 | 33.172 | 33.057 | 1.00 | 47.85 |
| ATOM | 461 | C | ALA | A | 279 | 17.588 | 33.271 | 34.468 | 1.00 | 47.85 |
| ATOM | 462 | O | ALA | A | 279 | 18.519 | 32.561 | 34.851 | 1.00 | 47.85 |
| ATOM | 463 | CB | ALA | A | 279 | 17.440 | 34.378 | 32.279 | 1.00 | 44.05 |
| ATOM | 464 | N | ILE | A | 280 | 16.968 | 34.144 | 35.251 | 1.00 | 44.23 |
| ATOM | 465 | CA | ILE | A | 280 | 17.392 | 34.322 | 36.623 | 1.00 | 44.23 |
| ATOM | 466 | C | ILE | A | 280 | 17.201 | 33.025 | 37.392 | 1.00 | 44.23 |
| ATOM | 467 | O | ILE | A | 280 | 18.088 | 32.606 | 38.133 | 1.00 | 44.23 |
| ATOM | 468 | CB | ILE | A | 280 | 16.616 | 35.455 | 37.297 | 1.00 | 39.34 |
| ATOM | 469 | CG1 | ILE | A | 280 | 16.852 | 36.757 | 36.541 | 1.00 | 39.34 |
| ATOM | 470 | CG2 | ILE | A | 280 | 17.062 | 35.605 | 38.721 | 1.00 | 39.34 |
| ATOM | 471 | CD1 | ILE | A | 280 | 16.284 | 37.966 | 37.238 | 1.00 | 39.34 |
| ATOM | 472 | N | THR | A | 281 | 16.059 | 32.375 | 37.189 | 1.00 | 43.46 |
| ATOM | 473 | CA | THR | A | 281 | 15.792 | 31.119 | 37.879 | 1.00 | 43.46 |
| ATOM | 474 | C | THR | A | 281 | 16.976 | 30.173 | 37.710 | 1.00 | 43.46 |
| ATOM | 475 | O | THR | A | 281 | 17.415 | 29.548 | 38.680 | 1.00 | 43.46 |
| ATOM | 476 | CB | THR | A | 281 | 14.519 | 30.404 | 37.347 | 1.00 | 52.33 |
| ATOM | 477 | OG1 | THR | A | 281 | 14.671 | 30.149 | 35.948 | 1.00 | 52.33 |
| ATOM | 478 | CG2 | THR | A | 281 | 13.280 | 31.252 | 37.562 | 1.00 | 52.33 |
| ATOM | 479 | N | ARG | A | 282 | 17.495 | 30.071 | 36.486 | 1.00 | 47.94 |
| ATOM | 480 | CA | ARG | A | 282 | 18.634 | 29.199 | 36.202 | 1.00 | 47.94 |
| ATOM | 481 | C | ARG | A | 282 | 19.775 | 29.579 | 37.128 | 1.00 | 47.94 |
| ATOM | 482 | O | ARG | A | 282 | 20.358 | 28.732 | 37.806 | 1.00 | 47.94 |
| ATOM | 483 | CB | ARG | A | 282 | 19.099 | 29.381 | 34.765 | 1.00 | 74.21 |
| ATOM | 484 | CG | ARG | A | 282 | 19.187 | 28.100 | 33.973 | 1.00 | 74.21 |
| ATOM | 485 | CD | ARG | A | 282 | 18.007 | 27.962 | 33.025 | 1.00 | 74.21 |
| ATOM | 486 | NE | ARG | A | 282 | 17.893 | 29.117 | 32.136 | 1.00 | 74.21 |
| ATOM | 487 | CZ | ARG | A | 282 | 18.885 | 29.602 | 31.390 | 1.00 | 74.21 |
| ATOM | 488 | NH1 | ARG | A | 282 | 20.093 | 29.045 | 31.411 | 1.00 | 74.21 |
| ATOM | 489 | NH2 | ARG | A | 282 | 18.675 | 30.670 | 30.633 | 1.00 | 74.21 |
| ATOM | 490 | N | VAL | A | 283 | 20.092 | 30.868 | 37.138 | 1.00 | 45.45 |
| ATOM | 491 | CA | VAL | A | 283 | 21.142 | 31.375 | 37.990 | 1.00 | 45.45 |

TABLE III-continued

Structure Coordinates for Site II in Various NHRs
Based on the Consensus Alignments in FIG.2

| ATOM | 492 | C | VAL | A | 283 | 20.852 | 30.908 | 39.405 | 1.00 | 45.45 |
|------|-----|-----|-----|---|-----|--------|--------|--------|------|-------|
| ATOM | 493 | O | VAL | A | 283 | 21.743 | 30.458 | 40.112 | 1.00 | 45.45 |
| ATOM | 494 | CB | VAL | A | 283 | 21.170 | 32.895 | 37.957 | 1.00 | 42.13 |
| ATOM | 495 | CG1 | VAL | A | 283 | 22.286 | 33.411 | 38.849 | 1.00 | 42.13 |
| ATOM | 496 | CG2 | VAL | A | 283 | 21.361 | 33.358 | 36.533 | 1.00 | 42.13 |
| ATOM | 497 | N | VAL | A | 284 | 19.597 | 31.008 | 39.822 | 1.00 | 42.56 |
| ATOM | 498 | CA | VAL | A | 284 | 19.247 | 30.549 | 41.157 | 1.00 | 42.56 |
| ATOM | 499 | C | VAL | A | 284 | 19.516 | 29.042 | 41.234 | 1.00 | 42.56 |
| ATOM | 500 | O | VAL | A | 284 | 20.202 | 28.575 | 42.140 | 1.00 | 42.56 |
| ATOM | 501 | CB | VAL | A | 284 | 17.762 | 30.790 | 41.492 | 1.00 | 42.15 |
| ATOM | 502 | CG1 | VAL | A | 284 | 17.499 | 30.381 | 42.909 | 1.00 | 42.15 |
| ATOM | 503 | CG2 | VAL | A | 284 | 17.416 | 32.242 | 41.313 | 1.00 | 42.15 |
| ATOM | 504 | N | ASP | A | 285 | 18.987 | 28.283 | 40.277 | 1.00 | 48.17 |
| ATOM | 505 | CA | ASP | A | 285 | 19.197 | 26.843 | 40.267 | 1.00 | 48.17 |
| ATOM | 506 | C | ASP | A | 285 | 20.676 | 26.473 | 40.291 | 1.00 | 48.17 |
| ATOM | 507 | O | ASP | A | 285 | 21.044 | 25.441 | 40.846 | 1.00 | 48.17 |
| ATOM | 508 | CB | ASP | A | 285 | 18.522 | 26.204 | 39.051 | 1.00 | 48.63 |
| ATOM | 509 | CG | ASP | A | 285 | 17.005 | 26.271 | 39.122 | 1.00 | 48.63 |
| ATOM | 510 | OD1 | ASP | A | 285 | 16.432 | 25.721 | 40.086 | 1.00 | 48.63 |
| ATOM | 511 | OD2 | ASP | A | 285 | 16.381 | 26.865 | 38.212 | 1.00 | 48.63 |
| ATOM | 512 | N | PHE | A | 286 | 21.522 | 27.308 | 39.694 | 1.00 | 49.87 |
| ATOM | 513 | CA | PHE | A | 286 | 22.954 | 27.030 | 39.687 | 1.00 | 49.87 |
| ATOM | 514 | C | PHE | A | 286 | 23.543 | 27.124 | 41.087 | 1.00 | 49.87 |
| ATOM | 515 | O | PHE | A | 286 | 24.226 | 26.213 | 41.538 | 1.00 | 49.87 |
| ATOM | 516 | CB | PHE | A | 286 | 23.687 | 27.997 | 38.760 | 1.00 | 50.22 |
| ATOM | 517 | CG | PHE | A | 286 | 25.176 | 28.000 | 38.940 | 1.00 | 50.22 |
| ATOM | 518 | CD1 | PHE | A | 286 | 25.906 | 26.828 | 38.855 | 1.00 | 50.22 |
| ATOM | 519 | CD2 | PHE | A | 286 | 25.843 | 29.186 | 39.197 | 1.00 | 50.22 |
| ATOM | 520 | CE1 | PHE | A | 286 | 27.283 | 26.841 | 39.025 | 1.00 | 50.22 |
| ATOM | 521 | CE2 | PHE | A | 286 | 27.214 | 29.210 | 39.367 | 1.00 | 50.22 |
| ATOM | 522 | CZ | PHE | A | 286 | 27.937 | 28.038 | 39.284 | 1.00 | 50.22 |
| ATOM | 687 | N | CYS | A | 308 | 25.191 | 39.069 | 42.212 | 1.00 | 44.63 |
| ATOM | 688 | CA | CYS | A | 308 | 25.837 | 38.359 | 41.123 | 1.00 | 44.63 |
| ATOM | 689 | C | CYS | A | 308 | 24.900 | 37.906 | 40.016 | 1.00 | 44.63 |
| ATOM | 690 | O | CYS | A | 308 | 25.366 | 37.375 | 39.015 | 1.00 | 44.63 |
| ATOM | 691 | CB | CYS | A | 308 | 26.554 | 37.125 | 41.658 | 1.00 | 42.54 |
| ATOM | 692 | SG | CYS | A | 308 | 25.409 | 35.829 | 42.131 | 1.00 | 42.54 |
| ATOM | 693 | N | CYS | A | 309 | 23.595 | 38.101 | 40.167 | 1.00 | 41.98 |
| ATOM | 694 | CA | CYS | A | 309 | 22.708 | 37.618 | 39.121 | 1.00 | 41.98 |
| ATOM | 695 | C | CYS | A | 309 | 23.019 | 38.142 | 37.746 | 1.00 | 41.98 |
| ATOM | 696 | O | CYS | A | 309 | 23.149 | 37.369 | 36.805 | 1.00 | 41.98 |
| ATOM | 697 | CB | CYS | A | 309 | 21.257 | 37.924 | 39.404 | 1.00 | 47.81 |
| ATOM | 698 | SG | CYS | A | 309 | 20.268 | 37.272 | 38.051 | 1.00 | 47.81 |
| ATOM | 699 | N | MET | A | 310 | 23.111 | 39.456 | 37.611 | 1.00 | 40.05 |
| ATOM | 700 | CA | MET | A | 310 | 23.419 | 40.020 | 36.308 | 1.00 | 40.05 |
| ATOM | 701 | C | MET | A | 310 | 24.800 | 39.539 | 35.896 | 1.00 | 40.05 |
| ATOM | 702 | O | MET | A | 310 | 24.988 | 39.040 | 34.788 | 1.00 | 40.05 |
| ATOM | 703 | CB | MET | A | 310 | 23.387 | 41.553 | 36.357 | 1.00 | 39.89 |
| ATOM | 704 | CG | MET | A | 310 | 23.777 | 42.209 | 35.045 | 1.00 | 39.89 |
| ATOM | 705 | SD | MET | A | 310 | 22.737 | 41.646 | 33.699 | 1.00 | 39.89 |
| ATOM | 706 | CE | MET | A | 310 | 23.594 | 42.336 | 32.298 | 1.00 | 39.89 |
| ATOM | 707 | N | GLU | A | 311 | 25.756 | 39.668 | 36.814 | 1.00 | 40.89 |
| ATOM | 708 | CA | GLU | A | 311 | 27.134 | 39.274 | 36.565 | 1.00 | 40.89 |
| ATOM | 709 | C | GLU | A | 311 | 27.213 | 37.868 | 35.958 | 1.00 | 40.89 |
| ATOM | 710 | O | GLU | A | 311 | 27.864 | 37.673 | 34.929 | 1.00 | 40.89 |
| ATOM | 711 | CB | GLU | A | 311 | 27.940 | 39.357 | 37.866 | 1.00 | 37.60 |
| ATOM | 712 | CG | GLU | A | 311 | 27.708 | 40.646 | 38.645 | 1.00 | 37.60 |
| ATOM | 713 | CD | GLU | A | 311 | 28.590 | 40.779 | 39.885 | 1.00 | 37.60 |
| ATOM | 714 | OE1 | GLU | A | 311 | 28.752 | 39.789 | 40.629 | 1.00 | 37.60 |
| ATOM | 715 | OE2 | GLU | A | 311 | 29.112 | 41.888 | 40.139 | 1.00 | 37.60 |
| ATOM | 716 | N | ILE | A | 312 | 26.536 | 36.896 | 36.566 | 1.00 | 40.84 |
| ATOM | 717 | CA | ILE | A | 312 | 26.569 | 35.533 | 36.035 | 1.00 | 40.84 |
| ATOM | 718 | C | ILE | A | 312 | 25.827 | 35.408 | 34.707 | 1.00 | 40.84 |
| ATOM | 719 | O | ILE | A | 312 | 26.255 | 34.664 | 33.825 | 1.00 | 40.84 |
| ATOM | 720 | CB | ILE | A | 312 | 25.983 | 34.485 | 37.033 | 1.00 | 34.15 |
| ATOM | 721 | CG1 | ILE | A | 312 | 26.836 | 34.423 | 38.306 | 1.00 | 34.15 |
| ATOM | 722 | CG2 | ILE | A | 312 | 25.970 | 33.106 | 36.388 | 1.00 | 34.15 |
| ATOM | 723 | CD1 | ILE | A | 312 | 26.350 | 33.418 | 39.331 | 1.00 | 34.15 |
| ATOM | 724 | N | MET | A | 313 | 24.718 | 36.131 | 34.558 | 1.00 | 41.96 |
| ATOM | 725 | CA | MET | A | 313 | 23.961 | 36.071 | 33.312 | 1.00 | 41.96 |
| ATOM | 726 | C | MET | A | 313 | 24.773 | 36.591 | 32.138 | 1.00 | 41.96 |
| ATOM | 727 | O | MET | A | 313 | 25.071 | 35.834 | 31.216 | 1.00 | 41.96 |
| ATOM | 728 | CB | MET | A | 313 | 22.635 | 36.843 | 33.423 | 1.00 | 52.96 |
| ATOM | 729 | CG | MET | A | 313 | 21.562 | 36.115 | 34.245 | 1.00 | 52.96 |
| ATOM | 730 | SD | MET | A | 313 | 19.862 | 36.769 | 34.098 | 1.00 | 52.96 |
| ATOM | 731 | CE | MET | A | 313 | 20.065 | 38.413 | 34.741 | 1.00 | 52.96 |

TABLE III-continued

Structure Coordinates for Site II in Various NHRs
Based on the Consensus Alignments in FIG.2

| ATOM | 732 | N | SER | A | 314 | 25.141 | 37.872 | 32.175 | 1.00 | 38.33 |
|---|---|---|---|---|---|---|---|---|---|---|
| ATOM | 733 | CA | SER | A | 314 | 25.928 | 38.462 | 31.094 | 1.00 | 38.33 |
| ATOM | 734 | C | SER | A | 314 | 27.198 | 37.658 | 30.774 | 1.00 | 38.33 |
| ATOM | 735 | O | SER | A | 314 | 27.604 | 37.587 | 29.616 | 1.00 | 38.33 |
| ATOM | 736 | CB | SER | A | 314 | 26.266 | 39.927 | 31.408 | 1.00 | 50.03 |
| ATOM | 737 | OG | SER | A | 314 | 26.887 | 40.065 | 32.665 | 1.00 | 50.03 |
| ATOM | 738 | N | LEU | A | 315 | 27.832 | 37.056 | 31.781 | 1.00 | 38.47 |
| ATOM | 739 | CA | LEU | A | 315 | 29.017 | 36.237 | 31.501 | 1.00 | 38.47 |
| ATOM | 740 | C | LEU | A | 315 | 28.558 | 35.167 | 30.527 | 1.00 | 38.47 |
| ATOM | 741 | O | LEU | A | 315 | 29.058 | 35.052 | 29.406 | 1.00 | 38.47 |
| ATOM | 742 | CB | LEU | A | 315 | 29.557 | 35.548 | 32.769 | 1.00 | 31.33 |
| ATOM | 743 | CG | LEU | A | 315 | 30.628 | 34.464 | 32.514 | 1.00 | 31.33 |
| ATOM | 744 | CD1 | LEU | A | 315 | 31.827 | 35.048 | 31.781 | 1.00 | 31.33 |
| ATOM | 745 | CD2 | LEU | A | 315 | 31.073 | 33.845 | 33.830 | 1.00 | 31.33 |
| ATOM | 746 | N | ARG | A | 316 | 27.572 | 34.405 | 30.981 | 1.00 | 42.55 |
| ATOM | 747 | CA | ARG | A | 316 | 26.994 | 33.320 | 30.217 | 1.00 | 42.55 |
| ATOM | 748 | C | ARG | A | 316 | 26.637 | 33.669 | 28.803 | 1.00 | 42.55 |
| ATOM | 749 | O | ARG | A | 316 | 26.555 | 32.788 | 27.963 | 1.00 | 42.55 |
| ATOM | 750 | CB | ARG | A | 316 | 25.752 | 32.799 | 30.916 | 1.00 | 40.97 |
| ATOM | 751 | CG | ARG | A | 316 | 26.060 | 32.162 | 32.237 | 1.00 | 40.97 |
| ATOM | 752 | CD | ARG | A | 316 | 24.851 | 31.475 | 32.762 | 1.00 | 40.97 |
| ATOM | 753 | NE | ARG | A | 316 | 25.222 | 30.313 | 33.542 | 1.00 | 40.97 |
| ATOM | 754 | CZ | ARG | A | 316 | 24.347 | 29.411 | 33.946 | 1.00 | 40.97 |
| ATOM | 755 | NH1 | ARG | A | 316 | 23.068 | 29.558 | 33.631 | 1.00 | 40.97 |
| ATOM | 756 | NH2 | ARG | A | 316 | 24.750 | 28.354 | 34.634 | 1.00 | 40.97 |
| ATOM | 767 | N | VAL | A | 319 | 30.221 | 34.487 | 26.650 | 1.00 | 50.27 |
| ATOM | 768 | CA | VAL | A | 319 | 30.869 | 33.230 | 26.290 | 1.00 | 50.27 |
| ATOM | 769 | C | VAL | A | 319 | 30.179 | 32.610 | 25.100 | 1.00 | 50.27 |
| ATOM | 770 | O | VAL | A | 319 | 30.602 | 31.575 | 24.606 | 1.00 | 50.27 |
| ATOM | 771 | CB | VAL | A | 319 | 30.823 | 32.209 | 27.430 | 1.00 | 43.16 |
| ATOM | 772 | CG1 | VAL | A | 319 | 31.272 | 32.861 | 28.722 | 1.00 | 43.16 |
| ATOM | 773 | CG2 | VAL | A | 319 | 29.432 | 31.637 | 27.550 | 1.00 | 43.16 |
| ATOM | 774 | N | ARG | A | 320 | 29.110 | 33.252 | 24.652 | 1.00 | 54.91 |
| ATOM | 775 | CA | ARG | A | 320 | 28.355 | 32.781 | 23.510 | 1.00 | 54.91 |
| ATOM | 776 | C | ARG | A | 320 | 28.265 | 33.790 | 22.377 | 1.00 | 54.91 |
| ATOM | 777 | O | ARG | A | 320 | 27.257 | 33.876 | 21.680 | 1.00 | 54.91 |
| ATOM | 778 | CB | ARG | A | 320 | 26.968 | 32.356 | 23.958 | 1.00 | 63.84 |
| ATOM | 779 | CG | ARG | A | 320 | 26.891 | 30.895 | 24.301 | 1.00 | 63.84 |
| ATOM | 780 | CD | ARG | A | 320 | 25.569 | 30.557 | 24.916 | 1.00 | 63.84 |
| ATOM | 781 | NE | ARG | A | 320 | 25.330 | 29.123 | 24.908 | 1.00 | 63.84 |
| ATOM | 782 | CZ | ARG | A | 320 | 24.358 | 28.541 | 25.594 | 1.00 | 63.84 |
| ATOM | 783 | NH1 | ARG | A | 320 | 23.552 | 29.283 | 26.341 | 1.00 | 63.84 |
| ATOM | 784 | NH2 | ARG | A | 320 | 24.177 | 27.230 | 25.517 | 1.00 | 63.84 |
| ATOM | 797 | N | ASP | A | 322 | 29.281 | 34.908 | 18.810 | 1.00 | 58.89 |
| ATOM | 798 | CA | ASP | A | 322 | 29.780 | 34.397 | 17.537 | 1.00 | 58.89 |
| ATOM | 799 | C | ASP | A | 322 | 30.428 | 35.585 | 16.827 | 1.00 | 58.89 |
| ATOM | 800 | O | ASP | A | 322 | 29.729 | 36.503 | 16.396 | 1.00 | 58.89 |
| ATOM | 801 | CB | ASP | A | 322 | 28.614 | 33.892 | 16.678 | 1.00 | 55.15 |
| ATOM | 802 | CG | ASP | A | 322 | 29.068 | 33.304 | 15.347 | 1.00 | 55.15 |
| ATOM | 803 | OD1 | ASP | A | 322 | 30.036 | 33.842 | 14.755 | 1.00 | 55.15 |
| ATOM | 804 | OD2 | ASP | A | 322 | 28.439 | 32.323 | 14.884 | 1.00 | 55.15 |
| ATOM | 805 | N | PRO | A | 323 | 31.770 | 35.612 | 16.709 | 1.00 | 61.57 |
| ATOM | 806 | CA | PRO | A | 323 | 32.317 | 36.775 | 16.017 | 1.00 | 61.57 |
| ATOM | 807 | C | PRO | A | 323 | 31.913 | 36.892 | 14.533 | 1.00 | 61.57 |
| ATOM | 808 | O | PRO | A | 323 | 31.828 | 38.003 | 14.009 | 1.00 | 61.57 |
| ATOM | 809 | CB | PRO | A | 323 | 33.815 | 36.566 | 16.199 | 1.00 | 58.50 |
| ATOM | 810 | CG | PRO | A | 323 | 33.915 | 35.076 | 16.059 | 1.00 | 58.50 |
| ATOM | 811 | CD | PRO | A | 323 | 32.892 | 34.762 | 17.138 | 1.00 | 58.50 |
| ATOM | 812 | N | GLU | A | 324 | 31.698 | 35.772 | 13.842 | 1.00 | 69.24 |
| ATOM | 813 | CA | GLU | A | 324 | 31.296 | 35.868 | 12.438 | 1.00 | 69.24 |
| ATOM | 814 | C | GLU | A | 324 | 30.010 | 36.700 | 12.397 | 1.00 | 69.24 |
| ATOM | 815 | O | GLU | A | 324 | 30.041 | 37.868 | 12.016 | 1.00 | 69.24 |
| ATOM | 816 | CB | GLU | A | 324 | 31.039 | 34.482 | 11.809 | 1.00 | 56.60 |
| ATOM | 817 | CG | GLU | A | 324 | 32.215 | 33.479 | 11.837 | 1.00 | 56.60 |
| ATOM | 818 | CD | GLU | A | 324 | 33.545 | 34.037 | 11.313 | 1.00 | 56.60 |
| ATOM | 819 | OE1 | GLU | A | 324 | 33.521 | 34.931 | 10.433 | 1.00 | 56.60 |
| ATOM | 820 | OE2 | GLU | A | 324 | 34.620 | 33.556 | 11.761 | 1.00 | 56.60 |
| ATOM | 874 | N | GLY | A | 332 | 20.090 | 31.110 | 25.121 | 1.00 | 73.02 |
| ATOM | 875 | CA | GLY | A | 332 | 20.316 | 30.023 | 24.190 | 1.00 | 73.02 |
| ATOM | 876 | C | GLY | A | 332 | 19.274 | 29.921 | 23.092 | 1.00 | 73.02 |
| ATOM | 877 | O | GLY | A | 332 | 19.303 | 28.984 | 22.297 | 1.00 | 73.02 |
| ATOM | 1148 | N | VAL | A | 370 | 34.003 | 28.455 | 32.872 | 1.00 | 40.00 |
| ATOM | 1149 | CA | VAL | A | 370 | 32.879 | 29.368 | 32.981 | 1.00 | 40.00 |
| ATOM | 1150 | C | VAL | A | 370 | 32.280 | 29.144 | 34.357 | 1.00 | 40.00 |
| ATOM | 1151 | O | VAL | A | 370 | 32.101 | 30.082 | 35.129 | 1.00 | 40.00 |
| ATOM | 1152 | CB | VAL | A | 370 | 31.778 | 29.065 | 31.943 | 1.00 | 37.32 |

TABLE III-continued

Structure Coordinates for Site II in Various NHRs
Based on the Consensus Alignments in FIG.2

| ATOM | 1153 | CG1 | VAL | A | 370 | 30.607 | 29.997 | 32.157 | 1.00 | 37.32 |
|---|---|---|---|---|---|---|---|---|---|---|
| ATOM | 1154 | CG2 | VAL | A | 370 | 32.327 | 29.220 | 30.542 | 1.00 | 37.32 |
| ATOM | 1155 | N | ALA | A | 371 | 31.993 | 27.882 | 34.655 | 1.00 | 37.67 |
| ATOM | 1156 | CA | ALA | A | 371 | 31.407 | 27.503 | 35.927 | 1.00 | 37.67 |
| ATOM | 1157 | C | ALA | A | 371 | 32.165 | 28.154 | 37.072 | 1.00 | 37.67 |
| ATOM | 1158 | O | ALA | A | 371 | 31.621 | 28.990 | 37.784 | 1.00 | 37.67 |
| ATOM | 1159 | CB | ALA | A | 371 | 31.418 | 25.989 | 36.075 | 1.00 | 32.11 |
| ATOM | 1176 | N | GLN | A | 374 | 31.828 | 31.691 | 37.341 | 1.00 | 36.73 |
| ATOM | 1177 | CA | GLN | A | 374 | 30.505 | 32.029 | 37.866 | 1.00 | 36.73 |
| ATOM | 1178 | C | GLN | A | 374 | 30.426 | 31.946 | 39.387 | 1.00 | 36.73 |
| ATOM | 1179 | O | GLN | A | 374 | 29.713 | 32.733 | 40.017 | 1.00 | 36.73 |
| ATOM | 1180 | CB | GLN | A | 374 | 29.428 | 31.110 | 37.293 | 1.00 | 37.11 |
| ATOM | 1181 | CG | GLN | A | 374 | 29.254 | 31.181 | 35.797 | 1.00 | 37.11 |
| ATOM | 1182 | CD | GLN | A | 374 | 28.133 | 30.278 | 35.318 | 1.00 | 37.11 |
| ATOM | 1183 | OE1 | GLN | A | 374 | 27.860 | 30.179 | 34.121 | 1.00 | 37.11 |
| ATOM | 1184 | NE2 | GLN | A | 374 | 27.476 | 29.614 | 36.257 | 1.00 | 37.11 |
| VitDR Site II Residues (ref. 1DB1.pdb) (highlighted residues of SEQ ID NO:9) | | | | | | | | | | |
| ATOM | 134 | N | LEU | A | 136 | 20.223 | 7.725 | 47.913 | 1.00 | 22.40 |
| ATOM | 135 | CA | LEU | A | 136 | 20.991 | 7.675 | 46.669 | 1.00 | 23.29 |
| ATOM | 136 | C | LEU | A | 136 | 20.302 | 6.721 | 45.705 | 1.00 | 23.50 |
| ATOM | 137 | O | LEU | A | 136 | 20.191 | 6.996 | 44.512 | 1.00 | 23.31 |
| ATOM | 138 | CB | LEU | A | 136 | 22.424 | 7.194 | 46.920 | 1.00 | 24.60 |
| ATOM | 139 | CG | LEU | A | 136 | 23.395 | 8.196 | 47.549 | 1.00 | 25.56 |
| ATOM | 140 | CD1 | LEU | A | 136 | 24.740 | 7.518 | 47.798 | 1.00 | 26.67 |
| ATOM | 141 | CD2 | LEU | A | 136 | 23.555 | 9.398 | 46.628 | 1.00 | 26.04 |
| ATOM | 142 | N | ASP | A | 137 | 19.845 | 5.591 | 46.232 | 1.00 | 23.87 |
| ATOM | 143 | CA | ASP | A | 137 | 19.156 | 4.589 | 45.427 | 1.00 | 23.95 |
| ATOM | 144 | C | ASP | A | 137 | 17.844 | 5.152 | 44.870 | 1.00 | 23.67 |
| ATOM | 145 | O | ASP | A | 137 | 17.513 | 4.943 | 43.697 | 1.00 | 22.79 |
| ATOM | 146 | CB | ASP | A | 137 | 18.886 | 3.348 | 46.282 | 1.00 | 26.93 |
| ATOM | 147 | CG | ASP | A | 137 | 18.158 | 2.266 | 45.524 | 1.00 | 31.10 |
| ATOM | 148 | OD1 | ASP | A | 137 | 17.010 | 1.947 | 45.900 | 1.00 | 34.78 |
| ATOM | 149 | OD2 | ASP | A | 137 | 18.730 | 1.734 | 44.552 | 1.00 | 34.13 |
| ATOM | 150 | N | ALA | A | 138 | 17.105 | 5.867 | 45.714 | 1.00 | 22.31 |
| ATOM | 151 | CA | ALA | A | 138 | 15.836 | 6.472 | 45.312 | 1.00 | 22.31 |
| ATOM | 152 | C | ALA | A | 138 | 16.063 | 7.435 | 44.157 | 1.00 | 21.39 |
| ATOM | 153 | O | ALA | A | 138 | 15.310 | 7.445 | 43.183 | 1.00 | 20.83 |
| ATOM | 154 | CB | ALA | A | 138 | 15.213 | 7.219 | 46.487 | 1.00 | 23.04 |
| ATOM | 155 | N | HIS | A | 139 | 17.107 | 8.249 | 44.263 | 1.00 | 21.06 |
| ATOM | 156 | CA | HIS | A | 139 | 17.408 | 9.202 | 43.208 | 1.00 | 21.28 |
| ATOM | 157 | C | HIS | A | 139 | 17.814 | 8.511 | 41.905 | 1.00 | 21.64 |
| ATOM | 158 | O | HIS | A | 139 | 17.385 | 8.913 | 40.824 | 1.00 | 21.17 |
| ATOM | 159 | CB | HIS | A | 139 | 18.528 | 10.152 | 43.631 | 1.00 | 21.21 |
| ATOM | 160 | CG | HIS | A | 139 | 18.730 | 11.288 | 42.680 | 1.00 | 22.53 |
| ATOM | 161 | ND1 | HIS | A | 139 | 19.955 | 11.593 | 42.126 | 1.00 | 25.49 |
| ATOM | 162 | CD2 | HIS | A | 139 | 17.850 | 12.173 | 42.157 | 1.00 | 19.49 |
| ATOM | 163 | CE1 | HIS | A | 139 | 19.820 | 12.615 | 41.300 | 1.00 | 20.82 |
| ATOM | 164 | NE2 | HIS | A | 139 | 18.552 | 12.986 | 41.301 | 1.00 | 23.99 |
| ATOM | 165 | N | HIS | A | 140 | 18.650 | 7.479 | 42.005 | 1.00 | 21.50 |
| ATOM | 166 | CA | HIS | A | 140 | 19.099 | 6.760 | 40.819 | 1.00 | 22.20 |
| ATOM | 167 | C | HIS | A | 140 | 17.947 | 6.088 | 40.082 | 1.00 | 21.95 |
| ATOM | 168 | O | HIS | A | 140 | 17.997 | 5.911 | 38.861 | 1.00 | 21.87 |
| ATOM | 169 | CB | HIS | A | 140 | 20.153 | 5.710 | 41.193 | 1.00 | 23.76 |
| ATOM | 170 | CG | HIS | A | 140 | 21.398 | 6.291 | 41.787 | 1.00 | 25.80 |
| ATOM | 171 | ND1 | HIS | A | 140 | 21.803 | 7.585 | 41.546 | 1.00 | 27.26 |
| ATOM | 172 | CD2 | HIS | A | 140 | 22.341 | 5.745 | 42.591 | 1.00 | 26.22 |
| ATOM | 173 | CE1 | HIS | A | 140 | 22.942 | 7.814 | 42.176 | 1.00 | 26.08 |
| ATOM | 174 | NE2 | HIS | A | 140 | 23.291 | 6.714 | 42.817 | 1.00 | 27.71 |
| ATOM | 175 | N | LYS | A | 141 | 16.908 | 5.719 | 40.821 | 1.00 | 20.41 |
| ATOM | 176 | CA | LYS | A | 141 | 15.745 | 5.071 | 40.225 | 1.00 | 21.89 |
| ATOM | 177 | C | LYS | A | 141 | 14.746 | 6.078 | 39.665 | 1.00 | 21.31 |
| ATOM | 178 | O | LYS | A | 141 | 13.916 | 5.730 | 38.832 | 1.00 | 22.47 |
| ATOM | 179 | CB | LYS | A | 141 | 15.031 | 4.203 | 41.265 | 1.00 | 23.28 |
| ATOM | 180 | CG | LYS | A | 141 | 15.804 | 2.960 | 41.668 | 1.00 | 26.83 |
| ATOM | 181 | CD | LYS | A | 141 | 15.080 | 2.209 | 42.771 | 1.00 | 30.63 |
| ATOM | 182 | CE | LYS | A | 141 | 15.781 | 0.902 | 43.093 | 1.00 | 33.64 |
| ATOM | 183 | NZ | LYS | A | 141 | 15.122 | 0.206 | 44.231 | 1.00 | 36.58 |
| ATOM | 184 | N | THR | A | 142 | 14.840 | 7.325 | 40.107 | 1.00 | 20.65 |
| ATOM | 185 | CA | THR | A | 142 | 13.893 | 8.348 | 39.664 | 1.00 | 20.68 |
| ATOM | 186 | C | THR | A | 142 | 14.440 | 9.502 | 38.833 | 1.00 | 20.45 |
| ATOM | 187 | O | THR | A | 142 | 13.682 | 10.375 | 38.420 | 1.00 | 20.32 |
| ATOM | 188 | CB | THR | A | 142 | 13.142 | 8.935 | 40.865 | 1.00 | 20.48 |
| ATOM | 189 | OG1 | THR | A | 142 | 14.081 | 9.474 | 41.805 | 1.00 | 18.91 |
| ATOM | 190 | CG2 | THR | A | 142 | 12.326 | 7.850 | 41.546 | 1.00 | 19.94 |

TABLE III-continued

Structure Coordinates for Site II in Various NHRs
Based on the Consensus Alignments in FIG.2

| ATOM | 191 | N | TYR | A | 143 | 15.747 | 9.520 | 38.595 | 1.00 | 20.03 |
|------|-----|-----|-----|---|-----|--------|--------|--------|------|-------|
| ATOM | 192 | CA | TYR | A | 143 | 16.342 | 10.566 | 37.768 | 1.00 | 20.44 |
| ATOM | 193 | C | TYR | A | 143 | 17.207 | 9.895 | 36.706 | 1.00 | 20.75 |
| ATOM | 194 | O | TYR | A | 143 | 18.248 | 9.323 | 37.013 | 1.00 | 21.56 |
| ATOM | 195 | CB | TYR | A | 143 | 17.198 | 11.529 | 38.610 | 1.00 | 20.88 |
| ATOM | 196 | CG | TYR | A | 143 | 17.673 | 12.742 | 37.835 | 1.00 | 20.90 |
| ATOM | 197 | CD1 | TYR | A | 143 | 18.721 | 12.650 | 36.915 | 1.00 | 21.44 |
| ATOM | 198 | CD2 | TYR | A | 143 | 17.048 | 13.980 | 37.994 | 1.00 | 21.13 |
| ATOM | 199 | CE1 | TYR | A | 143 | 19.132 | 13.762 | 36.170 | 1.00 | 21.80 |
| ATOM | 200 | CE2 | TYR | A | 143 | 17.449 | 15.090 | 37.253 | 1.00 | 20.26 |
| ATOM | 201 | CZ | TYR | A | 143 | 18.487 | 14.978 | 36.347 | 1.00 | 22.15 |
| ATOM | 202 | OH | TYR | A | 143 | 18.868 | 16.077 | 35.612 | 1.00 | 21.28 |
| ATOM | 203 | N | ASP | A | 144 | 16.750 | 9.959 | 35.461 | 1.00 | 20.48 |
| ATOM | 204 | CA | ASP | A | 144 | 17.449 | 9.365 | 34.326 | 1.00 | 21.36 |
| ATOM | 205 | C | ASP | A | 144 | 18.428 | 10.387 | 33.751 | 1.00 | 22.06 |
| ATOM | 206 | O | ASP | A | 144 | 18.016 | 11.348 | 33.102 | 1.00 | 21.75 |
| ATOM | 207 | CB | ASP | A | 144 | 16.412 | 8.955 | 33.274 | 1.00 | 21.65 |
| ATOM | 208 | CG | ASP | A | 144 | 17.032 | 8.481 | 31.976 | 1.00 | 22.22 |
| ATOM | 209 | OD1 | ASP | A | 144 | 18.261 | 8.286 | 31.921 | 1.00 | 22.12 |
| ATOM | 210 | OD2 | ASP | A | 144 | 16.266 | 8.294 | 31.007 | 1.00 | 23.20 |
| ATOM | 494 | N | LEU | A | 233 | 7.228 | 18.018 | 30.549 | 1.00 | 21.20 |
| ATOM | 495 | CA | LEU | A | 233 | 8.483 | 17.785 | 31.278 | 1.00 | 20.50 |
| ATOM | 496 | C | LEU | A | 233 | 8.267 | 17.940 | 32.785 | 1.00 | 20.58 |
| ATOM | 497 | O | LEU | A | 233 | 8.755 | 17.139 | 33.587 | 1.00 | 18.39 |
| ATOM | 498 | CB | LEU | A | 233 | 9.565 | 18.770 | 30.811 | 1.00 | 20.92 |
| ATOM | 499 | CG | LEU | A | 233 | 10.826 | 18.839 | 31.684 | 1.00 | 20.96 |
| ATOM | 500 | CD1 | LEU | A | 233 | 11.554 | 17.502 | 31.652 | 1.00 | 22.15 |
| ATOM | 501 | CD2 | LEU | A | 233 | 11.737 | 19.969 | 31.190 | 1.00 | 22.47 |
| ATOM | 502 | N | VAL | A | 234 | 7.539 | 18.981 | 33.172 | 1.00 | 20.09 |
| ATOM | 503 | CA | VAL | A | 234 | 7.263 | 19.217 | 34.583 | 1.00 | 20.15 |
| ATOM | 504 | C | VAL | A | 234 | 6.320 | 18.152 | 35.146 | 1.00 | 19.97 |
| ATOM | 505 | O | VAL | A | 234 | 6.500 | 17.691 | 36.268 | 1.00 | 19.99 |
| ATOM | 506 | CB | VAL | A | 234 | 6.665 | 20.630 | 34.796 | 1.00 | 21.02 |
| ATOM | 507 | CG1 | VAL | A | 234 | 6.104 | 20.778 | 36.209 | 1.00 | 23.20 |
| ATOM | 508 | CG2 | VAL | A | 234 | 7.754 | 21.679 | 34.566 | 1.00 | 21.83 |
| ATOM | 527 | N | SER | A | 237 | 8.241 | 15.105 | 35.711 | 1.00 | 17.93 |
| ATOM | 528 | CA | SER | A | 237 | 9.106 | 15.312 | 36.868 | 1.00 | 18.19 |
| ATOM | 529 | C | SER | A | 237 | 8.373 | 15.218 | 38.199 | 1.00 | 18.73 |
| ATOM | 530 | O | SER | A | 237 | 8.929 | 14.737 | 39.184 | 1.00 | 19.34 |
| ATOM | 531 | CB | SER | A | 237 | 9.830 | 16.654 | 36.730 | 1.00 | 18.72 |
| ATOM | 532 | OG | SER | A | 237 | 10.648 | 16.628 | 35.573 | 1.00 | 19.76 |
| ATOM | 533 | N | ILE | A | 238 | 7.128 | 15.680 | 38.237 | 1.00 | 18.89 |
| ATOM | 534 | CA | ILE | A | 238 | 6.343 | 15.597 | 39.460 | 1.00 | 20.25 |
| ATOM | 535 | C | ILE | A | 238 | 6.101 | 14.119 | 39.759 | 1.00 | 20.17 |
| ATOM | 536 | O | ILE | A | 238 | 6.129 | 13.705 | 40.914 | 1.00 | 20.62 |
| ATOM | 537 | CB | ILE | A | 238 | 4.984 | 16.337 | 39.317 | 1.00 | 21.21 |
| ATOM | 538 | CG1 | ILE | A | 238 | 5.226 | 17.847 | 39.236 | 1.00 | 23.61 |
| ATOM | 539 | CG2 | ILE | A | 238 | 4.068 | 16.001 | 40.502 | 1.00 | 23.76 |
| ATOM | 540 | CD1 | ILE | A | 238 | 3.972 | 18.668 | 38.937 | 1.00 | 24.70 |
| ATOM | 541 | N | GLN | A | 239 | 5.868 | 13.315 | 38.719 | 1.00 | 20.04 |
| ATOM | 542 | CA | GLN | A | 239 | 5.657 | 11.890 | 38.936 | 1.00 | 19.72 |
| ATOM | 543 | C | GLN | A | 239 | 6.911 | 11.261 | 39.531 | 1.00 | 20.24 |
| ATOM | 544 | O | GLN | A | 239 | 6.823 | 10.433 | 40.437 | 1.00 | 19.92 |
| ATOM | 545 | CB | GLN | A | 239 | 5.288 | 11.178 | 37.628 | 1.00 | 21.35 |
| ATOM | 546 | CG | GLN | A | 239 | 3.920 | 11.576 | 37.086 | 1.00 | 21.87 |
| ATOM | 547 | CD | GLN | A | 239 | 3.487 | 10.707 | 35.922 | 1.00 | 23.58 |
| ATOM | 548 | OE1 | GLN | A | 239 | 3.092 | 9.556 | 36.105 | 1.00 | 26.39 |
| ATOM | 549 | NE2 | GLN | A | 239 | 3.568 | 11.249 | 34.720 | 1.00 | 22.31 |
| ATOM | 550 | N | LYS | A | 240 | 8.080 | 11.661 | 39.037 | 1.00 | 19.37 |
| ATOM | 551 | CA | LYS | A | 240 | 9.336 | 11.116 | 39.557 | 1.00 | 19.49 |
| ATOM | 552 | C | LYS | A | 240 | 9.575 | 11.583 | 40.994 | 1.00 | 20.03 |
| ATOM | 553 | O | LYS | A | 240 | 10.086 | 10.826 | 41.826 | 1.00 | 20.81 |
| ATOM | 554 | CB | LYS | A | 240 | 10.509 | 11.525 | 38.658 | 1.00 | 19.27 |
| ATOM | 555 | CG | LYS | A | 240 | 10.385 | 11.015 | 37.216 | 1.00 | 19.70 |
| ATOM | 556 | CD | LYS | A | 240 | 10.174 | 9.491 | 37.165 | 1.00 | 20.85 |
| ATOM | 557 | CE | LYS | A | 240 | 10.201 | 8.986 | 35.734 | 1.00 | 20.78 |
| ATOM | 558 | NZ | LYS | A | 240 | 9.919 | 7.527 | 35.631 | 1.00 | 21.79 |
| ATOM | 559 | N | VAL | A | 241 | 9.203 | 12.827 | 41.284 | 1.00 | 19.95 |
| ATOM | 560 | CA | VAL | A | 241 | 9.355 | 13.380 | 42.630 | 1.00 | 21.18 |
| ATOM | 561 | C | VAL | A | 241 | 8.466 | 12.633 | 43.621 | 1.00 | 22.58 |
| ATOM | 562 | O | VAL | A | 241 | 8.845 | 12.418 | 44.769 | 1.00 | 22.01 |
| ATOM | 563 | CB | VAL | A | 241 | 9.006 | 14.890 | 42.658 | 1.00 | 22.53 |
| ATOM | 564 | CG1 | VAL | A | 241 | 8.893 | 15.392 | 44.104 | 1.00 | 23.49 |
| ATOM | 565 | CG2 | VAL | A | 241 | 10.092 | 15.671 | 41.929 | 1.00 | 22.43 |
| ATOM | 566 | N | ILE | A | 242 | 7.277 | 12.237 | 43.178 | 1.00 | 22.44 |
| ATOM | 567 | CA | ILE | A | 242 | 6.375 | 11.492 | 44.052 | 1.00 | 23.64 |

TABLE III-continued

Structure Coordinates for Site II in Various NHRs
Based on the Consensus Alignments in FIG.2

| ATOM | 568 | C | ILE | A | 242 | 7.027 | 10.157 | 44.416 | 1.00 | 23.45 |
|---|---|---|---|---|---|---|---|---|---|---|
| ATOM | 569 | O | ILE | A | 242 | 6.987 | 9.726 | 45.573 | 1.00 | 25.50 |
| ATOM | 570 | CB | ILE | A | 242 | 5.012 | 11.255 | 43.360 | 1.00 | 24.32 |
| ATOM | 571 | CG1 | ILE | A | 242 | 4.235 | 12.575 | 43.303 | 1.00 | 25.64 |
| ATOM | 572 | CG2 | ILE | A | 242 | 4.214 | 10.186 | 44.104 | 1.00 | 24.95 |
| ATOM | 573 | CD1 | ILE | A | 242 | 3.012 | 12.540 | 42.401 | 1.00 | 25.41 |
| ATOM | 574 | N | GLY | A | 243 | 7.652 | 9.521 | 43.431 | 1.00 | 22.76 |
| ATOM | 575 | CA | GLY | A | 243 | 8.310 | 8.246 | 43.665 | 1.00 | 23.14 |
| ATOM | 576 | C | GLY | A | 243 | 9.491 | 8.385 | 44.604 | 1.00 | 23.29 |
| ATOM | 577 | O | GLY | A | 243 | 9.719 | 7.525 | 45.454 | 1.00 | 24.26 |
| ATOM | 578 | N | PHE | A | 244 | 10.244 | 9.471 | 44.443 | 1.00 | 22.21 |
| ATOM | 579 | CA | PHE | A | 244 | 11.406 | 9.754 | 45.287 | 1.00 | 23.08 |
| ATOM | 580 | C | PHE | A | 244 | 10.962 | 9.960 | 46.734 | 1.00 | 23.33 |
| ATOM | 581 | O | PHE | A | 244 | 11.509 | 9.359 | 47.665 | 1.00 | 22.96 |
| ATOM | 582 | CB | PHE | A | 244 | 12.110 | 11.023 | 44.799 | 1.00 | 21.55 |
| ATOM | 583 | CG | PHE | A | 244 | 13.264 | 11.454 | 45.663 | 1.00 | 23.20 |
| ATOM | 584 | CD1 | PHE | A | 244 | 14.474 | 10.764 | 45.632 | 1.00 | 25.04 |
| ATOM | 585 | CD2 | PHE | A | 244 | 13.140 | 12.548 | 46.516 | 1.00 | 24.78 |
| ATOM | 586 | CE1 | PHE | A | 244 | 15.542 | 11.157 | 46.437 | 1.00 | 25.46 |
| ATOM | 587 | CE2 | PHE | A | 244 | 14.205 | 12.950 | 47.327 | 1.00 | 24.71 |
| ATOM | 588 | CZ | PHE | A | 244 | 15.407 | 12.254 | 47.286 | 1.00 | 24.22 |
| ATOM | 753 | N | SER | A | 266 | 5.847 | 21.434 | 47.757 | 1.00 | 25.17 |
| ATOM | 754 | CA | SER | A | 266 | 7.277 | 21.412 | 47.449 | 1.00 | 23.91 |
| ATOM | 755 | C | SER | A | 266 | 7.609 | 21.035 | 46.011 | 1.00 | 23.51 |
| ATOM | 756 | O | SER | A | 266 | 8.749 | 21.206 | 45.572 | 1.00 | 23.30 |
| ATOM | 757 | CB | SER | A | 266 | 8.001 | 20.445 | 48.385 | 1.00 | 24.45 |
| ATOM | 758 | OG | SER | A | 266 | 7.656 | 19.101 | 48.094 | 1.00 | 24.60 |
| ATOM | 759 | N | ALA | A | 267 | 6.619 | 20.519 | 45.285 | 1.00 | 22.67 |
| ATOM | 760 | CA | ALA | A | 267 | 6.801 | 20.089 | 43.898 | 1.00 | 23.39 |
| ATOM | 761 | C | ALA | A | 267 | 7.698 | 20.979 | 43.040 | 1.00 | 23.51 |
| ATOM | 762 | O | ALA | A | 267 | 8.716 | 20.517 | 42.515 | 1.00 | 23.55 |
| ATOM | 763 | CB | ALA | A | 267 | 5.436 | 19.938 | 43.217 | 1.00 | 24.51 |
| ATOM | 764 | N | ILE | A | 268 | 7.330 | 22.247 | 42.883 | 1.00 | 22.01 |
| ATOM | 765 | CA | ILE | A | 268 | 8.132 | 23.135 | 42.041 | 1.00 | 22.23 |
| ATOM | 766 | C | ILE | A | 268 | 9.539 | 23.374 | 42.592 | 1.00 | 22.05 |
| ATOM | 767 | O | ILE | A | 268 | 10.494 | 23.558 | 41.828 | 1.00 | 20.90 |
| ATOM | 768 | CB | ILE | A | 268 | 7.426 | 24.496 | 41.811 | 1.00 | 23.63 |
| ATOM | 769 | CG1 | ILE | A | 268 | 8.097 | 25.232 | 40.645 | 1.00 | 24.85 |
| ATOM | 770 | CG2 | ILE | A | 268 | 7.484 | 25.354 | 43.068 | 1.00 | 25.18 |
| ATOM | 771 | CD1 | ILE | A | 268 | 7.933 | 24.549 | 39.303 | 1.00 | 25.69 |
| ATOM | 772 | N | GLU | A | 269 | 9.674 | 23.352 | 43.911 | 1.00 | 20.40 |
| ATOM | 773 | CA | GLU | A | 269 | 10.979 | 23.561 | 44.529 | 1.00 | 20.63 |
| ATOM | 774 | C | GLU | A | 269 | 11.933 | 22.402 | 44.268 | 1.00 | 21.33 |
| ATOM | 775 | O | GLU | A | 269 | 13.109 | 22.620 | 43.976 | 1.00 | 20.99 |
| ATOM | 776 | CB | GLU | A | 269 | 10.823 | 23.770 | 46.030 | 1.00 | 20.38 |
| ATOM | 777 | CG | GLU | A | 269 | 10.206 | 25.110 | 46.396 | 1.00 | 22.10 |
| ATOM | 778 | CD | GLU | A | 269 | 10.009 | 25.261 | 47.892 | 1.00 | 23.72 |
| ATOM | 779 | OE1 | GLU | A | 269 | 10.803 | 24.670 | 48.656 | 1.00 | 22.73 |
| ATOM | 780 | OE2 | GLU | A | 269 | 9.067 | 25.974 | 48.301 | 1.00 | 24.58 |
| ATOM | 781 | N | VAL | A | 270 | 11.434 | 21.172 | 44.375 | 1.00 | 20.39 |
| ATOM | 782 | CA | VAL | A | 270 | 12.279 | 20.006 | 44.143 | 1.00 | 20.83 |
| ATOM | 783 | C | VAL | A | 270 | 12.644 | 19.911 | 42.670 | 1.00 | 20.52 |
| ATOM | 784 | O | VAL | A | 270 | 13.734 | 19.458 | 42.318 | 1.00 | 20.87 |
| ATOM | 785 | CB | VAL | A | 270 | 11.582 | 18.709 | 44.597 | 1.00 | 21.55 |
| ATOM | 786 | CG1 | VAL | A | 270 | 12.481 | 17.512 | 44.318 | 1.00 | 21.95 |
| ATOM | 787 | CG2 | VAL | A | 270 | 11.268 | 18.790 | 46.086 | 1.00 | 23.25 |
| ATOM | 788 | N | ILE | A | 271 | 11.731 | 20.337 | 41.804 | 1.00 | 20.29 |
| ATOM | 789 | CA | ILE | A | 271 | 12.010 | 20.318 | 40.376 | 1.00 | 20.71 |
| ATOM | 790 | C | ILE | A | 271 | 13.145 | 21.300 | 40.099 | 1.00 | 20.86 |
| ATOM | 791 | O | ILE | A | 271 | 14.083 | 20.990 | 39.361 | 1.00 | 20.78 |
| ATOM | 792 | CB | ILE | A | 271 | 10.755 | 20.684 | 39.563 | 1.00 | 21.89 |
| ATOM | 793 | CG1 | ILE | A | 271 | 9.842 | 19.450 | 39.483 | 1.00 | 24.21 |
| ATOM | 794 | CG2 | ILE | A | 271 | 11.149 | 21.173 | 38.170 | 1.00 | 23.03 |
| ATOM | 795 | CD1 | ILE | A | 271 | 8.489 | 19.711 | 38.852 | 1.00 | 27.85 |
| ATOM | 796 | N | MET | A | 272 | 13.076 | 22.481 | 40.701 | 1.00 | 21.17 |
| ATOM | 797 | CA | MET | A | 272 | 14.147 | 23.446 | 40.500 | 1.00 | 21.57 |
| ATOM | 798 | C | MET | A | 272 | 15.474 | 22.888 | 41.020 | 1.00 | 20.82 |
| ATOM | 799 | O | MET | A | 272 | 16.513 | 23.064 | 40.384 | 1.00 | 22.20 |
| ATOM | 800 | CB | MET | A | 272 | 13.800 | 24.770 | 41.183 | 1.00 | 22.31 |
| ATOM | 801 | CG | MET | A | 272 | 12.595 | 25.441 | 40.549 | 1.00 | 24.16 |
| ATOM | 802 | SD | MET | A | 272 | 12.222 | 27.036 | 41.296 | 1.00 | 26.22 |
| ATOM | 803 | CE | MET | A | 272 | 11.003 | 27.687 | 40.134 | 1.00 | 26.38 |
| ATOM | 804 | N | LEU | A | 273 | 15.442 | 22.204 | 42.163 | 1.00 | 21.17 |
| ATOM | 805 | CA | LEU | A | 273 | 16.661 | 21.606 | 42.717 | 1.00 | 21.28 |
| ATOM | 806 | C | LEU | A | 273 | 17.226 | 20.486 | 41.842 | 1.00 | 20.96 |
| ATOM | 807 | O | LEU | A | 273 | 18.408 | 20.494 | 41.487 | 1.00 | 20.75 |

TABLE III-continued

Structure Coordinates for Site II in Various NHRs
Based on the Consensus Alignments in FIG.2

| ATOM | 808 | CB | LEU | A | 273 | 16.405 | 21.026 | 44.116 | 1.00 | 22.98 |
|---|---|---|---|---|---|---|---|---|---|---|
| ATOM | 809 | CG | LEU | A | 273 | 16.367 | 21.940 | 45.337 | 1.00 | 25.62 |
| ATOM | 810 | CD1 | LEU | A | 273 | 15.959 | 21.129 | 46.572 | 1.00 | 25.83 |
| ATOM | 811 | CD2 | LEU | A | 273 | 17.736 | 22.571 | 45.543 | 1.00 | 26.65 |
| ATOM | 812 | N | ARG | A | 274 | 16.385 | 19.517 | 41.494 | 1.00 | 19.69 |
| ATOM | 813 | CA | ARG | A | 274 | 16.852 | 18.384 | 40.702 | 1.00 | 19.52 |
| ATOM | 814 | C | ARG | A | 274 | 17.317 | 18.787 | 39.309 | 1.00 | 19.10 |
| ATOM | 815 | O | ARG | A | 274 | 18.159 | 18.117 | 38.715 | 1.00 | 19.83 |
| ATOM | 816 | CB | ARG | A | 274 | 15.759 | 17.299 | 40.610 | 1.00 | 19.75 |
| ATOM | 817 | CG | ARG | A | 274 | 14.652 | 17.566 | 39.601 | 1.00 | 19.52 |
| ATOM | 818 | CD | ARG | A | 274 | 13.381 | 16.792 | 39.969 | 1.00 | 19.72 |
| ATOM | 819 | NE | ARG | A | 274 | 13.599 | 15.356 | 40.153 | 1.00 | 18.11 |
| ATOM | 820 | CZ | ARG | A | 274 | 13.580 | 14.453 | 39.175 | 1.00 | 19.01 |
| ATOM | 821 | NH1 | ARG | A | 274 | 13.357 | 14.824 | 37.919 | 1.00 | 18.53 |
| ATOM | 822 | NH2 | ARG | A | 274 | 13.759 | 13.168 | 39.458 | 1.00 | 19.51 |
| ATOM | 837 | N | GLU | A | 277 | 21.096 | 19.280 | 38.000 | 1.00 | 20.52 |
| ATOM | 838 | CA | GLU | A | 277 | 21.925 | 18.226 | 37.425 | 1.00 | 21.75 |
| ATOM | 839 | C | GLU | A | 277 | 22.103 | 18.370 | 35.908 | 1.00 | 21.79 |
| ATOM | 840 | O | GLU | A | 277 | 23.105 | 17.910 | 35.351 | 1.00 | 22.41 |
| ATOM | 841 | CB | GLU | A | 277 | 21.331 | 16.852 | 37.785 | 1.00 | 22.91 |
| ATOM | 842 | CG | GLU | A | 277 | 22.199 | 15.659 | 37.413 | 1.00 | 26.24 |
| ATOM | 843 | CD | GLU | A | 277 | 21.904 | 14.418 | 38.261 | 1.00 | 28.07 |
| ATOM | 844 | OE1 | GLU | A | 277 | 22.359 | 13.319 | 37.875 | 1.00 | 30.43 |
| ATOM | 845 | OE2 | GLU | A | 277 | 21.233 | 14.532 | 39.317 | 1.00 | 26.56 |
| ATOM | 846 | N | SER | A | 278 | 21.152 | 19.011 | 35.234 | 1.00 | 19.68 |
| ATOM | 847 | CA | SER | A | 278 | 21.266 | 19.194 | 33.789 | 1.00 | 20.64 |
| ATOM | 848 | C | SER | A | 278 | 21.712 | 20.607 | 33.448 | 1.00 | 21.58 |
| ATOM | 849 | O | SER | A | 278 | 22.008 | 20.910 | 32.292 | 1.00 | 22.05 |
| ATOM | 850 | CB | SER | A | 278 | 19.934 | 18.910 | 33.092 | 1.00 | 20.93 |
| ATOM | 851 | OG | SER | A | 278 | 18.941 | 19.829 | 33.497 | 1.00 | 22.00 |
| ATOM | 863 | N | THR | A | 280 | 24.077 | 23.728 | 33.010 | 1.00 | 24.73 |
| ATOM | 864 | CA | THR | A | 280 | 25.496 | 23.872 | 32.728 | 1.00 | 26.87 |
| ATOM | 865 | C | THR | A | 280 | 25.884 | 25.343 | 32.672 | 1.00 | 27.44 |
| ATOM | 866 | O | THR | A | 280 | 25.186 | 26.162 | 32.070 | 1.00 | 26.28 |
| ATOM | 867 | CB | THR | A | 280 | 25.897 | 23.198 | 31.399 | 1.00 | 27.76 |
| ATOM | 868 | OG1 | THR | A | 280 | 27.298 | 23.408 | 31.173 | 1.00 | 31.72 |
| ATOM | 869 | CG2 | THR | A | 280 | 25.107 | 23.768 | 30.236 | 1.00 | 27.79 |
| ATOM | 870 | N | MET | A | 281 | 26.991 | 25.676 | 33.326 | 1.00 | 28.33 |
| ATOM | 871 | CA | MET | A | 281 | 27.469 | 27.049 | 33.340 | 1.00 | 31.03 |
| ATOM | 872 | C | MET | A | 281 | 28.275 | 27.390 | 32.095 | 1.00 | 31.28 |
| ATOM | 873 | O | MET | A | 281 | 28.812 | 28.490 | 31.980 | 1.00 | 30.87 |
| ATOM | 874 | CB | MET | A | 281 | 28.298 | 27.306 | 34.596 | 1.00 | 33.43 |
| ATOM | 875 | CG | MET | A | 281 | 27.448 | 27.518 | 35.835 | 1.00 | 36.11 |
| ATOM | 876 | SD | MET | A | 281 | 28.429 | 27.829 | 37.295 | 1.00 | 39.85 |
| ATOM | 877 | CE | MET | A | 281 | 28.995 | 29.495 | 36.967 | 1.00 | 40.40 |
| ATOM | 878 | N | ASP | A | 282 | 28.364 | 26.448 | 31.159 | 1.00 | 31.72 |
| ATOM | 879 | CA | ASP | A | 282 | 29.097 | 26.709 | 29.925 | 1.00 | 32.91 |
| ATOM | 880 | C | ASP | A | 282 | 28.366 | 27.818 | 29.175 | 1.00 | 32.02 |
| ATOM | 881 | O | ASP | A | 282 | 28.989 | 28.764 | 28.683 | 1.00 | 31.15 |
| ATOM | 882 | CB | ASP | A | 282 | 29.172 | 25.455 | 29.050 | 1.00 | 35.93 |
| ATOM | 883 | CG | ASP | A | 282 | 29.947 | 24.328 | 29.708 | 1.00 | 39.91 |
| ATOM | 884 | OD1 | ASP | A | 282 | 30.940 | 24.619 | 30.412 | 1.00 | 42.35 |
| ATOM | 885 | OD2 | ASP | A | 282 | 29.573 | 23.150 | 29.508 | 1.00 | 42.45 |
| ATOM | 935 | N | GLY | A | 289 | 20.675 | 16.498 | 26.466 | 1.00 | 37.69 |
| ATOM | 936 | CA | GLY | A | 289 | 20.897 | 15.682 | 25.286 | 1.00 | 41.85 |
| ATOM | 937 | C | GLY | A | 289 | 21.072 | 16.536 | 24.044 | 1.00 | 44.11 |
| ATOM | 938 | O | GLY | A | 289 | 21.842 | 17.497 | 24.051 | 1.00 | 45.10 |
| ATOM | 1269 | N | HIS | A | 330 | 23.291 | 16.450 | 47.721 | 1.00 | 22.72 |
| ATOM | 1270 | CA | HIS | A | 330 | 22.225 | 16.836 | 46.803 | 1.00 | 22.97 |
| ATOM | 1271 | C | HIS | A | 330 | 20.908 | 16.139 | 47.150 | 1.00 | 23.43 |
| ATOM | 1272 | O | HIS | A | 330 | 19.863 | 16.790 | 47.257 | 1.00 | 22.10 |
| ATOM | 1273 | CB | HIS | A | 330 | 22.638 | 16.494 | 45.364 | 1.00 | 24.13 |
| ATOM | 1274 | CG | HIS | A | 330 | 21.648 | 16.916 | 44.321 | 1.00 | 25.22 |
| ATOM | 1275 | ND1 | HIS | A | 330 | 21.357 | 18.237 | 44.060 | 1.00 | 25.99 |
| ATOM | 1276 | CD2 | HIS | A | 330 | 20.913 | 16.190 | 43.444 | 1.00 | 25.76 |
| ATOM | 1277 | CE1 | HIS | A | 330 | 20.489 | 18.307 | 43.065 | 1.00 | 26.73 |
| ATOM | 1278 | NE2 | HIS | A | 330 | 20.203 | 17.078 | 42.674 | 1.00 | 25.08 |
| ATOM | 1279 | N | VAL | A | 331 | 20.955 | 14.823 | 47.334 | 1.00 | 22.22 |
| ATOM | 1280 | CA | VAL | A | 331 | 19.739 | 14.072 | 47.642 | 1.00 | 23.00 |
| ATOM | 1281 | C | VAL | A | 331 | 19.185 | 14.382 | 49.024 | 1.00 | 22.12 |
| ATOM | 1282 | O | VAL | A | 331 | 17.968 | 14.393 | 49.218 | 1.00 | 21.17 |
| ATOM | 1283 | CB | VAL | A | 331 | 19.952 | 12.544 | 47.490 | 1.00 | 22.74 |
| ATOM | 1284 | CG1 | VAL | A | 331 | 20.363 | 12.233 | 46.053 | 1.00 | 25.60 |
| ATOM | 1285 | CG2 | VAL | A | 331 | 21.008 | 12.045 | 48.466 | 1.00 | 25.97 |
| ATOM | 1302 | N | MET | A | 334 | 17.198 | 17.654 | 48.776 | 1.00 | 21.27 |
| ATOM | 1303 | CA | MET | A | 334 | 15.878 | 17.513 | 48.163 | 1.00 | 20.93 |

TABLE III-continued

Structure Coordinates for Site II in Various NHRs
Based on the Consensus Alignments in FIG.2

| ATOM | 1304 | C  | MET | A | 334 | 14.928 | 16.881 | 49.171 | 1.00 | 21.48 |
|------|------|----|-----|---|-----|--------|--------|--------|------|-------|
| ATOM | 1305 | O  | MET | A | 334 | 13.769 | 17.263 | 49.256 | 1.00 | 21.52 |
| ATOM | 1306 | CB | MET | A | 334 | 15.939 | 16.648 | 46.896 | 1.00 | 21.53 |
| ATOM | 1307 | CG | MET | A | 334 | 16.631 | 17.318 | 45.719 | 1.00 | 22.31 |
| ATOM | 1308 | SD | MET | A | 334 | 16.442 | 16.343 | 44.219 | 1.00 | 24.84 |
| ATOM | 1309 | CE | MET | A | 334 | 17.484 | 14.909 | 44.612 | 1.00 | 24.19 |

Example 23

X-ray Structure Coordinates of GR Site II Table IV

Below is Table IV, which gives the x-ray structure coordinates for GR Site II discerned from the disclosure in WO 03/015692 A2, Feb. 27, 2003, Apolito, et. al,. The format used is based on that commonly used in the RCSB (Research Collaboratory for Structural Bioinformatics, pdb file format), and the fields listed from left to right are defined as follows: record name, atom serial number, atom name, residue name, chain identifier, residue sequence number, orthogonal coordinate for x in Ångstroms, orthogonal cordinate for y in Ångstroms, orthogonal coordinate for z in Ångstroms, occupancy, and temperature factor.

TABLE IV

GR Homology Model Coordinates (SEQ ID NO:1) discerned from the disclosure in WO 03/015692 A2

| ATOM | 1  | N   | GLU | 537 | 49.171 | 2.415  | 43.840 | 1.00 | 59.21 |
|------|----|-----|-----|-----|--------|--------|--------|------|-------|
| ATOM | 2  | CA  | GLU | 537 | 48.231 | 3.343  | 43.210 | 1.00 | 59.76 |
| ATOM | 3  | C   | GLU | 537 | 47.139 | 2.698  | 42.370 | 1.00 | 61.66 |
| ATOM | 4  | O   | GLU | 537 | 45.973 | 3.101  | 42.430 | 1.00 | 60.28 |
| ATOM | 5  | CB  | GLU | 537 | 48.984 | 4.292  | 42.300 | 1.00 | 59.81 |
| ATOM | 6  | CG  | GLU | 537 | 48.816 | 5.744  | 42.620 | 1.00 | 60.10 |
| ATOM | 7  | CD  | GLU | 537 | 48.907 | 6.616  | 41.380 | 1.00 | 64.34 |
| ATOM | 8  | OE1 | GLU | 537 | 47.868 | 6.813  | 40.700 | 1.00 | 57.41 |
| ATOM | 9  | OE2 | GLU | 537 | 50.024 | 7.091  | 41.080 | 1.00 | 62.84 |
| ATOM | 10 | N   | VAL | 538 | 47.536 | 1.717  | 41.560 | 1.00 | 60.48 |
| ATOM | 11 | CA  | VAL | 538 | 46.606 | 1.045  | 40.670 | 1.00 | 63.41 |
| ATOM | 12 | C   | VAL | 538 | 45.768 | −0.046 | 41.310 | 1.00 | 57.99 |
| ATOM | 13 | O   | VAL | 538 | 44.828 | −0.530 | 40.680 | 1.00 | 58.71 |
| ATOM | 14 | CB  | VAL | 538 | 47.325 | 0.448  | 39.440 | 1.00 | 64.15 |
| ATOM | 15 | CG2 | VAL | 538 | 47.973 | −0.883 | 39.790 | 1.00 | 63.88 |
| ATOM | 16 | CG  | VAL | 538 | 48.334 | 1.444  | 38.900 | 1.00 | 60.29 |
| ATOM | 17 | N   | ILK | 539 | 46.094 | −0.454 | 42.530 | 1.00 | 61.14 |
| ATOM | 18 | CA  | ILK | 539 | 45.282 | −1.484 | 43.180 | 1.00 | 60.23 |
| ATOM | 19 | C   | ILK | 539 | 44.259 | −0.811 | 44.090 | 1.00 | 61.40 |
| ATOM | 20 | O   | ILK | 539 | 43.321 | −1.447 | 44.570 | 1.00 | 63.49 |
| ATOM | 21 | CB  | ILK | 539 | 46.141 | −2.499 | 44.010 | 1.00 | 65.32 |
| ATOM | 22 | CG2 | ILK | 539 | 47.243 | −3.066 | 43.140 | 1.00 | 61.32 |
| ATOM | 23 | CG  | ILK | 539 | 46.775 | −1.833 | 45.220 | 1.00 | 63.80 |
| ATOM | 24 | CD1 | ILK | 539 | 47.356 | −2.833 | 46.200 | 1.00 | 60.85 |
| ATOM | 25 | N   | GLU | 540 | 44.451 | 0.489  | 44.310 | 1.00 | 61.12 |
| ATOM | 26 | CA  | GLU | 540 | 43.584 | 1.307  | 45.153 | 1.00 | 60.76 |
| ATOM | 27 | C   | GLU | 540 | 42.169 | 1.264  | 44.585 | 1.00 | 61.78 |
| ATOM | 28 | O   | GLU | 540 | 41.928 | 1.709  | 43.459 | 1.00 | 61.36 |
| ATOM | 29 | CB  | GLU | 540 | 44.109 | 2.753  | 45.173 | 1.00 | 58.26 |
| ATOM | 30 | CG  | GLU | 540 | 43.466 | 3.684  | 46.191 | 1.00 | 61.15 |
| ATOM | 31 | CD  | GLU | 540 | 43.598 | 3.183  | 47.619 | 1.00 | 61.95 |
| ATOM | 32 | OE1 | GLU | 540 | 44.656 | 2.591  | 47.950 | 1.00 | 59.71 |
| ATOM | 33 | OE2 | GLU | 540 | 42.649 | 3.397  | 48.410 | 1.00 | 62.96 |
| ATOM | 34 | N   | PRO | 541 | 41.214 | 0.713  | 45.352 | 1.00 | 63.77 |
| ATOM | 35 | CA  | PRO | 541 | 39.830 | 0.632  | 44.876 | 1.00 | 60.14 |
| ATOM | 36 | C   | PRO | 541 | 39.180 | 1.991  | 44.592 | 1.00 | 62.36 |
| ATOM | 37 | O   | PRO | 541 | 39.455 | 2.982  | 45.283 | 1.00 | 59.45 |
| ATOM | 38 | CB  | PRO | 541 | 39.131 | −0.149 | 45.988 | 1.00 | 59.62 |
| ATOM | 39 | CG  | PRO | 541 | 39.978 | 0.122  | 47.195 | 1.00 | 60.56 |
| ATOM | 40 | CD  | PRO | 541 | 41.365 | 0.053  | 46.659 | 1.00 | 58.98 |
| ATOM | 41 | N   | GLU | 542 | 38.332 | 2.039  | 43.563 | 1.00 | 60.43 |
| ATOM | 42 | CA  | GLU | 542 | 37.653 | 3.279  | 43.198 | 1.00 | 62.04 |
| ATOM | 43 | C   | GLU | 542 | 36.548 | 3.515  | 44.208 | 1.00 | 63.11 |
| ATOM | 44 | O   | GLU | 542 | 35.941 | 2.564  | 44.697 | 1.00 | 59.70 |
| ATOM | 45 | CB  | GLU | 542 | 37.091 | 3.201  | 41.770 | 1.00 | 62.84 |
| ATOM | 46 | CG  | GLU | 542 | 36.130 | 2.050  | 41.511 | 1.00 | 63.24 |
| ATOM | 47 | CD  | GLU | 542 | 35.745 | 1.911  | 40.031 | 1.00 | 63.39 |
| ATOM | 48 | OE2 | GLU | 542 | 34.568 | 1.599  | 39.743 | 1.00 | 59.31 |
| ATOM | 49 | OE  | GLU | 542 | 36.622 | 2.095  | 39.153 | 1.00 | 60.50 |
| ATOM | 50 | N   | VAL | 543 | 36.304 | 4.783  | 44.528 | 1.00 | 61.53 |

TABLE IV-continued

GR Homology Model Coordinates (SEQ ID NO:1) discerned from the disclosure in WO 03/015692 A2

| | | | | | | | | | |
|---|---|---|---|---|---|---|---|---|---|
| ATOM | 51 | CA | VAL | 543 | 35.299 | 5.148 | 45.518 | 1.00 | 63.47 |
| ATOM | 52 | C | VAL | 543 | 33.886 | 4.748 | 45.126 | 1.00 | 61.39 |
| ATOM | 53 | O | VAL | 543 | 33.495 | 4.877 | 43.965 | 1.00 | 60.79 |
| ATOM | 54 | CB | VAL | 543 | 35.334 | 6.661 | 45.801 | 1.00 | 62.60 |
| ATOM | 55 | CG1 | VAL | 543 | 34.467 | 6.984 | 46.987 | 1.00 | 60.93 |
| ATOM | 56 | CG2 | VAL | 543 | 36.762 | 7.103 | 46.064 | 1.00 | 59.59 |
| TER | 57 | | VAL | 543 | | | | | |
| ATOM | 58 | N | LEU | 566 | 27.382 | 0.590 | 53.462 | 1.00 | 62.25 |
| ATOM | 59 | CA | LEU | 566 | 28.495 | 1.064 | 52.656 | 1.00 | 60.20 |
| ATOM | 60 | C | LEU | 566 | 29.756 | 0.424 | 53.218 | 1.00 | 62.85 |
| ATOM | 61 | O | LEU | 566 | 30.576 | −0.116 | 52.474 | 1.00 | 60.20 |
| ATOM | 62 | CB | LEU | 566 | 28.596 | 2.594 | 52.741 | 1.00 | 59.50 |
| ATOM | 63 | CG | LEU | 566 | 29.801 | 3.267 | 52.076 | 1.00 | 64.18 |
| ATOM | 64 | CD1 | LEU | 566 | 29.685 | 3.195 | 50.565 | 1.00 | 61.46 |
| ATOM | 65 | CD2 | LEU | 566 | 29.869 | 4.700 | 52.516 | 1.00 | 62.10 |
| ATOM | 66 | N | GLY | 567 | 29.886 | 0.477 | 54.542 | 1.00 | 59.45 |
| ATOM | 67 | CA | GLY | 567 | 31.040 | −0.095 | 55.207 | 1.00 | 59.94 |
| ATOM | 68 | C | GLY | 567 | 31.316 | −1.516 | 54.768 | 1.00 | 60.71 |
| ATOM | 69 | O | GLY | 567 | 32.461 | −1.890 | 54.520 | 1.00 | 59.79 |
| TER | 70 | | GLY | 567 | | | | | |
| ATOM | 71 | N | GLN | 570 | 32.788 | −1.713 | 51.295 | 1.00 | 60.73 |
| ATOM | 72 | CA | GLN | 570 | 34.123 | −1.132 | 51.300 | 1.00 | 62.31 |
| ATOM | 73 | C | GLN | 570 | 35.144 | −2.093 | 51.882 | 1.00 | 61.15 |
| ATOM | 74 | O | GLN | 570 | 36.293 | −2.134 | 51.441 | 1.00 | 60.50 |
| ATOM | 75 | CB | GLN | 570 | 34.143 | 0.150 | 52.120 | 1.00 | 59.04 |
| ATOM | 76 | CG | GLN | 570 | 33.608 | 1.361 | 51.417 | 1.00 | 62.03 |
| ATOM | 77 | CD | GLN | 570 | 33.782 | 2.606 | 52.247 | 1.00 | 56.35 |
| ATOM | 78 | OE1 | GLN | 570 | 33.460 | 3.698 | 51.801 | 1.00 | 62.86 |
| ATOM | 79 | NE2 | GLN | 570 | 34.295 | 2.449 | 53.467 | 1.00 | 63.17 |
| ATOM | 80 | N | VAL | 571 | 34.732 | −2.837 | 52.903 | 1.00 | 60.99 |
| ATOM | 81 | CA | VAL | 571 | 35.615 | −3.792 | 53.554 | 1.00 | 61.91 |
| ATOM | 82 | C | VAL | 571 | 35.805 | −5.007 | 52.665 | 1.00 | 62.66 |
| ATOM | 83 | O | VAL | 571 | 36.698 | −5.820 | 52.885 | 1.00 | 58.99 |
| ATOM | 84 | CB | VAL | 571 | 35.054 | −4.200 | 54.930 | 1.00 | 58.42 |
| ATOM | 85 | CG1 | VAL | 571 | 35.822 | −5.393 | 55.485 | 1.00 | 61.27 |
| ATOM | 86 | CG2 | VAL | 571 | 35.160 | −3.007 | 55.891 | 1.00 | 60.58 |
| ATOM | 87 | N | ILK | 572 | 34.958 | −5.116 | 51.652 | 1.00 | 63.61 |
| ATOM | 88 | CA | ILK | 572 | 35.042 | −6.206 | 50.695 | 1.00 | 63.76 |
| ATOM | 89 | C | ILK | 572 | 35.999 | −5.772 | 49.589 | 1.00 | 60.35 |
| ATOM | 90 | O | ILK | 572 | 36.733 | −6.587 | 49.042 | 1.00 | 62.13 |
| ATOM | 91 | CB | ILK | 572 | 33.649 | −6.539 | 50.103 | 1.00 | 60.98 |
| ATOM | 92 | CG2 | ILK | 572 | 33.794 | −7.443 | 48.883 | 1.00 | 63.63 |
| ATOM | 93 | CG1 | ILK | 572 | 32.782 | −7.192 | 51.183 | 1.00 | 61.03 |
| ATOM | 94 | CD1 | ILK | 572 | 31.346 | −7.366 | 50.801 | 1.00 | 62.17 |
| ATOM | 95 | N | ALA | 573 | 35.984 | −4.481 | 49.265 | 1.00 | 62.76 |
| ATOM | 96 | CA | ALA | 573 | 36.879 | −3.936 | 48.251 | 1.00 | 58.47 |
| ATOM | 97 | C | ALA | 573 | 38.271 | −3.997 | 48.872 | 1.00 | 61.14 |
| ATOM | 98 | O | ALA | 573 | 39.294 | −4.088 | 48.180 | 1.00 | 60.46 |
| ATOM | 99 | CB | ALA | 573 | 36.502 | −2.496 | 47.940 | 1.00 | 61.48 |
| ATOM | 100 | N | ALA | 574 | 38.273 | −3.964 | 50.200 | 1.00 | 60.84 |
| ATOM | 101 | CA | ALA | 574 | 39.477 | −4.008 | 51.003 | 1.00 | 61.42 |
| ATOM | 102 | C | ALA | 574 | 40.294 | −5.282 | 50.771 | 1.00 | 58.96 |
| ATOM | 103 | O | ALA | 574 | 41.506 | −5.217 | 50.518 | 1.00 | 61.38 |
| ATOM | 104 | CB | ALA | 574 | 39.098 | −3.888 | 52.465 | 1.00 | 60.18 |
| ATOM | 105 | N | VAL | 575 | 39.631 | −6.435 | 50.861 | 1.00 | 59.99 |
| ATOM | 106 | CA | VAL | 575 | 40.296 | −7.720 | 50.664 | 1.00 | 59.60 |
| ATOM | 107 | C | VAL | 575 | 41.009 | −7.779 | 49.318 | 1.00 | 60.96 |
| ATOM | 108 | O | VAL | 575 | 42.222 | −7.981 | 49.264 | 1.00 | 62.47 |
| ATOM | 109 | CB | VAL | 575 | 39.309 | −8.898 | 50.732 | 1.00 | 56.06 |
| ATOM | 110 | CG2 | VAL | 575 | 38.547 | −8.880 | 52.057 | 1.00 | 63.34 |
| ATOM | 111 | CG | VAL | 575 | 40.070 | −10.197 | 50.570 | 1.00 | 62.55 |
| ATOM | 112 | N | LYS | 576 | 40.265 | −7.584 | 48.236 | 1.00 | 59.97 |
| ATOM | 113 | CA | LYS | 576 | 40.851 | −7.628 | 46.901 | 1.00 | 62.25 |
| ATOM | 114 | C | LYS | 576 | 41.957 | −6.593 | 46.742 | 1.00 | 63.69 |
| ATOM | 115 | O | LYS | 576 | 42.673 | −6.573 | 45.742 | 1.00 | 59.32 |
| ATOM | 116 | CB | LYS | 576 | 39.770 | −7.391 | 45.860 | 1.00 | 60.99 |
| ATOM | 117 | CG | LYS | 576 | 40.115 | −7.866 | 44.462 | 1.00 | 61.35 |
| ATOM | 118 | CD | LYS | 576 | 38.905 | −7.708 | 43.568 | 1.00 | 63.13 |
| ATOM | 119 | CE | LYS | 576 | 37.667 | −8.234 | 44.276 | 1.00 | 62.07 |
| ATOM | 120 | NZ | LYS | 576 | 36.420 | −7.912 | 43.531 | 1.00 | 59.76 |
| ATOM | 121 | N | TRP | 577 | 42.074 | −5.723 | 47.734 | 1.00 | 62.59 |
| ATOM | 122 | CA | TRP | 577 | 43.091 | −4.694 | 47.734 | 1.00 | 62.15 |
| ATOM | 123 | C | TRP | 577 | 44.263 | −5.272 | 48.509 | 1.00 | 64.09 |
| ATOM | 124 | O | TRP | 577 | 45.403 | −5.238 | 48.055 | 1.00 | 61.89 |
| ATOM | 125 | CB | TRP | 577 | 42.556 | −3.432 | 48.424 | 1.00 | 60.50 |
| ATOM | 126 | CG | TRP | 577 | 43.620 | −2.458 | 48.780 | 1.00 | 63.03 |

TABLE IV-continued

GR Homology Model Coordinates (SEQ ID NO:1) discerned from the disclosure in WO 03/015692 A2

| | | | | | | | | | |
|---|---|---|---|---|---|---|---|---|---|
| ATOM | 127 | CD1 | TRP | 577 | 44.346 | −1.698 | 47.924 | 1.00 | 62.09 |
| ATOM | 128 | CD2 | TRP | 577 | 44.140 | −2.200 | 50.090 | 1.00 | 58.79 |
| ATOM | 129 | NE1 | TRP | 577 | 45.293 | −0.983 | 48.611 | 1.00 | 61.93 |
| ATOM | 130 | CE2 | TRP | 577 | 45.189 | −1.272 | 49.945 | 1.00 | 64.04 |
| ATOM | 131 | CE3 | TRP | 577 | 43.824 | −2.668 | 51.372 | 1.00 | 60.56 |
| ATOM | 132 | CZ2 | TRP | 577 | 45.930 | −0.798 | 51.032 | 1.00 | 61.40 |
| ATOM | 133 | CZ3 | TRP | 577 | 44.566 | −2.197 | 52.458 | 1.00 | 59.59 |
| ATOM | 134 | CH2 | TRP | 577 | 45.607 | −1.271 | 52.277 | 1.00 | 61.92 |
| TER | 135 | | TRP | 577 | | | | | |
| ATOM | 136 | N | SER | 599 | 42.278 | −4.312 | 61.305 | 1.00 | 58.28 |
| ATOM | 137 | CA | SER | 599 | 42.491 | −2.988 | 60.774 | 1.00 | 62.69 |
| ATOM | 138 | C | SER | 599 | 41.365 | −2.525 | 59.867 | 1.00 | 64.40 |
| ATOM | 139 | O | SER | 599 | 41.398 | −1.405 | 59.367 | 1.00 | 62.40 |
| ATOM | 140 | CB | SER | 599 | 43.837 | −2.949 | 60.046 | 1.00 | 62.55 |
| ATOM | 141 | OG | SER | 599 | 44.008 | −4.083 | 59.216 | 1.00 | 62.72 |
| ATOM | 142 | N | TRP | 600 | 40.358 | −3.375 | 59.677 | 1.00 | 59.48 |
| ATOM | 143 | CA | TRP | 600 | 39.245 | −3.026 | 58.807 | 1.00 | 62.88 |
| ATOM | 144 | C | TRP | 600 | 38.789 | −1.630 | 59.169 | 1.00 | 62.61 |
| ATOM | 145 | O | TRP | 600 | 38.533 | −0.805 | 58.308 | 1.00 | 62.45 |
| ATOM | 146 | CB | TRP | 600 | 38.073 | −4.031 | 58.932 | 1.00 | 64.17 |
| ATOM | 147 | CG | TRP | 600 | 37.282 | −3.951 | 60.198 | 1.00 | 62.02 |
| ATOM | 148 | CD1 | TRP | 600 | 37.583 | −4.533 | 61.395 | 1.00 | 58.92 |
| ATOM | 149 | CD2 | TRP | 600 | 36.105 | −3.166 | 60.420 | 1.00 | 58.67 |
| ATOM | 150 | NE1 | TRP | 600 | 36.672 | −4.151 | 62.355 | 1.00 | 64.28 |
| ATOM | 151 | CE2 | TRP | 600 | 35.754 | −3.311 | 61.781 | 1.00 | 61.68 |
| ATOM | 152 | CE3 | TRP | 600 | 35.314 | −2.350 | 59.603 | 1.00 | 62.68 |
| ATOM | 153 | CZ2 | TRP | 600 | 34.648 | −2.666 | 62.342 | 1.00 | 61.17 |
| ATOM | 154 | CZ3 | TRP | 600 | 34.217 | −1.711 | 60.159 | 1.00 | 58.94 |
| ATOM | 155 | CH2 | TRP | 600 | 33.894 | −1.871 | 61.516 | 1.00 | 61.08 |
| ATOM | 156 | N | MET | 601 | 38.744 | −1.344 | 60.458 | 1.00 | 63.90 |
| ATOM | 157 | CA | MET | 601 | 38.298 | −0.049 | 60.884 | 1.00 | 60.96 |
| ATOM | 158 | C | MET | 601 | 39.225 | 1.129 | 60.577 | 1.00 | 61.08 |
| ATOM | 159 | O | MET | 601 | 38.758 | 2.167 | 60.114 | 1.00 | 60.27 |
| ATOM | 160 | CB | MET | 601 | 37.968 | −0.064 | 62.351 | 1.00 | 60.46 |
| ATOM | 161 | CG | MET | 601 | 37.139 | 1.112 | 62.702 | 1.00 | 61.28 |
| ATOM | 162 | SD | MET | 601 | 35.774 | 1.420 | 61.631 | 1.00 | 59.33 |
| ATOM | 163 | CE | MET | 601 | 34.684 | 1.638 | 62.889 | 1.00 | 64.63 |
| ATOM | 164 | N | SER | 602 | 40.521 | 0.979 | 60.854 | 1.00 | 61.23 |
| ATOM | 165 | CA | SER | 602 | 41.488 | 2.035 | 60.581 | 1.00 | 59.98 |
| ATOM | 166 | C | SER | 602 | 41.536 | 2.214 | 59.079 | 1.00 | 60.99 |
| ATOM | 167 | O | SER | 602 | 41.609 | 3.327 | 58.581 | 1.00 | 64.11 |
| ATOM | 168 | CB | SER | 602 | 42.872 | 1.647 | 61.083 | 1.00 | 60.99 |
| ATOM | 169 | OG | SER | 602 | 42.783 | 1.022 | 62.350 | 1.00 | 66.17 |
| ATOM | 170 | N | LEU | 603 | 41.494 | 1.108 | 58.351 | 1.00 | 59.44 |
| ATOM | 171 | CA | LEU | 603 | 41.522 | 1.185 | 56.901 | 1.00 | 61.46 |
| ATOM | 172 | C | LEU | 603 | 40.386 | 2.061 | 56.408 | 1.00 | 60.47 |
| ATOM | 173 | O | LEU | 603 | 40.599 | 3.062 | 55.731 | 1.00 | 63.39 |
| ATOM | 174 | CB | LEU | 603 | 41.402 | −0.212 | 56.280 | 1.00 | 59.31 |
| ATOM | 175 | CG | LEU | 603 | 42.646 | −1.097 | 56.346 | 1.00 | 61.54 |
| ATOM | 176 | CD1 | LEU | 603 | 42.415 | −2.362 | 55.549 | 1.00 | 63.99 |
| ATOM | 177 | CD2 | LEU | 603 | 43.828 | −0.346 | 55.787 | 1.00 | 63.36 |
| ATOM | 178 | N | MET | 604 | 39.173 | 1.688 | 56.784 | 1.00 | 63.54 |
| ATOM | 179 | CA | MET | 604 | 38.000 | 2.417 | 56.365 | 1.00 | 62.81 |
| ATOM | 180 | C | MET | 604 | 37.898 | 3.832 | 56.856 | 1.00 | 60.43 |
| ATOM | 181 | O | MET | 604 | 37.397 | 4.695 | 56.132 | 1.00 | 62.37 |
| ATOM | 182 | CB | MET | 604 | 36.770 | 1.623 | 56.723 | 1.00 | 58.90 |
| ATOM | 183 | CG | MET | 604 | 36.632 | 0.429 | 55.842 | 1.00 | 59.86 |
| ATOM | 184 | SD | MET | 604 | 37.633 | 0.438 | 54.374 | 1.00 | 62.53 |
| ATOM | 185 | CE | MET | 604 | 36.663 | −0.510 | 53.559 | 1.00 | 60.72 |
| ATOM | 186 | N | ALA | 605 | 38.375 | 4.076 | 58.072 | 1.00 | 59.95 |
| ATOM | 187 | CA | ALA | 605 | 38.357 | 5.409 | 58.664 | 1.00 | 60.49 |
| ATOM | 188 | C | ALA | 605 | 39.381 | 6.309 | 57.985 | 1.00 | 61.50 |
| ATOM | 189 | O | ALA | 605 | 39.071 | 7.427 | 57.583 | 1.00 | 59.82 |
| ATOM | 190 | CB | ALA | 605 | 38.667 | 5.317 | 60.132 | 1.00 | 59.15 |
| ATOM | 191 | N | PHE | 606 | 40.608 | 5.810 | 57.870 | 1.00 | 63.59 |
| ATOM | 192 | CA | PHE | 606 | 41.700 | 6.554 | 57.258 | 1.00 | 60.15 |
| ATOM | 193 | C | PHE | 606 | 41.362 | 6.933 | 55.825 | 1.00 | 61.96 |
| ATOM | 194 | O | PHE | 606 | 41.751 | 7.991 | 55.356 | 1.00 | 60.07 |
| ATOM | 195 | CB | PHE | 606 | 42.981 | 5.713 | 57.285 | 1.00 | 63.75 |
| ATOM | 196 | CG | PHE | 606 | 44.237 | 6.490 | 56.999 | 1.00 | 64.30 |
| ATOM | 197 | CD1 | PHE | 606 | 44.723 | 7.424 | 57.913 | 1.00 | 61.77 |
| ATOM | 198 | CD2 | PHE | 606 | 44.957 | 6.265 | 55.829 | 1.00 | 60.74 |
| ATOM | 199 | CE1 | PHE | 606 | 45.910 | 8.118 | 57.665 | 1.00 | 64.00 |
| ATOM | 200 | CE2 | PHE | 606 | 46.145 | 6.955 | 55.575 | 1.00 | 62.47 |
| ATOM | 201 | CZ | PHE | 606 | 46.620 | 7.879 | 56.496 | 1.00 | 63.95 |
| ATOM | 202 | N | ALA | 607 | 40.644 | 6.063 | 55.126 | 1.00 | 62.00 |

TABLE IV-continued

GR Homology Model Coordinates (SEQ ID NO:1) discerned from the disclosure in WO 03/015692 A2

| | | | | | | | | | |
|---|---|---|---|---|---|---|---|---|---|
| ATOM | 203 | CA | ALA | 607 | 40.264 | 6.338 | 53.745 | 1.00 | 57.50 |
| ATOM | 204 | C | ALA | 607 | 39.105 | 7.324 | 53.684 | 1.00 | 64.88 |
| ATOM | 205 | O | ALA | 607 | 38.931 | 8.030 | 52.703 | 1.00 | 59.60 |
| ATOM | 206 | CB | ALA | 607 | 39.888 | 5.051 | 53.039 | 1.00 | 59.69 |
| TER | 207 | | ALA | 607 | | | | | |
| ATOM | 208 | N | TRP | 610 | 40.835 | 10.650 | 54.039 | 1.00 | 62.47 |
| ATOM | 209 | CA | TRP | 610 | 41.488 | 11.102 | 52.823 | 1.00 | 61.40 |
| ATOM | 210 | C | TRP | 610 | 40.517 | 11.797 | 51.874 | 1.00 | 60.80 |
| ATOM | 211 | O | TRP | 610 | 40.797 | 12.866 | 51.358 | 1.00 | 60.72 |
| ATOM | 212 | CB | TRP | 610 | 42.141 | 9.917 | 52.123 | 1.00 | 62.68 |
| ATOM | 213 | CG | TRP | 610 | 42.744 | 10.264 | 50.817 | 1.00 | 62.61 |
| ATOM | 214 | CD1 | TRP | 610 | 42.254 | 9.965 | 49.582 | 1.00 | 58.08 |
| ATOM | 215 | CD2 | TRP | 610 | 43.955 | 10.991 | 50.604 | 1.00 | 61.10 |
| ATOM | 216 | NE1 | TRP | 610 | 43.086 | 10.459 | 48.608 | 1.00 | 62.17 |
| ATOM | 217 | CE2 | TRP | 610 | 44.139 | 11.095 | 49.209 | 1.00 | 62.45 |
| ATOM | 218 | CE3 | TRP | 610 | 44.906 | 11.565 | 51.457 | 1.00 | 63.78 |
| ATOM | 219 | CZ2 | TRP | 610 | 45.238 | 11.751 | 48.646 | 1.00 | 60.53 |
| ATOM | 220 | CZ3 | TRP | 610 | 46.001 | 12.219 | 50.896 | 1.00 | 62.27 |
| ATOM | 221 | CH2 | TRP | 610 | 46.156 | 12.305 | 49.505 | 1.00 | 60.31 |
| ATOM | 222 | N | ARG | 611 | 39.368 | 11.191 | 51.639 | 1.00 | 61.36 |
| ATOM | 223 | CA | ARG | 611 | 38.412 | 11.790 | 50.738 | 1.00 | 58.33 |
| ATOM | 224 | C | ARG | 611 | 37.898 | 13.128 | 51.277 | 1.00 | 62.93 |
| ATOM | 225 | O | ARG | 611 | 37.610 | 14.051 | 50.502 | 1.00 | 61.13 |
| ATOM | 226 | CB | ARG | 611 | 37.254 | 10.817 | 50.486 | 1.00 | 62.33 |
| ATOM | 227 | CG | ARG | 611 | 37.684 | 9.490 | 49.873 | 1.00 | 60.18 |
| ATOM | 228 | CD | ARG | 611 | 36.476 | 8.686 | 49.426 | 1.00 | 59.83 |
| ATOM | 229 | NE | ARG | 611 | 35.604 | 8.333 | 50.544 | 1.00 | 61.17 |
| ATOM | 230 | CZ | ARG | 611 | 35.817 | 7.308 | 51.366 | 1.00 | 59.54 |
| ATOM | 231 | NH1 | ARG | 611 | 36.875 | 6.528 | 51.187 | 1.00 | 61.47 |
| ATOM | 232 | NH2 | ARG | 611 | 34.988 | 7.072 | 52.376 | 1.00 | 62.25 |
| TER | 233 | | ARG | 611 | | | | | |
| ATOM | 234 | N | ARG | 614 | 40.511 | 15.896 | 50.745 | 1.00 | 61.73 |
| ATOM | 235 | CA | ARG | 614 | 40.623 | 16.190 | 49.328 | 1.00 | 61.64 |
| ATOM | 236 | C | ARG | 614 | 39.440 | 16.960 | 48.776 | 1.00 | 58.09 |
| ATOM | 237 | O | ARG | 614 | 39.613 | 17.922 | 48.041 | 1.00 | 63.07 |
| ATOM | 238 | CB | ARG | 614 | 40.835 | 14.880 | 48.545 | 1.00 | 62.80 |
| ATOM | 239 | CG | ARG | 614 | 42.274 | 14.328 | 48.621 | 1.00 | 58.30 |
| ATOM | 240 | CD | ARG | 614 | 42.908 | 14.348 | 47.242 | 1.00 | 60.57 |
| ATOM | 241 | NE | ARG | 614 | 44.369 | 14.448 | 47.262 | 1.00 | 61.63 |
| ATOM | 242 | CZ | ARG | 614 | 45.056 | 15.421 | 47.868 | 1.00 | 63.66 |
| ATOM | 243 | NH1 | ARG | 614 | 44.414 | 16.386 | 48.521 | 1.00 | 61.59 |
| ATOM | 244 | NH2 | ARG | 614 | 46.389 | 15.451 | 47.797 | 1.00 | 64.70 |
| ATOM | 245 | N | GLN | 615 | 38.239 | 16.538 | 49.137 | 1.00 | 64.09 |
| ATOM | 246 | CA | GLN | 615 | 37.033 | 17.192 | 48.660 | 1.00 | 61.67 |
| ATOM | 247 | C | GLN | 615 | 36.677 | 18.478 | 49.396 | 1.00 | 59.82 |
| ATOM | 248 | O | GLN | 615 | 36.200 | 19.441 | 48.784 | 1.00 | 60.64 |
| ATOM | 249 | CB | GLN | 615 | 35.840 | 16.259 | 48.801 | 1.00 | 62.84 |
| ATOM | 250 | CG | GLN | 615 | 35.738 | 15.162 | 47.795 | 1.00 | 62.14 |
| ATOM | 251 | CD | GLN | 615 | 34.290 | 14.775 | 47.573 | 1.00 | 58.76 |
| ATOM | 252 | OE1 | GLN | 615 | 33.532 | 14.598 | 48.525 | 1.00 | 62.70 |
| ATOM | 253 | NE2 | GLN | 615 | 33.897 | 14.651 | 46.314 | 1.00 | 61.03 |
| TER | 254 | | GLN | 615 | | | | | |
| ATOM | 255 | N | PRO | 625 | 30.130 | 9.828 | 47.355 | 1.00 | 62.43 |
| ATOM | 256 | CA | PRO | 625 | 29.795 | 11.035 | 46.593 | 1.00 | 59.45 |
| ATOM | 257 | C | PRO | 625 | 28.366 | 11.397 | 46.928 | 1.00 | 62.94 |
| ATOM | 258 | O | PRO | 625 | 28.111 | 12.382 | 47.622 | 1.00 | 59.36 |
| ATOM | 259 | CB | PRO | 625 | 29.949 | 10.582 | 45.146 | 1.00 | 62.18 |
| ATOM | 260 | CG | PRO | 625 | 31.089 | 9.653 | 45.245 | 1.00 | 59.91 |
| ATOM | 261 | CD | PRO | 625 | 30.706 | 8.811 | 46.459 | 1.00 | 62.52 |
| TER | 262 | | PRO | 625 | | | | | |
| ATOM | 263 | N | TYR | 663 | 50.007 | 8.771 | 51.436 | 1.00 | 61.62 |
| ATOM | 264 | CA | TYR | 663 | 48.716 | 8.186 | 51.812 | 1.00 | 62.54 |
| ATOM | 265 | C | TYR | 663 | 48.565 | 6.680 | 51.537 | 1.00 | 59.94 |
| ATOM | 266 | O | TYR | 663 | 48.090 | 5.918 | 52.389 | 1.00 | 60.92 |
| ATOM | 267 | CB | TYR | 663 | 47.601 | 8.921 | 51.068 | 1.00 | 63.89 |
| ATOM | 268 | CG | TYR | 663 | 46.266 | 8.230 | 51.167 | 1.00 | 61.84 |
| ATOM | 269 | CD1 | TYR | 663 | 45.619 | 8.109 | 52.392 | 1.00 | 59.60 |
| ATOM | 270 | CD2 | TYR | 663 | 45.659 | 7.676 | 50.043 | 1.00 | 58.65 |
| ATOM | 271 | CE1 | TYR | 663 | 44.407 | 7.458 | 52.498 | 1.00 | 58.52 |
| ATOM | 272 | CE2 | TYR | 663 | 44.441 | 7.019 | 50.138 | 1.00 | 60.83 |
| ATOM | 273 | CZ | TYR | 663 | 43.820 | 6.916 | 51.368 | 1.00 | 62.58 |
| ATOM | 274 | OH | TYR | 663 | 42.601 | 6.287 | 51.477 | 1.00 | 61.21 |
| ATOM | 275 | N | LEU | 664 | 48.930 | 6.274 | 50.325 | 1.00 | 60.84 |
| ATOM | 276 | CA | LEU | 664 | 48.846 | 4.881 | 49.908 | 1.00 | 61.56 |
| ATOM | 277 | C | LEU | 664 | 49.744 | 4.001 | 50.777 | 1.00 | 60.21 |
| ATOM | 278 | O | LEU | 664 | 49.369 | 2.889 | 51.161 | 1.00 | 61.89 |

TABLE IV-continued

GR Homology Model Coordinates (SEQ ID NO:1) discerned from the disclosure in WO 03/015692 A2

| ATOM | 279 | CB  | LEU | 664 | 49.261 | 4.757  | 48.438 | 1.00 | 60.37 |
|------|-----|-----|-----|-----|--------|--------|--------|------|-------|
| ATOM | 280 | CG  | LEU | 664 | 48.363 | 5.402  | 47.382 | 1.00 | 64.33 |
| ATOM | 281 | CD1 | LEU | 664 | 49.036 | 5.350  | 46.023 | 1.00 | 64.49 |
| ATOM | 282 | CD2 | LEU | 664 | 47.032 | 4.687  | 47.351 | 1.00 | 59.02 |
| TER  | 283 |     | LEU | 664 |        |        |        |      |       |
| ATOM | 284 | N   | LYS | 667 | 48.446 | 3.950  | 54.421 | 1.00 | 58.08 |
| ATOM | 285 | CA  | LYS | 667 | 47.241 | 3.129  | 54.482 | 1.00 | 61.17 |
| ATOM | 286 | C   | LYS | 667 | 47.592 | 1.658  | 54.468 | 1.00 | 63.84 |
| ATOM | 287 | O   | LYS | 667 | 46.867 | 0.838  | 55.011 | 1.00 | 61.95 |
| ATOM | 288 | CB  | LYS | 667 | 46.318 | 3.429  | 53.305 | 1.00 | 66.33 |
| ATOM | 289 | CG  | LYS | 667 | 45.013 | 2.663  | 53.338 | 1.00 | 59.73 |
| ATOM | 290 | CD  | LYS | 667 | 43.951 | 3.382  | 52.532 | 1.00 | 60.07 |
| ATOM | 291 | CE  | LYS | 667 | 44.313 | 3.462  | 51.063 | 1.00 | 62.82 |
| ATOM | 292 | NZ  | LYS | 667 | 44.134 | 2.158  | 50.390 | 1.00 | 62.44 |
| TER  | 293 |     | LYS | 667 |        |        |        |      |       |

Example 24

X-ray Structure Coordinates of GR Site II, Table V

Below is Table V, which gives the x-ray structure coordinates for GR Site II discerned from the disclosure in Kauppi et. al., in the Journal of Biological Chemistry Online, JBC Papers In Press as doi: 10.1074/jbc.M212711200, Apr. 9, 2003, RCSB file: 1nhz.pdb (GR LBD bound to an antagonist, RU 486). The format used is based on that commonly used in the RCSB (Research Collaboratory for Structural Bioinformatics, pdb file format), and the fields listed from left to right are defined as follows: record name, atom serial number, atom name, residue name, chain identifier, residue sequence number, orthogonal coordinate for x in Ångstroms, orthogonal cordinate for y in Ångstroms, orthogonal coordinate for z in Ångstroms, occupancy, and temperature factor.

TABLE V

GR Homology Model Coordinates (SEQ ID NO:1) discerned from the disclosure in Kauppi et. al.

| ATOM | 1  | N   | GLU | 537 | 26.949 | 4.045  | 83.095 | 1.00 | 0.00 |
|------|----|-----|-----|-----|--------|--------|--------|------|------|
| ATOM | 2  | CA  | GLU | 537 | 25.828 | 3.147  | 82.817 | 1.00 | 0.00 |
| ATOM | 3  | C   | GLU | 537 | 24.510 | 3.903  | 82.903 | 1.00 | 0.00 |
| ATOM | 4  | O   | GLU | 537 | 23.672 | 3.737  | 82.043 | 1.00 | 0.00 |
| ATOM | 5  | CB  | GLU | 537 | 25.781 | 1.935  | 83.756 | 1.00 | 0.00 |
| ATOM | 6  | CG  | GLU | 537 | 24.445 | 1.183  | 83.643 | 1.00 | 0.00 |
| ATOM | 7  | CD  | GLU | 537 | 24.470 | -0.233 | 84.168 | 1.00 | 0.00 |
| ATOM | 8  | OE1 | GLU | 537 | 25.374 | -0.538 | 84.996 | 1.00 | 0.00 |
| ATOM | 9  | OE2 | GLU | 537 | 23.565 | -1.032 | 83.762 | 1.00 | 0.00 |
| ATOM | 10 | N   | VAL | 538 | 24.336 | 4.753  | 83.907 | 1.00 | 0.00 |
| ATOM | 11 | CA  | VAL | 538 | 23.045 | 5.402  | 84.089 | 1.00 | 0.00 |
| ATOM | 12 | C   | VAL | 538 | 22.743 | 6.413  | 82.968 | 1.00 | 0.00 |
| ATOM | 13 | O   | VAL | 538 | 21.598 | 6.534  | 82.552 | 1.00 | 0.00 |
| ATOM | 14 | CB  | VAL | 538 | 22.824 | 6.035  | 85.527 | 1.00 | 0.00 |
| ATOM | 15 | CG1 | VAL | 538 | 23.344 | 5.107  | 86.654 | 1.00 | 0.00 |
| ATOM | 16 | CG2 | VAL | 538 | 23.413 | 7.415  | 85.654 | 1.00 | 0.00 |
| ATOM | 17 | N   | ILE | 539 | 23.742 | 7.119  | 82.470 | 1.00 | 0.00 |
| ATOM | 18 | CA  | ILE | 539 | 23.496 | 8.120  | 81.427 | 1.00 | 0.00 |
| ATOM | 19 | C   | ILE | 539 | 23.537 | 7.549  | 79.994 | 1.00 | 0.00 |
| ATOM | 20 | O   | ILE | 539 | 23.320 | 8.285  | 79.043 | 1.00 | 0.00 |
| ATOM | 21 | CB  | ILE | 539 | 24.471 | 9.322  | 81.550 | 1.00 | 0.00 |
| ATOM | 22 | CG1 | ILE | 539 | 25.908 | 8.862  | 81.348 | 1.00 | 0.00 |
| ATOM | 23 | CG2 | ILE | 539 | 24.329 | 10.017 | 82.914 | 1.00 | 0.00 |
| ATOM | 24 | CD1 | ILE | 539 | 26.805 | 9.907  | 80.746 | 1.00 | 0.00 |
| ATOM | 25 | N   | GLU | 540 | 23.820 | 6.263  | 79.846 | 1.00 | 0.00 |
| ATOM | 26 | CA  | GLU | 540 | 23.875 | 5.614  | 78.522 | 1.00 | 0.00 |
| ATOM | 27 | C   | GLU | 540 | 22.497 | 5.764  | 77.805 | 1.00 | 0.00 |
| ATOM | 28 | O   | GLU | 540 | 21.463 | 5.478  | 78.377 | 1.00 | 0.00 |
| ATOM | 29 | CB  | GLU | 540 | 24.313 | 4.129  | 78.698 | 1.00 | 0.00 |
| ATOM | 30 | CG  | GLU | 540 | 24.605 | 3.310  | 77.424 | 1.00 | 0.00 |
| ATOM | 31 | CD  | GLU | 540 | 25.530 | 3.964  | 76.393 | 1.00 | 0.00 |
| ATOM | 32 | OE1 | GLU | 540 | 25.387 | 3.568  | 75.196 | 1.00 | 0.00 |
| ATOM | 33 | OE2 | GLU | 540 | 26.383 | 4.837  | 76.748 | 1.00 | 0.00 |
| ATOM | 34 | N   | PRO | 541 | 22.480 | 6.288  | 76.578 | 1.00 | 0.00 |
| ATOM | 35 | CA  | PRO | 541 | 21.219 | 6.557  | 75.887 | 1.00 | 0.00 |
| ATOM | 36 | C   | PRO | 541 | 20.356 | 5.307  | 75.680 | 1.00 | 0.00 |
| ATOM | 37 | O   | PRO | 541 | 20.873 | 4.266  | 75.401 | 1.00 | 0.00 |
| ATOM | 38 | CB  | PRO | 541 | 21.683 | 7.067  | 74.527 | 1.00 | 0.00 |
| ATOM | 39 | CG  | PRO | 541 | 23.067 | 7.581  | 74.749 | 1.00 | 0.00 |

TABLE V-continued

GR Homology Model Coordinates (SEQ ID NO:1) discerned from the disclosure in Kauppi et. al.

| | | | | | | | | |
|---|---|---|---|---|---|---|---|---|
| ATOM | 40 | CD | PRO | 541 | 23.639 | 6.678 | 75.759 | 1.00 | 0.00 |
| ATOM | 41 | N | GLU | 542 | 19.049 | 5.419 | 75.801 | 1.00 | 0.00 |
| ATOM | 42 | CA | GLU | 542 | 18.163 | 4.373 | 75.290 | 1.00 | 0.00 |
| ATOM | 43 | C | GLU | 542 | 18.327 | 4.201 | 73.782 | 1.00 | 0.00 |
| ATOM | 44 | O | GLU | 542 | 18.747 | 5.141 | 73.056 | 1.00 | 0.00 |
| ATOM | 45 | CB | GLU | 542 | 16.706 | 4.701 | 75.586 | 1.00 | 0.00 |
| ATOM | 46 | CG | GLU | 542 | 16.392 | 4.783 | 77.062 | 1.00 | 0.00 |
| ATOM | 47 | CD | GLU | 542 | 14.923 | 5.041 | 77.333 | 1.00 | 0.00 |
| ATOM | 48 | OE1 | GLU | 542 | 14.131 | 5.127 | 76.358 | 1.00 | 0.00 |
| ATOM | 49 | OE2 | GLU | 542 | 14.565 | 5.168 | 78.522 | 1.00 | 0.00 |
| ATOM | 50 | N | VAL | 543 | 18.014 | 2.994 | 73.322 | 1.00 | 0.00 |
| ATOM | 51 | CA | VAL | 543 | 18.041 | 2.659 | 71.904 | 1.00 | 0.00 |
| ATOM | 52 | C | VAL | 543 | 16.769 | 3.187 | 71.221 | 1.00 | 0.00 |
| ATOM | 53 | O | VAL | 543 | 15.652 | 2.913 | 71.645 | 1.00 | 0.00 |
| ATOM | 54 | CB | VAL | 543 | 18.231 | 1.127 | 71.699 | 1.00 | 0.00 |
| ATOM | 55 | CG1 | VAL | 543 | 17.014 | 0.387 | 72.184 | 1.00 | 0.00 |
| ATOM | 56 | CG2 | VAL | 543 | 18.414 | 0.803 | 70.241 | 1.00 | 0.00 |
| TER | 57 | | VAL | 543 | | | | | |
| ATOM | 58 | N | LEU | 566 | 17.090 | 9.013 | 61.502 | 1.00 | 0.00 |
| ATOM | 59 | CA | LEU | 566 | 17.579 | 8.376 | 62.706 | 1.00 | 0.00 |
| ATOM | 60 | C | LEU | 566 | 18.952 | 8.946 | 63.111 | 1.00 | 0.00 |
| ATOM | 61 | O | LEU | 566 | 19.208 | 9.149 | 64.289 | 1.00 | 0.00 |
| ATOM | 62 | CB | LEU | 566 | 17.630 | 6.849 | 62.519 | 1.00 | 0.00 |
| ATOM | 63 | CG | LEU | 566 | 18.276 | 6.057 | 63.667 | 1.00 | 0.00 |
| ATOM | 64 | CD1 | LEU | 566 | 17.436 | 6.181 | 64.939 | 1.00 | 0.00 |
| ATOM | 65 | CD2 | LEU | 566 | 18.455 | 4.644 | 63.275 | 1.00 | 0.00 |
| ATOM | 66 | N | GLY | 567 | 19.844 | 9.183 | 62.155 | 1.00 | 0.00 |
| ATOM | 67 | CA | GLY | 567 | 21.173 | 9.724 | 62.456 | 1.00 | 0.00 |
| ATOM | 68 | C | GLY | 567 | 21.184 | 11.113 | 63.098 | 1.00 | 0.00 |
| ATOM | 69 | O | GLY | 567 | 21.956 | 11.389 | 64.033 | 1.00 | 0.00 |
| TER | 70 | | GLY | 567 | | | | | |
| ATOM | 71 | N | GLN | 570 | 20.184 | 10.552 | 66.664 | 1.00 | 0.00 |
| ATOM | 72 | CA | GLN | 570 | 21.237 | 9.937 | 67.467 | 1.00 | 0.00 |
| ATOM | 73 | C | GLN | 570 | 22.303 | 10.951 | 67.864 | 1.00 | 0.00 |
| ATOM | 74 | O | GLN | 570 | 22.800 | 10.900 | 68.978 | 1.00 | 0.00 |
| ATOM | 75 | CB | GLN | 570 | 21.888 | 8.769 | 66.721 | 1.00 | 0.00 |
| ATOM | 76 | CG | GLN | 570 | 21.014 | 7.523 | 66.606 | 1.00 | 0.00 |
| ATOM | 77 | CD | GLN | 570 | 21.775 | 6.239 | 66.219 | 1.00 | 0.00 |
| ATOM | 78 | OE1 | GLN | 570 | 21.183 | 5.150 | 66.188 | 1.00 | 0.00 |
| ATOM | 79 | NE2 | GLN | 570 | 23.046 | 6.353 | 65.935 | 1.00 | 0.00 |
| ATOM | 80 | N | VAL | 571 | 22.632 | 11.873 | 66.948 | 1.00 | 0.00 |
| ATOM | 81 | CA | VAL | 571 | 23.474 | 13.031 | 67.233 | 1.00 | 0.00 |
| ATOM | 82 | C | VAL | 571 | 22.909 | 13.850 | 68.390 | 1.00 | 0.00 |
| ATOM | 83 | O | VAL | 571 | 23.632 | 14.163 | 69.310 | 1.00 | 0.00 |
| ATOM | 84 | CB | VAL | 571 | 23.685 | 13.922 | 65.994 | 1.00 | 0.00 |
| ATOM | 85 | CG1 | VAL | 571 | 24.439 | 15.225 | 66.326 | 1.00 | 0.00 |
| ATOM | 86 | CG2 | VAL | 571 | 24.492 | 13.214 | 64.979 | 1.00 | 0.00 |
| ATOM | 87 | N | ILE | 572 | 21.622 | 14.175 | 68.366 | 1.00 | 0.00 |
| ATOM | 88 | CA | ILE | 572 | 21.011 | 14.888 | 69.472 | 1.00 | 0.00 |
| ATOM | 89 | C | ILE | 572 | 21.175 | 14.114 | 70.772 | 1.00 | 0.00 |
| ATOM | 90 | O | ILE | 572 | 21.438 | 14.708 | 71.803 | 1.00 | 0.00 |
| ATOM | 91 | CB | ILE | 572 | 19.511 | 15.163 | 69.238 | 1.00 | 0.00 |
| ATOM | 92 | CG1 | ILE | 572 | 19.267 | 16.067 | 68.031 | 1.00 | 0.00 |
| ATOM | 93 | CG2 | ILE | 572 | 18.825 | 15.804 | 70.530 | 1.00 | 0.00 |
| ATOM | 94 | CD1 | ILE | 572 | 20.291 | 17.128 | 67.843 | 1.00 | 0.00 |
| ATOM | 95 | N | ALA | 573 | 21.006 | 12.800 | 70.727 | 1.00 | 0.00 |
| ATOM | 96 | CA | ALA | 573 | 21.188 | 11.972 | 71.920 | 1.00 | 0.00 |
| ATOM | 97 | C | ALA | 573 | 22.683 | 11.844 | 72.355 | 1.00 | 0.00 |
| ATOM | 98 | O | ALA | 573 | 22.946 | 11.714 | 73.538 | 1.00 | 0.00 |
| ATOM | 99 | CB | ALA | 573 | 20.555 | 10.598 | 71.713 | 1.00 | 0.00 |
| ATOM | 100 | N | ALA | 574 | 23.629 | 11.873 | 71.416 | 1.00 | 0.00 |
| ATOM | 101 | CA | ALA | 574 | 25.057 | 11.920 | 71.732 | 1.00 | 0.00 |
| ATOM | 102 | C | ALA | 574 | 25.470 | 13.202 | 72.483 | 1.00 | 0.00 |
| ATOM | 103 | O | ALA | 574 | 26.280 | 13.158 | 73.394 | 1.00 | 0.00 |
| ATOM | 104 | CB | ALA | 574 | 25.887 | 11.795 | 70.468 | 1.00 | 0.00 |
| ATOM | 105 | N | VAL | 575 | 24.897 | 14.339 | 72.085 | 1.00 | 0.00 |
| ATOM | 106 | CA | VAL | 575 | 25.196 | 15.612 | 72.722 | 1.00 | 0.00 |
| ATOM | 107 | C | VAL | 575 | 24.679 | 15.597 | 74.137 | 1.00 | 0.00 |
| ATOM | 108 | O | VAL | 575 | 25.403 | 15.925 | 75.107 | 1.00 | 0.00 |
| ATOM | 109 | CB | VAL | 575 | 24.568 | 16.781 | 71.924 | 1.00 | 0.00 |
| ATOM | 110 | CG1 | VAL | 575 | 24.768 | 18.084 | 72.645 | 1.00 | 0.00 |
| ATOM | 111 | CG2 | VAL | 575 | 25.179 | 16.813 | 70.517 | 1.00 | 0.00 |
| ATOM | 112 | N | LYS | 576 | 23.443 | 15.142 | 74.281 | 1.00 | 0.00 |
| ATOM | 113 | CA | LYS | 576 | 22.833 | 15.038 | 75.596 | 1.00 | 0.00 |
| ATOM | 114 | C | LYS | 576 | 23.602 | 14.088 | 76.541 | 1.00 | 0.00 |
| ATOM | 115 | O | LYS | 576 | 23.770 | 14.370 | 77.733 | 1.00 | 0.00 |

TABLE V-continued

GR Homology Model Coordinates (SEQ ID NO:1) discerned from
the disclosure in Kauppi et. al.

| ATOM | 116 | CB | LYS | 576 | 21.339 | 14.722 | 75.422 | 1.00 | 0.00 |
|------|-----|-----|-----|-----|--------|--------|--------|------|------|
| ATOM | 117 | CG | LYS | 576 | 20.637 | 13.971 | 76.547 | 1.00 | 0.00 |
| ATOM | 118 | CD | LYS | 576 | 20.466 | 14.768 | 77.796 | 1.00 | 0.00 |
| ATOM | 119 | CE | LYS | 576 | 19.157 | 14.388 | 78.557 | 1.00 | 0.00 |
| ATOM | 120 | NZ | LYS | 576 | 18.232 | 13.432 | 77.808 | 1.00 | 0.00 |
| ATOM | 121 | N | TRP | 577 | 24.091 | 12.987 | 76.012 | 1.00 | 0.00 |
| ATOM | 122 | CA | TRP | 577 | 24.939 | 12.051 | 76.760 | 1.00 | 0.00 |
| ATOM | 123 | C | TRP | 577 | 26.259 | 12.737 | 77.181 | 1.00 | 0.00 |
| ATOM | 124 | O | TRP | 577 | 26.604 | 12.777 | 78.340 | 1.00 | 0.00 |
| ATOM | 125 | CB | TRP | 577 | 25.224 | 10.833 | 75.872 | 1.00 | 0.00 |
| ATOM | 126 | CG | TRP | 577 | 26.324 | 9.975 | 76.319 | 1.00 | 0.00 |
| ATOM | 127 | CD1 | TRP | 577 | 26.276 | 9.030 | 77.295 | 1.00 | 0.00 |
| ATOM | 128 | CD2 | TRP | 577 | 27.639 | 9.915 | 75.762 | 1.00 | 0.00 |
| ATOM | 129 | NE1 | TRP | 577 | 27.494 | 8.424 | 77.423 | 1.00 | 0.00 |
| ATOM | 130 | CE2 | TRP | 577 | 28.351 | 8.943 | 76.481 | 1.00 | 0.00 |
| ATOM | 131 | CE3 | TRP | 577 | 28.297 | 10.604 | 74.730 | 1.00 | 0.00 |
| ATOM | 132 | CZ2 | TRP | 577 | 29.683 | 8.650 | 76.217 | 1.00 | 0.00 |
| ATOM | 133 | CZ3 | TRP | 577 | 29.600 | 10.333 | 74.488 | 1.00 | 0.00 |
| ATOM | 134 | CH2 | TRP | 577 | 30.285 | 9.354 | 75.207 | 1.00 | 0.00 |
| TER | 135 | | TRP | 577 | | | | | |
| ATOM | 136 | N | SER | 599 | 33.944 | 13.837 | 67.076 | 1.00 | 0.00 |
| ATOM | 137 | CA | SER | 599 | 33.791 | 12.478 | 67.530 | 1.00 | 0.00 |
| ATOM | 138 | C | SER | 599 | 32.416 | 11.902 | 67.351 | 1.00 | 0.00 |
| ATOM | 139 | O | SER | 599 | 32.274 | 10.694 | 67.529 | 1.00 | 0.00 |
| ATOM | 140 | CB | SER | 599 | 34.200 | 12.381 | 69.007 | 1.00 | 0.00 |
| ATOM | 141 | OG | SER | 599 | 33.158 | 12.943 | 69.797 | 1.00 | 0.00 |
| ATOM | 142 | N | TRP | 600 | 31.417 | 12.686 | 66.954 | 1.00 | 0.00 |
| ATOM | 143 | CA | TRP | 600 | 30.053 | 12.122 | 66.862 | 1.00 | 0.00 |
| ATOM | 144 | C | TRP | 600 | 29.906 | 10.885 | 65.951 | 1.00 | 0.00 |
| ATOM | 145 | O | TRP | 600 | 29.176 | 9.955 | 66.262 | 1.00 | 0.00 |
| ATOM | 146 | CB | TRP | 600 | 28.985 | 13.176 | 66.533 | 1.00 | 0.00 |
| ATOM | 147 | CG | TRP | 600 | 29.029 | 13.741 | 65.176 | 1.00 | 0.00 |
| ATOM | 148 | CD1 | TRP | 600 | 29.530 | 14.957 | 64.832 | 1.00 | 0.00 |
| ATOM | 149 | CD2 | TRP | 600 | 28.521 | 13.159 | 63.961 | 1.00 | 0.00 |
| ATOM | 150 | NE1 | TRP | 600 | 29.378 | 15.168 | 63.488 | 1.00 | 0.00 |
| ATOM | 151 | CE2 | TRP | 600 | 28.761 | 14.084 | 62.923 | 1.00 | 0.00 |
| ATOM | 152 | CE3 | TRP | 600 | 27.875 | 11.962 | 63.644 | 1.00 | 0.00 |
| ATOM | 153 | CZ2 | TRP | 600 | 28.389 | 13.842 | 61.584 | 1.00 | 0.00 |
| ATOM | 154 | CZ3 | TRP | 600 | 27.507 | 11.713 | 62.310 | 1.00 | 0.00 |
| ATOM | 155 | CH2 | TRP | 600 | 27.748 | 12.648 | 61.307 | 1.00 | 0.00 |
| ATOM | 156 | N | MET | 601 | 30.634 | 10.843 | 64.848 | 1.00 | 0.00 |
| ATOM | 157 | CA | MET | 601 | 30.494 | 9.691 | 63.964 | 1.00 | 0.00 |
| ATOM | 158 | C | MET | 601 | 31.122 | 8.461 | 64.655 | 1.00 | 0.00 |
| ATOM | 159 | O | MET | 601 | 30.582 | 7.387 | 64.607 | 1.00 | 0.00 |
| ATOM | 160 | CB | MET | 601 | 31.142 | 9.953 | 62.620 | 1.00 | 0.00 |
| ATOM | 161 | CG | MET | 601 | 31.047 | 8.813 | 61.588 | 1.00 | 0.00 |
| ATOM | 162 | SD | MET | 601 | 29.324 | 8.553 | 60.991 | 1.00 | 0.00 |
| ATOM | 163 | CE | MET | 601 | 29.347 | 9.653 | 59.543 | 1.00 | 0.00 |
| ATOM | 164 | N | SER | 602 | 32.284 | 8.637 | 65.271 | 1.00 | 0.00 |
| ATOM | 165 | CA | SER | 602 | 32.954 | 7.575 | 65.985 | 1.00 | 0.00 |
| ATOM | 166 | C | SER | 602 | 32.055 | 6.975 | 67.064 | 1.00 | 0.00 |
| ATOM | 167 | O | SER | 602 | 31.966 | 5.774 | 67.198 | 1.00 | 0.00 |
| ATOM | 168 | CB | SER | 602 | 34.224 | 8.119 | 66.622 | 1.00 | 0.00 |
| ATOM | 169 | OG | SER | 602 | 35.066 | 7.041 | 66.994 | 1.00 | 0.00 |
| ATOM | 170 | N | LEU | 603 | 31.383 | 7.822 | 67.825 | 1.00 | 0.00 |
| ATOM | 171 | CA | LEU | 603 | 30.530 | 7.383 | 68.933 | 1.00 | 0.00 |
| ATOM | 172 | C | LEU | 603 | 29.331 | 6.614 | 68.450 | 1.00 | 0.00 |
| ATOM | 173 | O | LEU | 603 | 28.976 | 5.602 | 69.021 | 1.00 | 0.00 |
| ATOM | 174 | CB | LEU | 603 | 30.008 | 8.560 | 69.746 | 1.00 | 0.00 |
| ATOM | 175 | CG | LEU | 603 | 31.053 | 9.411 | 70.448 | 1.00 | 0.00 |
| ATOM | 176 | CD1 | LEU | 603 | 30.409 | 10.692 | 70.907 | 1.00 | 0.00 |
| ATOM | 177 | CD2 | LEU | 603 | 31.573 | 8.704 | 71.615 | 1.00 | 0.00 |
| ATOM | 178 | N | MET | 604 | 28.716 | 7.098 | 67.385 | 1.00 | 0.00 |
| ATOM | 179 | CA | MET | 604 | 27.565 | 6.405 | 66.803 | 1.00 | 0.00 |
| ATOM | 180 | C | MET | 604 | 27.914 | 5.076 | 66.137 | 1.00 | 0.00 |
| ATOM | 181 | O | MET | 604 | 27.150 | 4.114 | 66.248 | 1.00 | 0.00 |
| ATOM | 182 | CB | MET | 604 | 26.834 | 7.333 | 65.826 | 1.00 | 0.00 |
| ATOM | 183 | CG | MET | 604 | 26.029 | 8.373 | 66.615 | 1.00 | 0.00 |
| ATOM | 184 | SD | MET | 604 | 25.459 | 9.825 | 65.626 | 1.00 | 0.00 |
| ATOM | 185 | CE | MET | 604 | 24.810 | 8.937 | 64.246 | 1.00 | 0.00 |
| ATOM | 186 | N | ALA | 605 | 29.062 | 5.018 | 65.465 | 1.00 | 0.00 |
| ATOM | 187 | CA | ALA | 605 | 29.507 | 3.760 | 64.823 | 1.00 | 0.00 |
| ATOM | 188 | C | ALA | 605 | 29.891 | 2.728 | 65.897 | 1.00 | 0.00 |
| ATOM | 189 | O | ALA | 605 | 29.656 | 1.535 | 65.720 | 1.00 | 0.00 |
| ATOM | 190 | CB | ALA | 605 | 30.712 | 4.035 | 63.882 | 1.00 | 0.00 |
| ATOM | 191 | N | PHE | 606 | 30.454 | 3.204 | 67.028 | 1.00 | 0.00 |

TABLE V-continued

GR Homology Model Coordinates (SEQ ID NO:1) discerned from the disclosure in Kauppi et. al.

| ATOM | 192 | CA | PHE | 606 | 30.868 | 2.345 | 68.135 | 1.00 | 0.00 |
|---|---|---|---|---|---|---|---|---|---|
| ATOM | 193 | C | PHE | 606 | 29.663 | 1.746 | 68.854 | 1.00 | 0.00 |
| ATOM | 194 | O | PHE | 606 | 29.642 | 0.569 | 69.130 | 1.00 | 0.00 |
| ATOM | 195 | CB | PHE | 606 | 31.741 | 3.102 | 69.128 | 1.00 | 0.00 |
| ATOM | 196 | CG | PHE | 606 | 32.577 | 2.209 | 69.997 | 1.00 | 0.00 |
| ATOM | 197 | CD1 | PHE | 606 | 33.528 | 1.379 | 69.442 | 1.00 | 0.00 |
| ATOM | 198 | CD2 | PHE | 606 | 32.423 | 2.207 | 71.378 | 1.00 | 0.00 |
| ATOM | 199 | CE1 | PHE | 606 | 34.303 | 0.556 | 70.248 | 1.00 | 0.00 |
| ATOM | 200 | CE2 | PHE | 606 | 33.195 | 1.399 | 72.194 | 1.00 | 0.00 |
| ATOM | 201 | CZ | PHE | 606 | 34.132 | 0.569 | 71.648 | 1.00 | 0.00 |
| ATOM | 202 | N | ALA | 607 | 28.655 | 2.552 | 69.116 | 1.00 | 0.00 |
| ATOM | 203 | CA | ALA | 607 | 27.432 | 2.068 | 69.751 | 1.00 | 0.00 |
| ATOM | 204 | C | ALA | 607 | 26.656 | 1.180 | 68.791 | 1.00 | 0.00 |
| ATOM | 205 | O | ALA | 607 | 26.075 | 0.162 | 69.213 | 1.00 | 0.00 |
| ATOM | 206 | CB | ALA | 607 | 26.606 | 3.233 | 70.199 | 1.00 | 0.00 |
| TER | 207 |  | ALA | 607 |  |  |  |  |  |
| ATOM | 208 | N | TRP | 610 | 28.346 | −2.104 | 69.065 | 1.00 | 0.00 |
| ATOM | 209 | CA | TRP | 610 | 27.953 | −2.735 | 70.319 | 1.00 | 0.00 |
| ATOM | 210 | C | TRP | 610 | 26.577 | −3.372 | 70.237 | 1.00 | 0.00 |
| ATOM | 211 | O | TRP | 610 | 26.421 | −4.534 | 70.610 | 1.00 | 0.00 |
| ATOM | 212 | CB | TRP | 610 | 28.040 | −1.731 | 71.469 | 1.00 | 0.00 |
| ATOM | 213 | CG | TRP | 610 | 27.584 | −2.314 | 72.758 | 1.00 | 0.00 |
| ATOM | 214 | CD1 | TRP | 610 | 26.347 | −2.161 | 73.356 | 1.00 | 0.00 |
| ATOM | 215 | CD2 | TRP | 610 | 28.334 | −3.183 | 73.609 | 1.00 | 0.00 |
| ATOM | 216 | NE1 | TRP | 610 | 26.310 | −2.864 | 74.532 | 1.00 | 0.00 |
| ATOM | 217 | CE2 | TRP | 610 | 27.507 | −3.517 | 74.704 | 1.00 | 0.00 |
| ATOM | 218 | CE3 | TRP | 610 | 29.630 | −3.712 | 73.564 | 1.00 | 0.00 |
| ATOM | 219 | CZ2 | TRP | 610 | 27.935 | −4.341 | 75.732 | 1.00 | 0.00 |
| ATOM | 220 | CZ3 | TRP | 610 | 30.040 | −4.541 | 74.584 | 1.00 | 0.00 |
| ATOM | 221 | CH2 | TRP | 610 | 29.202 | −4.842 | 75.652 | 1.00 | 0.00 |
| ATOM | 222 | N | ARG | 611 | 25.611 | −2.643 | 69.698 | 1.00 | 0.00 |
| ATOM | 223 | CA | ARG | 611 | 24.296 | −3.167 | 69.471 | 1.00 | 0.00 |
| ATOM | 224 | C | ARG | 611 | 24.337 | −4.398 | 68.582 | 1.00 | 0.00 |
| ATOM | 225 | O | ARG | 611 | 23.635 | −5.363 | 68.865 | 1.00 | 0.00 |
| ATOM | 226 | CB | ARG | 611 | 23.350 | −2.102 | 68.853 | 1.00 | 0.00 |
| ATOM | 227 | CG | ARG | 611 | 22.907 | −1.050 | 69.843 | 1.00 | 0.00 |
| ATOM | 228 | CD | ARG | 611 | 21.755 | −0.166 | 69.401 | 1.00 | 0.00 |
| ATOM | 229 | NE | ARG | 611 | 21.899 | 0.318 | 68.043 | 1.00 | 0.00 |
| ATOM | 230 | CZ | ARG | 611 | 22.496 | 1.444 | 67.662 | 1.00 | 0.00 |
| ATOM | 231 | NH1 | ARG | 611 | 23.083 | 2.262 | 68.503 | 1.00 | 0.00 |
| ATOM | 232 | NH2 | ARG | 611 | 22.551 | 1.737 | 66.376 | 1.00 | 0.00 |
| TER | 233 |  | ARG | 611 |  |  |  |  |  |
| ATOM | 234 | N | ARG | 614 | 25.776 | −7.384 | 70.378 | 1.00 | 0.00 |
| ATOM | 235 | CA | ARG | 614 | 24.958 | −7.840 | 71.479 | 1.00 | 0.00 |
| ATOM | 236 | C | ARG | 614 | 23.643 | −8.468 | 71.041 | 1.00 | 0.00 |
| ATOM | 237 | O | ARG | 614 | 23.239 | −9.504 | 71.557 | 1.00 | 0.00 |
| ATOM | 238 | CB | ARG | 614 | 24.681 | −6.657 | 72.407 | 1.00 | 0.00 |
| ATOM | 239 | CG | ARG | 614 | 24.963 | −6.918 | 73.839 | 1.00 | 0.00 |
| ATOM | 240 | CD | ARG | 614 | 26.436 | −7.104 | 74.156 | 1.00 | 0.00 |
| ATOM | 241 | NE | ARG | 614 | 26.731 | −8.517 | 74.370 | 1.00 | 0.00 |
| ATOM | 242 | CZ | ARG | 614 | 27.372 | −9.045 | 75.417 | 1.00 | 0.00 |
| ATOM | 243 | NH1 | ARG | 614 | 27.791 | −8.303 | 76.446 | 1.00 | 0.00 |
| ATOM | 244 | NH2 | ARG | 614 | 27.608 | −10.351 | 75.425 | 1.00 | 0.00 |
| ATOM | 245 | N | GLN | 615 | 22.973 | −7.828 | 70.100 | 1.00 | 0.00 |
| ATOM | 246 | CA | GLN | 615 | 21.685 | −8.299 | 69.591 | 1.00 | 0.00 |
| ATOM | 247 | C | GLN | 615 | 21.782 | −9.480 | 68.626 | 1.00 | 0.00 |
| ATOM | 248 | O | GLN | 615 | 20.869 | −10.301 | 68.601 | 1.00 | 0.00 |
| ATOM | 249 | CB | GLN | 615 | 20.942 | −7.142 | 68.923 | 1.00 | 0.00 |
| ATOM | 250 | CG | GLN | 615 | 20.559 | −6.039 | 69.902 | 1.00 | 0.00 |
| ATOM | 251 | CD | GLN | 615 | 19.647 | −6.546 | 70.990 | 1.00 | 0.00 |
| ATOM | 252 | OE1 | GLN | 615 | 18.595 | −7.114 | 70.687 | 1.00 | 0.00 |
| ATOM | 253 | NE2 | GLN | 615 | 20.066 | −6.416 | 72.251 | 1.00 | 0.00 |
| TER | 254 |  | GLN | 615 |  |  |  |  |  |
| ATOM | 255 | N | PRO | 625 | 16.074 | −1.390 | 66.522 | 1.00 | 0.00 |
| ATOM | 256 | CA | PRO | 625 | 15.326 | −2.645 | 66.670 | 1.00 | 0.00 |
| ATOM | 257 | C | PRO | 625 | 14.446 | −2.972 | 65.466 | 1.00 | 0.00 |
| ATOM | 258 | O | PRO | 625 | 14.219 | −4.123 | 65.155 | 1.00 | 0.00 |
| ATOM | 259 | CB | PRO | 625 | 14.451 | −2.387 | 67.917 | 1.00 | 0.00 |
| ATOM | 260 | CG | PRO | 625 | 15.230 | −1.373 | 68.700 | 1.00 | 0.00 |
| ATOM | 261 | CD | PRO | 625 | 15.816 | −0.460 | 67.630 | 1.00 | 0.00 |
| TER | 262 |  | PRO | 625 |  |  |  |  |  |
| ATOM | 263 | N | TYR | 663 | 33.300 | −1.331 | 77.384 | 1.00 | 0.00 |
| ATOM | 264 | CA | TYR | 663 | 32.605 | −0.587 | 76.345 | 1.00 | 0.00 |
| ATOM | 265 | C | TYR | 663 | 32.220 | 0.825 | 76.775 | 1.00 | 0.00 |
| ATOM | 266 | O | TYR | 663 | 32.422 | 1.772 | 76.039 | 1.00 | 0.00 |
| ATOM | 267 | CB | TYR | 663 | 31.366 | −1.372 | 75.911 | 1.00 | 0.00 |

TABLE V-continued

GR Homology Model Coordinates (SEQ ID NO:1) discerned from the disclosure in Kauppi et. al.

| | | | | | | | | | |
|---|---|---|---|---|---|---|---|---|---|
| ATOM | 268 | CG | TYR | 663 | 30.348 | −0.537 | 75.200 | 1.00 | 0.00 |
| ATOM | 269 | CD1 | TYR | 663 | 30.558 | −0.163 | 73.888 | 1.00 | 0.00 |
| ATOM | 270 | CD2 | TYR | 663 | 29.164 | −0.139 | 75.821 | 1.00 | 0.00 |
| ATOM | 271 | CE1 | TYR | 663 | 29.632 | 0.607 | 73.206 | 1.00 | 0.00 |
| ATOM | 272 | CE2 | TYR | 663 | 28.221 | 0.647 | 75.125 | 1.00 | 0.00 |
| ATOM | 273 | CZ | TYR | 663 | 28.493 | 1.012 | 73.822 | 1.00 | 0.00 |
| ATOM | 274 | OH | TYR | 663 | 27.616 | 1.758 | 73.058 | 1.00 | 0.00 |
| ATOM | 275 | N | LEU | 664 | 31.685 | 0.992 | 77.971 | 1.00 | 0.00 |
| ATOM | 276 | CA | LEU | 664 | 31.341 | 2.335 | 78.447 | 1.00 | 0.00 |
| ATOM | 277 | C | LEU | 664 | 32.559 | 3.273 | 78.520 | 1.00 | 0.00 |
| ATOM | 278 | O | LEU | 664 | 32.478 | 4.449 | 78.147 | 1.00 | 0.00 |
| ATOM | 279 | CB | LEU | 664 | 30.682 | 2.262 | 79.818 | 1.00 | 0.00 |
| ATOM | 280 | CG | LEU | 664 | 29.314 | 1.540 | 79.897 | 1.00 | 0.00 |
| ATOM | 281 | CD1 | LEU | 664 | 28.821 | 1.419 | 81.337 | 1.00 | 0.00 |
| ATOM | 282 | CD2 | LEU | 664 | 28.309 | 2.263 | 79.064 | 1.00 | 0.00 |
| TER | 283 | | LEU | 664 | | | | | |
| ATOM | 284 | N | LYS | 667 | 33.939 | 4.070 | 75.029 | 1.00 | 0.00 |
| ATOM | 285 | CA | LYS | 667 | 33.100 | 5.011 | 74.302 | 1.00 | 0.00 |
| ATOM | 286 | C | LYS | 667 | 33.330 | 6.463 | 74.740 | 1.00 | 0.00 |
| ATOM | 287 | O | LYS | 667 | 33.376 | 7.376 | 73.914 | 1.00 | 0.00 |
| ATOM | 288 | CB | LYS | 667 | 31.622 | 4.597 | 74.408 | 1.00 | 0.00 |
| ATOM | 289 | CG | LYS | 667 | 30.709 | 5.423 | 73.574 | 1.00 | 0.00 |
| ATOM | 290 | CD | LYS | 667 | 29.419 | 4.683 | 73.210 | 1.00 | 0.00 |
| ATOM | 291 | CE | LYS | 667 | 28.426 | 4.543 | 74.330 | 1.00 | 0.00 |
| ATOM | 292 | NZ | LYS | 667 | 28.369 | 5.641 | 75.303 | 1.00 | 0.00 |
| TER | 293 | | LYS | 667 | | | | | |

What is claimed is:

1. A method for evaluating the potential of a chemical entity to bind to a glucocorticoid receptor (GR) Site II comprising:
   (a) docking a chemical entity into the cavity circumscribed by said GR Site II, wherein said GR Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:1 according to Table I, Table IV or Table V;
   (b) analyzing structural and chemical feature complementarity between said chemical entity and said GR Site II; and
   (c) screening the chemical entity in an in vitro assay that characterizes binding to said GR Site II, thereby identifying the chemical entity that binds GR Site II.

2. A method of designing a ligand of a GR Site II comprising:
   (a) modeling the GR Site II, wherein said GR Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:1 according to Table I;
   (b) based on said modeling, designing a chemical entity that has structural and chemical feature complementarity with said GR Site II; and
   (c) screening the chemical entity in an in vitro assay that characterizes binding to said GR Site II, thereby identifying the chemical entity as a ligand of GR Site II.

3. A method for identifying a modulator of a GR comprising:
   (a) docking a test molecule into the cavity circumscribed by a GR Site II, wherein said GR Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:1 according to Table I;
   (b) analyzing structural and chemical feature complementarity between the test molecule and said GR Site II; and
   (c) screening the test molecule in an in vitro assay of modulation for the GR, thereby identifying the test molecule as a modulator of GR wherein said modulator of said GR induces transrepression.

4. The method of claim 3 further comprising one or more of the following:
   (d) screening the test molecule in an assay that characterizes binding to the GR Site II; and
   (e) screening the test molecule in an assay that characterizes binding to the GR Site I.

5. The method of claim 3, wherein the modulator of the GR is a dissociated non-covalent modulator.

6. The method of claim 3, wherein the modulator of the GR antagonizes a modulator that induces transactivation.

7. A method for identifying a ligand of a GR Site II comprising:
   (a) docking a test molecule into the cavity circumscribed by said GR Site II, wherein said GR Site II is a structure defined by structure coordinates that describe conserved residue backbone atoms having a root mean square deviation of not more than 2.0 Å from the conserved residue backbone atoms described by the structure coordinates of amino acids E537-V543, L566, G567, Q570-W577, S599-A607, W610, R611, R614, Q615, P625, Y663, L664 and K667 of SEQ ID NO:1 according to Table I;
   (b) analyzing structural and chemical feature complementarity between the test molecule and said Site II; and
   (c) screening the test molecule in an in vitro assay that characterizes binding to said GR Site II, thereby identifying t the test molecule as a ligand of Gr Site II.

* * * * *

UNITED STATES PATENT AND TRADEMARK OFFICE
CERTIFICATE OF CORRECTION

| | | |
|---|---|---|
| PATENT NO. | : 7,442,554 B2 | Page 1 of 1 |
| APPLICATION NO. | : 10/621807 | |
| DATED | : October 28, 2008 | |
| INVENTOR(S) | : Arthur M. P. Doweyko and Steven G. Nadler | |

It is certified that error appears in the above-identified patent and that said Letters Patent is hereby corrected as shown below:

Column 296, Claim 7(c), last line, the letter "t" after "identifying" should be deleted to read:

"..., thereby identifying the test molecule as a ligand of Gr Site II".

Signed and Sealed this

Twenty-fourth Day of February, 2009

JOHN DOLL
*Acting Director of the United States Patent and Trademark Office*

SEQUENCE LISTING

<160> NUMBER OF SEQ ID NOS: 21

<210> SEQ ID NO 1
<211> LENGTH: 255
<212> TYPE: PRT
<213> ORGANISM: Homo sapiens

<400> SEQUENCE: 1

```
Ala Thr Leu Pro Gln Leu Thr Pro Thr Leu Val Ser Leu Leu Glu Val
1               5                   10                  15

Ile Glu Pro Glu Val Leu Tyr Ala Gly Tyr Asp Ser Ser Val Pro Asp
            20                  25                  30

Ser Thr Trp Arg Ile Met Thr Thr Leu Asn Met Leu Gly Gly Arg Gln
        35                  40                  45

Val Ile Ala Ala Val Lys Trp Ala Lys Ala Ile Pro Gly Phe Arg Asn
    50                  55                  60

Leu His Leu Asp Asp Gln Met Thr Leu Leu Gln Tyr Ser Trp Met Phe
65                  70                  75                  80

Leu Met Ala Phe Ala Leu Gly Trp Arg Ser Tyr Arg Gln Ser Ser Ala
                85                  90                  95

Asn Leu Leu Cys Phe Ala Pro Asp Leu Ile Ile Asn Glu Gln Arg Met
            100                 105                 110

Thr Leu Pro Cys Met Tyr Asp Gln Cys Lys His Met Leu Tyr Val Ser
        115                 120                 125

Ser Glu Leu His Arg Leu Gln Val Ser Tyr Glu Glu Tyr Leu Cys Met
    130                 135                 140

Lys Thr Leu Leu Leu Leu Ser Ser Val Pro Lys Asp Gly Leu Lys Ser
145                 150                 155                 160

Gln Glu Leu Phe Asp Glu Ile Arg Met Thr Tyr Ile Lys Glu Leu Gly
                165                 170                 175
```

```
Lys Ala Ile Val Lys Arg Glu Gly Asn Ser Ser Gln Asn Trp Gln Arg
            180                 185                 190

Phe Tyr Gln Leu Thr Lys Leu Leu Asp Ser Met His Glu Val Val Glu
            195                 200                 205

Asn Leu Leu Asn Tyr Cys Phe Gln Thr Phe Leu Asp Lys Thr Met Ser
            210                 215                 220

Ile Glu Phe Pro Glu Met Leu Ala Glu Ile Ile Thr Asn Gln Ile Pro
225                 230                 235                 240

Lys Tyr Ser Asn Gly Asn Ile Lys Lys Leu Leu Phe His Gln Lys
            245                 250                 255

<210> SEQ ID NO 2
<211> LENGTH: 251
<212> TYPE: PRT
<213> ORGANISM: Homo sapiens

<400> SEQUENCE: 2

Gln Leu Ile Pro Pro Leu Ile Asn Leu Leu Met Ser Ile Glu Pro Asp
1               5                   10                  15

Val Ile Tyr Ala Gly His Asp Asn Thr Lys Pro Asp Thr Ser Ser Ser
            20                  25                  30

Leu Leu Thr Ser Leu Asn Gln Leu Gly Glu Arg Gln Leu Leu Ser Val
            35                  40                  45

Val Lys Trp Ser Lys Ser Leu Pro Gly Phe Arg Asn Leu His Ile Asp
        50                  55                  60

Asp Gln Ile Thr Leu Ile Gln Tyr Ser Trp Met Ser Leu Met Val Phe
65                  70                  75                  80

Gly Leu Gly Trp Arg Ser Tyr Lys His Val Ser Gly Gln Met Leu Tyr
                85                  90                  95

Phe Ala Pro Asp Leu Ile Leu Asn Glu Gln Arg Met Lys Glu Ser Ser
            100                 105                 110

Phe Tyr Ser Leu Cys Leu Thr Met Trp Gln Ile Pro Gln Glu Phe Val
            115                 120                 125

Lys Leu Gln Val Ser Gln Glu Glu Phe Leu Cys Met Lys Val Leu Leu
        130                 135                 140

Leu Leu Asn Thr Ile Pro Leu Glu Gly Leu Arg Ser Gln Thr Gln Phe
145                 150                 155                 160

Glu Glu Met Arg Ser Ser Tyr Ile Arg Glu Leu Ile Lys Ala Ile Gly
                165                 170                 175

Leu Arg Gln Lys Gly Val Val Ser Ser Ser Gln Arg Phe Tyr Gln Leu
            180                 185                 190

Thr Lys Leu Leu Asp Asn Leu His Asp Leu Val Lys Gln Leu His Leu
            195                 200                 205

Tyr Cys Leu Asn Thr Phe Ile Gln Ser Arg Ala Leu Ser Val Glu Phe
            210                 215                 220

Pro Glu Met Met Ser Glu Val Ile Ala Ala Gln Leu Pro Lys Ile Leu
225                 230                 235                 240

Ala Gly Met Val Lys Pro Leu Leu Phe His Lys
                245                 250

<210> SEQ ID NO 3
<211> LENGTH: 238
<212> TYPE: PRT
<213> ORGANISM: Homo sapiens

<400> SEQUENCE: 3
```

Ser Ala Asn Glu Asp Met Pro Val Glu Arg Ile Leu Glu Ala Glu Leu
1               5                   10                  15

Ala Val Glu Pro Lys Thr Glu Thr Tyr Val Glu Ala Asn Met Gly Leu
            20                  25                  30

Asn Pro Ser Ser Pro Asn Asp Pro Val Thr Asn Ile Cys Gln Ala Ala
        35                  40                  45

Asp Lys Gln Leu Phe Thr Leu Val Glu Trp Ala Lys Arg Ile Pro His
    50                  55                  60

Phe Ser Glu Leu Pro Leu Asp Asp Gln Val Ile Leu Leu Arg Ala Gly
65                  70                  75                  80

Trp Asn Glu Leu Leu Ile Ala Ser Phe Ser His Arg Ser Ile Ala Val
                85                  90                  95

Lys Asp Gly Ile Leu Leu Ala Thr Gly Leu His Val His Arg Asn Ser
            100                 105                 110

Ala His Ser Ala Gly Val Gly Ala Ile Phe Asp Arg Val Leu Thr Glu
        115                 120                 125

Leu Val Ser Lys Met Arg Asp Met Gln Met Asp Lys Thr Glu Leu Gly
    130                 135                 140

Cys Leu Arg Ala Ile Val Leu Phe Asn Pro Asp Ser Lys Gly Leu Ser
145                 150                 155                 160

Asn Pro Ala Glu Val Glu Ala Leu Arg Glu Lys Val Tyr Ala Ser Leu
                165                 170                 175

Glu Ala Tyr Cys Lys His Lys Tyr Pro Glu Gln Pro Gly Arg Phe Ala
            180                 185                 190

Lys Leu Leu Leu Arg Leu Pro Ala Leu Arg Ser Ile Gly Leu Lys Cys
    195                 200                 205

Leu Glu His Leu Phe Phe Phe Lys Leu Ile Gly Asp Thr Pro Ile Asp
        210                 215                 220

Thr Phe Leu Met Glu Met Leu Glu Ala Pro His Gln Met Thr
225                 230                 235

<210> SEQ ID NO 4
<211> LENGTH: 238
<212> TYPE: PRT
<213> ORGANISM: Homo sapiens

<400> SEQUENCE: 4

Leu Ser Pro Gln Leu Glu Glu Leu Ile Thr Lys Val Ser Lys Ala His
1               5                   10                  15

Gln Glu Thr Phe Pro Ser Leu Cys Gln Leu Gly Lys Tyr Thr Thr Asn
            20                  25                  30

Ser Ser Ala Asp His Arg Val Gln Leu Asp Leu Gly Leu Trp Asp Lys
        35                  40                  45

Phe Ser Glu Leu Ala Thr Lys Cys Ile Ile Lys Ile Val Glu Phe Ala
    50                  55                  60

Lys Arg Leu Pro Gly Phe Thr Gly Leu Ser Ile Ala Asp Gln Ile Thr
65                  70                  75                  80

Leu Leu Lys Ala Ala Cys Leu Asp Ile Leu Met Leu Arg Ile Cys Thr
                85                  90                  95

Arg Tyr Thr Pro Glu Gln Asp Thr Met Thr Phe Ser Asp Gly Leu Thr
            100                 105                 110

Leu Asn Arg Thr Gln Met His Asn Ala Gly Phe Gly Pro Leu Thr Asp
        115                 120                 125

Leu Val Phe Ala Phe Ala Gly Gln Leu Leu Pro Leu Glu Met Asp Asp

-continued

```
              130                 135                 140
Thr Glu Thr Gly Leu Leu Ser Ala Ile Cys Leu Ile Cys Gly Asp Arg
145                 150                 155                 160

Met Asp Leu Glu Glu Pro Glu Lys Val Asp Lys Leu Gln Glu Pro Leu
                165                 170                 175

Leu Glu Ala Leu Arg Leu Tyr Ala Arg Arg Arg Pro Ser Gln Pro
                180                 185                 190

Tyr Met Phe Pro Arg Met Leu Met Lys Ile Thr Asp Leu Arg Gly Ile
                195                 200                 205

Ser Thr Lys Gly Ala Glu Arg Ala Ile Thr Leu Lys Met Glu Ile Pro
                210                 215                 220

Gly Pro Met Pro Pro Leu Ile Arg Glu Met Leu Glu Asn Pro
225                 230                 235

<210> SEQ ID NO 5
<211> LENGTH: 251
<212> TYPE: PRT
<213> ORGANISM: Homo sapiens

<400> SEQUENCE: 5

Gln Leu Ile Pro Pro Leu Ile Asn Leu Leu Met Ser Ile Glu Pro Asp
1               5                   10                  15

Val Ile Tyr Ala Gly His Asp Asn Thr Lys Pro Asp Thr Ser Ser Ser
                20                  25                  30

Leu Leu Thr Ser Leu Asn Gln Leu Gly Glu Arg Gln Leu Leu Ser Val
                35                  40                  45

Val Lys Trp Ser Lys Ser Leu Pro Gly Phe Arg Asn Leu His Ile Asp
                50                  55                  60

Asp Gln Ile Thr Leu Ile Gln Tyr Ser Trp Met Ser Leu Met Val Phe
65                  70                  75                  80

Gly Leu Gly Trp Arg Ser Tyr Lys His Val Ser Gly Gln Met Leu Tyr
                85                  90                  95

Phe Ala Pro Asp Leu Ile Leu Asn Glu Gln Arg Met Lys Glu Ser Ser
                100                 105                 110

Phe Tyr Ser Leu Cys Leu Thr Met Trp Gln Ile Pro Gln Glu Phe Val
                115                 120                 125

Lys Leu Gln Val Ser Gln Glu Glu Phe Leu Cys Met Lys Val Leu Leu
                130                 135                 140

Leu Leu Asn Thr Ile Pro Leu Glu Gly Leu Arg Ser Gln Thr Gln Phe
145                 150                 155                 160

Glu Glu Met Arg Ser Ser Tyr Ile Arg Glu Leu Ile Lys Ala Ile Gly
                165                 170                 175

Leu Arg Gln Lys Gly Val Val Ser Ser Ser Gln Arg Phe Tyr Gln Leu
                180                 185                 190

Thr Lys Leu Leu Asp Asn Leu His Asp Leu Val Lys Gln Leu His Leu
                195                 200                 205

Tyr Cys Leu Asn Thr Phe Ile Gln Ser Arg Ala Leu Ser Val Glu Phe
                210                 215                 220

Pro Glu Met Met Ser Glu Val Ile Ala Ala Gln Leu Pro Lys Ile Leu
225                 230                 235                 240

Ala Gly Met Val Lys Pro Leu Leu Phe His Lys
                245                 250

<210> SEQ ID NO 6
<211> LENGTH: 250
```

```
<212> TYPE: PRT
<213> ORGANISM: Homo sapiens

<400> SEQUENCE: 6

Cys Gln Pro Ile Phe Leu Asn Val Leu Glu Ala Ile Glu Pro Gly Val
1               5                   10                  15

Val Cys Ala Gly His Asp Asn Asn Gln Pro Asp Ser Phe Ala Ala Leu
            20                  25                  30

Leu Ser Ser Leu Asn Glu Leu Gly Glu Arg Gln Leu His Val Val
        35                  40                  45

Lys Trp Ala Lys Ala Leu Pro Gly Phe Arg Asn Leu His Val Asp Asp
    50                  55                  60

Gln Met Ala Val Ile Gln Tyr Ser Trp Met Gly Leu Met Val Phe Ala
65                  70                  75                  80

Met Gly Trp Arg Ser Phe Thr Asn Val Asn Ser Arg Met Leu Tyr Phe
                85                  90                  95

Ala Pro Asp Leu Val Phe Asn Glu Tyr Arg Met His Lys Ser Arg Met
            100                 105                 110

Tyr Ser Gln Cys Val Arg Met Arg His Leu Ser Gln Glu Phe Gly Trp
        115                 120                 125

Leu Gln Ile Thr Pro Gln Glu Phe Leu Cys Met Lys Ala Leu Leu Leu
130                 135                 140

Phe Ser Ile Ile Pro Val Asp Gly Leu Lys Asn Gln Lys Phe Phe Asp
145                 150                 155                 160

Glu Leu Arg Met Asn Tyr Ile Lys Glu Leu Asp Arg Ile Ile Ala Cys
                165                 170                 175

Lys Arg Lys Asn Pro Thr Ser Cys Ser Arg Arg Phe Tyr Gln Leu Thr
            180                 185                 190

Lys Leu Leu Asp Ser Val Gln Pro Ile Ala Arg Glu Leu His Gln Phe
        195                 200                 205

Thr Phe Asp Leu Leu Ile Lys Ser His Met Val Ser Val Asp Phe Pro
210                 215                 220

Glu Met Met Ala Glu Ile Ile Ser Val Gln Val Pro Lys Ile Leu Ser
225                 230                 235                 240

Gly Lys Val Lys Pro Ile Tyr Phe His Thr
                245                 250

<210> SEQ ID NO 7
<211> LENGTH: 240
<212> TYPE: PRT
<213> ORGANISM: Homo sapiens

<400> SEQUENCE: 7

Ser Leu Ala Leu Ser Leu Thr Ala Asp Gln Met Val Ser Ala Leu Leu
1               5                   10                  15

Asp Ala Glu Pro Pro Ile Leu Tyr Ser Glu Tyr Asp Pro Thr Arg Pro
            20                  25                  30

Phe Ser Glu Ala Ser Met Met Gly Leu Leu Thr Asn Leu Ala Asp Arg
        35                  40                  45

Glu Leu Val His Met Ile Asn Trp Ala Lys Arg Val Pro Gly Phe Val
    50                  55                  60

Asp Leu Thr Leu His Asp Gln Val His Leu Leu Glu Cys Ala Trp Leu
65                  70                  75                  80

Glu Ile Leu Met Ile Gly Leu Val Trp Arg Ser Met Glu His Pro Gly
                85                  90                  95
```

```
Lys Leu Leu Phe Ala Pro Asn Leu Leu Leu Asp Arg Asn Gln Gly Lys
            100                 105                 110

Cys Val Glu Gly Met Val Glu Ile Phe Asp Met Leu Leu Ala Thr Ser
            115                 120                 125

Ser Arg Phe Arg Met Met Asn Leu Gln Gly Glu Glu Phe Val Cys Leu
        130                 135                 140

Lys Ser Ile Ile Leu Leu Asn Ser Gly Val Tyr Thr Phe Leu Ser Ser
145                 150                 155                 160

Thr Leu Lys Ser Leu Glu Glu Lys Asp His Ile His Arg Val Leu Asp
                165                 170                 175

Lys Ile Thr Asp Thr Leu Ile His Leu Met Ala Lys Ala Gly Leu Thr
            180                 185                 190

Leu Gln Gln Gln His Glu Arg Leu Ala Gln Leu Leu Leu Ile Leu Ser
            195                 200                 205

His Ile Arg His Met Ser Asn Lys Gly Met Glu His Leu Tyr Ser Met
        210                 215                 220

Lys Cys Lys Asn Val Val Pro Leu Tyr Asp Leu Leu Leu Glu Met Leu
225                 230                 235                 240

<210> SEQ ID NO 8
<211> LENGTH: 232
<212> TYPE: PRT
<213> ORGANISM: Homo sapiens

<400> SEQUENCE: 8

Asp Ala Leu Ser Pro Glu Gln Leu Val Leu Thr Leu Leu Glu Ala Glu
1               5                   10                  15

Pro Pro His Val Leu Ile Ser Arg Thr Glu Ala Ser Met Met Met Ser
            20                  25                  30

Leu Thr Lys Leu Ala Asp Lys Glu Leu Val His Met Ile Ser Trp Ala
        35                  40                  45

Lys Lys Ile Pro Gly Phe Val Glu Leu Ser Leu Phe Asp Gln Val Arg
    50                  55                  60

Leu Leu Glu Ser Cys Trp Met Glu Val Leu Met Met Gly Leu Met Trp
65                  70                  75                  80

Arg Ser Ile Asp His Pro Gly Lys Leu Ile Phe Ala Pro Asp Leu Val
                85                  90                  95

Leu Asp Arg Asp Glu Gly Lys Cys Val Glu Gly Ile Leu Glu Ile Phe
            100                 105                 110

Asp Met Leu Leu Ala Thr Thr Ser Arg Phe Arg Glu Leu Lys Leu Gln
            115                 120                 125

His Lys Glu Tyr Leu Cys Val Lys Ala Met Ile Leu Leu Asn Ser Leu
        130                 135                 140

Val Thr Ala Thr Gln Asp Ala Asp Ser Ser Arg Lys Leu Ala His Leu
145                 150                 155                 160

Leu Asn Ala Val Thr Asp Ala Leu Val Trp Val Ile Ala Lys Ser Gly
                165                 170                 175

Ile Ser Ser Gln Gln Gln Ser Met Arg Leu Ala Asn Leu Leu Met Leu
            180                 185                 190

Leu Ser His Val Arg His Ala Ser Asn Lys Gly Met Glu His Leu Leu
            195                 200                 205

Asn Met Lys Cys Lys Asn Val Val Pro Val Tyr Asp Leu Leu Leu Glu
        210                 215                 220

Met Leu Asn Ala His Val Leu Arg
225                 230
```

<210> SEQ ID NO 9
<211> LENGTH: 250
<212> TYPE: PRT
<213> ORGANISM: Homo sapiens

<400> SEQUENCE: 9

Leu Arg Pro Lys Leu Ser Glu Glu Gln Arg Ile Ile Ala Ile Leu
1               5                   10                  15

Leu Asp Ala His His Lys Thr Tyr Asp Pro Thr Tyr Ser Asp Phe Cys
            20                  25                  30

Gln Phe Arg Pro Pro Val Arg Val Asn Asp Gly Gly Ser Val Thr
            35                  40                  45

Leu Glu Leu Ser Gln Leu Ser Met Leu Pro His Leu Ala Asp Leu Val
    50                  55                  60

Ser Tyr Ser Ile Gln Lys Val Ile Gly Phe Ala Lys Met Ile Pro Gly
65                  70                  75                  80

Phe Arg Asp Leu Thr Ser Glu Asp Gln Ile Val Leu Leu Lys Ser Ser
                85                  90                  95

Ala Ile Glu Val Ile Met Leu Arg Ser Asn Glu Ser Phe Thr Met Asp
            100                 105                 110

Asp Met Ser Trp Thr Cys Gly Asn Gln Asp Tyr Lys Tyr Arg Val Ser
        115                 120                 125

Asp Val Thr Lys Ala Gly His Ser Leu Glu Leu Ile Glu Pro Leu Ile
    130                 135                 140

Lys Phe Gln Val Gly Leu Lys Lys Leu Asn Leu His Glu Glu Glu His
145                 150                 155                 160

Val Leu Leu Met Ala Ile Cys Ile Val Ser Pro Asp Arg Pro Gly Val
                165                 170                 175

Gln Asp Ala Ala Leu Ile Glu Ala Ile Gln Asp Arg Leu Ser Asn Thr
            180                 185                 190

Leu Gln Thr Tyr Ile Arg Cys Arg His Pro Pro Leu Leu Tyr Ala
        195                 200                 205

Lys Met Ile Gln Lys Leu Ala Asp Leu Arg Ser Leu Asn Glu Glu His
    210                 215                 220

Ser Lys Gln Tyr Arg Cys Leu Ser Phe Gln Pro Glu Cys Ser Met Lys
225                 230                 235                 240

Leu Thr Pro Leu Val Leu Glu Val Phe Gly
                245                 250

<210> SEQ ID NO 10
<211> LENGTH: 271
<212> TYPE: PRT
<213> ORGANISM: Homo sapiens

<400> SEQUENCE: 10

Glu Ser Ala Asp Leu Arg Ala Leu Ala Lys His Leu Tyr Asp Ser Tyr
1               5                   10                  15

Ile Lys Ser Phe Pro Leu Thr Lys Ala Lys Ala Arg Ala Ile Leu Thr
            20                  25                  30

Gly Lys Thr Thr Asp Lys Ser Pro Phe Val Ile Tyr Asp Met Asn Ser
        35                  40                  45

Leu Met Met Gly Glu Asp Lys Ile Lys Phe Lys His Ile Thr Pro Leu
    50                  55                  60

Gln Glu Gln Ser Lys Glu Val Ala Ile Arg Ile Phe Gln Gly Cys Gln
65                  70                  75                  80

```
Phe Arg Ser Val Glu Ala Val Gln Glu Ile Thr Glu Tyr Ala Lys Ser
                85                  90                  95

Ile Pro Gly Phe Val Asn Leu Asp Leu Asn Asp Gln Val Thr Leu Leu
           100                 105                 110

Lys Tyr Gly Val His Glu Ile Ile Tyr Thr Met Leu Ala Ser Leu Met
       115                 120                 125

Asn Lys Asp Gly Val Leu Ile Ser Glu Gly Gln Gly Phe Met Thr Arg
   130                 135                 140

Glu Phe Leu Lys Ser Leu Arg Lys Pro Phe Gly Asp Phe Met Glu Pro
145                 150                 155                 160

Lys Phe Glu Phe Ala Val Lys Phe Asn Ala Leu Glu Leu Asp Asp Ser
               165                 170                 175

Asp Leu Ala Ile Phe Ile Ala Val Ile Ile Leu Ser Gly Asp Arg Pro
           180                 185                 190

Gly Leu Leu Asn Val Lys Pro Ile Glu Asp Ile Gln Asp Asn Leu Leu
       195                 200                 205

Gln Ala Leu Glu Leu Gln Leu Lys Leu Asn His Pro Glu Ser Ser Gln
   210                 215                 220

Leu Phe Ala Lys Leu Leu Gln Lys Met Thr Asp Leu Arg Gln Ile Val
225                 230                 235                 240

Thr Glu His Val Gln Leu Leu Gln Val Ile Lys Lys Thr Glu Thr Asp
               245                 250                 255

Met Ser Leu His Pro Leu Leu Gln Glu Ile Tyr Lys Asp Leu Tyr
           260                 265                 270

<210> SEQ ID NO 11
<211> LENGTH: 254
<212> TYPE: PRT
<213> ORGANISM: Homo sapiens

<400> SEQUENCE: 11

Ser Arg Ala Leu Thr Pro Ser Pro Val Met Val Leu Glu Asn Ile Glu
1               5                   10                  15

Pro Glu Ile Val Tyr Ala Gly Tyr Asp Ser Ser Lys Pro Asp Thr Ala
               20                  25                  30

Glu Asn Leu Leu Ser Thr Leu Asn Arg Leu Ala Gly Lys Gln Met Ile
           35                  40                  45

Gln Val Val Lys Trp Ala Lys Val Leu Pro Gly Phe Lys Asn Leu Pro
       50                  55                  60

Leu Glu Asp Gln Ile Thr Leu Ile Gln Tyr Ser Trp Met Cys Leu Ser
65                  70                  75                  80

Ser Phe Ala Leu Ser Trp Arg Ser Tyr Lys His Thr Asn Ser Gln Phe
               85                  90                  95

Leu Tyr Phe Ala Pro Asp Leu Val Phe Asn Glu Glu Lys Met His Gln
           100                 105                 110

Ser Ala Met Tyr Glu Leu Cys Gln Gly Met His Gln Ile Ser Leu Gln
       115                 120                 125

Phe Val Arg Leu Gln Leu Thr Phe Glu Glu Tyr Thr Ile Met Lys Val
   130                 135                 140

Leu Leu Leu Leu Ser Thr Ile Pro Lys Asp Gly Leu Lys Ser Gln Ala
145                 150                 155                 160

Ala Phe Glu Glu Met Arg Thr Asn Tyr Ile Lys Glu Leu Arg Lys Met
               165                 170                 175

Val Thr Lys Cys Pro Asn Asn Ser Gly Gln Ser Trp Gln Arg Phe Tyr
```

-continued

```
                        180                 185                 190
Gln Leu Thr Lys Leu Leu Asp Ser Met His Asp Leu Val Ser Asp Leu
                195                 200                 205

Leu Glu Phe Cys Phe Tyr Thr Phe Arg Glu Ser His Ala Leu Lys Val
210                 215                 220

Glu Phe Pro Ala Met Leu Val Glu Ile Ile Ser Asp Gln Leu Pro Lys
225                 230                 235                 240

Val Glu Ser Gly Asn Ala Lys Pro Leu Tyr Phe His Arg Lys
                245                 250

<210> SEQ ID NO 12
<211> LENGTH: 242
<212> TYPE: PRT
<213> ORGANISM: Homo sapiens

<400> SEQUENCE: 12

Lys Pro Glu Pro Thr Asp Glu Glu Trp Glu Leu Ile Lys Thr Val Thr
1               5                   10                  15

Glu Ala His Val Ala Thr Asn Ala Gln Gly Ser His Trp Lys Gln Lys
                20                  25                  30

Arg Lys Phe Leu Pro Glu Asp Ile Gly Gln Ala Pro Lys Val Asp Leu
            35                  40                  45

Glu Ala Phe Ser His Phe Thr Lys Ile Ile Thr Pro Ala Ile Thr Arg
        50                  55                  60

Val Val Asp Phe Ala Lys Lys Leu Pro Met Phe Cys Glu Leu Pro Cys
65                  70                  75                  80

Glu Asp Gln Ile Ile Leu Leu Lys Gly Cys Cys Met Glu Ile Met Ser
                85                  90                  95

Leu Arg Ala Ala Val Arg Tyr Asp Pro Glu Ser Glu Thr Leu Thr Leu
            100                 105                 110

Asn Gly Glu Met Ala Val Thr Arg Gly Gln Leu Lys Asn Gly Gly Leu
        115                 120                 125

Gly Val Val Ser Asp Ala Ile Phe Asp Leu Gly Met Ser Leu Ser Ser
    130                 135                 140

Phe Asn Leu Asp Asp Thr Glu Val Ala Leu Leu Gln Ala Val Leu Leu
145                 150                 155                 160

Met Ser Ser Asp Arg Pro Gly Leu Ala Cys Val Glu Arg Ile Glu Lys
                165                 170                 175

Tyr Gln Asp Ser Phe Leu Leu Ala Phe Glu His Tyr Ile Asn Tyr Arg
            180                 185                 190

Lys His His Val Thr His Phe Trp Pro Lys Leu Leu Met Lys Val Thr
        195                 200                 205

Asp Leu Arg Met Ile Gly Ala Cys His Ala Ser Arg Phe Leu His Met
    210                 215                 220

Lys Val Glu Cys Pro Thr Glu Leu Phe Pro Pro Leu Phe Leu Glu Val
225                 230                 235                 240

Phe Glu

<210> SEQ ID NO 13
<211> LENGTH: 255
<212> TYPE: PRT
<213> ORGANISM: Homo sapiens

<400> SEQUENCE: 13

Ala Thr Leu Pro Gln Leu Thr Pro Thr Leu Val Ser Leu Leu Glu Val
1               5                   10                  15
```

```
Ile Glu Pro Glu Val Leu Tyr Ala Gly Tyr Asp Ser Ser Val Pro Asp
             20                  25                  30

Ser Thr Trp Arg Ile Met Thr Thr Leu Asn Met Leu Gly Gly Arg Gln
         35                  40                  45

Val Ile Ala Ala Val Lys Trp Ala Lys Ala Ile Pro Gly Phe Arg Asn
     50                  55                  60

Leu His Leu Asp Asp Gln Met Thr Leu Leu Gln Tyr Ser Trp Met Phe
 65                  70                  75                  80

Leu Met Ala Phe Ala Leu Gly Trp Arg Ser Tyr Arg Gln Ser Ser Ala
                 85                  90                  95

Asn Leu Leu Cys Phe Ala Pro Asp Leu Ile Ile Asn Glu Gln Arg Met
            100                 105                 110

Thr Leu Pro Cys Met Tyr Asp Gln Cys Lys His Met Leu Tyr Val Ser
        115                 120                 125

Ser Glu Leu His Arg Leu Gln Val Ser Tyr Glu Glu Tyr Leu Cys Met
    130                 135                 140

Lys Thr Leu Leu Leu Leu Ser Ser Val Pro Lys Asp Gly Leu Lys Ser
145                 150                 155                 160

Gln Glu Leu Phe Asp Glu Ile Arg Met Thr Tyr Ile Lys Glu Leu Gly
                165                 170                 175

Lys Ala Ile Val Lys Arg Glu Gly Asn Ser Ser Gln Asn Trp Gln Arg
            180                 185                 190

Phe Tyr Gln Leu Thr Lys Leu Leu Asp Ser Met His Glu Val Val Glu
        195                 200                 205

Asn Leu Leu Asn Tyr Cys Phe Gln Thr Phe Leu Asp Lys Thr Met Ser
    210                 215                 220

Ile Glu Phe Pro Glu Met Leu Ala Glu Ile Ile Thr Asn Gln Ile Pro
225                 230                 235                 240

Lys Tyr Ser Asn Gly Asn Ile Lys Lys Leu Leu Phe His Gln Lys
                245                 250                 255

<210> SEQ ID NO 14
<211> LENGTH: 777
<212> TYPE: PRT
<213> ORGANISM: Saimiri boliviensis

<400> SEQUENCE: 14

Met Asp Ser Lys Glu Ser Leu Thr Pro Gly Lys Glu Glu Asn Pro Ser
  1               5                  10                  15

Ser Val Leu Thr Gln Glu Arg Gly Asn Val Met Asp Phe Cys Lys Ile
             20                  25                  30

Leu Arg Gly Gly Ala Thr Leu Lys Val Ser Val Ser Ser Thr Ser Leu
         35                  40                  45

Ala Ala Ala Ser Gln Ser Asp Ser Lys Gln Gln Arg Leu Leu Val Asp
     50                  55                  60

Phe Pro Lys Gly Ser Val Ser Asn Ala Gln Gln Pro Asp Leu Ser Lys
 65                  70                  75                  80

Ala Val Ser Leu Ser Met Gly Leu Tyr Met Gly Glu Thr Glu Thr Lys
                 85                  90                  95

Val Met Gly Asn Asp Leu Gly Phe Pro Gln Gln Gly Gln Ile Ser Leu
            100                 105                 110

Ser Ser Gly Glu Thr Asp Leu Gln Leu Leu Glu Glu Ser Ile Ala Asn
        115                 120                 125

Leu Asn Arg Ser Thr Ser Val Pro Glu Asn Pro Lys Ser Ser Ala Ser
```

```
                130                 135                 140
Ser Ser Val Ser Ala Ala Pro Lys Glu Lys Glu Phe Pro Lys Thr His
145                 150                 155                 160

Ser Asp Val Ser Ser Glu Gln Gln Asn Leu Lys Gly Gln Thr Gly Ser
                165                 170                 175

Asn Gly Gly Asn Val Lys Leu Tyr Thr Ala Asp Gln Ser Thr Phe Asp
                180                 185                 190

Ile Leu Gln Asp Leu Glu Phe Ser Ser Gly Ser Pro Gly Lys Glu Thr
                195                 200                 205

Asn Gln Ser Pro Trp Lys Ser Asp Leu Leu Ile Asp Glu Asn Cys Leu
210                 215                 220

Leu Ser Pro Leu Ala Gly Glu Glu Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Ser Asn Val Thr
                260                 265                 270

Leu Pro Gln Val Lys Thr Glu Lys Glu Asp Phe Ile Glu Leu Cys Thr
                275                 280                 285

Pro Gly Val Ile Lys Gln Glu Lys Leu Ser Thr Val Tyr Cys Gln Ala
                290                 295                 300

Ser Phe Pro Gly Ala Asn Ile Ile Gly Asn Lys Met Ser Ala Ile Ser
305                 310                 315                 320

Ile His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
                340                 345                 350

Val Ile Pro Pro Ile Pro Val Gly Ser Glu Asn Trp Asn Arg Cys Gln
                355                 360                 365

Gly Ser Gly Asp Asp Asn Leu Thr Ser Leu Gly Thr Leu Asn Phe Pro
                370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Thr Gly Pro
                405                 410                 415

Pro Pro Lys Leu Cys Leu Val Cys Ser Asp Glu Ala Ser Gly Cys His
                420                 425                 430

Tyr Gly Val Leu Thr Cys Gly Ser Cys Lys Val Phe Phe Lys Arg Ala
                435                 440                 445

Val Glu Gly Gln His Asn Tyr Leu Cys Ala Gly Arg Asn Asp Cys Ile
450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
                500                 505                 510

Glu Asn Pro Ala Asn Lys Thr Ile Val Pro Ala Thr Leu Pro Gln Leu
                515                 520                 525

Thr Pro Thr Leu Val Ser Leu Leu Glu Val Ile Glu Pro Glu Val Leu
                530                 535                 540

Tyr Ala Gly Tyr Asp Ser Thr Val Pro Asp Ser Thr Trp Arg Ile Met
545                 550                 555                 560
```

```
Thr Thr Leu Asn Met Leu Gly Gly Arg Gln Val Ile Ala Ala Val Lys
                565                 570                 575
Trp Ala Lys Ala Ile Pro Gly Phe Arg Asn Leu His Leu Asp Asp Gln
            580                 585                 590
Met Thr Leu Leu Gln Tyr Ser Trp Met Phe Leu Met Ala Phe Ala Leu
        595                 600                 605
Gly Trp Arg Ser Tyr Arg Gln Ala Ser Ser Asn Leu Leu Cys Phe Ala
    610                 615                 620
Pro Asp Leu Ile Ile Asn Glu Gln Arg Met Thr Leu Pro Cys Met Tyr
625                 630                 635                 640
Asp Gln Cys Lys His Met Leu Tyr Val Ser Ser Glu Leu His Arg Leu
                645                 650                 655
Gln Val Ser Tyr Glu Glu Tyr Leu Cys Met Lys Thr Leu Leu Leu Leu
            660                 665                 670
Ser Ser Val Pro Lys Asp Gly Leu Lys Ser Gln Glu Leu Phe Asp Glu
        675                 680                 685
Ile Arg Met Thr Tyr Ile Lys Glu Leu Gly Lys Ala Ile Val Lys Arg
    690                 695                 700
Glu Gly Asn Ser Ser Gln Asn Trp Gln Arg Phe Tyr Gln Leu Thr Lys
705                 710                 715                 720
Leu Leu Asp Ser Met His Glu Val Val Glu Asn Leu Leu Asn Tyr Cys
                725                 730                 735
Phe Gln Thr Phe Leu Asp Lys Thr Met Ser Ile Glu Phe Pro Glu Met
            740                 745                 750
Leu Ala Glu Ile Ile Thr Asn Gln Leu Pro Lys Tyr Ser Asn Gly Asn
        755                 760                 765
Ile Lys Lys Leu Leu Phe His Gln Lys
    770                 775

<210> SEQ ID NO 15
<211> LENGTH: 703
<212> TYPE: PRT
<213> ORGANISM: Sus scrofa

<400> SEQUENCE: 15

Val Ser Ala Ser Ser Pro Ser Leu Ala Ala Val Ser Gln Pro Asp Ser
1               5                   10                  15
Lys Gln Gln Arg Leu Ala Val Asp Phe Pro Lys Gly Ser Gly Ser Asn
            20                  25                  30
Ala Gln Gln Pro Asp Leu Ser Lys Ala Val Ser Leu Ser Met Gly Leu
        35                  40                  45
Tyr Met Gly Glu Thr Glu Thr Lys Val Met Gly Ser Asp Leu Gly Phe
    50                  55                  60
Pro Gln Gln Gly Gln Ile Ser Leu Ser Ser Gly Glu Thr Asp Phe Arg
65                  70                  75                  80
Leu Leu Glu Glu Ser Ile Ala Asn Leu Ser Arg Ser Thr Ser Val Pro
                85                  90                  95
Glu Asn Pro Lys Ser Ser Ala Ser Ala Ala Gly Pro Ala Ala Pro Ala
            100                 105                 110
Glu Lys Ala Phe Pro Lys Thr His Ser Asp Gly Ala Pro Glu Gln Pro
        115                 120                 125
Asn Val Lys Gly Gln Thr Gly Thr Asn Gly Gly Asn Val Lys Leu Phe
    130                 135                 140
Thr Thr Asp Gln Ser Thr Phe Asp Ile Trp Arg Lys Lys Leu Gln Asp
```

```
            145                 150                 155                 160
Leu Glu Leu Pro Ser Gly Ser Pro Gly Lys Glu Thr Ser Glu Ser Pro
                165                 170                 175
Trp Ser Ser Asp Leu Leu Ile Asp Glu Asn Cys Leu Leu Ser Pro Leu
                180                 185                 190
Ala Gly Glu Glu Asp Pro Phe Leu Leu Glu Gly Ser Ser Thr Glu Asp
                195                 200                 205
Cys Lys Pro Leu Val Leu Pro Asp Thr Lys Pro Lys Val Lys Asp Asn
                210                 215                 220
Gly Glu Leu Ile Leu Pro Ser Pro Asn Ser Val Pro Leu Pro Gln Val
225                 230                 235                 240
Lys Thr Glu Lys Glu Asp Phe Ile Glu Leu Cys Thr Pro Gly Val Ile
                245                 250                 255
Lys Gln Glu Lys Leu Gly Pro Ala Tyr Cys Gln Ala Ser Phe Ser Gly
                260                 265                 270
Ala Asn Ile Ile Gly Gly Lys Met Ser Ala Ile Ser Val His Gly Val
                275                 280                 285
Ser Thr Ser Gly Gly Gln Leu Tyr His Tyr Asp Met Asn Thr Ala Ala
                290                 295                 300
Ser Leu Ser Lys Gln Gln Glu Gln Lys Pro Leu Phe Asn Val Ile Pro
305                 310                 315                 320
Pro Ile Pro Val Gly Ser Glu Asn Trp Asn Arg Cys Gln Gly Ser Gly
                325                 330                 335
Asp Asp Asn Leu Thr Ser Leu Gly Thr Leu Asn Phe Ser Gly Arg Ser
                340                 345                 350
Val Phe Ser Asn Gly Tyr Ser Ser Pro Gly Met Arg Pro Asp Val Ser
                355                 360                 365
Ser Pro Pro Ser Ser Ser Ala Ala Thr Gly Pro Pro Pro Lys Leu
                370                 375                 380
Cys Leu Val Cys Ser Asp Glu Ala Ser Gly Cys His Tyr Gly Val Leu
385                 390                 395                 400
Thr Cys Gly Ser Cys Lys Val Phe Phe Lys Arg Ala Val Glu Gly Gln
                405                 410                 415
His Asn Tyr Leu Cys Ala Gly Arg Asn Asp Cys Ile Ile Asp Lys Ile
                420                 425                 430
Arg Arg Lys Asn Cys Pro Ala Cys Arg Tyr Arg Lys Cys Leu Gln Ala
                435                 440                 445
Gly Met Asn Leu Glu Ala Arg Lys Thr Lys Lys Ile Lys Gly Ile
                450                 455                 460
Gln Gln Ala Thr Thr Gly Val Ser Gln Glu Thr Ser Glu Asn Ser Ala
465                 470                 475                 480
Asn Lys Thr Ile Val Pro Ala Thr Leu Pro Gln Leu Thr Pro Thr Leu
                485                 490                 495
Val Ser Leu Leu Glu Val Ile Glu Pro Glu Val Leu Tyr Ala Gly Tyr
                500                 505                 510
Asp Ser Ser Ile Pro Asp Ser Thr Trp Arg Ile Met Thr Ala Leu Asn
                515                 520                 525
Met Leu Gly Gly Arg Gln Val Ile Ala Ala Val Lys Trp Ala Lys Ala
                530                 535                 540
Ile Pro Gly Phe Arg Asn Leu His Leu Asp Asp Gln Met Thr Leu Leu
545                 550                 555                 560
Gln Tyr Ser Trp Met Phe Leu Met Val Phe Ala Leu Gly Trp Arg Ser
                565                 570                 575
```

```
Tyr Arg Gln Ser Ser Ala Ser Leu Leu Cys Phe Ala Pro Asp Leu Val
                580                 585                 590

Ile Asn Glu Gln Arg Met Ala Leu Pro Cys Met Tyr Asp Gln Cys Arg
            595                 600                 605

His Met Leu Tyr Val Ser Ser Glu Leu Gln Arg Leu Gln Val Ser Tyr
        610                 615                 620

Glu Glu Tyr Leu Cys Met Lys Thr Leu Leu Leu Ser Ser Val Pro
625                 630                 635                 640

Lys Asp Gly Leu Lys Ser Gln Glu Leu Phe Asp Glu Ile Arg Met Thr
                645                 650                 655

Tyr Ile Lys Glu Leu Gly Lys Ala Ile Val Lys Arg Glu Gly Asn Ser
            660                 665                 670

Ser Gln Asn Trp Gln Arg Phe Tyr Gln Leu Thr Lys Leu Leu Asp Ser
        675                 680                 685

Met His Asp Val Val Glu Asn Leu Leu Asn Tyr Cys Phe Gln Thr
690                 695                 700
```

<210> SEQ ID NO 16
<211> LENGTH: 771
<212> TYPE: PRT
<213> ORGANISM: Cavia porcellus

<400> SEQUENCE: 16

```
Met Asp Leu Lys Glu Ser Val Thr Ser Ser Lys Glu Val Pro Ser Ser
1               5                   10                  15

Val Leu Gly Ser Glu Arg Arg Asn Val Ile Asp Phe Tyr Lys Thr Val
            20                  25                  30

Arg Gly Gly Ala Thr Val Lys Val Ser Ala Ser Ser Pro Ser Leu Ala
        35                  40                  45

Ala Ala Ala Gln Ser Asp Ser Lys Gln Arg Arg Leu Leu Val Asp Phe
    50                  55                  60

Pro Lys Gly Ser Gly Ser Asn Ala Gln Gln Pro Asp Leu Ser Lys Ala
65                  70                  75                  80

Val Ser Leu Ser Met Gly Leu Tyr Met Gly Thr Glu Thr Lys Val
                85                  90                  95

Met Gly Asn Asp Leu Gly Phe Pro Gln Gln Gly Gln Ile Ser Leu Pro
            100                 105                 110

Ser Gly Glu Thr Asp Phe Arg Leu Leu Glu Glu Ser Ile Ala Asn Leu
        115                 120                 125

Ser Arg Ser Thr Ser Val Pro Glu Asn Pro Lys Asn Ser Ala Ser Ala
    130                 135                 140

Val Ser Gly Thr Pro Thr Glu Glu Phe Pro Lys Thr Gln Ser Asp Leu
145                 150                 155                 160

Ser Ser Glu Gln Glu Asn Leu Lys Ser Gln Ala Gly Thr Asn Gly Gly
                165                 170                 175

Asn Val Lys Phe Pro Pro Asp Gln Ser Thr Phe Asp Ile Leu Lys Asp
            180                 185                 190

Leu Glu Phe Ser Ser Gly Ser Pro Gly Lys Glu Arg Ser Glu Ser Pro
        195                 200                 205

Trp Arg Pro Asp Leu Leu Met Asp Glu Ser Cys Leu Leu Ser Pro Leu
    210                 215                 220

Ala Gly Glu Asp Asp Pro Phe Leu Leu Glu Gly Asn Ser Asn Glu Asp
225                 230                 235                 240

Cys Lys Pro Leu Ile Leu Pro Asp Thr Lys Pro Lys Ile Lys Asp Asn
```

-continued

```
                245                 250                 255
Gly Asp Gly Ile Leu Ser Ser Asn Ser Val Pro Gln Pro Gln Val
                260                 265                 270
Lys Ile Gly Lys Glu Asp Phe Ile Glu Leu Cys Thr Pro Gly Val Ile
                275                 280                 285
Lys Gln Glu Lys Leu Gly Pro Val Tyr Cys Gln Ala Ser Phe Ser Gly
                290                 295                 300
Ala Asn Ile Ile Gly Asn Lys Met Ser Ala Ile Ser Val His Gly Val
305                 310                 315                 320
Ser Thr Ser Gly Gly Gln Met Tyr His Tyr Asp Met Asn Thr Ala Ser
                325                 330                 335
Leu Ser Gln Gln Gln Asp Gln Lys Pro Ile Phe Asn Val Ile Pro Pro
                340                 345                 350
Ile Pro Val Gly Ser Glu Asn Trp Asn Arg Cys Gln Gly Ser Gly Glu
                355                 360                 365
Asp Asn Leu Thr Ser Leu Gly Thr Val Asn Phe Pro Gly Arg Ser Val
                370                 375                 380
Phe Ser Asn Gly Tyr Ser Ser Pro Gly Leu Arg Pro Asp Val Ser Ser
385                 390                 395                 400
Pro Pro Ser Ser Ser Thr Thr Thr Gly Pro Pro Lys Leu Cys
                405                 410                 415
Leu Val Cys Ser Asp Glu Leu Ser Gly Cys His Tyr Gly Val Leu Thr
                420                 425                 430
Cys Gly Ser Cys Lys Val Phe Phe Lys Arg Ala Val Glu Gly Gln His
                435                 440                 445
Asn Tyr Leu Cys Ala Gly Arg Asn Asp Cys Ile Ile Asp Lys Ile Arg
                450                 455                 460
Arg Glu Asn Cys Pro Ala Cys Arg Tyr Arg Lys Cys Leu Gln Ala Gly
465                 470                 475                 480
Met Asn Leu Gln Ala Arg Lys Thr Lys Lys Ile Lys Gly Ile Gln
                485                 490                 495
Gln Ala Thr Thr Gly Val Ser Gln Asn Thr Ser Glu Asn Pro Asn Lys
                500                 505                 510
Thr Ile Val Pro Ala Thr Leu Pro Gln Leu Thr Pro Thr Leu Val Ser
                515                 520                 525
Leu Leu Glu Val Ile Glu Pro Glu Val Ile His Ser Gly Tyr Asp Ser
                530                 535                 540
Thr Ser Pro Asp Ser Thr Trp Arg Ile Met Thr Thr Leu Asn Met Leu
545                 550                 555                 560
Gly Gly Arg Gln Val Ile Ala Ala Val Lys Trp Ala Lys Ala Ile Pro
                565                 570                 575
Gly Phe Lys Asn Leu His Leu Asp Asp Gln Met Thr Leu Leu Gln Tyr
                580                 585                 590
Ser Trp Met Phe Leu Met Ala Phe Ala Leu Gly Trp Arg Ser Tyr Lys
                595                 600                 605
Gln Ser Asn Gly Ser Leu Leu Cys Phe Ala Pro Asp Leu Ile Ile Asn
                610                 615                 620
Glu Gln Arg Met Ser Leu Pro Trp Met Tyr Asp Gln Cys Arg Tyr Met
625                 630                 635                 640
Leu Tyr Val Ser Ser Glu Leu Lys Arg Leu Gln Val Ser Tyr Glu Glu
                645                 650                 655
Tyr Leu Cys Met Lys Thr Leu Leu Leu Leu Ser Ser Val Pro Lys Glu
                660                 665                 670
```

```
Gly Leu Lys Ser Gln Glu Leu Phe Asp Glu Ile Arg Met Thr Tyr Ile
            675                 680                 685
Lys Glu Leu Gly Lys Ala Ile Val Lys Arg Glu Gly Asn Ser Ser Gln
        690                 695                 700
Asn Trp Gln Arg Phe Tyr Gln Leu Thr Lys Leu Leu Asp Ser Leu His
705                 710                 715                 720
Glu Ile Val Gly Asn Leu Leu Asn Ile Cys Phe Lys Thr Phe Leu Asp
                725                 730                 735
Lys Thr Met Asn Ile Glu Phe Pro Glu Met Leu Ala Glu Ile Ile Thr
            740                 745                 750
Asn Gln Leu Pro Lys Tyr Ser Asn Gly Asp Ile Lys Lys Leu Leu Phe
        755                 760                 765
His Gln Lys
    770

<210> SEQ ID NO 17
<211> LENGTH: 777
<212> TYPE: PRT
<213> ORGANISM: Saguinus oedipus

<400> SEQUENCE: 17

Met Asp Ser Lys Glu Ser Leu Thr Pro Gly Lys Glu Glu Asn Pro Ser
1               5                   10                  15
Ser Val Leu Thr Gln Glu Arg Gly Asn Val Met Asp Phe Cys Lys Ile
            20                  25                  30
Leu Arg Gly Gly Ala Thr Leu Lys Val Ser Val Ser Ser Thr Ser Leu
        35                  40                  45
Ala Ala Ala Ser Gln Ser Asp Ser Lys Gln Gln Arg Leu Leu Val Asp
    50                  55                  60
Phe Pro Lys Gly Ser Val Ser Asn Ala Gln Gln Pro Asp Leu Ser Lys
65                  70                  75                  80
Ala Val Ser Leu Ser Met Gly Leu Tyr Met Gly Glu Thr Glu Thr Lys
                85                  90                  95
Val Met Gly Asn Asp Leu Gly Phe Pro Gln Gln Gly Gln Ile Ser Leu
            100                 105                 110
Ser Ser Gly Glu Thr Asp Leu Gln Leu Leu Glu Glu Ser Ile Ala Asn
        115                 120                 125
Leu Asn Arg Ser Thr Ser Val Pro Glu Asn Pro Lys Ser Ser Ala Ser
    130                 135                 140
Ser Ser Val Ser Ala Ala Pro Lys Glu Lys Glu Phe Pro Lys Thr His
145                 150                 155                 160
Ser Asp Val Ser Ser Glu Gln Gln Asn Leu Lys Gly Gln Thr Gly Thr
                165                 170                 175
Asn Gly Gly Asn Ala Lys Leu Cys Thr Ala Asp Gln Ser Thr Phe Asp
            180                 185                 190
Ile Leu Gln Asp Leu Glu Phe Ser Ser Gly Ser Pro Gly Lys Glu Thr
        195                 200                 205
Asn Gln Ser Pro Trp Arg Ser Asp Leu Leu Ile Asp Glu Asn Cys Leu
    210                 215                 220
Leu Ser Pro Leu Ala Gly Glu Glu Asp Ser Phe Leu Leu Glu Gly Asn
225                 230                 235                 240
Ser Asn Glu Asp Cys Lys Pro Leu Ile Leu Pro Asp Thr Lys Pro Lys
                245                 250                 255
Ile Lys Asp Asn Gly Asp Leu Val Leu Ser Ser Ser Ser Asn Val Thr
```

```
                260                 265                 270
Leu Pro Gln Val Lys Thr Glu Lys Glu Asp Phe Ile Glu Leu Cys Thr
            275                 280                 285

Pro Gly Val Ile Lys Gln Glu Lys Leu Ser Thr Val Tyr Cys Gln Ala
290                 295                 300

Ser Phe Pro Gly Ala Asn Ile Ile Gly Asn Lys Met Ser Ala Ile Ser
305                 310                 315                 320

Ile His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
            355                 360                 365

Gly Ser Gly Asp Asp Asn Leu Thr Ser Leu Gly Thr Leu Asn Phe Pro
            370                 375                 380

Gly Arg Thr Val Phe Ser Asn Gly Tyr Ser Ser Pro Ser Met Arg Pro
385                 390                 395                 400

Asp Val Ser Ser Pro Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
            435                 440                 445

Val Glu Gly Gln His Asn Tyr Leu Cys Ala Gly Arg Asn Asp Cys Ile
450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Ala Asn Lys Thr Ile Val Pro Ala Thr Leu Pro Gln Leu
            515                 520                 525

Thr Pro Thr Leu Val Ser Leu Leu Glu Val Ile Glu Pro Glu Val Leu
530                 535                 540

Tyr Ala Gly Tyr Asp Ser Thr Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
            595                 600                 605

Gly Trp Arg Ser Tyr Arg Gln Ala Ser Ser Asn Leu Leu Cys Phe Ala
            610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
            675                 680                 685
```

```
Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Leu Pro Lys Tyr Ser Asn Gly Asn
        755                 760                 765

Ile Arg Lys Leu Leu Phe His Gln Lys
    770                 775

<210> SEQ ID NO 18
<211> LENGTH: 777
<212> TYPE: PRT
<213> ORGANISM: Aotus nancymaae

<400> SEQUENCE: 18

Met Asp Ser Lys Glu Ser Leu Thr Pro Gly Lys Glu Asn Pro Ser
1               5                   10                  15

Ser Val Leu Thr Gln Glu Arg Gly Asn Val Met Asp Phe Ser Lys Ile
            20                  25                  30

Leu Arg Gly Gly Ala Thr Leu Lys Val Ser Val Ser Ser Thr Ser Leu
        35                  40                  45

Ala Ala Ala Ser Gln Ser Asp Ser Lys Gln Gln Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Gln Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Ser Ser Val Ser Ala Ala Pro Lys Glu Lys Glu Phe Pro Lys Thr His
145                 150                 155                 160

Ser Asp Val Ser Ser Glu Gln Gln Asn Leu Lys Gly Gln Thr Gly Thr
                165                 170                 175

Asn Gly Gly Asn Val Lys Leu Tyr Thr Ala Asp Gln Ser Thr Phe Asp
            180                 185                 190

Ile Leu Gln Asp Leu Glu Phe Ser Gly Ser Pro Gly Lys Glu Thr
        195                 200                 205

Asn Gln Ser Pro Trp Arg Ser Asp Leu Leu Ile Asp Glu Asn Cys Leu
    210                 215                 220

Leu Ser Pro Leu Ala Gly Glu Glu Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Ser Asn Val Thr
            260                 265                 270

Leu Pro Gln Val Lys Thr Glu Lys Glu Asp Phe Ile Glu Leu Cys Thr
```

-continued

```
              275                 280                 285
Pro Gly Val Ile Lys Gln Glu Lys Leu Ser Thr Val Tyr Cys Gln Ala
    290                 295                 300

Ser Phe Pro Gly Ala Asn Val Ile Gly Asn Lys Met Ser Ala Ile Ser
305                 310                 315                 320

Ile His Gly Val Ser Thr Ser Gly Gln Met Tyr His Tyr Asp Met
                325                 330                 335

Asn Thr Ala Ser Leu Ser Gln Gln Gln Asp Gln Lys Pro Ile Phe Asn
                340                 345                 350

Val Ile Pro Pro Ile Pro Val Gly Ser Glu Asn Trp Asn Arg Cys Gln
            355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
    435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Ala Asn Lys Thr Ile Val Pro Ala Thr Leu Pro Gln Leu
            515                 520                 525

Thr Pro Thr Leu Val Ser Leu Leu Glu Val Ile Glu Pro Glu Val Leu
    530                 535                 540

Tyr Ala Gly Tyr Asp Ser Thr Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
            595                 600                 605

Gly Trp Arg Ser Tyr Arg Gln Ala Ser Ser Asn Leu Leu Cys Phe Ala
    610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
            675                 680                 685

Ile Arg Met Thr Tyr Ile Lys Glu Leu Gly Lys Ala Ile Val Lys Arg
    690                 695                 700
```

```
Glu Gly Asn Ser Ser Gln Asn Trp Gln Arg Phe Tyr Gln Leu Thr Lys
705                 710                 715                 720

Leu Leu Asp Ser Met His Glu Val Glu Asn Leu Leu Asn Tyr Cys
            725                 730                 735

Phe Gln Thr Phe Leu Asp Lys Thr Met Ser Ile Glu Phe Pro Glu Met
                740                 745                 750

Leu Ala Glu Ile Ile Thr Asn Gln Leu Pro Lys Tyr Ser Asn Gly Asn
            755                 760                 765

Ile Lys Lys Leu Leu Phe His Gln Lys
        770                 775

<210> SEQ ID NO 19
<211> LENGTH: 795
<212> TYPE: PRT
<213> ORGANISM: Rattus norvegicus

<400> SEQUENCE: 19

Met Asp Ser Lys Glu Ser Leu Ala Pro Pro Gly Arg Asp Glu Val Pro
1               5                   10                  15

Gly Ser Leu Leu Gly Gln Gly Arg Gly Ser Val Met Asp Phe Tyr Lys
            20                  25                  30

Ser Leu Arg Gly Gly Ala Thr Val Lys Val Ser Ala Ser Ser Pro Ser
        35                  40                  45

Val Ala Ala Ala Ser Gln Ala Asp Ser Lys Gln Gln Arg Ile Leu Leu
    50                  55                  60

Asp Phe Ser Lys Gly Ser Thr Ser Asn Val Gln Gln Arg Gln Gln Gln
65                  70                  75                  80

Gln Gln Gln Gln Gln Gln Gln Gln Gln Gln Gln Gln Gln Gln Gln Gln
                85                  90                  95

Pro Gly Leu Ser Lys Ala Val Ser Leu Ser Met Gly Leu Tyr Met Gly
            100                 105                 110

Glu Thr Glu Thr Lys Val Met Gly Asn Asp Leu Gly Tyr Pro Gln Gln
        115                 120                 125

Gly Gln Leu Gly Leu Ser Ser Gly Glu Thr Asp Phe Arg Leu Leu Glu
    130                 135                 140

Glu Ser Ile Ala Asn Leu Asn Arg Ser Thr Ser Val Pro Glu Asn Pro
145                 150                 155                 160

Lys Ser Ser Thr Ser Ala Thr Gly Cys Ala Thr Pro Thr Glu Lys Glu
                165                 170                 175

Phe Pro Lys Thr His Ser Asp Ala Ser Ser Glu Gln Gln Asn Arg Lys
            180                 185                 190

Ser Gln Thr Gly Thr Asn Gly Gly Ser Val Lys Leu Tyr Pro Thr Asp
        195                 200                 205

Gln Ser Thr Phe Asp Leu Leu Lys Asp Leu Glu Phe Ser Ala Gly Ser
    210                 215                 220

Pro Ser Lys Asp Thr Asn Glu Ser Pro Trp Arg Ser Asp Leu Leu Ile
225                 230                 235                 240

Asp Glu Asn Leu Leu Ser Pro Leu Ala Gly Glu Asp Asp Pro Phe Leu
                245                 250                 255

Leu Glu Gly Asn Thr Asn Glu Asp Cys Lys Pro Leu Ile Leu Pro Asp
            260                 265                 270

Thr Lys Pro Lys Ile Lys Asp Thr Gly Asp Thr Ile Leu Ser Ser Pro
        275                 280                 285

Ser Ser Val Ala Leu Pro Gln Val Lys Thr Glu Lys Asp Asp Phe Ile
```

```
                290                 295                 300
Glu Leu Cys Thr Pro Gly Val Ile Lys Gln Glu Lys Leu Gly Pro Val
305                 310                 315                 320

Tyr Cys Gln Ala Ser Phe Ser Gly Thr Asn Ile Ile Gly Asn Lys Met
                325                 330                 335

Ser Ala Ile Ser Val His Gly Val Ser Thr Ser Gly Gly Gln Met Tyr
                340                 345                 350

His Tyr Asp Met Asn Thr Ala Ser Leu Ser Gln Gln Gln Asp Gln Lys
                355                 360                 365

Pro Val Phe Asn Val Ile Pro Pro Ile Pro Val Gly Ser Glu Asn Trp
370                 375                 380

Asn Arg Cys Gln Gly Ser Gly Glu Asp Ser Leu Thr Ser Leu Gly Ala
385                 390                 395                 400

Leu Asn Phe Pro Gly Arg Ser Val Phe Ser Asn Gly Tyr Ser Ser Pro
                405                 410                 415

Gly Met Arg Pro Asp Val Ser Ser Pro Ser Ser Ser Ala Ala
                420                 425                 430

Thr Gly Pro Pro Pro Lys Leu Cys Leu Val Cys Ser Asp Glu Ala Ser
                435                 440                 445

Gly Cys His Tyr Gly Val Leu Thr Cys Gly Ser Cys Lys Val Phe Phe
                450                 455                 460

Lys Arg Ala Val Glu Gly Gln His Asn Tyr Leu Cys Ala Gly Arg Asn
465                 470                 475                 480

Asp Cys Ile Ile Asp Lys Ile Arg Arg Lys Asn Cys Pro Ala Cys Arg
                485                 490                 495

Tyr Arg Lys Cys Leu Gln Ala Gly Met Asn Leu Glu Ala Arg Lys Thr
                500                 505                 510

Lys Lys Lys Ile Lys Gly Ile Gln Gln Ala Thr Ala Gly Val Ser Gln
                515                 520                 525

Asp Thr Ser Glu Asn Pro Asn Lys Thr Ile Val Pro Ala Ala Leu Pro
                530                 535                 540

Gln Leu Thr Pro Thr Leu Val Ser Leu Leu Glu Val Ile Glu Pro Glu
545                 550                 555                 560

Val Leu Tyr Ala Gly Tyr Asp Ser Ser Val Pro Asp Ser Ala Trp Arg
                565                 570                 575

Ile Met Thr Thr Leu Asn Met Leu Gly Gly Arg Gln Val Ile Ala Ala
                580                 585                 590

Val Lys Trp Ala Lys Ala Ile Leu Gly Leu Arg Asn Leu His Leu Asp
                595                 600                 605

Asp Gln Met Thr Leu Leu Gln Tyr Ser Trp Met Phe Leu Met Ala Phe
                610                 615                 620

Ala Leu Gly Trp Arg Ser Tyr Arg Gln Ser Ser Gly Asn Leu Leu Cys
625                 630                 635                 640

Phe Ala Pro Asp Leu Ile Ile Asn Glu Gln Arg Met Ser Leu Pro Cys
                645                 650                 655

Met Tyr Asp Gln Cys Lys His Met Leu Phe Val Ser Ser Glu Leu Gln
                660                 665                 670

Arg Leu Gln Val Ser Tyr Glu Glu Tyr Leu Cys Met Lys Thr Leu Leu
                675                 680                 685

Leu Leu Ser Ser Val Pro Lys Glu Gly Leu Lys Ser Gln Glu Leu Phe
                690                 695                 700

Asp Glu Ile Arg Met Thr Tyr Ile Lys Glu Leu Gly Lys Ala Ile Val
705                 710                 715                 720
```

Lys Arg Glu Gly Asn Ser Ser Gln Asn Trp Gln Arg Phe Tyr Gln Leu
            725                 730                 735

Thr Lys Leu Leu Asp Ser Met His Glu Val Val Glu Asn Leu Leu Thr
            740                 745                 750

Tyr Cys Phe Gln Thr Phe Leu Asp Lys Thr Met Ser Ile Glu Phe Pro
            755                 760                 765

Glu Met Leu Ala Glu Ile Ile Thr Asn Gln Ile Pro Lys Tyr Ser Asn
            770                 775                 780

Gly Asn Ile Lys Lys Leu Leu Phe His Gln Lys
785                 790                 795

<210> SEQ ID NO 20
<211> LENGTH: 783
<212> TYPE: PRT
<213> ORGANISM: Mus musculus

<400> SEQUENCE: 20

Met Asp Ser Lys Glu Ser Leu Ala Pro Pro Gly Arg Asp Glu Val Pro
1               5                   10                  15

Ser Ser Leu Leu Gly Arg Gly Arg Gly Ser Val Met Asp Leu Tyr Lys
            20                  25                  30

Thr Leu Arg Gly Gly Ala Thr Val Lys Val Ser Ala Ser Ser Pro Ser
        35                  40                  45

Val Ala Ala Ala Ser Gln Ala Asp Ser Lys Gln Gln Arg Ile Leu Leu
    50                  55                  60

Asp Phe Ser Lys Gly Ser Ala Ser Asn Ala Gln Gln Gln Gln Gln Gln
65                  70                  75                  80

Gln Gln Pro Gln Pro Asp Leu Ser Lys Ala Val Ser Leu Ser Met Gly
            85                  90                  95

Leu Tyr Met Gly Glu Thr Glu Thr Lys Val Met Gly Asn Asp Leu Gly
            100                 105                 110

Tyr Pro Gln Gln Gly Gln Leu Gly Leu Ser Ser Gly Glu Thr Asp Phe
            115                 120                 125

Arg Leu Leu Glu Glu Ser Ile Ala Asn Leu Asn Arg Ser Thr Ser Arg
130                 135                 140

Pro Glu Asn Pro Lys Ser Ser Thr Pro Ala Ala Gly Cys Ala Thr Pro
145                 150                 155                 160

Thr Glu Lys Glu Phe Pro Gln Thr His Ser Asp Pro Ser Ser Glu Gln
            165                 170                 175

Gln Asn Arg Lys Ser Gln Pro Gly Thr Asn Gly Gly Ser Val Lys Leu
            180                 185                 190

Tyr Thr Thr Asp Gln Ser Thr Phe Asp Ile Leu Gln Asp Leu Glu Phe
            195                 200                 205

Ser Ala Gly Ser Pro Gly Lys Glu Thr Asn Glu Ser Pro Trp Arg Ser
    210                 215                 220

Asp Leu Leu Ile Asp Glu Asn Leu Leu Ser Pro Leu Ala Gly Glu Asp
225                 230                 235                 240

Asp Pro Phe Leu Leu Glu Gly Asp Val Asn Glu Asp Cys Lys Pro Leu
            245                 250                 255

Ile Leu Pro Asp Thr Lys Pro Lys Ile Gln Asp Thr Gly Asp Thr Ile
            260                 265                 270

Leu Ser Ser Pro Ser Ser Val Ala Leu Pro Gln Val Lys Thr Glu Lys
        275                 280                 285

Asp Asp Phe Ile Glu Leu Cys Thr Pro Gly Val Ile Lys Gln Glu Lys

-continued

```
          290                 295                 300
Leu Gly Pro Val Tyr Cys Gln Ala Ser Phe Ser Gly Thr Asn Ile Ile
305                 310                 315                 320

Gly Asn Lys Met Ser Ala Ile Ser Val His Gly Val Ser Thr Ser Gly
                325                 330                 335

Gly Gln Met Tyr His Tyr Asp Met Asn Thr Ala Ser Leu Ser Gln Gln
                340                 345                 350

Gln Asp Gln Lys Pro Val Phe Asn Val Ile Pro Ile Pro Val Gly
            355                 360                 365

Ser Glu Asn Trp Asn Arg Cys Gln Gly Ser Gly Glu Asp Asn Leu Thr
370                 375                 380

Ser Leu Gly Ala Met Asn Phe Ala Gly Arg Ser Val Phe Ser Asn Gly
385                 390                 395                 400

Tyr Ser Ser Pro Gly Met Arg Pro Asp Val Ser Ser Pro Pro Ser Ser
                405                 410                 415

Ser Ser Thr Ala Thr Gly Pro Pro Lys Leu Cys Leu Val Cys Ser
            420                 425                 430

Asp Glu Ala Ser Val Cys His Tyr Gly Val Leu Thr Cys Gly Ser Cys
                435                 440                 445

Lys Val Phe Phe Lys Arg Ala Val Glu Gly Gln His Asn Tyr Leu Cys
450                 455                 460

Ala Gly Arg Asn Asp Cys Ile Ile Asp Lys Ile Arg Arg Lys Asn Cys
465                 470                 475                 480

Pro Ala Cys Arg Tyr Arg Lys Cys Leu Gln Ala Gly Met Asn Leu Glu
                485                 490                 495

Ala Arg Lys Thr Lys Lys Lys Ile Lys Gly Ile Gln Gln Ala Thr Ala
            500                 505                 510

Gly Val Ser Gln Asp Thr Ser Glu Asn Ala Asn Lys Thr Ile Val Pro
        515                 520                 525

Ala Ala Leu Pro Gln Leu Thr Pro Thr Leu Val Ser Leu Leu Glu Val
        530                 535                 540

Ile Glu Pro Glu Val Leu Tyr Ala Gly Tyr Asp Ser Ser Val Pro Asp
545                 550                 555                 560

Ser Ala Trp Arg Ile Met Thr Thr Leu Asn Met Leu Gly Gly Arg Gln
                565                 570                 575

Val Ile Ala Ala Val Lys Trp Ala Lys Ala Ile Pro Gly Phe Arg Asn
            580                 585                 590

Leu His Leu Asp Asp Gln Met Thr Leu Leu Gln Tyr Ser Trp Met Phe
        595                 600                 605

Leu Met Ala Phe Ala Leu Gly Trp Arg Ser Tyr Arg Gln Ala Ser Gly
        610                 615                 620

Asn Leu Leu Cys Phe Ala Pro Asp Leu Ile Ile Asn Glu Gln Arg Met
625                 630                 635                 640

Thr Leu Pro Cys Met Tyr Asp Gln Cys Lys His Met Leu Phe Ile Ser
                645                 650                 655

Thr Glu Leu Gln Arg Leu Gln Val Ser Tyr Glu Glu Tyr Leu Cys Met
                660                 665                 670

Lys Thr Leu Leu Leu Leu Ser Ser Val Pro Lys Glu Gly Leu Lys Ser
            675                 680                 685

Gln Glu Leu Phe Asp Glu Ile Arg Met Thr Tyr Ile Lys Glu Leu Gly
        690                 695                 700

Lys Ala Ile Val Lys Arg Glu Gly Asn Ser Ser Gln Asn Trp Gln Arg
705                 710                 715                 720
```

Phe Tyr Gln Leu Thr Lys Leu Leu Asp Ser Met His Asp Val Val Glu
                725                 730                 735

Asn Leu Leu Ser Tyr Cys Phe Gln Thr Phe Leu Asp Lys Ser Met Ser
            740                 745                 750

Ile Glu Phe Pro Glu Met Leu Ala Glu Ile Ile Thr Asn Gln Ile Pro
        755                 760                 765

Lys Tyr Ser Asn Gly Asn Ile Lys Lys Leu Leu Phe His Gln Lys
    770                 775                 780

<210> SEQ ID NO 21
<211> LENGTH: 777
<212> TYPE: PRT
<213> ORGANISM: Homo sapiens

<400> SEQUENCE: 21

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Pro Ser Leu
        35                  40                  45

Ala Val Ala Ser Gln Ser Asp Ser Lys Gln Arg Arg Leu Leu Val Asp
50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser

-continued

```
            305                 310                 315                 320
Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
                340                 345                 350

Val Ile Pro Pro Ile Pro Val Gly Ser Glu Asn Trp Asn Arg Cys Gln
                355                 360                 365

Gly Ser Gly Asp Asp Asn Leu Thr Ser Leu Gly Thr Leu Asn Phe Pro
                370                 375                 380

Gly Arg Thr Val Phe Ser Asn Gly Tyr Ser Ser Pro Ser Met Arg Pro
385                 390                 395                 400

Asp Val Ser Ser Pro Ser Ser Ser Thr Ala Thr Thr Gly Pro
                405                 410                 415

Pro Pro Lys Leu Cys Leu Val Cys Ser Asp Glu Ala Ser Gly Cys His
                420                 425                 430

Tyr Gly Val Leu Thr Cys Gly Ser Cys Lys Val Phe Phe Lys Arg Ala
                435                 440                 445

Val Glu Gly Gln His Asn Tyr Leu Cys Ala Gly Arg Asn Asp Cys Ile
                450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
                500                 505                 510

Glu Asn Pro Gly Asn Lys Thr Ile Val Pro Ala Thr Leu Pro Gln Leu
                515                 520                 525

Thr Pro Thr Leu Val Ser Leu Leu Glu Val Ile Glu Pro Glu Val Leu
                530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
                580                 585                 590

Met Thr Leu Leu Gln Tyr Ser Trp Met Phe Leu Met Ala Phe Ala Leu
                595                 600                 605

Gly Trp Arg Ser Tyr Arg Gln Ser Ser Ala Asn Leu Leu Cys Phe Ala
                610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
                660                 665                 670

Ser Ser Val Pro Lys Asp Gly Leu Lys Ser Gln Glu Leu Phe Asp Glu
                675                 680                 685

Ile Arg Met Thr Tyr Ile Lys Glu Leu Gly Lys Ala Ile Val Lys Arg
                690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735
```

```
Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
            755             760                 765

Ile Lys Lys Leu Leu Phe His Gln Lys
    770             775
```